United States Patent
Patsalis et al.

(10) Patent No.: US 9,249,462 B2
(45) Date of Patent: Feb. 2, 2016

(54) METHODS AND COMPOSITIONS FOR NONINVASIVE PRENATAL DIAGNOSIS OF FETAL ANEUPLOIDIES

(75) Inventors: Philippos C. Patsalis, Nicosia (CY); Elisavet A. Papageorgiou, Nicosia (CY)

(73) Assignee: NIPD Genetics Ltd, Nicosia (CY)

( * ) Notice: Subject to any disclaimer, the term of this patent is extended or adjusted under 35 U.S.C. 154(b) by 0 days.

(21) Appl. No.: 13/520,708

(22) PCT Filed: Jan. 26, 2011

(86) PCT No.: PCT/IB2011/000217
§ 371 (c)(1),
(2), (4) Date: Jul. 5, 2012

(87) PCT Pub. No.: WO2011/092592
PCT Pub. Date: Aug. 4, 2011

(65) Prior Publication Data
US 2012/0282613 A1 Nov. 8, 2012

Related U.S. Application Data

(60) Provisional application No. 61/298,339, filed on Jan. 26, 2010, provisional application No. 61/405,421, filed on Oct. 21, 2010.

(51) Int. Cl.
*C12Q 1/68* (2006.01)

(52) U.S. Cl.
CPC ............ *C12Q 1/6883* (2013.01); *C12Q 1/6804* (2013.01); *C12Q 1/6806* (2013.01); *C12Q 1/6809* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 2001/0053519 A1* | 12/2001 | Fodor et al. | | 435/6 |
| 2007/0275402 A1* | 11/2007 | Lo et al. | | 435/6 |
| 2010/0105049 A1 | 4/2010 | Ehrich et al. | | |

FOREIGN PATENT DOCUMENTS

| | | |
|---|---|---|
| JP | 2008-502332 A | 1/2008 |
| JP | 2008-521389 A | 6/2008 |

(Continued)

OTHER PUBLICATIONS

Puszyk. University of Warwick. Department of Biological Sciences. Sep. 2008.*

(Continued)

*Primary Examiner* — Juliet Switzer
*Assistant Examiner* — Joseph G Dauner
(74) *Attorney, Agent, or Firm* — Nelson Mullins Riley & Scarborough LLP; Jill Gorny Sloper, Esq.

(57) ABSTRACT

The invention provides methods and compositions for non-invasive prenatal diagnosis of fetal aneuploidies. A large panel of differentially methylated regions (DMRs) have been identified. Certain of these DMRs are hypomethylated in adult female blood DNA and hypermethylated in fetal DNA, whereas others are hypermethylated in adult female blood DNA and hypomethylated in fetal DNA. Moreover, DMRs that are hypomethylated in adult female blood DNA and hypermethylated in fetal DNA have been shown to accurately predict a fetal aneuploidy in fetal DNA present in a maternal blood sample during pregnancy. In the methods of the invention, hypermethylated DNA is physically separated from hypomethylated DNA, preferably by methylated DNA immunoprecipitation.

7 Claims, 9 Drawing Sheets

(56) References Cited

FOREIGN PATENT DOCUMENTS

| JP | 2009-232767 A | 10/2009 |
|---|---|---|
| WO | 2005/028674 A2 | 3/2005 |
| WO | 2005123942 A2 | 12/2005 |
| WO | 2006056480 A2 | 6/2006 |
| WO | 2007/007337 A1 | 1/2007 |
| WO | 2007/044780 A2 | 4/2007 |
| WO | 2007/132167 A2 | 11/2007 |
| WO | 2009013492 A1 | 1/2009 |

OTHER PUBLICATIONS

Bianchi, Diana W. et al., "Noninvasive Prenatal Diagnosis of Fetal Rhesus D, Ready for Prime(r) Time," Obstetrics & Gynecology, vol. 106(4):841-844 (2005).

Chan, K.C. Allen et al., "Size Distributions of Maternal and Fetal DNA in Maternal Plasma," Clinical Chemistry, vol. 50 (1):88-92 (2004).

Chim, Stephen S.C. et al., "Detection of the placental epigenetic signature of the maspin gene in maternal plasma," PNAS, vol. 102(41):14753-14758 (2005).

Chim, Stephen S.C. et al., "Systematic Search for Placental DNA-Methylation Markers on Chromosome 21: Toward a Maternal Plasma-Based Epigenetic Test for Fetal Trisomy 21," Clinical Chemistry, vol. 54(3):500-511 (2008).

Chiu, Rossa W.K. et al., "Hypermethylation of RASSF1A in Human and Rhesus Placentas," The American Journal of Pathology, vol. 170(3):941-950 (2007).

Chiu, Rossa W.K. et al., "Maternal Plasma DNA Analysis with Massively Parallel Sequencing by Ligation for Noninvasive Prenatal Diagnosis of Trisomy 21," Clinical Chemistry, vol. 56(3):459-463 (2010).

Chiu, Rossa W.K. et al., "Noninvasive prenatal diagnosis of fetal chromosomal aneuploidy by massively parallel genomic sequencing of DNA in maternal plasma," PNAS, vol. 105(51):20458-20463 (2008).

Chu, Tianjiao et al., "A microarray-based approach for the identification of epigenetic biomarkers for the noninvasive diagnosis of fetal disease," Prenat. Diagn., vol. 29:1020-1030 (2009).

Fan, H. Christina et al., "Noninvasive diagnosis of fetal aneuploidy by shotgun sequencing DNA from maternal blood," PNAS, vol. 105(42):16266-16271 (2008).

Fazzari, Melissa J. et al., "Epigenomics: Beyond CpG Islands," Nature Reviews Genetics, vol. 5:446-455 (2004).

Flori, E. et al., "Circulating cell-free fetal DNA in maternal serum appears to originate from cyto- and syncytio-trophoblastic cells. Case Report," Human Reproduction, vol. 19(3):723-724 (2004).

Go, Attie T.J.I. et al., "Non-invasive aneuploidy detection using free fetal DNA and RNA in maternal plasma: recent progress and future possibilities," Human Reproduction Update, vol. 17(3):372-382 (2011).

Grunau, C. et al., "Bisulfite genomic sequencing: systematic investigation of critical experimental parameters," Nucleic Acids Research, vol. 29(13):e65, 1-7 (2001).

Honda, Hiroshi et al., "Fetal gender determination in early pregnancy through qualitative and quantitative analysis of fetal DNA in maternal serum," Hum. Genet., vol. 110:75-79 (2002).

Hulten, Maj A. et al., "Rapid and simple prenatal diagnosis of common chromosome disorders: advantages and disadvantages of the molecular methods FISH and QF-PCR," Reproduction, vol. 126:279-297 (2003).

Lo, Y.M. Dennis et al., "Plasma placental RNA allelic ratio permits noninvasive prenatal chromosomal aneuploidy detection," Nature Medicine, vol. 13(2):218-223 (2007).

Lo, Y.M. Dennis et al., "Prenatal Diagnosis of Fetal RhD Status by Molecular Analysis of Maternal Plasma," The New England Journal of Medicine, vol. 339:1734-1738 (1998).

Lo, Y.M. Dennis et al., "Presence of fetal DNA in maternal plasma and serum," Lancet, vol. 350:485-487 (1997).

Lo, Y.M. Dennis et al., "Quantitative Analysis of Fetal DNA in Maternal Plasma and Serum: Implications for Noninvasive Prenatal Diagnosis," Am. J. Hum. Genet., vol. 62:768-775 (1998).

Masuzaki, H. et al., "Detection of cell free placental DNA in maternal plasma: direct evidence from three cases of confined placental mosaicism," J. Med. Genet., vol. 41:289-292 (2004).

Old, Robert W. et al., "Candidate epigenetic biomarkers for non-invasive prenatal diagnosis of Down syndrome," Reproductive BioMedicine Online, vol. 15(2):227-235 (2007).

Papageorgiou, Elisavet A. et al., "Fetal-specific DNA methylation ratio permits noninvasive prenatal diagnosis of trisomy 21," Nature Medicine, vol. 17(4):510-513 (2011).

Papageorgiou, Elisavet A. et al., "Non-invasive prenatal diagnosis of aneuploidies: new technologies and clinical applications," Genome Medicine, vol. 4:46, 1-12 (2012).

Papageorgiou, Elisavet A. et al., "Sites of Differential DNA Methylation between Placenta and Peripheral Blood," The American Journal of Pathology, vol. 174(5):1609-1618 (2009).

Patsalis, Philippos C. et al., "A new non-invasive prenatal diagnosis of Down syndrome through epigenetic markers and real-time qPCR," Expert Opin. Biol. Ther., vol. 12(Suppl. 1):S155-S161 (2012).

Patsalis, Philippos C. et al., "Non-Invasive Prenatal Diagnosis (NIPD) of Down Syndrome using real time qPCR," European Cytogeneticists Association Newsletter, No. 30:5-10 (2012).

Poon, Leo L.M. et al., "Differential DNA Methylation between Fetus and Mother as a Strategy for Detecting Fetal DNA in Maternal Plasma," Clinical Chemistry, vol. 48(1):35-41 (2002).

Rakyan, Vardhman K. et al., "An integrated resource for genome-wide identification and analysis of human tissue-specific differentially methylated regions (tDMRs)," Genome Research, vol. 18:1518-1529 (2008).

Tong, Yu K. et al., "Noninvasive Prenatal Detection of Trisomy 21 by an Epigenetic-Genetic Chromosome-Dosage Approach," Clinical Chemistry, vol. 56(1):90-98 (2010).

Tsaliki, Evdokia et al., "MeDIP real-time qPCR of maternal peripheral blood reliably identifies trisomy 21," Prenatal Diagnosis, vol. 32:996-1001 (2012).

Tsui, Nancy B.Y. et al., "A Microarray Approach for Systematic Identification of Placental-Derived RNA Markers in Maternal Plasma," Methods in Molecular Biology, vol. 444:275-289 (2008).

Tsui, Nancy B.Y. et al., "Detection of Tisomy 21 by Quantitative Mass Spectrometric Analysis of Single-Nucleotide Polymorphisms," Clinical Chemistry, vol. 51(12):2358-2362 (2005).

Tsui, Nancy B.Y. et al., "Non-invasive prenatal detection of fetal trisomy 18 by RNA-SNP allelic ratio analysis using maternal plasma SERPINB2 mRNA: a feasibility study," Prenatal Diagnosis, vol. 29:1031-1037 (2009).

Wald, N.J. et al., "Integrated Screening for Down's Syndrome Based on Tests Performed During the First and Second Trimesters," The New England Journal of Medicine, vol. 341(7):461-467 (1999).

Weber, Michael et al., "Chromosome-wide and promoter-specific analyses identify sites of differential DNA methylation in normal and transformed human cells," Nature Genetics, vol. 37(8):853-862 (2005).

Weisz, Boaz et al., "An update on antenatal screening for Down's syndrome and specific implications for assisted reproduction pregnancies," Human Reproduction Update, vol. 12(5):513-518 (2006).

International Search Report and Written Opinion for Application No. PCT/IB2011/000217, 15 pages, dated Aug. 23, 2011.

International Preliminary Report on Patentability and Written Opinion for Application No. PCT/IB2011/000217, 6 pages, dated Jul. 31, 2012.

* cited by examiner

METHODS AND COMPOSITIONS FOR NONINVASIVE PRENATAL DIAGNOSIS OF FETAL ANEUPLOIDIES

BACKGROUND OF THE INVENTION

Prenatal diagnosis is currently performed using conventional cytogenetic analysis (such as karyotyping) or DNA analysis (such as QF-PCR), which require fetal genetic material to be obtained by amniocentesis, chorionic villus sampling or chordocentesis. However, these are invasive procedures and are associated with a significant risk of fetal loss (0.5 to 1% for chorionic villus sampling and amniocentesis) (Hultén, M. A. et al. (2003) *Reproduction* 126:279-297). The need for effective prenatal diagnostic tests is particularly acute in the case of Down Syndrome, also known as trisomy 21 syndrome, which is considered to be the most frequent form of mental retardation, with an incidence of 1 in 700 child births in all populations worldwide. However, due to the current risk of prenatal testing, prenatal diagnosis is only offered to high risk pregnancies (6-8% of all pregnancies), which are assessed based on maternal serum screening and fetal ultrasonography programs. Thus, there is an urgent need for the development of diagnostic procedures that do not put the fetus at risk, which is commonly termed as noninvasive prenatal diagnosis.

Free fetal DNA (ffDNA) has been discovered in the maternal circulation during pregnancy (Lo, Y. M. et al. (1997) *Lancet* 350:485-487), and has become a focus for alternative approaches toward the development of noninvasive prenatal tests. ffDNA has been successfully used for the determination of fetal sex and fetal RhD status in maternal plasma (Lo, Y. M. et al. (1998) *N. Engl. J. Med.* 339:1734-1738; Bianchi, D. W. et al. (2005) *Obstet. Gynecol.* 106:841-844). Nevertheless, direct analysis of the limited amount of ffDNA (3 to 6%) in the presence of excess of maternal DNA is a great challenge for the development of noninvasive testing for fetal aneuploidies.

Recent advances in the field have shown that physical and molecular characteristics of the ffDNA can be used for its discrimination from circulating maternal DNA or as a means of fetal DNA enrichment (Chan, K. C. et al. (2004) *Clin. Chem.* 50:88-92; Poon, L. L. et al. (2002) *Clin. Chem.* 48:35-41). For example, size fractionation has been used on plasma DNA to enrich for fetal DNA because fetal DNA is generally shorter in length than maternal DNA in the circulation (Chan, K. C. et al. (2004), supra). Furthermore, based on evidence that ffDNA in maternal plasma is of placental origin, epigenetic differences between maternal peripheral (whole) blood and placental DNA have been used to detect a hypomethylated gene sequence (maspin/SERPINB5) in maternal plasma derived from the fetus (Masuzaki, H. et al. (2004) *J. Med. Genet.* 41:289-292; Fiori, E. et al. (2004) *Hum. Reprod.* 19:723-724; Chim, S. S. et al. (2005) *Proc. Natl. Acad. Sci. USA* 102:14753-14758). Subsequently, a small number of additional differential fetal epigenetic molecular markers have been described, including the RASSF1A gene on chromosome 3, as well as a marker on chromosome 21 (Chiu, R. W. et al. (2007) *Am. J. Pathol.* 170:941-950; Old, R. W. et al. (2007) *Reprod. Biomed. Online* 15:227-235; Chim, S. S. et al. (2008) *Clin. Chem.* 54:500-511).

Although these studies have demonstrated that epigenetic differences between fetal DNA (placental DNA obtained from chorionic villus sampling) and maternal peripheral blood DNA may serve as potential fetal molecular markers for noninvasive prenatal diagnosis, only a limited number of genomic regions have been identified or tested to date. A number of studies have focused on single gene promoter regions (Chim, S. S. et al. (2005) supra; Chiu, R. W. et al. (2007, supra), whereas others have investigated CpG islands on chromosome 21 (Old, R. W. et al. (2007) supra; Chim, S. S. et al. (2008) supra), which however cover only a small fraction of the chromosome (Fazzari, M. J. et al. (2004) *Nat. Rev. Genet.* 5:446-455).

Current methods developed using ffDNA for noninvasive prenatal diagnosis are subject to a number of limitations. One method being investigated involves the use of methylation-sensitive restriction enzymes to remove hypomethylated maternal DNA thus allowing direct polymerase chain reaction (PCR) analysis of ffDNA (Old, R. W. et al. (2007), supra). However, the requirement for regions of differentially methylated DNA to contain a restriction site for recognition by methylation-sensitive restriction enzymes limits the number of regions suitable for testing. Another method being investigated involves the use of sodium bisulfite conversion to allow the discrimination of differential methylation between maternal and fetal DNA. In this approach, sodium bisulfite conversion is followed by either methylation-specific PCR or methylation sensitive single nucleotide primer extension and/or bisulfite sequencing (Chim, S. S. et al. (2005) supra; Chiu, R. W. et al. (2007) supra; Chim, S. S. et al. (2008) supra). This approach, however, has two main problems. Firstly, the accurate analysis of the methylation status after bisulfite conversion depends on the complete conversion of unmethylated cytosines to uracils, a condition rarely achieved. Secondly, the degradation of DNA obtained after bisulfite treatment (described in Grunau, C. et al. (2001) *Nucl. Acids Res.* 29:E65-5) complicates even further the testing and quantification of extremely low amounts of fetal DNA.

Another recent approach has been to directly sequence cell-free DNA from the plasma of pregnant women, using a high throughput shotgun sequencing technique (Fan, H. C. et. al (2008) *Proc. Natl. Acad. Sci. USA* 105:16266-71; Chiu, R. W. et. al. (2008) *Proc. Natl. Acad. Sci USA.* 105:20458-63). However, this approach is technologically demanding and the high cost of this approach makes its application extremely difficult to the majority of diagnostic laboratories.

Accordingly, additional approaches and methods for noninvasive prenatal diagnosis of fetal aneuploidies are needed, to reduce the risk of fetal loss and to allow for screening of all pregnancies, not just high risk pregnancies.

SUMMARY OF THE INVENTION

This invention provides a new approach for noninvasive prenatal diagnosis based on the detection of ffDNA. A large number (more than 2000) of differentially methylated regions (DMRs), on each of the chromosomes tested (chromosomes 13, 18, 21, X and Y), which are differentially methylated between female peripheral blood and fetal DNA (placental DNA), have now been identified, through use of a system coupling methylated DNA immunoprecipitation (MeDiP) with high-resolution tiling oligonucleotide array analysis to enable chromosome-wide identification of DNA methylation patterns in a high-throughput approach. Furthermore, representative examples of a subset of these DMRs which are hypermethylated in fetal DNA and hypomethylated in female peripheral blood, have been used to accurately predict trisomy 21, in a method based on physically separating hypermethylated DNA from hypomethylated DNA in a sample of maternal blood, typically during the first trimester of gestational age, without chemically altering or enzymatically digesting the hypermethylated DNA or hypomethylated DNA, and then determining the levels of a plurality of DMRs in the hypermethylated DNA sample. Thus, the effectiveness of the disclosed DMRs and methodologies for diagnosing fetal aneuploidies has been demonstrated.

Accordingly, in one aspect, the invention pertains to a method for prenatal diagnosis of a fetal aneuploidy using a sample of maternal blood, the method comprising:

a) in a sample of maternal blood, physically separating hypermethylated DNA from hypomethylated DNA, without chemically altering or enzymatically digesting the hypomethylated DNA or hypermethylated DNA, to obtain a hypermethylated DNA sample;

b) in the hypermethylated DNA sample, determining levels of a plurality of differentially methylated regions (DMRs) to obtain a hypermethylation value for the hypermethylated DNA sample;

c) comparing the hypermethylation value of the hypermethylated DNA sample to a standardized reference hypermethylation value for said plurality of DMRs (e.g., a normal maternal reference hypermethylation value of matched gestational age); and d) diagnosing a fetal aneuploidy based on said comparison.

In a preferred embodiment, the maternal blood sample is a maternal peripheral blood sample. Preferably, the hypermethylated DNA is physically separated from hypomethylated DNA by Methylation DNA Immunoprecipitation (MeDiP). Preferably, after physical separation of hypermethylated DNA from hypomethylated DNA, the hypermethylated DNA is amplified, such as by ligation mediated polymerase chain reaction (LM-PCR).

The plurality of DMRs preferably are chosen from the lists shown in Appendices A-E. In various embodiments, the levels of the plurality of DMRs are determined for at least three, at least five, at least eight, at least 10 or at least 12 DMRs, for example chosen from the lists shown in Appendices A-E. Furthermore, control regions (e.g., two control regions) can be used as well. Preferably, the levels of the plurality of DMRs in the hypermethylated DNA sample are determined by real time quantitative polymerase chain reaction (Real Time QPCR).

In one embodiment, the levels of the plurality of DMRs are also determined in a total untreated maternal blood DNA sample as a control of the LM-PCR efficiency.

Preferably, the hypermethylation value for the hypermethylated DNA sample is compared to a standardized reference hypermethylation value, for example determined from maternal DNA obtained from women bearing a normal fetus, and diagnosis of fetal aneuploidy is made when the hypermethylation value for the hypermethylated DNA sample is higher than the standardized normal reference hypermethylation value.

In a preferred embodiment, the plurality of DMRs are on chromosome 21 for diagnosis of trisomy 21. Preferably, the plurality of DMRs on chromosome 21 comprise three or more, five or more, or eight or more, regions selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof. Preferred DMRs on chromosome 21 for use in the diagnosis of trisomy 21 are SEQ ID NOs: 36, 37, 38, 39, 40, 42, 43 and 44. In other embodiments, the plurality of DMRs are on a chromosome selected from the group consisting of chromosome 13, chromosome 18, X chromosome and Y chromosome.

In another aspect, the invention pertains to a method for prenatal diagnosis of trisomy 21 using a sample of maternal peripheral blood, the method comprising:

a) in a sample of maternal peripheral blood, physically separating hypermethylated DNA from hypomethylated DNA, without chemically altering or enzymatically digesting the hypermethylated DNA or hypomethylated DNA, to obtain a hypermethylated DNA sample;

b) in the hypermethylated DNA sample, determining levels of a plurality of differentially methylated regions (DMRs) on chromosome 21 to obtain a hypermethylation value for the hypermethylated DNA sample, wherein the plurality of DMRs on chromosome 21 comprise eight or more regions selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof, and wherein the levels of the plurality of DMRs are determined by real time quantitative polymerase chain reaction (Real Time QPCR);

c) comparing the hypermethylation value of the hypermethylated DNA sample to a standardized normal reference hypermethylation value for said plurality of DMRs on chromosome 21; and d) diagnosing trisomy 21 based on said comparison.

Preferred DMRs on chromosome 21 for use in the diagnosis of trisomy 21 are SEQ ID NOs: 36, 37, 38, 39, 40, 42, 43 and 44. Preferably, the hypermethylated DNA is physically separated from hypomethylated DNA by Methylation DNA Immunoprecipitation (MeDiP). Preferably, after physical separation of hypermethylated DNA from hypomethylated DNA, the hypermethylated DNA is amplified, such as by ligation-mediated polymerase chain reaction (LM-PCR).

In one embodiment, the levels of the plurality of DMRs are also determined in a total untreated maternal blood DNA sample as a control of the LM-PCR efficiency.

In another embodiment, the hypermethylation value for the hypermethylated DNA sample is compared to a standardized normal reference hypermethylation value of a normal maternal blood sample, and diagnosis of trisomy 21 is made when the hypermethylation value for the hypermethylated DNA sample is higher than the standardized normal reference hypermethylation value.

In yet another aspect, the invention pertains to a method for identifying a differentially methylated region (DMR) on a chromosome of interest suitable for use in diagnosing a fetal aneuploidy, the method comprising:

a) providing:

(i) a normal adult female peripheral blood DNA sample (PB sample); and (ii)) a normal placental DNA sample (PL sample);

b) in each sample of a), physically separating hypermethylated DNA from hypomethylated DNA, without chemically altering or enzymatically digesting the hypermethylated DNA or hypomethylated DNA, to obtain:
(i) a separated PB sample; and
(iii) a separated PL sample;
c) in each separated sample of b), determining levels of a plurality of regions on a chromosome of interest; and
d) selecting a region that is hypomethylated in the separated PB sample and is hypermethylated in the separated PL sample to thereby identify a differentially methylated region (DMR) on the chromosome of interest.

In one embodiment, wherein the PL sample comprises two different samples, a first trimester PL sample and a third trimester PL sample, wherein step d) further comprises selecting a region having an equivalent degree of methylation in the first trimester separated PL sample and the third trimester separated PL sample. In a preferred embodiment, the chromosome of interest is chromosome 21. In other embodiments, the chromosome of interest is selected from the group consisting of chromosome 13, chromosome 18, X chromosome and Y chromosome. In a preferred embodiment, the aneuploidy is a trisomy. In another embodiment, the aneuploidy is a monosomy.

In yet another aspect, the invention pertains to a kit for prenatal diagnosis of trisomy 21, the kit comprising:
a) one or more nucleic acid compositions for determining levels of a plurality of differentially methylated regions (DMRs) on chromosome 21; and
b) instructions for using the nucleic acid compositions for prenatal diagnosis of trisomy 21.

Preferably, the plurality of DMRs on chromosome 21 are chosen from the list shown in Appendix A. More preferably, the plurality of DMRs on chromosome 21 comprise three or more, five or more, or eight or more, regions selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof. Preferred DMRs on chromosome 21 for use in the diagnosis of trisomy 21 are SEQ ID NOs: 36, 37, 38, 39, 40, 42, 43 and 44.

In a preferred embodiment of the kit, the nucleic acid compositions comprise one or more oligonucleotide primers selected from the group consisting of SEQ ID NOs: 1-24, and combinations thereof. In another embodiment, the kit further comprises oligonucleotide primers (e.g., two or more) for detection of control regions. In another embodiment, the kit further comprises means for physically separating hypermethylated DNA from hypomethylated DNA, without chemically altering or enzymatically digesting the hypermethylated DNA or hypomethylated DNA, in a blood sample. Preferably, the means for physically separating hypermethylated DNA from hypomethylated DNA comprises an antibody that immunoprecipitates methylated DNA. In another embodiment, the kit can further comprise means for amplifying hypermethylated DNA. In a preferred embodiment, the means for amplifying hypermethylated DNA comprises oligonucleotide linkers and/or oligonucleotide primers for performing ligation mediated polymerase chain reaction (LM-PCR).

In yet another aspect, the invention pertains to a nucleic acid composition comprising one or more isolated oligonucleotide primers selected from the group consisting of SEQ ID NOs: 1-24, and combinations thereof.

DETAILED DESCRIPTION

Figure 1:
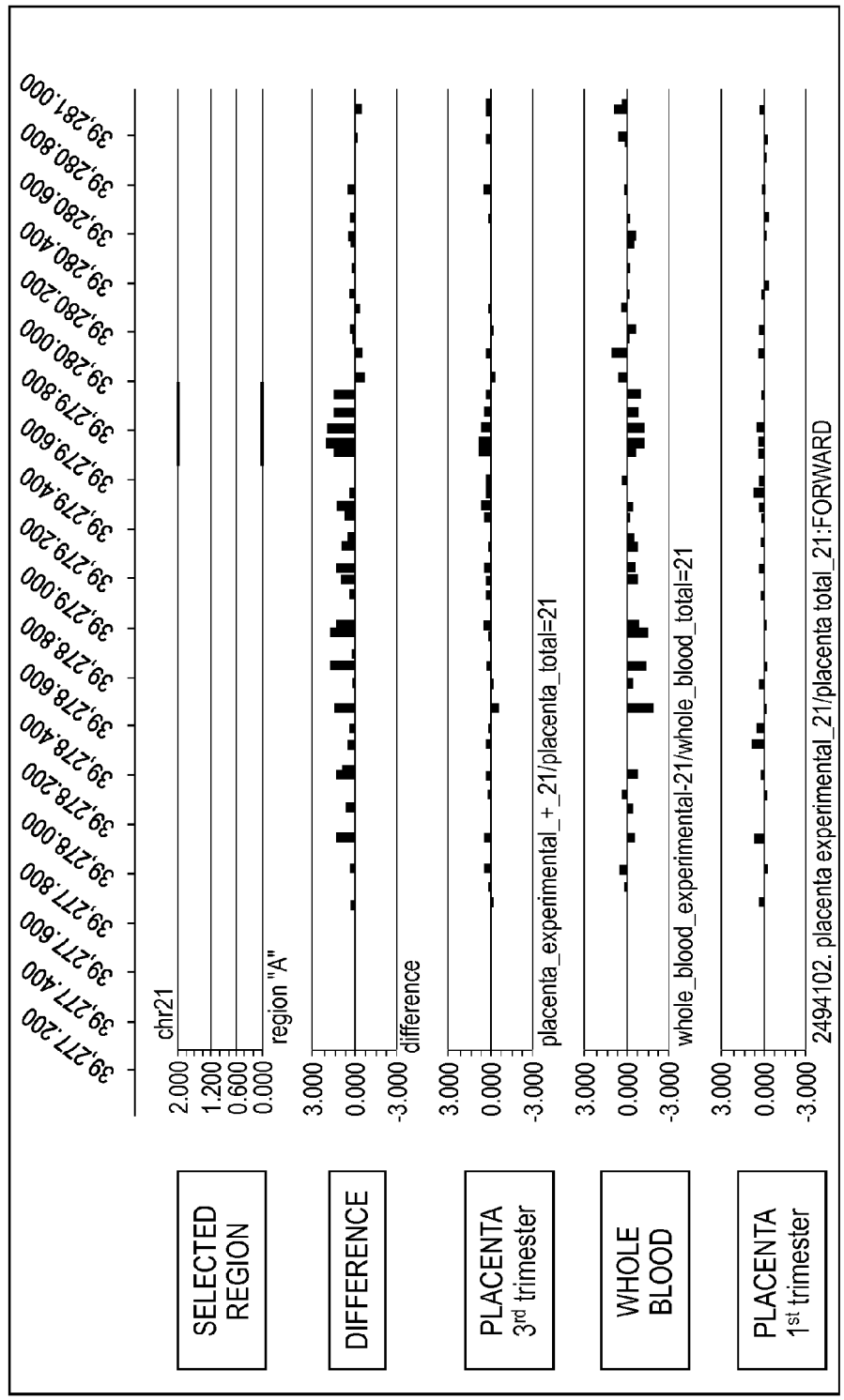
FIG. 1 is a diagram showing the DNA methylation enrichment of CHR21(A) region assayed by oligonucleotide array. The diagram shows methylation differences between $3^{rd}$ trimester placenta and peripheral (whole) blood and individual methylation status of peripheral (whole) blood, $1^{st}$ trimester and $3^{rd}$ trimester placental DNA samples.

The present invention is based, at least in part, on the inventors' identification of a large panel of differentially methylated regions (DMRs) that exhibit hypermethylation in fetal DNA and hypomethylation in maternal DNA. Still further, the invention is based, at least in part, on the inventors' demonstration that hypermethylated fetal DNA can be purified away from hypomethylated maternal DNA by physically separating the two DNA populations without chemically altering or enzymatically digesting the two DNA samples, thereby resulting in a sample enriched for hypermethylated fetal DNA. Still further, the inventors have accurately diagnosed trisomy 21 in a panel of maternal peripheral blood samples using representative examples of the DMRs disclosed herein, thereby demonstrating the effectiveness of the identified DMRs and disclosed methodologies in diagnosing fetal aneuploidies.

Various aspects of this disclosure are described in further detail in the following subsections.

I. METHODS FOR NONINVASIVE PRENATAL DIAGNOSIS OF FETAL ANEUPLOIDIES

In one aspect, the invention provides a method for prenatal diagnosis of a fetal aneuploidy using a sample of maternal blood, the method comprising:

a) in a sample of maternal blood, physically separating hypermethylated DNA from hypomethylated DNA, without chemically altering or enzymatically digesting the hypomethylated DNA or hypermethylated DNA, to obtain a hypermethylated DNA sample;

b) in the hypermethylated DNA sample, determining levels of a plurality of differentially methylated regions (DMRs) to obtain a hypermethylation value for the hypermethylated DNA sample;

c) comparing the hypermethylation value of the hypermethylated DNA sample to a standardized reference hypermethylation value (e.g., a standardized normal reference hypermethylation value, discussed further below) for said plurality of DMRs; and d) diagnosing a fetal aneuploidy based on said comparison.

Maternal Blood Sample

The sample of maternal blood can be obtained by standard techniques, such as using a needle and syringe. In a preferred embodiment, the maternal blood sample is a maternal peripheral blood sample. Alternatively, the maternal blood sample can be a fractionated portion of peripheral blood, such as a maternal plasma sample. Once the blood sample is obtained, total DNA can be extracted from the sample using standard techniques, a non-limiting example of which is the QIAmp DNA Blood Midi Kit (Qiagen). Typically, the total DNA is then fragmented, preferably to sizes of approximately 300 bp-800 bp. For example, the total DNA can be fragmented by sonication.

Separation of Hypermethylated DNA from Hypomethylated DNA

In the method, hypermethylated DNA is physically separated from hypomethylated DNA, without chemically altering or enzymatically digesting the hypomethylated DNA or hypermethylated DNA, to obtain a hypermethylated DNA sample. Preferably, this physical separation is accomplished by Methylated DNA Immunoprecipitation (MeDiP), a technique that has been described in the art (see e.g., Weber, M. et al. (2005) *Nat. Genet.* 37:853-862; and Rakyan, et al. (2008) *Genome Res.* 18:1518-1529; which are both expressly incorporated herein by reference).

In the MeDiP technique, the input DNA is denatured, incubated with an antibody directed against 5-methylcytosine and then the methylated DNA is isolated by immunoprecipitation. For example, to accomplish immunoprecipitation, the anti-5-methylcytosine antibody can be coupled to a solid support (e.g., magnetic dynabeads, microscopic agarose beads or paramagnetic beads) to allow for precipitation of the methylated DNA from solution (direct immunoprecipitation). Alternatively, a secondary antibody or reagent can be used that recognizes the anti-5-methylcytosine antibody (e.g., the constant region of the antibody) and that is coupled to a solid support, to thereby allow for precipitation of the methylated DNA from solution (indirect immunoprecipitation). For direct or indirect immunoprecipitation, other approaches known in the art for physical separation of components within a sample, such as the biotin/avidin or biotin/streptavidin systems, can be used. For example, the anti-5-methylcytosine antibody can be coupled to biotin and then avidin or streptavidin coupled to a solid support can be used to allow for precipitation of the methylated DNA from solution. It will be apparent to the ordinarily skilled artisan that other variations known in the art for causing immunoprecipitation are also suitable for use in the invention. Thus, as used herein, the term "Methylated DNA Immunoprecipitation" or "MeDiP" is intended to encompass any and all approaches in which an antibody that discriminates between hypermethylated DNA and hypomethylated DNA is contacted with DNA from the maternal blood sample, followed by precipitation of the hypermethylated DNA (i.e., the DNA that specifically binds to the antibody) out of solution.

In accomplishing the physical separation of the hypermethylated DNA from the hypomethylated DNA in the maternal blood sample, the DNA in the sample is not chemically altered or enzymatically digested. As used herein, the term "chemically altering" is intended to mean reacting the DNA with a non-antibody chemical substance that discriminates between hypermethylated DNA and hypomethylated DNA, such as sodium bisulfite conversion. Thus, in the instant method, the DNA of the maternal blood sample is not subjected to sodium bisulfite conversion or any other similar (non-antibody) chemical reaction that discriminates between hypermethylated DNA and hypomethylated DNA. Moreover, as used herein, the term "enzymatically digesting" is intended to mean reacting the DNA with one or more methylation-sensitive restriction enzymes to thereby remove hypomethylated DNA. Thus, in the instant method, the DNA of the maternal blood sample is not treated with a methylation-sensitive restriction enzyme(s) to discriminate between hypermethylated DNA and hypomethylated DNA.

It should be noted, however, that the fragmentation of the DNA from the maternal peripheral blood sample (that typically is performed prior to separation of the hypermethylated DNA from the hypomethylated DNA), while typically is accomplished by shearing by sonication, could also be accomplished by digestion of the DNA with restriction enzymes. However, such general digestion of the DNA to accomplish fragmentation is not performed with a methylation-sensitive restriction enzyme(s). Thus, the requirement that the DNA of the maternal blood sample not be "enzymatically digested" is not intended to preclude the use of non-methylation-sensitive restriction enzymes to achieve overall fragmentation (i.e., size reduction) of the maternal blood sample DNA.

DNA Amplification

In the diagnostic method, typically after physical separation of the hypermethylated DNA from the hypomethylated DNA in the maternal blood sample, the hypermethylated DNA is then amplified. As used herein, the term "amplified" is intended to mean that additional copies of the DNA are made to thereby increase the number of copies of the DNA", which is typically accomplished using the polymerase chain reaction (PCR). A preferred method for amplification of the hypermethylated DNA is ligation mediated polymerase chain reaction (LM-PCR), which has been described previously in the art (see e.g., Ren, B. et al. (2000) *Science* 22:2306-2309; and Oberley, M. J. et al. (2004) *Methods Enzymol.* 376:315-334; the contents of both of which are expressly incorporated herein by reference). In LM-PCR, linker ends are ligated onto a sample of DNA fragments through blunt-end ligation and then oligonucleotide primers that recognize the nucleotide sequences of the linker ends are used in PCR to thereby amplify the DNA fragments to which the linkers have been ligated. Thus, in a preferred embodiment of the instant diagnostic method, after the DNA from the maternal blood sample has been fragmented (e.g., into fragments of approximately 300-800 bp), and before the hypermethylated DNA is physically separated from the hypomethylated DNA (e.g., by MeDiP), linker arms are ligated onto the fragmented DNA by blunt-end ligation. Then, following physical separation of the hypermethylated DNA from hypomethylated DNA, the recovered hypermethylated DNA is subjected to PCR using oligonucleotide primers that recognized the linker ends that have been ligated onto the DNA. This results in amplification of the hypermethylated DNA sample.

Differentially Methylated Regions (DMRs)

The diagnostic method of the invention employs a plurality of differentially methylated regions (DMRs). As used herein, the term "differentially methylated region" or "DMR" is intended to refer to a region in chromosomic DNA that is differentially methylated between fetal and maternal DNA, and for the purposes of the invention the preferred, selected DMRs are those that are hypermethylated in fetal DNA and hypomethylated in maternal. That is, these regions (selected DMRs) exhibit a greater degree (i.e., more) methylation in fetal DNA as compared to maternal DNA.

In theory, any DMR with the above characteristics in a chromosome of interest can be used in the instant diagnostic method. In particular, methods for identifying such DMRs are described in detail below and in the Examples (see Examples 1 and 2). Moreover, a large panel (approximately 2000) of DMRs for each of the chromosomes 13, 18, 21, X and Y, suitable for use in the diagnostic methods, has now been identified. Such DMRs are shown in the lists of Appendices A-E, which provides selected DMRs for chromosomes 21, 13, 18, X and Y, respectively.

As used herein, the term "a plurality of DMRs" is intended to mean two or more DMRs. In a preferred embodiment, the plurality of DMRs are chosen from the lists shown in Appendices A-E, for chromosomes 21, 13, 18, X or Y, respectively. In various embodiments, the levels of the plurality of DMRs are determined for at least two, at least three, at least four, at least five, at least six, at least seven, at least eight, at least nine, at least ten, at least eleven or at least twelve DMRs. Again, most preferably, the plurality of DMRs are chosen from the lists shown in Appendices A-E.

In a preferred embodiment, the plurality of DMRs are on chromosome 21 for diagnosis of trisomy 21. In a particularly preferred embodiment, the plurality of DMRs on chromosome 21 comprise two or more, three or more, four or more, five or more, six or more, seven or more, eight or more, nine or more, ten or more, eleven or more, or twelve regions selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof. Regarding terminology of these regions, the term "base pairs 39279856-39280004" (and the like) refers to the first and last base pair position on chromosome 21 for the differentially methylated region. Thus, for the representative DMR at "base pairs 39279856-39280004" of chromosome 21, the DMR comprises a region on chromosome 21 that starts at base pair 39279856 and ends at base pair 39280004 (thus, this region comprises a 148 base pair region). Oligonucleotide primers for amplifying the above-listed DMRs are described further in Example 3 and in Table 7 and are shown in SEQ ID NOs: 1-24. The nucleotide sequences of the above-listed DMRs are shown in Table 8 and in SEQ ID NOs: 33-44.

As described in detail in Example 3, a subset of eight of the twelve DMRs shown in SEQ ID NOs: 33-44 have been selected and identified as being sufficient to accurately diagnose trisomy 21 in a maternal blood sample during pregnancy of a woman bearing a trisomy 21 fetus. These eight preferred DMRs on chromosome 21 for use in the trisomy 21 diagnosis methods of the invention consist of base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 32268843-32268943 (SEQ ID NO: 42), base pairs 44079235-44079322 (SEQ ID NO: 43) and base pairs 37841284-37841411 (SEQ ID NO: 44).

In various other embodiments, the plurality of DMRs are on a chromosome selected from the group consisting of chromosome 13, chromosome 18, X chromosome and Y chromosome, to allow for diagnosis of aneuploidies of any of these chromosomes.

Control DMRs also can be used in the diagnostic methods of the invention. For example, one more DMRs that are known to be hypermethylated can be included in the diagnostic method as a control for hypermethylation. Preferred control hypermethylated regions include CHR13(HYP1), primers for which are shown in SEQ ID NOs: 25 and 26, and CHR13(HYP2), primers for which are shown in SEQ ID NOs: 27 and 28. Furthermore, the nucleotide sequence of the amplified PCR product for CHR13 (HYP1) is shown in Table 8 and in SEQ ID NO: 45. Additionally or alternatively, one more DMRs that are known to be hypomethylated can be included in the diagnostic method as a control for hypomethylation. Preferred control hypomethylated regions include CHR22(U1), primers for which are shown in SEQ ID NOs: 29 and 30, and CHR22(U2), primers for which are shown in SEQ ID NOs: 31 and 32. Furthermore, the nucleotide sequence of the amplified PCR product for CHR22(U1) is shown in Table 8 and in SEQ ID NO: 46. Control DMRs, and primers therefore, are discussed further in Example 1 and described further in Tables 6, 7 and 8.

The actual nucleotide sequence of any of the DMRs shown in Appendices A-E is readily obtainable from the information provided herein together with other information known in the art. More specifically, each of the DMRs shown in Appendices A-E is defined by a beginning and ending base pair position on a particular chromosome, such as "base pair 39279856-39280004" of chromosome 21, as described above. The complete nucleotide sequences of each of human chromosome 21, 13, 18, X and Y have been determined and are publically available in the art. For example, the complete nucleotide sequences for each of these five chromosomes is obtainable from the UCSC Genome Browser, Build 36. Moreover, the specified beginning and ending base pair positions for each particular DMR in each of the five chromosomes can be input into Genome Browser to obtain the actual nucleotide sequence of that stretch of DNA on the chromosome. Furthermore, oligonucleotide primers for detecting and/or amplifying a DMR can then be designed, using standard molecular biology methods, based on the nucleotide sequence of the DMR. Accordingly, given the information provided herein for the beginning and ending base pair position for each of the DMRs shown in the Appendices A-E, along with the nucleotide sequences for these DMRs readily obtainable by the ordinarily skilled artisan from this information using other chromosomic sequences known in the art, such as those obtainable from the UCSC Genome Browser, the complete nucleotide sequences for each of the DMRs shown in Appendices A-E are hereby explicitly incorporated herein by reference.

Determining Levels of DMRs

In the instant diagnostic method, after physical separation of the hypermethylated DNA from the hypomethylated DNA, and preferably amplification of the recovered hypermethylated DNA, levels of a plurality of differentially methylated regions (DMRs) are determined in the hypermethylated DNA sample, to thereby obtain a hypermethylation value for the hypermethylated DNA sample.

As used herein, the term "the levels of the plurality of DMRs are determined" is intended to mean that the amount, or prevalence, or copy number, of the DMRs is determined. The basis for this is that in a fetus with a fetal aneuploidy, as compared to a normal fetus, there will be a larger amount (i.e., higher copy number) of the DMRs as a result of the aneuploidy. In a preferred embodiment, the levels of the plurality of DMRs in the hypermethylated DNA sample are determined by real time quantitative polymerase chain reaction (Real Time QPCR), a technique well-established in the art. Representative, non-limiting conditions for Real Time QPCR are given in the Examples.

In one embodiment, the levels of the plurality of DMRs are also determined (e.g., by Real Time QPCR) in a total untreated maternal blood DNA sample as a control of the LM-PCR efficiency. As used herein, the term "total untreated maternal blood DNA sample" is intended to refer to a sample of DNA obtained from maternal blood that has not been subjected to treatment to physically separate the hypermethylated DNA from the hypomethylated DNA.

The levels of the plurality of differentially methylated regions (DMRs) are determined in the hypermethylated DNA sample to thereby obtain a "hypermethylation value" for the hypermethylated DNA sample. As used herein, the term "hypermethylation value" is intended to encompass any quantitative representation of the level of DMRs in the sample. For example, the raw data obtained from Real Time QPCR can be normalized based on various controls and statistical analyses to obtain one or more numerical values that represent the level of each of the plurality of DMRs in the hypermethylated DNA sample. Representative, non-limiting examples of controls and statistical analyses that can be applied to the samples are described in detail in Example 3. However, it will be appreciated by the ordinarily skilled artisan that the specific statistical tests used to evaluate the data in the Examples are representative statistical approaches, and that alternative statistical approaches can also be applied to the instant invention, based on the guidance provided in the Examples and figures.

Comparison to a Standardized Reference Value

Once the hypermethylation value has been determined for the hypermethylated fetal DNA present in the maternal peripheral blood (also referred to herein as the "test DNA"), this value is compared to a standardized reference hypermethylation value for the same plurality of DMRs examined in the test DNA, and the diagnosis of fetal aneuploidy (or lack of such fetal aneuploidy) is made based on this comparison.

Typically, the hypermethylation value for the hypermethylated DNA sample is compared to a standardized normal reference hypermethylation value for a normal fetus, and diagnosis of fetal aneuploidy is made when the hypermethylation value for the hypermethylated DNA sample is higher than the standardized normal reference hypermethylation value for a normal fetus. That is, a "normal" hypermethylation value is set, based on data obtained from normal fetal DNA present in the maternal peripheral blood (i.e., DNA from fetus's without a fetal aneuploidy), and a diagnosis of fetal aneuploidy can be made for the test sample when the hypermethylation value for the test DNA is higher than the "normal" value. Most preferably, a standardized normal reference hypermethylation value is determined using maternal peripheral blood samples from women bearing a normal fetus (i.e., a fetus without fetal aneuploidies) of matched gestational age as compared to the "test DNA" (e.g., if the test DNA is from a fetus at 3 months gestational age, then the standardized normal reference hypermethylation value is determined using maternal peripheral blood samples from women bearing a normal fetus of 3 months gestational age). For example, a standardized normal reference hypermethylation value can be set as "1" and then a hypermethylation value for the test DNA that is above "1" indicates an abnormal fetus, whereas a hypermethylation value of "1" or lower indicates a normal fetus.

Additionally or alternatively, the hypermethylation value for the hypermethylated DNA sample can be compared to a standardized reference hypermethylation value for a fetal aneuploidy fetus, and diagnosis of fetal aneuploidy can be made when the hypermethylation value for the test DNA sample is comparable to the standardized reference hypermethylation value for a fetal aneuploidy fetus. That is, a standardized reference "abnormal" or "fetal aneuploidy" hypermethylation value can be set, based on data obtained from fetal aneuploidy fetal DNA present in maternal peripheral blood (i.e., DNA from fetus's that have a fetal aneuploidy), and a diagnosis of fetal aneuploidy can be made for the test sample when the hypermethylation value for the test DNA is comparable to (similar to, in the same range as) the "abnormal" or "fetal aneuploidy" value.

In order to establish the standardized normal reference hypermethylation values for a normal fetus, a group of healthy pregnant women carrying healthy fetuses are selected. These women are of similar gestational age, which is within the appropriate time period of pregnancy for screening of conditions such as preeclampsia, fetal chromosomal aneuploidy, and preterm labor using the methods of the present invention. Similarly, a standard reference value can be established using samples from a group of healthy non-pregnant women. The healthy status of the selected pregnant women and the fetuses they are carrying are confirmed by well established, routinely employed methods including but not limited to monitoring blood pressure of the women, recording the onset of labor, and conducting fetal genetic analysis using CVS and amniocentesis. Furthermore, the selected group of healthy pregnant women carrying healthy fetuses must be of a reasonable size to ensure that the standardized normal reference hypermethylation value for a normal fetus is statistically accurate. Preferably, the selected group comprises at least 10 women.

To establish the standardized normal reference hypermethylation values for a normal fetus, maternal blood samples from these pregnant women carrying a normal fetus are subjected to the same steps (a) and (b) described above for the diagnostic method, namely physically separation of hypermethylated DNA from hypomethylated DNA (without chemically altering or enzymatically digesting the hypomethylated DNA or hypermethylated DNA) to obtain a hypermethylated DNA sample, and then determining the levels of a plurality of differentially methylated regions (DMRs) in the hypermethylated DNA sample to obtain a hypermethylation value for the hypermethylated DNA sample.

Similarly, standardized reference hypermethylation values for an "abnormal" fetus can be established using the same approach as described above for establishing the standardized reference hypermethylation values for a "normal" fetus, except that the maternal blood samples used to establish the "abnormal" reference values are from pregnant women who have been determined to be carrying a fetus with a fetal aneuploidy, using conventional invasive diagnostic methods.

The Examples, in particular Example 3, described in detail appropriate statistical analysis approaches that can be used to analyze the data obtained from DNA samples. For example, statistical analysis using Mann-Whitney U test, Fisher test and stepwise model analysis can be employed as described in detail in the Examples. However, it will be appreciated by the ordinarily skilled artisan that the specific statistical tests used to evaluate the data in the Examples are representative statistical approaches, and that alternative statistical approaches can also be applied to the instant invention, based on the guidance provided in the Examples and figures.

II. NONINVASIVE PRENATAL DIAGNOSTIC TEST FOR TRISOMY 21

In another aspect, the invention provides a noninvasive prenatal diagnostic test for trisomy 21 (also referred to herein as an "NID21 test"). As discussed in detail in Example 3, an NID21 test has been developed and validated using DMRs identified as described in Examples 1 and 2. In the development of the test, twelve DMRs on chromosome 21 (as disclosed herein) were examined using maternal blood samples from 40 cases, 20 normal and 20 abnormal (i.e., from women known to be carrying a fetus with trisomy 21). Statistical analysis of the results (described in detail in Example 3) revealed the most informative chromosomal regions and has demonstrated that testing of only eight specific DMRs (from the total of twelve DMRs originally examined) was sufficient to reach 100% sensitivity and accuracy in the diagnosis of all normal and abnormal cases.

Accordingly, in another aspect, the invention provides a method for prenatal diagnosis of trisomy 21 using a sample of maternal peripheral blood, the method comprising:

a) in a sample of maternal peripheral blood, physically separating hypermethylated DNA from hypomethylated DNA, without chemically altering or enzymatically digesting the hypermethylated DNA or hypomethylated DNA, to obtain a hypermethylated DNA sample;

b) in the hypermethylated DNA sample, determining levels of a plurality of differentially methylated regions (DMRs) on chromosome 21 to obtain a hypermethylation value for the hypermethylated DNA sample, wherein the plurality of DMRs on chromosome 21 comprise eight or more regions selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof, and wherein the levels of the plurality of DMRs are determined by real time quantitative polymerase chain reaction (Real Time QPCR);

c) comparing the hypermethylation value of the hypermethylated DNA sample to a standardized normal reference hypermethylation value for said plurality of DMRs on chromosome 21; and d) diagnosing trisomy 21 based on said comparison.

In a preferred embodiment, the plurality of DMRs on chromosome 21 consist of eight regions having nucleotide sequences of base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 32268843-32268943 (SEQ ID NO: 42), base pairs 44079235-44079322 (SEQ ID NO: 43) and base pairs 37841284-37841411 (SEQ ID NO: 44).

Preferably, the hypermethylated DNA is physically separated from hypomethylated DNA by Methylation DNA Immunoprecipitation (MeDiP) (described further in Section I above). Preferably, after physical separation of hypermethylated DNA from hypomethylated DNA, the hypermethylated DNA is amplified, for example by ligation-mediated polymerase chain reaction (LM-PCR) (as described in detail in Section I above). Oligonucleotide primers for amplifying the above-listed DMRs for chromosome 21 are described in further detail in Example 3 and Table 7 and are shown in SEQ ID NOs: 1-24.

Additionally, control DMRs also can be used in the diagnostic method. For example, one more DMRs that are known to be hypermethylated can be included in the diagnostic method as a control for hypermethylation. Preferred control hypermethylated regions include CHR13(HYP1), primers for which are shown in SEQ ID NOs: 25 and 26 (and the nucleotide sequence of which is shown in SEQ ID NO: 45), and CHR13(HYP2), primers for which are shown in SEQ ID NOs: 27 and 28. Additionally or alternatively, one more DMRs that are known to be hypomethylated can be included in the diagnostic method as a control for hypomethylation. Preferred control hypomethylated regions include CHR22 (U1), primers for which are shown in SEQ ID NOs: 29 and 30 (and the nucleotide sequence of which is shown in SEQ ID NO: 46), and CHR22(U2), primers for which are shown in SEQ ID NOs: 31 and 32. Control DMRs, and primers therefore, are discussed further in Example 1 and described further in Table 6.

In one embodiment, the levels of the plurality of DMRs are also determined in a total untreated maternal blood DNA sample as a control of the LM-PCR efficiency (as described in Section I above).

Preferably, the hypermethylation value for the hypermethylated DNA sample is compared to a standardized normal reference hypermethylation value for a normal fetus, and diagnosis of trisomy 21 is made when the hypermethylation value for the hypermethylated DNA sample is higher than the standardized normal reference hypermethylation value for a normal fetus. That is, a "normal" hypermethylation value can be set for a plurality of DMRs on chromosome 21, based on data obtained from normal fetal DNA present in maternal peripheral blood (i.e., DNA from fetus's without a fetal aneuploidy) (as described in detail above), and a diagnosis of trisomy 21 can be made for the test sample when the hypermethylation value for the test DNA is higher than the "normal" value. For example, a "normal" hypermethylation value has been calculated for the twelve DMRs described in Example 3 and, based on this, eight preferred DMRs were selected as being sufficient to allow for an accurate diagnosis of trisomy 21 in a test sample.

Additionally or alternatively, the hypermethylation value for the hypermethylated DNA sample can be compared to a standardized reference hypermethylation value for a trisomy 21 fetus, and diagnosis of trisomy 21 can be made when the hypermethylation value for the test DNA sample is comparable to the standardized reference hypermethylation value for a trisomy 21 fetus. That is, an "abnormal" hypermethylation value can be set for a plurality of DMRs on chromosome 21, based on data obtained from trisomy 21 fetal DNA (i.e., DNA from fetus's with trisomy 21), and a diagnosis of trisomy 21 can be made for the test sample when the hypermethylation value for the test DNA is comparable to (similar to, in the same range as) the "abnormal" value.

III. METHODS FOR IDENTIFYING DIFFERENTIALLY METHYLATED REGIONS

In another aspect, the invention provides methods for identifying differentially methylated regions (DMRs) that are hypermethylated in fetal DNA and hypomethylated in maternal DNA, based on physically separating hypermethylated DNA from hypomethylated DNA. As described in detail in Examples 1 and 2, the approaches described herein have been applied chromosome-wide to identify a large panel of differentially methylated regions on chromosomes 21, 13, 18, X and Y, which exhibit a higher level of methylation (hypermethylation) in fetal DNA as compared to adult female peripheral blood DNA. Furthermore, these same approaches can be applied to identify additional DMRs on these same chromosomes and to identify new DMRs on other chromosomes.

Accordingly, in another aspect, the invention provides a method for identifying a differentially methylated region (DMR) on a chromosome of interest suitable for use in diagnosing a fetal aneuploidy, the method comprising:
 a) providing:
   (i) a normal adult female peripheral blood DNA sample (PB sample); and
   (ii) a normal placental DNA sample (PL sample);
 b) in each sample of a), physically separating hypermethylated DNA from hypomethylated DNA, without chemically altering or enzymatically digesting the hypermethylated DNA or hypomethylated DNA, to obtain:
   (i) a separated PB sample; and
   (iii) a separated PL sample;
 c) in each separated sample of b), determining levels of a plurality of regions on a chromosome of interest; and
 d) selecting a region that is hypomethylated in the separated PB sample and is hypermethylated in the separated PL sample to thereby identify a differentially methylated region (DMR) on the chromosome of interest that is suitable for use in the diagnostic methods described herein.

In one embodiment, the PL sample comprises two different samples, a first trimester PL sample and a third trimester PL sample, wherein step d) further comprises selecting a region having an equivalent degree of methylation in the first trimester separated PL sample and the third trimester separated PL sample.

In a preferred embodiment, the chromosome of interest is chromosome 21. In various other embodiments, the chromosome of interest is selected from the group consisting of chromosome 13, chromosome 18, X chromosome and Y chromosome. Preferably, the aneuploidy is a trisomy.

As used herein, a "normal adult female" is a female that does not have a chromosomal aneuploidy. As used herein, "normal placental DNA" is DNA from the placenta of a fetus that does not have a chromosomal aneuploidy.

In each sample, the hypermethylated DNA is physically separated from hypomethylated DNA, without chemically altering or enzymatically digesting the hypermethylated DNA or hypomethylated DNA, as described in detail above in Section I. Preferably, this separation is accomplished using Methylation DNA Immunoprecipitation (MeDiP), as described in Section I, to obtain the "separated" samples. As used herein, the terms "separated PB sample" and "separated PL sample" refer to the portion of the original peripheral blood sample or original placental DNA sample that putatively contains hypermethylated DNA that has been separated away from hypomethylated DNA. For example, when MeDiP is used for separation, the "separated" sample is the fraction of the peripheral blood or placental DNA sample that has been immunoprecipitated.

Preferably, after separation, the DNA of the separated PB sample and the separated PL sample is amplified, preferably by LM-PCR. Thus, in this embodiment, linker ends are blunt ligated to the DNA prior to separation, and then after separation, PCR is carried out on the separated DNA samples using oligonucleotide primers that recognize the linker ends, as described in detail above in Section I.

The levels of the plurality of regions on a chromosome of interest are determined in the separated samples as described above in Section I, preferably by Real Time QPCR. Also as described above, controls and statistical analyses can be applied to the raw data to determine a hypermethylation value for the plurality of regions. Finally, to identify a specific differentially methylated region (DMR) on the chromosome of interest, a region is selected that is hypomethylated in the separated peripheral blood (PB) sample from the normal adult female and is hypermethylated in the separated placental (PL) sample from the normal fetus.

IV. KITS OF THE INVENTION

In another aspect, the invention provides kits that can be used in the diagnostic methods of the invention. Such kits typically include at least one reagent and instructions for use of the kit. In a preferred embodiment, the invention provides a kit for prenatal diagnosis of trisomy 21, the kit comprising:
 a) one or more nucleic acid compositions for determining levels of a plurality of differentially methylated regions (DMRs) on chromosome 21; and
 b) instructions for using the nucleic acid compositions for noninvasive prenatal diagnosis of trisomy 21.

The plurality of DMRs on chromosome 21 can be chosen, for example, from the chromosome 21 DMRs shown in the list of Appendix A. Preferably, the plurality of DMRs on chromosome 21 comprise at least one region selected from the group consisting of base pairs 39279856-39280004 (SEQ ID NO: 33), base pairs 44161178-44161323 (SEQ ID NO: 34), base pairs 44161239-44161371 (SEQ ID NO: 35), base pairs 33320735-33320829 (SEQ ID NO: 36), base pairs 42189557-42189683 (SEQ ID NO: 37), base pairs 42355712-42355815 (SEQ ID NO: 38), base pairs 42357215-42357341 (SEQ ID NO: 39), base pairs 22403649-22403792 (SEQ ID NO: 40), base pairs 29136735-29136844 (SEQ ID NO: 41), base pairs 32268843-32268943 (SEQ ID NO: 42), base pairs 44079235-44079322 (SEQ ID NO: 43), base pairs 37841284-37841411 (SEQ ID NO: 44), and combinations thereof. In other embodiments, the plurality of DMRs on chromosome 21 comprise two or more, three or more, four or more, five or more, six or more, seven or more, eight or more, nine or more, or ten or more of the above-listed regions. In a preferred embodiment, the plurality of DMRs on chromosome 21 consist of eight regions having SEQ ID NOs: 36, 37, 38, 39, 40, 42, 43 and 44, respectively. Oligonucleotide primers for amplifying the above-listed twelve DMRs are described in further detail in Example 3 and Table 7 and are shown in SEQ ID NOs: 1-24.

Accordingly, in a preferred embodiment of the kit, the nucleic acid compositions comprise one or more oligonucleotide primers selected from the group consisting of SEQ ID NOs: 1-24, and combinations thereof. Additionally, one or more oligonucleotide primers for amplifying control hypermethylated or hypomethylated regions can be include in the kit. For example, preferred control hypermethylated regions include CHR13(HYP1), primers for which are shown in SEQ ID NOs: 25 and 26 (and having the nucleotide sequence shown in SEQ ID NO: 45), and CHR13(HYP2), primers for which are shown in SEQ ID NOs: 27 and 28. Preferred control hypomethylated regions include CHR22(U1), primers for which are shown in SEQ ID NOs: 29 and 30 (and having the nucleotide sequence shown in SEQ ID NO: 46), and CHR22 (U2), primers for which are shown in SEQ ID NOs: 31 and 32. Control DMRs, and primers therefore, are discussed further in Example 1 and described further in Table 6.

In another embodiment, the kit further comprises means for physically separating hypermethylated DNA from hypomethylated DNA, without chemically altering or enzymatically digesting the hypermethylated DNA or hypomethylated DNA, in a blood sample. A preferred means for physically separating hypermethylated DNA from hypomethylated DNA comprises an antibody that immunoprecipitates methylated DNA, such as an antibody that specifically binds 5-methylcytosine. In another embodiment, the kit further comprises means for amplifying hypermethylated DNA. A preferred means for amplifying hypermethylated DNA comprises oligonucleotide linkers and/or oligonucleotide primers for performing ligation mediated polymerase chain reaction (LM-PCR).

V. NUCLEIC ACID COMPOSITIONS

In another aspect, the invention provides nucleic acid compositions that can be used in the methods and kits of the invention. These nucleic acid compositions are effective for detecting DMRs. For example, in a preferred embodiment, the nucleic acid composition comprises one or more oligonucleotide primers that are effective for amplifying one or more DMRs of the invention, such as one or more DMRs chosen from the list shown as Appendix A. Preferably, the oligonucleotide primers are "isolated", meaning that they are purified away from, or separated away from, other primers having different (undesired) specificities. Moreover, the "isolated" oligonucleotide primers are purified away from, or separated away from, other nucleic acid that may flank the primer sequence in a natural or native location, such as in chromosomal DNA or other natural or native form of nucleic acid.

In a preferred embodiment, the invention provides a nucleic acid composition comprising one or more isolated oligonucleotide primers, for amplifying DMRs EP1-EP12 (as described in Table 7), selected from the group consisting of GCTGGACCAGAAAGTGTTGAG (SEQ ID NO: 1), GTGTGCTGCTTTGCAATGTG (SEQ ID NO: 2), GGTCGAGTTTTTGGTGGTGT (SEQ ID NO: 3), CCACCGTCACTGTTCCTAGA (SEQ ID NO: 4), CCTCGTGCTCGTGTCTGTAT (SEQ ID NO: 5), GAGGAAACAGCTTGGCTCTG (SEQ ID NO: 6), CTGTTGCATGAGAGCAGAGG (SEQ ID NO: 7), CGTCCCCCTCGCTACTATCT (SEQ ID NO: 8), TGCAGGATATTTGGCAAGGT (SEQ ID NO: 9), CTGTGCCGGTAGAAATGGTT (SEQ ID NO: 10), TGAATCAGTTCACCGACAGC (SEQ ID NO: 11), GAAACAACCTGGCCATTCTC (SEQ ID NO: 12), CCGTTATATGGATGCCTTGG (SEQ ID NO: 13), AAACTGTTGGGCTGAACTGC (SEQ ID NO: 14), CCAGGCAAGATGGCTTATGT (SEQ ID NO: 15), ACCATGCTCAGCCAATTTTT (SEQ ID NO: 16), GACCCAGACGATACCTGGAA (SEQ ID NO: 17), GCTGAACAAAACTCGGCTTC (SEQ ID NO: 18), CCACATCCTGGCCATCTACT (SEQ ID NO: 19), TTCCACAGACAGCAGAGACG (SEQ ID NO: 20), TGAGCTCACAGGTCTGGAAA (SEQ ID NO: 21), CCCCACAGGGTTCTGGTAAT (SEQ ID NO: 22), ATTCTCCACAGGGCAATGAG (SEQ ID NO: 23), TTATGTGGCCTTTCCTCCTG (SEQ ID NO: 24), and combinations thereof.

In another embodiment, the invention provides a nucleic acid composition comprising one or more isolated oligonucleotide primers, for amplifying a control hypermethylated or hypomethylated region(s), selected from the group consisting of: CAGGAAAGTGAAGGGAGCTG (SEQ ID NO: 25), CAAAACCCAATGGTCAATCC (SEQ ID NO: 26), AATGATTGTGCAGGTGGTGA (SEQ ID NO: 27), GAGCGCCTTGAGTAGAGGAA (SEQ ID NO: 28), AAGGTGCCCAATTCAAGGTA (SEQ ID NO: 29), CTTCCCCACCAGTCTTGAAA (SEQ ID NO: 30), TGAGAGCGGATGACAGATTG (SEQ ID NO: 31), GGTCCCTCCCTTTTCTGTCT (SEQ ID NO: 32), and combinations thereof.

VI. EXAMPLES

The present invention is further illustrated by the following examples, which should not be construed as further limiting. The contents of all references, appendices, Genbank entries, patents and published patent applications cited throughout this application are expressly incorporated herein by reference in their entirety.

Example 1

Identification of Sites of Differential DNA Methylation Between Placental and Peripheral Blood In this example, differentially methylated regions (DMRs) were identified for chromosomes 13, 18, 21, X and Y, using a system coupling MeDiP with high resolution tiling oligonucleotide array analysis to enable chromosome-wide identification of DNA methylation patterns in a high-throughput approach.

The experiments described in this example are also described in Papageorgiou, E. A. et al. (2009) *Am. J. Pathol.* 174:1609-1618, the entire contents of which, including all supplemental data and materials, is explicitly incorporated herein by reference.

Materials and Methods

Human Samples

The samples used in this study were obtained from AMS Biotechnology (Europe) Ltd (Oxon, UK). These samples, originally sourced from the Biochain Institute (Hayward, Calif.), were subject to consent using ethical Internal Review Board (IRB) approved protocols.

In total, five female normal peripheral blood samples and five normal placental DNA samples were used in this study. Three of the placental DNA samples were obtained from first trimester pregnancies of which one derived from a female fetus pregnancy and two from male fetus pregnancies. The remaining two placental DNA samples were derived from third trimester pregnancies of which one of them was obtained from a female fetus pregnancy and the other one from a male fetus pregnancy.

MeDiP Assay Combined with LM-PCR Amplification

The MeDiP assay (Weber, M. et al. (2005) Nat. Genet. 37:853-862) was followed by ligation-mediated PCR (LM-PCR) as described in Ren, B. et al. (2000) Science 22:2306-2309 and Oberley, M. J. et al. (2005) Methods Enzymol. 376:315-334, but with additional modifications. Briefly, 2.5 µg of DNA in a total volume of 100 µl was initially sheared by sonication into fragments of approximately 300 bp-1000 bp in size using the Virsonic300 sonicator (Virtis; Gardiner, N.Y.). The fragmented DNA was blunt-ended after combination with 1×NEB buffer 2 (New England BioLabs; Ipswich, UK), 10×BSA (New England BioLabs; Ipswich, UK), 100 mM dNTP mix, T4 DNA polymerase (3U/µl) (New England BioLabs; Ipswich, UK) and distilled water up to a final volume of 1204 After 20 minutes incubation at 12° C., the reaction was cleaned up using the DNA Clean and Concentrator-5™ (Zymo Research Corp; Glasgow, Scotland) according to the manufacturer's protocol. However, the final elution step was performed in 30 µl of EB buffer provided by the QiAquick PCR purification kit (Qiagen; West Sussex, UK). The cleaned sample was then mixed with 40 µl of annealed linkers (50 µM) (SIGMA Genosys; Gillingham, UK) prepared as previously described in Ren, B. et al. (2000) supra, Oberley, M. J. et al. (2004) supra, T4 DNA ligase 10× buffer (Roche; Mannheim, Germany), 6 µl of T4 DNA ligase (5U/µl) (Roche; Mannheim, Germany) and distilled water up to a final volume of 101 µl. The sample was then incubated overnight at 16° C. to allow ligation of the adaptors. Purification of the sample was performed using the DNA Clean and Concentrator-5™ as described above. The eluted sample was then combined with 100 mM dNTP mix, 1×PCR Gold Buffer (Roche; Mannheim, Germany), 1.5 mM $MgCl_2$ (Roche; Mannheim, Germany), and 5U AmpliTaq Polymerase. The sample was then incubated at 70° C. for 10 minutes to fill in DNA overhangs and purified using the DNA Clean and Concentrator-5™ as described above. 50 ng of DNA was removed and retained for use as input genomic control DNA. The remaining ligated DNA sample (700 ng-1.2 µg) was subjected to MeDiP as described previously (Weber, M. et al. (2005) supra), after scaling down the reaction accordingly. The immunoprecipitated DNA sample was then cleaned up using the DNA Clean and Concentrator-5™ binding buffer) according to the manufacturer's instructions.

Ligation-mediated PCR (LM-PCR) was performed using 10 ng of each input and immunoprecipitated DNA fraction using the Advantage-GC Genomic PCR kit (Clontech; Saint-Germain-en-Laye, France). The thermal cycling conditions applied were 95° C. for 2 minutes, 20 cycles at (94° C. for 30 seconds and 68° C. for 3 minutes) and 68° C. for 10 minutes. After PCR amplification, the reaction was purified using the QIAquick PCR Purification kit (Qiagen; West Sussex, UK) and eluted in 50 µl of distilled water preheated to 50° C.

Array Hybridizations

The input and the immunoprecipitated DNA fractions from a female peripheral blood DNA sample, a $3^{rd}$ trimester placental DNA sample and a $1^{st}$ trimester placental DNA sample (both placental samples were obtained from male fetus pregnancies) were sent to Roche NimbleGen Inc (Reykjsvik, Iceland) for hybridization. The array platforms used were high resolution tiling oligonucleotide arrays specific for chromosomes 13, 18, 21, X and Y with a median probe spacing of 225 bp for chromosome 13, 170 bp for chromosome 18, 70 bp for chromosome 21, 340 bp for chromosome X and 20 bp for chromosome Y.

Briefly, the input genomic control DNA and the immunoprecipitated DNA of each sample were differentially labeled with fluorescent dyes (Cy3, Cy5) and were then co-hybridized on the oligonucleotide arrays.

The raw data can be accessed in ArrayExpress with accession number E-TABM-507.

Data Analysis of the Tiling Oligonucleotide Arrays

To calculate the relative methylation differences between placenta and peripheral blood, the oligonucleotide array normalized $log_2$ ratio values obtained from peripheral blood DNA (immunoprecipitated versus input fraction), were subtracted from the $log_2$ ratio values (immunoprecipitated versus input fraction) obtained from placental DNA using the R statistical computing environment. Positive differences represent relative hypermethylation in placental DNA, negative differences relative hypomethylation. General Feature Format (GFF) files were then created for the subtracted $log_2$ ratio data and the results were viewed using the SignalMap viewer (NimbleGen systems; Reykjsvik, Iceland) together with genes, CpG islands and CG content across chromosomes 13, 18, 21, X and Y. Gene data were downloaded from the Ensembl genome browser (NCBI build36) whereas the CpG islands and CG content were downloaded from the UCSC genome browser, (NCBI build36). For the automated selection of regions with significant differential methylation enrichment between peripheral blood and placenta, we applied the Smith-Waterman dynamic programming algorithm adapted for Array-CGH (SW-ARRAY) which had previously been used for Copy Number Variation (CNV) calling (Price, T. S. et al. (2005) Nucl. Acids Res. 16:3455-3464). This algorithm was used to identify segments or "islands" of consecutive oligonucleotides showing methylation enrichment or methylation depletion in placental DNA compared to peripheral blood DNA. Each of the oligonucleotide array data was analyzed by chromosome arm. Threshold values ($t_0$) for SW-ARRAY of between 0.2 and 1 were tested to identify the optimal value for calling relative high-score segments or "islands" based on the identification of at least two consecutive oligonucleotides having the same methylation status and showing the highest score among the scores obtained with different threshold values ($t_0$). A direct comparison between the differentially methylated regions identifie by SW-ARRAY and the position of genes, promoter regions (which were defined as the region of up to 2 kb upstream of the 5' end of each gene) and CpG islands was performed.

While the above analysis identifies differentially methylated regions of the genome, for the use of MeDiP as an enrichment method prior to quantitative assays of copy number (i.e. for the identification of trisomy 21 for example) for non-invasive prenatal diagnosis, it is important that selected targets were hypermethylated in the fetus. Thus, MeDiP would be used to deplete maternal hypomethylated DNA allowing assay of fetal hypermethylated DNA. Therefore, we identified all regions where the immunoprecipitated versus input ratios were positive in the placenta and negative in the peripheral blood samples (hypermethylation in the placenta). For other assay systems being investigated by others, hypomethylation of DNA in the placenta is required and so we also recorded all regions where the immunoprecipitated versus input ratios were negative in the placenta and positive in the peripheral blood samples. To achieve this, the oligonucleotide array normalized $log_2$ ratio values obtained from peripheral blood DNA (immunoprecipitated versus input fraction), were subtracted from the log$_2$ ratio values (immunoprecipitated versus input fraction) obtained from placental DNA only where the sign of the ratios were different. A small number of the most differentially hypermethylated regions in the placenta (8 regions on chromosome 21 and one region on chromosome 18 plus the SERPINB5 promoter region) were selected from this data set for further validation and assay development by using an arbitrary differential ratio cut off of greater than 1.0 (at least one of the consecutive probes showing a log$_2$ ratio value >1).

Confirmation of Tiling Oligonuceotide Array Data by Real-Time Quantitative PCR

The methylation enrichment of the selected regions on chromosome 21 and chromosome 18 were confirmed by real-time quantitative PCR. For this purpose we used five female peripheral blood DNA samples and five placental DNA samples of both first and third trimester gestational age. Primers specific for the regions of interest were designed using the primer3 web site. The primer design was optimized to give a product of 80-150 bp in length as recommended for optimal SYBR Green fluorescence melting curve analysis. Additionally, the Tm of all the primers was chosen to be close to 60° C. The uniqueness of both primer sequences and PCR product sequences was confirmed by mapping these onto the human reference sequence using Blat. Primers were purchased from Sigma Genosys (Gillingham, UK).

Each quantitative PCR reaction was carried out in a final volume of 25 µl with 20 ng of either immunoprecipitated methylated DNA or input genomic DNA. We used the SYBR Green PCR master mix (Eurogentec; Seraing, Belgium) and an ABI Prism 7900HT Sequence Detection System (Applied Biosystems). Initially the optimal concentration of each primer was selected after testing a series of dilutions (150-900 nM) using normal genomic DNA. For each selected primer concentration, standard curves were calculated on 1:2 serial dilutions (200 ng down to 3.125 ng) and finally, the sample reactions were performed in triplicate. The amplification program consisted of 2 minutes at 50° C. and 10 minutes at 95° C., followed by 40 cycles of denaturation for 15 seconds at 95° C. and annealing/extension for 1 minute at 60° C. After amplification, melting curve analysis was performed by heating the reaction mixture from 60 to 95° C. at a rate of 0.2° C./s. Amplification reactions were routinely checked for nonspecific products by agarose gel electrophoresis. To evaluate the enrichment of target sequences after MeDiP, we calculated the ratios of the calculated cycle difference ($\Delta C_T$) between the test DNA (immunoprecipitated or input DNA) ($C_{Ttest}$) and an untreated normal genomic DNA ($C_{Tcontrol}$) ($\Delta C_T = C_{Tcontrol} - C_{Ttest}$) in the immunoprecipitated DNA versus input genomic DNA. In addition, to evaluate the methylation enrichment of placental samples compared to peripheral blood we calculated the ratio of placental immunoprecipitated DNA versus peripheral blood immunoprecipitated DNA. Moreover, control regions with similar DNA methylation status in peripheral blood and placental DNA samples as indicated by our oligonucleotide array results were used in every run to test for possible MeDiP or PCR amplification bias. The median variability and median reproducibility of methylation enrichment between individuals or between technical replicate experiments was obtained by calculating the average value of all the ratio values of the different samples tested or of the technical replicates of a specific region (average IP/INPUT) and then each ratio value was divided by the average ratio value to obtain the reproducibility of each test and expressed as a percentage (IPi/INPUTi)/mean (IPi/INPUTi, IPii/INPUTii, . . . )=Ri (IPi: Immunoprecipitated DNA of the "ith" sample, INPUTi: Input DNA of the "ith" sample, RI=reproducibility of the "ith" sample). The median reproducibility was obtained by calculating the median of all the different reproducibility values: median (Ri, Riis, . . . ). Finally, the variability was calculated using the following formula: (1−Ri)×100=Vi and median variability: median (Vi, Vii, . . . ). (Vi=variability of the "ith" sample).

Results

Selection of Differentially Methylated Marker Candidates

The normalized oligonucleotide array log$_2$ ratio values obtained for chromosomes 13, 18, 21, X and Y in both placenta and peripheral blood DNA samples were initially used to calculate the ratio difference (relative methylation) between placental and peripheral blood DNA. We used SW-ARRAY to identify differentially methylated regions between peripheral blood and placenta. The optimal SW-ARRAY threshold for the identification of regions was found to be 0.9 for all chromosomes. The differentially methylated regions identified by SW-ARRAY analysis in 1$^{st}$ and 3$^{rd}$ trimester compared to peripheral blood DNA are shown in Appendices A-E, for chromosomes 21, 13, 18, X and Y, respectively. We found that the number of regions identified to be hypermethylated was approximately equal to the number of regions being hypomethylated in all five chromosomes tested, as summarized below in Table 1. Additionally the total number of differentially methylated regions is comparable in 1$^{st}$ and 3$^{rd}$ trimester placentas, as summarized below in Table 1. A direct correlation of the identified loci with the position of genes, promoter regions as well as the position of CpG islands is shown in Appendices A-E.

TABLE 1

Differentially methylated regions in placental compared to peripheral blood DNA samples across chromosomes 13, 18, 21, X and Y.

| CHR.* | TRI-MESTER | N° OF HYPER.† | N° OF HYPO.‡ | TOTAL N°. | % OF HYPER.§ | % OF HYPO ‖ |
|---|---|---|---|---|---|---|
| 13 | FIRST | 1310 | 1336 | 2646 | 49.5 | 50.5 |
| 13 | THIRD | 1311 | 1318 | 2629 | 49.9 | 50.1 |
| 18 | FIRST | 1967 | 1888 | 3855 | 51.0 | 48.9 |
| 18 | THIRD | 1957 | 1944 | 3901 | 50.2 | 49.8 |
| 21 | FIRST | 1063 | 1015 | 2078 | 51.1 | 48.8 |
| 21 | THIRD | 1042 | 1040 | 2082 | 50.0 | 49.9 |
| X | FIRST | 1992 | 1951 | 3943 | 50.5 | 49.5 |
| X | THIRD | 1995 | 1989 | 3984 | 50.1 | 49.9 |
| Y | FIRST | 1192 | 1120 | 2312 | 51.6 | 48.4 |
| Y | THIRD | 1986 | 1990 | 3976 | 49.9 | 50.0 |

*Chromosome;
†Number of hypermethylated regions;
‡Number of hypomethylated regions;
§Percentage of hypermethylated regions;
‖Percentage of hypomethylated regions.

The 17.5-43.6% of the identified regions were located within genes and their methylation status varied between chromosomes as well as between trimesters, as summarized below in Table 2. For chromosomes 13 and Y, the majority of the differentially methylated regions (located within genes) are hypomethylated in 1$^{st}$ trimester placenta but the majority became hypermethylated in 3$^{rd}$ trimester placentas. In chromosomes 21 and X, most of the regions were hypomethylated in both 1$^{st}$ and 3$^{rd}$ trimester placentas whereas in chromosome 18 equal numbers of regions were found to be hypermethylated and hypomethylated, as summarized below in Table 2.

TABLE 2

Differentially methylated regions located within genes in chromosomes 13, 18, 21, X and Y.

| CHR.* | TRIMESTER | Nº OF HYPER.† | Nº OF HYPO.‡ | TOTAL Nº. | % OF TOTAL§ | % OF HYPER.‖ | % OF HYPO.¶ |
|---|---|---|---|---|---|---|---|
| 13 | FIRST | 374 | 671 | 1045 | 39.5 | 35.8 | 64.2 |
| 13 | THIRD | 554 | 480 | 1034 | 39.3 | 53.6 | 46.4 |
| 18 | FIRST | 734 | 728 | 1463 | 37.9 | 50.2 | 49.8 |
| 18 | THIRD | 746 | 673 | 1419 | 36.4 | 52.6 | 47.4 |
| 21 | FIRST | 362 | 545 | 907 | 43.6 | 39.9 | 60.1 |
| 21 | THIRD | 338 | 486 | 824 | 39.6 | 41.0 | 59.0 |
| X | FIRST | 700 | 884 | 1584 | 40.2 | 44.2 | 55.8 |
| X | THIRD | 604 | 897 | 1501 | 37.7 | 40.2 | 59.8 |
| Y | FIRST | 196 | 228 | 424 | 18.3 | 46.2 | 53.8 |
| Y | THIRD | 387 | 310 | 697 | 17.5 | 55.5 | 44.5 |

*Chromosome;
†Number of hypermethylated regions within genes;
‡Number of hypomethylated regions within genes;
§Percentage of differentially methylated regions within genes;
‖Percentage of hypermethylated regions within genes;
¶Percentage of hypomethylated regions within genes.

Additionally, a small percentage (1.6-11.0%) of the identified regions (both genic and non-genic regions) were overlapping with CpG islands, as summarized below in Table 3A. The majority of the CpG islands identified to be differentially methylated were located within genes (including the appropriate promoter sites defined as the regions up to 2 kb upstream the 5' end of each gene) with a significant number of these (up to 65.5%) located specifically within promoter regions. The methylation status of these regions in each chromosome and in $1^{st}$ and $3^{rd}$ trimester placentas is shown below in Table 3B.

TABLE 3A

Number of methylated regions overlapping with CpG islands in chromosomes 13, 18, 21, X and Y.

| CHR.* | TRIMESTER | REGIONS WITHIN CpGs† | % TOTAL‡ |
|---|---|---|---|
| 13 | FIRST | 250 | 9.4 |
| 13 | THIRD | 142 | 5.4 |
| 18 | FIRST | 182 | 5.4 |
| 18 | THIRD | 143 | 3.7 |
| 21 | FIRST | 162 | 7.8 |
| 21 | THIRD | 91 | 4.4 |
| X | FIRST | 435 | 11.0 |
| X | THIRD | 415 | 10.4 |
| Y | FIRST | 46 | 2.0 |
| Y | THIRD | 63 | 1.6 |

*Chromosome;
†Number of regions overlapping with CpG islands;
‡percentage differentially methylated regions overlapping with CpG islands.

TABLE 3B

Methylation status of genic, no-genic and promoter CpG islands located within the differentially methylated regions in chromosomes 13, 18, 21, X and Y.

| CHR.* | TRIMESTER | HYPER/HYPO (+/−)† | GENIC CpGs | NON-GENIC CpGs | TOTAL Nº | PROMOTER CpGs | % OF PROMOTER CpGs‡ |
|---|---|---|---|---|---|---|---|
| 13 | FIRST | + | 17 | 7 | 24 | 11 | 45.8 |
| 13 | FIRST | − | 226 | 84 | 310 | 102 | 32.9 |
| 13 | THIRD | + | 74 | 26 | 100 | 31 | 31.0 |
| 13 | THIRD | − | 57 | 25 | 82 | 21 | 25.6 |
| 18 | FIRST | + | 13 | 5 | 18 | 6 | 33.3 |
| 18 | FIRST | − | 166 | 90 | 256 | 65 | 25.4 |
| 18 | THIRD | + | 30 | 12 | 42 | 15 | 35.7 |
| 18 | THIRD | − | 102 | 60 | 162 | 28 | 17.3 |
| 21 | FIRST | + | 0 | 1 | 1 | 0 | 0.0 |
| 21 | FIRST | − | 220 | 41 | 261 | 121 | 46.4 |
| 21 | THIRD | + | 4 | 4 | 8 | 1 | 12.5 |
| 21 | THIRD | − | 90 | 37 | 127 | 49 | 38.6 |
| X | FIRST | + | 2 | 1 | 3 | 0 | 0.0 |
| X | FIRST | − | 592 | 103 | 695 | 414 | 59.6 |
| X | THIRD | + | 5 | 1 | 6 | 0 | 0.0 |
| X | THIRD | − | 609 | 93 | 702 | 460 | 65.5 |

TABLE 3B-continued

Methylation status of genic, no-genic and promoter CpG islands located within the differentially methylated regions in chromosomes 13, 18, 21, X and Y.

| CHR.* | TRIMESTER | HYPER/HYPO (+/−)† | GENIC CpGs | NON-GENIC CpGs | TOTAL N° | PROMOTER CpGs | % OF PROMOTER CpGs‡ |
|---|---|---|---|---|---|---|---|
| Y | FIRST | + | 3 | 2 | 5 | 0 | 0.0 |
| Y | FIRST | − | 49 | 21 | 70 | 35 | 50.0 |
| Y | THIRD | + | 28 | 33 | 61 | 3 | 4.9 |
| Y | THIRD | − | 12 | 11 | 23 | 8 | 34.8 |

*Chromosome;
†hypermethylated/hypomethylated;
‡Percentage of promoter CpGs compared to the total number of differentially methylated CpG islands.

Validation of the Tiling Oligonucleotide Array Results

To validate the array analysis, we first analyzed the methylation status of a previously investigated region by real time quantitative PCR. We found that the SERPINB5 promoter region was hypomethylated in placenta and hypermethylated in peripheral blood which is in agreement with the study of Chim, S. S. et. al (2005) *Proc. Natl. Acad. Sci. USA* 11:14753-14758. To further validate the methylation differences identified by high resolution array analysis, an additional 9 selected regions, including the SERPINB5 promoter region (Chim, S. S. et al. (2005) supra) were analyzed by real time quantitative PCR. Various primers were designed to cover each region. Each primer was tested prior to use and the optimal concentration for each one was determined.

Figure 2:
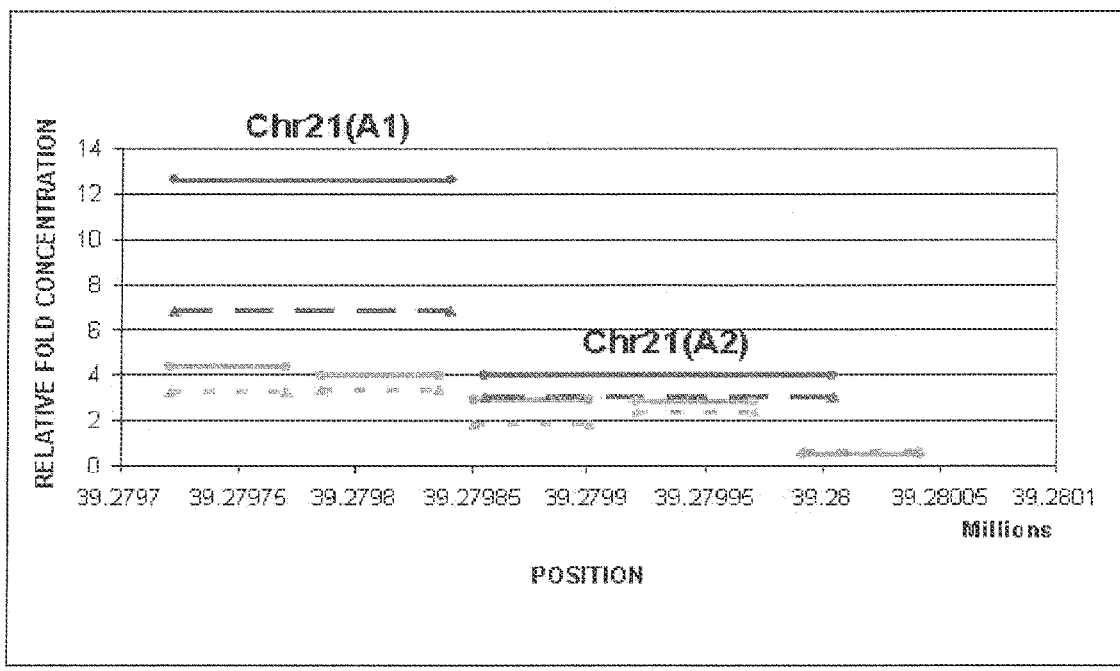
FIG. 2 is a diagram showing the comparison of the DNA methylation enrichment of CHR21(A) from oligonucleotide arrays and real time quantitative PCR using peripheral blood, $1^{st}$ trimester and $3^{rd}$ trimester placental DNA samples. The Y axis indicates the relative fold enrichment of placenta when compared to peripheral blood DNA sample and the X axis indicates the chromosomal position in bp. The grey lines represent the oligonucleotides covering the specific region on chromosome 21 whereas the black lines represent the PCR products (CHR21 (A1) & CHR21 (A2)) when real time quantitative PCR was applied. The dotted lines represent the results obtained from a $1^{st}$ trimester placenta whereas the solid lines represent the results obtained from a $3^{rd}$ trimester placenta.

As an example, the oligonucleotide array results for a region located on chromosome 21 (see FIG. 1) can be compared to the real-time quantitative PCR results as shown in FIG. 2. The same peripheral blood and placental DNA samples were used for PCR validation as had been used for oligonucleotide array hybridizations. Both methods reported enrichment for methylation in placenta compared to peripheral blood. Additionally, both oligonucleotide array and real time quantitative PCR demonstrated a lower degree of methylation enrichment in $1^{st}$ trimester placental DNA sample compared to $3^{rd}$ trimester placental DNA sample. Nevertheless, the methylation enrichment observed in the $1^{st}$ trimester placenta was higher compared to the methylation enrichment obtained from the peripheral blood DNA sample. We found concordance of differential methylation for all 9 selected regions as well as the SERPINB5 promoter region between array analysis and quantitative PCR. However, the relative fold enrichment obtained using real time quantitative PCR was generally found to be greater than the enrichment obtained by oligonucleotide array analysis.

Evaluation of MeDiP-LMPCR Efficiency

The experimental reproducibility of the MeDiP procedure was assessed by performing technical replicates of a single placental DNA sample with the methylation status of two regions on chromosome 21 being assessed by real time quantitative PCR. The median reproducibility was found to be 98.62% and 95.84% for the regions.

Evaluating the Methylation Status of Selected Regions in Different Individuals

Figure 3:
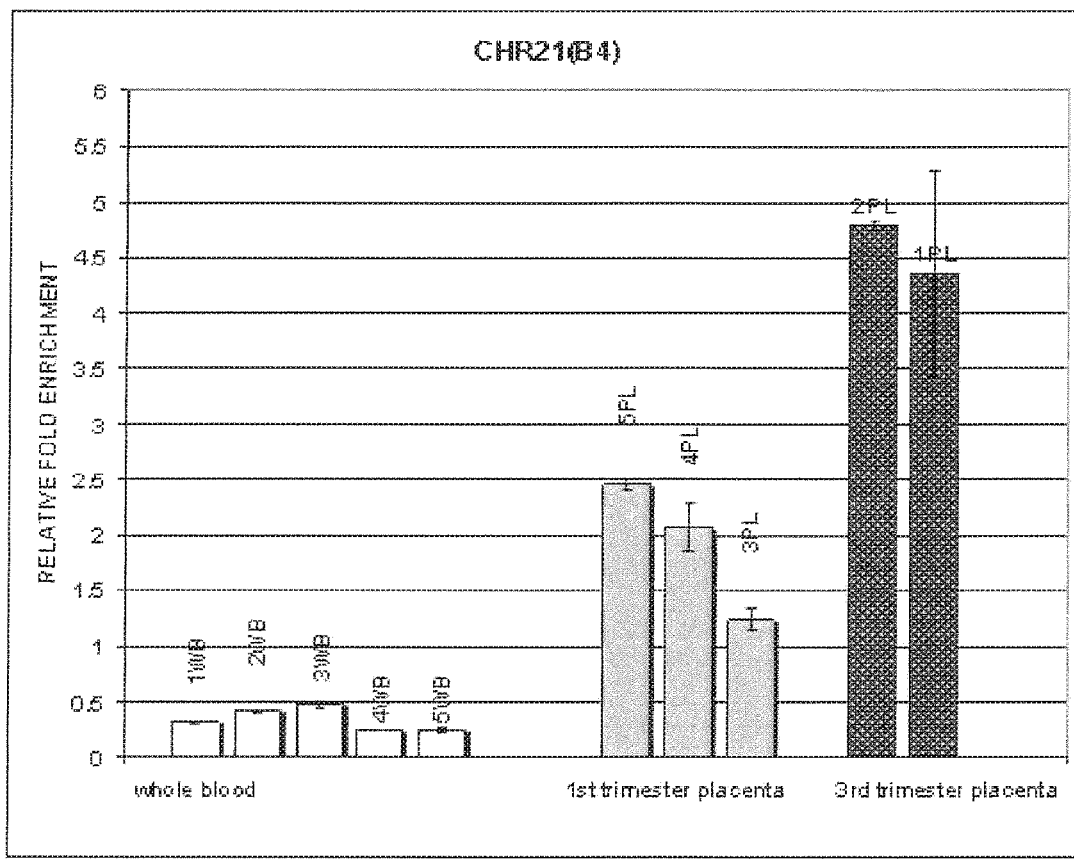
FIG. 3 is a bar graph showing DNA methylation enrichment of CHR21(B4) by real time quantitative PCR on MeDiP and input replicated DNA samples. Open bars are peripheral (whole) blood samples; grey bars are $1^{st}$ trimester placental DNA samples; solid black bars are $3^{rd}$ trimester placental DNA samples. The error bars indicate the standard deviation between technical replicates. WB: whole (peripheral) blood, PL: placenta.

In order to assess the normal variability in methylation status between individuals, we applied the real time quantitative PCR assay for the 9 selected regions to 5 different peripheral blood and 3 different $1^{st}$ trimester placentas. The methylation status of two $3^{rd}$ trimester placentas was tested in only 4 of the selected regions. Further investigation of inter-individual variability of $3^{rd}$ trimester placentas was not necessary in this study in which we preferably tested $1^{st}$ trimester placentas as their gestational age is the most appropriate for the development of non-invasive prenatal diagnosis. The results of the CHR21(B4) region are shown in FIG. 3. All five peripheral blood samples were found to be hypomethylated compared to the five placental DNA with a variability of DNA methylation enrichment between individuals, as summarized below in Table 4. Less methylation enrichment was observed in $1^{st}$ trimester placentas compared to $3^{rd}$ trimester placentas confirming the oligonucleotide array results (see FIG. 3). A lower level of variability was also observed between different placentas of the same gestational age.

TABLE 4

Percentage variability of methylation between different samples of the same tissue origin (peripheral blood (PB) or placenta (PL)) and gestational age (placenta) calculated for multiple regions located in chromosomes 18 and 21.

| Chr. | Region | Primer tested | PB_aver* | $1^{st}$ TR PL_aver† | $3^{st}$ TR PL_aver‡ | PB var (%)§ | $1^{st}$ TR PL var (%)∥ | $3^{st}$ TR PL var (%)¶ |
|---|---|---|---|---|---|---|---|---|
| 18 | CHR18(A) | CHR18(A-2) | 0.12 | 1.72 | 1.90 | 6.2 | 1.3 | 0 |
| 18 | ≫ | CHR18(A-3) | 0.08 | 1.89 | 2.30 | 5.9 | 10.2 | 0 |
| 21 | CHR21(A) | CHR21(A1) | 0.43 | 1.49 | 2.08 | 0.1 | 10.7 | 0 |
| 21 | ≫ | CHR21(A2) | 0.21 | 1.23 | 2.67 | 4.9 | 4.6 | 0 |
| 21 | CHR21(B) | CHR21(B3) | 0.38 | 2.09 | 4.85 | 12.7 | 3.3 | 0 |
| 21 | ≫ | CHR21(B4) | 0.34 | 1.92 | 4.57 | 7.6 | 7.6 | 0 |
| 21 | CHR21(C) | CHR21(C1) | 0.25 | 1.51 | — | 1.3 | 1.1 | — |
| 21 | ≫ | CHR21(C2) | 0.30 | 1.53 | — | 3.0 | 5.3 | — |
| 21 | ≫ | CHR21(C3) | 0.28 | 1.88 | — | 3.9 | 1.5 | — |
| 21 | CHR21(D) | CHR21(D2) | 0.66 | 6.13 | — | 3.3 | 4.5 | — |
| 21 | ≫ | CHR21(D3) | 0.27 | 2.71 | — | 1.9 | 6.2 | — |
| 21 | ≫ | CHR21(D4) | 0.35 | 2.58 | — | 4.8 | 4.8 | — |

TABLE 4-continued

Percentage variability of methylation between different samples of the same tissue origin (peripheral blood (PB) or placenta (PL)) and gestational age (placenta) calculated for multiple regions located in chromosomes 18 and 21.

| Chr. | Region | Primer tested | PB_aver* | $1^{st}$ TR PL_aver† | $3^{st}$ TR PL_aver‡ | PB var (%)§ | $1^{st}$ TR PL var (%)‖ | $3^{st}$ TR PL var (%)¶ |
|---|---|---|---|---|---|---|---|---|
| 21 | CHR21(EI) | CHR21(EI-1) | 0.05 | 1.85 | — | 58.3 | 18.7 | — |
| 21 | >> | CHR21(EI-2) | 0.07 | 1.86 | — | 45.2 | 15.1 | — |
| 21 | CHR21 (EII) | CHR21(EII-1) | 0.36 | 1.92 | 3.78 | 10.2 | 22.4 | 0 |
| 21 | CHR21(H) | CHR21(H1) | 0.57 | 2.03 | — | 2.4 | 0.8 | — |
| 21 | >> | CHR21(H2) | 0.50 | 1.90 | — | 1.0 | 5.3 | — |
| 21 | CHR21 (I) | CHR21(I1) | 0.41 | 1.67 | — | 0.3 | 0.1 | — |
| 21 | >> | CHR21(I2) | 0.30 | 1.48 | — | 3.8 | 4.8 | — |

*the mean of five different peripheral blood samples;
†the mean of three $1^{st}$ trimester placentas;
‡mean of two $3^{st}$ trimester placentas;
§median variability between the peripheral blood samples;
‖median variability between the $1^{st}$ trimester placental samples;
¶median variability between the $3^{st}$ trimester placental samples.

The majority of the regions tested so far by real time quantitative PCR showed methylation variability between placental DNA samples of different gestational ages (see Table 4). However, not all of the regions demonstrated this effect. One example is a region located on chromosome 18 (CHR18 (A)) shown in Table 4. Only minor differences of the methylation level between $1^{st}$ and $3^{rd}$ trimester placentas were found for this region. Additionally, we identified regions with opposite DNA methylation status between $1^{st}$ and $3^{rd}$ trimester placentas as well as other regions showing differential methylation, examples of which are shown below in Table 5.

TABLE 5

Example of regions found to have opposite methylation status between $1^{st}$ and $3^{rd}$ trimester placental DNA or being differentially methylated at a specific gestational age compared to peripheral blood DNA.

| Chr.* | Gene name | Meth. status $1^{st}$ TR_PL† | Meth. status $3^{st}$ TR_PL‡ |
|---|---|---|---|
| 13 | ALG5 | Hypomethylated | Non-differentially methylated |
| 13 | C13orf3 | Non-differentially methylated | Hypomethylated |
| 13 | EBPL | Hypomethylated | Non-differentially methylated |
| 13 | BRCA2 | Hypomethylated | Hypermethylated |
| 13 | C13orf21 | Hypomethylated | Hypermethylated |
| 18 | CPLX4 | Non-differentially methylated | Hypermethylated |
| 18 | CTDP1 | Hypomethylated | Non-differentially methylated |
| 18 | MCART2 | Hypomethylated | Non-differentially methylated |
| 18 | ME2 | Hypomethylated | Non-differentially methylated |
| 21 | SUMO3 | Hypomethylated | Non-differentially methylated |
| 21 | WRB | Hypomethylated | Non-differentially methylated |

*chromosome;
Meth. †Methylation status of $1^{st}$ trimester placenta;
Meth. ‡Methylation status of $3^{rd}$ trimester placenta.

Differentially Methylated Control Regions

To assess MeDiP efficiency in all experiments, we selected 2 hypermethylated and 2 hypomethylated regions that showed a similar degree of differential methylation from the array experiments for use as controls. The primers used to detect these control regions are summarized below in Table 6, wherein the CHR13(HYP1) and CHR13(HYP2) primers detect hypermethylated control regions and the CHR22(U1) and CHR22 (U2) primers detect hypomethylated control regions.

TABLE 6

Control primers used to assess the MeDiP efficiency on different samples using real time quantitative PCR.

| Primer name | Forward primer (top) and Reverse primer (bottom) | Position (bp) | Pr. size* | Selected conc.† |
|---|---|---|---|---|
| CHR13(HYP1)§ | CAGGAAAGTGAAGGGAGCTG (SEQ ID NO: 25) CAAAACCCAATGGTCAATCC (SEQ ID NO: 26) | 19991387-19991465 | 79 bp | 300 nM |
| CHR13(HYP2)‖ | AATGATTGTGCAGGTGGTGA (SEQ ID NO: 27) GAGCGCCTTGAGTAGAGGAA (SEQ ID NO: 28) | 20191970-20192091 | 122 bp | 300 nM |

TABLE 6-continued

Control primers used to assess the MeDiP efficiency on different samples using real time quantitative PCR.

| Primer name | Forward primer (top) and Reverse primer (bottom) | Position (bp) | Pr. size* | Selected conc.† |
|---|---|---|---|---|
| CHR22(U1)¶[22] | AAGGTGCCCAATTCAAGGTA (SEQ ID NO: 29) CTTCCCCACCAGTCTTGAAA (SEQ ID NO: 30) | 30214952-30215055 | 104 bp | 300 nM |
| CHR22(U2)**[22] | TGAGAGCGGATGACAGATTG (SEQ ID NO: 31) GGTCCCTCCCTTTTCTGTCT (SEQ ID NO: 32) | 35582634-35582737 | 104 bp | 300 nM |

*product size;
†Selected concentration;
‡methylation status;
§hypermethylated region 1 on chromosome 13;
∥hypermethylated region 2 on chromosome 13;
¶hypomethylated region 1 on chromosome 22;
**hypomethylated region 2 on chromosome 22.

Figure 4:
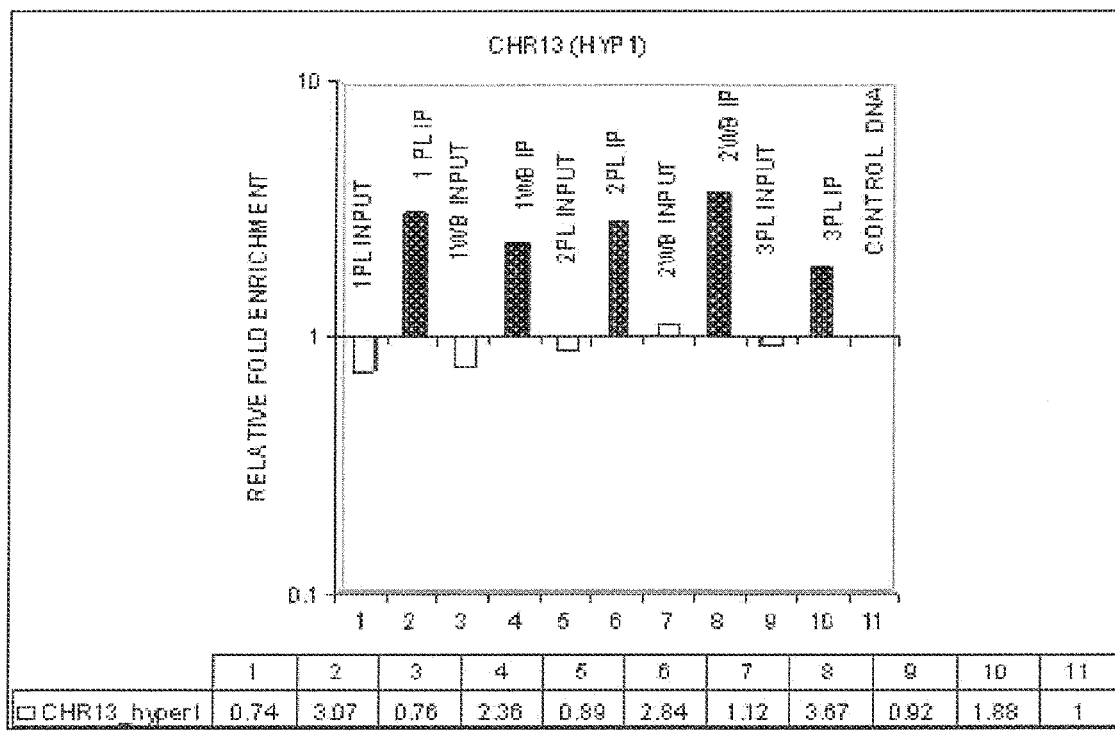
FIG. 4 is a bar graph showing DNA methylation enrichment of CHR13(HYP1) using real time quantitative PCR. Open bars are input DNA compared to peripheral (whole) blood; solid black bars are immunoprecipitated DNA compared to peripheral (whole) blood, 1PL & 2PL are $3^{rd}$ trimester placentas, 3PL is $1^{st}$ trimester placenta. WB is whole (peripheral) blood, P is placenta.

The methylation status of these regions was assessed by real time quantitative PCR in multiple samples of peripheral blood and placenta. The results for a region on chromosome 13, which was expected to be hypermethylated in both peripheral blood and placental DNA samples, are shown in FIG. 4. The same DNA samples were used for testing all the control primers. The median reproducibility of methylation enrichment between individuals was found to be 98.48% for the region CHR13 (HYP1), 96.02% for the region CHR13 (HYP2), 98.71% for the region CHR22 (U1) and 99.75% for the region CHR22(U2).

Example 2

Additional Description of Identification of Differentially Methylated Regions (DMRs)

Figure 5:
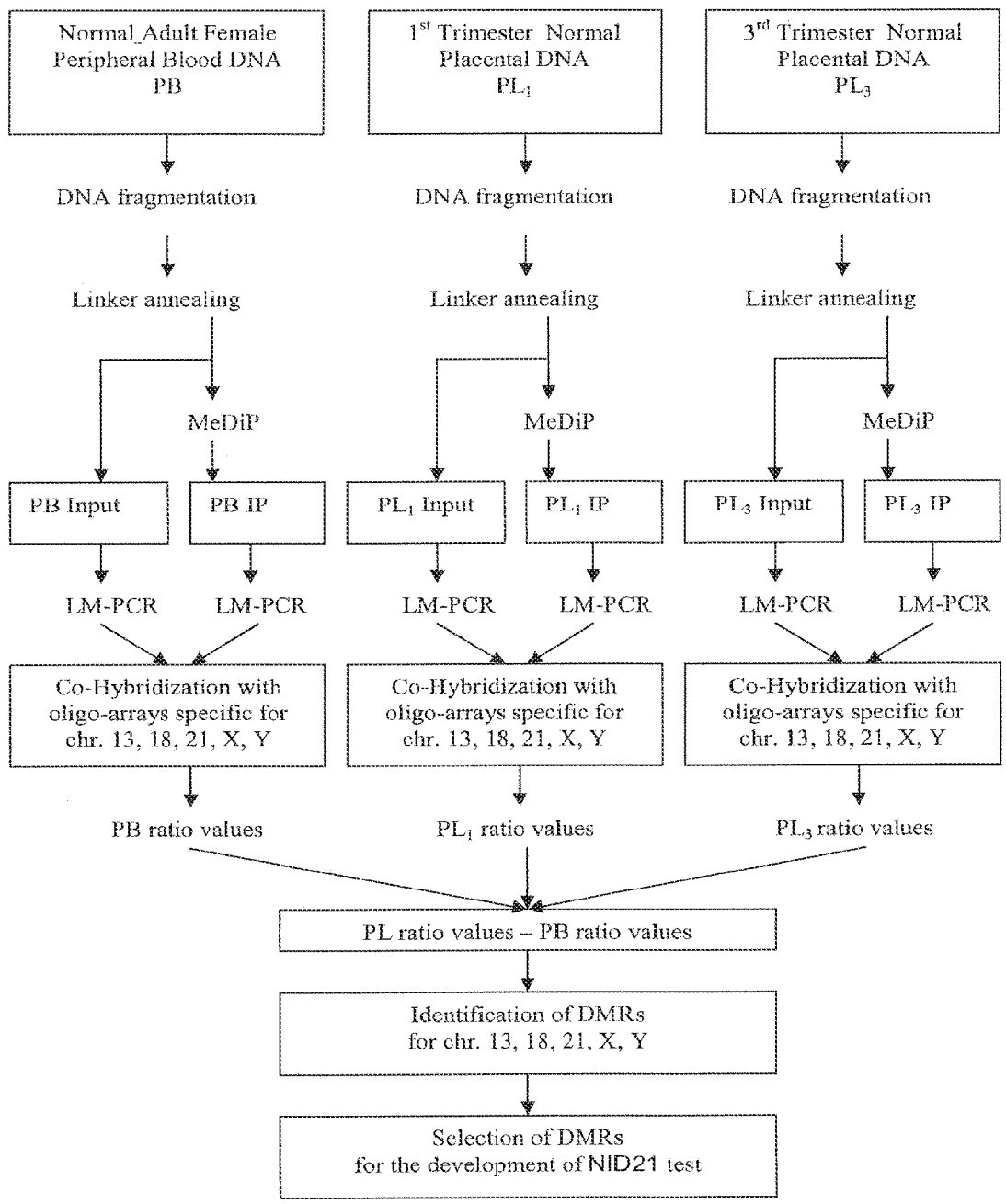
FIG. 5 is a flowchart diagram of the methodology for identification of Differentially Methylated Regions (DMRs).

This example provides an additional description of how differentially methylated regions (DMRs) were identified and, from those DMRs, the ones which are hypomethylated in maternal DNA and hypermethylated in fetal DNA were preferentially chosen. A flowchart diagram of the methodology is shown in FIG. 5. The diagram shows the application of the MeDiP LM-PCR methodology and the oligo-array hybridization procedure towards the identification of DMRs across chromosomes 13, 18, 21, X and Y.

Samples

The DNA samples from one normal adult female peripheral blood (PB), one normal first trimester placenta ($PL_1$) and one normal third trimester placenta ($PL_3$) were obtained from unrelated individuals and were supplied from AMS Biotechnology (Europe) Ltd (Oxon, UK) which were originally sourced from the Biochain Institute (Hayward, Calif.). Consent for these samples was obtained using the ethical Internal Review Board (IRB) approved protocols.

Identification of DMRs

Initially, Methylation DNA Immunoprecipitation (MeDiP) and Ligation Mediated PCR (LM-PCR) was applied to DNA samples from one normal adult female peripheral blood (PB), one normal first trimester placenta ($PL_1$) and one normal third trimester placenta ($PL_3$). In more detail, the MeDiP assay (described further in Weber, M. et al. (2005) *Nat. Genet.* 37:853-862) was followed by LM-PCR (described further in Ren, B. et al. (2000) *Science* 22:2306-2309; Oberley, M. J. et al. (2004) *Methods Enzymol.* 376:315-334). The methodology was as described previously (Rakyan, K. V. et al. (2008) *Genome Research* 18:1518-1529) with minor modifications. FIG. 5 provides a flow chart of the procedure.

DNA Fragmentation and Linker Annealing

Briefly, 2.5 µg of DNA samples in a total volume of 100 µl were separately sheared by sonication into fragments of approximately 300 bp-1000 bp in size using the VirSonic Digital 600 sonicator (Virtis; Gardiner, N.Y.) (FIG. 1).

The fragmented DNA from samples were blunt-ended after combination with 1×NEB buffer 2 (New England BioLabs; Ipswich, UK), 10×BSA (New England BioLabs; Ipswich, UK), 100 mM dNTP mix, T4 DNA polymerase (3U/µl) (New England BioLabs; Ipswich, UK) and distilled water up to a final volume of 120 µl (FIG. 5). After 20 minutes incubation at 12° C., the reactions were cleaned up using the QIAquick PCR Purification kit (Qiagen; West Sussex, UK) according to the manufacturer's protocol. However, the final elution step was performed in 30 µl of EB buffer. The cleaned samples were then mixed with 40 µl of annealed linkers (50 µM) (SIGMA Genosys; Gillingham, UK), prepared as previously described (Ren, B. et al. (2002), supra; Oberley, M. J. et al. (2004), supra), T4 DNA ligase 10× buffer (Roche; Mannheim, Germany), 6 µl of T4 DNA ligase (5U/µl) (Roche; Mannheim, Germany) and distilled water up to a final volume of 101 µl. The samples were then incubated overnight at 16° C. to allow ligation of the adaptors (FIG. 5). Purification of the sample was performed using the QIAquick PCR Purification kit as described above. The eluted samples were then combined with 100 mM dNTP mix, 1×PCR Gold Buffer (Roche; Mannheim, Germany), 1.5 mM $MgCl_2$ (Roche; Mannheim, Germany), and 5U AmpliTaq Polymerase. The samples were then incubated at 70° C. for 10 minutes to fill in DNA overhangs and purified using the QIAquick PCR Purification kit as described above (FIG. 5).

Input and MeDiP DNA Isolation

A total of 50 ng of ligated DNA from each sample was removed and retained for use as Input genomic control DNA (FIG. 5). The remaining ligated DNA samples (800 ng-1.2 µg) were subjected to MeDiP as described previously, after scaling down the reaction accordingly (Weber, M. et al. (2005) supra). The immunoprecipitated DNA samples were then purified using the QIAquick PCR Purification kit according to the manufacturer's instructions (FIG. 5).

LM-PCR

Ligation-mediated PCR amplification (LM-PCR) reactions were separately performed with 10 ng of each Input and IP DNA fraction using the Advantage GC Genomic LA Polymerase Mix (Clontech; Saint-Germain-en-Laye, France) (FIG. 5). The thermal cycling conditions applied were 94° C. for 1 minute, 20 cycles at (94° C. for 30 seconds, 60° C. for 30 seconds and 72° C. for 2 minutes) and 72° C. for 5 minutes. After PCR amplification, the reactions were purified using the QIAquick PCR Purification kit and eluted in 50 µl of distilled water preheated to 50° C. (FIG. 5).

Co-Hybridization with Oligo-Arrays Specific for Chromosomes 13, 18, 21, X, Y and Data Analysis The Input and IP DNA fragments of each sample were co-hybridized on oligo-arrays specific for chromosomes 13, 18, 21, X and Y. The PB ratio values were subtracted from the $PL_1$ ratio values and from the $PL_3$ ratio values to reveal the DMRs across the chromosomes of interest (Chromosomes 13, 18, 21, X and Y) in both first and third trimester placentas. Furthermore, data analysis was applied using the dynamic programming algorithm adapted for Array-CGH (SW-ARRAY) to automatically select regions with significant differential methylation in placental DNA compared to peripheral blood DNA (FIG. 5).

Several experiments were carried out to analyze and validate the above identified DMRs. These experiments include confirmation of the methylation status of a number of those DMRs by real-time quantitative PCR in multiple DNA samples. Comparison of the results obtained between first and third trimester placentas to identify any possible differential methylation between placentas of different gestational age. Additionally, evaluation of the variability and reproducibility of the methylation levels between different individuals and between technical replicates was performed (as in Example 1).

Example 3

Development and Validation of a Noninvasive Diagnostic Test for Trisomy 21

Figure 6:
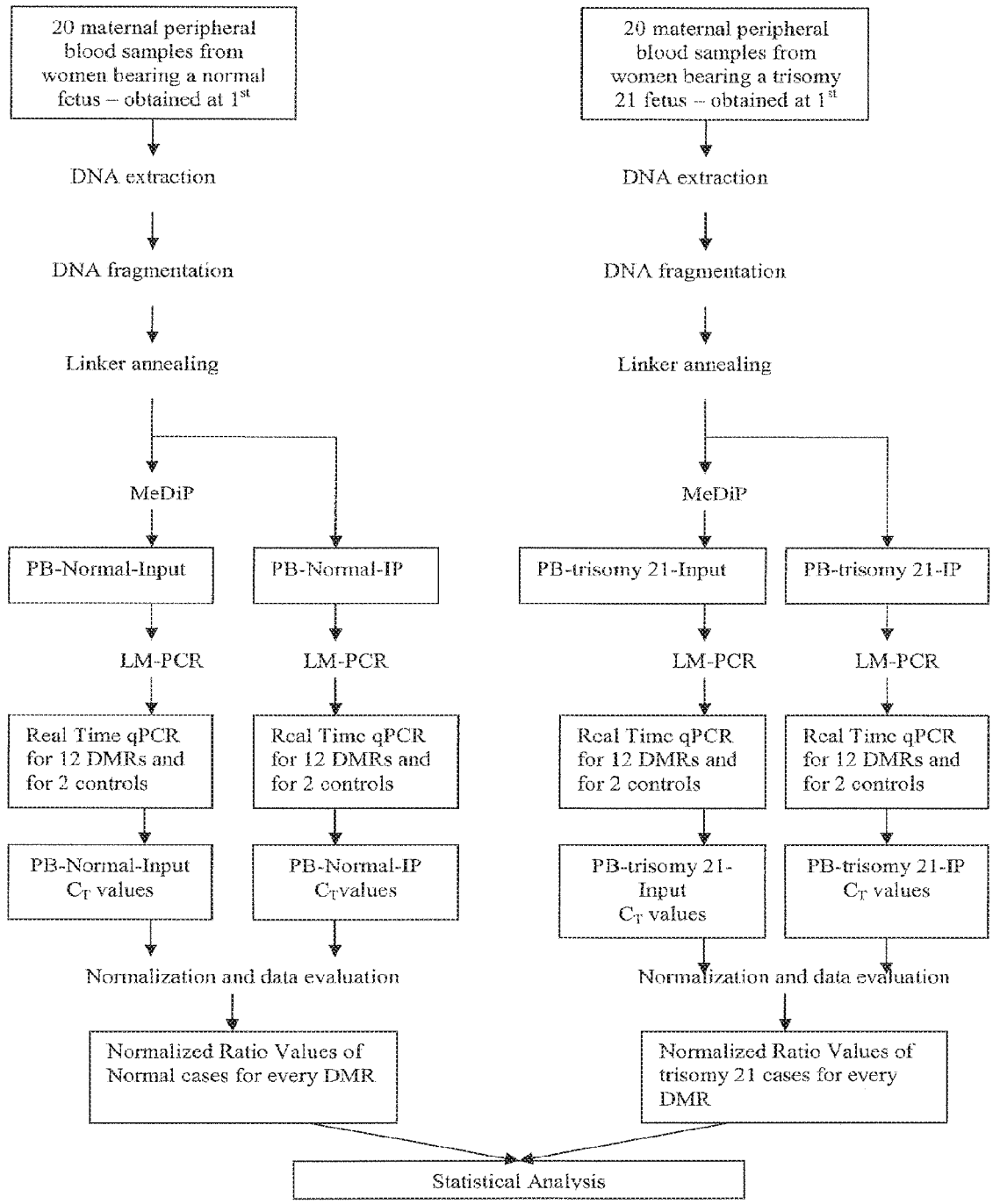
FIG. 6 is a flowchart diagram of the methodology for development and validation of a noninvasive diagnostic test for trisomy 21 (NID21).

In this example, DMRs identified according to the methodology described in Examples 1 and 2 were used in the development and validation of a noninvasive diagnostic test for trisomy 21 (referred to herein as NID21). A flowchart diagram of the methodology is shown in FIG. 6. The diagram shows the experimental procedure followed using 20 normal and 20 trisomy 21 cases towards the development and validation of the NID21 test.

Selection of DMRs for the Development of Noninvasive Diagnostic Test for Trisomy 21

An in depth investigation of the identified DMRs between female peripheral blood and placental DNA samples (Examples 1 and 2), has led to the selection of 12 regions located on chromosome 21. Along with the selected regions for the development of NID21 test, two additional regions located on chromosomes 13 and 22 were used as hypermethylated and hypomethylated controls respectively. The selection criteria of the 12 regions were based firstly on the methylation status of the regions in peripheral blood and placental DNA samples. More specifically, the selected regions should demonstrate a hypermethylated status in placenta and hypomethylated status in peripheral blood. Secondly, the regions selected should have common methylation status between first and third trimester placentas in order to ensure the tissue specificity of the methylation status. Finally, the level of differential methylation observed for these regions must be above the value of "1" in a logarithmic scale in order to ensure efficient discrimination of the methylation status when testing minute amounts of hypermethylated DNA samples presented in a high background of hypomethylated DNA.

Based on the above evaluation, the selected DMRs, or part of them, can be used as DMRs for the NID21 test. However, similar evaluation to that described herein can identify other DMRs from the lists shown in Appendices A-E that can be used for NID21 test. Furthermore, evaluation and selection of DMRs can be used in a similar or different methodology for NIPD of aneuploidies of chromosomes 13, 18, X and Y.

Samples

For the purpose of the development of NID21 test, we have used 20 maternal peripheral blood samples from women baring a normal fetus and 20 maternal peripheral blood samples from women baring a Down Syndrome (trisomy 21) fetus (T21 fetus). All the maternal peripheral blood DNA samples were obtained from first trimester pregnancies at the "Cyprus Institute of Neurology and Genetics" through collaboration with Centers in Cyprus and in Greece. Consent forms approved by the Cyprus National Bioethics Committee were collected for each of the samples participated.

Development and Validation of NID21 Test

MeDiP and LM-PCR Preparation

DNA was extracted from all samples using the QIAamp DNA blood Midi Kit (Qiagen; West Sussex, UK). The isolated DNA from the 20 maternal peripheral blood samples from women baring a normal fetus and 20 maternal peripheral blood samples from women baring a T21 fetus was processed for DNA fragmentation, linker annealing, MeDiP and LM-PCR resulting the Input and IP DNA fragments as shown in FIG. 6. The above methodologies are described in Examples 1 and 2.

Real Time qPCR and Data Evaluation

Real Time qPCR was applied in all 40 maternal peripheral blood samples in all Input and IP fragments for the 12 pre-selected DMRs on chromosome 21 and two control regions on chromosomes 13 and 22 (FIG. 6). Initially, primers specific for the regions of interest were designed using the primer3 web site (http://frodo.wi.mit.edu/.) Primers used real time qPCR are shown below in Table 7.

TABLE 7

The primers designed for the regions tested on chromosome 21 and control regions on chromosomes 13 and 22.

| Region | Forward primer (Top) Reverse primer (Bottom) | Position (bp) | Pr. size (bp) | Selected *conc.† |
|---|---|---|---|---|
| EP1 | GCTGGACCAGAAAGTGTTGAG (SEQ ID NO: 1) GTGTGCTGCTTTGCAATGTG (SEQ ID NO: 2) | 39279856-39280004 | 149 | 300 nM |

TABLE 7-continued

The primers designed for the regions tested on chromosome 21 and control regions on chromosomes 13 and 22.

| Region | Forward primer (Top) Reverse primer (Bottom) | Position (bp) | Pr. size (bp)* | Selected conc.† |
|---|---|---|---|---|
| EP2 | GGTCGAGTTTTTGGTGGTGT (SEQ ID NO: 3) CCACCGTCACTGTTCCTAGA (SEQ ID NO: 4) | 44161178-44161323 | 146 | 300 nM |
| EP3 | CCTCGTGCTCGTGTCTGTAT (SEQ ID NO: 5) GAGGAAACAGCTTGGCTCTG (SEQ ID NO: 6) | 44161239-44161371 | 133 | 300 nM |
| EP4 | CTGTTGCATGAGAGCAGAGG (SEQ ID NO: 7) CGTCCCCCTCGCTACTATCT (SEQ ID NO: 8) | 33320735-33320829 | 95 | 900 nM |
| EP5 | TGCAGGATATTTGGCAAGGT (SEQ ID NO: 9) CTGTGCCGGTAGAAATGGTT (SEQ ID NO: 10) | 42189557-42189683 | 127 | 450 nM |
| EP6 | TGAATCAGTTCACCGACAGC (SEQ ID NO: 11) GAAACAACCTGGCCATTCTC (SEQ ID NO: 12) | 42355712-42355815 | 104 | 900 nM |
| EP7 | CCGTTATATGGATGCCTTGG (SEQ ID NO: 13) AAACTGTTGGGCTGAACTGC (SEQ ID NO: 14) | 42357215-42357341 | 127 | 750 nM |
| EP8 | CCAGGCAAGATGGCTTATGT (SEQ ID NO: 15) ACCATGCTCAGCCAATTTTT (SEQ ID NO: 16) | 22403649-22403792 | 144 | 300 nM |
| EP9 | GACCCAGACGATACCTGGAA (SEQ ID NO: 17) GCTGAACAAAACTCGGCTTC (SEQ ID NO: 18) | 29136735-29136844 | 110 | 300 nM |
| EP10 | CCACATCCTGGCCATCTACT (SEQ ID NO: 19) TTCCACAGACAGCAGAGACG (SEQ ID NO: 20) | 32268843-32268943 | 101 | 300 nM |
| EP11 | TGAGCTCACAGGTCTGGAAA (SEQ ID NO: 21) CCCCACAGGGTTCTGGTAAT (SEQ ID NO: 22) | 44079235-44079322 | 88 | 300 nM |
| EP12 | ATTCTCCACAGGGCAATGAG (SEQ ID NO: 23) TTATGTGGCCTTTCCTCCTG (SEQ ID NO: 24) | 37841284-37841411 | 128 | 300 nM |
| HYP1$_{13}$§ | CAGGAAAGTGAAGGGAGCTG (SEQ ID NO: 25) CAAAACCCAATGGTCAATCC (SEQ ID NO: 26) | 19991387-19991465 | 79 | 300 nM |
| U1$_{22}$¶ | AAGGTGCCCAATTCAAGGTA (SEQ ID NO: 29) CTTCCCCACCAGTCTTGAAA (SEQ ID NO: 30) | <u>30214952-30215055</u> | 104 | 300 nM |

*product size;
†Selected concentration;
§hypermethylated control region on chromosome 13;;
¶hypomethylated control region on chromosome 22.

The primer design was optimized to give a product of 80-150 bp in length as recommended for optimal SYBR Green fluorescence melting curve analysis. Additionally, the Tm of all the primers was chosen to be close to 60° C.

The nucleotide sequences of the twelve DMRs (EP1-EP12) amplified by the primers set forth in Table 7 are shown below in Table 8, along with the nucleotide sequences of the two control regions (HYP1$_{13}$ and U1$_{22}$).

TABLE 8

The nucleotide sequences of the regions tested on chromosome 21 and control regions on chromosomes 13 and 22.

| Region | Position (b) | Nucleotide Sequence (build 36) |
|---|---|---|
| EP1 | 39279856-39280004 | GCTGGACCAGAAAGTGTTGAGTACCTGCTCATGCGTGCAAGAG GAGGAGGGAGGAGCACATCACTGAACTTCACATGAAATTGGAT ACCCGGGATTAGAGACAGTAGAGGGTTTTGGTGAAATCAGATA CACATTGCAAAGCAGCACAC (SEQ ID NO: 33) |
| EP2 | 44161178-44161323 | GGTCGAGTTTTTGGTGGTGTTGAGCGGATAGCCGGGGAAGTTG GAGTCTTGTTTGTGGCCGCCTCGTGCTCGTGTCTGTATCTAAGA TCCTCAGGCTGCTCCTTTTTGGGTAAGGTCTGTTGCTTCTCTAG GAACAGTGACGGTGG (SEQ ID NO: 34) |
| EP3 | 44161239-44161371 | CCTCGTGCTCGTGTCTGTATCTAAGATCCTCAGGCTGCTCCTTT TTGGGTAAGGTCTGTTGCTTCTCTAGGAACAGTGACGGTGGCA GAGCCCGTGGCCCCTCTCCTGTCCCAGAGCCAAGCTGTTTC CTC (SEQ ID NO: 35) |
| EP4 | 33320735-33320829 | CTGTTGCATGAGAGCAGAGGGGAGATAGAGAGAGCTTAATTATA GGTACCCGCGTGCAGCTAAAAGGAGGGCCAGAGATAGTAGCGA GGGGGACG (SEQ ID NO: 36) |
| EP5 | 42189557-42189683 | TGCAGGATATTTGGCAAGGTTTCTTACTGTTCCAAGTTTTTTTCC GAAAACCTCCCTTGAAACTTTTGTGCTTACTTGTGGTAACATACC CATAATATACCCTCTTAACCATTTCTACCGGCACAG (SEQ ID NO: 37) |
| EP6 | 42355712-42355815 | TGAATCAGTTCACCGACAGCCTTGGGGACATTCACCTTGGGCTC CACAACCTGTCAGAAATGCCCCCAAGCCCAAAGGCGTCGAGAG AATGGCCAGGTTGTTTC (SEQ ID NO: 38) |
| EP7 | 42357215-42357341 | CCGTTATATGGATGCCTTGGGGCTTGGGGGGTTTCTGGCAGTC TGTCGAGCCCGAGGTGAATGTCCCCAAGGCTGCTGGTGAATCA GATCCCTGGCGTTCTCCGTTGGCAGTTCAGCCCAACAGTTT (SEQ ID NO: 39) |
| EP8 | 22403649-22403792 | CCAGGCAAGATGGCTTATGTCTTTAATCTCAGCTGTTTGGGAAG CCAAGTGGAAAGATTGCTTGAGGCCAGGAGTTCAAGACCAACC TGGATAATGTAAGAAGACCTCGTCTCTATAAAAAATTAAAAATTG GCTGAGCATGGT (SEQ ID NO: 40) |
| EP9 | 29136735-29136844 | GACCCAGACGATACCTGGAAATTATTTGCTCATGTGGCAGTCAC TGTTGATTGCCTACCCAAAGCCATTACTCCTTCTCCCCACCTAA CAGAAGCCGAGTTTTGTTCAGC (SEQ ID NO: 41) |
| EP10 | 32268843-32268943 | CCACATCCTGGCCATCTACTTCCTCTTAAACAAGAAACTGGAGC GCTATTTGTCAGGGGTAAGTGCGACCCTAGAGGCGATCGTCTC TGCTGTCTGTGGAA (SEQ ID NO: 42) |
| EP11 | 44079235-44079322 | TGAGCTCACAGGTCTGGAAATGGTCTGAATAGAAAGGATTGGTC TCCGGAGGAAAGCATACTCTTCCTATTACCAGAACCCTGTGGGG (SEQ ID NO: 43) |
| EP12 | 37841284-37841411 | ATTCTCCACAGGGCAATGAGGCAAGAAATTTACAGCTTAGCCTGA TTAATGGGCCAGGCAGTTAAGAGTTCTTTGCCAAGCTATGAGCAT AATTTATAGTCATCACGGCAGGAGGAAAGGCCACATAA (SEQ ID NO: 44) |
| HYP1$_{13}$§ | 19991387-19991465 | CAGGAAAGTGAAGGGAGCTGCCATCTGCATCAAACGCTGCTGAT GAACACTTGAACTGAGGATTGACCATTGGGTTTTG (SEQ ID NO: 45) |

TABLE 8-continued

The nucleotide sequences of the regions tested on chromosome 21 and control regions on chromosomes 13 and 22.

| Region | Position (b) | Nucleotide Sequence (build 36) |
|---|---|---|
| U1$_{22}$¶ | 30214952-30215055 | AAGGTGCCCAATTCAAGGTATATAACCTTTAAGCAGCTTTAACAC AAGAGAAACCAAGATTAGTAGCTGCCACCCATGGGGATCTTTCA AGACTGGTGGGGAAG (SEQ ID NO: 46) |

§hypermethylated control region on chromosome 13;;
¶hypomethylated control region on chromosome 22.

The uniqueness of both primer sequences and PCR product sequences was confirmed by mapping these onto the human reference sequence using Blat. Primers were purchased from Sigma Genosys (Gillingham, UK). Each Real Time qPCR reaction was carried out in a final volume of 25 µl with 20 ng of either input or IP DNA. We used the SYBR Green PCR master mix (Eurogentec; Seraing, Belgium) and an ABI Prism 7900HT Sequence Detection System (Applied Biosystems). Initially the optimal concentration of each primer was selected after testing a series of dilutions (150-900 nM) using normal genomic DNA (Table 7). For each selected primer concentration, standard curves were calculated on 1:2 serial dilutions (200 ng down to 3.125 ng) and finally, the sample reactions were performed in triplicate. The amplification program consisted of 2 minutes at 50° C. and 10 minutes at 95° C., followed by 40 cycles of denaturation for 15 seconds at 95° C. and annealing/extension for 1 minute at 60° C. After amplification, melting curve analysis was performed by heating the reaction mixture from 60 to 95° C. at a rate of 0.2° C./s. The Real Time qPCR as described above provided the $C_T$ values for all Input and IP fragments (FIG. 6).

The $C_T$ values obtained underwent a series of normalization steps. Initially, the average $C_T$ value of the triplicate Real Time qPCR reactions was calculated for each Input and IP sample. Then, the efficiency of the PCR reactions performed during the MeDiP and LM-PCR applications was normalized using the formula:

$$\Delta C_T^{PB-Normal} = C_T^{PB-Normal-Input} - C_T^{PB-Normal-IP}$$

$$\Delta C_T^{PB-T21} = C_T^{PB-T21-Input} - C_T^{PB-T21-IP}.$$

wherein PB=Peripheral Blood and T21=Trisomy 21.

The above normalization is carried out for every sample and every one of the selected DMRs and controls separately.

Then, the Real Time qPCR primer's efficiency is used for further normalization using the formula:

$$\text{Norm } \Delta C_T \text{ value}^{PB-Normal} = E^{\Delta C_T^{PB-Normal}}$$

$$\text{Norm } \Delta C_T \text{ value}^{PB-T21} = E^{\Delta C_T^{PB-T21}}$$

where $E=10^{[-1/slope]}$=efficiency of the primer
Norm=normalized

The normalized values obtained from the control primers correspond to the methylation enrichment of every control region in each of the "test samples".

Following the normalization of PCR reactions, and normalization based on the Real Time qPCR primer's efficiency the median value of the Norm$\Delta C_T^{PB-Normal}$ was calculated for every selected DMR separately using the formula:

$$\text{Median Norm } \Delta C_T^{PB-Normal} = \text{Median}(\text{Norm } \Delta C_T^{PB-Normal-1}, \text{Norm } \Delta C_T^{PB-Normal-2}, \ldots \text{Norm } \Delta C_T^{PB-Normal-n})$$

The calculation of the Median Norm $\Delta C_T^{PB-Normal}$ is required to determine the ratio value of every sample in every DMR tested. This ratio value is determined by the formula:

$$\text{Ratio Value}^{Sample; DMR} = \text{Norm } \Delta C_T^{PB-Sample(Normal\ or\ T21)}/\text{Median}(\text{Norm } \Delta C_T^{PB-Normal})$$

The ratio values obtained from the normal cases were compared to the ones obtained from trisomy 21 samples for each of the DMR tested in order to evaluate the degree of discrimination of the normal cases from abnormal cases. However, statistical analysis of the above data was essential to determine with accuracy the statistical significance of discriminating normal from abnormal cases.

Statistical Analysis

The statistical significance of each of the 12 DMRs in discriminating normal from trisomy 21 cases was evaluated using the Mann-Whitney U Test. This test is a non-parametric test for assessing whether two independent sets of observations (in our case a set with normal samples and a set with trisomy 21 samples) come from the same distribution. The p value was then reported for each of the 12 DMRs. A p value of ≤0.05 was considered as significant.

In addition to the data evaluation of the results described above, the ratio values of normal cases and trisomy 21 cases for all DMRs tested were used to re-evaluate the statistical significance of discriminating normal from trisomy 21 cases.

Initially, the significance of each of the 12 regions in discriminating between normal and trisomy 21 cases was estimated. Firstly, the median values of the ratio values from all trisomy 21 cases and all the normal cases were calculated for each DMR separately. The formula used is the following:

$$\text{Median ratio values}^{PB-Normal} = \text{Median}(\text{ratio value}^{PB-Normal-1}, \text{ratio value}^{PB-Normal-2}, \ldots \text{ratio value}^{PB-Normal-n})$$

$$\text{Median ratio values}^{PB-T21} = \text{Median}(\text{ratio value}^{PB-T21-1}, \text{ratio value}^{PB-T21-2}, \ldots \text{ratio value}^{PB-T21-n})$$

Then the median ratio values of the trisomy 21 cases was divided by the median of the ratio values from the normal cases as indicated in the following formula:

$$\text{Median Ratio Value}^{DMR} = \text{Median ratio values}^{PB-T21}/\text{Median ratio values}^{PB-Normal}$$

The Median Ratio Values obtained from the DMRs were ranked in a descending order, showing the degree of separation between Normal and Trisomy 21 cases. We then performed a (nonparametric) median test. This test is a chi-square test that determines if two groups have the same median. The p value was then reported for each of the 12 DMRs. A p value of ≤0.05 was considered as significant. Furthermore, the Fisher's multiple test was applied. This test combined p values of various DMRs and gave an overall evaluation of the statistical significance of discriminating the normal from the trisomy 21 cases.

The final aim of our analysis was to be able to correctly interpret the results of a new case and accurately classify it as a normal or trisomy 21 case. In order to achieve this we have applied the so called "Discriminant Analysis (DA)" which was performed using the computational program SPSS v16.0. DA is a technique used to build a predictive model of group membership based on observed characteristics of each case. In other words in DA one wishes to predict group membership from a set of (usually continuous) predictor variables.

DA generates functions from a sample of cases for which group membership is known; the functions can then be applied to new cases with measurements for the predictor variables but unknown group membership. A "linear discriminant equation", is constructed such that the two groups differ as much as possible on D. The "linear discriminant equation" is the following:

$$D_i = a + b_1 X_1 + b_2 X_2 + \ldots + b_p X_p, \quad (1)$$

a=a constant, b=an unstandartized coefficient, $X_p$=ratio value$^{Sample; DMR}$.

In more detail, the "a" and "b" are values that have been calculated using the set of known samples and are used to construct the equation. Each "b" value is specific for one DMR and therefore in every new case classification the "X" Value of a specific DMR is multiplied by the "b" value of the same DMR previously calculated. Due to equal representation of normal and trisomy 21 cases in our study (20 normal and 20 trisomy 21 cases), the equation was constructed so that when the D gives a positive value (D>0), then the new case is considered as abnormal (trisomy 21 case) whereas when a negative value (D<0) is given then the new case is considered as normal.

An additional way for the classification of the cases as normal or trisomy 21 is the application of the so called "Fisher's classification function coefficients". For each case a D function is computed for each group and the sample is classified into the group for which the value of the corresponding D function is the highest. In our study two groups were created (one for normal cases and one for trisomy 21 cases) and therefore two functions like (1) were constructed. $D_1$ with the coefficients for Group 1 (normal cases) and $D_2$ with the coefficients for Group 2 (trisomy 21 cases). For the classification of a new case $(X_1, \ldots, X_p)$ the two functions are evaluated. If $D_1 > D_2$ the subject is classified into Group 1 (normal cases), otherwise into Group 2 (trisomy 21 cases).

For the purpose of our study, among the different types of DA we have been using the stepwise discriminating analysis in which statistical criteria determine the order of entry. Here we concentrate on stepwise DA employing the most economical selection technique, namely the Wilks lambda criterion. As with stepwise multiple regression, one may set the criteria for entry and removal (F criteria or p criteria). The ability of discriminant analysis to extract discriminant functions that are capable of producing accurate classifications is enhanced when the assumptions of normality, linearity, homogeneity of variance (homoscedasticity), independence of predictors, absence of multicollinearity, and influence of outliers are satisfied.

Although in our study we have used specific statistical tests to evaluate our data as described above, alternative statistical approaches could be followed to generate the same conclusions.

In our study, using the 12 DMRs having the nucleotide sequences set forth in Table 8 (EP1-EP12), it has been determined that a subset of only eight of those DMRs, EP4 (SEQ ID NO: 36), EP5 (SEQ ID NO: 37), EP6 (SEQ ID NO: 38), EP7 (SEQ ID NO: 39), EP8 (SEQ ID NO: 40), EP10 (SEQ ID NO: 42), EP11 (SEQ ID NO: 43) and EP12 (SEQ ID NO: 44), are sufficient to accurately identify trisomy 21 in maternal blood samples examined during pregnancy of woman bearing a trisomy 21 fetus.

Example 4

Additional Description and Validation of a Noninvasive Diagnostic Test for Trisomy 21

In this example, the noninvasive diagnostic test for trisomy 21 set forth in Example 3 is described in further detail. Moreover, the application of this fetal specific methylation ratio approach is shown to provide with 100% accuracy the correct diagnosis of 46 normal and 34 trisomy 21 pregnancies, thereby validating this diagnostic test.

Samples Used in this Example

For the purpose of the diagnostic strategy followed hereby, we have initially used 40 maternal peripheral blood samples with known karyotype (20 from normal pregnancies and 20 from trisomy 21 pregnancies). These 40 maternal peripheral blood samples were obtained at a gestational age of between 11.1-14.4 weeks. Furthermore, 40 additional samples were used in a blind fashion so that their identity and karyotype results were hidden from the investigator who carried out the test.

The 80 samples used were obtained from first trimester pregnancies at the "Cyprus Institute of Neurology and Genetics" through collaboration with gynecology centers in Cyprus and "Mitera" Hospital in Athens, Greece. The samples were collected in EDTA tubes and were stored within 6 hours of collection in −80° C. until further use. Consent forms approved by the Cyprus National Bioethics Committee were collected from all the participants.

The 40 samples were tested in groups of six (three normal and three trisomy 21 cases). The median value of three normal samples participated in one experiment were compared only with the trisomy 21 samples of the specific experiment.

Selection of DMRs for the Non-Invasive Prenatal Detection of Trisomy 21

An in depth investigation of our previously identified DMRs, described in Example 1, has led to the selection of 12 DMRs located on chromosome 21 for further investigation. The 12 DMRs were selected based on three criteria. Firstly, they should demonstrate a hypermethylated status in placenta and hypomethylated status in peripheral blood in order to achieve fetal specific DNA methylation enrichment and therefore increase the amount of ffDNA in maternal circulation. Secondly, they should have common methylation status between first and third trimester placentas in order to ensure the tissue specificity of the methylation status. Finally, the level of differential methylation observed for these DMRs must be above the value of "1" in a logarithmic scale in at least one of the oligonucleotide probes included in the region. Along with the 12 DMRs, two additional regions located on chromosomes 13 ($HYP1_{13}$) and 22 ($U1_{22}$) were used as hypermethylated and hypomethylated controls respectively, as described in Example 3.

Development and Validation of the Fetal Specific DNA Methylation Ratio Approach

Application of MeDiP and Real-time QPCR

DNA was extracted from 1 ml of each sample using the QIAamp DNA blood Midi Kit (Qiagen; West Sussex, UK). The isolated DNAs from 80 samples were processed for immunoprecipitation of methylated sites as described in Examples 1-3. Briefly, 2.5 µg of DNA were sheared by sonication into fragments of approximately 300 bp-1000 bp in size. The fragmented DNA was blunt-ended and annealed linkers were added to both ends generated. A total of 50 ng of ligated DNA from each sample was removed and retained for use as Input genomic control DNA. The remaining ligated DNA samples (800 ng-1.2 µg) were subjected to MeDiP as described in Examples 1-3. Finally, Ligation-Mediated PCR (LM-PCR) reactions were performed using 10 ng of each Input and IP DNA fraction to increase the amount of DNA.

Real-time QPCR was then applied to all Input and IP fragments for the selected DMRs on chromosome 21 and the two control regions. The procedure followed for primers' design, optimization and the cycle conditions used were as described in Examples 1-3. The primers used for the regions tested on chromosome 21 and the control regions on chromosomes 13 and 22 are set forth in Table 7 of Example 3.

Statistical Analysis Methodology

The 40 samples with known karyotype were used to evaluate the degree of discrimination of the 12 selected DMRs. To achieve this, the fetal specific methylation ratio values of the 20 normal cases were compared to the ratio values of the 20 trisomy 21 cases for each of the 12 DMRs. For normalization of the raw data, the Real Time qPCR as described above provided the $C_T$ values for all Input and IP fragments. The $C_T$ values obtained underwent a series of normalization steps. Initially, the average $C_T$ value of the triplicate Real Time qPCR reactions was calculated for each Input and IP sample. Then, the efficiency of the PCR reactions performed during the MeDiP and LM-PCR applications was normalized using the formula:

$$\Delta C_T^{PB\ Normal} = C_T^{PB\ Normal\ Input} - C_T^{PB\ Normal\ IP}$$

$$\Delta C_T^{PB\ T21} = C_T^{PB\ T21\ Input} - C_T^{PB\ T21\ IP}.$$

Where PB=Peripheral Blood
T21=Trisomy 21
IP=Immunoprecipitated

The above normalization was carried out for every sample and every one of the selected DMRs and controls separately.

Then, the Real Time qPCR primer's efficiency was used for further normalization using the formula:

$$\text{Norm}\ \Delta C_T\ \text{value}^{PB\ Normal} = E^{\Delta C_T^{PB\ Normal}}$$

$$\text{Norm}\ \Delta C_T\ \text{value}^{PB\ T21} = E^{\Delta C_T^{PB\ T21}}$$

where $E = 10^{[-1/slope]}$ = efficiency of the primer
Norm=Normalized

The normalized values obtained from the control primers correspond to the methylation enrichment of every control region in each of the tested samples.

Following the normalization of PCR reactions and normalization based on the Real Time qPCR primer's efficiency, the median value of the Norm$\Delta C_T^{PB\ Normal}$ was calculated for every selected DMRs separately using the formula:

$$\text{Median Norm}\ \Delta C_T^{PB\ Normal} = \text{Median}(\text{Norm}\ \Delta C_T^{PB\ Normal-1}, \text{Norm}\ \Delta C_T^{PB\ Normal-2}, \ldots \text{Norm}\ \Delta C_T^{PB\ Normal-n})$$

The calculation of the Median Norm $\Delta C_T^{PB\ Normal}$ was required to determine the fetal specific methylation ratio value of every sample in every DMR tested. This ratio value was determined by the formula:

$$\text{Ratio Value}^{Sample;\ DMR} = \text{Norm}\ \Delta C_T^{PB\ Sample(Normal\ or\ T21)} / \text{Median}(\text{Norm}\ \Delta C_T^{PB\ Normal})$$

In theory, the ratio value of normal cases should be 1 and 1.5 for trisomy 21 cases. However, the observed ratios are usually of a smaller value for normal cases and of a higher value for trisomy 21 cases as a result of inter-individual variability of the methylation levels (as described in Example 1) as well as due to the presence of maternal DNA background.

Further statistical analysis was essential to determine with accuracy the statistical significance of each DMR. The statistical evaluation was performed using the Mann-Whitney U test. This test is a non-parametric test for assessing whether two independent sets of observations come from the same distribution.

The final aim of our analysis was to correctly interpret the results of a case and accurately classify it as normal or trisomy 21. To achieve this we have applied the so called "Discriminant Analysis (DA)". DA generates functions from a set of cases for which group membership is known; the functions can then be applied to new cases with measurements for the predictor variables but unknown group membership. A "linear discriminant equation", is constructed such that the two groups differ as much as possible on the DA function. For the purpose of our study, among the different types of DA we have been using the stepwise discriminating analysis in which statistical criteria determine the order of entry. Here we concentrate on stepwise DA employing the most economical selection technique, namely the Wilks lambda criterion. In order for a DMR to enter the final model, a number of criteria need to be fulfilled (F criteria). The criteria are set by calculating the maximum significance of F for a DMR in order to enable the inclusion of the DMR to the final model and the minimum significance of F for a DMR to be removed from the final model.

Once the prediction equation was created, we aimed to further validate our results by performing a blind study. We have used 40 blind samples and tested the methylation enrichment of the 8 selected DMRs. The ratio values obtained from each sample were applied to the prediction equation and determined their status (normal or trisomy 21).

Evaluating the MeDiP Efficiency

In order to evaluate the efficiency of the MeDiP methodology, we tested a known hypermethylated ($HYP1_{13}$) and a hypomethylated ($U1_{22}$) control region using the 80 maternal peripheral blood samples described above. Samples P1-P40 are the samples with known karyotype used to create the Prediction Equation, whereas samples P41-P80 are the samples participated in the blind study. Samples P1-20 and P41-P66 are samples obtained from women bearing a normal fetus whereas samples P21-P40 and P67-P80 are samples obtained from women baring a fetus with trisomy 21.

For samples P1-20 and P41-66 ("normal" samples), methylation enrichment values for the $HYP1_{13}$ control region were in the range of 3.66-8.68 (median value=5.27) and for samples P21-P40 and P67-P80 ("trisomy 21" samples), methylation enrichment values for the $HYP1_{13}$ control region were in the range of 3.15-12.32 (median value=4.68). For samples P1-20 and P41-66 ("normal" samples), methylation enrichment values for the $U1_{22}$ control region were in the range of 0.00-0.15 (median value=0.03) and for samples P21-P40 and P67-P80 ("trisomy 21" samples), methylation enrichment values for the $U1_{22}$ control region were in the range of 0.00-0.51 (median value=0.04). Thus, high methylation enrichment was observed when testing the $HYP1_{13}$ control region indicating a hypermethylated status with values of 3.15 fold change or above in both normal and trisomy 21 cases. On the other hand, testing the $U1_{22}$ control region, a hypomethylated status was shown as expected in both normal and trisomy 21 cases with values of 0.51 fold change or below.

Efficiency of the Fetal Specific DNA Methylation Ratio Approach

As described herein, we developed an approach for determining the DNA methylation ratio in normal and trisomy 21 cases using 40 samples of known karyotype (20 normal and 20 with trisomy 21).

Figure 7:
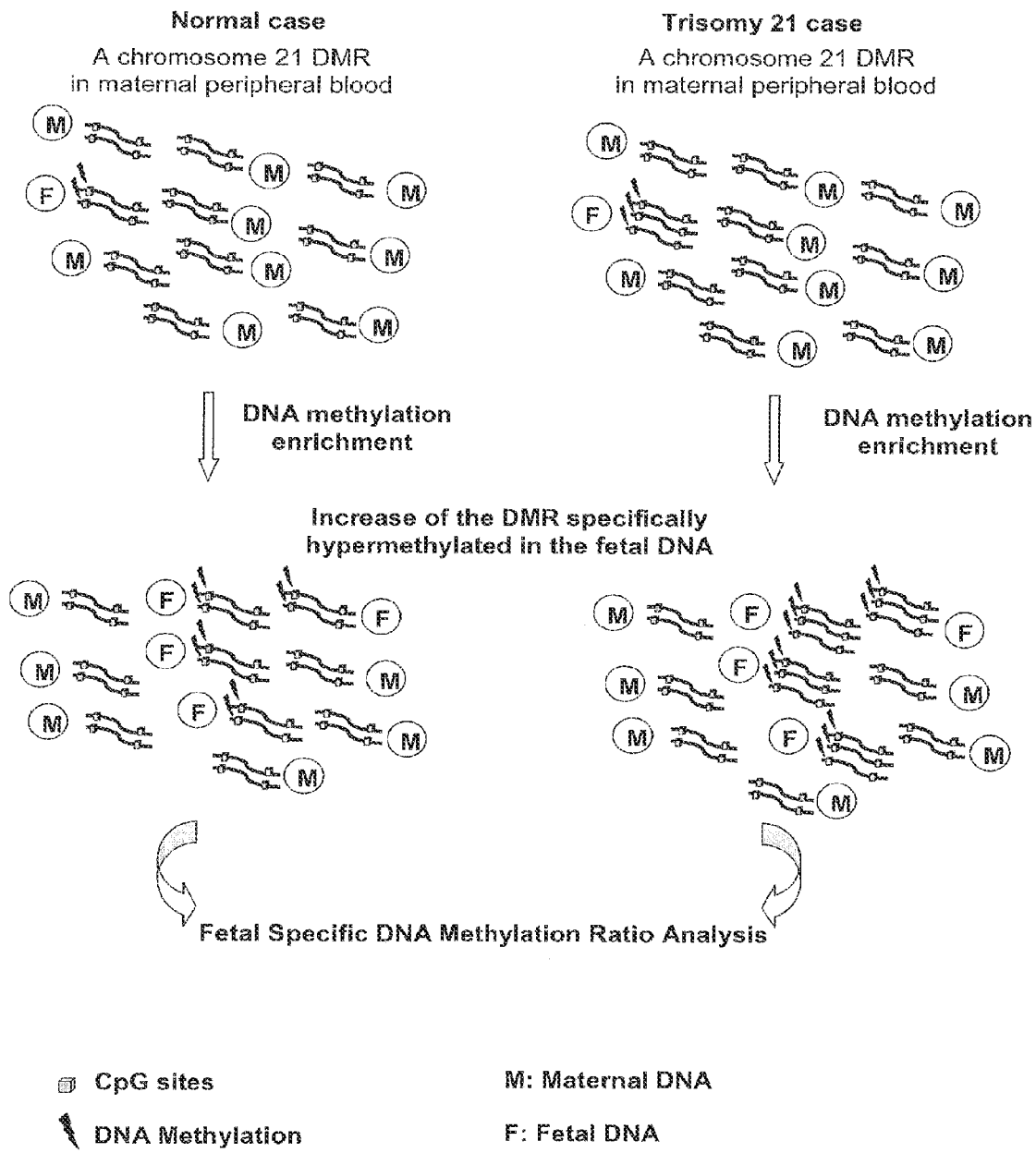
FIG. 7 is a schematic illustration of the DNA methylation ratio strategy for non-invasive detection of trisomy 21 through maternal peripheral blood analysis, by the relative quantification of fetal specific DNA methylated regions located on chromosome 21.

The fetal specific methylation ratio approach used herein is illustrated schematically in FIG. 7, wherein the ability to discriminate normal from trisomy 21 cases is achieved by comparing the ratio values obtained from normal and trisomy 21 cases using fetal specific methylated regions located on chromosome 21. The fetus with trisomy 21 has an extra copy of the fetal specific methylated region compared to the normal fetus. After the completion of the DNA methylation enrichment, the amount of fetal DNA increases in maternal circulation. However the amount of fetal specific methylated regions will increase more in fetuses with trisomy 21 compared to normal cases due to the extra copy of the region. Thus the maternal peripheral blood ratio of normal control cases with a normal testing sample will deviate from the ratio value of normal control cases in comparison to trisomy 21 cases.

Figure 8:
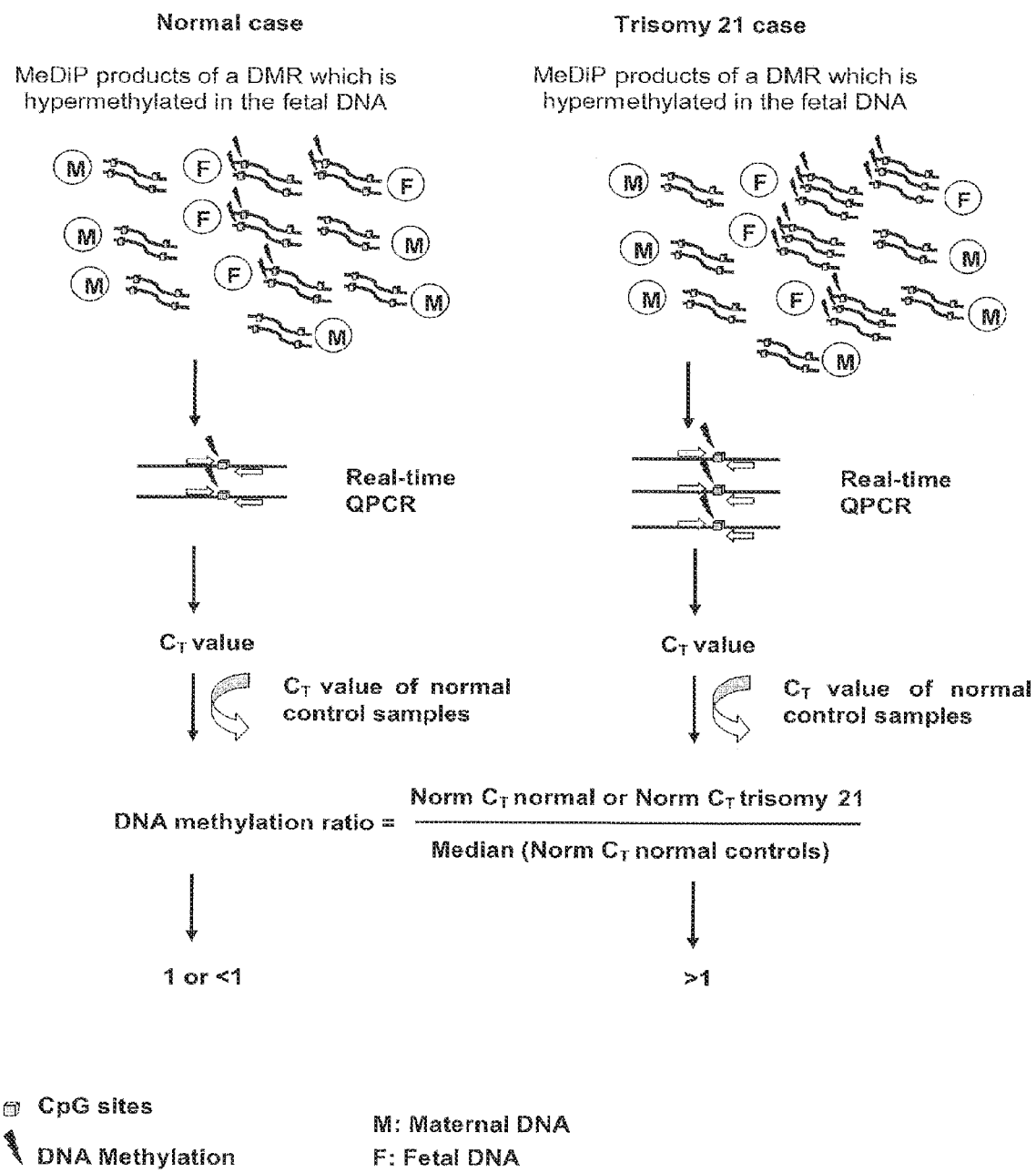
FIG. 8 is a schematic illustration of the analytical approach for DNA methylation ratio determination.

The analytical approach for determining the DNA methylation ratio in normal and trisomy 21 cases is illustrated schematically in FIG. 8. Once the methylation enrichment of a fetal specific methylated region is completed, real-time QPCR is applied to the fetal specific methylated region in order to proceed with relative quantification of the amount of fetal DNA in normal and trisomy 21 cases. To obtain the DNA methylation ratio, the Normalized (Norm) $C_T$ value obtained from a normal case is divided by the Median Norm value of normal control cases. The same procedure is followed for trisomy 21 cases. The expected ratio values for normal cases are equal or lower the value of 1 and for trisomy 21 cases above the value of 1.

The ratio values of 12 selected DMRs (EP1 to EP12) obtained from the 40 samples with known karyotype that participated in the creation of the discrimination/prediction equation are summarized below in Table 9:

TABLE 9

Summary of fetal specific methylation ratio values obtained for each of the 12 selected DMRs from each of the 40 samples with known karyotype

| DMR | Normal Ratio Range | Normal Median Ratio | Trisomy 21 Ratio Range | Trisomy 21 Median Ratio |
| --- | --- | --- | --- | --- |
| EP1 | 0.10-1.39 | 1.00 | 0.76-12.46 | 1.74 |
| EP2 | 0.10-1.40 | 1.00 | 0.07-9.15 | 1.37 |
| EP3 | 0.07-1.68 | 0.94 | 0.04-5.34 | 1.56 |
| EP4 | 0.31-1.71 | 1.00 | 0.24-4.30 | 1.79 |
| EP5 | 0.34-3.56 | 1.00 | 0.12-5.15 | 1.54 |
| EP6 | 0.00-2.22 | 1.00 | 0.00-10.70 | 1.56 |
| EP7 | 0.02-1.80 | 1.00 | 0.13-6.57 | 2.17 |
| EP8 | 0.06-5.15 | 0.85 | 0.00-78.63 | 0.84 |
| EP9 | 0.05-7.89 | 0.98 | 0.24-12.32 | 1.35 |
| EP10 | 0.00-2.47 | 1.00 | 0.42-6.71 | 2.03 |
| EP11 | 0.01-3.78 | 1.00 | 0.26-5.44 | 0.94 |
| EP12 | 0.00-2.43 | 0.89 | 0.18-6.82 | 1.53 |

As indicated in Table 9, the normal cases have median ratio values at or below the value of 1.00, whereas the trisomy 21 cases have median ratio values above the value of 1.00 with the exception of EP8 (which exhibited a wide range of methylation ratio values) and EP11.

Figure 9:
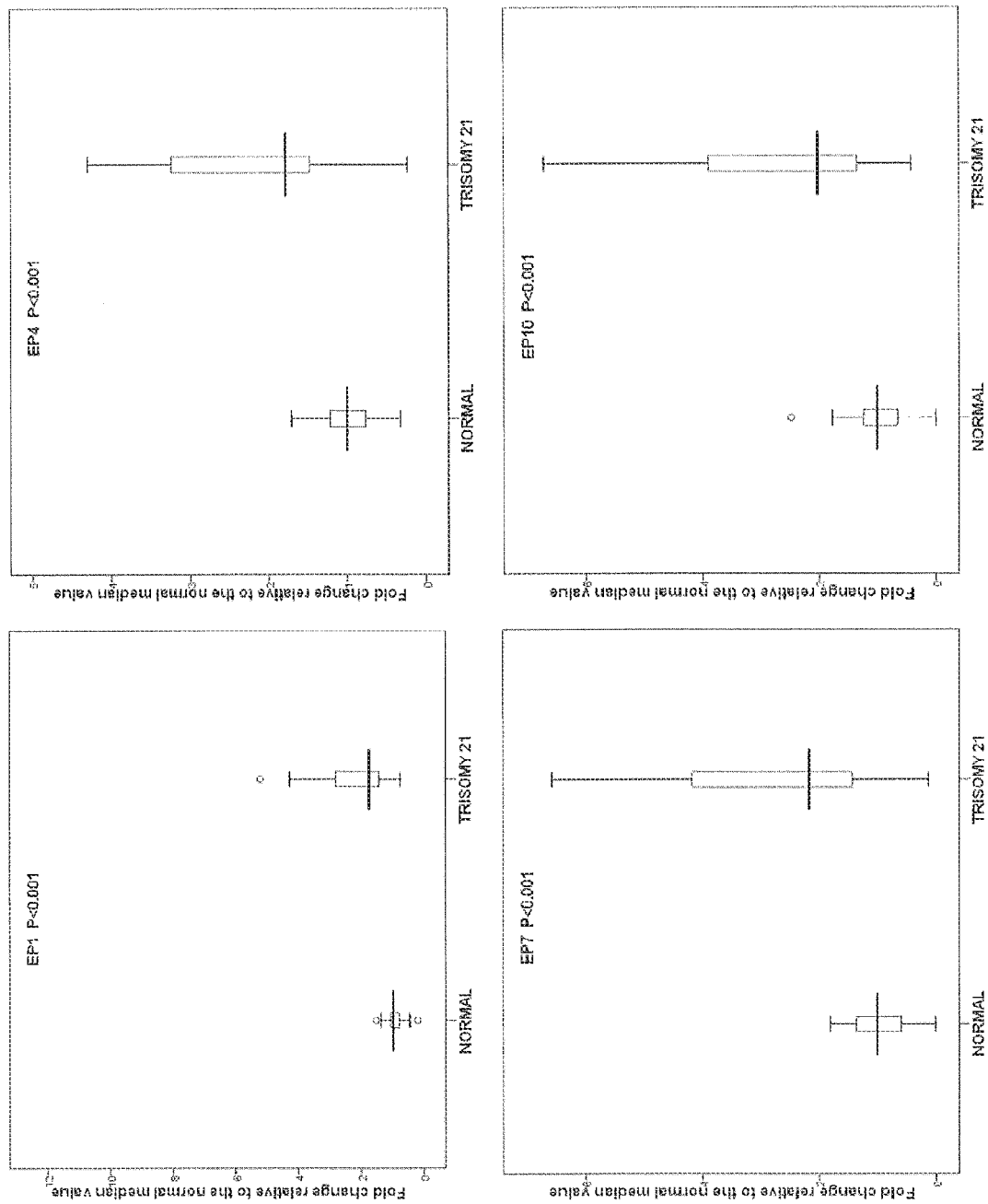
FIG. 9 is a BoxPlot representation of the results obtained from four DMRs, EP1, EP4, EP7 and EP10 in normal and trisomy 21 cases.

FIG. 9 shows a BoxPlot representation of the results obtained from four DMRs, EP1, EP4, EP7 and EP10 in normal and trisomy 21 cases. The boxplots depict the 5-number summaries, namely the minimum and maximum values, the upper (Q3) and lower ($Q_1$) quartiles, and the median. The median is identified by a line inside the box. The length of the box represents the interquartile range (IQR=$Q_3$-$Q_1$). Values more than three IQR's from either end of the box are labeled as extremes and denoted by an asterisk (*). Values more than 1.5 IQR's but less than 3 IQR's from either end of the box are labeled as outliers (o).

Statistical Analysis

Further to the evaluation of the fetal specific methylation ratio values it was essential in our study to proceed with a detailed univariate statistical analysis that would eventually reveal the statistical significance of each of the 12 DMRs in discriminating normal from trisomy 21 cases. To achieve this we have employed the Mann-Whitney U Test which estimates the significance of each of the DMRs in terms of p values. The p values given by the two-tailed test for each of the DMRs is shown below in Table 10.

TABLE 10

Statistical significance of each of the DMRs estimated by the calculation of p value.

| DMR* | P value |
| --- | --- |
| EP1 | <0.001 |
| EP2 | <0.05 |
| EP3 | >0.05 |
| EP4 | <0.001 |
| EP5 | <0.05 |
| EP6 | <0.05 |
| EP7 | <0.001 |
| EP8 | >0.05 |
| EP9 | >0.05 |
| EP10 | <0.001 |
| EP11 | >0.05 |
| EP12 | <0.05 |

DMRs that can discriminate efficiently normal cases from trisomy 21 cases such as EP1, EP4, EP7 and EP10 (p<0.001) show a clear separation of the range of values obtained from normal cases compared to the ones obtained from trisomy 21 cases. The difference of the median value of the normal cases (value=1.00) compared to the one obtained from the trisomy 21 cases (value=1.74, 1.79, 2.17 and 2.03 respectively) for the specific DMRs give an additional estimation of the statistical significance of the DMRs. On the other hand, in DMRs which are not statistically significant (p>0.05) such as EP8 and EP11, the median values obtained from both normal and trisomy 21 cases are close to the value of 1.00. For example in EP11, the median value is 1.00 in normal cases and 0.94 in trisomy 21 cases.

Although a single DMR may not lead to the correct diagnosis of a normal or a trisomy 21 pregnancy with confidence, we hypothesize that a combination of DMRs may be able to achieve it. To test the above hypothesis we have used statistical tools that would generate the ideal combination of a subset or the total number of DMRs, which can give the highest possible diagnostic sensitivity and specificity. We have concluded that the application of the so called "Discriminant Analysis (DA)" provides a statistical approach, which determines accurately a normal or a trisomy 21 pregnancy.

As discussed in the methods, the stepwise selection procedure was followed to select the most appropriate DMRs for the construction of the equation. The implementation of the DA on 40 cases showed that 8 DMRs out of 12, entered the final model of the prediction equation and none was removed so that the stepwise analysis was consisted of 8 steps in each of which a new predictor variable was chosen. The predictors were chosen in the following order according to the Wilks' Lambda statistic: EP4 (0.646), EP12 (0.456), EP6 (0.340), EP5 (0.251), EP7 (0.210), EP11 (0.159), EP10 (0.133), and EP8 (0.122). The DMRs EP1, EP2, EP3 and EP9 were excluded from the model.

Once the selection of the DMRs was completed, the discriminant function coefficients were calculated for each of the DMRs. These values would be used to construct the prediction equation which can be used to classify cases. Table 11 below shows the estimated coefficients for each of the 8 selected DMRs in the DA function.

TABLE 11

Discriminant Function Coefficients

| | Discriminant Function Coefficients |
|---|---|
| EP4 | .959 |
| EP5 | 1.188 |
| EP6 | .424 |
| EP7 | .621 |
| EP8 | .028 |
| EP10 | .387 |
| EP11 | −.683 |
| EP12 | .897 |
| (Constant) | −6.331 |

The interpretation of the coefficients in the prediction equation is simple. For instance, 1 unit of increase in EP5 increases the value of the prediction equation by 1.188 units (Table 11). The resulting prediction equation is shown below.

$$D = -6.331 + 0.959 X_{EP4} + 1.188 X_{EP5} + 0.424 X_{EP6} + 0.621 X_{EP7} + 0.028 X_{EP8} + 0.387 X_{EP10} - 0.683 X_{EP11} + 0.897 X_{EP12}$$

where $X_{EPi}$=ratio value$^{Sample;\ EPi}$, i=1, ... 12

Classification of Normal and Trisomy 21 cases

Cases that give a prediction value, or "D value", above the cutting point are classified as "trisomy 21" while those evaluating below the cutting point are evaluated as "normal". As the two groups of cases are of equal size, the cutting point is "0". Hence when D>0 the case is classified as "trisomy 21" otherwise is classified as "normal". All of the samples that were obtained from known normal pregnancies had negative D values, whereas all of the samples obtained from known trisomy 21 pregnancies had positive D values. The range of D values as well as the median values are shown below in Table 12 for the 40 known cases.

TABLE 12

Prediction values obtained from 40 samples with known karyotype when using the prediction equation.

| Status | Range of prediction values | Median prediction value |
|---|---|---|
| Normal | −4.29 to −1.05 | −2.63 |
| | | Values over −1.00:None |
| Trisomy 21 | +0.58 to +4.35 | +2.54 |
| | | Values below +1.00:0.58 & 0.96 |

Statistical evaluation of the diagnostic efficiency of the DA function using the original validatory method, showed a perfect classification for all normal and trisomy 21 cases. These results correspond to 100% specificity and 100% sensitivity of the methodology.

Since we are interested in a decision rule for the accurate classification of cases, we must check all assumptions in order to enhance the capability of the resulting discrimination function. In the DA function, the assumption of linearity applies only to the relationships between pairs of predictors. Since non-linearity only reduces the power to detect relationships, researchers usually attend to it only when it is clearly known that a predictor consistently demonstrated non-linear relationships with other predictors. In the present analysis, there is no evidence for such a possibility.

Multivariate normality of the predictors is assumed but it has easily been tested for all predictors involved. The appropriate confidence intervals for skewness and kyrtosis cover at least partly the range (−1, 1) which is the range for a normally distributed variable. In regard to the outliers the usual Mahalanobis distance between each case and the centroid of the group which the case belongs to has been evaluated. No significant deviations have been reported and no indication of any influential observations was found. The assumption of homogeneous covariance matrices for groups defined by the dependent variable only affects the classification phase of the discriminant analysis and is evaluated via the Box's M test. Note that the Discriminant function analysis is robust even when the homogeneity of variances assumption is not met, provided the data do not contain important outliers which is the case in the present analysis. Multicollinearity occurs when one predictor is so strongly correlated with one or more other predictors so that its relationship to the dependent variable is likely to be misinterpreted. As a result, its potential unique contribution to explaining the dependent variable is minimized by its strong relationship to other predictors. Multicollinearity is indicated when the tolerance value for an independent variable is less than 0.10. The tolerance values for all independent variables in the resulting DA function are larger than 0.10. Multicollinearity is not a problem in this discriminant analysis.

For assessing the appropriateness of the proposed DA function we have obtained the relevant eigenvalue which indicates the proportion of the variance in the dependent variable which is explained by the DA function. The larger the value the stronger the function. Furthermore, the canonical correlation has been evaluated, the squared of which represents the percent of variation in the dependent variable discriminated by the predictors in DA. Sometimes these values are used to decide how many functions are important. This issue does not arise here since there is only one discriminant function, though we may note that the function is extremely important since the eigenvalue is much larger than 1, it is 7.207 and its canonical correlation is very high, 93.7%. Finally note that the appropriate Wilks' Lambda test for the significance of the eigenvalue has been performed and found to be statistically significant (Wilks' Lambda=1.222, p-value=0.00).

Blind Study of Normal and Trisomy 21 Cases

The specificity and sensitivity of the methodology was re-evaluated by performing a blind study consisting of 40 samples. The blind study was performed by evaluating the methylation status of the 8 DMRs which constituted the prediction equation. The ratio values obtained from the 8 DMRs for the 40 samples in the blind study were applied to the prediction equation for each sample separately in order to reveal the D value which determines the status of the sample (normal or trisomy 21). A total of 26 cases have given a negative D value and 14 cases a positive D value. Therefore, according to the prediction equation 26 of these cases are normal and 14 are trisomy 21, as summarized below in Table 13:

TABLE 13

Prediction values obtained from the 40 samples participated in the blind study when using the prediction equation.

| SAMPLE | STATUS | Prediction value |
|---|---|---|
| P41 | NORMAL | −2.34 |
| P42 | NORMAL | −1.16 |
| P43 | NORMAL | −3.54 |
| P44 | NORMAL | −2.79 |
| P45 | NORMAL | −3.19 |
| P46 | NORMAL | −2.88 |
| P47 | NORMAL | −3.66 |
| P48 | NORMAL | −3.24 |
| P49 | NORMAL | −4.66 |
| P50 | NORMAL | −3.86 |
| P51 | NORMAL | −4.30 |
| P52 | NORMAL | −4.35 |
| P53 | NORMAL | −2.81 |
| P54 | NORMAL | −2.37 |
| P55 | NORMAL | −2.41 |
| P56 | NORMAL | −2.47 |
| P57 | NORMAL | −2.10 |
| P58 | NORMAL | −3.36 |
| P59 | NORMAL | −2.26 |
| P60 | NORMAL | −2.99 |
| P61 | NORMAL | −2.80 |
| P62 | NORMAL | −3.53 |
| P63 | NORMAL | −3.76 |
| P64 | NORMAL | −2.48 |
| P65 | NORMAL | −1.93 |
| P66 | NORMAL | −2.63 |
| P67 | TRISOMY 21 | 4.14 |
| P68 | TRISOMY 21 | 1.58 |
| P69 | TRISOMY 21 | 60.52 |
| P70 | TRISOMY 21 | 10.05 |
| P71 | TRISOMY 21 | 2.41 |
| P72 | TRISOMY 21 | 7.27 |
| P73 | TRISOMY 21 | 1.62 |
| P74 | TRISOMY 21 | 6.26 |
| P75 | TRISOMY 21 | 24.16 |
| P76 | TRISOMY 21 | 6.31 |
| P77 | TRISOMY 21 | 35.97 |
| P78 | TRISOMY 21 | 23.54 |
| P79 | TRISOMY 21 | 20.63 |
| P80 | TRISOMY 21 | 86.41 |

The above results were confirmed after cross referencing the samples's karyotype, indicating 100% specificity and 100% sensitivity of our NIPD approach as previously estimated.

Interestingly, our results have shown a higher diagnostic sensitivity and specificity compared to a previous study which used the RNA-SNP strategy (90% and 96.5% respectively) (Lo, Y. M. et al. (2007) Nat. Med. 13:218-223). The RNA-SNP study included only 10 trisomy 21 cases in the range of 12-20 weeks with one of the trisomy 21 cases being incorrectly classified. In our study a total number of 40 samples with known karyotype (20 normal and 20 with trisomy 21) as well as 40 blind samples (26 normal and 14 with trisomy 21), were correctly classified providing 100% sensitivity and specificity. All the samples were obtained specifically during the first trimester of gestational age (11.1-14.4). Moreover, the diagnostic sensitivity and specificity of our strategy are found to be more significant compared to currently applied first trimester screening protocols involving the use of nuchal translucency and biochemical markers (Wald, N. J. et al. (1999) New Eng. J. Med. 341:461-467; Weisz, B. and Rodeck, C. H. (2006) Hum. Reprod. Update 12:513-518).

An additional advantage of our methodology is observed when compared to newly developed methodologies such as the application of next generation sequencing technologies which are of high cost and not easily accessible to diagnostic laboratories. Our approach involves the application of the MeDiP and Real-time QPCR methodologies which are accessible in all basic diagnostic laboratories as they require no major and expensive infrastructure, are technically easier and of lower cost.

Moreover, our approach is an improvement in comparison to the currently applied methodologies such as the use of sodium bisulfite conversion of the DNA which can cause up to 96% DNA degradation (Grunau, C. et al. (2001) Nucl. Acids Res. 29:E65-E65) and can complicate even further the quantification of limited amounts of ffDNA. Additionally, our diagnostic approach is not affected by fetal gender or the presence of informative polymorphic sites in contrast to previous studies (Lo, Y. M. et al. (2007) Nat. Med. 13:218-223; Tsui, N. B. et al. (2009) Prenat. Diagn. 29:1031-1037; Tsui, N. B. et al. (2005) Clin. Chem. 51:2358-2362; Tsui, N. B. and Lo, Y. M. (2008) Methods Mol. Biol. 444:275-289; Tong, Y. K. et al. (2009) Clin. Chem. 56:90-98). This advantage is of high importance as the technology will be available population wide.

The approach described here has opened the way to NIPD of trisomy 21 to be potentially employed into the routine practice of all diagnostic laboratories and be applicable to all pregnancies. Such a non-invasive approach will avoid the risk of miscarriages of normal pregnancies due to current invasive procedures.

SUMMARY OF SEQUENCE LISTING

SEQ ID NO: 1:
GCTGGACCAGAAAGTGTTGAG

SEQ ID NO: 2
GTGTGCTGCTTTGCAATGTG

SEQ ID NO: 3:
GGTCGAGTTTTTGGTGGTGT

SEQ ID NO: 4:
CCACCGTCACTGTTCCTAGA

SEQ ID NO: 5:
CCTCGTGCTCGTGTCTGTAT

SEQ ID NO: 6:
GAGGAAACAGCTTGGCTCTG

SEQ ID NO: 7:
CTGTTGCATGAGAGCAGAGG

SEQ ID NO: 8:
CGTCCCCCTCGCTACTATCT

SEQ ID NO: 9:
TGCAGGATATTTGGCAAGGT

SEQ ID NO: 10:
CTGTGCCGGTAGAAATGGTT

SEQ ID NO: 11:
TGAATCAGTTCACCGACAGC

SEQ ID NO: 12:
GAAACAACCTGGCCATTCTC

SEQ ID NO: 13:
CCGTTATATGGATGCCTTGG

SEQ ID NO: 14:
AAACTGTTGGGCTGAACTGC

SEQ ID NO: 15:
CCAGGCAAGATGGCTTATGT

SEQ ID NO: 16:
ACCATGCTCAGCCAATTTTT

SEQ ID NO: 17:
GACCCAGACGATACCTGGAA

SEQ ID NO: 18:
GCTGAACAAAACTCGGCTTC

SEQ ID NO: 19:
CCACATCCTGGCCATCTACT

SEQ ID NO: 20:
TTCCACAGACAGCAGAGACG

SEQ ID NO: 21:
TGAGCTCACAGGTCTGGAAA

SEQ ID NO: 22:
CCCCACAGGGTTCTGGTAAT

SEQ ID NO: 23:
ATTCTCCACAGGGCAATGAG

SEQ ID NO: 24:
TTATGTGGCCTTTCCTCCTG

SEQ ID NO: 25:
CAGGAAAGTGAAGGGAGCTG

SEQ ID NO: 26:
CAAAACCCAATGGTCAATCC

SEQ ID NO: 27:
AATGATTGTGCAGGTGGTGA

SEQ ID NO: 28:
GAGCGCCTTGAGTAGAGGAA

SEQ ID NO: 29:
AAGGTGCCCAATTCAAGGTA

SEQ ID NO: 30:
CTTCCCCACCAGTCTTGAAA

SEQ ID NO: 31:
TGAGAGCGGATGACAGATTG

SEQ ID NO: 32:
GGTCCCTCCCTTTTCTGTCT

SEQ ID NO: 33:
GCTGGACCAGAAAGTGTTGAGTACCTGCTCATGCGTGCAAGAG

GAGGAGGGAGGAGCACATCACTGAACTTCACATGAAATTGGAT

ACCCGGGATTAGAGACAGTAGAGGGTTTTGGTGAAATCAGATA

CACATTGCAAAGCAGCACAC

SEQ ID NO: 34:
GGTCGAGTTTTGGTGGTGTTGAGCGGATAGCCGGGGAAGTTG

GAGTCTTGTTTGTGGCCGCCTCGTGCTCGTGTCTGTATCTAAGA

TCCTCAGGCTGCTCCTTTTTGGGTAAGGTCTGTTGCTTCTCTAG

GAACAGTGACGGTGG

SEQ ID NO: 35:
CCTCGTGCTCGTGTCTGTATCTAAGATCCTCAGGCTGCTCCTTT

TTGGGTAAGGTCTGTTGCTTCTCTAGGAACAGTGACGGTGGCA

GAGCCCGTGGCCCCTCTCTCCTGTCCCAGAGCCAAGCTGTTTC

CTC

SEQ ID NO: 36:
CTGTTGCATGAGAGCAGAGGGGAGATAGAGAGAGCTTAATTATA

GGTACCCGCGTGCAGCTAAAAGGAGGGCCAGAGATAGTAGCGA

GGGGGACG

SEQ ID NO: 37:
TGCAGGATATTTGGCAAGGTTTCTTACTGTTCCAAGTTTTTTTCC

GAAAACCTCCCTTGAAACTTTTGTGCTTACTTGTGGTAACATACC

CATAATATACCCTCTTAACCATTTCTACCGGCACAG

SEQ ID NO: 38:
TGAATCAGTTCACCGACAGCCTTGGGGACATTCACCTTGGGCTC

CACAACCTGTCAGAAATGCCCCCAAGCCCAAAGGCGTCGAGAG

AATGGCCAGGTTGTTTC

SEQ ID NO: 39:
CCGTTATATGGATGCCTTGGGGCTTGGGGGGTTTCTGGCAGTC

TGTCGAGCCCGAGGTGAATGTCCCCAAGGCTGCTGGTGAATCA

GATCCCTGGCGTTCTCCGTTGGCAGTTCAGCCCAACAGTTT

SEQ ID NO: 40:
CCAGGCAAGATGGCTTATGTCTTTAATCTCAGCTGTTTGGGAAG

CCAAGTGGAAAGATTGCTTGAGGCCAGGAGTTCAAGACCAACC

TGGATAATGTAAGAAGACCTCGTCTCTATAAAAAATTAAAAATTG

GCTGAGCATGGT

SEQ ID NO: 41:
GACCCAGACGATACCTGGAAATTATTTGCTCATGTGGCAGTCAC

TGTTGATTGCCTACCCAAAGCCATTACTCCTTCTCCCCACCTAA

CAGAAGCCGAGTTTTGTTCAGC

SEQ ID NO: 42:
CCACATCCTGGCCATCTACTTCCTCTTAAACAAGAAACTGGAGC

GCTATTTGTCAGGGGTAAGTGCGACCCTAGAGGCGATCGTCTC

TGCTGTCTGTGGAA

SEQ ID NO: 43:
TGAGCTCACAGGTCTGGAAATGGTCTGAATAGAAAGGATTGGTC

TCCGGAGGAAAGCATACTCTTCCTATTACCAGAACCCTGTGGGG

SEQ ID NO: 44:
ATTCTCCACAGGGCAATGAGGCAAGAAATTTACAGCTTAGCCTGA

TTAATGGGCCAGGCAGTTAAGAGTTCTTTGCCAAGCTATGAGCAT

AATTTATAGTCATCACGGCAGGAGGAAAGGCCACATAA

SEQ ID NO: 45:
CAGGAAAGTGAAGGGAGCTGCCATCTGCATCAAACGCTGCTGAT

GAACACTTGAACTGAGGATTGACCATTGGGTTTTG

SEQ ID NO: 46:
AAGGTGCCCAATTCAAGGTATATAACCTTTAAGCAGCTTTAACAC

AAGAGAAACCAAGATTAGTAGCTGCCACCCATGGGGATCTTTCA

AGACTGGTGGGGAAG

Appendix A: Chromosome 21

Page 1 of 39

| Chr | Start | End | | | Chr | Start | End |
|---|---|---|---|---|---|---|---|
| 21 | 9719879 | 9788237 | | | 21 | 9982354 | 9986088 |
| 21 | 9800293 | 9800303 | | | 21 | 9986698 | 9987013 |
| 21 | 9800492 | 9800557 | | | 21 | 9987108 | 9987578 |
| 21 | 9800898 | 9801307 | | | 21 | 9988925 | 9988934 |
| 21 | 9801424 | 9801551 | | | 21 | 9991015 | 9991498 |
| 21 | 9803743 | 9804112 | | | 21 | 9993413 | 9993608 |
| 21 | 9804471 | 9804787 | | | 21 | 9995206 | 9995274 |
| 21 | 9805107 | 9806143 | | | 21 | 9997702 | 9999606 |
| 21 | 9810134 | 9810137 | | | 21 | 9999933 | 10000909 |
| 21 | 9810928 | 9811012 | | | 21 | 10001897 | 10005675 |
| 21 | 9814541 | 9814557 | | | 21 | 10009266 | 10010320 |
| 21 | 9815417 | 9815647 | | | 21 | 10012021 | 10013281 |
| 21 | 9815903 | 9815982 | | | 21 | 10014215 | 10014483 |
| 21 | 9817087 | 9817201 | | | 21 | 10018063 | 10019018 |
| 21 | 9818874 | 9819121 | | | 21 | 10019207 | 10019371 |
| 21 | 9823128 | 9823748 | | | 21 | 10022985 | 10023537 |
| 21 | 9826942 | 9827957 | | | 21 | 10023775 | 10046057 |
| 21 | 9832778 | 9832943 | | | 21 | 10048126 | 10048271 |
| 21 | 9838977 | 9839142 | | | 21 | 10054493 | 10055570 |
| 21 | 9839652 | 9839761 | | | 21 | 10057203 | 10057602 |
| 21 | 9840822 | 9841015 | | | 21 | 10058671 | 10062521 |
| 21 | 9844566 | 9845022 | | | 21 | 10063217 | 10063389 |
| 21 | 9846669 | 9847272 | | | 21 | 10063798 | 10065346 |
| 21 | 9847303 | 9847426 | | | 21 | 10066359 | 10068104 |
| 21 | 9849283 | 9852801 | | | 21 | 10068277 | 10068592 |
| 21 | 9858830 | 9859265 | | | 21 | 10070397 | 10071814 |
| 21 | 9863924 | 9864795 | | | 21 | 10076754 | 10077173 |
| 21 | 9872835 | 9872864 | | | 21 | 10079555 | 10079682 |
| 21 | 9873050 | 9873593 | | | 21 | 10082054 | 10082633 |
| 21 | 9876920 | 9877899 | | | 21 | 10085048 | 10085978 |
| 21 | 9880395 | 9880489 | | | 21 | 10089321 | 10089658 |
| 21 | 9882709 | 9882820 | | | 21 | 10090215 | 10090777 |
| 21 | 9883095 | 9883180 | | | 21 | 10091531 | 10093380 |
| 21 | 9884062 | 9884146 | | | 21 | 10094944 | 10095582 |
| 21 | 9884521 | 9884586 | | | 21 | 10095617 | 10096001 |
| 21 | 9886032 | 9887558 | | | 21 | 10098820 | 10098826 |
| 21 | 9891832 | 9891907 | | | 21 | 10099792 | 10099863 |
| 21 | 9892963 | 9895463 | | | 21 | 10103573 | 10103836 |
| 21 | 9895712 | 9896110 | | | 21 | 10104238 | 10105530 |
| 21 | 9903321 | 9903588 | | | 21 | 10106397 | 10106818 |
| 21 | 9903609 | 9904690 | | | 21 | 10111103 | 10111646 |
| 21 | 9906591 | 9906878 | | | 21 | 10115548 | 10115683 |
| 21 | 9911893 | 9911931 | | | 21 | 10117698 | 10117951 |
| 21 | 9912693 | 9912704 | | | 21 | 10118698 | 10123058 |
| 21 | 9914528 | 9915256 | | | 21 | 10123799 | 10123960 |
| 21 | 9917679 | 9918409 | | | 21 | 10127342 | 10133562 |
| 21 | 9921310 | 9924471 | | | 21 | 10135183 | 10135348 |
| 21 | 9927144 | 9927549 | | | 21 | 10136404 | 10136887 |
| 21 | 9929405 | 9930565 | | | 21 | 10137186 | 10137982 |
| 21 | 9932141 | 9932275 | | | 21 | 10139418 | 10140772 |
| 21 | 9934921 | 9935381 | | | 21 | 10140797 | 10141017 |
| 21 | 9937653 | 9938242 | | | 21 | 10141557 | 10142301 |
| 21 | 9940750 | 9940761 | | | 21 | 10142839 | 10142844 |
| 21 | 9945228 | 9949391 | | | 21 | 10143698 | 10145027 |
| 21 | 9953232 | 9956144 | | | 21 | 10145288 | 10145487 |

*The chromosomal position was obtained from UCSC genome browser (http://genome.ucsc.edu/) build 36.

Appendix A: Chromosome 21

Page 2 of 39

| Chr | Start | End | | | Chr | Start | End |
|---|---|---|---|---|---|---|---|
| 21 | 9961609 | 9962926 | | | 21 | 10149070 | 10149185 |
| 21 | 9964665 | 9965899 | | | 21 | 10150435 | 10150585 |
| 21 | 9977213 | 9980568 | | | 21 | 10152366 | 10158157 |
| 21 | 9982223 | 9982283 | | | 21 | 10158734 | 10159211 |
| | | | | | 21 | 10161344 | 10162737 |
| | | | | | 21 | 10163353 | 10164012 |
| | | | | | 21 | 10165542 | 10170098 |
| | | | | | 21 | 10173462 | 10174308 |
| | | | | | 21 | 10177812 | 10178035 |
| | | | | | 21 | 10187305 | 10190984 |
| | | | | | 21 | 10202774 | 10202864 |
| | | | | | 21 | 10203469 | 10206602 |
| | | | | | 21 | 10208168 | 10208207 |
| 21 | 13261321 | 13267274 | | | 21 | 31641438 | 31642548 |
| 21 | 13635318 | 13649802 | | | 21 | 31643308 | 31644148 |
| 21 | 13654625 | 13670992 | | | 21 | 31652145 | 31653040 |
| 21 | 13774804 | 13803296 | | | 21 | 31668339 | 31669200 |
| 21 | 13841527 | 13869597 | | | 21 | 31676198 | 31677079 |
| 21 | 13898914 | 13905107 | | | 21 | 31691303 | 31691839 |
| 21 | 13936916 | 13992039 | | | 21 | 31707383 | 31708945 |
| 21 | 13998933 | 14000578 | | | 21 | 31738424 | 31740627 |
| 21 | 14056242 | 14061245 | | | 21 | 31743001 | 31743071 |
| 21 | 14085736 | 14088907 | | | 21 | 31780137 | 31781492 |
| 21 | 14120949 | 14121654 | | | 21 | 31802896 | 31804096 |
| 21 | 14134014 | 14145636 | | | 21 | 31824101 | 31825266 |
| 21 | 14200837 | 14203444 | | | 21 | 31832897 | 31833978 |
| 21 | 14274034 | 14312456 | | | 21 | 31836777 | 31839414 |
| 21 | 14330740 | 14332072 | | | 21 | 31847463 | 31848785 |
| 21 | 14333320 | 14336106 | | | 21 | 31860762 | 31861199 |
| 21 | 14349684 | 14380474 | | | 21 | 31869512 | 31871291 |
| 21 | 14433496 | 14434172 | | | 21 | 31890986 | 31892429 |
| 21 | 14446701 | 14452633 | | | 21 | 31907242 | 31907803 |
| 21 | 14457072 | 14459170 | | | 21 | 31923685 | 31923850 |
| 21 | 14459635 | 14460437 | | | 21 | 31935088 | 31935982 |
| 21 | 14475153 | 14476641 | | | 21 | 31951900 | 31954860 |
| 21 | 14489531 | 14499260 | | | 21 | 31960122 | 31961400 |
| 21 | 14567699 | 14568890 | | | 21 | 31970413 | 31971010 |
| 21 | 14584973 | 14588669 | | | 21 | 32024412 | 32028025 |
| 21 | 14590998 | 14591170 | | | 21 | 32042656 | 32045204 |
| 21 | 14602804 | 14607383 | | | 21 | 32073354 | 32073974 |
| 21 | 14618953 | 14619569 | | | 21 | 32078693 | 32080945 |
| 21 | 14634072 | 14636487 | | | 21 | 32086055 | 32086793 |
| 21 | 14648182 | 14649718 | | | 21 | 32093063 | 32099541 |
| 21 | 14656934 | 14658098 | | | 21 | 32154899 | 32155559 |
| 21 | 14687511 | 14688595 | | | 21 | 32166428 | 32170970 |
| 21 | 14703677 | 14706532 | | | 21 | 32179795 | 32182237 |
| 21 | 14710408 | 14711833 | | | 21 | 32205389 | 32208643 |
| 21 | 14747353 | 14754489 | | | 21 | 32212835 | 32214434 |
| 21 | 14758766 | 14762705 | | | 21 | 32225564 | 32228108 |
| 21 | 14765151 | 14768597 | | | 21 | 32231923 | 32234476 |
| 21 | 14778140 | 14779531 | | | 21 | 32237616 | 32243482 |
| 21 | 14780644 | 14782769 | | | 21 | 32267980 | 32269625 |
| 21 | 14803774 | 14804613 | | | 21 | 32279612 | 32281172 |
| 21 | 14808703 | 14810031 | | | 21 | 32290070 | 32290770 |
| 21 | 14843928 | 14844801 | | | 21 | 32292473 | 32293418 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| 21 | 14846042 | 14846577 | | | 21 | 32316106 | 32318094 |
| 21 | 14873730 | 14874605 | | | 21 | 32324058 | 32328998 |
| 21 | 14886131 | 14889905 | | | 21 | 32337086 | 32338976 |
| 21 | 14891560 | 14892465 | | | 21 | 32344264 | 32344760 |
| 21 | 14950874 | 14953422 | | | 21 | 32350189 | 32351314 |
| 21 | 14965176 | 14965911 | | | 21 | 32351904 | 32352434 |
| 21 | 14971921 | 14972992 | | | 21 | 32359510 | 32361993 |
| 21 | 14989217 | 14994834 | | | 21 | 32364744 | 32365298 |
| 21 | 15000460 | 15001484 | | | 21 | 32370247 | 32371477 |
| 21 | 15005414 | 15006955 | | | 21 | 32385620 | 32386115 |
| 21 | 15014829 | 15015907 | | | 21 | 32408866 | 32409486 |
| 21 | 15086840 | 15087687 | | | 21 | 32414448 | 32417536 |
| 21 | 15090655 | 15093462 | | | 21 | 32422393 | 32423192 |
| 21 | 15108091 | 15109181 | | | 21 | 32426065 | 32432839 |
| 21 | 15111325 | 15112839 | | | 21 | 32456236 | 32457106 |
| 21 | 15117130 | 15118789 | | | 21 | 32463037 | 32464112 |
| 21 | 15135228 | 15137063 | | | 21 | 32477922 | 32479819 |
| 21 | 15147725 | 15151047 | | | 21 | 32499721 | 32501716 |
| 21 | 15165274 | 15166148 | | | 21 | 32504810 | 32507279 |
| 21 | 15168825 | 15169528 | | | 21 | 32508839 | 32509551 |
| 21 | 15174003 | 15174829 | | | 21 | 32539321 | 32544752 |
| 21 | 15183454 | 15184434 | | | 21 | 32547157 | 32547917 |
| 21 | 15187492 | 15189596 | | | 21 | 32550561 | 32555722 |
| 21 | 15209667 | 15211053 | | | 21 | 32558815 | 32561299 |
| 21 | 15216818 | 15219574 | | | 21 | 32564414 | 32567007 |
| 21 | 15236858 | 15239830 | | | 21 | 32583304 | 32585090 |
| 21 | 15248470 | 15249677 | | | 21 | 32592915 | 32595011 |
| 21 | 15251930 | 15254328 | | | 21 | 32599951 | 32600791 |
| 21 | 15257545 | 15261665 | | | 21 | 32620534 | 32621164 |
| 21 | 15284118 | 15285604 | | | 21 | 32628773 | 32630293 |
| 21 | 15302699 | 15304633 | | | 21 | 32641041 | 32647168 |
| 21 | 15315705 | 15317049 | | | 21 | 32678743 | 32679269 |
| 21 | 15319472 | 15321588 | | | 21 | 32684199 | 32684507 |
| 21 | 15331790 | 15334715 | | | 21 | 32686844 | 32688190 |
| 21 | 15345604 | 15345913 | | | 21 | 32703799 | 32711722 |
| 21 | 15348456 | 15350908 | | | 21 | 32742320 | 32747482 |
| 21 | 15351325 | 15352055 | | | 21 | 32750474 | 32758466 |
| 21 | 15360256 | 15360537 | | | 21 | 32763089 | 32763704 |
| 21 | 15361194 | 15362739 | | | 21 | 32767445 | 32769991 |
| 21 | 15370098 | 15371264 | | | 21 | 32776482 | 32777998 |
| 21 | 15375125 | 15375743 | | | 21 | 32790840 | 32794940 |
| 21 | 15378715 | 15380203 | | | 21 | 32800834 | 32807129 |
| 21 | 15384947 | 15391566 | | | 21 | 32813378 | 32824835 |
| 21 | 15394000 | 15394892 | | | 21 | 32833457 | 32834044 |
| 21 | 15402847 | 15406019 | | | 21 | 32867031 | 32881734 |
| 21 | 15425424 | 15426340 | | | 21 | 32884302 | 32890271 |
| 21 | 15435026 | 15437101 | | | 21 | 32907066 | 32914608 |
| 21 | 15451094 | 15455562 | | | 21 | 33048249 | 33049925 |
| 21 | 15463430 | 15464140 | | | 21 | 33059221 | 33059542 |
| 21 | 15480193 | 15480478 | | | 21 | 33061542 | 33063391 |
| 21 | 15501981 | 15502661 | | | 21 | 33065144 | 33066464 |
| 21 | 15530281 | 15531152 | | | 21 | 33128920 | 33129615 |
| 21 | 15538797 | 15540718 | | | 21 | 33131411 | 33131696 |
| 21 | 15554318 | 15559727 | | | 21 | 33134335 | 33144784 |
| 21 | 15568102 | 15569596 | | | 21 | 33161860 | 33163580 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 15574617 | 15575046 | 21 | 33173582 | 33174835 |
| 21 | 15596641 | 15597375 | 21 | 33180341 | 33182186 |
| 21 | 15603720 | 15603923 | 21 | 33183267 | 33183737 |
| 21 | 15617064 | 15617790 | 21 | 33200185 | 33204831 |
| 21 | 15620255 | 15621665 | 21 | 33214709 | 33216389 |
| 21 | 15625851 | 15628274 | 21 | 33227140 | 33228852 |
| 21 | 15648811 | 15651490 | 21 | 33244308 | 33247192 |
| 21 | 15663934 | 15665859 | 21 | 33252714 | 33254109 |
| 21 | 15670561 | 15671496 | 21 | 33255190 | 33257768 |
| 21 | 15687852 | 15688539 | 21 | 33267615 | 33270321 |
| 21 | 15712918 | 15713917 | 21 | 33279900 | 33283414 |
| 21 | 15719644 | 15720157 | 21 | 33305757 | 33310602 |
| 21 | 15726816 | 15729882 | 21 | 33322596 | 33323129 |
| 21 | 15731916 | 15735546 | 21 | 33323808 | 33330608 |
| 21 | 15737208 | 15737655 | 21 | 33335302 | 33337618 |
| 21 | 15745921 | 15748713 | 21 | 33339342 | 33339408 |
| 21 | 15756658 | 15761144 | 21 | 33340669 | 33343693 |
| 21 | 15791586 | 15793337 | 21 | 33349535 | 33358959 |
| 21 | 15795468 | 15796862 | 21 | 33371833 | 33373283 |
| 21 | 15800762 | 15801063 | 21 | 33397636 | 33399861 |
| 21 | 15821868 | 15827468 | 21 | 33402694 | 33412482 |
| 21 | 15829069 | 15833267 | 21 | 33416182 | 33417904 |
| 21 | 15835832 | 15836897 | 21 | 33425513 | 33431465 |
| 21 | 15844315 | 15846827 | 21 | 33437929 | 33444201 |
| 21 | 15853701 | 15860173 | 21 | 33447701 | 33449751 |
| 21 | 15863757 | 15864302 | 21 | 33456731 | 33457427 |
| 21 | 15872335 | 15872660 | 21 | 33459028 | 33461657 |
| 21 | 15895244 | 15902137 | 21 | 33462772 | 33466557 |
| 21 | 15903653 | 15904232 | 21 | 33477047 | 33478657 |
| 21 | 15908921 | 15910130 | 21 | 33480176 | 33484688 |
| 21 | 15914538 | 15915880 | 21 | 33501015 | 33502457 |
| 21 | 15920289 | 15920493 | 21 | 33520661 | 33525123 |
| 21 | 15980028 | 15981867 | 21 | 33526505 | 33527508 |
| 21 | 15988104 | 15990286 | 21 | 33532050 | 33533548 |
| 21 | 15994402 | 15995154 | 21 | 33557996 | 33561156 |
| 21 | 15998433 | 16000801 | 21 | 33563475 | 33566139 |
| 21 | 16018279 | 16020207 | 21 | 33579475 | 33583944 |
| 21 | 16051139 | 16054372 | 21 | 33586015 | 33587031 |
| 21 | 16057320 | 16059643 | 21 | 33626228 | 33627096 |
| 21 | 16061238 | 16061993 | 21 | 33649872 | 33652167 |
| 21 | 16063442 | 16064963 | 21 | 33654802 | 33655783 |
| 21 | 16080404 | 16081533 | 21 | 33662985 | 33663922 |
| 21 | 16085744 | 16092703 | 21 | 33683691 | 33685053 |
| 21 | 16095259 | 16100067 | 21 | 33691571 | 33698316 |
| 21 | 16125512 | 16126222 | 21 | 33705106 | 33706296 |
| 21 | 16132518 | 16136167 | 21 | 33735761 | 33736536 |
| 21 | 16181366 | 16182944 | 21 | 33775750 | 33776452 |
| 21 | 16231400 | 16232203 | 21 | 33789943 | 33792759 |
| 21 | 16234247 | 16235375 | 21 | 33811146 | 33811783 |
| 21 | 16237605 | 16239727 | 21 | 33844818 | 33846988 |
| 21 | 16242539 | 16250937 | 21 | 33864430 | 33868179 |
| 21 | 16283374 | 16288517 | 21 | 33889966 | 33890915 |
| 21 | 16293547 | 16294672 | 21 | 33935818 | 33938284 |
| 21 | 16300771 | 16304880 | 21 | 33977403 | 33977947 |
| 21 | 16306051 | 16307352 | 21 | 33983310 | 33983387 |

*The chromosomal position was obtained from UCSC genome browser (http://genome.ucsc.edu/) build 36.

Appendix A: Chromosome 21
Page 5 of 39

| Chr | Start | End | Chr | Start | End |
|---|---|---|---|---|---|
| 21 | 16342881 | 16343212 | 21 | 34006462 | 34006802 |
| 21 | 16369397 | 16374696 | 21 | 34087813 | 34088683 |
| 21 | 16384057 | 16384136 | 21 | 34125469 | 34126714 |
| 21 | 16417394 | 16419623 | 21 | 34138428 | 34145516 |
| 21 | 16449502 | 16450623 | 21 | 34148562 | 34154904 |
| 21 | 16469512 | 16470850 | 21 | 34172896 | 34179529 |
| 21 | 16473729 | 16475483 | 21 | 34187231 | 34190082 |
| 21 | 16546830 | 16548678 | 21 | 34241308 | 34241913 |
| 21 | 16553102 | 16554268 | 21 | 34242668 | 34243498 |
| 21 | 16603946 | 16605738 | 21 | 34246035 | 34247278 |
| 21 | 16610516 | 16610818 | 21 | 34257114 | 34257734 |
| 21 | 16610901 | 16612432 | 21 | 34265812 | 34266346 |
| 21 | 16613751 | 16616345 | 21 | 34270470 | 34271738 |
| 21 | 16622801 | 16626550 | 21 | 34278034 | 34281636 |
| 21 | 16637091 | 16638306 | 21 | 34330427 | 34331405 |
| 21 | 16640375 | 16642290 | 21 | 34348734 | 34349694 |
| 21 | 16659943 | 16661136 | 21 | 34360580 | 34361669 |
| 21 | 16709477 | 16711317 | 21 | 34368474 | 34369640 |
| 21 | 16718319 | 16719351 | 21 | 34370052 | 34371091 |
| 21 | 16721628 | 16722740 | 21 | 34374046 | 34375203 |
| 21 | 16741842 | 16742662 | 21 | 34376285 | 34378178 |
| 21 | 16753553 | 16754080 | 21 | 34387012 | 34389142 |
| 21 | 16760138 | 16762057 | 21 | 34391608 | 34397909 |
| 21 | 16766451 | 16768455 | 21 | 34410183 | 34410736 |
| 21 | 16774644 | 16780245 | 21 | 34413749 | 34416120 |
| 21 | 16782485 | 16782843 | 21 | 34437845 | 34441627 |
| 21 | 16790228 | 16791688 | 21 | 34450561 | 34454241 |
| 21 | 16826397 | 16827329 | 21 | 34468137 | 34469323 |
| 21 | 16833521 | 16833544 | 21 | 34492738 | 34493631 |
| 21 | 16867701 | 16869313 | 21 | 34496410 | 34499990 |
| 21 | 16869674 | 16870227 | 21 | 34514874 | 34517077 |
| 21 | 16873263 | 16874377 | 21 | 34529444 | 34530119 |
| 21 | 16877321 | 16878481 | 21 | 34547065 | 34547659 |
| 21 | 16882280 | 16883139 | 21 | 34581779 | 34584429 |
| 21 | 16903746 | 16904272 | 21 | 34586213 | 34587755 |
| 21 | 16912783 | 16913095 | 21 | 34600067 | 34601197 |
| 21 | 16930178 | 16931515 | 21 | 34610654 | 34611061 |
| 21 | 16940180 | 16941122 | 21 | 34617975 | 34618390 |
| 21 | 17005903 | 17007770 | 21 | 34629816 | 34631811 |
| 21 | 17013524 | 17014605 | 21 | 34636244 | 34638147 |
| 21 | 17019327 | 17020905 | 21 | 34639000 | 34640931 |
| 21 | 17035882 | 17042245 | 21 | 34649130 | 34651262 |
| 21 | 17044857 | 17046413 | 21 | 34693784 | 34694769 |
| 21 | 17081462 | 17082946 | 21 | 34698677 | 34699651 |
| 21 | 17091850 | 17096200 | 21 | 34720197 | 34725276 |
| 21 | 17100166 | 17106367 | 21 | 34738092 | 34745741 |
| 21 | 17127834 | 17132850 | 21 | 34749512 | 34750616 |
| 21 | 17134605 | 17145364 | 21 | 34753713 | 34754436 |
| 21 | 17145878 | 17148266 | 21 | 34761398 | 34762898 |
| 21 | 17149809 | 17156452 | 21 | 34799646 | 34801509 |
| 21 | 17159618 | 17164263 | 21 | 34804362 | 34804847 |
| 21 | 17165452 | 17167801 | 21 | 34811906 | 34816333 |
| 21 | 17176149 | 17181672 | 21 | 34818785 | 34820370 |
| 21 | 17185499 | 17186010 | 21 | 34822088 | 34822919 |
| 21 | 17202169 | 17203853 | 21 | 34830190 | 34832858 |

*The chromosomal position was obtained from UCSC genome browser (http://genome.ucsc.edu/) build 36.

Appendix A: Chromosome 21

Page 6 of 39

| Chr | Start | End | Chr | Start | End |
|---|---|---|---|---|---|
| 21 | 17218543 | 17219674 | 21 | 34838380 | 34839760 |
| 21 | 17254738 | 17257357 | 21 | 34841322 | 34842001 |
| 21 | 17268519 | 17270209 | 21 | 34874499 | 34875044 |
| 21 | 17274214 | 17276839 | 21 | 34876007 | 34878320 |
| 21 | 17288453 | 17294404 | 21 | 34885291 | 34886796 |
| 21 | 17307858 | 17310535 | 21 | 34908216 | 34909896 |
| 21 | 17311076 | 17314798 | 21 | 34919441 | 34923806 |
| 21 | 17339103 | 17339469 | 21 | 34926037 | 34931728 |
| 21 | 17350092 | 17353202 | 21 | 34940644 | 34943654 |
| 21 | 17358358 | 17360527 | 21 | 34947140 | 34948670 |
| 21 | 17426183 | 17427273 | 21 | 34957962 | 34958649 |
| 21 | 17441449 | 17444036 | 21 | 34961442 | 34963437 |
| 21 | 17452903 | 17456584 | 21 | 34969003 | 34970188 |
| 21 | 17489099 | 17490292 | 21 | 34982058 | 34985187 |
| 21 | 17494454 | 17496898 | 21 | 34990384 | 34990669 |
| 21 | 17502012 | 17505405 | 21 | 34993806 | 34999799 |
| 21 | 17511949 | 17517223 | 21 | 35002909 | 35004135 |
| 21 | 17519530 | 17523233 | 21 | 35009398 | 35025159 |
| 21 | 17530993 | 17532169 | 21 | 35034401 | 35049663 |
| 21 | 17575634 | 17577085 | 21 | 35054184 | 35055986 |
| 21 | 17590323 | 17591318 | 21 | 35076544 | 35077775 |
| 21 | 17713675 | 17716077 | 21 | 35085838 | 35087353 |
| 21 | 17724189 | 17724793 | 21 | 35089002 | 35093745 |
| 21 | 17730734 | 17731956 | 21 | 35105192 | 35108313 |
| 21 | 17736088 | 17736628 | 21 | 35112174 | 35115290 |
| 21 | 17745926 | 17748478 | 21 | 35130064 | 35131583 |
| 21 | 17755017 | 17758085 | 21 | 35136755 | 35139684 |
| 21 | 17805305 | 17806032 | 21 | 35155238 | 35159746 |
| 21 | 17814649 | 17817187 | 21 | 35164166 | 35166345 |
| 21 | 17904768 | 17907676 | 21 | 35176364 | 35178077 |
| 21 | 17937446 | 17937574 | 21 | 35179296 | 35186102 |
| 21 | 18008264 | 18009086 | 21 | 35187105 | 35187605 |
| 21 | 18040238 | 18041380 | 21 | 35192602 | 35193767 |
| 21 | 18078269 | 18082974 | 21 | 35205824 | 35209599 |
| 21 | 18088872 | 18091950 | 21 | 35226048 | 35227775 |
| 21 | 18113355 | 18113915 | 21 | 35234450 | 35235946 |
| 21 | 18114466 | 18114527 | 21 | 35241604 | 35243938 |
| 21 | 18152116 | 18153860 | 21 | 35249708 | 35252278 |
| 21 | 18155214 | 18156585 | 21 | 35253903 | 35255110 |
| 21 | 18164515 | 18166281 | 21 | 35257443 | 35260293 |
| 21 | 18180844 | 18180863 | 21 | 35273674 | 35275041 |
| 21 | 18194734 | 18196963 | 21 | 35282002 | 35285872 |
| 21 | 18236282 | 18237799 | 21 | 35291990 | 35294257 |
| 21 | 18251336 | 18254560 | 21 | 35319661 | 35320332 |
| 21 | 18259117 | 18259996 | 21 | 35340135 | 35340926 |
| 21 | 18288629 | 18289409 | 21 | 35341898 | 35344652 |
| 21 | 18328505 | 18331524 | 21 | 35355557 | 35356897 |
| 21 | 18334306 | 18338590 | 21 | 35366946 | 35367865 |
| 21 | 18339747 | 18343629 | 21 | 35382171 | 35384412 |
| 21 | 18349676 | 18350083 | 21 | 35394436 | 35395415 |
| 21 | 18354955 | 18355803 | 21 | 35400195 | 35401259 |
| 21 | 18387896 | 18392008 | 21 | 35498974 | 35499775 |
| 21 | 18413634 | 18417724 | 21 | 35521345 | 35521885 |
| 21 | 18465861 | 18466805 | 21 | 35526699 | 35527433 |
| 21 | 18504747 | 18505693 | 21 | 35545118 | 35546669 |

*The chromosomal position was obtained from UCSC genome browser (http://genome.ucsc.edu/) build 36.

Appendix A: Chromosome 21
Page 7 of 39

| Chr | Start | End | | | Chr | Start | End |
|---|---|---|---|---|---|---|---|
| 21 | 18523133 | 18523983 | | | 21 | 35578477 | 35580684 |
| 21 | 18541589 | 18544449 | | | 21 | 35588365 | 35590256 |
| 21 | 18547614 | 18548853 | | | 21 | 35593235 | 35594025 |
| 21 | 18599954 | 18606355 | | | 21 | 35603129 | 35603614 |
| 21 | 18617504 | 18619755 | | | 21 | 35608008 | 35615927 |
| 21 | 18643217 | 18644568 | | | 21 | 35617459 | 35618438 |
| 21 | 18646022 | 18647110 | | | 21 | 35620529 | 35621564 |
| 21 | 18647809 | 18650113 | | | 21 | 35646868 | 35647707 |
| 21 | 18650471 | 18651938 | | | 21 | 35670903 | 35671586 |
| 21 | 18655753 | 18656571 | | | 21 | 35673233 | 35676220 |
| 21 | 18661842 | 18664473 | | | 21 | 35690710 | 35691510 |
| 21 | 18677697 | 18678212 | | | 21 | 35696942 | 35700037 |
| 21 | 18699308 | 18702178 | | | 21 | 35710678 | 35711577 |
| 21 | 18771617 | 18775161 | | | 21 | 35732943 | 35737180 |
| 21 | 18783124 | 18783572 | | | 21 | 35782191 | 35782651 |
| 21 | 18800719 | 18802631 | | | 21 | 35802832 | 35803608 |
| 21 | 18837155 | 18838045 | | | 21 | 35813671 | 35814885 |
| 21 | 18840167 | 18842670 | | | 21 | 35818488 | 35823864 |
| 21 | 18845715 | 18849382 | | | 21 | 35857301 | 35860293 |
| 21 | 18885729 | 18888310 | | | 21 | 35874407 | 35875344 |
| 21 | 18899745 | 18900121 | | | 21 | 35898185 | 35899070 |
| 21 | 18904054 | 18904408 | | | 21 | 35909507 | 35912354 |
| 21 | 18905075 | 18908767 | | | 21 | 35936003 | 35938701 |
| 21 | 18912317 | 18918001 | | | 21 | 35942701 | 35946543 |
| 21 | 18922626 | 18932943 | | | 21 | 35957473 | 35958317 |
| 21 | 18934435 | 18939526 | | | 21 | 35986169 | 35988102 |
| 21 | 18964554 | 18966460 | | | 21 | 35991145 | 35992596 |
| 21 | 18972215 | 18973918 | | | 21 | 36001451 | 36003409 |
| 21 | 18994466 | 18995329 | | | 21 | 36005868 | 36007478 |
| 21 | 19010490 | 19011323 | | | 21 | 36026513 | 36027974 |
| 21 | 19031390 | 19036027 | | | 21 | 36042415 | 36043451 |
| 21 | 19037729 | 19038732 | | | 21 | 36059444 | 36062193 |
| 21 | 19062447 | 19063792 | | | 21 | 36076406 | 36077811 |
| 21 | 19070717 | 19071240 | | | 21 | 36104009 | 36105871 |
| 21 | 19089655 | 19089783 | | | 21 | 36113110 | 36114327 |
| 21 | 19113540 | 19114031 | | | 21 | 36125610 | 36127783 |
| 21 | 19118483 | 19120416 | | | 21 | 36138097 | 36139979 |
| 21 | 19123007 | 19123313 | | | 21 | 36144463 | 36149033 |
| 21 | 19129380 | 19135635 | | | 21 | 36156225 | 36157676 |
| 21 | 19142274 | 19142991 | | | 21 | 36172729 | 36173799 |
| 21 | 19149636 | 19150132 | | | 21 | 36180675 | 36181597 |
| 21 | 19173944 | 19174949 | | | 21 | 36198365 | 36200103 |
| 21 | 19181735 | 19182602 | | | 21 | 36215590 | 36216301 |
| 21 | 19215608 | 19220026 | | | 21 | 36285059 | 36289091 |
| 21 | 19223514 | 19226018 | | | 21 | 36292046 | 36292895 |
| 21 | 19248202 | 19248794 | | | 21 | 36299908 | 36301647 |
| 21 | 19250850 | 19252584 | | | 21 | 36321971 | 36328668 |
| 21 | 19281380 | 19282242 | | | 21 | 36338900 | 36339860 |
| 21 | 19298030 | 19305035 | | | 21 | 36365103 | 36366152 |
| 21 | 19319657 | 19320539 | | | 21 | 36371430 | 36373835 |
| 21 | 19322560 | 19326518 | | | 21 | 36419734 | 36420943 |
| 21 | 19345719 | 19350833 | | | 21 | 36449649 | 36451692 |
| 21 | 19380343 | 19381574 | | | 21 | 36477676 | 36479198 |
| 21 | 19384143 | 19386815 | | | 21 | 36486179 | 36487614 |
| 21 | 19401938 | 19406160 | | | 21 | 36501214 | 36505991 |

*The chromosomal position was obtained from UCSC genome browser (http://genome.ucsc.edu/) build 36.

Appendix A: Chromosome 21
Page 8 of 39

| Chr | Start | End | Chr | Start | End |
|---|---|---|---|---|---|
| 21 | 19490029 | 19491714 | 21 | 36524673 | 36525353 |
| 21 | 19496486 | 19496959 | 21 | 36531280 | 36533322 |
| 21 | 19522427 | 19524485 | 21 | 36539086 | 36541372 |
| 21 | 19538494 | 19540333 | 21 | 36544269 | 36545153 |
| 21 | 19547184 | 19548646 | 21 | 36560778 | 36564356 |
| 21 | 19549743 | 19554453 | 21 | 36589341 | 36590578 |
| 21 | 19559714 | 19562892 | 21 | 36614055 | 36615129 |
| 21 | 19564592 | 19569774 | 21 | 36678910 | 36680629 |
| 21 | 19586111 | 19586558 | 21 | 36702613 | 36702952 |
| 21 | 19588400 | 19593579 | 21 | 36714667 | 36717486 |
| 21 | 19595619 | 19600572 | 21 | 36753319 | 36757564 |
| 21 | 19609126 | 19611041 | 21 | 36759364 | 36760335 |
| 21 | 19615821 | 19616068 | 21 | 36767701 | 36769640 |
| 21 | 19638395 | 19641512 | 21 | 36772650 | 36775155 |
| 21 | 19662539 | 19663611 | 21 | 36782322 | 36789013 |
| 21 | 19676010 | 19677202 | 21 | 36793841 | 36794919 |
| 21 | 19681022 | 19682579 | 21 | 36816621 | 36817495 |
| 21 | 19683102 | 19683963 | 21 | 36819295 | 36819775 |
| 21 | 19745234 | 19749739 | 21 | 36827031 | 36829137 |
| 21 | 19762859 | 19763595 | 21 | 36832842 | 36834414 |
| 21 | 19789071 | 19789346 | 21 | 36843718 | 36845386 |
| 21 | 19798509 | 19798514 | 21 | 36848105 | 36850250 |
| 21 | 19843259 | 19846444 | 21 | 36859504 | 36866633 |
| 21 | 19861152 | 19863563 | 21 | 36872638 | 36875088 |
| 21 | 19896196 | 19896783 | 21 | 36881335 | 36887685 |
| 21 | 19914255 | 19915572 | 21 | 36899076 | 36901236 |
| 21 | 19926598 | 19929705 | 21 | 36904979 | 36907874 |
| 21 | 19941378 | 19941828 | 21 | 36920880 | 36928755 |
| 21 | 19951528 | 19964499 | 21 | 36934596 | 36937855 |
| 21 | 19965598 | 19967655 | 21 | 36956449 | 36957860 |
| 21 | 19989572 | 19992712 | 21 | 36963505 | 36964280 |
| 21 | 20031734 | 20033214 | 21 | 36986315 | 36987261 |
| 21 | 20043049 | 20043169 | 21 | 36987969 | 36989871 |
| 21 | 20062783 | 20063327 | 21 | 37012141 | 37018840 |
| 21 | 20111341 | 20112152 | 21 | 37022700 | 37032911 |
| 21 | 20147277 | 20148882 | 21 | 37042238 | 37042718 |
| 21 | 20157408 | 20158041 | 21 | 37081271 | 37082998 |
| 21 | 20194408 | 20195408 | 21 | 37114204 | 37115997 |
| 21 | 20214430 | 20217136 | 21 | 37117063 | 37119075 |
| 21 | 20225748 | 20227770 | 21 | 37129186 | 37129618 |
| 21 | 20228840 | 20230419 | 21 | 37154333 | 37155523 |
| 21 | 20239857 | 20241816 | 21 | 37181977 | 37182335 |
| 21 | 20244779 | 20248572 | 21 | 37204344 | 37205560 |
| 21 | 20272521 | 20273510 | 21 | 37212829 | 37213208 |
| 21 | 20274366 | 20275244 | 21 | 37216634 | 37217954 |
| 21 | 20325458 | 20326965 | 21 | 37230478 | 37231411 |
| 21 | 20339159 | 20339834 | 21 | 37288749 | 37289204 |
| 21 | 20355366 | 20361239 | 21 | 37355986 | 37356921 |
| 21 | 20401784 | 20410139 | 21 | 37365800 | 37368800 |
| 21 | 20416207 | 20416924 | 21 | 37377400 | 37377732 |
| 21 | 20442045 | 20442198 | 21 | 37413847 | 37417480 |
| 21 | 20451639 | 20454062 | 21 | 37445665 | 37446201 |
| 21 | 20461115 | 20462589 | 21 | 37466441 | 37468789 |
| 21 | 20463860 | 20464781 | 21 | 37475418 | 37476522 |
| 21 | 20486274 | 20493418 | 21 | 37519965 | 37520174 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| 21 | 20518096 | 20519164 | | | 21 | 37521330 | 37522865 |
| 21 | 20554065 | 20554802 | | | 21 | 37525011 | 37526861 |
| 21 | 20572505 | 20572608 | | | 21 | 37561097 | 37562537 |
| 21 | 20574474 | 20575676 | | | 21 | 37632755 | 37635598 |
| 21 | 20579790 | 20581093 | | | 21 | 37639760 | 37640021 |
| 21 | 20604730 | 20605416 | | | 21 | 37643210 | 37644576 |
| 21 | 20641228 | 20641988 | | | 21 | 37658136 | 37659891 |
| 21 | 20679547 | 20680141 | | | 21 | 37677529 | 37678707 |
| 21 | 20690803 | 20691824 | | | 21 | 37692044 | 37694115 |
| 21 | 20714156 | 20716775 | | | 21 | 37699165 | 37700161 |
| 21 | 20719207 | 20720167 | | | 21 | 37707527 | 37708699 |
| 21 | 20722023 | 20726365 | | | 21 | 37712909 | 37717053 |
| 21 | 20754777 | 20756452 | | | 21 | 37729313 | 37731431 |
| 21 | 20763339 | 20766451 | | | 21 | 37783498 | 37784365 |
| 21 | 20773923 | 20775897 | | | 21 | 37785690 | 37786286 |
| 21 | 20788737 | 20790044 | | | 21 | 37813274 | 37814219 |
| 21 | 20801018 | 20802638 | | | 21 | 37827013 | 37827961 |
| 21 | 20816715 | 20817196 | | | 21 | 37833667 | 37834472 |
| 21 | 20901558 | 20904914 | | | 21 | 37841075 | 37841806 |
| 21 | 20913466 | 20915135 | | | 21 | 37845244 | 37849111 |
| 21 | 21007855 | 21012380 | | | 21 | 37857321 | 37859560 |
| 21 | 21022251 | 21024275 | | | 21 | 37900139 | 37901495 |
| 21 | 21033641 | 21034136 | | | 21 | 37925414 | 37926328 |
| 21 | 21036928 | 21038329 | | | 21 | 37930284 | 37931079 |
| 21 | 21042490 | 21042877 | | | 21 | 37935844 | 37937744 |
| 21 | 21056953 | 21064269 | | | 21 | 37939936 | 37941341 |
| 21 | 21078189 | 21079062 | | | 21 | 37941853 | 37945919 |
| 21 | 21082762 | 21084457 | | | 21 | 37967393 | 37968698 |
| 21 | 21105505 | 21107583 | | | 21 | 37970233 | 37971517 |
| 21 | 21154825 | 21156062 | | | 21 | 38001368 | 38003039 |
| 21 | 21158901 | 21163204 | | | 21 | 38028501 | 38031055 |
| 21 | 21173030 | 21175421 | | | 21 | 38043070 | 38048263 |
| 21 | 21178639 | 21181510 | | | 21 | 38049951 | 38057811 |
| 21 | 21183111 | 21186757 | | | 21 | 38067216 | 38067896 |
| 21 | 21187810 | 21188808 | | | 21 | 38126474 | 38127934 |
| 21 | 21197452 | 21198913 | | | 21 | 38136434 | 38137029 |
| 21 | 21209746 | 21211680 | | | 21 | 38142209 | 38143964 |
| 21 | 21224421 | 21225910 | | | 21 | 38172595 | 38186058 |
| 21 | 21235453 | 21237191 | | | 21 | 38189833 | 38192825 |
| 21 | 21240673 | 21241242 | | | 21 | 38206983 | 38208809 |
| 21 | 21251261 | 21252037 | | | 21 | 38209897 | 38211832 |
| 21 | 21289085 | 21291348 | | | 21 | 38213495 | 38213840 |
| 21 | 21296370 | 21296670 | | | 21 | 38250947 | 38253103 |
| 21 | 21302262 | 21303573 | | | 21 | 38269002 | 38269781 |
| 21 | 21305858 | 21306542 | | | 21 | 38273876 | 38275935 |
| 21 | 21384029 | 21385945 | | | 21 | 38339776 | 38340168 |
| 21 | 21387263 | 21400066 | | | 21 | 38344616 | 38346495 |
| 21 | 21441065 | 21441415 | | | 21 | 38348729 | 38349366 |
| 21 | 21456617 | 21457757 | | | 21 | 38350070 | 38350446 |
| 21 | 21510600 | 21511324 | | | 21 | 38359122 | 38360401 |
| 21 | 21513775 | 21517567 | | | 21 | 38384055 | 38387728 |
| 21 | 21518902 | 21521203 | | | 21 | 38392206 | 38393282 |
| 21 | 21523731 | 21525263 | | | 21 | 38411653 | 38411821 |
| 21 | 21528174 | 21529303 | | | 21 | 38414905 | 38416139 |
| 21 | 21538723 | 21540095 | | | 21 | 38424657 | 38427293 |

*The chromosomal position was obtained from UCSC genome browser (http://genome.ucsc.edu/) build 36.

Appendix A: Chromosome 21

Page 10 of 39

| Chr | Start | End | Chr | Start | End |
|---|---|---|---|---|---|
| 21 | 21555520 | 21561893 | 21 | 38434793 | 38437242 |
| 21 | 21581434 | 21582170 | 21 | 38449319 | 38450376 |
| 21 | 21584467 | 21587837 | 21 | 38464326 | 38466346 |
| 21 | 21590271 | 21591143 | 21 | 38500687 | 38502537 |
| 21 | 21608819 | 21609737 | 21 | 38549008 | 38550009 |
| 21 | 21621805 | 21622167 | 21 | 38577717 | 38579186 |
| 21 | 21639208 | 21644100 | 21 | 38584884 | 38585804 |
| 21 | 21658326 | 21660767 | 21 | 38588007 | 38588899 |
| 21 | 21662538 | 21664003 | 21 | 38590446 | 38590826 |
| 21 | 21699834 | 21701631 | 21 | 38591816 | 38593893 |
| 21 | 21736819 | 21743537 | 21 | 38598974 | 38602717 |
| 21 | 21744840 | 21745763 | 21 | 38614075 | 38615341 |
| 21 | 21750288 | 21751323 | 21 | 38619258 | 38622135 |
| 21 | 21757358 | 21764832 | 21 | 38637207 | 38638155 |
| 21 | 21765622 | 21766784 | 21 | 38640190 | 38645229 |
| 21 | 21769308 | 21770439 | 21 | 38669819 | 38670103 |
| 21 | 21790657 | 21791454 | 21 | 38674646 | 38678322 |
| 21 | 21795090 | 21795880 | 21 | 38695432 | 38697694 |
| 21 | 21799249 | 21799389 | 21 | 38720310 | 38725228 |
| 21 | 21805922 | 21806615 | 21 | 38734069 | 38739979 |
| 21 | 21813847 | 21815863 | 21 | 38741964 | 38743090 |
| 21 | 21820430 | 21822925 | 21 | 38748100 | 38748960 |
| 21 | 21832569 | 21834866 | 21 | 38791388 | 38792277 |
| 21 | 21842906 | 21852955 | 21 | 38797329 | 38800114 |
| 21 | 21865065 | 21865259 | 21 | 38805167 | 38805508 |
| 21 | 21884507 | 21885640 | 21 | 38809259 | 38812384 |
| 21 | 21903574 | 21905302 | 21 | 38818964 | 38819448 |
| 21 | 21916765 | 21919020 | 21 | 38860761 | 38863222 |
| 21 | 21954549 | 21956531 | 21 | 38867783 | 38868423 |
| 21 | 21975506 | 21978300 | 21 | 38870489 | 38875193 |
| 21 | 22005795 | 22006755 | 21 | 38882075 | 38883610 |
| 21 | 22008318 | 22010370 | 21 | 38885556 | 38894368 |
| 21 | 22033599 | 22034525 | 21 | 38896311 | 38897571 |
| 21 | 22044201 | 22044615 | 21 | 38905078 | 38905767 |
| 21 | 22054928 | 22057740 | 21 | 38936633 | 38937703 |
| 21 | 22106195 | 22114906 | 21 | 38940275 | 38941154 |
| 21 | 22176290 | 22177709 | 21 | 38942190 | 38943248 |
| 21 | 22218361 | 22219141 | 21 | 38945427 | 38947887 |
| 21 | 22261682 | 22262574 | 21 | 38951439 | 38952239 |
| 21 | 22283871 | 22286383 | 21 | 38955052 | 38955926 |
| 21 | 22349605 | 22360100 | 21 | 38957916 | 38958844 |
| 21 | 22372909 | 22374896 | 21 | 38990512 | 38991707 |
| 21 | 22378295 | 22379612 | 21 | 38994362 | 38997792 |
| 21 | 22392439 | 22393392 | 21 | 39033596 | 39035929 |
| 21 | 22394297 | 22399414 | 21 | 39049688 | 39050774 |
| 21 | 22414756 | 22415334 | 21 | 39053686 | 39054338 |
| 21 | 22424388 | 22430456 | 21 | 39061021 | 39061324 |
| 21 | 22431164 | 22432184 | 21 | 39071163 | 39071895 |
| 21 | 22448807 | 22451864 | 21 | 39078997 | 39079332 |
| 21 | 22459941 | 22466808 | 21 | 39089235 | 39090921 |
| 21 | 22484503 | 22485304 | 21 | 39095907 | 39096816 |
| 21 | 22496782 | 22497677 | 21 | 39098888 | 39100953 |
| 21 | 22510767 | 22511650 | 21 | 39111899 | 39116825 |
| 21 | 22518585 | 22522777 | 21 | 39169051 | 39169774 |
| 21 | 22525351 | 22529324 | 21 | 39171027 | 39171952 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 22534622 | 22535212 | 21 | 39182792 | 39184196 |
| 21 | 22538955 | 22541862 | 21 | 39192148 | 39194195 |
| 21 | 22547305 | 22548023 | 21 | 39196678 | 39197923 |
| 21 | 22548724 | 22548754 | 21 | 39200505 | 39201657 |
| 21 | 22580159 | 22581424 | 21 | 39206668 | 39208146 |
| 21 | 22595136 | 22596175 | 21 | 39209020 | 39209979 |
| 21 | 22598136 | 22600876 | 21 | 39215912 | 39216960 |
| 21 | 22605512 | 22608008 | 21 | 39222509 | 39223218 |
| 21 | 22609821 | 22611485 | 21 | 39229107 | 39230320 |
| 21 | 22614551 | 22616093 | 21 | 39237887 | 39239574 |
| 21 | 22649772 | 22650318 | 21 | 39242573 | 39243912 |
| 21 | 22684290 | 22687978 | 21 | 39257494 | 39260774 |
| 21 | 22715444 | 22717878 | 21 | 39275790 | 39276810 |
| 21 | 22740110 | 22742903 | 21 | 39278140 | 39279946 |
| 21 | 22748797 | 22749583 | 21 | 39282940 | 39286255 |
| 21 | 22829233 | 22829968 | 21 | 39287530 | 39289649 |
| 21 | 22843233 | 22844671 | 21 | 39302429 | 39303105 |
| 21 | 22855913 | 22856512 | 21 | 39304126 | 39307250 |
| 21 | 22884139 | 22884250 | 21 | 39314401 | 39317622 |
| 21 | 22906869 | 22908999 | 21 | 39323050 | 39325791 |
| 21 | 22911716 | 22913176 | 21 | 39327751 | 39329842 |
| 21 | 22924800 | 22927436 | 21 | 39333504 | 39334728 |
| 21 | 22931138 | 22931752 | 21 | 39349950 | 39350423 |
| 21 | 22932704 | 22936145 | 21 | 39354550 | 39357065 |
| 21 | 22937511 | 22938527 | 21 | 39372389 | 39372688 |
| 21 | 22939368 | 22940901 | 21 | 39375005 | 39377933 |
| 21 | 22955227 | 22956607 | 21 | 39381091 | 39382172 |
| 21 | 22984001 | 22992745 | 21 | 39390541 | 39392427 |
| 21 | 23001579 | 23005127 | 21 | 39430739 | 39432893 |
| 21 | 23023678 | 23024609 | 21 | 39438242 | 39438834 |
| 21 | 23037330 | 23039191 | 21 | 39471618 | 39472518 |
| 21 | 23050381 | 23054230 | 21 | 39477994 | 39478306 |
| 21 | 23080794 | 23081790 | 21 | 39479637 | 39486094 |
| 21 | 23098380 | 23099168 | 21 | 39488326 | 39493021 |
| 21 | 23103325 | 23103361 | 21 | 39505033 | 39505191 |
| 21 | 23115502 | 23116690 | 21 | 39510353 | 39514295 |
| 21 | 23123655 | 23125223 | 21 | 39607609 | 39608666 |
| 21 | 23126694 | 23129139 | 21 | 39612866 | 39616723 |
| 21 | 23132305 | 23133288 | 21 | 39630360 | 39630790 |
| 21 | 23147145 | 23147805 | 21 | 39642019 | 39643008 |
| 21 | 23157161 | 23157518 | 21 | 39670677 | 39671635 |
| 21 | 23185228 | 23186517 | 21 | 39678831 | 39680586 |
| 21 | 23195209 | 23195990 | 21 | 39683438 | 39684815 |
| 21 | 23210513 | 23211373 | 21 | 39735785 | 39738685 |
| 21 | 23229490 | 23233338 | 21 | 39753739 | 39754053 |
| 21 | 23235207 | 23237408 | 21 | 39819534 | 39820809 |
| 21 | 23249370 | 23252870 | 21 | 39822569 | 39825524 |
| 21 | 23274535 | 23275056 | 21 | 39832110 | 39832682 |
| 21 | 23295298 | 23296315 | 21 | 39856825 | 39857759 |
| 21 | 23325653 | 23327901 | 21 | 39860923 | 39863174 |
| 21 | 23334475 | 23335036 | 21 | 39894979 | 39896464 |
| 21 | 23340308 | 23341377 | 21 | 39931716 | 39933685 |
| 21 | 23355904 | 23357017 | 21 | 39949076 | 39950466 |
| 21 | 23378279 | 23379808 | 21 | 39954166 | 39961896 |
| 21 | 23404484 | 23405748 | 21 | 39966457 | 39971601 |

*The chromosomal position was obtained from UCSC genome browser (http://genome.ucsc.edu/) build 36.

Appendix A: Chromosome 21
Page 12 of 39

| Chr | Start | End | | Chr | Start | End |
|---|---|---|---|---|---|---|
| 21 | 23407262 | 23408971 | | 21 | 40004034 | 40006164 |
| 21 | 23411359 | 23412493 | | 21 | 40021107 | 40022377 |
| 21 | 23413686 | 23414268 | | 21 | 40030292 | 40031701 |
| 21 | 23433008 | 23434775 | | 21 | 40044565 | 40044954 |
| 21 | 23456058 | 23456872 | | 21 | 40047918 | 40048258 |
| 21 | 23472870 | 23477952 | | 21 | 40050142 | 40052107 |
| 21 | 23519061 | 23521435 | | 21 | 40052670 | 40053222 |
| 21 | 23525519 | 23526497 | | 21 | 40056772 | 40058822 |
| 21 | 23527893 | 23528940 | | 21 | 40082149 | 40083354 |
| 21 | 23536027 | 23545758 | | 21 | 40116120 | 40117636 |
| 21 | 23572092 | 23574673 | | 21 | 40119371 | 40127480 |
| 21 | 23598417 | 23598651 | | 21 | 40161074 | 40164670 |
| 21 | 23609958 | 23611137 | | 21 | 40188038 | 40189812 |
| 21 | 23613475 | 23618407 | | 21 | 40230792 | 40233622 |
| 21 | 23661270 | 23661823 | | 21 | 40234412 | 40235657 |
| 21 | 23692215 | 23694101 | | 21 | 40244105 | 40245513 |
| 21 | 23704990 | 23706276 | | 21 | 40266203 | 40267653 |
| 21 | 23707580 | 23708487 | | 21 | 40270727 | 40272978 |
| 21 | 23727878 | 23728348 | | 21 | 40278179 | 40280194 |
| 21 | 23738915 | 23740302 | | 21 | 40288642 | 40289872 |
| 21 | 23775474 | 23776201 | | 21 | 40303017 | 40304333 |
| 21 | 23779963 | 23781608 | | 21 | 40307170 | 40308753 |
| 21 | 23789717 | 23789746 | | 21 | 40326018 | 40333557 |
| 21 | 23827026 | 23827970 | | 21 | 40341489 | 40342390 |
| 21 | 23832971 | 23833952 | | 21 | 40346903 | 40347745 |
| 21 | 23838565 | 23839332 | | 21 | 40359473 | 40359973 |
| 21 | 23856460 | 23857907 | | 21 | 40368139 | 40369255 |
| 21 | 23898710 | 23900269 | | 21 | 40381721 | 40383386 |
| 21 | 23917602 | 23918515 | | 21 | 40426217 | 40428201 |
| 21 | 23935587 | 23936683 | | 21 | 40432150 | 40434528 |
| 21 | 23939382 | 23941190 | | 21 | 40437133 | 40439311 |
| 21 | 23965876 | 23965961 | | 21 | 40463306 | 40464076 |
| 21 | 23982775 | 23983179 | | 21 | 40474426 | 40479545 |
| 21 | 24012488 | 24015645 | | 21 | 40492349 | 40492884 |
| 21 | 24025935 | 24028434 | | 21 | 40496398 | 40497562 |
| 21 | 24044361 | 24047907 | | 21 | 40514710 | 40516462 |
| 21 | 24055873 | 24056961 | | 21 | 40525934 | 40526601 |
| 21 | 24083165 | 24086869 | | 21 | 40579700 | 40580587 |
| 21 | 24106526 | 24107053 | | 21 | 40618093 | 40620316 |
| 21 | 24114985 | 24115212 | | 21 | 40665912 | 40670158 |
| 21 | 24126795 | 24131579 | | 21 | 40733972 | 40734063 |
| 21 | 24145550 | 24147319 | | 21 | 40810437 | 40811465 |
| 21 | 24150480 | 24150967 | | 21 | 40813047 | 40813497 |
| 21 | 24152755 | 24153324 | | 21 | 40824585 | 40825810 |
| 21 | 24156157 | 24157726 | | 21 | 40841447 | 40842031 |
| 21 | 24181040 | 24181705 | | 21 | 40855449 | 40856945 |
| 21 | 24257573 | 24259577 | | 21 | 40857925 | 40858211 |
| 21 | 24288042 | 24288509 | | 21 | 40909143 | 40910193 |
| 21 | 24295183 | 24295338 | | 21 | 40930393 | 40932527 |
| 21 | 24312448 | 24313256 | | 21 | 40977480 | 40978287 |
| 21 | 24322042 | 24323083 | | 21 | 40984509 | 40985615 |
| 21 | 24325551 | 24327755 | | 21 | 40986734 | 40988600 |
| 21 | 24329808 | 24333070 | | 21 | 40989824 | 40990976 |
| 21 | 24362897 | 24368777 | | 21 | 41036451 | 41037322 |
| 21 | 24381186 | 24386097 | | 21 | 41040278 | 41040497 |

*The chromosomal position was obtained from UCSC genome browser (http://genome.ucsc.edu/) build 36.

Appendix A: Chromosome 21
Page 13 of 39

| Chr | Start | End | Chr | Start | End |
|---|---|---|---|---|---|
| 21 | 24387033 | 24390762 | 21 | 41052905 | 41053390 |
| 21 | 24398864 | 24401465 | 21 | 41070177 | 41070790 |
| 21 | 24426928 | 24427953 | 21 | 41082346 | 41083104 |
| 21 | 24432042 | 24433229 | 21 | 41105817 | 41106442 |
| 21 | 24449399 | 24450916 | 21 | 41126299 | 41127057 |
| 21 | 24517553 | 24518345 | 21 | 41129974 | 41130584 |
| 21 | 24522821 | 24522985 | 21 | 41134119 | 41135178 |
| 21 | 24526258 | 24527179 | 21 | 41276283 | 41277293 |
| 21 | 24529944 | 24530604 | 21 | 41304359 | 41307345 |
| 21 | 24559295 | 24560824 | 21 | 41315944 | 41317898 |
| 21 | 24595924 | 24596780 | 21 | 41319929 | 41326035 |
| 21 | 24649314 | 24653437 | 21 | 41355552 | 41359986 |
| 21 | 24662005 | 24662711 | 21 | 41395380 | 41396731 |
| 21 | 24678551 | 24681253 | 21 | 41404593 | 41407386 |
| 21 | 24683172 | 24690309 | 21 | 41408894 | 41413278 |
| 21 | 24696659 | 24698278 | 21 | 41414701 | 41416888 |
| 21 | 24715842 | 24717293 | 21 | 41429282 | 41431390 |
| 21 | 24727054 | 24728091 | 21 | 41432485 | 41436740 |
| 21 | 24743821 | 24744933 | 21 | 41440715 | 41445197 |
| 21 | 24754112 | 24756692 | 21 | 41470996 | 41474195 |
| 21 | 24788446 | 24791328 | 21 | 41480092 | 41481032 |
| 21 | 24816887 | 24817223 | 21 | 41501286 | 41503421 |
| 21 | 24837811 | 24841401 | 21 | 41508653 | 41511511 |
| 21 | 24861724 | 24862226 | 21 | 41514948 | 41518296 |
| 21 | 24865916 | 24866455 | 21 | 41529837 | 41531826 |
| 21 | 24870013 | 24872588 | 21 | 41534627 | 41536668 |
| 21 | 24915715 | 24917627 | 21 | 41542136 | 41546718 |
| 21 | 24920512 | 24923680 | 21 | 41548738 | 41549313 |
| 21 | 24925619 | 24927475 | 21 | 41573536 | 41575020 |
| 21 | 24930505 | 24931092 | 21 | 41575882 | 41576998 |
| 21 | 24961517 | 24964533 | 21 | 41583136 | 41584575 |
| 21 | 24973637 | 24976313 | 21 | 41585979 | 41586189 |
| 21 | 25012456 | 25018585 | 21 | 41598588 | 41599058 |
| 21 | 25021877 | 25022447 | 21 | 41609634 | 41617658 |
| 21 | 25023794 | 25024723 | 21 | 41651380 | 41655418 |
| 21 | 25027233 | 25028870 | 21 | 41657324 | 41658164 |
| 21 | 25050576 | 25052726 | 21 | 41659976 | 41662406 |
| 21 | 25105156 | 25106043 | 21 | 41667168 | 41674540 |
| 21 | 25155688 | 25167215 | 21 | 41681031 | 41682696 |
| 21 | 25174663 | 25175884 | 21 | 41687065 | 41688280 |
| 21 | 25196736 | 25198609 | 21 | 41695653 | 41702255 |
| 21 | 25271633 | 25273081 | 21 | 41706614 | 41711946 |
| 21 | 25304889 | 25309334 | 21 | 41719937 | 41724104 |
| 21 | 25317122 | 25320789 | 21 | 41752020 | 41754675 |
| 21 | 25326343 | 25326730 | 21 | 41760164 | 41774023 |
| 21 | 25329965 | 25336311 | 21 | 41786473 | 41788341 |
| 21 | 25379714 | 25380660 | 21 | 41791294 | 41796244 |
| 21 | 25420682 | 25421644 | 21 | 41803888 | 41804298 |
| 21 | 25425987 | 25427043 | 21 | 41829594 | 41831422 |
| 21 | 25453439 | 25454615 | 21 | 41842286 | 41843053 |
| 21 | 25471004 | 25472029 | 21 | 41854465 | 41858769 |
| 21 | 25497351 | 25499400 | 21 | 41860195 | 41862628 |
| 21 | 25526459 | 25534874 | 21 | 41876956 | 41880169 |
| 21 | 25570181 | 25571140 | 21 | 41886011 | 41887082 |
| 21 | 25719416 | 25720669 | 21 | 41893786 | 41900410 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 25762458 | 25763531 | 21 | 41902867 | 41907731 |
| 21 | 25766213 | 25766729 | 21 | 41913745 | 41915759 |
| 21 | 25781228 | 25781812 | 21 | 41923402 | 41929697 |
| 21 | 25790719 | 25792556 | 21 | 41949880 | 41950753 |
| 21 | 25813489 | 25814202 | 21 | 41957520 | 41959805 |
| 21 | 25855395 | 25855733 | 21 | 41965142 | 41967044 |
| 21 | 25857484 | 25858035 | 21 | 41971394 | 41978395 |
| 21 | 25885942 | 25886940 | 21 | 41981325 | 41983897 |
| 21 | 25902951 | 25903752 | 21 | 41998020 | 41999559 |
| 21 | 25933436 | 25935227 | 21 | 42005989 | 42006646 |
| 21 | 25976221 | 25977752 | 21 | 42006870 | 42009915 |
| 21 | 26027636 | 26028506 | 21 | 42015601 | 42017758 |
| 21 | 26046757 | 26047333 | 21 | 42019329 | 42021699 |
| 21 | 26058714 | 26061979 | 21 | 42033812 | 42040258 |
| 21 | 26082896 | 26083621 | 21 | 42043890 | 42050398 |
| 21 | 26086515 | 26087188 | 21 | 42058502 | 42060331 |
| 21 | 26099606 | 26100746 | 21 | 42064586 | 42066312 |
| 21 | 26148181 | 26150945 | 21 | 42071206 | 42072263 |
| 21 | 26313059 | 26313796 | 21 | 42079533 | 42080694 |
| 21 | 26349788 | 26351253 | 21 | 42093635 | 42095391 |
| 21 | 26383199 | 26384254 | 21 | 42097777 | 42098196 |
| 21 | 26406186 | 26408397 | 21 | 42103358 | 42110029 |
| 21 | 26418949 | 26420226 | 21 | 42113173 | 42119719 |
| 21 | 26463495 | 26464375 | 21 | 42121745 | 42129705 |
| 21 | 26471729 | 26472045 | 21 | 42138798 | 42141088 |
| 21 | 26475669 | 26476529 | 21 | 42144782 | 42148761 |
| 21 | 26567245 | 26569071 | 21 | 42151015 | 42156007 |
| 21 | 26633427 | 26636312 | 21 | 42157736 | 42158816 |
| 21 | 26637345 | 26638507 | 21 | 42166068 | 42168756 |
| 21 | 26644277 | 26646805 | 21 | 42177142 | 42178434 |
| 21 | 26660499 | 26661043 | 21 | 42178832 | 42179742 |
| 21 | 26672451 | 26672841 | 21 | 42184311 | 42187818 |
| 21 | 26675906 | 26677438 | 21 | 42188846 | 42189688 |
| 21 | 26686514 | 26687432 | 21 | 42190302 | 42192348 |
| 21 | 26724423 | 26725482 | 21 | 42194418 | 42195485 |
| 21 | 26731954 | 26733724 | 21 | 42223219 | 42227306 |
| 21 | 26758874 | 26760656 | 21 | 42245113 | 42251942 |
| 21 | 26760782 | 26760791 | 21 | 42255726 | 42260704 |
| 21 | 26768832 | 26769886 | 21 | 42265978 | 42269363 |
| 21 | 26777430 | 26778158 | 21 | 42278424 | 42278651 |
| 21 | 26779114 | 26780417 | 21 | 42297916 | 42298436 |
| 21 | 26803096 | 26804655 | 21 | 42302347 | 42306518 |
| 21 | 26812291 | 26815762 | 21 | 42312248 | 42321325 |
| 21 | 26826127 | 26831801 | 21 | 42330458 | 42335278 |
| 21 | 26833866 | 26834279 | 21 | 42336648 | 42337448 |
| 21 | 26847103 | 26849086 | 21 | 42349455 | 42352752 |
| 21 | 26866785 | 26867968 | 21 | 42355416 | 42357610 |
| 21 | 26935691 | 26939516 | 21 | 42360606 | 42377832 |
| 21 | 26944549 | 26946234 | 21 | 42382854 | 42387844 |
| 21 | 26947004 | 26948256 | 21 | 42391378 | 42393528 |
| 21 | 26954687 | 26955486 | 21 | 42396613 | 42409184 |
| 21 | 26956877 | 26957829 | 21 | 42414401 | 42422737 |
| 21 | 26968593 | 26969479 | 21 | 42425855 | 42440157 |
| 21 | 26977198 | 26978234 | 21 | 42443600 | 42457054 |
| 21 | 26986968 | 26988186 | 21 | 42464428 | 42467004 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 27018296 | 27018816 | 21 | 42487639 | 42488834 |
| 21 | 27026404 | 27027094 | 21 | 42502020 | 42503640 |
| 21 | 27030878 | 27032533 | 21 | 42509861 | 42511599 |
| 21 | 27035000 | 27035797 | 21 | 42514777 | 42516677 |
| 21 | 27048975 | 27050226 | 21 | 42523827 | 42524552 |
| 21 | 27075398 | 27078330 | 21 | 42525676 | 42526231 |
| 21 | 27101643 | 27102266 | 21 | 42527323 | 42528558 |
| 21 | 27104637 | 27114470 | 21 | 42532665 | 42559758 |
| 21 | 27124976 | 27126355 | 21 | 42565636 | 42604604 |
| 21 | 27135955 | 27141021 | 21 | 42605049 | 42613508 |
| 21 | 27178627 | 27188693 | 21 | 42614035 | 42616231 |
| 21 | 27193411 | 27196995 | 21 | 42633785 | 42641436 |
| 21 | 27198194 | 27198519 | 21 | 42643873 | 42646717 |
| 21 | 27201331 | 27211902 | 21 | 42650701 | 42659458 |
| 21 | 27219614 | 27220999 | 21 | 42662477 | 42679897 |
| 21 | 27253449 | 27254397 | 21 | 42688961 | 42692063 |
| 21 | 27258706 | 27261931 | 21 | 42703082 | 42709622 |
| 21 | 27266950 | 27274682 | 21 | 42716636 | 42728223 |
| 21 | 27288895 | 27289495 | 21 | 42729863 | 42749027 |
| 21 | 27293027 | 27294576 | 21 | 42786113 | 42786828 |
| 21 | 27295996 | 27297751 | 21 | 42788744 | 42790445 |
| 21 | 27311290 | 27313547 | 21 | 42796937 | 42797820 |
| 21 | 27334638 | 27338190 | 21 | 42808621 | 42811881 |
| 21 | 27356442 | 27368971 | 21 | 42815211 | 42817304 |
| 21 | 27370819 | 27372947 | 21 | 42825891 | 42827081 |
| 21 | 27391343 | 27393277 | 21 | 42836205 | 42838494 |
| 21 | 27394118 | 27395587 | 21 | 42840669 | 42841954 |
| 21 | 27402235 | 27409497 | 21 | 42851947 | 42859176 |
| 21 | 27415057 | 27416053 | 21 | 42861156 | 42866621 |
| 21 | 27423511 | 27423964 | 21 | 42872486 | 42872991 |
| 21 | 27427220 | 27427903 | 21 | 42874979 | 42889282 |
| 21 | 27442584 | 27443756 | 21 | 42891216 | 42893066 |
| 21 | 27446587 | 27449392 | 21 | 42909862 | 42915072 |
| 21 | 27450349 | 27451016 | 21 | 42918379 | 42920279 |
| 21 | 27473574 | 27474369 | 21 | 42925010 | 42932099 |
| 21 | 27500582 | 27501985 | 21 | 42933833 | 42963652 |
| 21 | 27507722 | 27511755 | 21 | 42965354 | 42974865 |
| 21 | 27513326 | 27515161 | 21 | 42975851 | 42988806 |
| 21 | 27520108 | 27527433 | 21 | 42991315 | 42992161 |
| 21 | 27529838 | 27536899 | 21 | 42995290 | 43005566 |
| 21 | 27540682 | 27543220 | 21 | 43013359 | 43019321 |
| 21 | 27544993 | 27545522 | 21 | 43023949 | 43026472 |
| 21 | 27550664 | 27554738 | 21 | 43034206 | 43038891 |
| 21 | 27565570 | 27567328 | 21 | 43039761 | 43040392 |
| 21 | 27578718 | 27578985 | 21 | 43040536 | 43050579 |
| 21 | 27589017 | 27591755 | 21 | 43051655 | 43076318 |
| 21 | 27607874 | 27609470 | 21 | 43078139 | 43080609 |
| 21 | 27625054 | 27631480 | 21 | 43114160 | 43122612 |
| 21 | 27652314 | 27654345 | 21 | 43123021 | 43128184 |
| 21 | 27656406 | 27658517 | 21 | 43129788 | 43150798 |
| 21 | 27665421 | 27667944 | 21 | 43153076 | 43162492 |
| 21 | 27686045 | 27686585 | 21 | 43166195 | 43166931 |
| 21 | 27688487 | 27704571 | 21 | 43172034 | 43173556 |
| 21 | 27714356 | 27715236 | 21 | 43206515 | 43220664 |
| 21 | 27730968 | 27731972 | 21 | 43223674 | 43227834 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 27741413 | 27743851 | 21 | 43233193 | 43236225 |
| 21 | 27745508 | 27747571 | 21 | 43247977 | 43249205 |
| 21 | 27754238 | 27756723 | 21 | 43266605 | 43267715 |
| 21 | 27770649 | 27771113 | 21 | 43285327 | 43286648 |
| 21 | 27773090 | 27776932 | 21 | 43294303 | 43296947 |
| 21 | 27779090 | 27779787 | 21 | 43314372 | 43319401 |
| 21 | 27806296 | 27807246 | 21 | 43329468 | 43343802 |
| 21 | 27813499 | 27817773 | 21 | 43346884 | 43376923 |
| 21 | 27820164 | 27822544 | 21 | 43382488 | 43388736 |
| 21 | 27830834 | 27834150 | 21 | 43392623 | 43393981 |
| 21 | 27841558 | 27843163 | 21 | 43397600 | 43398450 |
| 21 | 27852797 | 27854736 | 21 | 43401736 | 43402766 |
| 21 | 27856360 | 27857894 | 21 | 43421434 | 43424730 |
| 21 | 27862961 | 27864866 | 21 | 43431705 | 43456683 |
| 21 | 27889393 | 27889856 | 21 | 43459900 | 43477239 |
| 21 | 27892463 | 27893449 | 21 | 43484261 | 43490396 |
| 21 | 27907912 | 27910092 | 21 | 43499516 | 43540162 |
| 21 | 27913885 | 27914995 | 21 | 43541447 | 43552329 |
| 21 | 27926417 | 27927901 | 21 | 43557763 | 43568751 |
| 21 | 27938285 | 27945679 | 21 | 43572847 | 43607024 |
| 21 | 27987140 | 27987523 | 21 | 43608144 | 43656706 |
| 21 | 27991259 | 27991882 | 21 | 43658894 | 43659356 |
| 21 | 28001584 | 28006376 | 21 | 43661218 | 43666218 |
| 21 | 28031219 | 28033412 | 21 | 43670361 | 43681337 |
| 21 | 28043953 | 28045147 | 21 | 43684757 | 43697672 |
| 21 | 28060587 | 28065771 | 21 | 43701377 | 43716690 |
| 21 | 28067329 | 28068359 | 21 | 43720738 | 43733180 |
| 21 | 28076565 | 28076693 | 21 | 43735566 | 43739625 |
| 21 | 28082258 | 28083718 | 21 | 43742444 | 43750514 |
| 21 | 28093327 | 28093852 | 21 | 43761253 | 43762778 |
| 21 | 28107601 | 28109232 | 21 | 43772044 | 43772555 |
| 21 | 28110409 | 28110739 | 21 | 43796900 | 43797744 |
| 21 | 28126072 | 28127521 | 21 | 43815615 | 43816845 |
| 21 | 28283370 | 28284864 | 21 | 43826034 | 43828574 |
| 21 | 28312354 | 28315544 | 21 | 43842395 | 43843338 |
| 21 | 28339615 | 28349603 | 21 | 43846600 | 43847126 |
| 21 | 28368814 | 28369559 | 21 | 43855022 | 43856641 |
| 21 | 28390126 | 28392474 | 21 | 43875702 | 43876947 |
| 21 | 28395026 | 28397083 | 21 | 43889725 | 43890288 |
| 21 | 28416449 | 28417315 | 21 | 43901798 | 43904550 |
| 21 | 28454240 | 28461227 | 21 | 43944407 | 43946736 |
| 21 | 28464388 | 28465855 | 21 | 43956066 | 43957243 |
| 21 | 28495410 | 28498985 | 21 | 43962490 | 44015892 |
| 21 | 28509939 | 28510715 | 21 | 44020596 | 44023135 |
| 21 | 28534662 | 28536945 | 21 | 44030248 | 44078097 |
| 21 | 28537310 | 28537435 | 21 | 44079242 | 44079393 |
| 21 | 28541106 | 28541596 | 21 | 44096257 | 44098704 |
| 21 | 28545513 | 28548236 | 21 | 44102931 | 44105353 |
| 21 | 28549390 | 28550862 | 21 | 44122074 | 44130401 |
| 21 | 28566248 | 28567384 | 21 | 44146911 | 44156620 |
| 21 | 28569897 | 28570702 | 21 | 44161019 | 44161517 |
| 21 | 28574631 | 28576193 | 21 | 44166515 | 44170320 |
| 21 | 28594285 | 28594459 | 21 | 44172233 | 44190607 |
| 21 | 28601973 | 28607336 | 21 | 44195816 | 44206183 |
| 21 | 28620427 | 28620967 | 21 | 44210781 | 44220093 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 28648935 | 28651394 | 21 | 44224142 | 44241124 |
| 21 | 28652164 | 28656309 | 21 | 44244579 | 44251401 |
| 21 | 28672858 | 28675976 | 21 | 44258303 | 44259383 |
| 21 | 28680030 | 28681018 | 21 | 44261347 | 44261826 |
| 21 | 28682263 | 28683104 | 21 | 44282919 | 44283520 |
| 21 | 28689533 | 28690953 | 21 | 44298530 | 44299974 |
| 21 | 28704223 | 28705629 | 21 | 44332444 | 44333619 |
| 21 | 28720789 | 28722411 | 21 | 44346595 | 44348514 |
| 21 | 28729702 | 28742073 | 21 | 44351950 | 44352735 |
| 21 | 28748029 | 28748703 | 21 | 44357183 | 44388835 |
| 21 | 28749891 | 28753615 | 21 | 44390224 | 44393244 |
| 21 | 28761941 | 28774153 | 21 | 44403260 | 44415851 |
| 21 | 28786887 | 28787043 | 21 | 44419511 | 44433165 |
| 21 | 28805192 | 28805781 | 21 | 44438245 | 44444072 |
| 21 | 28834581 | 28834840 | 21 | 44446300 | 44456062 |
| 21 | 28842500 | 28843985 | 21 | 44467995 | 44512459 |
| 21 | 28870131 | 28870884 | 21 | 44513558 | 44519331 |
| 21 | 28891771 | 28893725 | 21 | 44528247 | 44540418 |
| 21 | 28903462 | 28907884 | 21 | 44544206 | 44580559 |
| 21 | 28909920 | 28910421 | 21 | 44588745 | 44603090 |
| 21 | 28933312 | 28933639 | 21 | 44608116 | 44628067 |
| 21 | 28947953 | 28953962 | 21 | 44634875 | 44650620 |
| 21 | 28980931 | 28981363 | 21 | 44657398 | 44673346 |
| 21 | 28984627 | 28987163 | 21 | 44676601 | 44697628 |
| 21 | 28994131 | 28998316 | 21 | 44700624 | 44712418 |
| 21 | 29009255 | 29012613 | 21 | 44721447 | 44732741 |
| 21 | 29033182 | 29033890 | 21 | 44738457 | 44744553 |
| 21 | 29134410 | 29137669 | 21 | 44750193 | 44766962 |
| 21 | 29236152 | 29237892 | 21 | 44769678 | 44777557 |
| 21 | 29286335 | 29287513 | 21 | 44782147 | 44785258 |
| 21 | 29312549 | 29314396 | 21 | 44791784 | 44798903 |
| 21 | 29317712 | 29319942 | 21 | 44801094 | 44803751 |
| 21 | 29350501 | 29351080 | 21 | 44811766 | 44814947 |
| 21 | 29355118 | 29356807 | 21 | 44815934 | 44820248 |
| 21 | 29361619 | 29362015 | 21 | 44822822 | 44828172 |
| 21 | 29390338 | 29391627 | 21 | 44829982 | 44838974 |
| 21 | 29449363 | 29450415 | 21 | 44844393 | 44848973 |
| 21 | 29452304 | 29452920 | 21 | 44855919 | 44861902 |
| 21 | 29487301 | 29489296 | 21 | 44869932 | 44874637 |
| 21 | 29501518 | 29503306 | 21 | 44880687 | 44885434 |
| 21 | 29505249 | 29506000 | 21 | 44890593 | 44900680 |
| 21 | 29521925 | 29524610 | 21 | 44909260 | 44911856 |
| 21 | 29550282 | 29550878 | 21 | 44925503 | 44933488 |
| 21 | 29554029 | 29555158 | 21 | 44936401 | 44938444 |
| 21 | 29591853 | 29593639 | 21 | 44939498 | 44947508 |
| 21 | 29594000 | 29595054 | 21 | 44953664 | 44954287 |
| 21 | 29605499 | 29607282 | 21 | 44964539 | 44965014 |
| 21 | 29664024 | 29666382 | 21 | 44967824 | 44981004 |
| 21 | 29694888 | 29697548 | 21 | 44993428 | 44998455 |
| 21 | 29708931 | 29710723 | 21 | 45001743 | 45013653 |
| 21 | 29729788 | 29730256 | 21 | 45015482 | 45018086 |
| 21 | 29743282 | 29751183 | 21 | 45040188 | 45040955 |
| 21 | 29752965 | 29754363 | 21 | 45044499 | 45046976 |
| 21 | 29766502 | 29767519 | 21 | 45057203 | 45058433 |
| 21 | 29785437 | 29786674 | 21 | 45060804 | 45064963 |

*The chromosomal position was obtained from UCSC genome browser (http://genome.ucsc.edu/) build 36.

Appendix A: Chromosome 21
Page 18 of 39

| Chr | Start | End | Chr | Start | End |
|---|---|---|---|---|---|
| 21 | 29792801 | 29794256 | 21 | 45078632 | 45094204 |
| 21 | 29807809 | 29808899 | 21 | 45097897 | 45109738 |
| 21 | 29811058 | 29811854 | 21 | 45114130 | 45117239 |
| 21 | 29824799 | 29828189 | 21 | 45126671 | 45154064 |
| 21 | 29850704 | 29852168 | 21 | 45162104 | 45165279 |
| 21 | 29866196 | 29866925 | 21 | 45170688 | 45171199 |
| 21 | 29874709 | 29875449 | 21 | 45172400 | 45181402 |
| 21 | 29876590 | 29878230 | 21 | 45186734 | 45204593 |
| 21 | 29879471 | 29880486 | 21 | 45210501 | 45249436 |
| 21 | 29896975 | 29897504 | 21 | 45251011 | 45252834 |
| 21 | 29899006 | 29901550 | 21 | 45255200 | 45266468 |
| 21 | 29902523 | 29907668 | 21 | 45270399 | 45280084 |
| 21 | 29914700 | 29916782 | 21 | 45282485 | 45289098 |
| 21 | 29929775 | 29931536 | 21 | 45293384 | 45306195 |
| 21 | 29934264 | 29934992 | 21 | 45308829 | 45309689 |
| 21 | 29941458 | 29942278 | 21 | 45311857 | 45317894 |
| 21 | 29954971 | 29956795 | 21 | 45339384 | 45345920 |
| 21 | 29957775 | 29959801 | 21 | 45355552 | 45356944 |
| 21 | 30022791 | 30023957 | 21 | 45364160 | 45365455 |
| 21 | 30062509 | 30064628 | 21 | 45370513 | 45374483 |
| 21 | 30114505 | 30117282 | 21 | 45377991 | 45382341 |
| 21 | 30120649 | 30126201 | 21 | 45386870 | 45388163 |
| 21 | 30130292 | 30137909 | 21 | 45391830 | 45393575 |
| 21 | 30159539 | 30161106 | 21 | 45401946 | 45402556 |
| 21 | 30173897 | 30185470 | 21 | 45404995 | 45409276 |
| 21 | 30208216 | 30209867 | 21 | 45415492 | 45416953 |
| 21 | 30213650 | 30215100 | 21 | 45420037 | 45426572 |
| 21 | 30238827 | 30239350 | 21 | 45429275 | 45429773 |
| 21 | 30254586 | 30255012 | 21 | 45443668 | 45447473 |
| 21 | 30260694 | 30265707 | 21 | 45464784 | 45474591 |
| 21 | 30273057 | 30275463 | 21 | 45478080 | 45480799 |
| 21 | 30282097 | 30283211 | 21 | 45489176 | 45493573 |
| 21 | 30288486 | 30289262 | 21 | 45495622 | 45512123 |
| 21 | 30292309 | 30292844 | 21 | 45515405 | 45519630 |
| 21 | 30326128 | 30328201 | 21 | 45521030 | 45532071 |
| 21 | 30359050 | 30360430 | 21 | 45534411 | 45540808 |
| 21 | 30384843 | 30391467 | 21 | 45543118 | 45598950 |
| 21 | 30393036 | 30393425 | 21 | 45600612 | 45690669 |
| 21 | 30398563 | 30399093 | 21 | 45692021 | 45705792 |
| 21 | 30406887 | 30410055 | 21 | 45707389 | 45722649 |
| 21 | 30432735 | 30433577 | 21 | 45723974 | 45761654 |
| 21 | 30435073 | 30435921 | 21 | 45763812 | 45764286 |
| 21 | 30440933 | 30441469 | 21 | 45770706 | 45790912 |
| 21 | 30448998 | 30449767 | 21 | 45795066 | 45796178 |
| 21 | 30456047 | 30456865 | 21 | 45796358 | 45807533 |
| 21 | 30490466 | 30492160 | 21 | 45815783 | 45826793 |
| 21 | 30496711 | 30497041 | 21 | 45828285 | 45829863 |
| 21 | 30516637 | 30517797 | 21 | 45835582 | 45846001 |
| 21 | 30524308 | 30528366 | 21 | 45849002 | 45864439 |
| 21 | 30554666 | 30555728 | 21 | 45866861 | 45887923 |
| 21 | 30579872 | 30583740 | 21 | 45902207 | 45903132 |
| 21 | 30604917 | 30605561 | 21 | 45924493 | 45924674 |
| 21 | 30608678 | 30611205 | 21 | 45926587 | 45927605 |
| 21 | 30613566 | 30614255 | 21 | 45941168 | 45941576 |
| 21 | 30620859 | 30621868 | 21 | 45942358 | 45942880 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| 21 | 30652876 | 30655014 | | | 21 | 45944923 | 45952815 |
| 21 | 30693184 | 30695648 | | | 21 | 45957645 | 45958115 |
| 21 | 30702944 | 30703715 | | | 21 | 45968597 | 45970926 |
| 21 | 30737665 | 30743825 | | | 21 | 45978421 | 45985668 |
| 21 | 30762576 | 30770211 | | | 21 | 45989308 | 45995113 |
| 21 | 30773414 | 30774033 | | | 21 | 46005553 | 46015267 |
| 21 | 30777522 | 30780052 | | | 21 | 46027671 | 46038171 |
| 21 | 30815948 | 30816249 | | | 21 | 46044394 | 46054308 |
| 21 | 30861165 | 30862568 | | | 21 | 46061370 | 46082424 |
| 21 | 30909193 | 30910398 | | | 21 | 46088390 | 46088925 |
| 21 | 30926510 | 30928160 | | | 21 | 46089775 | 46094967 |
| 21 | 30944258 | 30947292 | | | 21 | 46096329 | 46128242 |
| 21 | 30971221 | 30974548 | | | 21 | 46131017 | 46199070 |
| 21 | 31020131 | 31021420 | | | 21 | 46203591 | 46207480 |
| 21 | 31039506 | 31043894 | | | 21 | 46214555 | 46216143 |
| 21 | 31050856 | 31052874 | | | 21 | 46221986 | 46256428 |
| 21 | 31054998 | 31056932 | | | 21 | 46265758 | 46268403 |
| 21 | 31065848 | 31067613 | | | 21 | 46273291 | 46273866 |
| 21 | 31106735 | 31107621 | | | 21 | 46275049 | 46286751 |
| 21 | 31114545 | 31116276 | | | 21 | 46290902 | 46305144 |
| 21 | 31124604 | 31124875 | | | 21 | 46307306 | 46316244 |
| 21 | 31142047 | 31142698 | | | 21 | 46319440 | 46330287 |
| 21 | 31158711 | 31160478 | | | 21 | 46333804 | 46345397 |
| 21 | 31173741 | 31175789 | | | 21 | 46354395 | 46407945 |
| 21 | 31179770 | 31183705 | | | 21 | 46412348 | 46413554 |
| 21 | 31185031 | 31186946 | | | 21 | 46424213 | 46428633 |
| 21 | 31220861 | 31223437 | | | 21 | 46432872 | 46441288 |
| 21 | 31257429 | 31258561 | | | 21 | 46445349 | 46446826 |
| 21 | 31289054 | 31289721 | | | 21 | 46449404 | 46470624 |
| 21 | 31294904 | 31299163 | | | 21 | 46475635 | 46476384 |
| 21 | 31313908 | 31315503 | | | 21 | 46478751 | 46479181 |
| 21 | 31324681 | 31326753 | | | 21 | 46499292 | 46501370 |
| 21 | 31363686 | 31364137 | | | 21 | 46508744 | 46511864 |
| 21 | 31366416 | 31367850 | | | 21 | 46536756 | 46541736 |
| 21 | 31391934 | 31394055 | | | 21 | 46558738 | 46563621 |
| 21 | 31395960 | 31396482 | | | 21 | 46590142 | 46603640 |
| 21 | 31397916 | 31398401 | | | 21 | 46605908 | 46612146 |
| 21 | 31409607 | 31411344 | | | 21 | 46613161 | 46613517 |
| 21 | 31417215 | 31417614 | | | 21 | 46623242 | 46634383 |
| 21 | 31426781 | 31427526 | | | 21 | 46637339 | 46648176 |
| 21 | 31441205 | 31445828 | | | 21 | 46655289 | 46661443 |
| 21 | 31455031 | 31455971 | | | 21 | 46663055 | 46681374 |
| 21 | 31470951 | 31471326 | | | 21 | 46686249 | 46687340 |
| 21 | 31474893 | 31475533 | | | 21 | 46733882 | 46735656 |
| 21 | 31479051 | 31479445 | | | 21 | 46782145 | 46784660 |
| 21 | 31481502 | 31486405 | | | 21 | 46795106 | 46795994 |
| 21 | 31540641 | 31540970 | | | 21 | 46799339 | 46802624 |
| 21 | 31560560 | 31561531 | | | 21 | 46803997 | 46804858 |
| 21 | 31562011 | 31562940 | | | 21 | 46804939 | 46811005 |
| 21 | 31620819 | 31621487 | | | 21 | 46840367 | 46847181 |
| 21 | 31628767 | 31633512 | | | 21 | 46870451 | 46870863 |
| | | | | | 21 | 46892756 | 46896266 |
| | | | | | 21 | 46905700 | 46909083 |
| | | | | | 21 | 46914502 | 46915092 |
| 21 | 9719878 | 9788426 | | | 21 | 9988929 | 9989124 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 9797728 | 9797833 | 21 | 9997703 | 10009267 |
| 21 | 9798258 | 9798383 | 21 | 10012732 | 10013282 |
| 21 | 9800293 | 9800383 | 21 | 10016379 | 10016384 |
| 21 | 9807218 | 9807393 | 21 | 10018061 | 10019015 |
| 21 | 9808858 | 9808913 | 21 | 10019205 | 10019370 |
| 21 | 9813988 | 9814153 | 21 | 10021519 | 10021534 |
| 21 | 9820563 | 9820718 | 21 | 10023538 | 10027590 |
| 21 | 9827453 | 9828203 | 21 | 10048131 | 10062812 |
| 21 | 9832023 | 9832173 | 21 | 10063389 | 10063794 |
| 21 | 9832488 | 9832693 | 21 | 10065347 | 10068103 |
| 21 | 9834578 | 9835268 | 21 | 10069278 | 10071149 |
| 21 | 9836253 | 9836398 | 21 | 10073705 | 10073780 |
| 21 | 9842043 | 9843008 | 21 | 10074920 | 10081303 |
| 21 | 9844453 | 9845018 | 21 | 10085350 | 10086145 |
| 21 | 9846588 | 9846663 | 21 | 10087067 | 10087167 |
| 21 | 9849278 | 9849603 | 21 | 10089320 | 10091528 |
| 21 | 9850573 | 9850723 | 21 | 10093946 | 10094056 |
| 21 | 9852636 | 9852801 | 21 | 10095123 | 10098822 |
| 21 | 9853581 | 9854206 | 21 | 10100349 | 10101652 |
| 21 | 9855206 | 9855216 | 21 | 10103834 | 10104234 |
| 21 | 9862341 | 9862976 | 21 | 10106064 | 10106094 |
| 21 | 9868086 | 9868336 | 21 | 10106604 | 10106639 |
| 21 | 9871011 | 9872861 | 21 | 10106889 | 10107199 |
| 21 | 9873046 | 9874131 | 21 | 10108279 | 10109447 |
| 21 | 9877096 | 9877896 | 21 | 10109742 | 10109872 |
| 21 | 9879831 | 9880486 | 21 | 10110924 | 10111469 |
| 21 | 9883221 | 9883636 | 21 | 10115310 | 10115985 |
| 21 | 9884031 | 9886772 | 21 | 10117130 | 10117370 |
| 21 | 9887152 | 9887332 | 21 | 10118697 | 10119542 |
| 21 | 9887702 | 9888418 | 21 | 10120392 | 10120652 |
| 21 | 9889528 | 9889543 | 21 | 10121320 | 10121771 |
| 21 | 9891183 | 9892624 | 21 | 10125021 | 10125976 |
| 21 | 9893639 | 9894319 | 21 | 10128774 | 10139128 |
| 21 | 9894859 | 9895539 | 21 | 10140108 | 10140773 |
| 21 | 9896104 | 9896189 | 21 | 10142313 | 10142843 |
| 21 | 9896264 | 9896379 | 21 | 10143438 | 10143698 |
| 21 | 9896589 | 9912702 | 21 | 10145488 | 10145876 |
| 21 | 9913947 | 9913952 | 21 | 10148881 | 10153426 |
| 21 | 9914527 | 9915257 | 21 | 10157563 | 10157693 |
| 21 | 9923447 | 9924472 | 21 | 10158108 | 10158158 |
| 21 | 9927546 | 9927561 | 21 | 10159128 | 10159548 |
| 21 | 9928097 | 9930739 | 21 | 10161345 | 10170099 |
| 21 | 9939690 | 9940160 | 21 | 10173459 | 10178029 |
| 21 | 9953231 | 9957943 | 21 | 10179129 | 10183172 |
| 21 | 9964912 | 9984104 | 21 | 10189836 | 10190678 |
| 21 | 9985374 | 9985639 | 21 | 10194484 | 10195214 |
| 21 | 9987109 | 9987579 | 21 | 10200219 | 10202865 |
|  |  |  | 21 | 10203850 | 10209860 |
| 21 | 13262506 | 13290836 | 21 | 32093053 | 32101062 |
| 21 | 13349713 | 13434482 | 21 | 32103907 | 32104982 |
| 21 | 13555603 | 13561359 | 21 | 32121587 | 32122427 |
| 21 | 13583857 | 13599167 | 21 | 32132316 | 32133828 |
| 21 | 13635803 | 13649799 | 21 | 32134173 | 32134968 |
| 21 | 13659657 | 13670773 | 21 | 32138875 | 32142418 |
| 21 | 13734190 | 13746952 | 21 | 32162772 | 32163677 |

*The chromosomal position was obtained from UCSC genome browser (http://genome.ucsc.edu/) build 36.

Appendix A: Chromosome 21

Page 21 of 39

| Chr | Start | End | Chr | Start | End |
|---|---|---|---|---|---|
| 21 | 13841528 | 13854681 | 21 | 32168488 | 32170723 |
| 21 | 13868804 | 13875590 | 21 | 32181214 | 32182234 |
| 21 | 13903490 | 13905107 | 21 | 32187631 | 32188762 |
| 21 | 13958252 | 13976374 | 21 | 32202212 | 32203036 |
| 21 | 13989205 | 13992040 | 21 | 32209971 | 32212186 |
| 21 | 13998229 | 14001569 | 21 | 32226171 | 32228108 |
| 21 | 14018290 | 14018485 | 21 | 32232648 | 32234114 |
| 21 | 14056242 | 14060356 | 21 | 32238221 | 32240250 |
| 21 | 14120001 | 14126926 | 21 | 32253974 | 32256818 |
| 21 | 14127720 | 14134125 | 21 | 32268212 | 32269272 |
| 21 | 14234411 | 14269538 | 21 | 32316104 | 32318090 |
| 21 | 14273690 | 14276391 | 21 | 32323529 | 32324919 |
| 21 | 14330734 | 14335971 | 21 | 32327749 | 32328872 |
| 21 | 14364092 | 14378793 | 21 | 32336737 | 32338977 |
| 21 | 14383668 | 14385230 | 21 | 32350325 | 32351385 |
| 21 | 14416763 | 14417983 | 21 | 32359510 | 32361994 |
| 21 | 14451103 | 14452078 | 21 | 32362514 | 32363829 |
| 21 | 14489067 | 14489652 | 21 | 32374349 | 32375460 |
| 21 | 14500289 | 14501219 | 21 | 32383339 | 32384679 |
| 21 | 14528345 | 14529210 | 21 | 32399340 | 32399926 |
| 21 | 14553771 | 14554301 | 21 | 32408479 | 32409791 |
| 21 | 14567839 | 14568964 | 21 | 32427751 | 32430262 |
| 21 | 14579213 | 14580003 | 21 | 32454809 | 32457111 |
| 21 | 14593615 | 14594385 | 21 | 32477915 | 32485460 |
| 21 | 14602478 | 14603278 | 21 | 32500977 | 32502252 |
| 21 | 14619065 | 14620195 | 21 | 32511797 | 32512487 |
| 21 | 14647443 | 14648908 | 21 | 32529319 | 32530710 |
| 21 | 14650908 | 14651499 | 21 | 32539559 | 32552999 |
| 21 | 14652908 | 14653438 | 21 | 32632937 | 32634447 |
| 21 | 14661780 | 14662660 | 21 | 32641166 | 32647169 |
| 21 | 14677441 | 14679198 | 21 | 32653989 | 32656360 |
| 21 | 14686776 | 14688012 | 21 | 32670758 | 32673447 |
| 21 | 14699163 | 14699748 | 21 | 32694539 | 32696343 |
| 21 | 14701194 | 14709453 | 21 | 32703795 | 32705205 |
| 21 | 14737886 | 14738356 | 21 | 32707187 | 32708107 |
| 21 | 14740036 | 14740321 | 21 | 32727639 | 32728959 |
| 21 | 14744786 | 14746093 | 21 | 32732719 | 32734760 |
| 21 | 14747657 | 14748989 | 21 | 32740020 | 32745183 |
| 21 | 14767309 | 14768789 | 21 | 32749950 | 32757873 |
| 21 | 14770931 | 14771887 | 21 | 32759992 | 32763705 |
| 21 | 14777077 | 14778152 | 21 | 32768061 | 32770975 |
| 21 | 14784608 | 14785228 | 21 | 32776813 | 32778832 |
| 21 | 14803775 | 14804829 | 21 | 32789431 | 32791152 |
| 21 | 14846043 | 14846578 | 21 | 32800835 | 32807175 |
| 21 | 14854020 | 14855011 | 21 | 32812919 | 32821181 |
| 21 | 14855871 | 14856626 | 21 | 32828921 | 32836147 |
| 21 | 14861245 | 14863164 | 21 | 32839087 | 32840811 |
| 21 | 14886031 | 14887076 | 21 | 32845950 | 32849146 |
| 21 | 14896894 | 14897614 | 21 | 32866374 | 32881935 |
| 21 | 14898983 | 14899593 | 21 | 32885250 | 32891634 |
| 21 | 14930338 | 14930678 | 21 | 32907757 | 32914606 |
| 21 | 14931784 | 14932329 | 21 | 32924362 | 32924427 |
| 21 | 14936439 | 14937189 | 21 | 32948310 | 32949800 |
| 21 | 14951908 | 14953183 | 21 | 32955157 | 32956317 |
| 21 | 14971922 | 14972872 | 21 | 33011769 | 33012379 |

*The chromosomal position was obtained from UCSC genome browser (http://genome.ucsc.edu/) build 36.

Appendix A: Chromosome 21

Page 22 of 39

| Chr | Start | End | Chr | Start | End |
|---|---|---|---|---|---|
| 21 | 14981699 | 14982844 | 21 | 33053210 | 33053705 |
| 21 | 14988416 | 14995024 | 21 | 33081990 | 33083120 |
| 21 | 15000460 | 15002355 | 21 | 33086972 | 33087984 |
| 21 | 15022820 | 15024650 | 21 | 33103755 | 33105161 |
| 21 | 15031401 | 15035884 | 21 | 33126530 | 33127798 |
| 21 | 15069250 | 15069809 | 21 | 33134026 | 33135927 |
| 21 | 15090377 | 15091523 | 21 | 33138148 | 33139174 |
| 21 | 15124518 | 15125178 | 21 | 33145991 | 33147423 |
| 21 | 15130561 | 15132803 | 21 | 33157760 | 33160968 |
| 21 | 15147720 | 15149700 | 21 | 33162672 | 33163710 |
| 21 | 15151602 | 15151977 | 21 | 33172806 | 33173346 |
| 21 | 15153318 | 15154778 | 21 | 33174471 | 33181142 |
| 21 | 15158063 | 15158510 | 21 | 33185277 | 33188343 |
| 21 | 15164081 | 15166145 | 21 | 33196030 | 33196820 |
| 21 | 15167752 | 15169920 | 21 | 33198030 | 33199035 |
| 21 | 15171705 | 15172707 | 21 | 33200271 | 33204828 |
| 21 | 15173637 | 15174827 | 21 | 33211938 | 33215195 |
| 21 | 15179752 | 15184434 | 21 | 33215965 | 33216480 |
| 21 | 15187648 | 15189368 | 21 | 33234270 | 33236235 |
| 21 | 15209448 | 15211218 | 21 | 33244818 | 33248010 |
| 21 | 15236856 | 15239626 | 21 | 33249350 | 33252355 |
| 21 | 15243264 | 15246031 | 21 | 33255808 | 33256703 |
| 21 | 15251691 | 15254401 | 21 | 33267561 | 33273733 |
| 21 | 15259510 | 15263594 | 21 | 33279740 | 33281530 |
| 21 | 15284495 | 15285600 | 21 | 33284925 | 33285628 |
| 21 | 15336560 | 15337195 | 21 | 33307083 | 33309433 |
| 21 | 15357144 | 15358017 | 21 | 33320555 | 33323129 |
| 21 | 15360256 | 15363776 | 21 | 33324044 | 33330419 |
| 21 | 15366102 | 15371171 | 21 | 33335348 | 33337224 |
| 21 | 15375122 | 15377107 | 21 | 33340663 | 33342896 |
| 21 | 15378711 | 15380987 | 21 | 33345217 | 33346991 |
| 21 | 15389531 | 15391451 | 21 | 33349686 | 33358745 |
| 21 | 15393994 | 15395629 | 21 | 33376949 | 33378329 |
| 21 | 15401385 | 15403835 | 21 | 33395452 | 33400308 |
| 21 | 15425425 | 15426669 | 21 | 33402309 | 33407913 |
| 21 | 15427669 | 15431225 | 21 | 33411393 | 33412728 |
| 21 | 15443158 | 15446809 | 21 | 33424734 | 33426279 |
| 21 | 15451775 | 15457851 | 21 | 33428724 | 33431466 |
| 21 | 15459202 | 15460302 | 21 | 33447702 | 33449752 |
| 21 | 15477784 | 15480529 | 21 | 33455340 | 33457206 |
| 21 | 15491334 | 15493660 | 21 | 33458626 | 33465592 |
| 21 | 15501972 | 15503402 | 21 | 33470119 | 33471790 |
| 21 | 15528314 | 15529169 | 21 | 33480408 | 33484689 |
| 21 | 15537418 | 15541555 | 21 | 33485320 | 33486135 |
| 21 | 15544829 | 15545864 | 21 | 33526505 | 33527290 |
| 21 | 15554204 | 15559726 | 21 | 33532645 | 33534368 |
| 21 | 15568101 | 15570256 | 21 | 33538544 | 33539159 |
| 21 | 15585001 | 15585406 | 21 | 33557997 | 33558800 |
| 21 | 15587366 | 15587916 | 21 | 33563476 | 33565953 |
| 21 | 15591004 | 15592054 | 21 | 33601708 | 33603473 |
| 21 | 15595742 | 15597102 | 21 | 33606704 | 33607752 |
| 21 | 15603721 | 15604330 | 21 | 33612429 | 33613781 |
| 21 | 15606153 | 15607508 | 21 | 33635806 | 33637609 |
| 21 | 15617061 | 15618732 | 21 | 33680333 | 33684917 |
| 21 | 15640488 | 15640973 | 21 | 33693377 | 33697952 |

*The chromosomal position was obtained from UCSC genome browser (http://genome.ucsc.edu/) build 36.

Appendix A: Chromosome 21
Page 23 of 39

| Chr | Start | End | Chr | Start | End |
|---|---|---|---|---|---|
| 21 | 15648812 | 15653184 | 21 | 33770597 | 33773013 |
| 21 | 15665686 | 15666906 | 21 | 33790375 | 33792755 |
| 21 | 15692712 | 15696862 | 21 | 33870802 | 33872617 |
| 21 | 15726816 | 15729027 | 21 | 33950007 | 33951545 |
| 21 | 15735014 | 15740828 | 21 | 33977283 | 33978383 |
| 21 | 15791585 | 15793333 | 21 | 33992198 | 33992728 |
| 21 | 15795548 | 15797783 | 21 | 34033569 | 34034379 |
| 21 | 15805894 | 15806284 | 21 | 34048060 | 34049295 |
| 21 | 15822141 | 15827116 | 21 | 34093110 | 34094193 |
| 21 | 15834907 | 15837326 | 21 | 34142434 | 34143044 |
| 21 | 15844382 | 15847023 | 21 | 34167677 | 34171784 |
| 21 | 15853702 | 15862928 | 21 | 34177162 | 34179149 |
| 21 | 15882867 | 15884122 | 21 | 34189077 | 34190752 |
| 21 | 15886901 | 15888405 | 21 | 34251270 | 34252660 |
| 21 | 15892827 | 15896002 | 21 | 34265512 | 34266257 |
| 21 | 15897202 | 15901990 | 21 | 34269712 | 34271735 |
| 21 | 15906865 | 15910127 | 21 | 34278125 | 34281032 |
| 21 | 15914537 | 15915877 | 21 | 34284438 | 34286412 |
| 21 | 15926849 | 15930194 | 21 | 34311184 | 34311779 |
| 21 | 15980028 | 15981993 | 21 | 34328821 | 34331181 |
| 21 | 15988390 | 15993591 | 21 | 34355852 | 34358129 |
| 21 | 15996309 | 15999804 | 21 | 34368470 | 34369221 |
| 21 | 16009972 | 16012089 | 21 | 34369752 | 34372492 |
| 21 | 16018276 | 16020867 | 21 | 34376282 | 34377839 |
| 21 | 16051214 | 16055115 | 21 | 34380979 | 34381854 |
| 21 | 16088515 | 16092540 | 21 | 34391705 | 34399194 |
| 21 | 16112001 | 16113091 | 21 | 34405408 | 34409188 |
| 21 | 16125615 | 16126425 | 21 | 34444478 | 34445728 |
| 21 | 16132596 | 16136375 | 21 | 34446253 | 34447733 |
| 21 | 16243820 | 16250419 | 21 | 34492084 | 34493539 |
| 21 | 16258451 | 16259994 | 21 | 34496001 | 34498886 |
| 21 | 16262895 | 16263962 | 21 | 34515058 | 34516583 |
| 21 | 16270860 | 16271365 | 21 | 34553406 | 34554493 |
| 21 | 16283810 | 16284620 | 21 | 34586200 | 34587755 |
| 21 | 16286543 | 16287413 | 21 | 34594454 | 34595524 |
| 21 | 16300664 | 16302901 | 21 | 34600044 | 34600633 |
| 21 | 16304226 | 16305141 | 21 | 34612008 | 34612913 |
| 21 | 16330670 | 16332785 | 21 | 34626507 | 34631942 |
| 21 | 16333770 | 16335618 | 21 | 34640036 | 34641312 |
| 21 | 16364594 | 16365801 | 21 | 34649496 | 34651263 |
| 21 | 16367091 | 16367721 | 21 | 34684481 | 34685414 |
| 21 | 16371052 | 16374577 | 21 | 34693785 | 34694535 |
| 21 | 16402040 | 16403965 | 21 | 34720191 | 34721963 |
| 21 | 16428881 | 16431652 | 21 | 34723777 | 34724762 |
| 21 | 16469508 | 16470698 | 21 | 34738782 | 34745792 |
| 21 | 16474191 | 16475550 | 21 | 34753243 | 34755195 |
| 21 | 16492845 | 16493925 | 21 | 34757719 | 34758964 |
| 21 | 16499622 | 16500601 | 21 | 34761484 | 34762739 |
| 21 | 16506715 | 16507884 | 21 | 34775098 | 34777966 |
| 21 | 16552624 | 16553729 | 21 | 34784802 | 34785655 |
| 21 | 16564239 | 16565234 | 21 | 34799047 | 34802075 |
| 21 | 16570384 | 16571284 | 21 | 34804363 | 34805288 |
| 21 | 16611848 | 16612843 | 21 | 34809836 | 34811060 |
| 21 | 16615193 | 16616137 | 21 | 34813102 | 34815233 |
| 21 | 16622781 | 16625684 | 21 | 34822950 | 34823510 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 16637227 | 16638037 | 21 | 34830874 | 34831604 |
| 21 | 16641591 | 16644966 | 21 | 34860706 | 34862762 |
| 21 | 16648726 | 16649322 | 21 | 34885292 | 34886797 |
| 21 | 16710115 | 16711026 | 21 | 34895652 | 34897712 |
| 21 | 16721776 | 16722738 | 21 | 34916531 | 34918106 |
| 21 | 16756014 | 16759369 | 21 | 34919627 | 34920983 |
| 21 | 16770850 | 16774215 | 21 | 34925827 | 34929502 |
| 21 | 16779740 | 16780245 | 21 | 34937848 | 34943580 |
| 21 | 16803419 | 16805034 | 21 | 34947141 | 34948786 |
| 21 | 16862826 | 16864805 | 21 | 34953843 | 34954733 |
| 21 | 16870224 | 16870349 | 21 | 34958646 | 34960426 |
| 21 | 16873264 | 16874614 | 21 | 34962008 | 34963328 |
| 21 | 16882277 | 16883327 | 21 | 34970989 | 34971893 |
| 21 | 16902721 | 16903816 | 21 | 34982059 | 34984078 |
| 21 | 16916783 | 16918763 | 21 | 34992920 | 35000819 |
| 21 | 16929275 | 16931516 | 21 | 35002734 | 35010454 |
| 21 | 16968099 | 16970142 | 21 | 35013018 | 35017522 |
| 21 | 16985512 | 16987242 | 21 | 35022987 | 35025511 |
| 21 | 17002805 | 17004426 | 21 | 35031857 | 35038725 |
| 21 | 17013876 | 17014606 | 21 | 35043442 | 35050229 |
| 21 | 17045035 | 17046413 | 21 | 35053040 | 35055882 |
| 21 | 17066508 | 17067168 | 21 | 35060836 | 35061566 |
| 21 | 17087871 | 17088481 | 21 | 35074555 | 35077085 |
| 21 | 17093363 | 17093838 | 21 | 35105193 | 35105938 |
| 21 | 17119104 | 17121088 | 21 | 35112094 | 35115229 |
| 21 | 17130964 | 17132847 | 21 | 35127600 | 35128230 |
| 21 | 17142920 | 17145364 | 21 | 35130370 | 35131655 |
| 21 | 17159615 | 17164264 | 21 | 35136378 | 35139815 |
| 21 | 17166222 | 17166632 | 21 | 35154924 | 35159747 |
| 21 | 17179719 | 17181589 | 21 | 35163727 | 35166339 |
| 21 | 17185303 | 17186143 | 21 | 35179557 | 35180622 |
| 21 | 17192825 | 17194075 | 21 | 35184696 | 35186100 |
| 21 | 17221909 | 17222200 | 21 | 35189558 | 35191253 |
| 21 | 17226475 | 17229580 | 21 | 35192603 | 35193513 |
| 21 | 17236653 | 17237458 | 21 | 35200468 | 35202992 |
| 21 | 17268584 | 17270728 | 21 | 35205700 | 35208975 |
| 21 | 17273810 | 17274650 | 21 | 35213855 | 35214717 |
| 21 | 17286045 | 17286530 | 21 | 35219257 | 35221519 |
| 21 | 17296860 | 17297425 | 21 | 35223238 | 35223628 |
| 21 | 17310844 | 17312704 | 21 | 35224613 | 35230777 |
| 21 | 17345642 | 17346077 | 21 | 35236192 | 35239203 |
| 21 | 17351411 | 17353203 | 21 | 35241598 | 35243398 |
| 21 | 17359173 | 17361773 | 21 | 35251659 | 35255109 |
| 21 | 17369764 | 17370024 | 21 | 35257694 | 35259768 |
| 21 | 17371889 | 17373209 | 21 | 35261541 | 35262641 |
| 21 | 17434282 | 17435127 | 21 | 35265960 | 35267590 |
| 21 | 17439277 | 17440274 | 21 | 35274063 | 35274903 |
| 21 | 17455240 | 17456585 | 21 | 35279180 | 35280447 |
| 21 | 17476715 | 17479205 | 21 | 35282113 | 35288327 |
| 21 | 17494450 | 17496190 | 21 | 35293744 | 35295565 |
| 21 | 17502961 | 17505402 | 21 | 35297561 | 35299179 |
| 21 | 17512467 | 17516794 | 21 | 35319662 | 35323229 |
| 21 | 17520808 | 17524126 | 21 | 35329178 | 35330113 |
| 21 | 17543807 | 17544247 | 21 | 35340041 | 35341026 |
| 21 | 17551450 | 17552120 | 21 | 35342261 | 35345378 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 17553320 | 17554805 | 21 | 35355558 | 35356898 |
| 21 | 17597888 | 17601920 | 21 | 35359115 | 35359460 |
| 21 | 17656926 | 17657356 | 21 | 35379559 | 35381104 |
| 21 | 17684349 | 17685627 | 21 | 35381993 | 35383734 |
| 21 | 17688272 | 17689353 | 21 | 35387124 | 35387344 |
| 21 | 17706989 | 17708105 | 21 | 35390872 | 35393632 |
| 21 | 17713669 | 17714289 | 21 | 35394286 | 35396501 |
| 21 | 17719307 | 17725246 | 21 | 35399163 | 35402012 |
| 21 | 17731360 | 17731529 | 21 | 35425934 | 35427909 |
| 21 | 17735305 | 17737173 | 21 | 35450882 | 35452147 |
| 21 | 17737543 | 17739910 | 21 | 35453527 | 35456440 |
| 21 | 17747543 | 17750937 | 21 | 35460698 | 35461698 |
| 21 | 17775675 | 17776940 | 21 | 35474290 | 35475090 |
| 21 | 17778654 | 17780325 | 21 | 35498658 | 35499812 |
| 21 | 17813598 | 17817293 | 21 | 35515015 | 35517350 |
| 21 | 17822077 | 17826495 | 21 | 35520916 | 35522016 |
| 21 | 17828669 | 17829754 | 21 | 35523361 | 35523846 |
| 21 | 17832084 | 17833059 | 21 | 35526700 | 35527430 |
| 21 | 17847552 | 17849236 | 21 | 35533959 | 35534369 |
| 21 | 17872701 | 17874035 | 21 | 35542738 | 35543468 |
| 21 | 17904576 | 17905532 | 21 | 35558711 | 35560996 |
| 21 | 17914762 | 17915663 | 21 | 35578333 | 35581034 |
| 21 | 17928599 | 17929842 | 21 | 35595001 | 35595952 |
| 21 | 17933119 | 17934549 | 21 | 35611050 | 35619970 |
| 21 | 17985230 | 17986060 | 21 | 35628667 | 35629607 |
| 21 | 17987331 | 17988759 | 21 | 35631771 | 35632141 |
| 21 | 18008260 | 18009300 | 21 | 35644298 | 35644933 |
| 21 | 18023347 | 18023902 | 21 | 35645698 | 35646493 |
| 21 | 18040430 | 18041870 | 21 | 35646868 | 35648458 |
| 21 | 18054061 | 18056376 | 21 | 35654211 | 35654776 |
| 21 | 18063192 | 18071580 | 21 | 35657287 | 35659188 |
| 21 | 18077827 | 18081404 | 21 | 35667594 | 35668019 |
| 21 | 18088768 | 18091027 | 21 | 35669119 | 35669489 |
| 21 | 18116780 | 18117235 | 21 | 35672129 | 35675957 |
| 21 | 18123311 | 18124531 | 21 | 35690711 | 35691851 |
| 21 | 18129310 | 18130000 | 21 | 35695587 | 35695862 |
| 21 | 18134891 | 18136029 | 21 | 35697093 | 35700038 |
| 21 | 18152115 | 18156696 | 21 | 35710513 | 35711578 |
| 21 | 18164616 | 18170769 | 21 | 35733910 | 35735331 |
| 21 | 18179564 | 18180219 | 21 | 35736496 | 35737181 |
| 21 | 18180844 | 18180864 | 21 | 35754356 | 35755062 |
| 21 | 18195920 | 18197219 | 21 | 35761989 | 35763315 |
| 21 | 18214789 | 18216684 | 21 | 35766354 | 35767464 |
| 21 | 18234106 | 18238193 | 21 | 35770364 | 35773349 |
| 21 | 18254899 | 18255034 | 21 | 35778357 | 35779547 |
| 21 | 18289985 | 18290830 | 21 | 35812211 | 35816531 |
| 21 | 18328499 | 18329504 | 21 | 35818588 | 35824553 |
| 21 | 18337153 | 18338318 | 21 | 35834122 | 35834577 |
| 21 | 18339560 | 18342045 | 21 | 35838614 | 35839449 |
| 21 | 18349674 | 18350079 | 21 | 35859434 | 35860239 |
| 21 | 18358360 | 18359965 | 21 | 35872698 | 35873378 |
| 21 | 18360880 | 18362347 | 21 | 35874513 | 35875343 |
| 21 | 18401415 | 18405921 | 21 | 35878086 | 35881014 |
| 21 | 18413635 | 18415840 | 21 | 35881759 | 35882424 |
| 21 | 18432804 | 18434339 | 21 | 35886918 | 35887658 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 18441127 | 18441797 | 21 | 35897391 | 35898966 |
| 21 | 18446433 | 18447653 | 21 | 35905384 | 35905744 |
| 21 | 18449003 | 18450443 | 21 | 35909104 | 35910757 |
| 21 | 18466135 | 18467010 | 21 | 35917742 | 35918087 |
| 21 | 18488131 | 18489066 | 21 | 35927494 | 35928964 |
| 21 | 18517125 | 18518970 | 21 | 35937218 | 35938548 |
| 21 | 18547734 | 18548849 | 21 | 35942702 | 35943497 |
| 21 | 18560907 | 18562867 | 21 | 35949924 | 35951935 |
| 21 | 18628640 | 18629265 | 21 | 35953279 | 35956158 |
| 21 | 18649583 | 18650108 | 21 | 35968439 | 35969444 |
| 21 | 18662247 | 18663967 | 21 | 35973377 | 35974177 |
| 21 | 18677694 | 18678901 | 21 | 35975532 | 35976377 |
| 21 | 18717279 | 18717959 | 21 | 35979525 | 35980521 |
| 21 | 18734060 | 18734713 | 21 | 35981971 | 35982641 |
| 21 | 18771281 | 18775282 | 21 | 35985928 | 35989258 |
| 21 | 18786338 | 18787189 | 21 | 35994179 | 35997065 |
| 21 | 18795884 | 18795914 | 21 | 36006389 | 36007779 |
| 21 | 18818573 | 18818898 | 21 | 36009113 | 36011607 |
| 21 | 18840831 | 18842114 | 21 | 36015505 | 36019000 |
| 21 | 18845787 | 18847054 | 21 | 36026329 | 36029718 |
| 21 | 18871005 | 18876002 | 21 | 36037441 | 36039211 |
| 21 | 18883892 | 18884933 | 21 | 36059589 | 36068550 |
| 21 | 18905450 | 18908766 | 21 | 36074558 | 36076538 |
| 21 | 18914899 | 18915959 | 21 | 36104455 | 36106393 |
| 21 | 18923773 | 18924183 | 21 | 36110193 | 36112075 |
| 21 | 18927881 | 18932849 | 21 | 36117490 | 36119650 |
| 21 | 18936619 | 18938419 | 21 | 36125611 | 36126239 |
| 21 | 18971989 | 18973189 | 21 | 36138360 | 36142109 |
| 21 | 19031386 | 19035549 | 21 | 36144927 | 36145392 |
| 21 | 19044415 | 19048149 | 21 | 36147693 | 36149278 |
| 21 | 19060584 | 19061379 | 21 | 36150420 | 36151661 |
| 21 | 19062804 | 19063949 | 21 | 36170455 | 36173410 |
| 21 | 19118700 | 19120120 | 21 | 36176865 | 36177370 |
| 21 | 19134022 | 19135342 | 21 | 36180431 | 36181691 |
| 21 | 19142462 | 19143070 | 21 | 36198476 | 36200018 |
| 21 | 19156488 | 19156913 | 21 | 36214779 | 36216206 |
| 21 | 19215551 | 19219731 | 21 | 36228726 | 36229611 |
| 21 | 19248330 | 19249060 | 21 | 36236254 | 36237789 |
| 21 | 19278785 | 19280680 | 21 | 36248985 | 36249680 |
| 21 | 19281090 | 19282282 | 21 | 36268667 | 36269998 |
| 21 | 19284153 | 19284588 | 21 | 36278292 | 36279129 |
| 21 | 19327073 | 19328182 | 21 | 36282130 | 36283150 |
| 21 | 19335050 | 19337635 | 21 | 36283420 | 36289091 |
| 21 | 19345846 | 19349636 | 21 | 36294711 | 36296331 |
| 21 | 19364596 | 19370333 | 21 | 36298750 | 36301523 |
| 21 | 19384871 | 19385758 | 21 | 36324578 | 36328949 |
| 21 | 19402569 | 19406161 | 21 | 36338371 | 36339431 |
| 21 | 19412232 | 19413398 | 21 | 36356571 | 36359364 |
| 21 | 19419799 | 19421104 | 21 | 36364802 | 36366639 |
| 21 | 19479484 | 19480599 | 21 | 36373328 | 36374027 |
| 21 | 19488501 | 19489163 | 21 | 36417575 | 36418270 |
| 21 | 19490026 | 19491856 | 21 | 36436276 | 36437506 |
| 21 | 19496688 | 19496758 | 21 | 36487200 | 36488215 |
| 21 | 19499704 | 19500812 | 21 | 36501934 | 36505637 |
| 21 | 19517167 | 19518041 | 21 | 36539698 | 36540928 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 19538664 | 19540334 | 21 | 36589342 | 36590698 |
| 21 | 19549861 | 19552233 | 21 | 36671908 | 36672523 |
| 21 | 19559725 | 19560440 | 21 | 36676663 | 36682368 |
| 21 | 19564592 | 19567745 | 21 | 36702224 | 36707991 |
| 21 | 19597758 | 19600894 | 21 | 36713301 | 36714313 |
| 21 | 19615020 | 19616065 | 21 | 36724140 | 36724947 |
| 21 | 19680204 | 19680919 | 21 | 36756012 | 36757565 |
| 21 | 19683210 | 19684220 | 21 | 36759545 | 36762086 |
| 21 | 19735283 | 19735893 | 21 | 36772751 | 36774696 |
| 21 | 19748676 | 19749884 | 21 | 36782953 | 36789014 |
| 21 | 19761115 | 19768318 | 21 | 36803523 | 36804693 |
| 21 | 19793603 | 19795538 | 21 | 36833288 | 36834628 |
| 21 | 19817444 | 19818019 | 21 | 36848666 | 36850191 |
| 21 | 19847603 | 19848723 | 21 | 36857719 | 36858715 |
| 21 | 19861218 | 19863748 | 21 | 36860761 | 36866694 |
| 21 | 19877425 | 19878315 | 21 | 36881686 | 36883693 |
| 21 | 19894933 | 19896521 | 21 | 36891350 | 36893172 |
| 21 | 19951431 | 19952151 | 21 | 36898472 | 36901107 |
| 21 | 19957961 | 19959342 | 21 | 36905134 | 36907874 |
| 21 | 19989758 | 19992913 | 21 | 36917665 | 36918325 |
| 21 | 20016177 | 20017567 | 21 | 36922151 | 36923821 |
| 21 | 20053696 | 20054516 | 21 | 36934821 | 36937217 |
| 21 | 20079350 | 20080818 | 21 | 36941887 | 36945744 |
| 21 | 20089980 | 20090360 | 21 | 36957346 | 36964281 |
| 21 | 20121973 | 20123483 | 21 | 36988130 | 36989867 |
| 21 | 20127317 | 20128231 | 21 | 36991202 | 36992396 |
| 21 | 20146853 | 20149028 | 21 | 36994989 | 36996174 |
| 21 | 20193716 | 20195284 | 21 | 36998924 | 37000063 |
| 21 | 20215706 | 20216881 | 21 | 37001294 | 37003058 |
| 21 | 20225684 | 20226577 | 21 | 37004655 | 37005116 |
| 21 | 20229845 | 20230390 | 21 | 37012542 | 37018837 |
| 21 | 20244828 | 20246238 | 21 | 37022761 | 37032905 |
| 21 | 20272515 | 20275240 | 21 | 37035061 | 37036810 |
| 21 | 20334689 | 20335879 | 21 | 37146943 | 37147538 |
| 21 | 20357901 | 20360897 | 21 | 37204213 | 37205561 |
| 21 | 20387694 | 20389154 | 21 | 37283066 | 37284911 |
| 21 | 20463994 | 20464778 | 21 | 37288305 | 37289120 |
| 21 | 20512886 | 20513981 | 21 | 37339218 | 37339842 |
| 21 | 20542349 | 20542769 | 21 | 37360785 | 37363134 |
| 21 | 20551397 | 20553062 | 21 | 37365800 | 37368270 |
| 21 | 20566290 | 20567248 | 21 | 37378261 | 37380169 |
| 21 | 20641229 | 20642089 | 21 | 37429887 | 37432975 |
| 21 | 20679937 | 20680223 | 21 | 37451337 | 37452587 |
| 21 | 20701189 | 20702061 | 21 | 37465156 | 37468725 |
| 21 | 20713145 | 20715380 | 21 | 37519536 | 37520376 |
| 21 | 20719318 | 20720398 | 21 | 37551631 | 37552755 |
| 21 | 20721975 | 20722885 | 21 | 37564979 | 37565644 |
| 21 | 20735795 | 20738326 | 21 | 37633214 | 37634094 |
| 21 | 20763334 | 20766097 | 21 | 37634614 | 37635804 |
| 21 | 20788734 | 20790474 | 21 | 37641692 | 37642526 |
| 21 | 20801394 | 20802634 | 21 | 37643306 | 37644916 |
| 21 | 20827042 | 20827315 | 21 | 37666683 | 37667708 |
| 21 | 20859917 | 20859952 | 21 | 37669997 | 37671237 |
| 21 | 20970931 | 20971451 | 21 | 37677529 | 37679884 |
| 21 | 20989515 | 20990470 | 21 | 37708451 | 37710460 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| 21 | 21023641 | 21024401 | | | 21 | 37714469 | 37717724 |
| 21 | 21033582 | 21034137 | | | 21 | 37729070 | 37729780 |
| 21 | 21035027 | 21036016 | | | 21 | 37756654 | 37758034 |
| 21 | 21059966 | 21061761 | | | 21 | 37760193 | 37760363 |
| 21 | 21063965 | 21064380 | | | 21 | 37783302 | 37784363 |
| 21 | 21077658 | 21079683 | | | 21 | 37805614 | 37806806 |
| 21 | 21087883 | 21089201 | | | 21 | 37812254 | 37814217 |
| 21 | 21102070 | 21102730 | | | 21 | 37827221 | 37828655 |
| 21 | 21116854 | 21117144 | | | 21 | 37831037 | 37832311 |
| 21 | 21154710 | 21156236 | | | 21 | 37841076 | 37841866 |
| 21 | 21161602 | 21163187 | | | 21 | 37846840 | 37847925 |
| 21 | 21178782 | 21179597 | | | 21 | 37881643 | 37884376 |
| 21 | 21183613 | 21184743 | | | 21 | 37899530 | 37901190 |
| 21 | 21197372 | 21200084 | | | 21 | 37908363 | 37909638 |
| 21 | 21228120 | 21228650 | | | 21 | 37915292 | 37916302 |
| 21 | 21240685 | 21241243 | | | 21 | 37930285 | 37931075 |
| 21 | 21290759 | 21291294 | | | 21 | 37934212 | 37935315 |
| 21 | 21293932 | 21296666 | | | 21 | 37935835 | 37937095 |
| 21 | 21387260 | 21388245 | | | 21 | 37940149 | 37941309 |
| 21 | 21393274 | 21395130 | | | 21 | 37942204 | 37946790 |
| 21 | 21405659 | 21406028 | | | 21 | 37967759 | 37968404 |
| 21 | 21430551 | 21431022 | | | 21 | 38018295 | 38019701 |
| 21 | 21440354 | 21441416 | | | 21 | 38021381 | 38021961 |
| 21 | 21457115 | 21459728 | | | 21 | 38024706 | 38027091 |
| 21 | 21463563 | 21466068 | | | 21 | 38028206 | 38029646 |
| 21 | 21483625 | 21484997 | | | 21 | 38042661 | 38043951 |
| 21 | 21485992 | 21487088 | | | 21 | 38050037 | 38056367 |
| 21 | 21506552 | 21507562 | | | 21 | 38080485 | 38082025 |
| 21 | 21510599 | 21511324 | | | 21 | 38104269 | 38106844 |
| 21 | 21515588 | 21517917 | | | 21 | 38126375 | 38128510 |
| 21 | 21538720 | 21539657 | | | 21 | 38136345 | 38136925 |
| 21 | 21584688 | 21585583 | | | 21 | 38138120 | 38139290 |
| 21 | 21590351 | 21591136 | | | 21 | 38141400 | 38143965 |
| 21 | 21603346 | 21604156 | | | 21 | 38165511 | 38165876 |
| 21 | 21609221 | 21610101 | | | 21 | 38167866 | 38168596 |
| 21 | 21636009 | 21637035 | | | 21 | 38172695 | 38175601 |
| 21 | 21700420 | 21701500 | | | 21 | 38178185 | 38178975 |
| 21 | 21735850 | 21736410 | | | 21 | 38180653 | 38181503 |
| 21 | 21757712 | 21758802 | | | 21 | 38184208 | 38186134 |
| 21 | 21762428 | 21763413 | | | 21 | 38190003 | 38192448 |
| 21 | 21773883 | 21776334 | | | 21 | 38196351 | 38198539 |
| 21 | 21787417 | 21788029 | | | 21 | 38198911 | 38199446 |
| 21 | 21814659 | 21815799 | | | 21 | 38239642 | 38241688 |
| 21 | 21843381 | 21844206 | | | 21 | 38248443 | 38251185 |
| 21 | 21846350 | 21853813 | | | 21 | 38260470 | 38261100 |
| 21 | 21871880 | 21872540 | | | 21 | 38273302 | 38276350 |
| 21 | 21894955 | 21895595 | | | 21 | 38305222 | 38306748 |
| 21 | 21961515 | 21963575 | | | 21 | 38313712 | 38314587 |
| 21 | 21976840 | 21977641 | | | 21 | 38319561 | 38320572 |
| 21 | 21982509 | 21983233 | | | 21 | 38321252 | 38321907 |
| 21 | 21990429 | 21991036 | | | 21 | 38326298 | 38326968 |
| 21 | 22042755 | 22043309 | | | 21 | 38338632 | 38340162 |
| 21 | 22053383 | 22056561 | | | 21 | 38348727 | 38350472 |
| 21 | 22105717 | 22106732 | | | 21 | 38351572 | 38354338 |
| 21 | 22112809 | 22114902 | | | 21 | 38359121 | 38360396 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 22210629 | 22212335 | 21 | 38383778 | 38385852 |
| 21 | 22244796 | 22245771 | 21 | 38392492 | 38394009 |
| 21 | 22261253 | 22264237 | 21 | 38406361 | 38407473 |
| 21 | 22326593 | 22327752 | 21 | 38414900 | 38415785 |
| 21 | 22336469 | 22337594 | 21 | 38425293 | 38427495 |
| 21 | 22378292 | 22379605 | 21 | 38434792 | 38439805 |
| 21 | 22392443 | 22393058 | 21 | 38441459 | 38445083 |
| 21 | 22399023 | 22400183 | 21 | 38453173 | 38455003 |
| 21 | 22403320 | 22403825 | 21 | 38465082 | 38466553 |
| 21 | 22428547 | 22429792 | 21 | 38466998 | 38468463 |
| 21 | 22448344 | 22451939 | 21 | 38474349 | 38475652 |
| 21 | 22468137 | 22470657 | 21 | 38511157 | 38513484 |
| 21 | 22528096 | 22530981 | 21 | 38530163 | 38530673 |
| 21 | 22547300 | 22548130 | 21 | 38550899 | 38551290 |
| 21 | 22548725 | 22548755 | 21 | 38578008 | 38579733 |
| 21 | 22548805 | 22549585 | 21 | 38595424 | 38596084 |
| 21 | 22568307 | 22570198 | 21 | 38598305 | 38599264 |
| 21 | 22604729 | 22607964 | 21 | 38601189 | 38602504 |
| 21 | 22615877 | 22616372 | 21 | 38609166 | 38609371 |
| 21 | 22637166 | 22638731 | 21 | 38619941 | 38622033 |
| 21 | 22673234 | 22673839 | 21 | 38640535 | 38645115 |
| 21 | 22694945 | 22696255 | 21 | 38650208 | 38651363 |
| 21 | 22715572 | 22717920 | 21 | 38652630 | 38655425 |
| 21 | 22741402 | 22743755 | 21 | 38669819 | 38670969 |
| 21 | 22798825 | 22799640 | 21 | 38674959 | 38678323 |
| 21 | 22899276 | 22899778 | 21 | 38690662 | 38692439 |
| 21 | 22911716 | 22913367 | 21 | 38695583 | 38697689 |
| 21 | 22917605 | 22919960 | 21 | 38710732 | 38711257 |
| 21 | 22921879 | 22922874 | 21 | 38714911 | 38715561 |
| 21 | 22939368 | 22941432 | 21 | 38716939 | 38722382 |
| 21 | 22948668 | 22949328 | 21 | 38725108 | 38727120 |
| 21 | 22975658 | 22978097 | 21 | 38731200 | 38739680 |
| 21 | 22983875 | 22985720 | 21 | 38755528 | 38757771 |
| 21 | 23004109 | 23005117 | 21 | 38759316 | 38759682 |
| 21 | 23012391 | 23014224 | 21 | 38760307 | 38761622 |
| 21 | 23037190 | 23037735 | 21 | 38762327 | 38763329 |
| 21 | 23050171 | 23054317 | 21 | 38771177 | 38772207 |
| 21 | 23098377 | 23098727 | 21 | 38789356 | 38792242 |
| 21 | 23101419 | 23102024 | 21 | 38794702 | 38797755 |
| 21 | 23151428 | 23152951 | 21 | 38801409 | 38804464 |
| 21 | 23165387 | 23166034 | 21 | 38814094 | 38815354 |
| 21 | 23185993 | 23187883 | 21 | 38818885 | 38819836 |
| 21 | 23191631 | 23193236 | 21 | 38837832 | 38840654 |
| 21 | 23209584 | 23211162 | 21 | 38858517 | 38863073 |
| 21 | 23229058 | 23232905 | 21 | 38869393 | 38874288 |
| 21 | 23314245 | 23315199 | 21 | 38881526 | 38883421 |
| 21 | 23352158 | 23355311 | 21 | 38888467 | 38889682 |
| 21 | 23404411 | 23405614 | 21 | 38892044 | 38895094 |
| 21 | 23411275 | 23412490 | 21 | 38897008 | 38899242 |
| 21 | 23455838 | 23456956 | 21 | 38904189 | 38905764 |
| 21 | 23472955 | 23476360 | 21 | 38906433 | 38907770 |
| 21 | 23544006 | 23546004 | 21 | 38910396 | 38910986 |
| 21 | 23572965 | 23575158 | 21 | 38915823 | 38918534 |
| 21 | 23596982 | 23599282 | 21 | 38932105 | 38932490 |
| 21 | 23616956 | 23618322 | 21 | 38936629 | 38937704 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 23707733 | 23708483 | 21 | 38940130 | 38947874 |
| 21 | 23726874 | 23728344 | 21 | 38960219 | 38961761 |
| 21 | 23735867 | 23736987 | 21 | 38968845 | 38969857 |
| 21 | 23789602 | 23789742 | 21 | 38971192 | 38972480 |
| 21 | 23797357 | 23798317 | 21 | 38977803 | 38980556 |
| 21 | 23826746 | 23828138 | 21 | 38993288 | 38997579 |
| 21 | 23830871 | 23831897 | 21 | 39008166 | 39009746 |
| 21 | 23892524 | 23893342 | 21 | 39029516 | 39030006 |
| 21 | 24012672 | 24015366 | 21 | 39033597 | 39036064 |
| 21 | 24026471 | 24027371 | 21 | 39037162 | 39038964 |
| 21 | 24030653 | 24031483 | 21 | 39049949 | 39050774 |
| 21 | 24044228 | 24045324 | 21 | 39071064 | 39072100 |
| 21 | 24065807 | 24068030 | 21 | 39095906 | 39096711 |
| 21 | 24068460 | 24068796 | 21 | 39103608 | 39105031 |
| 21 | 24084759 | 24086404 | 21 | 39112050 | 39115331 |
| 21 | 24115812 | 24116459 | 21 | 39136967 | 39139145 |
| 21 | 24119102 | 24120217 | 21 | 39169042 | 39174267 |
| 21 | 24127252 | 24131510 | 21 | 39177696 | 39180712 |
| 21 | 24165000 | 24166247 | 21 | 39192119 | 39194194 |
| 21 | 24170216 | 24170992 | 21 | 39197259 | 39201631 |
| 21 | 24173727 | 24175002 | 21 | 39206669 | 39207379 |
| 21 | 24181041 | 24181616 | 21 | 39215738 | 39217148 |
| 21 | 24194986 | 24197006 | 21 | 39220520 | 39221835 |
| 21 | 24207291 | 24208006 | 21 | 39244672 | 39245537 |
| 21 | 24231873 | 24234736 | 21 | 39250887 | 39251642 |
| 21 | 24244469 | 24245609 | 21 | 39258720 | 39260775 |
| 21 | 24254854 | 24255485 | 21 | 39275790 | 39277211 |
| 21 | 24258653 | 24260218 | 21 | 39278141 | 39279946 |
| 21 | 24304520 | 24305802 | 21 | 39283056 | 39284641 |
| 21 | 24319461 | 24321251 | 21 | 39287388 | 39289650 |
| 21 | 24351663 | 24352183 | 21 | 39306161 | 39308117 |
| 21 | 24362803 | 24363783 | 21 | 39314917 | 39317621 |
| 21 | 24365643 | 24369268 | 21 | 39321131 | 39321891 |
| 21 | 24449396 | 24450236 | 21 | 39323902 | 39325602 |
| 21 | 24522866 | 24522986 | 21 | 39333979 | 39334729 |
| 21 | 24678549 | 24685273 | 21 | 39349844 | 39350424 |
| 21 | 24687600 | 24690160 | 21 | 39374901 | 39377604 |
| 21 | 24716221 | 24717291 | 21 | 39412975 | 39415293 |
| 21 | 24730441 | 24730791 | 21 | 39427890 | 39429145 |
| 21 | 24782071 | 24782356 | 21 | 39432318 | 39433584 |
| 21 | 24839302 | 24841677 | 21 | 39449854 | 39452974 |
| 21 | 24857275 | 24858010 | 21 | 39480908 | 39486385 |
| 21 | 24859580 | 24860648 | 21 | 39491458 | 39493041 |
| 21 | 24861228 | 24864589 | 21 | 39535814 | 39536934 |
| 21 | 24922383 | 24922884 | 21 | 39556693 | 39556953 |
| 21 | 24925620 | 24926840 | 21 | 39583394 | 39586145 |
| 21 | 24944918 | 24945813 | 21 | 39612700 | 39617163 |
| 21 | 24951220 | 24952245 | 21 | 39623533 | 39626574 |
| 21 | 24966304 | 24966679 | 21 | 39630297 | 39630787 |
| 21 | 24998934 | 25000824 | 21 | 39652387 | 39653182 |
| 21 | 25025625 | 25026135 | 21 | 39671296 | 39673123 |
| 21 | 25027230 | 25028595 | 21 | 39745428 | 39746158 |
| 21 | 25065769 | 25067684 | 21 | 39772889 | 39773694 |
| 21 | 25150185 | 25150953 | 21 | 39802912 | 39805834 |
| 21 | 25159379 | 25162450 | 21 | 39806994 | 39807999 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 25198278 | 25198820 | 21 | 39819535 | 39820810 |
| 21 | 25204307 | 25205302 | 21 | 39822365 | 39826045 |
| 21 | 25242630 | 25243705 | 21 | 39842703 | 39843976 |
| 21 | 25264010 | 25265398 | 21 | 39852651 | 39853636 |
| 21 | 25271525 | 25273385 | 21 | 39860924 | 39863610 |
| 21 | 25285792 | 25289115 | 21 | 39866397 | 39867737 |
| 21 | 25317229 | 25319144 | 21 | 39873226 | 39874361 |
| 21 | 25325810 | 25326735 | 21 | 39914239 | 39914744 |
| 21 | 25334174 | 25335977 | 21 | 39931952 | 39933686 |
| 21 | 25340567 | 25341327 | 21 | 39960417 | 39961492 |
| 21 | 25357286 | 25357766 | 21 | 40003955 | 40005265 |
| 21 | 25370404 | 25377884 | 21 | 40016085 | 40019303 |
| 21 | 25379711 | 25380741 | 21 | 40020998 | 40022038 |
| 21 | 25415288 | 25416359 | 21 | 40030274 | 40032612 |
| 21 | 25420206 | 25422975 | 21 | 40049936 | 40050701 |
| 21 | 25429954 | 25430684 | 21 | 40052203 | 40053118 |
| 21 | 25453501 | 25456286 | 21 | 40056773 | 40058133 |
| 21 | 25464317 | 25465072 | 21 | 40061171 | 40062701 |
| 21 | 25494773 | 25495398 | 21 | 40069230 | 40075381 |
| 21 | 25505292 | 25507722 | 21 | 40082150 | 40082555 |
| 21 | 25528699 | 25530824 | 21 | 40083670 | 40085205 |
| 21 | 25545362 | 25546752 | 21 | 40109932 | 40111270 |
| 21 | 25550235 | 25551728 | 21 | 40116771 | 40117496 |
| 21 | 25598903 | 25600078 | 21 | 40129276 | 40131591 |
| 21 | 25601560 | 25602805 | 21 | 40150465 | 40151135 |
| 21 | 25634970 | 25637826 | 21 | 40174227 | 40175567 |
| 21 | 25646767 | 25651174 | 21 | 40188464 | 40189569 |
| 21 | 25675337 | 25675857 | 21 | 40213261 | 40214756 |
| 21 | 25682732 | 25683152 | 21 | 40235483 | 40235938 |
| 21 | 25706113 | 25709499 | 21 | 40244105 | 40246281 |
| 21 | 25719411 | 25720490 | 21 | 40258202 | 40260347 |
| 21 | 25746710 | 25747815 | 21 | 40271583 | 40272973 |
| 21 | 25758368 | 25759163 | 21 | 40274273 | 40275323 |
| 21 | 25783701 | 25784980 | 21 | 40278265 | 40280315 |
| 21 | 25854998 | 25860407 | 21 | 40298387 | 40300194 |
| 21 | 25861399 | 25861984 | 21 | 40326029 | 40326614 |
| 21 | 26013085 | 26013825 | 21 | 40333944 | 40335269 |
| 21 | 26026525 | 26028182 | 21 | 40368630 | 40369125 |
| 21 | 26053947 | 26055008 | 21 | 40381116 | 40381947 |
| 21 | 26060269 | 26062071 | 21 | 40398481 | 40399620 |
| 21 | 26073359 | 26075566 | 21 | 40431886 | 40434356 |
| 21 | 26084222 | 26085077 | 21 | 40437128 | 40437853 |
| 21 | 26086509 | 26087049 | 21 | 40442280 | 40444000 |
| 21 | 26094519 | 26095960 | 21 | 40461037 | 40464077 |
| 21 | 26118696 | 26119651 | 21 | 40528180 | 40529370 |
| 21 | 26122293 | 26123088 | 21 | 40545249 | 40546330 |
| 21 | 26132458 | 26133123 | 21 | 40577021 | 40578526 |
| 21 | 26140380 | 26147577 | 21 | 40650795 | 40651826 |
| 21 | 26149084 | 26151046 | 21 | 40665741 | 40669884 |
| 21 | 26153381 | 26154406 | 21 | 40697339 | 40698124 |
| 21 | 26165129 | 26165861 | 21 | 40734063 | 40735488 |
| 21 | 26195773 | 26196328 | 21 | 40737738 | 40743444 |
| 21 | 26261809 | 26262219 | 21 | 40748619 | 40749225 |
| 21 | 26302733 | 26303358 | 21 | 40755747 | 40757002 |
| 21 | 26323932 | 26324458 | 21 | 40757197 | 40759268 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 26364911 | 26366326 | 21 | 40777779 | 40778359 |
| 21 | 26399645 | 26401289 | 21 | 40806213 | 40806658 |
| 21 | 26406187 | 26408393 | 21 | 40812969 | 40815162 |
| 21 | 26419296 | 26419837 | 21 | 40824191 | 40825806 |
| 21 | 26420217 | 26422155 | 21 | 40847688 | 40850492 |
| 21 | 26429288 | 26430719 | 21 | 40855716 | 40857041 |
| 21 | 26442608 | 26443723 | 21 | 40859066 | 40860761 |
| 21 | 26448235 | 26448805 | 21 | 40917645 | 40918554 |
| 21 | 26452486 | 26453761 | 21 | 40926228 | 40926983 |
| 21 | 26489127 | 26489667 | 21 | 40979568 | 40980417 |
| 21 | 26519083 | 26519973 | 21 | 40984371 | 40985610 |
| 21 | 26556886 | 26557878 | 21 | 41009974 | 41011104 |
| 21 | 26594657 | 26596167 | 21 | 41034004 | 41038098 |
| 21 | 26614713 | 26615208 | 21 | 41081446 | 41082568 |
| 21 | 26640477 | 26641162 | 21 | 41089450 | 41091170 |
| 21 | 26645136 | 26646932 | 21 | 41093671 | 41096558 |
| 21 | 26660378 | 26661273 | 21 | 41104214 | 41106409 |
| 21 | 26673528 | 26679276 | 21 | 41122374 | 41123834 |
| 21 | 26692999 | 26695004 | 21 | 41126296 | 41127147 |
| 21 | 26703157 | 26704887 | 21 | 41130305 | 41131005 |
| 21 | 26730557 | 26733625 | 21 | 41133971 | 41135186 |
| 21 | 26735767 | 26737127 | 21 | 41154175 | 41154585 |
| 21 | 26738230 | 26740775 | 21 | 41159472 | 41160112 |
| 21 | 26747670 | 26752811 | 21 | 41194804 | 41195262 |
| 21 | 26757739 | 26760479 | 21 | 41236903 | 41238173 |
| 21 | 26778671 | 26778766 | 21 | 41259830 | 41260485 |
| 21 | 26803157 | 26804412 | 21 | 41273726 | 41275361 |
| 21 | 26825664 | 26831462 | 21 | 41305701 | 41307436 |
| 21 | 26858224 | 26859923 | 21 | 41310851 | 41312451 |
| 21 | 26887500 | 26888295 | 21 | 41316030 | 41316590 |
| 21 | 26892314 | 26894110 | 21 | 41319930 | 41324485 |
| 21 | 26913543 | 26914108 | 21 | 41332366 | 41333576 |
| 21 | 26918051 | 26918637 | 21 | 41339001 | 41340046 |
| 21 | 26928470 | 26930696 | 21 | 41375886 | 41376533 |
| 21 | 26936353 | 26939512 | 21 | 41389392 | 41390152 |
| 21 | 26954687 | 26955483 | 21 | 41401062 | 41401967 |
| 21 | 26977195 | 26977785 | 21 | 41404594 | 41405984 |
| 21 | 27026730 | 27027030 | 21 | 41407972 | 41412989 |
| 21 | 27030183 | 27035798 | 21 | 41428415 | 41430866 |
| 21 | 27048971 | 27054198 | 21 | 41435656 | 41436966 |
| 21 | 27069788 | 27070954 | 21 | 41440622 | 41445190 |
| 21 | 27075654 | 27078093 | 21 | 41459967 | 41460630 |
| 21 | 27103012 | 27106157 | 21 | 41470996 | 41474196 |
| 21 | 27112148 | 27114471 | 21 | 41508879 | 41515078 |
| 21 | 27120680 | 27122155 | 21 | 41529838 | 41531824 |
| 21 | 27146273 | 27147878 | 21 | 41544122 | 41547339 |
| 21 | 27178019 | 27179359 | 21 | 41572926 | 41574966 |
| 21 | 27187470 | 27188690 | 21 | 41579488 | 41581215 |
| 21 | 27193812 | 27195459 | 21 | 41583572 | 41584442 |
| 21 | 27200999 | 27203154 | 21 | 41586100 | 41586190 |
| 21 | 27205780 | 27209335 | 21 | 41610975 | 41613122 |
| 21 | 27218920 | 27220534 | 21 | 41614347 | 41617318 |
| 21 | 27229772 | 27230747 | 21 | 41652691 | 41655322 |
| 21 | 27237234 | 27238999 | 21 | 41655692 | 41656502 |
| 21 | 27242513 | 27244145 | 21 | 41657505 | 41661847 |

*The chromosomal position was obtained from UCSC genome browser (http://genome.ucsc.edu/) build 36.

Appendix A: Chromosome 21
Page 33 of 39

| Chr | Start | End | | | Chr | Start | End |
|---|---|---|---|---|---|---|---|
| 21 | 27254043 | 27256478 | | | 21 | 41664499 | 41665364 |
| 21 | 27266461 | 27269121 | | | 21 | 41698737 | 41702481 |
| 21 | 27287756 | 27288351 | | | 21 | 41772252 | 41774024 |
| 21 | 27295913 | 27296693 | | | 21 | 41786281 | 41793562 |
| 21 | 27304505 | 27308447 | | | 21 | 41794811 | 41796405 |
| 21 | 27339877 | 27341582 | | | 21 | 41819438 | 41820742 |
| 21 | 27347292 | 27350297 | | | 21 | 41829594 | 41830914 |
| 21 | 27356759 | 27358058 | | | 21 | 41842285 | 41843465 |
| 21 | 27360363 | 27363203 | | | 21 | 41861744 | 41862809 |
| 21 | 27368547 | 27373193 | | | 21 | 41876956 | 41879705 |
| 21 | 27399396 | 27400211 | | | 21 | 41884455 | 41886632 |
| 21 | 27403545 | 27405999 | | | 21 | 41898763 | 41899218 |
| 21 | 27418492 | 27420343 | | | 21 | 41903863 | 41904617 |
| 21 | 27427214 | 27428834 | | | 21 | 41905917 | 41906992 |
| 21 | 27445401 | 27450746 | | | 21 | 41914046 | 41915756 |
| 21 | 27452793 | 27453816 | | | 21 | 41926453 | 41929698 |
| 21 | 27513201 | 27514601 | | | 21 | 41934980 | 41935835 |
| 21 | 27520625 | 27522276 | | | 21 | 41949960 | 41950835 |
| 21 | 27534382 | 27537204 | | | 21 | 41971665 | 41978551 |
| 21 | 27540676 | 27543215 | | | 21 | 41981411 | 41982818 |
| 21 | 27551395 | 27552500 | | | 21 | 42005986 | 42006261 |
| 21 | 27553900 | 27554739 | | | 21 | 42007076 | 42009916 |
| 21 | 27563263 | 27564082 | | | 21 | 42020375 | 42021460 |
| 21 | 27566046 | 27567566 | | | 21 | 42042982 | 42045911 |
| 21 | 27581101 | 27583009 | | | 21 | 42047390 | 42049479 |
| 21 | 27586236 | 27591750 | | | 21 | 42058635 | 42060332 |
| 21 | 27597576 | 27598392 | | | 21 | 42067439 | 42068559 |
| 21 | 27608176 | 27609471 | | | 21 | 42071062 | 42072581 |
| 21 | 27611581 | 27614781 | | | 21 | 42077571 | 42080900 |
| 21 | 27622940 | 27623879 | | | 21 | 42088097 | 42089888 |
| 21 | 27662081 | 27665807 | | | 21 | 42098655 | 42100743 |
| 21 | 27672346 | 27674124 | | | 21 | 42107100 | 42109650 |
| 21 | 27695740 | 27696926 | | | 21 | 42121746 | 42124309 |
| 21 | 27699681 | 27701006 | | | 21 | 42173757 | 42174492 |
| 21 | 27722729 | 27724568 | | | 21 | 42176893 | 42178223 |
| 21 | 27755009 | 27756396 | | | 21 | 42178628 | 42179638 |
| 21 | 27774805 | 27775670 | | | 21 | 42184210 | 42186165 |
| 21 | 27799520 | 27800875 | | | 21 | 42188845 | 42189824 |
| 21 | 27806412 | 27807357 | | | 21 | 42192629 | 42193039 |
| 21 | 27820412 | 27821929 | | | 21 | 42223220 | 42227157 |
| 21 | 27856443 | 27857908 | | | 21 | 42245804 | 42250154 |
| 21 | 27861912 | 27865367 | | | 21 | 42251083 | 42251888 |
| 21 | 27887597 | 27890715 | | | 21 | 42312079 | 42313294 |
| 21 | 27892460 | 27893445 | | | 21 | 42315334 | 42321599 |
| 21 | 27916168 | 27917648 | | | 21 | 42326501 | 42328302 |
| 21 | 27939306 | 27939941 | | | 21 | 42332929 | 42333934 |
| 21 | 27959523 | 27960633 | | | 21 | 42349841 | 42350703 |
| 21 | 27986548 | 27987523 | | | 21 | 42355391 | 42357611 |
| 21 | 28006989 | 28008252 | | | 21 | 42363894 | 42364719 |
| 21 | 28018911 | 28019785 | | | 21 | 42369408 | 42370473 |
| 21 | 28029398 | 28029898 | | | 21 | 42384317 | 42387795 |
| 21 | 28031332 | 28033852 | | | 21 | 42407000 | 42409580 |
| 21 | 28039902 | 28040467 | | | 21 | 42415695 | 42417140 |
| 21 | 28041327 | 28042422 | | | 21 | 42420290 | 42440348 |
| 21 | 28049789 | 28052747 | | | 21 | 42449968 | 42451408 |

*The chromosomal position was obtained from UCSC genome browser (http://genome.ucsc.edu/) build 36.

Appendix A: Chromosome 21

Page 34 of 39

| Chr | Start | End | | | Chr | Start | End |
|---|---|---|---|---|---|---|---|
| 21 | 28059558 | 28065873 | | | 21 | 42476332 | 42477800 |
| 21 | 28079236 | 28079801 | | | 21 | 42487640 | 42488715 |
| 21 | 28080785 | 28081615 | | | 21 | 42491481 | 42493029 |
| 21 | 28093463 | 28093523 | | | 21 | 42502056 | 42504072 |
| 21 | 28097112 | 28097692 | | | 21 | 42525673 | 42526228 |
| 21 | 28103535 | 28104325 | | | 21 | 42529876 | 42531941 |
| 21 | 28119777 | 28123455 | | | 21 | 42536179 | 42538380 |
| 21 | 28126487 | 28127712 | | | 21 | 42542886 | 42546271 |
| 21 | 28138102 | 28139720 | | | 21 | 42549456 | 42550996 |
| 21 | 28151218 | 28174214 | | | 21 | 42559944 | 42561144 |
| 21 | 28291626 | 28298404 | | | 21 | 42587969 | 42590091 |
| 21 | 28319684 | 28320955 | | | 21 | 42592411 | 42604605 |
| 21 | 28327823 | 28337967 | | | 21 | 42607040 | 42612529 |
| 21 | 28344607 | 28349703 | | | 21 | 42618195 | 42619175 |
| 21 | 28416788 | 28417316 | | | 21 | 42640132 | 42641367 |
| 21 | 28425744 | 28427686 | | | 21 | 42650277 | 42658237 |
| 21 | 28454031 | 28454841 | | | 21 | 42661626 | 42680419 |
| 21 | 28495686 | 28499075 | | | 21 | 42685172 | 42686197 |
| 21 | 28509395 | 28510590 | | | 21 | 42688928 | 42691330 |
| 21 | 28519662 | 28520473 | | | 21 | 42702155 | 42706543 |
| 21 | 28535785 | 28536567 | | | 21 | 42709288 | 42713107 |
| 21 | 28553484 | 28554985 | | | 21 | 42717022 | 42717837 |
| 21 | 28570077 | 28571662 | | | 21 | 42719473 | 42725644 |
| 21 | 28594281 | 28594456 | | | 21 | 42726729 | 42729214 |
| 21 | 28601690 | 28602895 | | | 21 | 42730404 | 42744263 |
| 21 | 28605032 | 28606487 | | | 21 | 42747568 | 42749283 |
| 21 | 28619663 | 28621188 | | | 21 | 42753507 | 42754372 |
| 21 | 28633580 | 28634310 | | | 21 | 42761692 | 42762402 |
| 21 | 28638661 | 28640876 | | | 21 | 42781923 | 42783021 |
| 21 | 28645738 | 28646668 | | | 21 | 42785849 | 42786904 |
| 21 | 28650755 | 28654046 | | | 21 | 42796853 | 42797756 |
| 21 | 28687849 | 28688824 | | | 21 | 42811407 | 42811882 |
| 21 | 28711414 | 28712994 | | | 21 | 42850227 | 42850887 |
| 21 | 28721515 | 28722405 | | | 21 | 42884659 | 42886129 |
| 21 | 28724714 | 28726256 | | | 21 | 42908255 | 42911954 |
| 21 | 28734579 | 28735969 | | | 21 | 42914479 | 42915069 |
| 21 | 28739069 | 28740654 | | | 21 | 42916404 | 42921306 |
| 21 | 28751296 | 28753711 | | | 21 | 42926531 | 42931726 |
| 21 | 28768167 | 28773319 | | | 21 | 42934080 | 42957497 |
| 21 | 28801467 | 28803555 | | | 21 | 42962238 | 42964438 |
| 21 | 28828705 | 28830875 | | | 21 | 42965485 | 42977057 |
| 21 | 28833149 | 28835508 | | | 21 | 42977897 | 43018782 |
| 21 | 28840566 | 28843986 | | | 21 | 43032354 | 43038892 |
| 21 | 28933308 | 28935927 | | | 21 | 43039762 | 43040412 |
| 21 | 28939319 | 28940779 | | | 21 | 43040632 | 43064984 |
| 21 | 28943740 | 28945213 | | | 21 | 43066503 | 43076315 |
| 21 | 28947985 | 28950680 | | | 21 | 43078345 | 43084550 |
| 21 | 28952050 | 28953453 | | | 21 | 43094001 | 43100609 |
| 21 | 28968997 | 28970077 | | | 21 | 43124470 | 43128185 |
| 21 | 28981147 | 28986152 | | | 21 | 43133435 | 43138246 |
| 21 | 28997375 | 28998212 | | | 21 | 43141136 | 43143721 |
| 21 | 29010461 | 29013116 | | | 21 | 43149508 | 43150799 |
| 21 | 29026759 | 29028345 | | | 21 | 43203673 | 43226458 |
| 21 | 29033176 | 29035079 | | | 21 | 43229624 | 43236311 |
| 21 | 29048221 | 29049576 | | | 21 | 43248598 | 43253165 |

*The chromosomal position was obtained from UCSC genome browser (http://genome.ucsc.edu/) build 36.

Appendix A: Chromosome 21

Page 35 of 39

| Chr | Start | End | | | Chr | Start | End |
|---|---|---|---|---|---|---|---|
| 21 | 29055679 | 29057316 | | | 21 | 43284153 | 43286479 |
| 21 | 29061717 | 29062692 | | | 21 | 43315613 | 43319398 |
| 21 | 29075430 | 29076090 | | | 21 | 43339847 | 43343796 |
| 21 | 29111755 | 29112455 | | | 21 | 43354215 | 43356687 |
| 21 | 29136241 | 29137666 | | | 21 | 43373234 | 43377149 |
| 21 | 29181071 | 29183744 | | | 21 | 43381164 | 43387313 |
| 21 | 29194908 | 29198034 | | | 21 | 43397595 | 43398856 |
| 21 | 29209995 | 29211357 | | | 21 | 43401737 | 43402767 |
| 21 | 29255879 | 29258019 | | | 21 | 43423391 | 43425071 |
| 21 | 29300914 | 29301963 | | | 21 | 43431706 | 43432551 |
| 21 | 29312346 | 29314391 | | | 21 | 43439109 | 43442078 |
| 21 | 29317563 | 29318688 | | | 21 | 43446811 | 43456274 |
| 21 | 29350497 | 29351237 | | | 21 | 43461461 | 43469739 |
| 21 | 29380057 | 29380752 | | | 21 | 43472674 | 43477240 |
| 21 | 29402526 | 29403676 | | | 21 | 43479984 | 43491254 |
| 21 | 29439280 | 29443751 | | | 21 | 43499517 | 43535342 |
| 21 | 29449500 | 29450410 | | | 21 | 43537842 | 43540039 |
| 21 | 29462627 | 29464143 | | | 21 | 43543065 | 43546035 |
| 21 | 29479532 | 29482300 | | | 21 | 43547695 | 43552330 |
| 21 | 29497479 | 29499122 | | | 21 | 43558154 | 43568847 |
| 21 | 29501170 | 29503301 | | | 21 | 43573663 | 43587558 |
| 21 | 29520553 | 29524717 | | | 21 | 43595862 | 43606365 |
| 21 | 29529778 | 29531003 | | | 21 | 43609155 | 43615180 |
| 21 | 29550197 | 29550947 | | | 21 | 43622288 | 43625168 |
| 21 | 29553854 | 29554964 | | | 21 | 43626903 | 43630767 |
| 21 | 29556279 | 29558799 | | | 21 | 43632991 | 43635176 |
| 21 | 29577001 | 29578176 | | | 21 | 43644697 | 43654977 |
| 21 | 29583531 | 29587036 | | | 21 | 43658396 | 43659779 |
| 21 | 29588077 | 29588949 | | | 21 | 43672329 | 43675513 |
| 21 | 29592129 | 29593640 | | | 21 | 43680678 | 43681533 |
| 21 | 29635765 | 29639016 | | | 21 | 43684758 | 43685918 |
| 21 | 29678981 | 29681140 | | | 21 | 43695583 | 43696873 |
| 21 | 29695870 | 29696655 | | | 21 | 43708062 | 43712934 |
| 21 | 29703978 | 29704428 | | | 21 | 43722194 | 43723114 |
| 21 | 29717406 | 29718478 | | | 21 | 43731455 | 43732966 |
| 21 | 29747286 | 29754070 | | | 21 | 43743630 | 43747770 |
| 21 | 29766290 | 29767520 | | | 21 | 43761814 | 43762764 |
| 21 | 29784093 | 29787084 | | | 21 | 43847853 | 43848458 |
| 21 | 29792902 | 29794327 | | | 21 | 43875553 | 43876948 |
| 21 | 29799214 | 29800324 | | | 21 | 43902104 | 43904079 |
| 21 | 29804450 | 29805420 | | | 21 | 43955552 | 43957244 |
| 21 | 29807809 | 29810539 | | | 21 | 43982487 | 43985836 |
| 21 | 29817725 | 29818470 | | | 21 | 43997245 | 43999415 |
| 21 | 29822641 | 29823811 | | | 21 | 44011301 | 44013601 |
| 21 | 29827328 | 29828210 | | | 21 | 44053441 | 44056331 |
| 21 | 29887148 | 29891404 | | | 21 | 44057646 | 44059765 |
| 21 | 29896240 | 29900008 | | | 21 | 44070599 | 44076868 |
| 21 | 29902910 | 29907668 | | | 21 | 44079243 | 44079883 |
| 21 | 29919230 | 29922246 | | | 21 | 44104512 | 44105354 |
| 21 | 29924012 | 29924757 | | | 21 | 44111442 | 44112002 |
| 21 | 29933520 | 29934993 | | | 21 | 44125621 | 44129021 |
| 21 | 29947290 | 29948580 | | | 21 | 44147432 | 44152115 |
| 21 | 29949028 | 29950775 | | | 21 | 44161018 | 44161518 |
| 21 | 29969535 | 29970295 | | | 21 | 44161943 | 44165616 |
| 21 | 29995614 | 29996169 | | | 21 | 44182296 | 44183983 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 29997294 | 29998064 | 21 | 44187143 | 44191798 |
| 21 | 30008922 | 30010012 | 21 | 44197059 | 44204070 |
| 21 | 30023159 | 30025738 | 21 | 44218325 | 44221200 |
| 21 | 30061899 | 30064444 | 21 | 44228368 | 44238139 |
| 21 | 30069867 | 30070906 | 21 | 44249128 | 44251905 |
| 21 | 30071611 | 30072316 | 21 | 44298966 | 44299975 |
| 21 | 30074521 | 30075176 | 21 | 44326707 | 44327827 |
| 21 | 30085329 | 30085931 | 21 | 44389396 | 44390115 |
| 21 | 30097270 | 30099396 | 21 | 44390925 | 44392290 |
| 21 | 30114576 | 30117348 | 21 | 44401561 | 44402391 |
| 21 | 30122353 | 30123893 | 21 | 44406646 | 44416542 |
| 21 | 30130737 | 30134581 | 21 | 44421520 | 44424572 |
| 21 | 30143535 | 30144951 | 21 | 44425647 | 44434862 |
| 21 | 30174586 | 30181134 | 21 | 44436668 | 44440555 |
| 21 | 30188949 | 30189954 | 21 | 44443372 | 44444308 |
| 21 | 30191332 | 30192107 | 21 | 44445863 | 44450674 |
| 21 | 30208212 | 30209547 | 21 | 44452006 | 44453266 |
| 21 | 30230009 | 30231069 | 21 | 44455066 | 44456786 |
| 21 | 30235998 | 30236521 | 21 | 44479334 | 44481979 |
| 21 | 30238821 | 30239380 | 21 | 44485907 | 44488132 |
| 21 | 30241125 | 30241855 | 21 | 44491051 | 44510680 |
| 21 | 30248553 | 30249178 | 21 | 44517887 | 44519172 |
| 21 | 30252041 | 30252976 | 21 | 44530731 | 44540314 |
| 21 | 30260435 | 30261115 | 21 | 44572640 | 44574615 |
| 21 | 30273759 | 30275349 | 21 | 44584362 | 44599601 |
| 21 | 30284396 | 30285187 | 21 | 44604767 | 44618270 |
| 21 | 30287542 | 30291189 | 21 | 44620080 | 44627710 |
| 21 | 30313566 | 30315842 | 21 | 44634495 | 44655483 |
| 21 | 30322213 | 30324614 | 21 | 44659276 | 44670137 |
| 21 | 30330652 | 30331063 | 21 | 44675761 | 44677802 |
| 21 | 30340727 | 30342192 | 21 | 44683982 | 44697729 |
| 21 | 30345263 | 30351155 | 21 | 44701890 | 44703481 |
| 21 | 30395469 | 30396670 | 21 | 44707703 | 44712999 |
| 21 | 30406158 | 30409859 | 21 | 44716735 | 44719645 |
| 21 | 30412246 | 30414211 | 21 | 44722012 | 44722407 |
| 21 | 30433750 | 30434815 | 21 | 44726579 | 44727734 |
| 21 | 30440815 | 30441635 | 21 | 44744417 | 44749081 |
| 21 | 30442635 | 30443330 | 21 | 44751187 | 44777448 |
| 21 | 30448124 | 30449259 | 21 | 44781834 | 44785715 |
| 21 | 30452575 | 30453642 | 21 | 44792907 | 44794440 |
| 21 | 30517433 | 30517833 | 21 | 44799900 | 44803986 |
| 21 | 30521167 | 30522647 | 21 | 44811763 | 44828167 |
| 21 | 30524282 | 30525062 | 21 | 44829647 | 44843179 |
| 21 | 30526027 | 30528363 | 21 | 44844394 | 44848749 |
| 21 | 30538614 | 30539678 | 21 | 44855990 | 44862072 |
| 21 | 30578665 | 30579030 | 21 | 44869421 | 44873518 |
| 21 | 30590204 | 30591014 | 21 | 44880618 | 44886068 |
| 21 | 30606598 | 30607188 | 21 | 44890162 | 44900881 |
| 21 | 30613481 | 30614756 | 21 | 44903341 | 44905833 |
| 21 | 30619862 | 30622899 | 21 | 44909816 | 44911551 |
| 21 | 30627951 | 30629066 | 21 | 44925499 | 44933489 |
| 21 | 30640633 | 30641313 | 21 | 44939614 | 44947454 |
| 21 | 30643193 | 30644848 | 21 | 44953665 | 44954285 |
| 21 | 30652869 | 30654142 | 21 | 44967825 | 44978890 |
| 21 | 30661105 | 30664675 | 21 | 44991511 | 44993273 |

*The chromosomal position was obtained from UCSC genome browser (http://genome.ucsc.edu/) build 36.

Appendix A: Chromosome 21

| Chr | Start | End | Chr | Start | End |
|---|---|---|---|---|---|
| 21 | 30681149 | 30681869 | 21 | 44996943 | 44997836 |
| 21 | 30712068 | 30713014 | 21 | 45001414 | 45003632 |
| 21 | 30720729 | 30721224 | 21 | 45005612 | 45011833 |
| 21 | 30737530 | 30743555 | 21 | 45017632 | 45018087 |
| 21 | 30751862 | 30752108 | 21 | 45030243 | 45031071 |
| 21 | 30762535 | 30764836 | 21 | 45089044 | 45090322 |
| 21 | 30779153 | 30781481 | 21 | 45097547 | 45098687 |
| 21 | 30824752 | 30825387 | 21 | 45102097 | 45103992 |
| 21 | 30873509 | 30874524 | 21 | 45114061 | 45117475 |
| 21 | 30889078 | 30889678 | 21 | 45126737 | 45130007 |
| 21 | 30909192 | 30911027 | 21 | 45138194 | 45149509 |
| 21 | 30935452 | 30935808 | 21 | 45170685 | 45171200 |
| 21 | 30964527 | 30967372 | 21 | 45180061 | 45181403 |
| 21 | 30972270 | 30972640 | 21 | 45199250 | 45204014 |
| 21 | 30977831 | 30979743 | 21 | 45224007 | 45224352 |
| 21 | 31033997 | 31035212 | 21 | 45227152 | 45245886 |
| 21 | 31035957 | 31036807 | 21 | 45248802 | 45249377 |
| 21 | 31045059 | 31045734 | 21 | 45250922 | 45252928 |
| 21 | 31052032 | 31053033 | 21 | 45256071 | 45258594 |
| 21 | 31054995 | 31056286 | 21 | 45265869 | 45266854 |
| 21 | 31074601 | 31076671 | 21 | 45270210 | 45274980 |
| 21 | 31079226 | 31080314 | 21 | 45276150 | 45280235 |
| 21 | 31087198 | 31088208 | 21 | 45281248 | 45289765 |
| 21 | 31102152 | 31106506 | 21 | 45294351 | 45305390 |
| 21 | 31106861 | 31107800 | 21 | 45308830 | 45309690 |
| 21 | 31115310 | 31116455 | 21 | 45311533 | 45312378 |
| 21 | 31118805 | 31120071 | 21 | 45323933 | 45326096 |
| 21 | 31127934 | 31129124 | 21 | 45329969 | 45331036 |
| 21 | 31139396 | 31140388 | 21 | 45331991 | 45333241 |
| 21 | 31151054 | 31153940 | 21 | 45339194 | 45346108 |
| 21 | 31173666 | 31175865 | 21 | 45350412 | 45351265 |
| 21 | 31176465 | 31177340 | 21 | 45355685 | 45357340 |
| 21 | 31178902 | 31183876 | 21 | 45362952 | 45366299 |
| 21 | 31185027 | 31186771 | 21 | 45369784 | 45374509 |
| 21 | 31205416 | 31206426 | 21 | 45380116 | 45385089 |
| 21 | 31211266 | 31212956 | 21 | 45386944 | 45388359 |
| 21 | 31236906 | 31238220 | 21 | 45389555 | 45391065 |
| 21 | 31239736 | 31240466 | 21 | 45391711 | 45393801 |
| 21 | 31255169 | 31256064 | 21 | 45395874 | 45397389 |
| 21 | 31259207 | 31260377 | 21 | 45401400 | 45403372 |
| 21 | 31270040 | 31271295 | 21 | 45407692 | 45409492 |
| 21 | 31282645 | 31284735 | 21 | 45416088 | 45417628 |
| 21 | 31288956 | 31290626 | 21 | 45420234 | 45426242 |
| 21 | 31294255 | 31299160 | 21 | 45428613 | 45429769 |
| 21 | 31300633 | 31302395 | 21 | 45443669 | 45449084 |
| 21 | 31311207 | 31312137 | 21 | 45451386 | 45452037 |
| 21 | 31314469 | 31315499 | 21 | 45454732 | 45456787 |
| 21 | 31317153 | 31317748 | 21 | 45464785 | 45474883 |
| 21 | 31325229 | 31326973 | 21 | 45478447 | 45481175 |
| 21 | 31327973 | 31328898 | 21 | 45489177 | 45494027 |
| 21 | 31346895 | 31348498 | 21 | 45494987 | 45507714 |
| 21 | 31354118 | 31355261 | 21 | 45525839 | 45527439 |
| 21 | 31376372 | 31377873 | 21 | 45535148 | 45540729 |
| 21 | 31381347 | 31383423 | 21 | 45543459 | 45598459 |
| 21 | 31390350 | 31394056 | 21 | 45600613 | 45641280 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| 21 | 31398211 | 31398291 | | | 21 | 45643583 | 45690875 |
| 21 | 31409643 | 31411344 | | | 21 | 45692125 | 45694875 |
| 21 | 31417002 | 31417612 | | | 21 | 45696377 | 45703968 |
| 21 | 31426667 | 31427588 | | | 21 | 45707388 | 45727006 |
| 21 | 31443748 | 31445828 | | | 21 | 45729943 | 45761520 |
| 21 | 31452916 | 31453912 | | | 21 | 45770700 | 45774790 |
| 21 | 31470813 | 31471323 | | | 21 | 45777677 | 45779997 |
| 21 | 31474788 | 31482884 | | | 21 | 45788485 | 45793199 |
| 21 | 31495102 | 31495884 | | | 21 | 45797034 | 45797864 |
| 21 | 31498788 | 31499458 | | | 21 | 45805320 | 45807534 |
| 21 | 31515106 | 31516491 | | | 21 | 45819004 | 45826584 |
| 21 | 31561746 | 31562862 | | | 21 | 45828316 | 45830866 |
| 21 | 31575684 | 31576024 | | | 21 | 45832879 | 45846457 |
| 21 | 31620820 | 31621475 | | | 21 | 45848683 | 45864095 |
| 21 | 31629053 | 31633368 | | | 21 | 45866181 | 45885751 |
| 21 | 31641389 | 31642149 | | | 21 | 45910129 | 45913120 |
| 21 | 31642884 | 31643729 | | | 21 | 45917892 | 45918532 |
| 21 | 31647882 | 31649443 | | | 21 | 45939852 | 45941577 |
| 21 | 31676194 | 31676986 | | | 21 | 45947745 | 45949605 |
| 21 | 31703729 | 31704850 | | | 21 | 45950505 | 45952600 |
| 21 | 31707324 | 31708531 | | | 21 | 45957386 | 45958526 |
| 21 | 31736834 | 31737174 | | | 21 | 45968596 | 45970587 |
| 21 | 31795535 | 31798180 | | | 21 | 45978705 | 45985959 |
| 21 | 31824102 | 31825327 | | | 21 | 45989309 | 45996426 |
| 21 | 31832318 | 31833979 | | | 21 | 46004585 | 46014953 |
| 21 | 31836230 | 31839416 | | | 21 | 46027671 | 46039847 |
| 21 | 31847359 | 31848394 | | | 21 | 46041360 | 46082520 |
| 21 | 31857940 | 31865395 | | | 21 | 46085586 | 46087526 |
| 21 | 31868410 | 31870940 | | | 21 | 46088391 | 46089046 |
| 21 | 31871836 | 31874093 | | | 21 | 46089856 | 46128086 |
| 21 | 31891840 | 31892550 | | | 21 | 46132013 | 46178936 |
| 21 | 31907143 | 31908280 | | | 21 | 46181318 | 46202038 |
| 21 | 31950426 | 31953405 | | | 21 | 46211243 | 46213169 |
| 21 | 31960831 | 31963056 | | | 21 | 46214399 | 46214984 |
| 21 | 32042657 | 32045415 | | | 21 | 46221437 | 46256422 |
| 21 | 32076729 | 32080846 | | | 21 | 46265103 | 46268404 |
| 21 | 32086054 | 32088529 | | | 21 | 46273367 | 46273692 |
| | | | | | 21 | 46275115 | 46286752 |
| | | | | | 21 | 46287682 | 46288763 |
| | | | | | 21 | 46290773 | 46301419 |
| | | | | | 21 | 46302334 | 46317285 |
| | | | | | 21 | 46321695 | 46330288 |
| | | | | | 21 | 46334763 | 46345238 |
| | | | | | 21 | 46354646 | 46407946 |
| | | | | | 21 | 46412155 | 46415680 |
| | | | | | 21 | 46419145 | 46428494 |
| | | | | | 21 | 46428709 | 46428784 |
| | | | | | 21 | 46432233 | 46433928 |
| | | | | | 21 | 46445235 | 46448762 |
| | | | | | 21 | 46457718 | 46458688 |
| | | | | | 21 | 46518852 | 46520204 |
| | | | | | 21 | 46536847 | 46541987 |
| | | | | | 21 | 46579100 | 46586818 |
| | | | | | 21 | 46602690 | 46607688 |
| | | | | | 21 | 46613158 | 46613974 |

*The chromosomal position was obtained from UCSC genome browser (http://genome.ucsc.edu/) build 36.

Appendix A: Chromosome 21

| Chr | Start | End | | | Chr | Start | End |
|---|---|---|---|---|---|---|---|
| | | | | | 21 | 46623093 | 46624425 |
| | | | | | 21 | 46637075 | 46638881 |
| | | | | | 21 | 46644376 | 46648547 |
| | | | | | 21 | 46794750 | 46797260 |
| | | | | | 21 | 46843260 | 46846099 |
| | | | | | 21 | 46889222 | 46891261 |
| | | | | | 21 | 46913878 | 46915683 |

*The chromosomal position was obtained from UCSC genome browser (http://genome.ucsc.edu/) build 36.

APPENDIX B: Chromosome 13
Page 1 of 49

| Chr | Start | End | | | Chr | Start | End |
|---|---|---|---|---|---|---|---|
| 13 | 18069149 | 18122861 | | | 13 | 63986228 | 63989146 |
| 13 | 18197974 | 18264583 | | | 13 | 63998703 | 64001832 |
| 13 | 18314534 | 18317489 | | | 13 | 64010828 | 64024160 |
| 13 | 18355374 | 18379270 | | | 13 | 64062827 | 64067979 |
| 13 | 18415034 | 18438564 | | | 13 | 64091085 | 64092414 |
| 13 | 18454749 | 18487551 | | | 13 | 64211066 | 64220758 |
| 13 | 18519853 | 18564151 | | | 13 | 64222830 | 64223292 |
| 13 | 18584051 | 18593171 | | | 13 | 64269440 | 64276131 |
| 13 | 18608137 | 18662596 | | | 13 | 64283582 | 64287766 |
| 13 | 18791588 | 18792688 | | | 13 | 64327755 | 64333333 |
| 13 | 18816548 | 18887276 | | | 13 | 64339197 | 64341549 |
| 13 | 19032639 | 19036973 | | | 13 | 64396621 | 64398327 |
| 13 | 19059674 | 19080262 | | | 13 | 64429052 | 64431758 |
| 13 | 19133739 | 19138274 | | | 13 | 64471681 | 64477398 |
| 13 | 19254055 | 19291417 | | | 13 | 64480946 | 64496743 |
| 13 | 19335696 | 19339625 | | | 13 | 64513825 | 64515042 |
| 13 | 19567197 | 19626447 | | | 13 | 64518574 | 64526686 |
| 13 | 19633328 | 19651373 | | | 13 | 64651646 | 64659225 |
| 13 | 19661120 | 19664266 | | | 13 | 64669180 | 64673242 |
| 13 | 19678329 | 19686057 | | | 13 | 64812948 | 64819167 |
| 13 | 19695012 | 19748263 | | | 13 | 64855973 | 64857713 |
| 13 | 19766997 | 19776742 | | | 13 | 64940999 | 64952234 |
| 13 | 19784233 | 19853888 | | | 13 | 64960287 | 64966360 |
| 13 | 19862474 | 19878714 | | | 13 | 65018544 | 65022738 |
| 13 | 19884828 | 19913671 | | | 13 | 65029172 | 65030103 |
| 13 | 19937796 | 19947210 | | | 13 | 65091247 | 65099210 |
| 13 | 19967554 | 19970920 | | | 13 | 65105819 | 65108665 |
| 13 | 19974110 | 19980481 | | | 13 | 65127727 | 65132454 |
| 13 | 19989375 | 19991782 | | | 13 | 65138409 | 65141196 |
| 13 | 20078482 | 20081474 | | | 13 | 65171992 | 65175208 |
| 13 | 20150984 | 20159041 | | | 13 | 65266357 | 65271699 |
| 13 | 20170825 | 20203974 | | | 13 | 65315100 | 65317180 |
| 13 | 20374827 | 20377032 | | | 13 | 65428372 | 65432801 |
| 13 | 20410763 | 20428973 | | | 13 | 65500079 | 65517554 |
| 13 | 20446802 | 20471475 | | | 13 | 65549479 | 65551301 |
| 13 | 20484546 | 20493674 | | | 13 | 65579937 | 65581043 |
| 13 | 20531160 | 20536554 | | | 13 | 65582151 | 65588280 |
| 13 | 20548539 | 20552914 | | | 13 | 65598346 | 65601692 |
| 13 | 20572894 | 20588500 | | | 13 | 65636602 | 65638253 |
| 13 | 20612763 | 20620326 | | | 13 | 65642667 | 65644311 |
| 13 | 20674818 | 20688806 | | | 13 | 65669922 | 65677467 |
| 13 | 20706196 | 20707393 | | | 13 | 65707822 | 65713740 |
| 13 | 20712014 | 20717589 | | | 13 | 65792317 | 65794437 |
| 13 | 20731745 | 20734115 | | | 13 | 65830572 | 65834460 |
| 13 | 20759566 | 20766490 | | | 13 | 65900284 | 65903445 |
| 13 | 20791096 | 20843833 | | | 13 | 65930706 | 65932715 |
| 13 | 20848648 | 20850004 | | | 13 | 66015128 | 66019412 |
| 13 | 20864046 | 20864172 | | | 13 | 66038091 | 66038672 |
| 13 | 20955908 | 20962422 | | | 13 | 66050595 | 66053603 |
| 13 | 21072795 | 21085887 | | | 13 | 66204093 | 66206419 |
| 13 | 21097674 | 21099591 | | | 13 | 66283502 | 66284164 |
| 13 | 21129584 | 21131957 | | | 13 | 66315274 | 66318203 |
| 13 | 21159422 | 21167485 | | | 13 | 66388652 | 66395148 |
| 13 | 21192872 | 21211874 | | | 13 | 66414524 | 66420167 |
| 13 | 21256576 | 21258027 | | | 13 | 66437874 | 66449484 |

The chromosomal positon was obtained from UCSC genome browser (http://genome.ucsc.edu/) build 36.

APPENDIX B: Chromosome 13
Page 2 of 49

| Chr | Start | End | Chr | Start | End |
|---|---|---|---|---|---|
| 13 | 21262915 | 21268021 | 13 | 66588642 | 66591449 |
| 13 | 21282742 | 21292431 | 13 | 66628036 | 66629706 |
| 13 | 21319437 | 21321939 | 13 | 66648414 | 66653524 |
| 13 | 21344389 | 21388803 | 13 | 66686126 | 66692976 |
| 13 | 21391441 | 21403484 | 13 | 66697622 | 66700267 |
| 13 | 21408258 | 21411257 | 13 | 66725479 | 66731862 |
| 13 | 21433584 | 21453579 | 13 | 66755928 | 66757853 |
| 13 | 21467453 | 21477440 | 13 | 66761694 | 66775364 |
| 13 | 21499380 | 21503090 | 13 | 66798173 | 66801003 |
| 13 | 21512215 | 21513594 | 13 | 66869696 | 66877866 |
| 13 | 21531897 | 21537603 | 13 | 66889251 | 66895960 |
| 13 | 21562959 | 21564555 | 13 | 67022979 | 67024271 |
| 13 | 21606613 | 21608403 | 13 | 67028165 | 67047579 |
| 13 | 21679468 | 21685319 | 13 | 67079583 | 67083889 |
| 13 | 21784091 | 21789111 | 13 | 67113237 | 67117502 |
| 13 | 21877313 | 21885926 | 13 | 67135716 | 67138177 |
| 13 | 21898383 | 21901359 | 13 | 67147438 | 67151629 |
| 13 | 21961229 | 21964075 | 13 | 67224975 | 67228650 |
| 13 | 22018358 | 22019485 | 13 | 67241565 | 67246172 |
| 13 | 22113575 | 22124805 | 13 | 67374213 | 67388679 |
| 13 | 22168245 | 22169105 | 13 | 67396595 | 67405128 |
| 13 | 22173507 | 22178879 | 13 | 67416762 | 67422176 |
| 13 | 22207356 | 22209302 | 13 | 67439385 | 67443717 |
| 13 | 22223820 | 22224828 | 13 | 67448504 | 67453587 |
| 13 | 22242335 | 22243869 | 13 | 67500555 | 67503839 |
| 13 | 22264863 | 22268324 | 13 | 67508342 | 67511546 |
| 13 | 22397146 | 22421799 | 13 | 67551697 | 67553541 |
| 13 | 22431369 | 22456831 | 13 | 67590038 | 67592979 |
| 13 | 22552134 | 22558960 | 13 | 67632685 | 67641209 |
| 13 | 22569532 | 22574316 | 13 | 67645074 | 67649726 |
| 13 | 22586720 | 22589818 | 13 | 67747397 | 67752282 |
| 13 | 22619050 | 22621189 | 13 | 67788374 | 67792991 |
| 13 | 22628989 | 22633597 | 13 | 67875061 | 67876355 |
| 13 | 22656954 | 22674510 | 13 | 67909975 | 67912808 |
| 13 | 22716235 | 22720530 | 13 | 67915430 | 67919086 |
| 13 | 22739827 | 22748976 | 13 | 67943049 | 67944068 |
| 13 | 22795438 | 22800546 | 13 | 67953756 | 67954653 |
| 13 | 22847322 | 22880785 | 13 | 68075124 | 68075536 |
| 13 | 22883375 | 22885670 | 13 | 68183566 | 68184720 |
| 13 | 22918039 | 22929120 | 13 | 68227755 | 68235375 |
| 13 | 22938120 | 22942969 | 13 | 68249798 | 68251427 |
| 13 | 22958719 | 23007298 | 13 | 68277784 | 68279510 |
| 13 | 23024431 | 23040963 | 13 | 68329815 | 68333054 |
| 13 | 23085726 | 23099393 | 13 | 68344592 | 68346861 |
| 13 | 23108524 | 23112355 | 13 | 68384888 | 68392325 |
| 13 | 23125560 | 23132267 | 13 | 68419963 | 68424687 |
| 13 | 23146253 | 23153783 | 13 | 68431127 | 68445321 |
| 13 | 23166457 | 23179084 | 13 | 68468715 | 68479940 |
| 13 | 23185467 | 23189447 | 13 | 68549144 | 68551031 |
| 13 | 23241507 | 23245215 | 13 | 68557744 | 68567386 |
| 13 | 23261643 | 23264060 | 13 | 68694090 | 68697461 |
| 13 | 23338388 | 23340986 | 13 | 68707518 | 68736458 |
| 13 | 23361131 | 23376585 | 13 | 68745517 | 68750346 |
| 13 | 23390803 | 23392206 | 13 | 68755784 | 68760224 |
| 13 | 23407345 | 23412244 | 13 | 68784159 | 68786607 |

The chromosomal positon was obtained from UCSC genome browser (http://genome.ucsc.edu/) build 36.

APPENDIX B: Chromosome 13
Page 3 of 49

| Chr | Start | End | Chr | Start | End |
|---|---|---|---|---|---|
| 13 | 23417981 | 23430606 | 13 | 68833006 | 68835386 |
| 13 | 23472476 | 23489840 | 13 | 68863586 | 68866316 |
| 13 | 23513155 | 23536895 | 13 | 68909641 | 68915443 |
| 13 | 23548382 | 23564077 | 13 | 68922260 | 68925486 |
| 13 | 23605326 | 23622529 | 13 | 68981798 | 68986300 |
| 13 | 23632151 | 23638777 | 13 | 68996885 | 68997647 |
| 13 | 23664085 | 23666707 | 13 | 69011751 | 69013555 |
| 13 | 23693169 | 23701258 | 13 | 69094501 | 69096171 |
| 13 | 23718057 | 23721951 | 13 | 69100046 | 69102095 |
| 13 | 23748953 | 23796111 | 13 | 69299483 | 69300850 |
| 13 | 23808926 | 23844842 | 13 | 69317198 | 69320934 |
| 13 | 23855755 | 23867868 | 13 | 69352267 | 69353446 |
| 13 | 23889639 | 23924443 | 13 | 69386950 | 69395830 |
| 13 | 23941897 | 23947898 | 13 | 69399921 | 69402500 |
| 13 | 23959606 | 23962394 | 13 | 69418169 | 69434914 |
| 13 | 23977952 | 23980467 | 13 | 69441992 | 69444923 |
| 13 | 23983313 | 23984486 | 13 | 69466009 | 69474407 |
| 13 | 24010161 | 24015575 | 13 | 69524231 | 69528940 |
| 13 | 24083699 | 24112383 | 13 | 69621799 | 69623954 |
| 13 | 24121172 | 24125922 | 13 | 69651093 | 69655009 |
| 13 | 24140888 | 24196228 | 13 | 69747591 | 69749520 |
| 13 | 24210841 | 24220199 | 13 | 69752439 | 69755309 |
| 13 | 24234051 | 24237612 | 13 | 69818996 | 69820810 |
| 13 | 24264086 | 24266196 | 13 | 69825915 | 69827412 |
| 13 | 24361774 | 24368007 | 13 | 69836348 | 69841372 |
| 13 | 24453919 | 24500193 | 13 | 69941379 | 69944281 |
| 13 | 24503543 | 24506642 | 13 | 69985547 | 69990113 |
| 13 | 24519497 | 24521765 | 13 | 70013908 | 70018783 |
| 13 | 24540409 | 24541959 | 13 | 70027445 | 70035694 |
| 13 | 24565738 | 24570124 | 13 | 70122709 | 70123400 |
| 13 | 24586997 | 24591681 | 13 | 70152441 | 70168964 |
| 13 | 24641923 | 24650028 | 13 | 70201112 | 70203487 |
| 13 | 24657392 | 24710022 | 13 | 70216442 | 70230250 |
| 13 | 24839656 | 24848370 | 13 | 70254032 | 70258682 |
| 13 | 24871172 | 24877806 | 13 | 70312864 | 70314953 |
| 13 | 24885778 | 24886933 | 13 | 70352310 | 70354675 |
| 13 | 24896062 | 24935664 | 13 | 70368334 | 70371127 |
| 13 | 24953378 | 24977260 | 13 | 70394528 | 70396821 |
| 13 | 24990034 | 24992248 | 13 | 70400723 | 70402410 |
| 13 | 25004046 | 25005879 | 13 | 70478010 | 70481940 |
| 13 | 25042273 | 25044780 | 13 | 70513875 | 70518360 |
| 13 | 25236797 | 25244669 | 13 | 70551893 | 70553539 |
| 13 | 25308471 | 25310836 | 13 | 70562550 | 70565504 |
| 13 | 25340587 | 25344255 | 13 | 70582117 | 70589716 |
| 13 | 25353840 | 25378568 | 13 | 70667676 | 70669051 |
| 13 | 25386497 | 25395123 | 13 | 70671990 | 70673373 |
| 13 | 25400655 | 25440924 | 13 | 70692532 | 70697199 |
| 13 | 25445147 | 25452845 | 13 | 70785583 | 70788936 |
| 13 | 25461358 | 25463556 | 13 | 70795791 | 70797884 |
| 13 | 25485108 | 25485867 | 13 | 70831097 | 70833056 |
| 13 | 25490040 | 25495408 | 13 | 70853692 | 70853913 |
| 13 | 25499796 | 25502846 | 13 | 70870279 | 70872958 |
| 13 | 25517874 | 25525081 | 13 | 70880741 | 70882843 |
| 13 | 25546924 | 25550417 | 13 | 70913290 | 70916911 |
| 13 | 25568110 | 25592454 | 13 | 70930714 | 70933455 |

The chromosomal positon was obtained from UCSC genome browser (http://genome.ucsc.edu/) build 36.

APPENDIX B: Chromosome 13
Page 4 of 49

| Chr | Start | End | Chr | Start | End |
|---|---|---|---|---|---|
| 13 | 25700783 | 25704113 | 13 | 70955808 | 70956735 |
| 13 | 25713305 | 25718567 | 13 | 70977020 | 70978125 |
| 13 | 25877185 | 25883559 | 13 | 70985221 | 70990747 |
| 13 | 25911888 | 25913933 | 13 | 71010405 | 71013705 |
| 13 | 25928991 | 25938552 | 13 | 71027964 | 71034199 |
| 13 | 25946379 | 25998724 | 13 | 71039392 | 71042765 |
| 13 | 26003796 | 26035844 | 13 | 71082647 | 71084237 |
| 13 | 26063135 | 26066690 | 13 | 71105322 | 71106986 |
| 13 | 26100812 | 26113624 | 13 | 71134240 | 71137709 |
| 13 | 26131228 | 26135954 | 13 | 71189200 | 71191417 |
| 13 | 26150705 | 26158345 | 13 | 71195194 | 71199393 |
| 13 | 26162539 | 26191337 | 13 | 71242789 | 71258537 |
| 13 | 26200247 | 26219737 | 13 | 71270311 | 71272183 |
| 13 | 26230287 | 26276232 | 13 | 71280482 | 71283055 |
| 13 | 26283709 | 26305826 | 13 | 71325459 | 71329365 |
| 13 | 26322138 | 26336515 | 13 | 71346878 | 71350782 |
| 13 | 26342548 | 26412528 | 13 | 71421137 | 71422116 |
| 13 | 26421029 | 26467540 | 13 | 71438762 | 71448187 |
| 13 | 26470381 | 26479856 | 13 | 71491175 | 71496039 |
| 13 | 26486542 | 26529081 | 13 | 71521299 | 71528786 |
| 13 | 26571057 | 26573034 | 13 | 71583113 | 71594826 |
| 13 | 26654233 | 26658319 | 13 | 71643736 | 71645102 |
| 13 | 26665254 | 26667844 | 13 | 71712816 | 71722367 |
| 13 | 26683273 | 26688123 | 13 | 71835944 | 71843225 |
| 13 | 26740109 | 26744611 | 13 | 71873185 | 71877739 |
| 13 | 26766880 | 26781866 | 13 | 71882736 | 71884599 |
| 13 | 26788641 | 26870396 | 13 | 71889216 | 71892155 |
| 13 | 26875326 | 26897046 | 13 | 71901040 | 71902718 |
| 13 | 26898181 | 26899071 | 13 | 71972478 | 71974253 |
| 13 | 26913701 | 26915596 | 13 | 71985152 | 71986666 |
| 13 | 26920758 | 26926574 | 13 | 72003103 | 72009415 |
| 13 | 26931099 | 26936643 | 13 | 72049999 | 72052045 |
| 13 | 26947013 | 26949390 | 13 | 72166060 | 72167186 |
| 13 | 26953222 | 26985202 | 13 | 72216779 | 72217730 |
| 13 | 26992504 | 27013074 | 13 | 72458494 | 72460426 |
| 13 | 27071641 | 27075659 | 13 | 72515532 | 72519471 |
| 13 | 27174908 | 27175881 | 13 | 72530321 | 72534857 |
| 13 | 27179824 | 27192595 | 13 | 72641029 | 72645395 |
| 13 | 27201885 | 27208407 | 13 | 72705198 | 72709228 |
| 13 | 27212603 | 27250710 | 13 | 72840376 | 72843503 |
| 13 | 27254213 | 27260538 | 13 | 72937312 | 72938009 |
| 13 | 27261358 | 27263351 | 13 | 73129935 | 73136469 |
| 13 | 27278159 | 27291219 | 13 | 73145536 | 73146941 |
| 13 | 27299288 | 27334699 | 13 | 73162903 | 73164920 |
| 13 | 27352688 | 27355120 | 13 | 73166861 | 73168087 |
| 13 | 27371396 | 27380880 | 13 | 73312136 | 73314963 |
| 13 | 27449579 | 27521811 | 13 | 73384398 | 73388982 |
| 13 | 27568548 | 27578274 | 13 | 73619761 | 73623013 |
| 13 | 27589842 | 27597883 | 13 | 73673298 | 73678612 |
| 13 | 27648166 | 27650733 | 13 | 73785657 | 73790162 |
| 13 | 27653886 | 27658824 | 13 | 73809547 | 73810965 |
| 13 | 27679650 | 27680963 | 13 | 73818090 | 73819370 |
| 13 | 27724709 | 27728723 | 13 | 73947358 | 73959794 |
| 13 | 27768761 | 27770800 | 13 | 74149871 | 74152148 |
| 13 | 27787919 | 27791924 | 13 | 74328573 | 74335115 |

The chromosomal positon was obtained from UCSC genome browser (http://genome.ucsc.edu/) build 36.

APPENDIX B: Chromosome 13
Page 5 of 49

| Chr | Start | End | Chr | Start | End |
|---|---|---|---|---|---|
| 13 | 27799830 | 27801953 | 13 | 74342562 | 74345361 |
| 13 | 27809347 | 27816787 | 13 | 74442671 | 74448654 |
| 13 | 27888876 | 27894892 | 13 | 74457975 | 74461982 |
| 13 | 27922978 | 27924563 | 13 | 74510633 | 74512483 |
| 13 | 27957394 | 27978131 | 13 | 74574669 | 74579894 |
| 13 | 28009559 | 28056495 | 13 | 74605956 | 74607644 |
| 13 | 28090059 | 28099306 | 13 | 74709811 | 74720624 |
| 13 | 28106557 | 28111817 | 13 | 74842283 | 74846408 |
| 13 | 28112042 | 28117262 | 13 | 74871068 | 74873944 |
| 13 | 28152559 | 28157614 | 13 | 75105837 | 75110339 |
| 13 | 28188439 | 28207018 | 13 | 75166037 | 75169325 |
| 13 | 28248596 | 28261506 | 13 | 75195605 | 75198442 |
| 13 | 28313379 | 28336773 | 13 | 75235213 | 75240317 |
| 13 | 28357365 | 28359949 | 13 | 75310358 | 75311668 |
| 13 | 28405569 | 28410643 | 13 | 75385839 | 75396821 |
| 13 | 28420999 | 28431362 | 13 | 75452177 | 75453720 |
| 13 | 28453576 | 28473653 | 13 | 75456314 | 75461925 |
| 13 | 28484298 | 28487324 | 13 | 75469251 | 75479137 |
| 13 | 28493032 | 28500763 | 13 | 75491408 | 75492354 |
| 13 | 28521396 | 28523490 | 13 | 75498597 | 75501505 |
| 13 | 28524779 | 28526728 | 13 | 75510106 | 75518665 |
| 13 | 28536053 | 28541233 | 13 | 75522413 | 75524033 |
| 13 | 28571176 | 28577111 | 13 | 75553743 | 75556067 |
| 13 | 28584171 | 28585323 | 13 | 75572545 | 75580398 |
| 13 | 28597798 | 28603098 | 13 | 75626151 | 75632364 |
| 13 | 28698197 | 28701624 | 13 | 75648632 | 75650510 |
| 13 | 28712698 | 28717604 | 13 | 75655832 | 75660798 |
| 13 | 28736224 | 28743525 | 13 | 75747834 | 75751134 |
| 13 | 28790089 | 28812735 | 13 | 75762017 | 75763288 |
| 13 | 28823664 | 28832217 | 13 | 75796826 | 75799121 |
| 13 | 28851783 | 28854896 | 13 | 75839488 | 75843054 |
| 13 | 28870690 | 28878797 | 13 | 75903290 | 75908864 |
| 13 | 28906813 | 28913383 | 13 | 75911435 | 75916819 |
| 13 | 28933998 | 28943174 | 13 | 75920135 | 75923700 |
| 13 | 28950372 | 29084340 | 13 | 75946711 | 75955520 |
| 13 | 29088479 | 29092888 | 13 | 75974411 | 75975827 |
| 13 | 29121490 | 29123291 | 13 | 76013863 | 76016778 |
| 13 | 29146815 | 29153351 | 13 | 76135514 | 76143331 |
| 13 | 29159510 | 29161722 | 13 | 76240496 | 76245921 |
| 13 | 29175110 | 29194990 | 13 | 76355825 | 76362521 |
| 13 | 29200606 | 29205820 | 13 | 76449788 | 76451669 |
| 13 | 29213835 | 29219081 | 13 | 76459493 | 76464249 |
| 13 | 29225951 | 29233556 | 13 | 76507991 | 76510985 |
| 13 | 29287090 | 29289554 | 13 | 76556059 | 76559548 |
| 13 | 29416262 | 29436905 | 13 | 76564163 | 76570155 |
| 13 | 29460775 | 29469115 | 13 | 76571864 | 76576637 |
| 13 | 29484871 | 29511698 | 13 | 76583257 | 76587417 |
| 13 | 29543808 | 29555372 | 13 | 76596597 | 76600329 |
| 13 | 29570403 | 29598124 | 13 | 76871819 | 76874374 |
| 13 | 29602551 | 29616533 | 13 | 77056390 | 77059812 |
| 13 | 29622861 | 29640060 | 13 | 77097114 | 77104758 |
| 13 | 29650452 | 29658063 | 13 | 77131085 | 77135368 |
| 13 | 29664811 | 29667816 | 13 | 77167193 | 77169423 |
| 13 | 29806691 | 29814739 | 13 | 77173531 | 77175095 |
| 13 | 29832712 | 29842435 | 13 | 77216478 | 77217967 |

The chromosomal positon was obtained from UCSC genome browser (http://genome.ucsc.edu/) build 36.

APPENDIX B: Chromosome 13
Page 6 of 49

| Chr | Start | End | | | Chr | Start | End |
|---|---|---|---|---|---|---|---|
| 13 | 29858629 | 29862143 | | | 13 | 77232634 | 77233791 |
| 13 | 29872839 | 29882191 | | | 13 | 77277561 | 77284634 |
| 13 | 29892554 | 29894387 | | | 13 | 77290658 | 77293575 |
| 13 | 29899594 | 29902297 | | | 13 | 77325584 | 77327001 |
| 13 | 29917518 | 29918668 | | | 13 | 77348596 | 77367981 |
| 13 | 29934040 | 29936259 | | | 13 | 77378469 | 77380081 |
| 13 | 29952960 | 29962613 | | | 13 | 77390230 | 77392888 |
| 13 | 29998624 | 30001500 | | | 13 | 77399309 | 77401568 |
| 13 | 30011447 | 30015172 | | | 13 | 77404927 | 77411526 |
| 13 | 30134366 | 30178194 | | | 13 | 77415427 | 77418502 |
| 13 | 30187660 | 30192831 | | | 13 | 77438775 | 77440859 |
| 13 | 30199530 | 30207453 | | | 13 | 77452835 | 77455163 |
| 13 | 30215144 | 30245739 | | | 13 | 77468922 | 77477699 |
| 13 | 30251279 | 30361542 | | | 13 | 77483245 | 77491340 |
| 13 | 30367878 | 30378914 | | | 13 | 77498905 | 77504472 |
| 13 | 30386926 | 30389556 | | | 13 | 77530342 | 77535166 |
| 13 | 30400623 | 30409621 | | | 13 | 77543551 | 77549323 |
| 13 | 30427528 | 30439300 | | | 13 | 77578785 | 77579478 |
| 13 | 30448249 | 30455876 | | | 13 | 77616903 | 77622211 |
| 13 | 30462732 | 30553984 | | | 13 | 77652638 | 77656981 |
| 13 | 30559153 | 30602404 | | | 13 | 77659231 | 77662565 |
| 13 | 30614280 | 30616739 | | | 13 | 77707613 | 77712845 |
| 13 | 30640650 | 30668057 | | | 13 | 77722183 | 77733231 |
| 13 | 30673733 | 30681176 | | | 13 | 77757563 | 77760375 |
| 13 | 30701419 | 30712421 | | | 13 | 77766715 | 77774821 |
| 13 | 30794640 | 30803043 | | | 13 | 77959910 | 77968505 |
| 13 | 30819152 | 30847376 | | | 13 | 77969369 | 77970701 |
| 13 | 30882292 | 30883769 | | | 13 | 78055378 | 78056386 |
| 13 | 30891289 | 30898251 | | | 13 | 78088486 | 78093030 |
| 13 | 30904869 | 30914814 | | | 13 | 78155261 | 78163147 |
| 13 | 30944517 | 30946659 | | | 13 | 78242828 | 78246828 |
| 13 | 30981694 | 30985934 | | | 13 | 78251210 | 78253925 |
| 13 | 31065026 | 31067034 | | | 13 | 78281283 | 78285726 |
| 13 | 31187801 | 31190447 | | | 13 | 78397861 | 78399467 |
| 13 | 31202401 | 31207323 | | | 13 | 78432435 | 78433131 |
| 13 | 31214871 | 31232125 | | | 13 | 78482230 | 78486034 |
| 13 | 31251530 | 31263728 | | | 13 | 78499043 | 78500485 |
| 13 | 31281398 | 31283332 | | | 13 | 78522102 | 78523056 |
| 13 | 31317473 | 31324800 | | | 13 | 78540852 | 78542960 |
| 13 | 31391121 | 31393135 | | | 13 | 78643587 | 78649340 |
| 13 | 31399682 | 31401468 | | | 13 | 78689661 | 78690987 |
| 13 | 31424761 | 31425734 | | | 13 | 78723788 | 78725687 |
| 13 | 31443580 | 31445809 | | | 13 | 78783951 | 78787933 |
| 13 | 31579851 | 31580577 | | | 13 | 78813503 | 78816079 |
| 13 | 31613781 | 31615326 | | | 13 | 78941093 | 78943399 |
| 13 | 31620552 | 31622689 | | | 13 | 79167955 | 79169550 |
| 13 | 31643298 | 31644792 | | | 13 | 79193908 | 79195195 |
| 13 | 31782468 | 31787966 | | | 13 | 79247741 | 79249820 |
| 13 | 31854202 | 31856934 | | | 13 | 79269739 | 79276492 |
| 13 | 31881548 | 31882703 | | | 13 | 79374663 | 79377584 |
| 13 | 31940822 | 31942443 | | | 13 | 79382025 | 79383075 |
| 13 | 32054248 | 32056684 | | | 13 | 79389937 | 79391103 |
| 13 | 32117582 | 32119279 | | | 13 | 79442775 | 79444391 |
| 13 | 32157718 | 32161350 | | | 13 | 79457164 | 79460578 |
| 13 | 32292886 | 32303083 | | | 13 | 79466568 | 79476080 |

The chromosomal positon was obtained from UCSC genome browser (http://genome.ucsc.edu/) build 36.

APPENDIX B: Chromosome 13
Page 7 of 49

| Chr | Start | End | | | Chr | Start | End |
|---|---|---|---|---|---|---|---|
| 13 | 32426022 | 32430226 | | | 13 | 79550624 | 79553791 |
| 13 | 32486960 | 32487804 | | | 13 | 79567669 | 79570989 |
| 13 | 32491254 | 32493567 | | | 13 | 79972869 | 79979509 |
| 13 | 32528112 | 32536181 | | | 13 | 79999427 | 80003751 |
| 13 | 32590294 | 32603605 | | | 13 | 80021116 | 80023492 |
| 13 | 32623846 | 32627518 | | | 13 | 80056111 | 80057818 |
| 13 | 32645012 | 32649242 | | | 13 | 80065282 | 80068082 |
| 13 | 32689572 | 32692060 | | | 13 | 80102545 | 80106058 |
| 13 | 32696770 | 32697051 | | | 13 | 80114255 | 80123195 |
| 13 | 32791552 | 32792382 | | | 13 | 80168083 | 80171154 |
| 13 | 32967725 | 32970881 | | | 13 | 80176986 | 80181486 |
| 13 | 33040022 | 33046200 | | | 13 | 80240853 | 80241597 |
| 13 | 33114335 | 33116570 | | | 13 | 80246183 | 80257662 |
| 13 | 33118880 | 33120254 | | | 13 | 80300387 | 80302262 |
| 13 | 33148256 | 33150635 | | | 13 | 80426680 | 80430099 |
| 13 | 33262041 | 33264314 | | | 13 | 80446737 | 80450731 |
| 13 | 33549846 | 33552766 | | | 13 | 80458730 | 80460073 |
| 13 | 33671762 | 33674905 | | | 13 | 80580775 | 80585134 |
| 13 | 33698732 | 33703265 | | | 13 | 80594555 | 80601405 |
| 13 | 33749416 | 33764695 | | | 13 | 80622988 | 80624869 |
| 13 | 33908984 | 33910990 | | | 13 | 80654472 | 80656122 |
| 13 | 33958446 | 33963156 | | | 13 | 80767434 | 80769339 |
| 13 | 34419721 | 34424411 | | | 13 | 80841311 | 80843011 |
| 13 | 34438680 | 34440050 | | | 13 | 80898064 | 80909335 |
| 13 | 34519824 | 34525920 | | | 13 | 80913981 | 80914669 |
| 13 | 34530653 | 34541084 | | | 13 | 80928399 | 80929643 |
| 13 | 34567010 | 34582495 | | | 13 | 80961183 | 80966780 |
| 13 | 34693110 | 34694916 | | | 13 | 81003275 | 81007866 |
| 13 | 34705796 | 34711867 | | | 13 | 81052879 | 81054777 |
| 13 | 34761617 | 34765314 | | | 13 | 81065413 | 81073694 |
| 13 | 34821042 | 34824052 | | | 13 | 81107549 | 81112291 |
| 13 | 34884940 | 34894141 | | | 13 | 81164403 | 81165433 |
| 13 | 34961312 | 34965982 | | | 13 | 81174382 | 81177335 |
| 13 | 34997322 | 34999989 | | | 13 | 81189922 | 81194782 |
| 13 | 35150998 | 35179799 | | | 13 | 81197664 | 81198806 |
| 13 | 35184052 | 35194075 | | | 13 | 81211184 | 81212542 |
| 13 | 35216653 | 35219718 | | | 13 | 81237764 | 81257443 |
| 13 | 35231168 | 35239618 | | | 13 | 81298246 | 81304396 |
| 13 | 35241758 | 35244098 | | | 13 | 81309821 | 81313024 |
| 13 | 35256618 | 35258568 | | | 13 | 81347912 | 81353086 |
| 13 | 35267430 | 35282620 | | | 13 | 81374689 | 81377296 |
| 13 | 35296662 | 35315058 | | | 13 | 81415674 | 81422463 |
| 13 | 35349038 | 35356542 | | | 13 | 81438317 | 81441468 |
| 13 | 35381280 | 35384826 | | | 13 | 81478573 | 81494397 |
| 13 | 35392624 | 35400861 | | | 13 | 81546066 | 81551387 |
| 13 | 35404436 | 35414955 | | | 13 | 81571468 | 81572376 |
| 13 | 35442225 | 35462001 | | | 13 | 81596557 | 81598998 |
| 13 | 35561661 | 35565023 | | | 13 | 81604481 | 81609119 |
| 13 | 35571504 | 35576847 | | | 13 | 81624139 | 81625758 |
| 13 | 35596824 | 35599247 | | | 13 | 81627091 | 81628856 |
| 13 | 35616481 | 35620593 | | | 13 | 81779075 | 81783034 |
| 13 | 35631075 | 35635945 | | | 13 | 81893719 | 81898215 |
| 13 | 35685597 | 35688201 | | | 13 | 81941237 | 81943242 |
| 13 | 35884069 | 35886965 | | | 13 | 81949913 | 81962669 |
| 13 | 35903680 | 35907779 | | | 13 | 81983455 | 81986043 |

The chromosomal positon was obtained from UCSC genome browser (http://genome.ucsc.edu/) build 36.

APPENDIX B: Chromosome 13
Page 8 of 49

| Chr | Start | End | | | Chr | Start | End |
|---|---|---|---|---|---|---|---|
| 13 | 35918506 | 35922876 | | | 13 | 82089220 | 82092851 |
| 13 | 35999515 | 36001806 | | | 13 | 82103999 | 82105346 |
| 13 | 36006982 | 36012383 | | | 13 | 82165658 | 82175478 |
| 13 | 36018062 | 36020749 | | | 13 | 82180396 | 82189493 |
| 13 | 36079998 | 36083006 | | | 13 | 82198361 | 82207972 |
| 13 | 36087584 | 36090382 | | | 13 | 82221022 | 82223867 |
| 13 | 36137088 | 36146238 | | | 13 | 82324892 | 82326174 |
| 13 | 36167064 | 36174449 | | | 13 | 82351340 | 82352126 |
| 13 | 36182214 | 36184572 | | | 13 | 82376259 | 82380958 |
| 13 | 36266691 | 36269854 | | | 13 | 82452599 | 82457407 |
| 13 | 36310810 | 36313071 | | | 13 | 82521704 | 82527123 |
| 13 | 36319890 | 36323656 | | | 13 | 82533861 | 82537241 |
| 13 | 36327510 | 36331607 | | | 13 | 82538895 | 82566302 |
| 13 | 36351158 | 36352531 | | | 13 | 82590617 | 82594175 |
| 13 | 36470855 | 36473574 | | | 13 | 82598718 | 82603376 |
| 13 | 36576594 | 36578792 | | | 13 | 82654977 | 82656487 |
| 13 | 36682563 | 36688697 | | | 13 | 82681364 | 82706868 |
| 13 | 36698109 | 36706881 | | | 13 | 82760519 | 82762734 |
| 13 | 36728958 | 36731270 | | | 13 | 82828048 | 82834469 |
| 13 | 36758596 | 36762622 | | | 13 | 82916303 | 82922643 |
| 13 | 36840794 | 36844029 | | | 13 | 82924324 | 82925925 |
| 13 | 36958756 | 36963278 | | | 13 | 83015382 | 83019683 |
| 13 | 37042253 | 37044786 | | | 13 | 83039177 | 83040928 |
| 13 | 37069342 | 37085476 | | | 13 | 83151270 | 83156356 |
| 13 | 37242957 | 37246186 | | | 13 | 83340179 | 83341751 |
| 13 | 37265165 | 37269436 | | | 13 | 83354335 | 83356505 |
| 13 | 37274086 | 37283749 | | | 13 | 83377998 | 83385157 |
| 13 | 37319348 | 37323290 | | | 13 | 83448819 | 83452779 |
| 13 | 37337894 | 37341242 | | | 13 | 83513351 | 83521619 |
| 13 | 37342162 | 37343597 | | | 13 | 83564948 | 83568504 |
| 13 | 37354941 | 37359824 | | | 13 | 83608390 | 83613433 |
| 13 | 37380768 | 37384953 | | | 13 | 83695133 | 83714789 |
| 13 | 37395245 | 37397028 | | | 13 | 83748909 | 83759082 |
| 13 | 37417811 | 37420173 | | | 13 | 83760569 | 83768572 |
| 13 | 37429971 | 37432551 | | | 13 | 83774876 | 83778317 |
| 13 | 37484571 | 37487971 | | | 13 | 83835576 | 83840014 |
| 13 | 37553856 | 37555362 | | | 13 | 83930494 | 83931406 |
| 13 | 37603026 | 37605817 | | | 13 | 83946055 | 83950585 |
| 13 | 37612274 | 37620234 | | | 13 | 83958058 | 83959292 |
| 13 | 37639817 | 37643483 | | | 13 | 83987373 | 83990124 |
| 13 | 37651638 | 37653970 | | | 13 | 83996975 | 83999087 |
| 13 | 37699143 | 37702898 | | | 13 | 84008185 | 84009174 |
| 13 | 37721579 | 37730396 | | | 13 | 84063536 | 84064996 |
| 13 | 37771007 | 37776178 | | | 13 | 84097558 | 84100848 |
| 13 | 37832309 | 37834800 | | | 13 | 84197632 | 84206957 |
| 13 | 37838687 | 37841174 | | | 13 | 84302436 | 84304871 |
| 13 | 37875866 | 37880074 | | | 13 | 84341963 | 84343078 |
| 13 | 37901299 | 37907346 | | | 13 | 84366164 | 84371578 |
| 13 | 37955930 | 37958473 | | | 13 | 84391769 | 84393908 |
| 13 | 37961576 | 37965114 | | | 13 | 84405714 | 84408293 |
| 13 | 37982958 | 37983724 | | | 13 | 84665576 | 84672329 |
| 13 | 38042981 | 38046577 | | | 13 | 84676868 | 84678632 |
| 13 | 38090382 | 38100651 | | | 13 | 84713486 | 84719638 |
| 13 | 38105788 | 38110226 | | | 13 | 84729818 | 84732469 |
| 13 | 38159232 | 38162053 | | | 13 | 84785323 | 84787592 |

The chromosomal positon was obtained from UCSC genome browser (http://genome.ucsc.edu/) build 36.

APPENDIX B: Chromosome 13
Page 9 of 49

| Chr | Start | End | Chr | Start | End |
|---|---|---|---|---|---|
| 13 | 38169553 | 38172894 | 13 | 84838443 | 84841480 |
| 13 | 38213645 | 38217123 | 13 | 84855355 | 84866204 |
| 13 | 38258145 | 38260079 | 13 | 84997750 | 85009472 |
| 13 | 38352952 | 38358174 | 13 | 85087393 | 85091095 |
| 13 | 38365890 | 38367021 | 13 | 85101956 | 85104147 |
| 13 | 38429780 | 38431573 | 13 | 85110712 | 85112068 |
| 13 | 38448916 | 38452542 | 13 | 85128367 | 85129829 |
| 13 | 38484545 | 38486560 | 13 | 85131403 | 85132727 |
| 13 | 38509697 | 38512481 | 13 | 85134909 | 85136280 |
| 13 | 38722676 | 38724824 | 13 | 85142286 | 85145824 |
| 13 | 38751046 | 38756182 | 13 | 85161654 | 85170918 |
| 13 | 38795739 | 38797491 | 13 | 85175951 | 85178817 |
| 13 | 38866859 | 38867918 | 13 | 85425110 | 85432386 |
| 13 | 39035520 | 39037629 | 13 | 85463699 | 85474630 |
| 13 | 39046062 | 39048732 | 13 | 85561438 | 85577839 |
| 13 | 39172492 | 39173613 | 13 | 85590922 | 85599902 |
| 13 | 39187033 | 39196180 | 13 | 85610153 | 85612178 |
| 13 | 39231230 | 39232041 | 13 | 85715451 | 85717077 |
| 13 | 39281230 | 39284059 | 13 | 85844964 | 85849670 |
| 13 | 39329069 | 39330013 | 13 | 85875577 | 85876928 |
| 13 | 39390296 | 39393250 | 13 | 85885357 | 85888598 |
| 13 | 39425599 | 39429459 | 13 | 85914452 | 85916416 |
| 13 | 39464111 | 39469453 | 13 | 86068155 | 86069981 |
| 13 | 39545257 | 39579918 | 13 | 86141946 | 86144085 |
| 13 | 39608279 | 39619412 | 13 | 86207518 | 86216480 |
| 13 | 39630063 | 39650511 | 13 | 86259264 | 86264046 |
| 13 | 39661821 | 39711172 | 13 | 86294878 | 86298269 |
| 13 | 39743998 | 39749657 | 13 | 86306497 | 86308381 |
| 13 | 39784244 | 39790056 | 13 | 86453949 | 86459854 |
| 13 | 39810272 | 39839556 | 13 | 86529792 | 86531212 |
| 13 | 39845832 | 39857475 | 13 | 86556343 | 86562310 |
| 13 | 39862479 | 39864779 | 13 | 86730882 | 86734749 |
| 13 | 39872118 | 39879542 | 13 | 86741323 | 86748463 |
| 13 | 39895917 | 39899429 | 13 | 86842384 | 86845210 |
| 13 | 39911362 | 39915015 | 13 | 86893117 | 86895693 |
| 13 | 39928862 | 39980787 | 13 | 86946376 | 86949270 |
| 13 | 40005931 | 40009873 | 13 | 86958502 | 86964793 |
| 13 | 40031578 | 40038339 | 13 | 86979785 | 86985471 |
| 13 | 40136668 | 40139759 | 13 | 87026623 | 87032284 |
| 13 | 40152268 | 40171780 | 13 | 87047929 | 87052469 |
| 13 | 40240969 | 40244759 | 13 | 87072317 | 87079641 |
| 13 | 40249455 | 40268464 | 13 | 87123800 | 87124923 |
| 13 | 40347491 | 40352743 | 13 | 87125915 | 87127455 |
| 13 | 40388579 | 40394879 | 13 | 87128475 | 87135569 |
| 13 | 40449848 | 40456829 | 13 | 87151900 | 87156269 |
| 13 | 40484997 | 40487587 | 13 | 87168293 | 87188223 |
| 13 | 40603480 | 40607260 | 13 | 87227452 | 87229531 |
| 13 | 40665255 | 40667015 | 13 | 87282530 | 87285885 |
| 13 | 40758797 | 40763290 | 13 | 87310846 | 87314572 |
| 13 | 40777673 | 40784622 | 13 | 87320914 | 87325160 |
| 13 | 40800700 | 40803148 | 13 | 87343395 | 87345677 |
| 13 | 40852857 | 40860456 | 13 | 87400476 | 87404498 |
| 13 | 40893696 | 40914333 | 13 | 87417605 | 87420185 |
| 13 | 40923353 | 40929429 | 13 | 87477226 | 87501883 |
| 13 | 40932272 | 40935882 | 13 | 87522922 | 87526457 |

The chromosomal positon was obtained from UCSC genome browser (http://genome.ucsc.edu/) build 36.

APPENDIX B: Chromosome 13
Page 10 of 49

| Chr | Start | End | | | Chr | Start | End |
|---|---|---|---|---|---|---|---|
| 13 | 40985216 | 40989572 | | | 13 | 87534596 | 87536215 |
| 13 | 41005603 | 41027445 | | | 13 | 87550839 | 87556217 |
| 13 | 41068297 | 41071705 | | | 13 | 87586073 | 87587800 |
| 13 | 41136060 | 41138641 | | | 13 | 87620450 | 87628953 |
| 13 | 41281808 | 41293019 | | | 13 | 87662971 | 87667730 |
| 13 | 41431437 | 41434007 | | | 13 | 87697282 | 87711393 |
| 13 | 41445138 | 41447914 | | | 13 | 87724242 | 87725622 |
| 13 | 41481509 | 41485148 | | | 13 | 87747639 | 87751114 |
| 13 | 41510601 | 41514476 | | | 13 | 87764326 | 87765416 |
| 13 | 41524363 | 41526601 | | | 13 | 87846283 | 87847554 |
| 13 | 41555482 | 41556524 | | | 13 | 87935573 | 87937074 |
| 13 | 41578508 | 41586397 | | | 13 | 87937874 | 87946511 |
| 13 | 41631736 | 41632866 | | | 13 | 87992210 | 88003438 |
| 13 | 41715268 | 41717154 | | | 13 | 88060625 | 88075972 |
| 13 | 41760593 | 41762735 | | | 13 | 88129015 | 88131929 |
| 13 | 41805080 | 41807437 | | | 13 | 88244819 | 88246415 |
| 13 | 41853282 | 41859315 | | | 13 | 88249585 | 88252964 |
| 13 | 41891066 | 41892087 | | | 13 | 88277166 | 88285716 |
| 13 | 41937941 | 41939010 | | | 13 | 88368812 | 88370793 |
| 13 | 41948060 | 41951812 | | | 13 | 88416387 | 88426892 |
| 13 | 42060624 | 42067750 | | | 13 | 88449590 | 88456861 |
| 13 | 42142036 | 42145661 | | | 13 | 88465766 | 88466933 |
| 13 | 42189259 | 42190488 | | | 13 | 88513152 | 88523310 |
| 13 | 42202803 | 42207419 | | | 13 | 88530221 | 88533504 |
| 13 | 42259777 | 42260122 | | | 13 | 88578333 | 88581007 |
| 13 | 42260502 | 42265263 | | | 13 | 88602349 | 88603040 |
| 13 | 42317955 | 42322598 | | | 13 | 88633590 | 88634075 |
| 13 | 42333496 | 42345555 | | | 13 | 88678789 | 88684053 |
| 13 | 42393834 | 42399445 | | | 13 | 88811493 | 88813796 |
| 13 | 42402594 | 42407107 | | | 13 | 88909016 | 88915127 |
| 13 | 42493078 | 42496891 | | | 13 | 88991033 | 88992667 |
| 13 | 42598890 | 42606625 | | | 13 | 89007848 | 89015967 |
| 13 | 42915646 | 42919582 | | | 13 | 89114274 | 89115764 |
| 13 | 42973036 | 42980709 | | | 13 | 89124384 | 89128332 |
| 13 | 43082038 | 43085354 | | | 13 | 89194468 | 89199475 |
| 13 | 43217311 | 43223168 | | | 13 | 89233594 | 89236547 |
| 13 | 43257029 | 43262627 | | | 13 | 89238513 | 89240501 |
| 13 | 43301752 | 43302922 | | | 13 | 89244950 | 89247690 |
| 13 | 43339482 | 43340377 | | | 13 | 89261478 | 89262244 |
| 13 | 43375644 | 43377104 | | | 13 | 89408901 | 89410270 |
| 13 | 43415150 | 43417325 | | | 13 | 89443348 | 89446321 |
| 13 | 43438783 | 43448902 | | | 13 | 89503674 | 89507272 |
| 13 | 43481379 | 43482735 | | | 13 | 89509785 | 89516812 |
| 13 | 43486396 | 43489094 | | | 13 | 89616993 | 89620331 |
| 13 | 43510606 | 43513055 | | | 13 | 89634568 | 89637168 |
| 13 | 43525075 | 43525606 | | | 13 | 89737859 | 89740436 |
| 13 | 43631038 | 43632285 | | | 13 | 89959909 | 89964369 |
| 13 | 43655056 | 43657312 | | | 13 | 90061902 | 90068413 |
| 13 | 43684099 | 43685852 | | | 13 | 90072336 | 90078361 |
| 13 | 43701253 | 43705115 | | | 13 | 90108077 | 90120367 |
| 13 | 43705894 | 43708490 | | | 13 | 90151674 | 90152382 |
| 13 | 43715988 | 43718445 | | | 13 | 90164994 | 90174932 |
| 13 | 43730944 | 43732260 | | | 13 | 90193841 | 90199033 |
| 13 | 43809810 | 43812162 | | | 13 | 90240809 | 90243324 |
| 13 | 43844985 | 43846667 | | | 13 | 90266426 | 90270894 |

The chromosomal positon was obtained from UCSC genome browser (http://genome.ucsc.edu/) build 36.

APPENDIX B: Chromosome 13

| Chr | Start | End | | Chr | Start | End |
|---|---|---|---|---|---|---|
| 13 | 43866217 | 43870443 | | 13 | 90281275 | 90282641 |
| 13 | 43874963 | 43889927 | | 13 | 90376829 | 90378781 |
| 13 | 43892943 | 43897289 | | 13 | 90419229 | 90424970 |
| 13 | 43904170 | 43907230 | | 13 | 90521011 | 90526963 |
| 13 | 43922071 | 43924981 | | 13 | 90585401 | 90587843 |
| 13 | 44012701 | 44016989 | | 13 | 90623475 | 90626071 |
| 13 | 44048575 | 44053016 | | 13 | 90650902 | 90654139 |
| 13 | 44061184 | 44069660 | | 13 | 90662998 | 90666464 |
| 13 | 44131088 | 44150800 | | 13 | 90673919 | 90678383 |
| 13 | 44198499 | 44205154 | | 13 | 90823114 | 90825761 |
| 13 | 44230935 | 44231870 | | 13 | 90829307 | 90831063 |
| 13 | 44269055 | 44273335 | | 13 | 90848735 | 90851326 |
| 13 | 44289735 | 44294844 | | 13 | 90956138 | 90958884 |
| 13 | 44307671 | 44310698 | | 13 | 90962312 | 90962938 |
| 13 | 44339627 | 44345642 | | 13 | 91067817 | 91070851 |
| 13 | 44365988 | 44373623 | | 13 | 91204128 | 91211016 |
| 13 | 44512781 | 44535808 | | 13 | 91278515 | 91281906 |
| 13 | 44576940 | 44588283 | | 13 | 91357475 | 91359387 |
| 13 | 44771883 | 44798314 | | 13 | 91385493 | 91387649 |
| 13 | 44812911 | 44819582 | | 13 | 91437160 | 91439093 |
| 13 | 44830123 | 44864555 | | 13 | 91489629 | 91493806 |
| 13 | 44886242 | 44887471 | | 13 | 91528490 | 91532264 |
| 13 | 44916777 | 44940314 | | 13 | 91601045 | 91604679 |
| 13 | 44983340 | 44989481 | | 13 | 91708932 | 91710030 |
| 13 | 45011963 | 45022503 | | 13 | 91775624 | 91780968 |
| 13 | 45046400 | 45052744 | | 13 | 91787381 | 91790105 |
| 13 | 45056988 | 45079002 | | 13 | 91834934 | 91836407 |
| 13 | 45100407 | 45103503 | | 13 | 91975146 | 91976786 |
| 13 | 45203803 | 45221760 | | 13 | 92005258 | 92008999 |
| 13 | 45232139 | 45233812 | | 13 | 92052223 | 92053230 |
| 13 | 45251255 | 45262358 | | 13 | 92059996 | 92065703 |
| 13 | 45268429 | 45275781 | | 13 | 92173423 | 92184512 |
| 13 | 45283181 | 45298667 | | 13 | 92228553 | 92234334 |
| 13 | 45306874 | 45323452 | | 13 | 92249954 | 92255003 |
| 13 | 45336142 | 45354179 | | 13 | 92291549 | 92297512 |
| 13 | 45360735 | 45384289 | | 13 | 92305425 | 92310278 |
| 13 | 45391211 | 45395888 | | 13 | 92383757 | 92386675 |
| 13 | 45401552 | 45408740 | | 13 | 92539797 | 92547473 |
| 13 | 45416364 | 45421581 | | 13 | 92576400 | 92580458 |
| 13 | 45555363 | 45559085 | | 13 | 92639793 | 92641444 |
| 13 | 45586522 | 45587328 | | 13 | 92693305 | 92695105 |
| 13 | 45614499 | 45619712 | | 13 | 92761721 | 92763583 |
| 13 | 45637663 | 45652667 | | 13 | 92778164 | 92781404 |
| 13 | 45802643 | 45818623 | | 13 | 92969983 | 92978353 |
| 13 | 45837486 | 45847874 | | 13 | 93018046 | 93020216 |
| 13 | 45857107 | 45861778 | | 13 | 93156316 | 93164065 |
| 13 | 45931131 | 45940547 | | 13 | 93173073 | 93174462 |
| 13 | 46024200 | 46026705 | | 13 | 93300330 | 93321716 |
| 13 | 46087829 | 46089784 | | 13 | 93335368 | 93342051 |
| 13 | 46105835 | 46109987 | | 13 | 93377994 | 93379088 |
| 13 | 46112467 | 46116707 | | 13 | 93403951 | 93406808 |
| 13 | 46181330 | 46183311 | | 13 | 93473615 | 93477253 |
| 13 | 46190406 | 46191770 | | 13 | 93524575 | 93531619 |
| 13 | 46250808 | 46264452 | | 13 | 93548117 | 93551260 |
| 13 | 46364417 | 46370931 | | 13 | 93601674 | 93604347 |

The chromosomal positon was obtained from UCSC genome browser (http://genome.ucsc.edu/) build 36.

APPENDIX B: Chromosome 13
Page 12 of 49

| Chr | Start | End | Chr | Start | End |
|---|---|---|---|---|---|
| 13 | 46492288 | 46499182 | 13 | 93620615 | 93624915 |
| 13 | 46508677 | 46515200 | 13 | 93667454 | 93671491 |
| 13 | 46531393 | 46533563 | 13 | 93730608 | 93738648 |
| 13 | 46548668 | 46551269 | 13 | 93752550 | 93754480 |
| 13 | 46566546 | 46567908 | 13 | 93775103 | 93780372 |
| 13 | 46574393 | 46583699 | 13 | 93786395 | 93795018 |
| 13 | 46648304 | 46652358 | 13 | 93829492 | 93833913 |
| 13 | 46758018 | 46760385 | 13 | 93912423 | 93921799 |
| 13 | 46795743 | 46797706 | 13 | 93950804 | 93955224 |
| 13 | 46896973 | 46901416 | 13 | 93959631 | 93965640 |
| 13 | 46918668 | 46925436 | 13 | 93995774 | 94002881 |
| 13 | 46960296 | 46965196 | 13 | 94127034 | 94135909 |
| 13 | 47027127 | 47030644 | 13 | 94139732 | 94143086 |
| 13 | 47180764 | 47194562 | 13 | 94160642 | 94163895 |
| 13 | 47308342 | 47310723 | 13 | 94241949 | 94246397 |
| 13 | 47472641 | 47474363 | 13 | 94278997 | 94289592 |
| 13 | 47520999 | 47534750 | 13 | 94296891 | 94299637 |
| 13 | 47701029 | 47706088 | 13 | 94305685 | 94337372 |
| 13 | 47788315 | 47794357 | 13 | 94384291 | 94402523 |
| 13 | 47805165 | 47806661 | 13 | 94449317 | 94454623 |
| 13 | 47829117 | 47831188 | 13 | 94457651 | 94464725 |
| 13 | 47869880 | 47872689 | 13 | 94488793 | 94493125 |
| 13 | 47919538 | 47924743 | 13 | 94507379 | 94512282 |
| 13 | 47928960 | 47930756 | 13 | 94563982 | 94575292 |
| 13 | 47977731 | 47978008 | 13 | 94606937 | 94608371 |
| 13 | 48040682 | 48043421 | 13 | 94617964 | 94626385 |
| 13 | 48056710 | 48058785 | 13 | 94641139 | 94663940 |
| 13 | 48135215 | 48138407 | 13 | 94695124 | 94696502 |
| 13 | 48149574 | 48153953 | 13 | 94705471 | 94756203 |
| 13 | 48163097 | 48165604 | 13 | 94794566 | 94797589 |
| 13 | 48211087 | 48213910 | 13 | 94824336 | 94835694 |
| 13 | 48234880 | 48236523 | 13 | 94894871 | 94901938 |
| 13 | 48245317 | 48245803 | 13 | 94920678 | 94930057 |
| 13 | 48254417 | 48257113 | 13 | 95062542 | 95068349 |
| 13 | 48336433 | 48344181 | 13 | 95072603 | 95075964 |
| 13 | 48381555 | 48382086 | 13 | 95081915 | 95083386 |
| 13 | 48492067 | 48495772 | 13 | 95093801 | 95094801 |
| 13 | 48569543 | 48575334 | 13 | 95140007 | 95146717 |
| 13 | 48689273 | 48695952 | 13 | 95547074 | 95548596 |
| 13 | 48769658 | 48786811 | 13 | 95607849 | 95609673 |
| 13 | 48819814 | 48824149 | 13 | 95616516 | 95620595 |
| 13 | 48870890 | 48874551 | 13 | 95672607 | 95672905 |
| 13 | 48967146 | 48971190 | 13 | 95680287 | 95685579 |
| 13 | 49031493 | 49039405 | 13 | 95740078 | 95741603 |
| 13 | 49122968 | 49140855 | 13 | 95954905 | 95957866 |
| 13 | 49156925 | 49164612 | 13 | 96024241 | 96026671 |
| 13 | 49310796 | 49321469 | 13 | 96092135 | 96095671 |
| 13 | 49468171 | 49470005 | 13 | 96130822 | 96133266 |
| 13 | 49748924 | 49752280 | 13 | 96179396 | 96181489 |
| 13 | 49796258 | 49799985 | 13 | 96192204 | 96199366 |
| 13 | 49806792 | 49808183 | 13 | 96299635 | 96307577 |
| 13 | 49810953 | 49813770 | 13 | 96334057 | 96335481 |
| 13 | 49857678 | 49859676 | 13 | 96365655 | 96366588 |
| 13 | 50001373 | 50002268 | 13 | 96396504 | 96399778 |
| 13 | 50024757 | 50025977 | 13 | 96443807 | 96445495 |

The chromosomal positon was obtained from UCSC genome browser (http://genome.ucsc.edu/) build 36.

APPENDIX B: Chromosome 13
Page 13 of 49

| Chr | Start | End | | | Chr | Start | End |
|---|---|---|---|---|---|---|---|
| 13 | 50068177 | 50070767 | | | 13 | 96517320 | 96520902 |
| 13 | 50163832 | 50167128 | | | 13 | 96559934 | 96563868 |
| 13 | 50259448 | 50263644 | | | 13 | 96581454 | 96585114 |
| 13 | 50315019 | 50316524 | | | 13 | 96592045 | 96595798 |
| 13 | 50470279 | 50473408 | | | 13 | 96634521 | 96638992 |
| 13 | 50497657 | 50502133 | | | 13 | 96684582 | 96694204 |
| 13 | 50515725 | 50518325 | | | 13 | 96706810 | 96714684 |
| 13 | 50542338 | 50560176 | | | 13 | 96730422 | 96735225 |
| 13 | 50582813 | 50584348 | | | 13 | 96766211 | 96771704 |
| 13 | 50608342 | 50610098 | | | 13 | 96787243 | 96790195 |
| 13 | 50619133 | 50626087 | | | 13 | 96838738 | 96839509 |
| 13 | 50671699 | 50675816 | | | 13 | 96901378 | 96908874 |
| 13 | 50681828 | 50703240 | | | 13 | 97066095 | 97069925 |
| 13 | 50712245 | 50725016 | | | 13 | 97070316 | 97078210 |
| 13 | 50728485 | 50735478 | | | 13 | 97089652 | 97104771 |
| 13 | 50752638 | 50765696 | | | 13 | 97172222 | 97187780 |
| 13 | 50785148 | 50796531 | | | 13 | 97195084 | 97208846 |
| 13 | 50807679 | 50817452 | | | 13 | 97331711 | 97335885 |
| 13 | 50829055 | 50841074 | | | 13 | 97355939 | 97357304 |
| 13 | 50891505 | 50894381 | | | 13 | 97477537 | 97514758 |
| 13 | 50954190 | 50959422 | | | 13 | 97546945 | 97565196 |
| 13 | 51028721 | 51031970 | | | 13 | 97574244 | 97595054 |
| 13 | 51048567 | 51052511 | | | 13 | 97621586 | 97628922 |
| 13 | 51201050 | 51203094 | | | 13 | 97635666 | 97643713 |
| 13 | 51240307 | 51255291 | | | 13 | 97658249 | 97677130 |
| 13 | 51287994 | 51290771 | | | 13 | 97685117 | 97692360 |
| 13 | 51293456 | 51294201 | | | 13 | 97696773 | 97699048 |
| 13 | 51311014 | 51312954 | | | 13 | 97715520 | 97718659 |
| 13 | 51316656 | 51318066 | | | 13 | 97727777 | 97730706 |
| 13 | 51337260 | 51338985 | | | 13 | 97735915 | 97740029 |
| 13 | 51376190 | 51428985 | | | 13 | 97746213 | 97773080 |
| 13 | 51441903 | 51442823 | | | 13 | 97777969 | 97802555 |
| 13 | 51444093 | 51444738 | | | 13 | 97816381 | 97823437 |
| 13 | 51468221 | 51484382 | | | 13 | 97832809 | 97841082 |
| 13 | 51661817 | 51663721 | | | 13 | 97843452 | 97846578 |
| 13 | 51666403 | 51684087 | | | 13 | 97851753 | 97861479 |
| 13 | 51782126 | 51790838 | | | 13 | 97865626 | 97958184 |
| 13 | 51848737 | 51857985 | | | 13 | 97970526 | 98022339 |
| 13 | 51926807 | 51927937 | | | 13 | 98104143 | 98115006 |
| 13 | 52066586 | 52098345 | | | 13 | 98123505 | 98149365 |
| 13 | 52210535 | 52280857 | | | 13 | 98173698 | 98178344 |
| 13 | 52304861 | 52320413 | | | 13 | 98200317 | 98248946 |
| 13 | 52324637 | 52326122 | | | 13 | 98266567 | 98267121 |
| 13 | 52363407 | 52384251 | | | 13 | 98358282 | 98360173 |
| 13 | 52392277 | 52409007 | | | 13 | 98409846 | 98428961 |
| 13 | 52446311 | 52448357 | | | 13 | 98463246 | 98464720 |
| 13 | 52474368 | 52479512 | | | 13 | 98512872 | 98515795 |
| 13 | 52486301 | 52488373 | | | 13 | 98528193 | 98538376 |
| 13 | 52529528 | 52534080 | | | 13 | 98624324 | 98631243 |
| 13 | 52539714 | 52549603 | | | 13 | 98648734 | 98660511 |
| 13 | 52610643 | 52614828 | | | 13 | 98727995 | 98728904 |
| 13 | 52632173 | 52633267 | | | 13 | 98790811 | 98806112 |
| 13 | 52671355 | 52677673 | | | 13 | 98835141 | 98896974 |
| 13 | 52701688 | 52722306 | | | 13 | 98904473 | 98917230 |
| 13 | 52795378 | 52801447 | | | 13 | 98944284 | 98952431 |

The chromosomal positon was obtained from UCSC genome browser (http://genome.ucsc.edu/) build 36.

APPENDIX B: Chromosome 13
Page 14 of 49

| Chr | Start | End | Chr | Start | End |
|---|---|---|---|---|---|
| 13 | 52804018 | 52805781 | 13 | 98973850 | 98977485 |
| 13 | 52880605 | 52882695 | 13 | 99015636 | 99040808 |
| 13 | 53021178 | 53022967 | 13 | 99063598 | 99076739 |
| 13 | 53058127 | 53062932 | 13 | 99101136 | 99106652 |
| 13 | 53072740 | 53077639 | 13 | 99113154 | 99117511 |
| 13 | 53114277 | 53117226 | 13 | 99139189 | 99163209 |
| 13 | 53127086 | 53129322 | 13 | 99175437 | 99181419 |
| 13 | 53143355 | 53147485 | 13 | 99190433 | 99206606 |
| 13 | 53163314 | 53170778 | 13 | 99252456 | 99307842 |
| 13 | 53179230 | 53181916 | 13 | 99327085 | 99344260 |
| 13 | 53191575 | 53192268 | 13 | 99345120 | 99345989 |
| 13 | 53216718 | 53220444 | 13 | 99347689 | 99352290 |
| 13 | 53247048 | 53251191 | 13 | 99361024 | 99406524 |
| 13 | 53267265 | 53270119 | 13 | 99429614 | 99432832 |
| 13 | 53282261 | 53292048 | 13 | 99831237 | 99833059 |
| 13 | 53309921 | 53314122 | 13 | 99866383 | 99870223 |
| 13 | 53351620 | 53357967 | 13 | 99901506 | 99917523 |
| 13 | 53380400 | 53383289 | 13 | 99937828 | 99947677 |
| 13 | 53410951 | 53415784 | 13 | 99958750 | 100005287 |
| 13 | 53460895 | 53462092 | 13 | 100015369 | 100016723 |
| 13 | 53528160 | 53529818 | 13 | 100036791 | 100045832 |
| 13 | 53543616 | 53544735 | 13 | 100056794 | 100058878 |
| 13 | 53553367 | 53555044 | 13 | 100074266 | 100097631 |
| 13 | 53558468 | 53560125 | 13 | 100110875 | 100126442 |
| 13 | 53625823 | 53629496 | 13 | 100155771 | 100157759 |
| 13 | 53664431 | 53668470 | 13 | 100165917 | 100173522 |
| 13 | 53671593 | 53678083 | 13 | 100223815 | 100227203 |
| 13 | 53701108 | 53705715 | 13 | 100395514 | 100399909 |
| 13 | 53713941 | 53715707 | 13 | 100434338 | 100435087 |
| 13 | 53724168 | 53735277 | 13 | 100477949 | 100480663 |
| 13 | 53785319 | 53790654 | 13 | 100511361 | 100518080 |
| 13 | 53799148 | 53804346 | 13 | 100534852 | 100538759 |
| 13 | 53821278 | 53828851 | 13 | 100638813 | 100641701 |
| 13 | 53858140 | 53862206 | 13 | 100672574 | 100678299 |
| 13 | 53870263 | 53873160 | 13 | 100706050 | 100709232 |
| 13 | 53903296 | 53904503 | 13 | 100722083 | 100726582 |
| 13 | 54011139 | 54016357 | 13 | 100844808 | 100851721 |
| 13 | 54100240 | 54109511 | 13 | 100858310 | 100859990 |
| 13 | 54145230 | 54148262 | 13 | 100875474 | 100877377 |
| 13 | 54227796 | 54229465 | 13 | 100895421 | 100896895 |
| 13 | 54230766 | 54233008 | 13 | 100960479 | 100964127 |
| 13 | 54266595 | 54269170 | 13 | 100985412 | 100987445 |
| 13 | 54324657 | 54327006 | 13 | 101058201 | 101059759 |
| 13 | 54409772 | 54414781 | 13 | 101099900 | 101105583 |
| 13 | 54439222 | 54443029 | 13 | 101133978 | 101138108 |
| 13 | 54451720 | 54455197 | 13 | 101298621 | 101303288 |
| 13 | 54519528 | 54523829 | 13 | 101305592 | 101308794 |
| 13 | 54524255 | 54533910 | 13 | 101322288 | 101323845 |
| 13 | 54590375 | 54592784 | 13 | 101438181 | 101441794 |
| 13 | 54640831 | 54648098 | 13 | 101468739 | 101472125 |
| 13 | 54685958 | 54690003 | 13 | 101523665 | 101524280 |
| 13 | 54695118 | 54699831 | 13 | 101560838 | 101567972 |
| 13 | 54728171 | 54739416 | 13 | 101581896 | 101585707 |
| 13 | 54814183 | 54816636 | 13 | 101654530 | 101657746 |
| 13 | 54841931 | 54848212 | 13 | 101691126 | 101694138 |

The chromosomal positon was obtained from UCSC genome browser (http://genome.ucsc.edu/) build 36.

APPENDIX B: Chromosome 13
Page 15 of 49

| Chr | Start | End | Chr | Start | End |
|---|---|---|---|---|---|
| 13 | 54868550 | 54874144 | 13 | 101709889 | 101710972 |
| 13 | 54934356 | 54937214 | 13 | 101788408 | 101796339 |
| 13 | 54947690 | 54949007 | 13 | 101823129 | 101827857 |
| 13 | 54975878 | 54980820 | 13 | 101830893 | 101832897 |
| 13 | 54985366 | 54988655 | 13 | 101842904 | 101845994 |
| 13 | 55007473 | 55011195 | 13 | 101870696 | 101875146 |
| 13 | 55024469 | 55026013 | 13 | 101902849 | 101923988 |
| 13 | 55082944 | 55084944 | 13 | 101982726 | 101988408 |
| 13 | 55197482 | 55198162 | 13 | 102006713 | 102010188 |
| 13 | 55209724 | 55216679 | 13 | 102137146 | 102152618 |
| 13 | 55230008 | 55234449 | 13 | 102190361 | 102200621 |
| 13 | 55240271 | 55243441 | 13 | 102222343 | 102224955 |
| 13 | 55268035 | 55277092 | 13 | 102226742 | 102230762 |
| 13 | 55307669 | 55317161 | 13 | 102312454 | 102316420 |
| 13 | 55357514 | 55362424 | 13 | 102352453 | 102355629 |
| 13 | 55389775 | 55392893 | 13 | 102364527 | 102373748 |
| 13 | 55526204 | 55533323 | 13 | 102387909 | 102391156 |
| 13 | 55542668 | 55545748 | 13 | 102401138 | 102407567 |
| 13 | 55598587 | 55601534 | 13 | 102489788 | 102492386 |
| 13 | 55607490 | 55608209 | 13 | 102498885 | 102501962 |
| 13 | 55622837 | 55623269 | 13 | 102551057 | 102560973 |
| 13 | 55647594 | 55651587 | 13 | 102582164 | 102589848 |
| 13 | 55668801 | 55679800 | 13 | 102611722 | 102618226 |
| 13 | 55686731 | 55687864 | 13 | 102637688 | 102638323 |
| 13 | 55696182 | 55698574 | 13 | 102663882 | 102667562 |
| 13 | 55791873 | 55793094 | 13 | 102700736 | 102704172 |
| 13 | 55799890 | 55802066 | 13 | 102732840 | 102733618 |
| 13 | 55856783 | 55859744 | 13 | 102783655 | 102784649 |
| 13 | 55879659 | 55882720 | 13 | 102815414 | 102821225 |
| 13 | 55931037 | 55935841 | 13 | 102862787 | 102865280 |
| 13 | 55957311 | 55960679 | 13 | 102978987 | 102982071 |
| 13 | 55987822 | 55990398 | 13 | 102992564 | 102995095 |
| 13 | 55999470 | 56003407 | 13 | 103007728 | 103012521 |
| 13 | 56073520 | 56074928 | 13 | 103018609 | 103019599 |
| 13 | 56111853 | 56125438 | 13 | 103029547 | 103032622 |
| 13 | 56157154 | 56166125 | 13 | 103075748 | 103081908 |
| 13 | 56176656 | 56185536 | 13 | 103095572 | 103098888 |
| 13 | 56200235 | 56201926 | 13 | 103113383 | 103119736 |
| 13 | 56260263 | 56275659 | 13 | 103196265 | 103203495 |
| 13 | 56346334 | 56348814 | 13 | 103313091 | 103315790 |
| 13 | 56399669 | 56405472 | 13 | 103358524 | 103361301 |
| 13 | 56427480 | 56435675 | 13 | 103407373 | 103409942 |
| 13 | 56476792 | 56489209 | 13 | 103417779 | 103422360 |
| 13 | 56542730 | 56544218 | 13 | 103514788 | 103516140 |
| 13 | 56579329 | 56589990 | 13 | 103521445 | 103525507 |
| 13 | 56670582 | 56675877 | 13 | 103550867 | 103553391 |
| 13 | 56712889 | 56715151 | 13 | 103615105 | 103617082 |
| 13 | 56729949 | 56735202 | 13 | 103685980 | 103695020 |
| 13 | 56747414 | 56750497 | 13 | 103763150 | 103767310 |
| 13 | 56768254 | 56771036 | 13 | 103785741 | 103797235 |
| 13 | 56854766 | 56863827 | 13 | 103805270 | 103808986 |
| 13 | 56885059 | 56888404 | 13 | 103831872 | 103835552 |
| 13 | 56919488 | 56926915 | 13 | 103860604 | 103866323 |
| 13 | 56930068 | 56934175 | 13 | 103936335 | 103940824 |
| 13 | 56970890 | 56984827 | 13 | 103992061 | 103995784 |

The chromosomal positon was obtained from UCSC genome browser (http://genome.ucsc.edu/) build 36.

APPENDIX B: Chromosome 13

| Chr | Start | End | | | Chr | Start | End |
|---|---|---|---|---|---|---|---|
| 13 | 56997427 | 57000554 | | | 13 | 104014719 | 104020913 |
| 13 | 57020758 | 57022492 | | | 13 | 104030387 | 104036086 |
| 13 | 57035697 | 57051004 | | | 13 | 104045838 | 104053228 |
| 13 | 57115685 | 57122092 | | | 13 | 104136191 | 104139221 |
| 13 | 57159778 | 57161931 | | | 13 | 104162816 | 104164846 |
| 13 | 57182739 | 57186826 | | | 13 | 104178117 | 104179997 |
| 13 | 57214999 | 57224994 | | | 13 | 104210171 | 104211322 |
| 13 | 57229197 | 57233907 | | | 13 | 104230651 | 104234807 |
| 13 | 57272893 | 57277328 | | | 13 | 104321184 | 104329572 |
| 13 | 57280635 | 57284091 | | | 13 | 104351961 | 104358390 |
| 13 | 57311289 | 57314022 | | | 13 | 104432719 | 104436323 |
| 13 | 57328431 | 57331654 | | | 13 | 104462525 | 104464514 |
| 13 | 57347727 | 57349350 | | | 13 | 104509504 | 104516115 |
| 13 | 57368467 | 57371628 | | | 13 | 104732291 | 104735632 |
| 13 | 57404059 | 57413423 | | | 13 | 104811018 | 104816419 |
| 13 | 57425855 | 57429290 | | | 13 | 104887396 | 104888911 |
| 13 | 57464056 | 57469513 | | | 13 | 105056343 | 105057716 |
| 13 | 57527934 | 57535793 | | | 13 | 105235982 | 105237001 |
| 13 | 57557296 | 57561330 | | | 13 | 105249367 | 105250539 |
| 13 | 57566180 | 57575910 | | | 13 | 105278771 | 105286309 |
| 13 | 57638294 | 57640160 | | | 13 | 105341499 | 105342793 |
| 13 | 57660370 | 57670149 | | | 13 | 105356414 | 105359300 |
| 13 | 57813247 | 57817781 | | | 13 | 105367804 | 105370492 |
| 13 | 57874759 | 57884002 | | | 13 | 105419710 | 105424072 |
| 13 | 57888872 | 57891207 | | | 13 | 105447094 | 105449634 |
| 13 | 57898632 | 57901929 | | | 13 | 105486959 | 105491800 |
| 13 | 57927772 | 57930759 | | | 13 | 105538310 | 105546970 |
| 13 | 58087081 | 58090593 | | | 13 | 105569353 | 105578667 |
| 13 | 58096605 | 58098124 | | | 13 | 105603021 | 105604366 |
| 13 | 58183201 | 58184653 | | | 13 | 105608517 | 105610685 |
| 13 | 58207826 | 58216668 | | | 13 | 105617731 | 105618926 |
| 13 | 58328590 | 58333515 | | | 13 | 105684307 | 105687745 |
| 13 | 58433861 | 58435072 | | | 13 | 105708246 | 105714211 |
| 13 | 58435908 | 58436829 | | | 13 | 105723384 | 105725303 |
| 13 | 58534397 | 58536032 | | | 13 | 105778719 | 105782271 |
| 13 | 58537567 | 58539170 | | | 13 | 105823576 | 105829902 |
| 13 | 58561470 | 58563905 | | | 13 | 105835272 | 105845307 |
| 13 | 58660422 | 58662032 | | | 13 | 105857917 | 105874717 |
| 13 | 58664775 | 58677098 | | | 13 | 105881100 | 105886913 |
| 13 | 58702161 | 58705839 | | | 13 | 105895674 | 105899378 |
| 13 | 58715831 | 58720873 | | | 13 | 105911112 | 105926885 |
| 13 | 58724152 | 58726443 | | | 13 | 105942048 | 105943503 |
| 13 | 58739813 | 58740700 | | | 13 | 105979535 | 105981820 |
| 13 | 58780429 | 58788048 | | | 13 | 106041823 | 106048619 |
| 13 | 58881391 | 58883403 | | | 13 | 106137030 | 106155699 |
| 13 | 58917583 | 58921023 | | | 13 | 106186563 | 106189093 |
| 13 | 58967484 | 58979299 | | | 13 | 106448173 | 106451178 |
| 13 | 59042867 | 59044371 | | | 13 | 106484779 | 106486305 |
| 13 | 59104735 | 59109952 | | | 13 | 106545111 | 106545455 |
| 13 | 59144267 | 59145673 | | | 13 | 106564875 | 106568282 |
| 13 | 59150258 | 59156814 | | | 13 | 106585962 | 106590701 |
| 13 | 59269763 | 59273393 | | | 13 | 106648352 | 106671455 |
| 13 | 59275650 | 59278539 | | | 13 | 106681067 | 106685502 |
| 13 | 59295190 | 59307881 | | | 13 | 106702351 | 106714318 |
| 13 | 59350101 | 59353493 | | | 13 | 106732480 | 106740023 |

The chromosomal positon was obtained from UCSC genome browser (http://genome.ucsc.edu/) build 36.

APPENDIX B: Chromosome 13
Page 17 of 49

| Chr | Start | End | Chr | Start | End |
|---|---|---|---|---|---|
| 13 | 59453489 | 59462657 | 13 | 106897439 | 106902484 |
| 13 | 59554822 | 59558824 | 13 | 106933644 | 106935595 |
| 13 | 59630847 | 59635881 | 13 | 106945555 | 106950696 |
| 13 | 59738384 | 59741821 | 13 | 107003508 | 107010968 |
| 13 | 59754780 | 59759321 | 13 | 107035960 | 107041947 |
| 13 | 59784091 | 59789964 | 13 | 107067914 | 107069770 |
| 13 | 59850822 | 59854816 | 13 | 107128300 | 107139518 |
| 13 | 59897807 | 59902491 | 13 | 107170169 | 107174054 |
| 13 | 59955467 | 59957959 | 13 | 107181607 | 107184060 |
| 13 | 60055451 | 60078181 | 13 | 107267856 | 107271740 |
| 13 | 60085861 | 60088782 | 13 | 107281623 | 107284088 |
| 13 | 60097635 | 60099956 | 13 | 107293701 | 107298891 |
| 13 | 60126760 | 60137198 | 13 | 107597541 | 107599362 |
| 13 | 60174823 | 60176842 | 13 | 107607013 | 107615306 |
| 13 | 60221705 | 60224999 | 13 | 107625479 | 107629586 |
| 13 | 60230992 | 60234355 | 13 | 107664686 | 107669338 |
| 13 | 60332282 | 60334972 | 13 | 107777298 | 107780153 |
| 13 | 60371511 | 60372705 | 13 | 107785174 | 107788566 |
| 13 | 60391608 | 60397336 | 13 | 107794083 | 107805887 |
| 13 | 60412922 | 60414716 | 13 | 107817779 | 107825780 |
| 13 | 60426887 | 60428887 | 13 | 107836448 | 107854678 |
| 13 | 60468841 | 60474846 | 13 | 107869558 | 107873194 |
| 13 | 60514509 | 60518747 | 13 | 107878552 | 107882113 |
| 13 | 60559969 | 60567575 | 13 | 107884991 | 107890950 |
| 13 | 60606981 | 60608403 | 13 | 107948533 | 107952713 |
| 13 | 60650958 | 60652902 | 13 | 107987874 | 107993040 |
| 13 | 60662716 | 60664395 | 13 | 107996130 | 107998976 |
| 13 | 60727766 | 60733826 | 13 | 108032550 | 108033735 |
| 13 | 60762108 | 60767553 | 13 | 108041517 | 108045355 |
| 13 | 60821570 | 60826440 | 13 | 108058537 | 108062067 |
| 13 | 60851813 | 60860502 | 13 | 108066912 | 108073821 |
| 13 | 60865759 | 60868944 | 13 | 108084165 | 108092701 |
| 13 | 60878695 | 60881198 | 13 | 108131703 | 108135260 |
| 13 | 60906135 | 60914588 | 13 | 108182493 | 108192697 |
| 13 | 60918497 | 60919744 | 13 | 108273088 | 108274612 |
| 13 | 60945525 | 60947393 | 13 | 108332717 | 108337612 |
| 13 | 60972448 | 60973142 | 13 | 108370455 | 108376831 |
| 13 | 60996478 | 60999513 | 13 | 108413781 | 108416206 |
| 13 | 61046978 | 61049583 | 13 | 108535302 | 108542347 |
| 13 | 61179750 | 61180558 | 13 | 108589641 | 108592940 |
| 13 | 61187109 | 61189975 | 13 | 108606901 | 108611397 |
| 13 | 61221104 | 61224326 | 13 | 108626461 | 108629477 |
| 13 | 61237778 | 61238618 | 13 | 108715037 | 108722646 |
| 13 | 61243654 | 61247384 | 13 | 108740837 | 108746020 |
| 13 | 61275389 | 61282526 | 13 | 108754558 | 108758032 |
| 13 | 61309499 | 61319524 | 13 | 108767500 | 108770041 |
| 13 | 61348704 | 61349637 | 13 | 108782970 | 108785307 |
| 13 | 61412963 | 61418140 | 13 | 108786046 | 108788424 |
| 13 | 61553848 | 61560570 | 13 | 108819950 | 108824954 |
| 13 | 61620791 | 61630448 | 13 | 108842452 | 108845272 |
| 13 | 61647294 | 61652684 | 13 | 108963708 | 108964808 |
| 13 | 61715261 | 61717697 | 13 | 108985784 | 108995440 |
| 13 | 61772408 | 61775514 | 13 | 109035561 | 109037483 |
| 13 | 61798015 | 61802356 | 13 | 109076180 | 109086346 |
| 13 | 61924117 | 61927650 | 13 | 109089795 | 109097733 |

The chromosomal positon was obtained from UCSC genome browser (http://genome.ucsc.edu/) build 36.

APPENDIX B: Chromosome 13
Page 18 of 49

| Chr | Start | End | | Chr | Start | End |
|---|---|---|---|---|---|---|
| 13 | 61933608 | 61935767 | | 13 | 109102057 | 109112661 |
| 13 | 61945795 | 61946460 | | 13 | 109119529 | 109121559 |
| 13 | 61959789 | 61963116 | | 13 | 109129950 | 109141064 |
| 13 | 61972590 | 61977212 | | 13 | 109177566 | 109197707 |
| 13 | 62012174 | 62014330 | | 13 | 109215689 | 109223881 |
| 13 | 62017433 | 62021309 | | 13 | 109230559 | 109237332 |
| 13 | 62027424 | 62035574 | | 13 | 109246061 | 109248364 |
| 13 | 62041672 | 62044530 | | 13 | 109254662 | 109262918 |
| 13 | 62096176 | 62100061 | | 13 | 109268418 | 109271892 |
| 13 | 62116488 | 62121121 | | 13 | 109284034 | 109287834 |
| 13 | 62152509 | 62159130 | | 13 | 109290258 | 109291414 |
| 13 | 62187761 | 62192414 | | 13 | 109291599 | 109332970 |
| 13 | 62205643 | 62218605 | | 13 | 109390389 | 109393206 |
| 13 | 62295344 | 62298843 | | 13 | 109411093 | 109424051 |
| 13 | 62326421 | 62331585 | | 13 | 109449859 | 109454819 |
| 13 | 62368874 | 62371183 | | 13 | 109467939 | 109473446 |
| 13 | 62377398 | 62380357 | | 13 | 109492992 | 109496704 |
| 13 | 62433360 | 62440757 | | 13 | 109504222 | 109523271 |
| 13 | 62450549 | 62461390 | | 13 | 109555222 | 109583439 |
| 13 | 62500176 | 62511507 | | 13 | 109588537 | 109592028 |
| 13 | 62542593 | 62550602 | | 13 | 109600586 | 109603108 |
| 13 | 62560027 | 62567124 | | 13 | 109609538 | 109616941 |
| 13 | 62646068 | 62648982 | | 13 | 109628934 | 109651997 |
| 13 | 62691505 | 62704426 | | 13 | 109662758 | 109667548 |
| 13 | 62748942 | 62750605 | | 13 | 109672290 | 109672822 |
| 13 | 62792662 | 62793868 | | 13 | 109678038 | 109688065 |
| 13 | 62800265 | 62801497 | | 13 | 109698406 | 109722003 |
| 13 | 62828927 | 62830404 | | 13 | 109725758 | 109743456 |
| 13 | 62863113 | 62866919 | | 13 | 109751733 | 109790333 |
| 13 | 62884343 | 62886499 | | 13 | 109793416 | 109816181 |
| 13 | 62950512 | 62954052 | | 13 | 109829165 | 109839702 |
| 13 | 62960595 | 62964645 | | 13 | 109842415 | 109843382 |
| 13 | 62971606 | 62975479 | | 13 | 109854880 | 109870371 |
| 13 | 63091996 | 63094158 | | 13 | 109886705 | 109958558 |
| 13 | 63103351 | 63109152 | | 13 | 109961542 | 110106903 |
| 13 | 63130991 | 63141848 | | 13 | 110112508 | 110149001 |
| 13 | 63209582 | 63219066 | | 13 | 110167338 | 110175763 |
| 13 | 63305208 | 63315443 | | 13 | 110208894 | 110222882 |
| 13 | 63349544 | 63354367 | | 13 | 110243204 | 110252551 |
| 13 | 63363678 | 63365765 | | 13 | 110260339 | 110307479 |
| 13 | 63426415 | 63431259 | | 13 | 110317052 | 110324835 |
| 13 | 63434106 | 63435138 | | 13 | 110385387 | 110407883 |
| 13 | 63497703 | 63498428 | | 13 | 110439863 | 110442782 |
| 13 | 63533010 | 63536074 | | 13 | 110453502 | 110458858 |
| 13 | 63547500 | 63551040 | | 13 | 110477665 | 110520243 |
| 13 | 63554526 | 63556206 | | 13 | 110527223 | 110532334 |
| 13 | 63577422 | 63579573 | | 13 | 110543419 | 110548869 |
| 13 | 63593930 | 63600377 | | 13 | 110561683 | 110601591 |
| 13 | 63603949 | 63614566 | | 13 | 110618244 | 110671132 |
| 13 | 63628655 | 63631505 | | 13 | 110678847 | 110683296 |
| 13 | 63657721 | 63659612 | | 13 | 110688233 | 110692683 |
| 13 | 63717869 | 63724424 | | 13 | 110695429 | 110707002 |
| 13 | 63730285 | 63731087 | | 13 | 110713354 | 110738992 |
| 13 | 63774229 | 63779397 | | 13 | 110748720 | 110781513 |
| 13 | 63793703 | 63797234 | | 13 | 110785565 | 110800669 |

The chromosomal positon was obtained from UCSC genome browser (http://genome.ucsc.edu/) build 36.

APPENDIX B: Chromosome 13
Page 19 of 49

| Chr | Start | End | | Chr | Start | End |
|---|---|---|---|---|---|---|
| 13 | 63809633 | 63815155 | | 13 | 110804311 | 110824843 |
| 13 | 63828872 | 63833593 | | 13 | 110831976 | 111128082 |
| 13 | 63850185 | 63851011 | | 13 | 111129440 | 111151969 |
| 13 | 63865441 | 63871967 | | | | |
| 13 | 63893943 | 63896498 | | | | |
| 13 | 63941628 | 63945631 | | | | |
| 13 | 63948872 | 63951266 | | | | |
| 13 | 63968119 | 63972287 | | | | |
| 13 | 111552789 | 111552860 | | 13 | 112669592 | 112669743 |
| 13 | 111553218 | 111553924 | | 13 | 112670042 | 112670379 |
| 13 | 111555784 | 111557329 | | 13 | 112671237 | 112671252 |
| 13 | 111559649 | 111561881 | | 13 | 112675192 | 112703590 |
| 13 | 111562873 | 111563122 | | 13 | 112704665 | 112704800 |
| 13 | 111564372 | 111564572 | | 13 | 112706302 | 112706807 |
| 13 | 111568485 | 111568620 | | 13 | 112707697 | 112707757 |
| 13 | 111569110 | 111570016 | | 13 | 112710556 | 112710885 |
| 13 | 111572323 | 111572506 | | 13 | 112711073 | 112711772 |
| 13 | 111574406 | 111574761 | | 13 | 112713523 | 112713649 |
| 13 | 111581840 | 111583614 | | 13 | 112715433 | 112729850 |
| 13 | 111585864 | 111586112 | | 13 | 112730560 | 112730674 |
| 13 | 111586982 | 111587398 | | 13 | 112731709 | 112731729 |
| 13 | 111589148 | 111597179 | | 13 | 112733014 | 112739267 |
| 13 | 111598228 | 111598578 | | 13 | 112740280 | 112740444 |
| 13 | 111602018 | 111602173 | | 13 | 112741100 | 112741559 |
| 13 | 111605366 | 111607454 | | 13 | 112742069 | 112742111 |
| 13 | 111610007 | 111610237 | | 13 | 112742824 | 112758546 |
| 13 | 111610257 | 111610583 | | 13 | 112745982 | 112746358 |
| 13 | 111611372 | 111611636 | | 13 | 112760496 | 112760696 |
| 13 | 111615162 | 111616251 | | 13 | 112764715 | 112768886 |
| 13 | 111618883 | 111619078 | | 13 | 112769201 | 112769461 |
| 13 | 111621301 | 111623071 | | 13 | 112772736 | 112772763 |
| 13 | 111625401 | 111625891 | | 13 | 112774058 | 112774578 |
| 13 | 111626492 | 111626719 | | 13 | 112774933 | 112775691 |
| 13 | 111628207 | 111628701 | | 13 | 112779365 | 112801445 |
| 13 | 111629846 | 111629968 | | 13 | 112802337 | 112802760 |
| 13 | 111631466 | 111632222 | | 13 | 112807756 | 112811857 |
| 13 | 111632460 | 111632521 | | 13 | 112813647 | 112815452 |
| 13 | 111635222 | 111638540 | | 13 | 112815857 | 112816082 |
| 13 | 111640616 | 111641719 | | 13 | 112816891 | 112817606 |
| 13 | 111644985 | 111645080 | | 13 | 112818166 | 112818441 |
| 13 | 111646180 | 111648846 | | 13 | 112819861 | 112820261 |
| 13 | 111649246 | 111649382 | | 13 | 112823707 | 112826307 |
| 13 | 111650317 | 111650557 | | 13 | 112828103 | 112828993 |
| 13 | 111652295 | 111652385 | | 13 | 112829673 | 112831394 |
| 13 | 111652863 | 111653095 | | 13 | 112832545 | 112832775 |
| 13 | 111653785 | 111654091 | | 13 | 112833560 | 112839894 |
| 13 | 111654299 | 111654600 | | 13 | 112840403 | 112840928 |
| 13 | 111656819 | 111657597 | | 13 | 112843847 | 112844162 |
| 13 | 111665090 | 111666040 | | 13 | 112845548 | 112845854 |
| 13 | 111670694 | 111670738 | | 13 | 112849445 | 112849875 |
| 13 | 111671918 | 111672163 | | 13 | 112851740 | 112851830 |
| 13 | 111672592 | 111672913 | | 13 | 112853531 | 112854106 |
| 13 | 111674719 | 111675023 | | 13 | 112855252 | 112855347 |
| 13 | 111677754 | 111678414 | | 13 | 112856087 | 112856228 |
| 13 | 111679880 | 111681111 | | 13 | 112857518 | 112857817 |

The chromosomal positon was obtained from UCSC genome browser (http://genome.ucsc.edu/) build 36.

APPENDIX B: Chromosome 13
Page 20 of 49

| Chr | Start | End | | | Chr | Start | End |
|---|---|---|---|---|---|---|---|
| 13 | 111684037 | 111693123 | | | 13 | 112860810 | 112861095 |
| 13 | 111694408 | 111694697 | | | 13 | 112862666 | 112863293 |
| 13 | 111696549 | 111696667 | | | 13 | 112865546 | 112865866 |
| 13 | 111697735 | 111697972 | | | 13 | 112869614 | 112870123 |
| 13 | 111699204 | 111699706 | | | 13 | 112871866 | 112872557 |
| 13 | 111703385 | 111703969 | | | 13 | 112874250 | 112874435 |
| 13 | 111710674 | 111711049 | | | 13 | 112875640 | 112876621 |
| 13 | 111712345 | 111712434 | | | 13 | 112878509 | 112879420 |
| 13 | 111714362 | 111714400 | | | 13 | 112880640 | 112880863 |
| 13 | 111714889 | 111715024 | | | 13 | 112882846 | 112888130 |
| 13 | 111717463 | 111718558 | | | 13 | 112888738 | 112889391 |
| 13 | 111718873 | 111726400 | | | 13 | 112891993 | 112892635 |
| 13 | 111728692 | 111729192 | | | 13 | 112892878 | 112893203 |
| 13 | 111730038 | 111732393 | | | 13 | 112893700 | 112893857 |
| 13 | 111733913 | 111735108 | | | 13 | 112894691 | 112910350 |
| 13 | 111736338 | 111736903 | | | 13 | 112912075 | 112912311 |
| 13 | 111737080 | 111737374 | | | 13 | 112912680 | 112912741 |
| 13 | 111738584 | 111739629 | | | 13 | 112915406 | 112916627 |
| 13 | 111740699 | 111740717 | | | 13 | 112917031 | 112918540 |
| 13 | 111741803 | 111742558 | | | 13 | 112919303 | 112920689 |
| 13 | 111743309 | 111796873 | | | 13 | 112921565 | 112921689 |
| 13 | 111770343 | 111770718 | | | 13 | 112922014 | 112922079 |
| 13 | 111798602 | 111799050 | | | 13 | 112927548 | 112928494 |
| 13 | 111799825 | 111800109 | | | 13 | 112929800 | 112930446 |
| 13 | 111801034 | 111801334 | | | 13 | 112933498 | 112933708 |
| 13 | 111801643 | 111809525 | | | 13 | 112935028 | 112935405 |
| 13 | 111812520 | 111814527 | | | 13 | 112936268 | 112936803 |
| 13 | 111816816 | 111820653 | | | 13 | 112940989 | 112941411 |
| 13 | 111821856 | 111822031 | | | 13 | 112947245 | 112962949 |
| 13 | 111822864 | 111823139 | | | 13 | 112954296 | 112954466 |
| 13 | 111825602 | 111826664 | | | 13 | 112963954 | 112964489 |
| 13 | 111827758 | 111828013 | | | 13 | 112965853 | 112967170 |
| 13 | 111829907 | 111829928 | | | 13 | 112968199 | 112968719 |
| 13 | 111833380 | 111834010 | | | 13 | 112970294 | 112971214 |
| 13 | 111834555 | 111834770 | | | 13 | 112974502 | 112974508 |
| 13 | 111836505 | 111837145 | | | 13 | 112976716 | 112976907 |
| 13 | 111839864 | 111842594 | | | 13 | 112981237 | 112981645 |
| 13 | 111843026 | 111843236 | | | 13 | 112983461 | 112983897 |
| 13 | 111843832 | 111845985 | | | 13 | 112991139 | 112991565 |
| 13 | 111848549 | 111849010 | | | 13 | 112992195 | 112992430 |
| 13 | 111849234 | 111851884 | | | 13 | 112994447 | 112995001 |
| 13 | 111853918 | 111854620 | | | 13 | 112996559 | 112997542 |
| 13 | 111856054 | 111856060 | | | 13 | 112998567 | 112998888 |
| 13 | 111858274 | 111858434 | | | 13 | 113000669 | 113006845 |
| 13 | 111859131 | 111861031 | | | 13 | 113009981 | 113011857 |
| 13 | 111863724 | 111864274 | | | 13 | 113019637 | 113019697 |
| 13 | 111864771 | 111865129 | | | 13 | 113021741 | 113022517 |
| 13 | 111865787 | 111866212 | | | 13 | 113024302 | 113024832 |
| 13 | 111867430 | 111867597 | | | 13 | 113027996 | 113028111 |
| 13 | 111868732 | 111868847 | | | 13 | 113031408 | 113031543 |
| 13 | 111869886 | 111870377 | | | 13 | 113032459 | 113033554 |
| 13 | 111871958 | 111872154 | | | 13 | 113033904 | 113033909 |
| 13 | 111874403 | 111876139 | | | 13 | 113034876 | 113035026 |
| 13 | 111881328 | 111881803 | | | 13 | 113037571 | 113037774 |
| 13 | 111885209 | 111885551 | | | 13 | 113040764 | 113040959 |

The chromosomal positon was obtained from UCSC genome browser (http://genome.ucsc.edu/) build 36.

APPENDIX B: Chromosome 13
Page 21 of 49

| Chr | Start | End | Chr | Start | End |
|---|---|---|---|---|---|
| 13 | 111887531 | 111887891 | 13 | 113041961 | 113043166 |
| 13 | 111888235 | 111888646 | 13 | 113045212 | 113045577 |
| 13 | 111889337 | 111889667 | 13 | 113046536 | 113047432 |
| 13 | 111890077 | 111890237 | 13 | 113052202 | 113053067 |
| 13 | 111890976 | 111891437 | 13 | 113054493 | 113055163 |
| 13 | 111892198 | 111894513 | 13 | 113056531 | 113056795 |
| 13 | 111895245 | 111896028 | 13 | 113057177 | 113057440 |
| 13 | 111896864 | 111896924 | 13 | 113059112 | 113062332 |
| 13 | 111897504 | 111897936 | 13 | 113063109 | 113064752 |
| 13 | 111903623 | 111904042 | 13 | 113065897 | 113067119 |
| 13 | 111904507 | 111904737 | 13 | 113067499 | 113068289 |
| 13 | 111905332 | 111905812 | 13 | 113068784 | 113069290 |
| 13 | 111907023 | 111909599 | 13 | 113069420 | 113069600 |
| 13 | 111910894 | 111911639 | 13 | 113070954 | 113071345 |
| 13 | 111914268 | 111914469 | 13 | 113072247 | 113073055 |
| 13 | 111915465 | 111915835 | 13 | 113074361 | 113075148 |
| 13 | 111916654 | 111916846 | 13 | 113076413 | 113076458 |
| 13 | 111918755 | 111919133 | 13 | 113079051 | 113079056 |
| 13 | 111921698 | 111921857 | 13 | 113079377 | 113080163 |
| 13 | 111922167 | 111922393 | 13 | 113081713 | 113082486 |
| 13 | 111922932 | 111923382 | 13 | 113084101 | 113091760 |
| 13 | 111925687 | 111925931 | 13 | 113097719 | 113097897 |
| 13 | 111928844 | 111929789 | 13 | 113100499 | 113100724 |
| 13 | 111931519 | 111931664 | 13 | 113103359 | 113108944 |
| 13 | 111932518 | 111932663 | 13 | 113111414 | 113111884 |
| 13 | 111933679 | 111934233 | 13 | 113113572 | 113114262 |
| 13 | 111936670 | 111936995 | 13 | 113115492 | 113115572 |
| 13 | 111939519 | 111939974 | 13 | 113116642 | 113117368 |
| 13 | 111941988 | 111942099 | 13 | 113120059 | 113120730 |
| 13 | 111946895 | 111958577 | 13 | 113123009 | 113123139 |
| 13 | 111959080 | 111959323 | 13 | 113127483 | 113128403 |
| 13 | 111960103 | 111960288 | 13 | 113129961 | 113130096 |
| 13 | 111961577 | 111962374 | 13 | 113130666 | 113133351 |
| 13 | 111963857 | 111964152 | 13 | 113134901 | 113135236 |
| 13 | 111965487 | 111965747 | 13 | 113140506 | 113142660 |
| 13 | 111965857 | 111966187 | 13 | 113145449 | 113146512 |
| 13 | 111966603 | 111973617 | 13 | 113146767 | 113146892 |
| 13 | 111974809 | 111975344 | 13 | 113148814 | 113148884 |
| 13 | 111975817 | 111976450 | 13 | 113149679 | 113149895 |
| 13 | 112013979 | 112015193 | 13 | 113151358 | 113151678 |
| 13 | 112015894 | 112021298 | 13 | 113154623 | 113154723 |
| 13 | 112022095 | 112022360 | 13 | 113155418 | 113155848 |
| 13 | 112024222 | 112024784 | 13 | 113160524 | 113160915 |
| 13 | 112027928 | 112028194 | 13 | 113164040 | 113169518 |
| 13 | 112028603 | 112029188 | 13 | 113171269 | 113171439 |
| 13 | 112031558 | 112032613 | 13 | 113174468 | 113175585 |
| 13 | 112033823 | 112034041 | 13 | 113175810 | 113175939 |
| 13 | 112034911 | 112035552 | 13 | 113176397 | 113176966 |
| 13 | 112038460 | 112043668 | 13 | 113178657 | 113189445 |
| 13 | 112044449 | 112046264 | 13 | 113185828 | 113186168 |
| 13 | 112048926 | 112050299 | 13 | 113189923 | 113190232 |
| 13 | 112051688 | 112051760 | 13 | 113191433 | 113192193 |
| 13 | 112051990 | 112052370 | 13 | 113194817 | 113196459 |
| 13 | 112054086 | 112054385 | 13 | 113197818 | 113198485 |
| 13 | 112056295 | 112057000 | 13 | 113198930 | 113208217 |

The chromosomal positon was obtained from UCSC genome browser (http://genome.ucsc.edu/) build 36.

APPENDIX B: Chromosome 13
Page 22 of 49

| Chr | Start | End | Chr | Start | End |
|---|---|---|---|---|---|
| 13 | 112058420 | 112058807 | 13 | 113209206 | 113209371 |
| 13 | 112061290 | 112065156 | 13 | 113211822 | 113212089 |
| 13 | 112066593 | 112067088 | 13 | 113214827 | 113215487 |
| 13 | 112068083 | 112068268 | 13 | 113218364 | 113220527 |
| 13 | 112068618 | 112068828 | 13 | 113225593 | 113226971 |
| 13 | 112070115 | 112070759 | 13 | 113228334 | 113229069 |
| 13 | 112072193 | 112072735 | 13 | 113232408 | 113233488 |
| 13 | 112073588 | 112076025 | 13 | 113234184 | 113235008 |
| 13 | 112077738 | 112077943 | 13 | 113236084 | 113236373 |
| 13 | 112078333 | 112078663 | 13 | 113236541 | 113236756 |
| 13 | 112079462 | 112079792 | 13 | 113237918 | 113238043 |
| 13 | 112080518 | 112092369 | 13 | 113240471 | 113241325 |
| 13 | 112097410 | 112098110 | 13 | 113242674 | 113242832 |
| 13 | 112099465 | 112099900 | 13 | 113243535 | 113243905 |
| 13 | 112100438 | 112100680 | 13 | 113245166 | 113245949 |
| 13 | 112101254 | 112101483 | 13 | 113248247 | 113251988 |
| 13 | 112102662 | 112132211 | 13 | 113252316 | 113252650 |
| 13 | 112132859 | 112133735 | 13 | 113253835 | 113254545 |
| 13 | 112134054 | 112134532 | 13 | 113254970 | 113256123 |
| 13 | 112135002 | 112135307 | 13 | 113257718 | 113258772 |
| 13 | 112136532 | 112136783 | 13 | 113261805 | 113263003 |
| 13 | 112137684 | 112138090 | 13 | 113265663 | 113268253 |
| 13 | 112139400 | 112141620 | 13 | 113270151 | 113270345 |
| 13 | 112146085 | 112146315 | 13 | 113270641 | 113280132 |
| 13 | 112146500 | 112160289 | 13 | 113281314 | 113281834 |
| 13 | 112162055 | 112163328 | 13 | 113284241 | 113284476 |
| 13 | 112164533 | 112165098 | 13 | 113284727 | 113286732 |
| 13 | 112165379 | 112166536 | 13 | 113288622 | 113289414 |
| 13 | 112167263 | 112170415 | 13 | 113291670 | 113292240 |
| 13 | 112171319 | 112172299 | 13 | 113292929 | 113294007 |
| 13 | 112172544 | 112207368 | 13 | 113301855 | 113304695 |
| 13 | 112177069 | 112177489 | 13 | 113306138 | 113306620 |
| 13 | 112198741 | 112198891 | 13 | 113307850 | 113308625 |
| 13 | 112207776 | 112208106 | 13 | 113309019 | 113309260 |
| 13 | 112209535 | 112209796 | 13 | 113311022 | 113312972 |
| 13 | 112211256 | 112211601 | 13 | 113313320 | 113313455 |
| 13 | 112212972 | 112214131 | 13 | 113316442 | 113316702 |
| 13 | 112215652 | 112216391 | 13 | 113320087 | 113321153 |
| 13 | 112217641 | 112218293 | 13 | 113322729 | 113322970 |
| 13 | 112219010 | 112226445 | 13 | 113326589 | 113328754 |
| 13 | 112227823 | 112228024 | 13 | 113329578 | 113329813 |
| 13 | 112231934 | 112246414 | 13 | 113331068 | 113331168 |
| 13 | 112248525 | 112248750 | 13 | 113333943 | 113334198 |
| 13 | 112254322 | 112254601 | 13 | 113335884 | 113336747 |
| 13 | 112255647 | 112255657 | 13 | 113338033 | 113338908 |
| 13 | 112258520 | 112261574 | 13 | 113340827 | 113341393 |
| 13 | 112264305 | 112264665 | 13 | 113343862 | 113346949 |
| 13 | 112265185 | 112265510 | 13 | 113349262 | 113349268 |
| 13 | 112266242 | 112300909 | 13 | 113355682 | 113355785 |
| 13 | 112303765 | 112304112 | 13 | 113356760 | 113359066 |
| 13 | 112307026 | 112307181 | 13 | 113359716 | 113360001 |
| 13 | 112307728 | 112308281 | 13 | 113360416 | 113360561 |
| 13 | 112308581 | 112308921 | 13 | 113362860 | 113363307 |
| 13 | 112309786 | 112313026 | 13 | 113364184 | 113365430 |
| 13 | 112316533 | 112316715 | 13 | 113366341 | 113372757 |

The chromosomal positon was obtained from UCSC genome browser (http://genome.ucsc.edu/) build 36.

APPENDIX B: Chromosome 13
Page 23 of 49

| Chr | Start | End | Chr | Start | End |
|---|---|---|---|---|---|
| 13 | 112317561 | 112318077 | 13 | 113373713 | 113475259 |
| 13 | 112318297 | 112318501 | 13 | 113475889 | 113476359 |
| 13 | 112319001 | 112319656 | 13 | 113477009 | 113477144 |
| 13 | 112324483 | 112324569 | 13 | 113478811 | 113480076 |
| 13 | 112325244 | 112325638 | 13 | 113480676 | 113481326 |
| 13 | 112327553 | 112327768 | 13 | 113483136 | 113483506 |
| 13 | 112331604 | 112331840 | 13 | 113483731 | 113483841 |
| 13 | 112332197 | 112333134 | 13 | 113485556 | 113485791 |
| 13 | 112333349 | 112333536 | 13 | 113486461 | 113486906 |
| 13 | 112334047 | 112334271 | 13 | 113489329 | 113489683 |
| 13 | 112335217 | 112335968 | 13 | 113490553 | 113490952 |
| 13 | 112338665 | 112341410 | 13 | 113492974 | 113497474 |
| 13 | 112344573 | 112344733 | 13 | 113497712 | 113502496 |
| 13 | 112346166 | 112346178 | 13 | 113507681 | 113507926 |
| 13 | 112347688 | 112348133 | 13 | 113510281 | 113512436 |
| 13 | 112348423 | 112348577 | 13 | 113514285 | 113522221 |
| 13 | 112349193 | 112350263 | 13 | 113522796 | 113523061 |
| 13 | 112351461 | 112351896 | 13 | 113524207 | 113524473 |
| 13 | 112353715 | 112353827 | 13 | 113525048 | 113525488 |
| 13 | 112355875 | 112356324 | 13 | 113527178 | 113528285 |
| 13 | 112360349 | 112360840 | 13 | 113528709 | 113528821 |
| 13 | 112362913 | 112365593 | 13 | 113534801 | 113535611 |
| 13 | 112366730 | 112367129 | 13 | 113537166 | 113542620 |
| 13 | 112368474 | 112368709 | 13 | 113545566 | 113545662 |
| 13 | 112371661 | 112372262 | 13 | 113546353 | 113546687 |
| 13 | 112373220 | 112373760 | 13 | 113546777 | 113547357 |
| 13 | 112374401 | 112374841 | 13 | 113548161 | 113550448 |
| 13 | 112377404 | 112377824 | 13 | 113553549 | 113553698 |
| 13 | 112381852 | 112382052 | 13 | 113554429 | 113554989 |
| 13 | 112383527 | 112383633 | 13 | 113562440 | 113562534 |
| 13 | 112384237 | 112384990 | 13 | 113563077 | 113563148 |
| 13 | 112387196 | 112387724 | 13 | 113566275 | 113568478 |
| 13 | 112389651 | 112391480 | 13 | 113569738 | 113569878 |
| 13 | 112396826 | 112397451 | 13 | 113573903 | 113574896 |
| 13 | 112397826 | 112398113 | 13 | 113575409 | 113575499 |
| 13 | 112398773 | 112398908 | 13 | 113576064 | 113577410 |
| 13 | 112400722 | 112400975 | 13 | 113578025 | 113578370 |
| 13 | 112402926 | 112404346 | 13 | 113579278 | 113579950 |
| 13 | 112410958 | 112411825 | 13 | 113584701 | 113584716 |
| 13 | 112413617 | 112416945 | 13 | 113586184 | 113586859 |
| 13 | 112418211 | 112418506 | 13 | 113591347 | 113591578 |
| 13 | 112420903 | 112421497 | 13 | 113592907 | 113593352 |
| 13 | 112425168 | 112425218 | 13 | 113594184 | 113594655 |
| 13 | 112427192 | 112427567 | 13 | 113595940 | 113599305 |
| 13 | 112427907 | 112428372 | 13 | 113603469 | 113604039 |
| 13 | 112429101 | 112429108 | 13 | 113604889 | 113606479 |
| 13 | 112432027 | 112432997 | 13 | 113608862 | 113608957 |
| 13 | 112435479 | 112436666 | 13 | 113611024 | 113621249 |
| 13 | 112438084 | 112438785 | 13 | 113624362 | 113625297 |
| 13 | 112439719 | 112440031 | 13 | 113626527 | 113627390 |
| 13 | 112441095 | 112442071 | 13 | 113628085 | 113628155 |
| 13 | 112442873 | 112446835 | 13 | 113629166 | 113631133 |
| 13 | 112450476 | 112450611 | 13 | 113632226 | 113632776 |
| 13 | 112455652 | 112455976 | 13 | 113634036 | 113635471 |
| 13 | 112456522 | 112457703 | 13 | 113636516 | 113636914 |

The chromosomal positon was obtained from UCSC genome browser (http://genome.ucsc.edu/) build 36.

APPENDIX B: Chromosome 13
Page 24 of 49

| Chr | Start | End | Chr | Start | End |
| --- | --- | --- | --- | --- | --- |
| 13 | 112461397 | 112462273 | 13 | 113638349 | 113638936 |
| 13 | 112465029 | 112465243 | 13 | 113641421 | 113641628 |
| 13 | 112465495 | 112465756 | 13 | 113642559 | 113642693 |
| 13 | 112467141 | 112468486 | 13 | 113644107 | 113646200 |
| 13 | 112468698 | 112469082 | 13 | 113646500 | 113646770 |
| 13 | 112471023 | 112471318 | 13 | 113649331 | 113649626 |
| 13 | 112472008 | 112472263 | 13 | 113651166 | 113651386 |
| 13 | 112472938 | 112473794 | 13 | 113653428 | 113654098 |
| 13 | 112475269 | 112475685 | 13 | 113655110 | 113655124 |
| 13 | 112476619 | 112476635 | 13 | 113758080 | 113762620 |
| 13 | 112476894 | 112478485 | 13 | 113765501 | 113770221 |
| 13 | 112480406 | 112484408 | 13 | 113771426 | 113771651 |
| 13 | 112485563 | 112485738 | 13 | 113774992 | 113775046 |
| 13 | 112487362 | 112487587 | 13 | 113776282 | 113778088 |
| 13 | 112489157 | 112490527 | 13 | 113780085 | 113780195 |
| 13 | 112492589 | 112492677 | 13 | 113781020 | 113823843 |
| 13 | 112493878 | 112493958 | 13 | 113826083 | 113827098 |
| 13 | 112494929 | 112495198 | 13 | 113827363 | 113828341 |
| 13 | 112496618 | 112496783 | 13 | 113828775 | 113829090 |
| 13 | 112498017 | 112503923 | 13 | 113830213 | 113831057 |
| 13 | 112507083 | 112507221 | 13 | 113833722 | 113836162 |
| 13 | 112509671 | 112510061 | 13 | 113839119 | 113840704 |
| 13 | 112516160 | 112516715 | 13 | 113841742 | 113841752 |
| 13 | 112516960 | 112517735 | 13 | 113843102 | 113844067 |
| 13 | 112519361 | 112519825 | 13 | 113844352 | 113844665 |
| 13 | 112520425 | 112520742 | 13 | 113846066 | 113846466 |
| 13 | 112521380 | 112521620 | 13 | 113846611 | 113847111 |
| 13 | 112522028 | 112522669 | 13 | 113848876 | 113851772 |
| 13 | 112523010 | 112524582 | 13 | 113852062 | 113852977 |
| 13 | 112528619 | 112528919 | 13 | 113855543 | 113856968 |
| 13 | 112529537 | 112529607 | 13 | 113860050 | 113860185 |
| 13 | 112530572 | 112530932 | 13 | 113860805 | 113860970 |
| 13 | 112532525 | 112532955 | 13 | 113862048 | 113862296 |
| 13 | 112533579 | 112542341 | 13 | 113862856 | 113863085 |
| 13 | 112544106 | 112544776 | 13 | 113863786 | 113864111 |
| 13 | 112545646 | 112546137 | 13 | 113865287 | 113866263 |
| 13 | 112546597 | 112546616 | 13 | 113870878 | 113871318 |
| 13 | 112548496 | 112549355 | 13 | 113871773 | 113872068 |
| 13 | 112550714 | 112551953 | 13 | 113876269 | 113878763 |
| 13 | 112552793 | 112552893 | 13 | 113879895 | 113889334 |
| 13 | 112553304 | 112553795 | 13 | 113890985 | 113892505 |
| 13 | 112554340 | 112555064 | 13 | 113893221 | 113893450 |
| 13 | 112555788 | 112555989 | 13 | 113893981 | 113894017 |
| 13 | 112557101 | 112559887 | 13 | 113896762 | 113897107 |
| 13 | 112561013 | 112561213 | 13 | 113899091 | 113900087 |
| 13 | 112562308 | 112564003 | 13 | 113902548 | 113902870 |
| 13 | 112564817 | 112567797 | 13 | 113904994 | 113910979 |
| 13 | 112570493 | 112570633 | 13 | 113912259 | 113913228 |
| 13 | 112572188 | 112572403 | 13 | 113913304 | 113914044 |
| 13 | 112573193 | 112574293 | 13 | 113914464 | 113914979 |
| 13 | 112575768 | 112576233 | 13 | 113916480 | 113916495 |
| 13 | 112578113 | 112578363 | 13 | 113921650 | 113923135 |
| 13 | 112580395 | 112580550 | 13 | 113923981 | 113924580 |
| 13 | 112581115 | 112581347 | 13 | 113925671 | 113926205 |
| 13 | 112582887 | 112583073 | 13 | 113928060 | 113930566 |

The chromosomal positon was obtained from UCSC genome browser (http://genome.ucsc.edu/) build 36.

APPENDIX B: Chromosome 13
Page 25 of 49

| Chr | Start | End | | | Chr | Start | End |
|---|---|---|---|---|---|---|---|
| 13 | 112583747 | 112585967 | | | 13 | 113932513 | 113933296 |
| 13 | 112588952 | 112589529 | | | 13 | 113934645 | 113937292 |
| 13 | 112589704 | 112592729 | | | 13 | 113941949 | 113942204 |
| 13 | 112594898 | 112595519 | | | 13 | 113942990 | 113943744 |
| 13 | 112595834 | 112595900 | | | 13 | 113944739 | 113944794 |
| 13 | 112598362 | 112603039 | | | 13 | 113946314 | 113947020 |
| 13 | 112605654 | 112605894 | | | 13 | 113948050 | 113949618 |
| 13 | 112609026 | 112611788 | | | 13 | 113951851 | 113956472 |
| 13 | 112613846 | 112614056 | | | 13 | 113957808 | 113958588 |
| 13 | 112618953 | 112620149 | | | 13 | 113960278 | 113961448 |
| 13 | 112620783 | 112621133 | | | 13 | 113962273 | 113962734 |
| 13 | 112627276 | 112627918 | | | 13 | 113967274 | 113967794 |
| 13 | 112630575 | 112630946 | | | 13 | 113969892 | 113978056 |
| 13 | 112633351 | 112634011 | | | 13 | 113980697 | 113980925 |
| 13 | 112635596 | 112636031 | | | 13 | 113984466 | 113984984 |
| 13 | 112639297 | 112639957 | | | 13 | 113986699 | 113987126 |
| 13 | 112640258 | 112640388 | | | 13 | 113988343 | 113989179 |
| 13 | 112642926 | 112645422 | | | 13 | 113993003 | 113993412 |
| 13 | 112646800 | 112647258 | | | 13 | 113994676 | 113995531 |
| 13 | 112648530 | 112649027 | | | 13 | 113998563 | 114002824 |
| 13 | 112651775 | 112653216 | | | 13 | 114003535 | 114003847 |
| 13 | 112653536 | 112656386 | | | 13 | 114005156 | 114005673 |
| 13 | 112656822 | 112657061 | | | 13 | 114015992 | 114016701 |
| 13 | 112659141 | 112662932 | | | 13 | 114017802 | 114018398 |
| 13 | 112664466 | 112664686 | | | 13 | 114020042 | 114020259 |
| 13 | 112666053 | 112668354 | | | 13 | 114021440 | 114069998 |
| 13 | 112669160 | 112669424 | | | 13 | 114064918 | 114065304 |
| | | | | | 13 | 114071702 | 114071877 |
| | | | | | 13 | 114072127 | 114072567 |
| | | | | | 13 | 114073423 | 114075535 |
| | | | | | 13 | 114077404 | 114077798 |
| | | | | | 13 | 114083629 | 114102879 |
| | | | | | 13 | 114103456 | 114103771 |
| | | | | | 13 | 114104806 | 114107850 |
| | | | | | 13 | 114108409 | 114108774 |
| | | | | | 13 | 114109308 | 114112184 |
| | | | | | 13 | 114113066 | 114113887 |
| | | | | | 13 | 114116340 | 114116592 |
| | | | | | 13 | 114117936 | 114118277 |
| | | | | | 13 | 114121226 | 114121325 |
| | | | | | 13 | 114123427 | 114123902 |
| 13 | 18314037 | 18317486 | | | 13 | 62983568 | 62985060 |
| 13 | 18418360 | 18429692 | | | 13 | 63136131 | 63139678 |
| 13 | 18449199 | 18455725 | | | 13 | 63176707 | 63180049 |
| 13 | 18470229 | 18480731 | | | 13 | 63209578 | 63219067 |
| 13 | 18522549 | 18553742 | | | 13 | 63283953 | 63320180 |
| 13 | 18556267 | 18564797 | | | 13 | 63375395 | 63377113 |
| 13 | 18584050 | 18592670 | | | 13 | 63430469 | 63432179 |
| 13 | 18601265 | 18608138 | | | 13 | 63434103 | 63438363 |
| 13 | 18643205 | 18646756 | | | 13 | 63455200 | 63456800 |
| 13 | 18707350 | 18709090 | | | 13 | 63847990 | 63850706 |
| 13 | 18762813 | 18763838 | | | 13 | 63867661 | 63870461 |
| 13 | 18790874 | 18792689 | | | 13 | 64029494 | 64031328 |
| 13 | 18814987 | 18822419 | | | 13 | 64056794 | 64059377 |
| 13 | 18836655 | 18857040 | | | 13 | 64063499 | 64068506 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 18874805 | 18888122 | 13 | 64126714 | 64128844 |
| 13 | 19281340 | 19290988 | 13 | 64427424 | 64432564 |
| 13 | 19492057 | 19493817 | 13 | 64495489 | 64496740 |
| 13 | 19573617 | 19575087 | 13 | 64668909 | 64671708 |
| 13 | 19601186 | 19605268 | 13 | 64809793 | 64810443 |
| 13 | 19665764 | 19666149 | 13 | 64824972 | 64826597 |
| 13 | 19666688 | 19668840 | 13 | 64855974 | 64858997 |
| 13 | 19678329 | 19681022 | 13 | 65129056 | 65131880 |
| 13 | 19694758 | 19698584 | 13 | 65186852 | 65190428 |
| 13 | 19719890 | 19721969 | 13 | 65473637 | 65474587 |
| 13 | 19730310 | 19730982 | 13 | 65500086 | 65502811 |
| 13 | 19767078 | 19796528 | 13 | 65579934 | 65584298 |
| 13 | 19806795 | 19808555 | 13 | 65639382 | 65640283 |
| 13 | 19826017 | 19828918 | 13 | 65654509 | 65655054 |
| 13 | 19847857 | 19848926 | 13 | 65660576 | 65662570 |
| 13 | 19853395 | 19857632 | 13 | 65694694 | 65695274 |
| 13 | 19883487 | 19884347 | 13 | 65711272 | 65713462 |
| 13 | 19885009 | 19889080 | 13 | 65760161 | 65761706 |
| 13 | 19947606 | 19948311 | 13 | 65792313 | 65796805 |
| 13 | 20000947 | 20001222 | 13 | 65819751 | 65820773 |
| 13 | 20117022 | 20119143 | 13 | 65901990 | 65903290 |
| 13 | 20152490 | 20153700 | 13 | 65912426 | 65915359 |
| 13 | 20184782 | 20192521 | 13 | 65929485 | 65933485 |
| 13 | 20423259 | 20425924 | 13 | 66154446 | 66159862 |
| 13 | 20446533 | 20447668 | 13 | 66203715 | 66204847 |
| 13 | 20516129 | 20519128 | 13 | 66421725 | 66424360 |
| 13 | 20531158 | 20534140 | 13 | 66445202 | 66446113 |
| 13 | 20546815 | 20547820 | 13 | 66523875 | 66524900 |
| 13 | 20551405 | 20552915 | 13 | 66559040 | 66560816 |
| 13 | 20628475 | 20629355 | 13 | 66618375 | 66619892 |
| 13 | 20640985 | 20641668 | 13 | 66626030 | 66629391 |
| 13 | 20804192 | 20811502 | 13 | 66650702 | 66653239 |
| 13 | 20826680 | 20834447 | 13 | 66672210 | 66673000 |
| 13 | 20840300 | 20845298 | 13 | 66697483 | 66700268 |
| 13 | 20924911 | 20928113 | 13 | 66700518 | 66702354 |
| 13 | 20946197 | 20947592 | 13 | 66770047 | 66773087 |
| 13 | 20952122 | 20953225 | 13 | 66776822 | 66778117 |
| 13 | 20994265 | 20996195 | 13 | 66788398 | 66791943 |
| 13 | 21096826 | 21101676 | 13 | 66829273 | 66831062 |
| 13 | 21119438 | 21120803 | 13 | 66984876 | 66987692 |
| 13 | 21122012 | 21124003 | 13 | 67027503 | 67029150 |
| 13 | 21138664 | 21141936 | 13 | 67045325 | 67047579 |
| 13 | 21178449 | 21179505 | 13 | 67081034 | 67082354 |
| 13 | 21195490 | 21201364 | 13 | 67107116 | 67110157 |
| 13 | 21263159 | 21264844 | 13 | 67113538 | 67114953 |
| 13 | 21286305 | 21288421 | 13 | 67119341 | 67120571 |
| 13 | 21510123 | 21513842 | 13 | 67211855 | 67213115 |
| 13 | 21532093 | 21533388 | 13 | 67270888 | 67271847 |
| 13 | 21534433 | 21535033 | 13 | 67378783 | 67388535 |
| 13 | 21535374 | 21536589 | 13 | 67521056 | 67523087 |
| 13 | 21563331 | 21564556 | 13 | 67551593 | 67553176 |
| 13 | 21583434 | 21584604 | 13 | 67588435 | 67592979 |
| 13 | 21606984 | 21607859 | 13 | 67617456 | 67619324 |
| 13 | 21611045 | 21613002 | 13 | 67637776 | 67641206 |
| 13 | 21658772 | 21661662 | 13 | 67648708 | 67650196 |

The chromosomal positon was obtained from UCSC genome browser (http://genome.ucsc.edu/) build 36.

APPENDIX B: Chromosome 13

| Chr | Start | End | | Chr | Start | End |
|---|---|---|---|---|---|---|
| 13 | 21858952 | 21862720 | | 13 | 67662441 | 67663204 |
| 13 | 21942428 | 21946276 | | 13 | 67670746 | 67672822 |
| 13 | 21962023 | 21964076 | | 13 | 67736813 | 67742921 |
| 13 | 21978554 | 21979539 | | 13 | 67766832 | 67768022 |
| 13 | 22013471 | 22016178 | | 13 | 67845409 | 67847642 |
| 13 | 22263908 | 22269372 | | 13 | 67874965 | 67876245 |
| 13 | 22309792 | 22311332 | | 13 | 68044444 | 68046274 |
| 13 | 22363544 | 22364364 | | 13 | 68068860 | 68069025 |
| 13 | 22398411 | 22401498 | | 13 | 68081350 | 68083114 |
| 13 | 22417653 | 22421800 | | 13 | 68183561 | 68185281 |
| 13 | 22586713 | 22589408 | | 13 | 68234287 | 68235372 |
| 13 | 22672894 | 22676965 | | 13 | 68277783 | 68280846 |
| 13 | 22703261 | 22705187 | | 13 | 68378883 | 68380038 |
| 13 | 22716893 | 22721427 | | 13 | 68455291 | 68457613 |
| 13 | 22741574 | 22748281 | | 13 | 68598007 | 68599740 |
| 13 | 22768714 | 22770200 | | 13 | 68716924 | 68723079 |
| 13 | 22772502 | 22776006 | | 13 | 68821296 | 68824607 |
| 13 | 22795629 | 22796494 | | 13 | 69057243 | 69058895 |
| 13 | 22798294 | 22799789 | | 13 | 69088429 | 69092115 |
| 13 | 22811859 | 22813304 | | 13 | 69098881 | 69101416 |
| 13 | 22824313 | 22825683 | | 13 | 69155908 | 69157311 |
| 13 | 22851670 | 22855764 | | 13 | 69230140 | 69235853 |
| 13 | 22863389 | 22880046 | | 13 | 69325229 | 69328162 |
| 13 | 22939465 | 22944297 | | 13 | 69359036 | 69361777 |
| 13 | 22960783 | 22988393 | | 13 | 69463008 | 69472149 |
| 13 | 23005494 | 23008991 | | 13 | 69496860 | 69500187 |
| 13 | 23025390 | 23031720 | | 13 | 69525454 | 69526114 |
| 13 | 23087401 | 23098872 | | 13 | 69747217 | 69749517 |
| 13 | 23152188 | 23155023 | | 13 | 69838863 | 69840363 |
| 13 | 23196645 | 23198385 | | 13 | 69864064 | 69866833 |
| 13 | 23237180 | 23238655 | | 13 | 69977962 | 69978487 |
| 13 | 23302625 | 23304680 | | 13 | 70055570 | 70057844 |
| 13 | 23476909 | 23478554 | | 13 | 70065956 | 70068631 |
| 13 | 23510507 | 23512822 | | 13 | 70143469 | 70145436 |
| 13 | 23588762 | 23590524 | | 13 | 70153576 | 70154471 |
| 13 | 23602542 | 23603142 | | 13 | 70222287 | 70225083 |
| 13 | 23617721 | 23622185 | | 13 | 70312125 | 70314954 |
| 13 | 23721592 | 23727630 | | 13 | 70319441 | 70322756 |
| 13 | 23736119 | 23737444 | | 13 | 70373554 | 70374728 |
| 13 | 23743082 | 23744550 | | 13 | 70394525 | 70396822 |
| 13 | 23841858 | 23843818 | | 13 | 70410978 | 70411932 |
| 13 | 23881043 | 23892052 | | 13 | 70418292 | 70420111 |
| 13 | 23983314 | 23984486 | | 13 | 70429778 | 70430193 |
| 13 | 24099123 | 24100603 | | 13 | 70567680 | 70569260 |
| 13 | 24123465 | 24125922 | | 13 | 70604674 | 70606829 |
| 13 | 24140489 | 24141099 | | 13 | 70786174 | 70789241 |
| 13 | 24171771 | 24175259 | | 13 | 70831236 | 70833333 |
| 13 | 24181611 | 24182628 | | 13 | 70880741 | 70882036 |
| 13 | 24242412 | 24242887 | | 13 | 70924847 | 70927728 |
| 13 | 24341853 | 24344406 | | 13 | 70955801 | 70956731 |
| 13 | 24349171 | 24351582 | | 13 | 70977021 | 70979356 |
| 13 | 24457114 | 24461855 | | 13 | 70989553 | 70992237 |
| 13 | 24489840 | 24498524 | | 13 | 71049642 | 71050444 |
| 13 | 24512599 | 24514114 | | 13 | 71098569 | 71100611 |
| 13 | 24527369 | 24528545 | | 13 | 71124543 | 71125993 |

The chromosomal positon was obtained from UCSC genome browser (http://genome.ucsc.edu/) build 36.

APPENDIX B: Chromosome 13
Page 28 of 49

| Chr | Start | End | Chr | Start | End |
|---|---|---|---|---|---|
| 13 | 24538475 | 24542689 | 13 | 71208871 | 71211438 |
| 13 | 24565518 | 24569594 | 13 | 71257520 | 71258833 |
| 13 | 24587363 | 24589792 | 13 | 71317020 | 71318980 |
| 13 | 24592619 | 24594504 | 13 | 71325045 | 71327730 |
| 13 | 24652076 | 24652895 | 13 | 71343437 | 71349647 |
| 13 | 24825807 | 24846234 | 13 | 71375285 | 71376590 |
| 13 | 24854589 | 24860445 | 13 | 71404573 | 71406249 |
| 13 | 24875542 | 24877937 | 13 | 71438763 | 71444846 |
| 13 | 24885774 | 24887709 | 13 | 71491175 | 71496040 |
| 13 | 24895536 | 24901160 | 13 | 71572956 | 71573836 |
| 13 | 24901562 | 24901902 | 13 | 71657622 | 71659612 |
| 13 | 24917127 | 24931704 | 13 | 71681372 | 71684131 |
| 13 | 24946077 | 24980907 | 13 | 71730511 | 71732463 |
| 13 | 24990349 | 24993820 | 13 | 71774565 | 71778181 |
| 13 | 24999322 | 25001333 | 13 | 71785802 | 71788992 |
| 13 | 25225073 | 25226677 | 13 | 71839317 | 71841502 |
| 13 | 25235072 | 25235872 | 13 | 71873185 | 71875980 |
| 13 | 25242826 | 25244467 | 13 | 71984550 | 71989070 |
| 13 | 25335396 | 25337826 | 13 | 72002764 | 72009411 |
| 13 | 25353841 | 25355201 | 13 | 72045220 | 72045680 |
| 13 | 25419373 | 25433413 | 13 | 72117412 | 72122009 |
| 13 | 25450429 | 25454094 | 13 | 72166057 | 72167042 |
| 13 | 25485102 | 25486484 | 13 | 72458495 | 72459659 |
| 13 | 25493151 | 25495407 | 13 | 72528047 | 72534858 |
| 13 | 25574306 | 25583264 | 13 | 72610328 | 72613354 |
| 13 | 25588328 | 25593015 | 13 | 72635566 | 72636538 |
| 13 | 25658825 | 25659759 | 13 | 72641030 | 72642280 |
| 13 | 25693229 | 25695154 | 13 | 72712100 | 72713845 |
| 13 | 25793818 | 25795728 | 13 | 72730669 | 72737668 |
| 13 | 25928990 | 25931260 | 13 | 72853458 | 72854383 |
| 13 | 25978063 | 25988361 | 13 | 72862416 | 72862961 |
| 13 | 25991109 | 25999630 | 13 | 72883159 | 72887392 |
| 13 | 26003100 | 26017276 | 13 | 72924633 | 72929965 |
| 13 | 26031695 | 26037732 | 13 | 72952562 | 72960535 |
| 13 | 26039417 | 26041032 | 13 | 73104796 | 73106617 |
| 13 | 26063606 | 26067311 | 13 | 73141884 | 73144882 |
| 13 | 26077511 | 26083712 | 13 | 73166862 | 73168467 |
| 13 | 26085971 | 26087247 | 13 | 73385689 | 73387365 |
| 13 | 26098222 | 26101688 | 13 | 73499007 | 73499532 |
| 13 | 26155679 | 26168576 | 13 | 73542168 | 73543373 |
| 13 | 26178023 | 26191338 | 13 | 73625555 | 73627298 |
| 13 | 26193148 | 26194178 | 13 | 73662851 | 73664276 |
| 13 | 26194768 | 26201368 | 13 | 73672602 | 73676336 |
| 13 | 26204448 | 26223123 | 13 | 73720297 | 73733102 |
| 13 | 26233300 | 26246419 | 13 | 73760308 | 73760853 |
| 13 | 26250599 | 26253649 | 13 | 73834922 | 73835957 |
| 13 | 26261635 | 26271648 | 13 | 73843634 | 73845994 |
| 13 | 26285704 | 26289223 | 13 | 73923475 | 73924745 |
| 13 | 26327315 | 26328070 | 13 | 73926241 | 73928641 |
| 13 | 26331921 | 26335896 | 13 | 73999950 | 74002531 |
| 13 | 26344479 | 26345714 | 13 | 74085650 | 74088939 |
| 13 | 26349919 | 26356248 | 13 | 74209086 | 74210189 |
| 13 | 26364592 | 26400523 | 13 | 74261020 | 74261055 |
| 13 | 26444661 | 26447675 | 13 | 74444882 | 74448304 |
| 13 | 26470382 | 26471050 | 13 | 74454770 | 74461580 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 26508226 | 26512808 | 13 | 74670422 | 74673332 |
| 13 | 26527208 | 26529906 | 13 | 74711279 | 74719674 |
| 13 | 26667381 | 26668376 | 13 | 74798254 | 74799484 |
| 13 | 26788863 | 26793564 | 13 | 74824035 | 74826535 |
| 13 | 26801497 | 26803026 | 13 | 74836311 | 74839046 |
| 13 | 26810740 | 26814142 | 13 | 74871065 | 74872510 |
| 13 | 26819143 | 26820700 | 13 | 75104892 | 75109975 |
| 13 | 26839613 | 26848368 | 13 | 75176784 | 75177399 |
| 13 | 26858766 | 26868788 | 13 | 75210919 | 75216383 |
| 13 | 26883592 | 26891672 | 13 | 75234885 | 75238139 |
| 13 | 26897242 | 26899667 | 13 | 75249689 | 75250775 |
| 13 | 26923344 | 26926569 | 13 | 75346706 | 75348590 |
| 13 | 26953532 | 26954561 | 13 | 75380226 | 75380706 |
| 13 | 26972381 | 26977156 | 13 | 75390329 | 75392556 |
| 13 | 26979915 | 26984973 | 13 | 75421988 | 75423310 |
| 13 | 26996863 | 27000473 | 13 | 75491401 | 75492026 |
| 13 | 27007384 | 27012656 | 13 | 75522414 | 75523815 |
| 13 | 27079449 | 27080204 | 13 | 75629168 | 75631418 |
| 13 | 27094344 | 27096590 | 13 | 75696378 | 75697243 |
| 13 | 27167035 | 27172562 | 13 | 75735529 | 75737416 |
| 13 | 27185146 | 27191446 | 13 | 75797838 | 75799116 |
| 13 | 27216971 | 27223031 | 13 | 75922165 | 75923315 |
| 13 | 27232324 | 27238146 | 13 | 75932766 | 75936331 |
| 13 | 27258520 | 27261089 | 13 | 75988098 | 75990842 |
| 13 | 27278665 | 27291638 | 13 | 75993353 | 75994568 |
| 13 | 27296790 | 27313473 | 13 | 76045995 | 76047390 |
| 13 | 27322828 | 27333880 | 13 | 76135864 | 76143212 |
| 13 | 27351287 | 27356237 | 13 | 76149087 | 76152562 |
| 13 | 27371818 | 27381116 | 13 | 76159150 | 76164214 |
| 13 | 27389240 | 27401678 | 13 | 76270765 | 76273024 |
| 13 | 27434010 | 27443520 | 13 | 76281121 | 76284313 |
| 13 | 27447820 | 27448850 | 13 | 76358822 | 76360313 |
| 13 | 27451492 | 27461615 | 13 | 76394908 | 76402059 |
| 13 | 27480528 | 27489114 | 13 | 76437583 | 76440453 |
| 13 | 27506296 | 27514451 | 13 | 76500094 | 76501024 |
| 13 | 27515751 | 27519423 | 13 | 76550873 | 76551738 |
| 13 | 27529871 | 27531603 | 13 | 76571864 | 76573539 |
| 13 | 27572981 | 27576139 | 13 | 76597113 | 76598601 |
| 13 | 27590356 | 27598693 | 13 | 76615541 | 76616826 |
| 13 | 27603099 | 27607067 | 13 | 76721481 | 76723222 |
| 13 | 27645533 | 27649594 | 13 | 76791911 | 76795365 |
| 13 | 27957395 | 27959816 | 13 | 76810923 | 76812943 |
| 13 | 27967907 | 27968617 | 13 | 76840836 | 76846353 |
| 13 | 28010099 | 28013066 | 13 | 76886649 | 76888369 |
| 13 | 28024781 | 28027803 | 13 | 76916845 | 76918472 |
| 13 | 28030476 | 28033283 | 13 | 76931651 | 76938141 |
| 13 | 28036120 | 28037175 | 13 | 77018422 | 77020484 |
| 13 | 28074935 | 28076595 | 13 | 77102141 | 77104755 |
| 13 | 28106557 | 28111813 | 13 | 77108347 | 77113645 |
| 13 | 28112839 | 28117101 | 13 | 77167377 | 77169037 |
| 13 | 28285726 | 28291555 | 13 | 77178353 | 77180154 |
| 13 | 28320902 | 28322742 | 13 | 77197638 | 77199781 |
| 13 | 28326889 | 28333419 | 13 | 77215028 | 77217237 |
| 13 | 28357360 | 28366137 | 13 | 77289729 | 77293571 |
| 13 | 28370253 | 28372805 | 13 | 77355119 | 77357451 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 28406329 | 28410639 | 13 | 77382578 | 77385579 |
| 13 | 28423096 | 28437546 | 13 | 77416750 | 77422821 |
| 13 | 28445754 | 28449523 | 13 | 77460782 | 77462817 |
| 13 | 28455972 | 28465167 | 13 | 77483035 | 77487012 |
| 13 | 28481295 | 28489096 | 13 | 77500823 | 77501513 |
| 13 | 28491183 | 28503428 | 13 | 77557821 | 77558661 |
| 13 | 28518571 | 28523931 | 13 | 77594110 | 77595170 |
| 13 | 28589568 | 28591727 | 13 | 77652635 | 77653600 |
| 13 | 28609027 | 28614382 | 13 | 77680640 | 77683344 |
| 13 | 28624810 | 28626080 | 13 | 77697417 | 77701288 |
| 13 | 28628800 | 28636741 | 13 | 77712981 | 77714311 |
| 13 | 28699038 | 28701698 | 13 | 77716926 | 77720615 |
| 13 | 28728192 | 28729982 | 13 | 77728702 | 77731009 |
| 13 | 28737249 | 28743620 | 13 | 77749957 | 77751833 |
| 13 | 28752905 | 28753745 | 13 | 77782647 | 77783907 |
| 13 | 28758762 | 28763479 | 13 | 77806192 | 77807762 |
| 13 | 28789985 | 28791900 | 13 | 77845690 | 77851298 |
| 13 | 28825988 | 28832791 | 13 | 77969370 | 77970503 |
| 13 | 28837797 | 28839987 | 13 | 78010174 | 78012250 |
| 13 | 28851359 | 28855422 | 13 | 78024640 | 78027098 |
| 13 | 28863540 | 28867390 | 13 | 78027988 | 78029645 |
| 13 | 28874811 | 28877788 | 13 | 78037536 | 78038884 |
| 13 | 28907829 | 28922962 | 13 | 78068859 | 78073853 |
| 13 | 28926704 | 28930581 | 13 | 78078627 | 78082400 |
| 13 | 28933999 | 28938084 | 13 | 78122368 | 78122928 |
| 13 | 28948902 | 28981570 | 13 | 78143973 | 78144918 |
| 13 | 28992058 | 29041779 | 13 | 78155258 | 78163498 |
| 13 | 29049840 | 29055465 | 13 | 78245818 | 78246829 |
| 13 | 29083095 | 29085260 | 13 | 78286682 | 78287327 |
| 13 | 29122571 | 29124291 | 13 | 78334312 | 78343105 |
| 13 | 29138745 | 29153797 | 13 | 78372976 | 78376139 |
| 13 | 29165386 | 29166326 | 13 | 78410698 | 78413053 |
| 13 | 29174709 | 29218662 | 13 | 78425655 | 78428320 |
| 13 | 29318966 | 29324934 | 13 | 78506517 | 78507256 |
| 13 | 29353462 | 29355132 | 13 | 78520895 | 78523532 |
| 13 | 29392324 | 29393599 | 13 | 78541658 | 78542958 |
| 13 | 29394474 | 29396344 | 13 | 78710867 | 78714017 |
| 13 | 29408171 | 29408961 | 13 | 78724124 | 78726107 |
| 13 | 29425305 | 29433729 | 13 | 78857459 | 78858465 |
| 13 | 29490877 | 29492457 | 13 | 78863935 | 78865954 |
| 13 | 29494723 | 29495968 | 13 | 78891723 | 78895348 |
| 13 | 29525254 | 29527843 | 13 | 78924233 | 78926270 |
| 13 | 29579512 | 29581534 | 13 | 79039900 | 79042140 |
| 13 | 29586355 | 29588576 | 13 | 79090881 | 79092831 |
| 13 | 29679618 | 29682746 | 13 | 79097037 | 79097742 |
| 13 | 29806760 | 29808105 | 13 | 79113302 | 79118969 |
| 13 | 29810365 | 29811215 | 13 | 79124039 | 79124565 |
| 13 | 29818600 | 29819080 | 13 | 79145426 | 79147088 |
| 13 | 29839282 | 29840711 | 13 | 79152540 | 79156985 |
| 13 | 29842994 | 29847777 | 13 | 79164886 | 79167443 |
| 13 | 29860628 | 29862140 | 13 | 79193240 | 79198408 |
| 13 | 29875766 | 29876122 | 13 | 79264976 | 79265936 |
| 13 | 29888828 | 29889158 | 13 | 79274776 | 79276613 |
| 13 | 29899595 | 29902198 | 13 | 79297085 | 79306922 |
| 13 | 29913422 | 29913932 | 13 | 79367028 | 79372923 |

The chromosomal positon was obtained from UCSC genome browser (http://genome.ucsc.edu/) build 36.

APPENDIX B: Chromosome 13
Page 31 of 49

| Chr | Start | End | | | Chr | Start | End |
|---|---|---|---|---|---|---|---|
| 13 | 29934357 | 29936259 | | | 13 | 79466345 | 79468959 |
| 13 | 29950714 | 29954235 | | | 13 | 79587556 | 79588486 |
| 13 | 29998624 | 30000586 | | | 13 | 79616966 | 79622598 |
| 13 | 30048386 | 30048871 | | | 13 | 79746440 | 79747475 |
| 13 | 30076726 | 30077811 | | | 13 | 79846711 | 79848006 |
| 13 | 30146682 | 30154562 | | | 13 | 79864502 | 79866218 |
| 13 | 30161518 | 30170648 | | | 13 | 79908838 | 79910647 |
| 13 | 30202553 | 30207454 | | | 13 | 79998236 | 80001181 |
| 13 | 30212551 | 30213486 | | | 13 | 80019664 | 80023491 |
| 13 | 30215145 | 30237218 | | | 13 | 80033522 | 80034997 |
| 13 | 30251609 | 30252399 | | | 13 | 80047868 | 80048573 |
| 13 | 30264347 | 30269482 | | | 13 | 80099802 | 80105870 |
| 13 | 30288251 | 30299093 | | | 13 | 80115896 | 80117516 |
| 13 | 30301569 | 30321984 | | | 13 | 80119658 | 80120038 |
| 13 | 30336631 | 30344903 | | | 13 | 80240728 | 80241943 |
| 13 | 30351873 | 30360435 | | | 13 | 80293537 | 80295111 |
| 13 | 30377510 | 30383467 | | | 13 | 80551652 | 80553152 |
| 13 | 30387147 | 30396959 | | | 13 | 80605909 | 80611656 |
| 13 | 30403923 | 30409621 | | | 13 | 80697524 | 80698226 |
| 13 | 30427439 | 30436595 | | | 13 | 80710771 | 80711156 |
| 13 | 30462718 | 30516584 | | | 13 | 80722309 | 80723639 |
| 13 | 30517029 | 30517369 | | | 13 | 80766224 | 80768480 |
| 13 | 30518204 | 30545421 | | | 13 | 80841243 | 80843328 |
| 13 | 30548366 | 30550614 | | | 13 | 80874890 | 80875743 |
| 13 | 30558236 | 30602405 | | | 13 | 80902328 | 80905021 |
| 13 | 30614051 | 30615061 | | | 13 | 80927122 | 80928075 |
| 13 | 30643401 | 30651464 | | | 13 | 81008325 | 81013429 |
| 13 | 30663141 | 30665399 | | | 13 | 81023349 | 81023854 |
| 13 | 30674119 | 30678544 | | | 13 | 81107956 | 81112292 |
| 13 | 30705806 | 30711562 | | | 13 | 81193542 | 81195074 |
| 13 | 30795006 | 30802168 | | | 13 | 81241612 | 81245053 |
| 13 | 30819854 | 30829622 | | | 13 | 81252513 | 81255553 |
| 13 | 30833898 | 30852114 | | | 13 | 81349220 | 81353262 |
| 13 | 30882023 | 30883520 | | | 13 | 81377533 | 81379458 |
| 13 | 30890696 | 30892380 | | | 13 | 81383354 | 81384624 |
| 13 | 30894345 | 30898037 | | | 13 | 81412297 | 81413137 |
| 13 | 30904869 | 30916134 | | | 13 | 81429258 | 81430738 |
| 13 | 30927097 | 30928278 | | | 13 | 81598316 | 81598971 |
| 13 | 30939254 | 30940376 | | | 13 | 81616464 | 81617029 |
| 13 | 30981905 | 30983845 | | | 13 | 81961251 | 81962806 |
| 13 | 31011131 | 31012776 | | | 13 | 82104000 | 82105782 |
| 13 | 31015611 | 31017506 | | | 13 | 82186006 | 82187871 |
| 13 | 31064002 | 31067308 | | | 13 | 82221199 | 82223868 |
| 13 | 31085833 | 31087713 | | | 13 | 82296601 | 82297381 |
| 13 | 31183296 | 31186637 | | | 13 | 82333874 | 82335139 |
| 13 | 31187802 | 31191997 | | | 13 | 82372387 | 82374279 |
| 13 | 31197435 | 31198735 | | | 13 | 82388514 | 82392196 |
| 13 | 31214868 | 31218303 | | | 13 | 82509758 | 82512898 |
| 13 | 31225174 | 31231229 | | | 13 | 82561905 | 82566295 |
| 13 | 31239099 | 31242839 | | | 13 | 82729086 | 82730096 |
| 13 | 31250001 | 31253860 | | | 13 | 82764985 | 82766060 |
| 13 | 31257117 | 31261553 | | | 13 | 82828047 | 82832152 |
| 13 | 31273757 | 31276536 | | | 13 | 82854198 | 82855468 |
| 13 | 31317143 | 31325914 | | | 13 | 82924321 | 82925461 |
| 13 | 31348063 | 31350972 | | | 13 | 82943581 | 82945960 |

The chromosomal positon was obtained from UCSC genome browser (http://genome.ucsc.edu/) build 36.

APPENDIX B: Chromosome 13
Page 32 of 49

| Chr | Start | End | Chr | Start | End |
|---|---|---|---|---|---|
| 13 | 31357817 | 31359682 | 13 | 82946749 | 82946884 |
| 13 | 31383497 | 31386674 | 13 | 83003646 | 83006091 |
| 13 | 31389776 | 31393456 | 13 | 83103237 | 83106250 |
| 13 | 31508082 | 31512858 | 13 | 83122104 | 83124206 |
| 13 | 31602822 | 31605247 | 13 | 83145816 | 83147549 |
| 13 | 31610744 | 31616198 | 13 | 83153380 | 83156355 |
| 13 | 31638596 | 31641576 | 13 | 83185914 | 83188425 |
| 13 | 31680432 | 31681403 | 13 | 83318481 | 83320734 |
| 13 | 31827191 | 31827196 | 13 | 83350539 | 83357089 |
| 13 | 31880973 | 31882698 | 13 | 83424749 | 83426412 |
| 13 | 31897635 | 31901066 | 13 | 83547563 | 83550117 |
| 13 | 31919998 | 31923282 | 13 | 83656442 | 83658987 |
| 13 | 32009686 | 32012989 | 13 | 83695134 | 83700320 |
| 13 | 32033650 | 32037579 | 13 | 83761451 | 83769458 |
| 13 | 32110286 | 32111526 | 13 | 83993821 | 83996161 |
| 13 | 32295449 | 32298822 | 13 | 84255778 | 84256878 |
| 13 | 32375594 | 32378234 | 13 | 84258596 | 84260556 |
| 13 | 32381830 | 32383717 | 13 | 84368980 | 84371573 |
| 13 | 32486744 | 32491250 | 13 | 84372607 | 84375007 |
| 13 | 32505864 | 32510492 | 13 | 84551348 | 84555774 |
| 13 | 32528131 | 32529641 | 13 | 84666366 | 84672330 |
| 13 | 32590294 | 32592879 | 13 | 84881297 | 84882372 |
| 13 | 32623615 | 32626681 | 13 | 84997120 | 84997425 |
| 13 | 32641641 | 32642928 | 13 | 85110713 | 85112068 |
| 13 | 32646911 | 32648500 | 13 | 85131403 | 85132724 |
| 13 | 32658995 | 32660732 | 13 | 85157245 | 85160265 |
| 13 | 32677240 | 32678471 | 13 | 85175948 | 85178813 |
| 13 | 32679466 | 32681806 | 13 | 85216138 | 85218524 |
| 13 | 32689783 | 32692056 | 13 | 85243065 | 85245830 |
| 13 | 32733710 | 32736020 | 13 | 85424939 | 85427871 |
| 13 | 32834420 | 32836035 | 13 | 85445952 | 85448347 |
| 13 | 32924192 | 32926818 | 13 | 85500349 | 85502742 |
| 13 | 32956169 | 32959881 | 13 | 85533562 | 85534504 |
| 13 | 32978958 | 32983600 | 13 | 85561544 | 85564795 |
| 13 | 33038334 | 33040709 | 13 | 85715450 | 85717250 |
| 13 | 33075098 | 33075912 | 13 | 85885355 | 85889462 |
| 13 | 33100479 | 33103920 | 13 | 85971350 | 85973686 |
| 13 | 33114334 | 33115946 | 13 | 86143414 | 86144079 |
| 13 | 33149066 | 33150632 | 13 | 86208346 | 86216255 |
| 13 | 33215668 | 33216973 | 13 | 86366878 | 86368682 |
| 13 | 33229419 | 33230654 | 13 | 86399661 | 86401418 |
| 13 | 33233775 | 33234250 | 13 | 86453949 | 86457726 |
| 13 | 33260228 | 33263240 | 13 | 86470945 | 86472110 |
| 13 | 33397982 | 33401491 | 13 | 86528973 | 86531842 |
| 13 | 33427208 | 33429401 | 13 | 86703709 | 86705570 |
| 13 | 33470298 | 33474862 | 13 | 86743729 | 86749847 |
| 13 | 33516659 | 33517769 | 13 | 86802079 | 86807294 |
| 13 | 33587577 | 33593290 | 13 | 86847799 | 86850654 |
| 13 | 33618407 | 33619627 | 13 | 86905121 | 86908731 |
| 13 | 33682137 | 33684548 | 13 | 86950774 | 86952395 |
| 13 | 33699788 | 33700628 | 13 | 86962603 | 86965173 |
| 13 | 33748555 | 33750322 | 13 | 87007415 | 87007850 |
| 13 | 33761580 | 33765275 | 13 | 87072773 | 87080114 |
| 13 | 33813135 | 33819168 | 13 | 87120969 | 87124924 |
| 13 | 33917573 | 33925339 | 13 | 87171874 | 87180939 |

The chromosomal positon was obtained from UCSC genome browser (http://genome.ucsc.edu/) build 36.

APPENDIX B: Chromosome 13
Page 33 of 49

| Chr | Start | End | Chr | Start | End |
|---|---|---|---|---|---|
| 13 | 33958585 | 33963884 | 13 | 87227687 | 87232722 |
| 13 | 34092163 | 34094854 | 13 | 87310583 | 87313447 |
| 13 | 34101865 | 34107629 | 13 | 87342656 | 87345406 |
| 13 | 34143254 | 34145388 | 13 | 87416569 | 87419590 |
| 13 | 34221806 | 34224807 | 13 | 87433024 | 87433614 |
| 13 | 34371551 | 34373617 | 13 | 87453152 | 87455597 |
| 13 | 34522941 | 34524362 | 13 | 87495296 | 87496966 |
| 13 | 34564297 | 34565746 | 13 | 87792784 | 87796552 |
| 13 | 34576445 | 34577745 | 13 | 87806579 | 87808198 |
| 13 | 34703877 | 34706929 | 13 | 87994586 | 87997616 |
| 13 | 34758746 | 34759638 | 13 | 88064700 | 88068671 |
| 13 | 34774057 | 34780330 | 13 | 88081151 | 88082949 |
| 13 | 34835199 | 34838303 | 13 | 88116527 | 88117272 |
| 13 | 34906126 | 34908394 | 13 | 88126724 | 88127276 |
| 13 | 34927379 | 34928213 | 13 | 88179422 | 88180567 |
| 13 | 34942710 | 34944295 | 13 | 88230381 | 88233221 |
| 13 | 34950201 | 34951672 | 13 | 88240060 | 88241328 |
| 13 | 35026550 | 35027620 | 13 | 88244238 | 88246109 |
| 13 | 35152209 | 35156630 | 13 | 88419181 | 88422169 |
| 13 | 35171640 | 35175039 | 13 | 88466477 | 88468069 |
| 13 | 35185122 | 35187202 | 13 | 88512851 | 88514724 |
| 13 | 35198517 | 35201162 | 13 | 88518873 | 88523359 |
| 13 | 35231161 | 35239844 | 13 | 88584015 | 88585134 |
| 13 | 35264841 | 35266271 | 13 | 88611917 | 88613719 |
| 13 | 35267711 | 35273856 | 13 | 88617723 | 88621328 |
| 13 | 35309902 | 35315056 | 13 | 88671455 | 88672814 |
| 13 | 35342127 | 35343582 | 13 | 88680675 | 88682943 |
| 13 | 35349484 | 35359284 | 13 | 88812639 | 88814411 |
| 13 | 35380780 | 35398600 | 13 | 88902054 | 88904115 |
| 13 | 35406937 | 35416906 | 13 | 89139268 | 89143761 |
| 13 | 35443164 | 35453175 | 13 | 89147597 | 89152475 |
| 13 | 35458136 | 35461999 | 13 | 89184264 | 89185404 |
| 13 | 35570817 | 35575596 | 13 | 89210085 | 89211130 |
| 13 | 35597400 | 35598924 | 13 | 89219313 | 89220551 |
| 13 | 35618382 | 35620809 | 13 | 89231338 | 89236543 |
| 13 | 35631076 | 35635945 | 13 | 89236978 | 89242267 |
| 13 | 35639502 | 35641484 | 13 | 89554042 | 89555442 |
| 13 | 35658464 | 35659259 | 13 | 89616994 | 89619390 |
| 13 | 35686006 | 35687787 | 13 | 89634565 | 89635926 |
| 13 | 35690323 | 35694356 | 13 | 89674523 | 89677624 |
| 13 | 35732784 | 35739206 | 13 | 89684946 | 89688335 |
| 13 | 35826047 | 35827497 | 13 | 89738699 | 89743977 |
| 13 | 35872930 | 35874554 | 13 | 89868474 | 89869274 |
| 13 | 35904876 | 35907950 | 13 | 89910025 | 89911983 |
| 13 | 35918242 | 35918507 | 13 | 90065413 | 90068954 |
| 13 | 35918722 | 35922877 | 13 | 90109180 | 90120493 |
| 13 | 35948521 | 35949416 | 13 | 90193630 | 90200994 |
| 13 | 36000151 | 36002336 | 13 | 90369411 | 90371230 |
| 13 | 36087965 | 36090113 | 13 | 90376501 | 90378572 |
| 13 | 36095315 | 36098186 | 13 | 90534804 | 90539785 |
| 13 | 36131845 | 36133300 | 13 | 90627601 | 90631322 |
| 13 | 36137088 | 36140074 | 13 | 90651768 | 90654138 |
| 13 | 36143478 | 36148473 | 13 | 90662049 | 90664315 |
| 13 | 36166629 | 36172982 | 13 | 90673919 | 90678114 |
| 13 | 36190518 | 36192428 | 13 | 90686582 | 90689397 |

The chromosomal positon was obtained from UCSC genome browser (http://genome.ucsc.edu/) build 36.

APPENDIX B: Chromosome 13
Page 34 of 49

| Chr | Start | End | Chr | Start | End |
|---|---|---|---|---|---|
| 13 | 36518081 | 36520046 | 13 | 90762891 | 90764689 |
| 13 | 36614680 | 36617347 | 13 | 90817511 | 90820511 |
| 13 | 36662770 | 36667412 | 13 | 90843896 | 90845836 |
| 13 | 36701405 | 36702825 | 13 | 90930321 | 90932739 |
| 13 | 36718512 | 36720882 | 13 | 90943235 | 90950356 |
| 13 | 36879166 | 36879731 | 13 | 90962310 | 90964540 |
| 13 | 36917456 | 36922255 | 13 | 91087443 | 91092842 |
| 13 | 36981139 | 36983403 | 13 | 91133855 | 91135760 |
| 13 | 37056120 | 37059281 | 13 | 91144888 | 91145973 |
| 13 | 37070799 | 37076996 | 13 | 91162825 | 91168313 |
| 13 | 37099335 | 37103116 | 13 | 91196135 | 91198290 |
| 13 | 37109011 | 37109901 | 13 | 91214338 | 91215158 |
| 13 | 37205625 | 37207535 | 13 | 91247125 | 91248211 |
| 13 | 37301031 | 37301484 | 13 | 91254601 | 91258997 |
| 13 | 37340485 | 37341242 | 13 | 91357472 | 91360207 |
| 13 | 37342333 | 37343598 | 13 | 91385097 | 91390277 |
| 13 | 37395231 | 37396146 | 13 | 91395467 | 91396555 |
| 13 | 37414984 | 37418837 | 13 | 91431394 | 91433753 |
| 13 | 37474593 | 37475814 | 13 | 91437121 | 91439593 |
| 13 | 37662889 | 37668518 | 13 | 91490306 | 91496159 |
| 13 | 37722200 | 37729125 | 13 | 91528487 | 91531809 |
| 13 | 37771911 | 37774786 | 13 | 91589311 | 91591105 |
| 13 | 37871135 | 37879894 | 13 | 91666398 | 91668905 |
| 13 | 37881959 | 37882994 | 13 | 91723626 | 91725906 |
| 13 | 37903197 | 37904360 | 13 | 91833977 | 91836734 |
| 13 | 37909317 | 37911952 | 13 | 91882167 | 91884080 |
| 13 | 37917086 | 37917651 | 13 | 91911839 | 91913246 |
| 13 | 37924615 | 37927900 | 13 | 91929272 | 91932594 |
| 13 | 37955702 | 37958138 | 13 | 92041666 | 92046252 |
| 13 | 37983132 | 37983437 | 13 | 92052676 | 92053231 |
| 13 | 37997176 | 38003749 | 13 | 92128676 | 92129547 |
| 13 | 38085468 | 38088420 | 13 | 92156036 | 92156826 |
| 13 | 38097680 | 38100797 | 13 | 92176189 | 92179918 |
| 13 | 38104338 | 38110561 | 13 | 92182981 | 92183752 |
| 13 | 38142567 | 38146147 | 13 | 92270206 | 92271331 |
| 13 | 38189940 | 38196396 | 13 | 92361255 | 92365673 |
| 13 | 38238045 | 38241969 | 13 | 92454627 | 92458317 |
| 13 | 38289271 | 38292291 | 13 | 92610226 | 92611166 |
| 13 | 38343141 | 38344651 | 13 | 92638139 | 92643236 |
| 13 | 38353262 | 38356875 | 13 | 92676226 | 92679247 |
| 13 | 38426682 | 38429774 | 13 | 92733425 | 92735022 |
| 13 | 38511339 | 38513498 | 13 | 92739173 | 92741668 |
| 13 | 38725404 | 38729130 | 13 | 92745007 | 92748397 |
| 13 | 38753227 | 38755638 | 13 | 92802442 | 92804360 |
| 13 | 38866856 | 38868466 | 13 | 92865332 | 92867729 |
| 13 | 38873589 | 38877725 | 13 | 92886284 | 92888290 |
| 13 | 38919619 | 38921304 | 13 | 92936440 | 92937915 |
| 13 | 38955807 | 38961347 | 13 | 92965829 | 92967110 |
| 13 | 39034901 | 39036944 | 13 | 92971180 | 92975365 |
| 13 | 39169615 | 39170430 | 13 | 93022082 | 93023567 |
| 13 | 39274856 | 39274876 | 13 | 93194114 | 93195954 |
| 13 | 39282430 | 39282660 | 13 | 93247820 | 93248540 |
| 13 | 39413194 | 39416269 | 13 | 93264703 | 93265193 |
| 13 | 39436988 | 39437143 | 13 | 93299794 | 93302944 |
| 13 | 39464112 | 39469447 | 13 | 93305414 | 93307609 |

The chromosomal positon was obtained from UCSC genome browser (http://genome.ucsc.edu/) build 36.

APPENDIX B: Chromosome 13
Page 35 of 49

| Chr | Start | End | Chr | Start | End |
|---|---|---|---|---|---|
| 13 | 39502093 | 39507302 | 13 | 93312718 | 93320526 |
| 13 | 39520677 | 39522330 | 13 | 93335279 | 93340116 |
| 13 | 39533740 | 39535905 | 13 | 93383531 | 93386171 |
| 13 | 39536340 | 39537506 | 13 | 93473611 | 93477385 |
| 13 | 39548873 | 39551988 | 13 | 93479763 | 93482402 |
| 13 | 39558188 | 39566487 | 13 | 93529789 | 93531614 |
| 13 | 39575810 | 39579035 | 13 | 93555602 | 93556756 |
| 13 | 39611265 | 39619412 | 13 | 93589429 | 93590502 |
| 13 | 39639318 | 39640127 | 13 | 93592682 | 93594580 |
| 13 | 39650187 | 39652223 | 13 | 93621721 | 93624218 |
| 13 | 39663854 | 39672291 | 13 | 93642731 | 93645263 |
| 13 | 39683577 | 39686108 | 13 | 93646333 | 93647837 |
| 13 | 39688048 | 39689238 | 13 | 93656790 | 93660027 |
| 13 | 39704416 | 39712706 | 13 | 93687268 | 93689352 |
| 13 | 39719788 | 39720568 | 13 | 93711583 | 93712618 |
| 13 | 39747968 | 39750505 | 13 | 93719648 | 93723421 |
| 13 | 39758929 | 39759629 | 13 | 93737379 | 93746221 |
| 13 | 39786063 | 39790056 | 13 | 93759985 | 93761843 |
| 13 | 39799052 | 39802288 | 13 | 93775259 | 93777094 |
| 13 | 39816771 | 39824806 | 13 | 93786791 | 93795014 |
| 13 | 39834683 | 39852448 | 13 | 93818115 | 93818851 |
| 13 | 39860810 | 39861925 | 13 | 93821655 | 93833879 |
| 13 | 39880919 | 39882089 | 13 | 93841940 | 93844912 |
| 13 | 39939472 | 39943235 | 13 | 93883925 | 93884665 |
| 13 | 39958690 | 39972550 | 13 | 93888960 | 93890096 |
| 13 | 40003965 | 40006962 | 13 | 93917160 | 93921011 |
| 13 | 40069625 | 40070405 | 13 | 93951119 | 93952165 |
| 13 | 40071040 | 40074381 | 13 | 93999984 | 94003579 |
| 13 | 40085217 | 40086129 | 13 | 94031004 | 94033570 |
| 13 | 40135701 | 40136454 | 13 | 94044896 | 94045831 |
| 13 | 40240445 | 40244756 | 13 | 94127515 | 94132026 |
| 13 | 40347232 | 40348637 | 13 | 94150028 | 94151074 |
| 13 | 40446523 | 40457025 | 13 | 94151974 | 94154449 |
| 13 | 40608718 | 40610110 | 13 | 94169990 | 94174270 |
| 13 | 40692544 | 40693869 | 13 | 94244050 | 94246396 |
| 13 | 40888618 | 40891532 | 13 | 94274027 | 94275826 |
| 13 | 40895291 | 40907619 | 13 | 94278640 | 94290361 |
| 13 | 40923349 | 40929035 | 13 | 94308307 | 94318249 |
| 13 | 40932662 | 40937708 | 13 | 94330613 | 94334582 |
| 13 | 40985567 | 40986903 | 13 | 94387287 | 94390637 |
| 13 | 41005389 | 41006729 | 13 | 94393864 | 94396394 |
| 13 | 41020776 | 41021845 | 13 | 94400409 | 94402209 |
| 13 | 41052844 | 41053635 | 13 | 94426795 | 94428483 |
| 13 | 41057161 | 41060078 | 13 | 94450772 | 94452513 |
| 13 | 41067191 | 41080788 | 13 | 94460879 | 94464726 |
| 13 | 41082466 | 41087504 | 13 | 94473875 | 94475878 |
| 13 | 41104527 | 41107350 | 13 | 94568830 | 94570052 |
| 13 | 41143261 | 41147112 | 13 | 94626066 | 94627374 |
| 13 | 41247290 | 41248942 | 13 | 94750781 | 94752811 |
| 13 | 41283429 | 41287578 | 13 | 94780807 | 94782912 |
| 13 | 41290898 | 41293019 | 13 | 94810836 | 94813756 |
| 13 | 41431413 | 41432339 | 13 | 94834688 | 94840709 |
| 13 | 41444659 | 41447911 | 13 | 94864964 | 94865629 |
| 13 | 41483010 | 41485801 | 13 | 95003677 | 95005055 |
| 13 | 41524914 | 41527333 | 13 | 95014314 | 95019079 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 41553072 | 41554382 | 13 | 95019929 | 95021404 |
| 13 | 41555102 | 41555868 | 13 | 95072604 | 95072924 |
| 13 | 41594342 | 41599284 | 13 | 95093432 | 95094027 |
| 13 | 41715982 | 41717475 | 13 | 95152626 | 95158569 |
| 13 | 41771273 | 41775727 | 13 | 95220101 | 95222282 |
| 13 | 41805077 | 41806466 | 13 | 95333573 | 95335594 |
| 13 | 41826146 | 41827726 | 13 | 95447209 | 95450888 |
| 13 | 41839844 | 41841705 | 13 | 95503981 | 95506087 |
| 13 | 41894675 | 41896968 | 13 | 95533073 | 95534882 |
| 13 | 42046641 | 42047665 | 13 | 95600045 | 95603572 |
| 13 | 42106554 | 42110784 | 13 | 95608080 | 95611505 |
| 13 | 42189548 | 42191084 | 13 | 95681559 | 95684289 |
| 13 | 42194041 | 42194856 | 13 | 95771994 | 95774354 |
| 13 | 42237707 | 42242829 | 13 | 95833787 | 95835505 |
| 13 | 42261113 | 42266532 | 13 | 95845838 | 95847711 |
| 13 | 42303372 | 42305077 | 13 | 96010344 | 96016019 |
| 13 | 42317951 | 42325868 | 13 | 96168513 | 96170589 |
| 13 | 42333497 | 42337894 | 13 | 96187199 | 96190200 |
| 13 | 42349315 | 42351553 | 13 | 96214552 | 96215934 |
| 13 | 42437563 | 42439727 | 13 | 96223033 | 96232107 |
| 13 | 42443276 | 42444796 | 13 | 96300416 | 96302101 |
| 13 | 42493856 | 42496430 | 13 | 96355892 | 96361262 |
| 13 | 42513745 | 42514935 | 13 | 96365650 | 96367312 |
| 13 | 42620848 | 42625104 | 13 | 96395749 | 96399119 |
| 13 | 42627889 | 42630889 | 13 | 96434301 | 96435524 |
| 13 | 42642721 | 42644551 | 13 | 96451258 | 96452691 |
| 13 | 42673722 | 42675352 | 13 | 96518654 | 96519859 |
| 13 | 42711725 | 42714200 | 13 | 96564080 | 96572165 |
| 13 | 42736047 | 42737532 | 13 | 96579455 | 96581140 |
| 13 | 42748011 | 42752076 | 13 | 96591811 | 96592991 |
| 13 | 42835854 | 42837770 | 13 | 96610648 | 96614213 |
| 13 | 42844443 | 42851572 | 13 | 96635197 | 96638575 |
| 13 | 42957094 | 42959401 | 13 | 96658475 | 96666758 |
| 13 | 43017952 | 43019202 | 13 | 96707016 | 96711012 |
| 13 | 43030572 | 43031842 | 13 | 96782397 | 96786019 |
| 13 | 43082469 | 43084686 | 13 | 96826372 | 96827312 |
| 13 | 43135169 | 43136134 | 13 | 96875090 | 96876365 |
| 13 | 43138849 | 43140834 | 13 | 96905804 | 96907032 |
| 13 | 43147091 | 43155058 | 13 | 97064992 | 97070317 |
| 13 | 43243438 | 43244567 | 13 | 97077642 | 97082305 |
| 13 | 43301818 | 43302919 | 13 | 97102512 | 97105282 |
| 13 | 43303674 | 43306142 | 13 | 97145112 | 97148241 |
| 13 | 43415381 | 43417326 | 13 | 97160495 | 97161400 |
| 13 | 43453683 | 43457863 | 13 | 97178192 | 97187586 |
| 13 | 43477350 | 43482376 | 13 | 97286727 | 97289059 |
| 13 | 43510604 | 43514638 | 13 | 97324810 | 97328570 |
| 13 | 43524721 | 43525802 | 13 | 97334961 | 97336081 |
| 13 | 43579627 | 43581102 | 13 | 97477116 | 97485892 |
| 13 | 43583822 | 43591165 | 13 | 97512613 | 97517116 |
| 13 | 43599162 | 43600209 | 13 | 97594415 | 97595260 |
| 13 | 43604065 | 43609370 | 13 | 97664590 | 97665415 |
| 13 | 43616387 | 43618019 | 13 | 97705279 | 97707330 |
| 13 | 43631037 | 43632282 | 13 | 97717390 | 97718590 |
| 13 | 43632502 | 43637725 | 13 | 97861837 | 97862657 |
| 13 | 43650191 | 43652845 | 13 | 97926403 | 97928445 |

The chromosomal positon was obtained from UCSC genome browser (http://genome.ucsc.edu/) build 36.

APPENDIX B: Chromosome 13
Page 37 of 49

| Chr | Start | End | | Chr | Start | End |
|---|---|---|---|---|---|---|
| 13 | 43657676 | 43662595 | | 13 | 97992920 | 97994554 |
| 13 | 43667674 | 43670394 | | 13 | 98027936 | 98029092 |
| 13 | 43678301 | 43684719 | | 13 | 98108088 | 98109138 |
| 13 | 43695743 | 43698810 | | 13 | 98144495 | 98149111 |
| 13 | 43701249 | 43704756 | | 13 | 98155829 | 98157687 |
| 13 | 43705681 | 43715719 | | 13 | 98179772 | 98180670 |
| 13 | 43728746 | 43735094 | | 13 | 98225555 | 98232690 |
| 13 | 43757906 | 43767134 | | 13 | 98236175 | 98238578 |
| 13 | 43792393 | 43806676 | | 13 | 98349877 | 98352111 |
| 13 | 43815415 | 43816655 | | 13 | 98357587 | 98374926 |
| 13 | 43841246 | 43844616 | | 13 | 98402957 | 98404533 |
| 13 | 43851660 | 43853155 | | 13 | 98410831 | 98413076 |
| 13 | 43859823 | 43862209 | | 13 | 98414486 | 98415256 |
| 13 | 43865249 | 43866104 | | 13 | 98422021 | 98423441 |
| 13 | 43875513 | 43876748 | | 13 | 98430145 | 98432572 |
| 13 | 43899845 | 43903766 | | 13 | 98438768 | 98439752 |
| 13 | 43906143 | 43907847 | | 13 | 98449043 | 98452290 |
| 13 | 44011612 | 44014649 | | 13 | 98463245 | 98464535 |
| 13 | 44045861 | 44048576 | | 13 | 98489594 | 98492043 |
| 13 | 44051678 | 44052992 | | 13 | 98504352 | 98506820 |
| 13 | 44195235 | 44196435 | | 13 | 98582004 | 98584371 |
| 13 | 44204090 | 44205450 | | 13 | 98649134 | 98653015 |
| 13 | 44206465 | 44207485 | | 13 | 98664648 | 98679915 |
| 13 | 44224282 | 44227398 | | 13 | 98727475 | 98733463 |
| 13 | 44274191 | 44275704 | | 13 | 98754098 | 98756499 |
| 13 | 44286539 | 44287569 | | 13 | 98769904 | 98773076 |
| 13 | 44288161 | 44290706 | | 13 | 98806443 | 98808076 |
| 13 | 44313015 | 44313986 | | 13 | 98824923 | 98827280 |
| 13 | 44534860 | 44535664 | | 13 | 98859448 | 98865748 |
| 13 | 44614182 | 44615953 | | 13 | 98882447 | 98885057 |
| 13 | 44665796 | 44667833 | | 13 | 98887493 | 98890669 |
| 13 | 44781345 | 44783138 | | 13 | 98933418 | 98935183 |
| 13 | 44848103 | 44855454 | | 13 | 99016539 | 99019739 |
| 13 | 44862793 | 44864226 | | 13 | 99105898 | 99110268 |
| 13 | 44866983 | 44868984 | | 13 | 99123128 | 99127831 |
| 13 | 44917222 | 44919752 | | 13 | 99141326 | 99143069 |
| 13 | 44982324 | 44989212 | | 13 | 99190949 | 99193035 |
| 13 | 45041836 | 45043416 | | 13 | 99278150 | 99280830 |
| 13 | 45046811 | 45053024 | | 13 | 99287991 | 99300416 |
| 13 | 45056989 | 45059699 | | 13 | 99335445 | 99341972 |
| 13 | 45062424 | 45065159 | | 13 | 99344666 | 99347260 |
| 13 | 45102983 | 45104343 | | 13 | 99350518 | 99352287 |
| 13 | 45168879 | 45170076 | | 13 | 99367347 | 99404661 |
| 13 | 45212386 | 45217410 | | 13 | 99406190 | 99429195 |
| 13 | 45256488 | 45258395 | | 13 | 99433073 | 99434881 |
| 13 | 45264098 | 45270031 | | 13 | 99437507 | 99448018 |
| 13 | 45283182 | 45285422 | | 13 | 99538749 | 99540154 |
| 13 | 45307965 | 45322993 | | 13 | 99661761 | 99665305 |
| 13 | 45336143 | 45342441 | | 13 | 99831043 | 99831781 |
| 13 | 45362834 | 45370543 | | 13 | 99939889 | 99942007 |
| 13 | 45375988 | 45380125 | | 13 | 99960715 | 99962705 |
| 13 | 45520052 | 45521391 | | 13 | 99974759 | 99977786 |
| 13 | 45567719 | 45570635 | | 13 | 100107848 | 100109013 |
| 13 | 45595403 | 45597632 | | 13 | 100243092 | 100244370 |
| 13 | 45637663 | 45657606 | | 13 | 100290687 | 100291792 |

The chromosomal positon was obtained from UCSC genome browser (http://genome.ucsc.edu/) build 36.

APPENDIX B: Chromosome 13
Page 38 of 49

| Chr | Start | End | Chr | Start | End |
| --- | --- | --- | --- | --- | --- |
| 13 | 45794048 | 45796735 | 13 | 100432893 | 100441856 |
| 13 | 45802253 | 45805733 | 13 | 100456841 | 100458173 |
| 13 | 45857841 | 45861179 | 13 | 100461945 | 100462795 |
| 13 | 45919805 | 45924705 | 13 | 100468886 | 100469751 |
| 13 | 45980373 | 45985412 | 13 | 100469986 | 100475542 |
| 13 | 46015530 | 46016690 | 13 | 100529608 | 100531519 |
| 13 | 46033357 | 46034652 | 13 | 100589990 | 100593631 |
| 13 | 46052727 | 46054474 | 13 | 100704803 | 100709230 |
| 13 | 46055799 | 46058043 | 13 | 100721728 | 100726581 |
| 13 | 46087829 | 46090129 | 13 | 100789041 | 100791056 |
| 13 | 46131671 | 46132121 | 13 | 100820814 | 100821545 |
| 13 | 46135601 | 46144162 | 13 | 100847617 | 100849187 |
| 13 | 46151658 | 46153444 | 13 | 100865857 | 100867769 |
| 13 | 46165477 | 46168424 | 13 | 100948866 | 100953297 |
| 13 | 46223418 | 46225106 | 13 | 101097886 | 101098736 |
| 13 | 46230239 | 46231494 | 13 | 101136057 | 101137112 |
| 13 | 46284762 | 46285876 | 13 | 101168993 | 101170957 |
| 13 | 46325673 | 46328554 | 13 | 101281746 | 101283403 |
| 13 | 46333283 | 46337225 | 13 | 101303118 | 101306390 |
| 13 | 46358422 | 46360732 | 13 | 101365393 | 101371162 |
| 13 | 46364411 | 46368422 | 13 | 101381226 | 101383319 |
| 13 | 46378569 | 46380335 | 13 | 101395194 | 101396857 |
| 13 | 46398551 | 46399471 | 13 | 101536434 | 101538285 |
| 13 | 46429734 | 46431810 | 13 | 101560448 | 101562773 |
| 13 | 46582104 | 46582639 | 13 | 101569922 | 101572064 |
| 13 | 46609344 | 46610694 | 13 | 101650912 | 101652992 |
| 13 | 46661243 | 46662938 | 13 | 101679291 | 101682071 |
| 13 | 46685339 | 46687139 | 13 | 101691463 | 101693458 |
| 13 | 46801786 | 46803086 | 13 | 101709882 | 101711222 |
| 13 | 46947377 | 46948921 | 13 | 101735530 | 101736905 |
| 13 | 47069039 | 47070324 | 13 | 101825599 | 101827819 |
| 13 | 47100936 | 47101721 | 13 | 101895291 | 101911277 |
| 13 | 47184581 | 47200453 | 13 | 101983053 | 101987488 |
| 13 | 47219240 | 47224074 | 13 | 102016651 | 102021789 |
| 13 | 47282459 | 47284226 | 13 | 102136016 | 102137146 |
| 13 | 47515345 | 47516560 | 13 | 102147053 | 102147898 |
| 13 | 47581525 | 47582080 | 13 | 102150818 | 102152053 |
| 13 | 47632562 | 47634484 | 13 | 102183753 | 102184533 |
| 13 | 47692590 | 47693943 | 13 | 102191998 | 102193248 |
| 13 | 47694348 | 47695413 | 13 | 102196807 | 102198277 |
| 13 | 47696709 | 47698148 | 13 | 102226743 | 102230455 |
| 13 | 47701030 | 47702575 | 13 | 102353039 | 102355430 |
| 13 | 47707440 | 47710618 | 13 | 102364528 | 102365253 |
| 13 | 47901621 | 47901886 | 13 | 102372305 | 102378495 |
| 13 | 47974081 | 47975999 | 13 | 102383785 | 102384792 |
| 13 | 47976744 | 47978229 | 13 | 102387053 | 102391156 |
| 13 | 47979444 | 47980024 | 13 | 102433233 | 102434103 |
| 13 | 48004028 | 48004743 | 13 | 102499491 | 102501418 |
| 13 | 48104683 | 48106103 | 13 | 102517699 | 102519044 |
| 13 | 48149684 | 48153234 | 13 | 102525097 | 102527121 |
| 13 | 48235139 | 48236282 | 13 | 102542132 | 102547889 |
| 13 | 48242745 | 48246148 | 13 | 102553370 | 102555683 |
| 13 | 48255103 | 48255883 | 13 | 102557593 | 102560873 |
| 13 | 48292519 | 48294085 | 13 | 102573862 | 102577128 |
| 13 | 48330425 | 48332767 | 13 | 102582363 | 102589849 |

The chromosomal positon was obtained from UCSC genome browser (http://genome.ucsc.edu/) build 36.

APPENDIX B: Chromosome 13

| Chr | Start | End | | Chr | Start | End |
|---|---|---|---|---|---|---|
| 13 | 48353402 | 48358793 | | 13 | 102613068 | 102618529 |
| 13 | 48378394 | 48384210 | | 13 | 102637429 | 102639163 |
| 13 | 48390460 | 48392502 | | 13 | 102663882 | 102667277 |
| 13 | 48412265 | 48427961 | | 13 | 102696151 | 102704113 |
| 13 | 48431528 | 48433700 | | 13 | 102732372 | 102733618 |
| 13 | 48689274 | 48695142 | | 13 | 102749281 | 102751475 |
| 13 | 48785761 | 48786811 | | 13 | 102758980 | 102761223 |
| 13 | 48819585 | 48821225 | | 13 | 102784646 | 102786275 |
| 13 | 48871014 | 48873740 | | 13 | 102813803 | 102814143 |
| 13 | 48905005 | 48906565 | | 13 | 102863049 | 102865276 |
| 13 | 49012744 | 49013234 | | 13 | 102959031 | 102964303 |
| 13 | 49047063 | 49050664 | | 13 | 103007365 | 103011927 |
| 13 | 49265485 | 49267042 | | 13 | 103038108 | 103038733 |
| 13 | 49329705 | 49333234 | | 13 | 103048815 | 103052055 |
| 13 | 49598884 | 49605381 | | 13 | 103067003 | 103068413 |
| 13 | 49694696 | 49696946 | | 13 | 103109613 | 103112503 |
| 13 | 49749040 | 49752780 | | 13 | 103129403 | 103130348 |
| 13 | 49756449 | 49757169 | | 13 | 103148195 | 103149430 |
| 13 | 49829642 | 49829972 | | 13 | 103186425 | 103187680 |
| 13 | 49967448 | 49970572 | | 13 | 103248412 | 103251431 |
| 13 | 49984151 | 49985855 | | 13 | 103301300 | 103302655 |
| 13 | 50022234 | 50024120 | | 13 | 103351149 | 103351434 |
| 13 | 50116737 | 50118422 | | 13 | 103358835 | 103361816 |
| 13 | 50154273 | 50158164 | | 13 | 103400967 | 103404897 |
| 13 | 50185580 | 50191003 | | 13 | 103417778 | 103421054 |
| 13 | 50231674 | 50236175 | | 13 | 103457081 | 103457571 |
| 13 | 50317704 | 50319204 | | 13 | 103461687 | 103462357 |
| 13 | 50363683 | 50365256 | | 13 | 103551218 | 103553507 |
| 13 | 50461744 | 50464995 | | 13 | 103584149 | 103588678 |
| 13 | 50507938 | 50509421 | | 13 | 103597040 | 103599616 |
| 13 | 50596187 | 50598242 | | 13 | 103637695 | 103638839 |
| 13 | 50670922 | 50676212 | | 13 | 103686282 | 103690418 |
| 13 | 50681829 | 50687510 | | 13 | 103693410 | 103695021 |
| 13 | 50693252 | 50697576 | | 13 | 103710289 | 103712520 |
| 13 | 50715295 | 50720315 | | 13 | 103732145 | 103733824 |
| 13 | 50758664 | 50759699 | | 13 | 103742448 | 103744708 |
| 13 | 50829359 | 50835371 | | 13 | 103773868 | 103775960 |
| 13 | 50892970 | 50894377 | | 13 | 103786022 | 103790311 |
| 13 | 50958719 | 50959849 | | 13 | 103805764 | 103809587 |
| 13 | 51028722 | 51029167 | | 13 | 103816541 | 103820278 |
| 13 | 51065666 | 51076608 | | 13 | 103831273 | 103833099 |
| 13 | 51141923 | 51142798 | | 13 | 103864736 | 103866083 |
| 13 | 51154562 | 51156112 | | 13 | 103896821 | 103897766 |
| 13 | 51189472 | 51191862 | | 13 | 103908899 | 103914099 |
| 13 | 51236300 | 51237725 | | 13 | 103996919 | 103998774 |
| 13 | 51259064 | 51267614 | | 13 | 104014569 | 104021134 |
| 13 | 51274188 | 51277493 | | 13 | 104036384 | 104037174 |
| 13 | 51282353 | 51283892 | | 13 | 104100314 | 104102919 |
| 13 | 51290647 | 51297129 | | 13 | 104120745 | 104121800 |
| 13 | 51306375 | 51310631 | | 13 | 104187735 | 104191679 |
| 13 | 51351229 | 51358498 | | 13 | 104218860 | 104222193 |
| 13 | 51363520 | 51368557 | | 13 | 104230357 | 104234807 |
| 13 | 51389432 | 51393980 | | 13 | 104328943 | 104329573 |
| 13 | 51403221 | 51405676 | | 13 | 104399381 | 104403390 |
| 13 | 51441904 | 51443134 | | 13 | 104432523 | 104435118 |

The chromosomal positon was obtained from UCSC genome browser (http://genome.ucsc.edu/) build 36.

APPENDIX B: Chromosome 13
Page 40 of 49

| Chr | Start | End | | | Chr | Start | End |
|---|---|---|---|---|---|---|---|
| 13 | 51446684 | 51448182 | | | 13 | 104486278 | 104490282 |
| 13 | 51451479 | 51452378 | | | 13 | 104509504 | 104514199 |
| 13 | 51452978 | 51453655 | | | 13 | 104813551 | 104816420 |
| 13 | 51462059 | 51463692 | | | 13 | 104860481 | 104862276 |
| 13 | 51469887 | 51472142 | | | 13 | 104941429 | 104941579 |
| 13 | 51501906 | 51507139 | | | 13 | 104956521 | 104961573 |
| 13 | 51589417 | 51592352 | | | 13 | 105018144 | 105018684 |
| 13 | 51660867 | 51662203 | | | 13 | 105266095 | 105267092 |
| 13 | 52071704 | 52072103 | | | 13 | 105267622 | 105268492 |
| 13 | 52212195 | 52225839 | | | 13 | 105311006 | 105312176 |
| 13 | 52234353 | 52236124 | | | 13 | 105325781 | 105327759 |
| 13 | 52240599 | 52280452 | | | 13 | 105358100 | 105361381 |
| 13 | 52299143 | 52301203 | | | 13 | 105369577 | 105370427 |
| 13 | 52304056 | 52312802 | | | 13 | 105420120 | 105423837 |
| 13 | 52319549 | 52323952 | | | 13 | 105424422 | 105428947 |
| 13 | 52376253 | 52376938 | | | 13 | 105454308 | 105457694 |
| 13 | 52396645 | 52398730 | | | 13 | 105540670 | 105542200 |
| 13 | 52446308 | 52448653 | | | 13 | 105581462 | 105582454 |
| 13 | 52477962 | 52479677 | | | 13 | 105583254 | 105586010 |
| 13 | 52500677 | 52506867 | | | 13 | 105608192 | 105610374 |
| 13 | 52529527 | 52533901 | | | 13 | 105708247 | 105713093 |
| 13 | 52540530 | 52550575 | | | 13 | 105763942 | 105765377 |
| 13 | 52610369 | 52618758 | | | 13 | 105778947 | 105782877 |
| 13 | 52709847 | 52716774 | | | 13 | 105793539 | 105794886 |
| 13 | 52750959 | 52751839 | | | 13 | 105818995 | 105819940 |
| 13 | 52755336 | 52756941 | | | 13 | 105825871 | 105830228 |
| 13 | 52764354 | 52767886 | | | 13 | 105860079 | 105865120 |
| 13 | 52935125 | 52937645 | | | 13 | 105872799 | 105874179 |
| 13 | 53019570 | 53022960 | | | 13 | 105922258 | 105923194 |
| 13 | 53072737 | 53076634 | | | 13 | 105940677 | 105947115 |
| 13 | 53122775 | 53123548 | | | 13 | 105980356 | 105981819 |
| 13 | 53137066 | 53138266 | | | 13 | 105982465 | 105984464 |
| 13 | 53146807 | 53147482 | | | 13 | 106151931 | 106155259 |
| 13 | 53199588 | 53205997 | | | 13 | 106187299 | 106188348 |
| 13 | 53230778 | 53231518 | | | 13 | 106203002 | 106204615 |
| 13 | 53247048 | 53248112 | | | 13 | 106210598 | 106211123 |
| 13 | 53267696 | 53268546 | | | 13 | 106239279 | 106243641 |
| 13 | 53282255 | 53284910 | | | 13 | 106278498 | 106283737 |
| 13 | 53312671 | 53314116 | | | 13 | 106309328 | 106310605 |
| 13 | 53327127 | 53327832 | | | 13 | 106337903 | 106339945 |
| 13 | 53334472 | 53339729 | | | 13 | 106352589 | 106353144 |
| 13 | 53349239 | 53357717 | | | 13 | 106369560 | 106370665 |
| 13 | 53384224 | 53384874 | | | 13 | 106436401 | 106438503 |
| 13 | 53440799 | 53441934 | | | 13 | 106449177 | 106452795 |
| 13 | 53493668 | 53496102 | | | 13 | 106468664 | 106469604 |
| 13 | 53543735 | 53545510 | | | 13 | 106482993 | 106485483 |
| 13 | 53671265 | 53671280 | | | 13 | 106585443 | 106588421 |
| 13 | 53671590 | 53678544 | | | 13 | 106618649 | 106631302 |
| 13 | 53711517 | 53715706 | | | 13 | 106648350 | 106671036 |
| 13 | 53724350 | 53727422 | | | 13 | 106707044 | 106709754 |
| 13 | 53733775 | 53735936 | | | 13 | 106718188 | 106720048 |
| 13 | 53799959 | 53801799 | | | 13 | 106729079 | 106730912 |
| 13 | 53853147 | 53863961 | | | 13 | 106732627 | 106735549 |
| 13 | 54100241 | 54103571 | | | 13 | 106797764 | 106802588 |
| 13 | 54108477 | 54109289 | | | 13 | 106816822 | 106819507 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 54268276 | 54270386 | 13 | 106826758 | 106827738 |
| 13 | 54346306 | 54347341 | 13 | 106830278 | 106832128 |
| 13 | 54409772 | 54414319 | 13 | 106841816 | 106842946 |
| 13 | 54439446 | 54440911 | 13 | 106861345 | 106862498 |
| 13 | 54635743 | 54636803 | 13 | 106896814 | 106902485 |
| 13 | 54643418 | 54644378 | 13 | 106904501 | 106906989 |
| 13 | 54679478 | 54680470 | 13 | 106914391 | 106917220 |
| 13 | 54691310 | 54694045 | 13 | 107003702 | 107010234 |
| 13 | 54701002 | 54701597 | 13 | 107060937 | 107063032 |
| 13 | 54733410 | 54738575 | 13 | 107113175 | 107115437 |
| 13 | 54917189 | 54917681 | 13 | 107128841 | 107134705 |
| 13 | 54943697 | 54950197 | 13 | 107156954 | 107167907 |
| 13 | 55020463 | 55027031 | 13 | 107169910 | 107173520 |
| 13 | 55082937 | 55086771 | 13 | 107181606 | 107183820 |
| 13 | 55210338 | 55212597 | 13 | 107229989 | 107237757 |
| 13 | 55308446 | 55310503 | 13 | 107249389 | 107249994 |
| 13 | 55396264 | 55398159 | 13 | 107268408 | 107270676 |
| 13 | 55569718 | 55572233 | 13 | 107276001 | 107278631 |
| 13 | 55669374 | 55670789 | 13 | 107293698 | 107295984 |
| 13 | 55674022 | 55680097 | 13 | 107303865 | 107306091 |
| 13 | 55703684 | 55705524 | 13 | 107314715 | 107317186 |
| 13 | 55727399 | 55730269 | 13 | 107356993 | 107359802 |
| 13 | 55754377 | 55755752 | 13 | 107418553 | 107421055 |
| 13 | 55828518 | 55830353 | 13 | 107538185 | 107540287 |
| 13 | 55969163 | 55970663 | 13 | 107591186 | 107591421 |
| 13 | 55973409 | 55975503 | 13 | 107605835 | 107612091 |
| 13 | 56018654 | 56019209 | 13 | 107626301 | 107632960 |
| 13 | 56244376 | 56247841 | 13 | 107674798 | 107680676 |
| 13 | 56263146 | 56264891 | 13 | 107760477 | 107766966 |
| 13 | 56336121 | 56336756 | 13 | 107778074 | 107787056 |
| 13 | 56426915 | 56432436 | 13 | 107794083 | 107802420 |
| 13 | 56670741 | 56672331 | 13 | 107852698 | 107853820 |
| 13 | 56712885 | 56714700 | 13 | 107869739 | 107880477 |
| 13 | 56729726 | 56734971 | 13 | 107932173 | 107933518 |
| 13 | 56768252 | 56770733 | 13 | 107946559 | 107947854 |
| 13 | 56971865 | 56972860 | 13 | 107949802 | 107952784 |
| 13 | 56976700 | 56981262 | 13 | 107997000 | 108005579 |
| 13 | 57010096 | 57013600 | 13 | 108032550 | 108034170 |
| 13 | 57035593 | 57036758 | 13 | 108042273 | 108044946 |
| 13 | 57051984 | 57054309 | 13 | 108066987 | 108073122 |
| 13 | 57102743 | 57108261 | 13 | 108123969 | 108129790 |
| 13 | 57215615 | 57223947 | 13 | 108131903 | 108137362 |
| 13 | 57225558 | 57227426 | 13 | 108216245 | 108218316 |
| 13 | 57230011 | 57233421 | 13 | 108227051 | 108240907 |
| 13 | 57271306 | 57278135 | 13 | 108312324 | 108312474 |
| 13 | 57299418 | 57300910 | 13 | 108408360 | 108412793 |
| 13 | 57309838 | 57310443 | 13 | 108413502 | 108415257 |
| 13 | 57327616 | 57333198 | 13 | 108430764 | 108431587 |
| 13 | 57371622 | 57378174 | 13 | 108557718 | 108558118 |
| 13 | 57410501 | 57413505 | 13 | 108569558 | 108570940 |
| 13 | 57449941 | 57452896 | 13 | 108580666 | 108582954 |
| 13 | 57554921 | 57560871 | 13 | 108595397 | 108596123 |
| 13 | 57586643 | 57588249 | 13 | 108605416 | 108608898 |
| 13 | 57660193 | 57665115 | 13 | 108612571 | 108613281 |
| 13 | 57879130 | 57880700 | 13 | 108659869 | 108663681 |

The chromosomal positon was obtained from UCSC genome browser (http://genome.ucsc.edu/) build 36.

APPENDIX B: Chromosome 13

| Chr | Start | End | | | Chr | Start | End |
|---|---|---|---|---|---|---|---|
| 13 | 57889036 | 57891206 | | | 13 | 108684997 | 108687375 |
| 13 | 57907386 | 57909076 | | | 13 | 108722972 | 108728046 |
| 13 | 58181754 | 58184880 | | | 13 | 108747567 | 108749803 |
| 13 | 58209384 | 58216662 | | | 13 | 108777949 | 108780336 |
| 13 | 58266874 | 58268841 | | | 13 | 108902027 | 108904943 |
| 13 | 58281616 | 58283651 | | | 13 | 109035562 | 109037484 |
| 13 | 58534203 | 58536647 | | | 13 | 109134820 | 109136570 |
| 13 | 58550408 | 58554628 | | | 13 | 109154764 | 109156929 |
| 13 | 58559304 | 58562029 | | | 13 | 109173928 | 109176020 |
| 13 | 58563694 | 58567709 | | | 13 | 109177962 | 109180252 |
| 13 | 58622848 | 58625200 | | | 13 | 109187962 | 109189152 |
| 13 | 58691322 | 58693423 | | | 13 | 109193642 | 109195577 |
| 13 | 58702162 | 58707022 | | | 13 | 109230555 | 109232200 |
| 13 | 58716622 | 58721059 | | | 13 | 109252065 | 109255413 |
| 13 | 58724248 | 58732293 | | | 13 | 109265649 | 109268059 |
| 13 | 58815531 | 58819312 | | | 13 | 109284513 | 109285893 |
| 13 | 58828903 | 58830583 | | | 13 | 109290100 | 109291265 |
| 13 | 58833647 | 58836482 | | | 13 | 109319589 | 109334709 |
| 13 | 58881452 | 58883404 | | | 13 | 109395361 | 109397201 |
| 13 | 58916823 | 58917388 | | | 13 | 109412053 | 109422284 |
| 13 | 58918108 | 58921378 | | | 13 | 109425737 | 109428207 |
| 13 | 58933144 | 58934992 | | | 13 | 109450209 | 109451199 |
| 13 | 58967485 | 58968600 | | | 13 | 109467940 | 109469475 |
| 13 | 59036219 | 59038293 | | | 13 | 109492583 | 109495814 |
| 13 | 59091899 | 59094160 | | | 13 | 109544962 | 109545507 |
| 13 | 59108636 | 59109951 | | | 13 | 109572781 | 109574636 |
| 13 | 59124848 | 59126193 | | | 13 | 109579031 | 109580496 |
| 13 | 59158589 | 59160109 | | | 13 | 109583725 | 109586373 |
| 13 | 59170002 | 59171847 | | | 13 | 109672291 | 109672823 |
| 13 | 59289869 | 59292395 | | | 13 | 109687635 | 109689295 |
| 13 | 59296518 | 59308303 | | | 13 | 109716054 | 109717214 |
| 13 | 59556832 | 59558382 | | | 13 | 109735318 | 109738098 |
| 13 | 59738385 | 59741821 | | | 13 | 109748731 | 109750870 |
| 13 | 60062498 | 60066456 | | | 13 | 109751730 | 109752500 |
| 13 | 60095809 | 60099957 | | | 13 | 109754675 | 109756522 |
| 13 | 60126866 | 60138311 | | | 13 | 109757307 | 109759592 |
| 13 | 60154576 | 60157116 | | | 13 | 109763144 | 109766372 |
| 13 | 60221452 | 60223926 | | | 13 | 109769412 | 109770737 |
| 13 | 60263919 | 60265469 | | | 13 | 109784190 | 109785505 |
| 13 | 60292892 | 60293652 | | | 13 | 109791027 | 109792447 |
| 13 | 60332538 | 60335895 | | | 13 | 109797147 | 109798747 |
| 13 | 60361855 | 60363073 | | | 13 | 109812394 | 109813029 |
| 13 | 60613370 | 60616410 | | | 13 | 109822685 | 109827446 |
| 13 | 60662710 | 60664540 | | | 13 | 109837633 | 109839138 |
| 13 | 60770922 | 60771772 | | | 13 | 109842078 | 109843652 |
| 13 | 60802483 | 60804232 | | | 13 | 109865736 | 109870372 |
| 13 | 60853274 | 60855247 | | | 13 | 109871017 | 109877258 |
| 13 | 60878689 | 60880692 | | | 13 | 109896871 | 109899451 |
| 13 | 60886442 | 60887824 | | | 13 | 109934510 | 109941964 |
| 13 | 60889835 | 60890951 | | | 13 | 109946860 | 109947700 |
| 13 | 60945935 | 60947735 | | | 13 | 109977439 | 109979024 |
| 13 | 60995514 | 60999509 | | | 13 | 109996163 | 109996813 |
| 13 | 61029392 | 61032741 | | | 13 | 110025703 | 110026668 |
| 13 | 61080930 | 61081950 | | | 13 | 110040342 | 110051813 |
| 13 | 61136438 | 61138108 | | | 13 | 110060225 | 110061750 |

The chromosomal positon was obtained from UCSC genome browser (http://genome.ucsc.edu/) build 36.

APPENDIX B: Chromosome 13
Page 43 of 49

| Chr | Start | End | Chr | Start | End |
|---|---|---|---|---|---|
| 13 | 61142416 | 61147211 | 13 | 110106764 | 110108646 |
| 13 | 61149766 | 61151058 | 13 | 110220934 | 110223227 |
| 13 | 61166771 | 61168321 | 13 | 110225787 | 110228084 |
| 13 | 61323990 | 61324655 | 13 | 110244570 | 110252125 |
| 13 | 61377596 | 61385015 | 13 | 110274666 | 110276256 |
| 13 | 61413565 | 61418140 | 13 | 110279772 | 110285452 |
| 13 | 61441437 | 61443568 | 13 | 110320306 | 110321311 |
| 13 | 61532276 | 61532876 | 13 | 110389572 | 110389852 |
| 13 | 61620612 | 61629528 | 13 | 110414563 | 110415904 |
| 13 | 61681734 | 61682479 | 13 | 110484451 | 110487358 |
| 13 | 61932744 | 61935442 | 13 | 110500197 | 110503422 |
| 13 | 61972966 | 61975059 | 13 | 110540065 | 110548659 |
| 13 | 62095987 | 62101978 | 13 | 110561684 | 110564494 |
| 13 | 62117032 | 62120117 | 13 | 110587853 | 110596292 |
| 13 | 62177785 | 62179195 | 13 | 110600705 | 110601590 |
| 13 | 62193479 | 62195154 | 13 | 110611304 | 110613406 |
| 13 | 62450546 | 62453042 | 13 | 110617190 | 110618020 |
| 13 | 62457560 | 62460532 | 13 | 110633856 | 110635732 |
| 13 | 62500500 | 62502220 | 13 | 110660440 | 110663185 |
| 13 | 62507454 | 62510890 | 13 | 110773125 | 110796688 |
| 13 | 62542588 | 62549094 | 13 | 110804393 | 110824844 |
| 13 | 62795796 | 62798009 | 13 | 110832291 | 110834836 |
| 13 | 62814477 | 62815687 | 13 | 110838101 | 110895690 |
|  |  |  | 13 | 110898473 | 110902478 |
|  |  |  | 13 | 110904731 | 111097980 |
|  |  |  | 13 | 111102289 | 111127718 |
|  |  |  | 13 | 111128083 | 111129280 |
|  |  |  | 13 | 111129786 | 111151970 |
| 13 | 111552786 | 111552861 | 13 | 112761742 | 112762282 |
| 13 | 111555785 | 111566438 | 13 | 112763940 | 112773412 |
| 13 | 111568936 | 111569842 | 13 | 112774053 | 112774358 |
| 13 | 111573149 | 111575491 | 13 | 112777986 | 112778441 |
| 13 | 111575976 | 111576171 | 13 | 112781536 | 112782056 |
| 13 | 111576981 | 111576996 | 13 | 112785286 | 112785306 |
| 13 | 111578281 | 111579701 | 13 | 112786271 | 112804646 |
| 13 | 111580838 | 111580948 | 13 | 112802337 | 112802757 |
| 13 | 111583151 | 111583611 | 13 | 112807122 | 112808092 |
| 13 | 111584121 | 111584843 | 13 | 112811843 | 112811858 |
| 13 | 111586318 | 111586588 | 13 | 112812610 | 112813415 |
| 13 | 111588237 | 111588487 | 13 | 112814323 | 112814668 |
| 13 | 111589142 | 111589372 | 13 | 112816752 | 112819232 |
| 13 | 111589812 | 111591019 | 13 | 112822597 | 112822767 |
| 13 | 111591269 | 111591670 | 13 | 112833706 | 112836752 |
| 13 | 111591685 | 111592356 | 13 | 112838148 | 112838401 |
| 13 | 111594282 | 111596609 | 13 | 112846699 | 112846899 |
| 13 | 111597400 | 111597934 | 13 | 112848586 | 112850256 |
| 13 | 111599954 | 111600519 | 13 | 112854107 | 112854387 |
| 13 | 111604585 | 111605900 | 13 | 112857208 | 112857218 |
| 13 | 111609373 | 111609393 | 13 | 112860811 | 112861106 |
| 13 | 111611373 | 111612053 | 13 | 112865842 | 112865867 |
| 13 | 111613773 | 111613958 | 13 | 112866725 | 112868195 |
| 13 | 111615163 | 111623072 | 13 | 112869525 | 112869775 |
| 13 | 111623527 | 111623742 | 13 | 112872557 | 112872776 |
| 13 | 111624472 | 111625892 | 13 | 112873721 | 112874251 |
| 13 | 111628087 | 111628827 | 13 | 112874946 | 112876241 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 111630176 | 111630716 | 13 | 112878101 | 112879417 |
| 13 | 111631176 | 111631251 | 13 | 112880344 | 112880864 |
| 13 | 111631666 | 111632221 | 13 | 112881309 | 112888131 |
| 13 | 111632516 | 111633453 | 13 | 112889523 | 112889893 |
| 13 | 111639221 | 111639981 | 13 | 112891990 | 112892000 |
| 13 | 111641324 | 111641465 | 13 | 112895090 | 112899901 |
| 13 | 111642005 | 111644176 | 13 | 112901631 | 112901851 |
| 13 | 111645356 | 111652386 | 13 | 112903499 | 112903674 |
| 13 | 111654601 | 111655026 | 13 | 112905045 | 112906045 |
| 13 | 111656818 | 111657598 | 13 | 112907100 | 112907420 |
| 13 | 111663956 | 111665941 | 13 | 112908060 | 112908625 |
| 13 | 111668909 | 111669071 | 13 | 112909400 | 112910351 |
| 13 | 111669564 | 111669719 | 13 | 112910671 | 112910946 |
| 13 | 111670694 | 111675024 | 13 | 112912677 | 112913052 |
| 13 | 111679207 | 111679877 | 13 | 112915402 | 112916625 |
| 13 | 111683239 | 111684184 | 13 | 112918306 | 112918541 |
| 13 | 111684459 | 111687110 | 13 | 112920690 | 112921565 |
| 13 | 111687690 | 111687805 | 13 | 112927669 | 112928650 |
| 13 | 111688615 | 111688777 | 13 | 112930447 | 112933979 |
| 13 | 111695753 | 111696278 | 13 | 112936804 | 112937174 |
| 13 | 111696928 | 111697283 | 13 | 112939400 | 112941678 |
| 13 | 111697518 | 111697733 | 13 | 112948642 | 112949032 |
| 13 | 111700054 | 111700209 | 13 | 112950907 | 112951722 |
| 13 | 111701544 | 111701929 | 13 | 112953492 | 112954187 |
| 13 | 111702644 | 111702789 | 13 | 112954797 | 112954897 |
| 13 | 111707880 | 111708010 | 13 | 112956980 | 112962210 |
| 13 | 111708665 | 111708890 | 13 | 112963955 | 112964590 |
| 13 | 111711455 | 111715800 | 13 | 112965090 | 112965887 |
| 13 | 111719062 | 111720132 | 13 | 112969030 | 112969110 |
| 13 | 111722315 | 111722355 | 13 | 112970735 | 112970935 |
| 13 | 111723040 | 111724585 | 13 | 112974503 | 112975422 |
| 13 | 111726400 | 111726720 | 13 | 112977192 | 112977407 |
| 13 | 111731319 | 111731474 | 13 | 112978821 | 112979086 |
| 13 | 111732239 | 111735494 | 13 | 112981236 | 112981466 |
| 13 | 111737580 | 111738115 | 13 | 112982519 | 112982854 |
| 13 | 111740339 | 111740699 | 13 | 112984018 | 112986257 |
| 13 | 111744592 | 111745428 | 13 | 112988462 | 112989871 |
| 13 | 111748227 | 111748590 | 13 | 112991146 | 112991866 |
| 13 | 111748735 | 111749036 | 13 | 112992746 | 112993602 |
| 13 | 111749526 | 111750936 | 13 | 112994327 | 112994447 |
| 13 | 111751371 | 111752847 | 13 | 112994767 | 112995082 |
| 13 | 111755369 | 111779552 | 13 | 112997738 | 112998113 |
| 13 | 111780435 | 111780640 | 13 | 113000128 | 113002401 |
| 13 | 111781520 | 111782045 | 13 | 113003486 | 113004101 |
| 13 | 111782265 | 111782605 | 13 | 113007697 | 113007782 |
| 13 | 111784361 | 111784977 | 13 | 113009788 | 113009978 |
| 13 | 111786160 | 111787360 | 13 | 113015768 | 113017673 |
| 13 | 111788156 | 111788416 | 13 | 113021312 | 113021412 |
| 13 | 111789923 | 111791323 | 13 | 113021897 | 113022518 |
| 13 | 111794495 | 111794975 | 13 | 113023963 | 113024303 |
| 13 | 111804718 | 111809931 | 13 | 113033910 | 113035492 |
| 13 | 111811132 | 111811847 | 13 | 113037775 | 113037875 |
| 13 | 111812232 | 111812517 | 13 | 113040365 | 113040555 |
| 13 | 111813661 | 111813861 | 13 | 113046023 | 113046537 |
| 13 | 111814142 | 111814157 | 13 | 113053208 | 113055164 |

The chromosomal positon was obtained from UCSC genome browser (http://genome.ucsc.edu/) build 36.

APPENDIX B: Chromosome 13
Page 45 of 49

| Chr | Start | End | Chr | Start | End |
|---|---|---|---|---|---|
| 13 | 111814807 | 111815562 | 13 | 113056532 | 113056793 |
| 13 | 111817172 | 111817982 | 13 | 113057437 | 113058057 |
| 13 | 111821512 | 111822032 | 13 | 113058462 | 113064062 |
| 13 | 111822865 | 111823140 | 13 | 113069601 | 113069961 |
| 13 | 111825601 | 111827124 | 13 | 113070951 | 113071341 |
| 13 | 111827759 | 111828194 | 13 | 113072977 | 113073397 |
| 13 | 111830243 | 111830513 | 13 | 113076724 | 113077334 |
| 13 | 111834556 | 111836131 | 13 | 113080812 | 113081713 |
| 13 | 111838345 | 111838365 | 13 | 113089288 | 113089868 |
| 13 | 111839380 | 111840370 | 13 | 113092903 | 113093163 |
| 13 | 111841790 | 111842090 | 13 | 113104075 | 113104270 |
| 13 | 111842591 | 111843236 | 13 | 113105220 | 113107650 |
| 13 | 111843651 | 111854620 | 13 | 113109665 | 113110080 |
| 13 | 111855005 | 111855660 | 13 | 113111650 | 113111735 |
| 13 | 111857940 | 111858275 | 13 | 113113573 | 113114158 |
| 13 | 111860166 | 111861026 | 13 | 113116643 | 113117369 |
| 13 | 111864069 | 111864519 | 13 | 113120059 | 113120109 |
| 13 | 111865773 | 111866208 | 13 | 113122430 | 113122830 |
| 13 | 111869789 | 111870244 | 13 | 113124928 | 113125895 |
| 13 | 111875274 | 111884175 | 13 | 113126585 | 113128404 |
| 13 | 111885225 | 111885802 | 13 | 113130667 | 113130892 |
| 13 | 111889338 | 111889668 | 13 | 113133352 | 113133892 |
| 13 | 111890648 | 111892078 | 13 | 113137667 | 113139347 |
| 13 | 111892817 | 111893207 | 13 | 113140507 | 113141208 |
| 13 | 111894088 | 111894303 | 13 | 113146513 | 113149130 |
| 13 | 111895239 | 111895404 | 13 | 113149910 | 113150215 |
| 13 | 111900278 | 111900473 | 13 | 113150405 | 113152044 |
| 13 | 111900783 | 111903623 | 13 | 113154724 | 113155004 |
| 13 | 111905553 | 111906163 | 13 | 113156800 | 113158676 |
| 13 | 111907023 | 111907943 | 13 | 113161636 | 113162466 |
| 13 | 111908517 | 111908756 | 13 | 113164841 | 113165056 |
| 13 | 111909600 | 111913325 | 13 | 113165895 | 113166255 |
| 13 | 111915466 | 111915946 | 13 | 113166640 | 113166855 |
| 13 | 111918756 | 111963438 | 13 | 113167705 | 113167949 |
| 13 | 111921288 | 111921418 | 13 | 113175586 | 113175811 |
| 13 | 111959549 | 111959854 | 13 | 113176392 | 113176792 |
| 13 | 111966599 | 111970003 | 13 | 113177132 | 113177622 |
| 13 | 111971498 | 111972428 | 13 | 113178352 | 113178657 |
| 13 | 111974810 | 111975810 | 13 | 113180475 | 113181035 |
| 13 | 111976317 | 111976447 | 13 | 113181704 | 113182164 |
| 13 | 111978514 | 112024784 | 13 | 113183704 | 113183895 |
| 13 | 112031559 | 112031759 | 13 | 113184274 | 113184629 |
| 13 | 112032839 | 112034902 | 13 | 113184902 | 113185524 |
| 13 | 112035708 | 112036698 | 13 | 113187019 | 113189924 |
| 13 | 112037221 | 112038246 | 13 | 113192339 | 113192559 |
| 13 | 112039221 | 112039261 | 13 | 113195456 | 113195526 |
| 13 | 112040090 | 112040638 | 13 | 113198926 | 113199196 |
| 13 | 112040974 | 112041304 | 13 | 113201481 | 113211068 |
| 13 | 112044050 | 112044285 | 13 | 113213163 | 113214213 |
| 13 | 112044450 | 112044770 | 13 | 113217848 | 113218358 |
| 13 | 112046890 | 112047662 | 13 | 113219847 | 113220812 |
| 13 | 112048497 | 112050300 | 13 | 113227395 | 113231135 |
| 13 | 112051526 | 112051761 | 13 | 113233794 | 113236754 |
| 13 | 112052996 | 112053251 | 13 | 113237544 | 113239116 |
| 13 | 112054796 | 112055276 | 13 | 113241492 | 113242302 |

The chromosomal positon was obtained from UCSC genome browser (http://genome.ucsc.edu/) build 36.

APPENDIX B: Chromosome 13

| Chr | Start | End | | Chr | Start | End |
|---|---|---|---|---|---|---|
| 13 | 112055691 | 112056121 | | 13 | 113246923 | 113247288 |
| 13 | 112058421 | 112060190 | | 13 | 113249543 | 113249898 |
| 13 | 112062157 | 112063432 | | 13 | 113252089 | 113264279 |
| 13 | 112066594 | 112067784 | | 13 | 113267824 | 113267909 |
| 13 | 112068599 | 112070110 | | 13 | 113268254 | 113268904 |
| 13 | 112070330 | 112071930 | | 13 | 113269269 | 113270342 |
| 13 | 112073050 | 112073165 | | 13 | 113270638 | 113271308 |
| 13 | 112077084 | 112077264 | | 13 | 113278333 | 113279407 |
| 13 | 112080439 | 112080519 | | 13 | 113284397 | 113284477 |
| 13 | 112080909 | 112080914 | | 13 | 113287925 | 113289768 |
| 13 | 112081344 | 112081559 | | 13 | 113291856 | 113292521 |
| 13 | 112082803 | 112083200 | | 13 | 113294441 | 113294796 |
| 13 | 112084011 | 112084466 | | 13 | 113298067 | 113298077 |
| 13 | 112085772 | 112086067 | | 13 | 113298972 | 113300090 |
| 13 | 112087860 | 112088837 | | 13 | 113300910 | 113301856 |
| 13 | 112089464 | 112090199 | | 13 | 113303376 | 113304061 |
| 13 | 112091494 | 112091509 | | 13 | 113309016 | 113311083 |
| 13 | 112093361 | 112095351 | | 13 | 113313321 | 113313816 |
| 13 | 112099931 | 112100681 | | 13 | 113317063 | 113319283 |
| 13 | 112103166 | 112105838 | | 13 | 113325185 | 113326165 |
| 13 | 112114194 | 112115437 | | 13 | 113328745 | 113329220 |
| 13 | 112117104 | 112117364 | | 13 | 113330799 | 113331069 |
| 13 | 112120144 | 112120874 | | 13 | 113333479 | 113333674 |
| 13 | 112123200 | 112123365 | | 13 | 113334794 | 113336744 |
| 13 | 112124015 | 112125003 | | 13 | 113340824 | 113341394 |
| 13 | 112126328 | 112127683 | | 13 | 113343866 | 113346266 |
| 13 | 112130198 | 112130492 | | 13 | 113346828 | 113346943 |
| 13 | 112131395 | 112131817 | | 13 | 113349259 | 113349854 |
| 13 | 112132208 | 112132443 | | 13 | 113350954 | 113351114 |
| 13 | 112134013 | 112135003 | | 13 | 113351929 | 113352139 |
| 13 | 112136988 | 112138574 | | 13 | 113354668 | 113355683 |
| 13 | 112142681 | 112143121 | | 13 | 113356501 | 113358126 |
| 13 | 112144529 | 112144961 | | 13 | 113359342 | 113359452 |
| 13 | 112145106 | 112145336 | | 13 | 113360212 | 113360562 |
| 13 | 112146086 | 112146501 | | 13 | 113361667 | 113362576 |
| 13 | 112147096 | 112147451 | | 13 | 113362856 | 113363301 |
| 13 | 112150006 | 112150536 | | 13 | 113363946 | 113365429 |
| 13 | 112151671 | 112153596 | | 13 | 113365862 | 113366917 |
| 13 | 112158398 | 112159293 | | 13 | 113367882 | 113368412 |
| 13 | 112160520 | 112160675 | | 13 | 113371143 | 113371878 |
| 13 | 112162054 | 112162484 | | 13 | 113372493 | 113372758 |
| 13 | 112167059 | 112168649 | | 13 | 113372878 | 113373444 |
| 13 | 112170022 | 112172545 | | 13 | 113474920 | 113475260 |
| 13 | 112173691 | 112174046 | | 13 | 113475890 | 113476360 |
| 13 | 112177290 | 112177490 | | 13 | 113476610 | 113476845 |
| 13 | 112179075 | 112179260 | | 13 | 113477470 | 113477620 |
| 13 | 112185206 | 112187621 | | 13 | 113479322 | 113480077 |
| 13 | 112190673 | 112191708 | | 13 | 113481592 | 113481942 |
| 13 | 112192323 | 112192883 | | 13 | 113482512 | 113483272 |
| 13 | 112194313 | 112197427 | | 13 | 113483732 | 113484262 |
| 13 | 112198402 | 112198422 | | 13 | 113490283 | 113490353 |
| 13 | 112199451 | 112202106 | | 13 | 113491325 | 113491605 |
| 13 | 112204681 | 112208107 | | 13 | 113493605 | 113493880 |
| 13 | 112209536 | 112209797 | | 13 | 113495025 | 113496285 |
| 13 | 112212532 | 112213122 | | 13 | 113498223 | 113498653 |

The chromosomal positon was obtained from UCSC genome browser (http://genome.ucsc.edu/) build 36.

APPENDIX B: Chromosome 13

| Chr | Start | End | | | Chr | Start | End |
|---|---|---|---|---|---|---|---|
| 13 | 112213492 | 112213797 | | | 13 | 113500200 | 113500398 |
| 13 | 112215652 | 112215857 | | | 13 | 113502186 | 113502750 |
| 13 | 112217332 | 112218042 | | | 13 | 113506270 | 113506300 |
| 13 | 112221718 | 112226090 | | | 13 | 113507512 | 113507927 |
| 13 | 112227400 | 112227820 | | | 13 | 113514282 | 113515321 |
| 13 | 112229710 | 112229745 | | | 13 | 113515950 | 113516020 |
| 13 | 112230755 | 112244179 | | | 13 | 113517471 | 113517961 |
| 13 | 112246335 | 112246415 | | | 13 | 113519469 | 113521452 |
| 13 | 112248526 | 112249721 | | | 13 | 113524388 | 113524473 |
| 13 | 112254323 | 112254598 | | | 13 | 113525709 | 113525859 |
| 13 | 112255658 | 112255933 | | | 13 | 113527739 | 113528710 |
| 13 | 112256233 | 112289188 | | | 13 | 113529781 | 113530086 |
| 13 | 112290258 | 112291557 | | | 13 | 113531656 | 113531926 |
| 13 | 112293312 | 112293697 | | | 13 | 113536752 | 113537167 |
| 13 | 112295242 | 112296097 | | | 13 | 113541086 | 113541311 |
| 13 | 112299171 | 112299781 | | | 13 | 113542186 | 113542616 |
| 13 | 112301446 | 112301466 | | | 13 | 113545057 | 113546688 |
| 13 | 112302279 | 112302359 | | | 13 | 113548162 | 113548627 |
| 13 | 112303563 | 112304556 | | | 13 | 113549499 | 113549824 |
| 13 | 112307727 | 112309012 | | | 13 | 113552834 | 113553079 |
| 13 | 112310067 | 112312440 | | | 13 | 113555540 | 113556695 |
| 13 | 112313450 | 112314475 | | | 13 | 113562441 | 113564913 |
| 13 | 112315127 | 112315522 | | | 13 | 113565861 | 113566091 |
| 13 | 112317082 | 112317707 | | | 13 | 113567959 | 113568199 |
| 13 | 112320817 | 112320897 | | | 13 | 113568724 | 113569569 |
| 13 | 112322358 | 112323649 | | | 13 | 113570879 | 113571674 |
| 13 | 112324484 | 112327159 | | | 13 | 113573579 | 113573904 |
| 13 | 112327879 | 112328129 | | | 13 | 113577296 | 113577656 |
| 13 | 112333132 | 112334042 | | | 13 | 113580769 | 113580894 |
| 13 | 112334287 | 112334819 | | | 13 | 113583517 | 113583627 |
| 13 | 112336869 | 112336969 | | | 13 | 113584702 | 113584717 |
| 13 | 112338331 | 112342861 | | | 13 | 113585267 | 113585497 |
| 13 | 112344734 | 112345010 | | | 13 | 113587395 | 113587575 |
| 13 | 112349194 | 112349679 | | | 13 | 113589687 | 113589978 |
| 13 | 112350564 | 112350809 | | | 13 | 113590228 | 113590333 |
| 13 | 112351216 | 112351461 | | | 13 | 113594656 | 113595091 |
| 13 | 112355901 | 112356268 | | | 13 | 113596565 | 113597170 |
| 13 | 112360350 | 112361030 | | | 13 | 113598778 | 113599306 |
| 13 | 112363198 | 112363358 | | | 13 | 113601110 | 113601241 |
| 13 | 112365053 | 112367130 | | | 13 | 113606150 | 113606480 |
| 13 | 112369850 | 112370230 | | | 13 | 113606744 | 113607223 |
| 13 | 112372260 | 112374672 | | | 13 | 113608958 | 113609275 |
| 13 | 112376629 | 112376917 | | | 13 | 113611025 | 113612040 |
| 13 | 112377405 | 112377510 | | | 13 | 113615730 | 113618280 |
| 13 | 112378550 | 112379829 | | | 13 | 113619920 | 113621555 |
| 13 | 112383528 | 112383633 | | | 13 | 113624608 | 113624863 |
| 13 | 112385586 | 112385941 | | | 13 | 113626528 | 113626683 |
| 13 | 112387196 | 112387872 | | | 13 | 113628086 | 113628156 |
| 13 | 112390147 | 112391477 | | | 13 | 113630525 | 113631130 |
| 13 | 112396827 | 112399149 | | | 13 | 113631777 | 113632637 |
| 13 | 112399759 | 112400972 | | | 13 | 113634037 | 113634662 |
| 13 | 112404182 | 112404347 | | | 13 | 113636517 | 113637680 |
| 13 | 112405669 | 112405794 | | | 13 | 113637990 | 113639228 |
| 13 | 112406586 | 112406671 | | | 13 | 113641033 | 113650582 |
| 13 | 112412816 | 112413116 | | | 13 | 113651167 | 113651982 |

The chromosomal positon was obtained from UCSC genome browser (http://genome.ucsc.edu/) build 36.

APPENDIX B: Chromosome 13
Page 48 of 49

| Chr | Start | End | | | Chr | Start | End |
|---|---|---|---|---|---|---|---|
| 13 | 112413616 | 112414511 | | | 13 | 113652313 | 113652338 |
| 13 | 112419722 | 112419967 | | | 13 | 113657759 | 113758471 |
| 13 | 112420904 | 112421763 | | | 13 | 113763581 | 113764206 |
| 13 | 112423750 | 112424555 | | | 13 | 113765496 | 113765551 |
| 13 | 112425169 | 112425219 | | | 13 | 113769217 | 113769512 |
| 13 | 112426298 | 112426693 | | | 13 | 113770897 | 113771652 |
| 13 | 112427568 | 112428808 | | | 13 | 113774992 | 113775047 |
| 13 | 112431568 | 112431803 | | | 13 | 113777809 | 113777819 |
| 13 | 112434841 | 112435246 | | | 13 | 113778658 | 113778703 |
| 13 | 112438084 | 112438784 | | | 13 | 113781021 | 113788932 |
| 13 | 112440031 | 112440331 | | | 13 | 113792832 | 113793227 |
| 13 | 112442871 | 112443236 | | | 13 | 113800637 | 113800892 |
| 13 | 112445936 | 112448321 | | | 13 | 113802442 | 113803180 |
| 13 | 112451932 | 112453482 | | | 13 | 113805070 | 113805640 |
| 13 | 112455408 | 112456158 | | | 13 | 113806491 | 113821369 |
| 13 | 112457939 | 112458419 | | | 13 | 113825374 | 113830893 |
| 13 | 112463247 | 112464409 | | | 13 | 113833968 | 113834303 |
| 13 | 112464849 | 112465029 | | | 13 | 113835648 | 113836163 |
| 13 | 112465494 | 112465757 | | | 13 | 113837003 | 113837288 |
| 13 | 112467597 | 112467917 | | | 13 | 113839790 | 113841753 |
| 13 | 112469083 | 112470744 | | | 13 | 113845331 | 113845436 |
| 13 | 112475270 | 112475685 | | | 13 | 113846467 | 113846816 |
| 13 | 112480406 | 112480716 | | | 13 | 113848472 | 113848667 |
| 13 | 112482357 | 112483072 | | | 13 | 113849153 | 113851773 |
| 13 | 112486079 | 112486549 | | | 13 | 113853954 | 113854874 |
| 13 | 112487588 | 112488073 | | | 13 | 113856414 | 113856969 |
| 13 | 112491458 | 112492263 | | | 13 | 113857441 | 113857601 |
| 13 | 112493038 | 112493043 | | | 13 | 113860806 | 113860971 |
| 13 | 112493559 | 112493879 | | | 13 | 113862047 | 113862297 |
| 13 | 112494929 | 112495444 | | | 13 | 113863172 | 113863467 |
| 13 | 112496344 | 112496779 | | | 13 | 113865288 | 113865653 |
| 13 | 112503824 | 112504071 | | | 13 | 113872965 | 113874929 |
| 13 | 112507215 | 112507550 | | | 13 | 113875144 | 113875289 |
| 13 | 112511647 | 112511972 | | | 13 | 113876266 | 113877626 |
| 13 | 112512697 | 112513017 | | | 13 | 113881026 | 113885703 |
| 13 | 112513874 | 112514384 | | | 13 | 113889265 | 113889335 |
| 13 | 112518641 | 112519751 | | | 13 | 113890410 | 113890651 |
| 13 | 112521827 | 112522214 | | | 13 | 113893221 | 113893586 |
| 13 | 112524350 | 112525653 | | | 13 | 113893978 | 113895571 |
| 13 | 112537615 | 112537830 | | | 13 | 113895746 | 113896011 |
| 13 | 112543332 | 112543837 | | | 13 | 113898808 | 113905355 |
| 13 | 112546612 | 112548876 | | | 13 | 113907060 | 113908390 |
| 13 | 112549356 | 112549986 | | | 13 | 113910195 | 113911925 |
| 13 | 112553325 | 112553790 | | | 13 | 113912800 | 113912965 |
| 13 | 112556655 | 112557095 | | | 13 | 113913225 | 113913305 |
| 13 | 112557839 | 112558494 | | | 13 | 113914465 | 113916481 |
| 13 | 112561434 | 112561699 | | | 13 | 113923776 | 113924581 |
| 13 | 112562618 | 112564643 | | | 13 | 113926436 | 113926776 |
| 13 | 112569529 | 112569779 | | | 13 | 113927111 | 113927721 |
| 13 | 112571014 | 112571539 | | | 13 | 113928866 | 113930566 |
| 13 | 112573604 | 112573729 | | | 13 | 113932511 | 113942205 |
| 13 | 112576004 | 112577739 | | | 13 | 113945565 | 113945825 |
| 13 | 112579481 | 112579681 | | | 13 | 113946315 | 113949746 |
| 13 | 112581843 | 112582213 | | | 13 | 113951957 | 113952227 |
| 13 | 112588922 | 112589530 | | | 13 | 113952757 | 113953077 |

The chromosomal positon was obtained from UCSC genome browser (http://genome.ucsc.edu/) build 36.

APPENDIX B: Chromosome 13

| Chr | Start | End | Chr | Start | End |
|---|---|---|---|---|---|
| 13 | 112590075 | 112590455 | 13 | 113954393 | 113955244 |
| 13 | 112592025 | 112592255 | 13 | 113957469 | 113965298 |
| 13 | 112592965 | 112595520 | 13 | 113966633 | 113967223 |
| 13 | 112597498 | 112597903 | 13 | 113971425 | 113971977 |
| 13 | 112598363 | 112599231 | 13 | 113976848 | 113978056 |
| 13 | 112601746 | 112602745 | 13 | 113983797 | 113984732 |
| 13 | 112604045 | 112605020 | 13 | 113985700 | 113986695 |
| 13 | 112609422 | 112618989 | 13 | 113988714 | 113989179 |
| 13 | 112621114 | 112621384 | 13 | 113990798 | 113995982 |
| 13 | 112624804 | 112625394 | 13 | 114003536 | 114003848 |
| 13 | 112626366 | 112626936 | 13 | 114004348 | 114004488 |
| 13 | 112627171 | 112627566 | 13 | 114006084 | 114007243 |
| 13 | 112628472 | 112628532 | 13 | 114015993 | 114016378 |
| 13 | 112629642 | 112630947 | 13 | 114018399 | 114019009 |
| 13 | 112631777 | 112632257 | 13 | 114020039 | 114020260 |
| 13 | 112633352 | 112634012 | 13 | 114021436 | 114022246 |
| 13 | 112637206 | 112638021 | 13 | 114023511 | 114029473 |
| 13 | 112640259 | 112643159 | 13 | 114031059 | 114031544 |
| 13 | 112645422 | 112646225 | 13 | 114034267 | 114036362 |
| 13 | 112646801 | 112647254 | 13 | 114038634 | 114040033 |
| 13 | 112648099 | 112648139 | 13 | 114044133 | 114063828 |
| 13 | 112648673 | 112649028 | 13 | 114065315 | 114068587 |
| 13 | 112652155 | 112652985 | 13 | 114072128 | 114072388 |
| 13 | 112653432 | 112653537 | 13 | 114073624 | 114074204 |
| 13 | 112655472 | 112670378 | 13 | 114080115 | 114081106 |
| 13 | 112670623 | 112671673 | 13 | 114083889 | 114091122 |
| 13 | 112672358 | 112694193 | 13 | 114091242 | 114091597 |
| 13 | 112696239 | 112696349 | 13 | 114095247 | 114095452 |
| 13 | 112698185 | 112698831 | 13 | 114101240 | 114102987 |
| 13 | 112704801 | 112705156 | 13 | 114104567 | 114105011 |
| 13 | 112707473 | 112708318 | 13 | 114106223 | 114106670 |
| 13 | 112709443 | 112711769 | 13 | 114107450 | 114107850 |
| 13 | 112712319 | 112712739 | 13 | 114109305 | 114109955 |
| 13 | 112715874 | 112716179 | 13 | 114111010 | 114114757 |
| 13 | 112719414 | 112749440 | 13 | 114117354 | 114118064 |
| 13 | 112753761 | 112758077 | 13 | 114123903 | 114124068 |
| 13 | 112760497 | 112760697 | 13 | 114124708 | 114125504 |

The chromosomal positon was obtained from UCSC genome browser (http://genome.ucsc.edu/) build 36.

APPENDIX C: Chromosome 18
Page 1 of 72

| Chr | Start | End | | | Chr | Start | End |
|---|---|---|---|---|---|---|---|
| 18 | 1187 | 50745 | | | 18 | 7121546 | 7122446 |
| 18 | 62955 | 77222 | | | 18 | 7135163 | 7136888 |
| 18 | 91515 | 98313 | | | 18 | 7143729 | 7144546 |
| 18 | 132169 | 133464 | | | 18 | 7148225 | 7150162 |
| 18 | 136020 | 140401 | | | 18 | 7159895 | 7163893 |
| 18 | 173859 | 174443 | | | 18 | 7174741 | 7176890 |
| 18 | 181180 | 182124 | | | 18 | 7178829 | 7178913 |
| 18 | 185176 | 185663 | | | 18 | 7188802 | 7189762 |
| 18 | 189689 | 191254 | | | 18 | 7191443 | 7192766 |
| 18 | 201701 | 202082 | | | 18 | 7195150 | 7196811 |
| 18 | 208583 | 209059 | | | 18 | 7220759 | 7224303 |
| 18 | 217447 | 218649 | | | 18 | 7230466 | 7230996 |
| 18 | 236134 | 236259 | | | 18 | 7235164 | 7235730 |
| 18 | 237234 | 237917 | | | 18 | 7238007 | 7238742 |
| 18 | 251548 | 251742 | | | 18 | 7241924 | 7242657 |
| 18 | 254726 | 254990 | | | 18 | 7249478 | 7250349 |
| 18 | 255052 | 255319 | | | 18 | 7254349 | 7254856 |
| 18 | 255854 | 255860 | | | 18 | 7258535 | 7259087 |
| 18 | 266431 | 269344 | | | 18 | 7266256 | 7266383 |
| 18 | 272041 | 274604 | | | 18 | 7274364 | 7275678 |
| 18 | 285253 | 287377 | | | 18 | 7296139 | 7296545 |
| 18 | 288626 | 289758 | | | 18 | 7301383 | 7301957 |
| 18 | 296923 | 297997 | | | 18 | 7303185 | 7303508 |
| 18 | 304513 | 305292 | | | 18 | 7313524 | 7313654 |
| 18 | 309440 | 310438 | | | 18 | 7331901 | 7332161 |
| 18 | 317494 | 319327 | | | 18 | 7342707 | 7344078 |
| 18 | 322828 | 323873 | | | 18 | 7346298 | 7346515 |
| 18 | 326069 | 326701 | | | 18 | 7348065 | 7350484 |
| 18 | 329187 | 329617 | | | 18 | 7356870 | 7357540 |
| 18 | 334321 | 334920 | | | 18 | 7360545 | 7361259 |
| 18 | 336136 | 336630 | | | 18 | 7367586 | 7368133 |
| 18 | 339063 | 343275 | | | 18 | 7371351 | 7376559 |
| 18 | 345331 | 346305 | | | 18 | 7416873 | 7418593 |
| 18 | 351969 | 353104 | | | 18 | 7426419 | 7426806 |
| 18 | 356503 | 357519 | | | 18 | 7441486 | 7442032 |
| 18 | 359184 | 360406 | | | 18 | 7445722 | 7446152 |
| 18 | 361702 | 361997 | | | 18 | 7447144 | 7447258 |
| 18 | 369472 | 374461 | | | 18 | 7450079 | 7451523 |
| 18 | 383970 | 384890 | | | 18 | 7452484 | 7453039 |
| 18 | 386053 | 387396 | | | 18 | 7457844 | 7458733 |
| 18 | 389611 | 390302 | | | 18 | 7471908 | 7473121 |
| 18 | 392509 | 393251 | | | 18 | 7476551 | 7477031 |
| 18 | 397639 | 397824 | | | 18 | 7479940 | 7482493 |
| 18 | 430121 | 430424 | | | 18 | 7494753 | 7495043 |
| 18 | 433055 | 433838 | | | 18 | 7496589 | 7496994 |
| 18 | 437630 | 439048 | | | 18 | 7500270 | 7503575 |
| 18 | 442468 | 442689 | | | 18 | 7507837 | 7509498 |
| 18 | 449196 | 451018 | | | 18 | 7517827 | 7520324 |
| 18 | 452328 | 452491 | | | 18 | 7535933 | 7535953 |
| 18 | 454189 | 454791 | | | 18 | 7545647 | 7548634 |
| 18 | 455768 | 456834 | | | 18 | 7549923 | 7550913 |
| 18 | 460970 | 461300 | | | 18 | 7553846 | 7554322 |
| 18 | 466263 | 466500 | | | 18 | 7554632 | 7555580 |
| 18 | 466713 | 467570 | | | 18 | 7556563 | 7557718 |
| 18 | 473534 | 476691 | | | 18 | 7562960 | 7564055 |

The chromosomal positon was obtained from UCSC genome browser (http://genome.ucsc.edu/) build 36.

APPENDIX C: Chromosome 18
Page 2 of 72

| Chr | Start | End | Chr | Start | End |
|---|---|---|---|---|---|
| 18 | 481252 | 482062 | 18 | 7565400 | 7566030 |
| 18 | 483911 | 484597 | 18 | 7566325 | 7566545 |
| 18 | 489791 | 489960 | 18 | 7570616 | 7571403 |
| 18 | 497304 | 497951 | 18 | 7573785 | 7574677 |
| 18 | 501771 | 506051 | 18 | 7584833 | 7585925 |
| 18 | 506187 | 509715 | 18 | 7601742 | 7602867 |
| 18 | 515181 | 515531 | 18 | 7607752 | 7608273 |
| 18 | 532715 | 533961 | 18 | 7609024 | 7609899 |
| 18 | 553782 | 553931 | 18 | 7611448 | 7612595 |
| 18 | 570239 | 571369 | 18 | 7616933 | 7617583 |
| 18 | 588497 | 590094 | 18 | 7619289 | 7619726 |
| 18 | 592262 | 592860 | 18 | 7623806 | 7624621 |
| 18 | 600546 | 600728 | 18 | 7624741 | 7625306 |
| 18 | 606526 | 608216 | 18 | 7637746 | 7638962 |
| 18 | 612296 | 613947 | 18 | 7640084 | 7640284 |
| 18 | 621061 | 621605 | 18 | 7644309 | 7647682 |
| 18 | 624545 | 624728 | 18 | 7652550 | 7653086 |
| 18 | 630144 | 630890 | 18 | 7653811 | 7654551 |
| 18 | 632872 | 633175 | 18 | 7662432 | 7662831 |
| 18 | 645719 | 647902 | 18 | 7663181 | 7663457 |
| 18 | 656315 | 656880 | 18 | 7668113 | 7668732 |
| 18 | 666766 | 668330 | 18 | 7690351 | 7694605 |
| 18 | 699026 | 700846 | 18 | 7707902 | 7708504 |
| 18 | 702932 | 703172 | 18 | 7713593 | 7713874 |
| 18 | 713455 | 714237 | 18 | 7714140 | 7715315 |
| 18 | 720975 | 721460 | 18 | 7716498 | 7716763 |
| 18 | 730408 | 730855 | 18 | 7729679 | 7731084 |
| 18 | 735314 | 736134 | 18 | 7737383 | 7738813 |
| 18 | 740480 | 740666 | 18 | 7739447 | 7739723 |
| 18 | 752404 | 753380 | 18 | 7744617 | 7745043 |
| 18 | 760845 | 762345 | 18 | 7748733 | 7749395 |
| 18 | 770753 | 773359 | 18 | 7750978 | 7751292 |
| 18 | 782966 | 783809 | 18 | 7759021 | 7761226 |
| 18 | 790748 | 791285 | 18 | 7766345 | 7766821 |
| 18 | 803237 | 804048 | 18 | 7777140 | 7777743 |
| 18 | 808412 | 809071 | 18 | 7790789 | 7790932 |
| 18 | 814004 | 814649 | 18 | 7799061 | 7800015 |
| 18 | 819947 | 820885 | 18 | 7803017 | 7805523 |
| 18 | 822084 | 822710 | 18 | 7809971 | 7814598 |
| 18 | 827852 | 828370 | 18 | 7820329 | 7821337 |
| 18 | 838898 | 839397 | 18 | 7827865 | 7828025 |
| 18 | 841205 | 841547 | 18 | 7840443 | 7840919 |
| 18 | 854771 | 855055 | 18 | 7844856 | 7845160 |
| 18 | 861588 | 862724 | 18 | 7849972 | 7851078 |
| 18 | 868849 | 871989 | 18 | 7852678 | 7856465 |
| 18 | 873932 | 874336 | 18 | 7875180 | 7876465 |
| 18 | 876515 | 876686 | 18 | 7883226 | 7884205 |
| 18 | 877751 | 878390 | 18 | 7885269 | 7885609 |
| 18 | 880736 | 882815 | 18 | 7886359 | 7887464 |
| 18 | 884401 | 887628 | 18 | 7888665 | 7889025 |
| 18 | 898583 | 899123 | 18 | 7917924 | 7918102 |
| 18 | 900098 | 900338 | 18 | 7918987 | 7920439 |
| 18 | 907192 | 907844 | 18 | 7930807 | 7931048 |
| 18 | 908258 | 909388 | 18 | 7934054 | 7934858 |
| 18 | 916415 | 917083 | 18 | 7936734 | 7938201 |

The chromosomal positon was obtained from UCSC genome browser (http://genome.ucsc.edu/) build 36.

APPENDIX C: Chromosome 18
Page 3 of 72

| Chr | Start | End | Chr | Start | End |
|---|---|---|---|---|---|
| 18 | 923729 | 924976 | 18 | 7947245 | 7947474 |
| 18 | 927215 | 927889 | 18 | 7948299 | 7950340 |
| 18 | 929000 | 929349 | 18 | 7952924 | 7953948 |
| 18 | 941335 | 941744 | 18 | 7964270 | 7964954 |
| 18 | 944487 | 945624 | 18 | 7970931 | 7971418 |
| 18 | 947026 | 948253 | 18 | 7971816 | 7977148 |
| 18 | 950255 | 952018 | 18 | 7980619 | 7982390 |
| 18 | 957446 | 969988 | 18 | 7985481 | 7986053 |
| 18 | 976584 | 976819 | 18 | 7987268 | 7988111 |
| 18 | 992329 | 992669 | 18 | 7988530 | 7988962 |
| 18 | 1010708 | 1012227 | 18 | 7989065 | 7992041 |
| 18 | 1026828 | 1027083 | 18 | 7993051 | 7994014 |
| 18 | 1041501 | 1041716 | 18 | 7995189 | 7996090 |
| 18 | 1042916 | 1043777 | 18 | 8008805 | 8009104 |
| 18 | 1049474 | 1050238 | 18 | 8010406 | 8012497 |
| 18 | 1055714 | 1055944 | 18 | 8013685 | 8015186 |
| 18 | 1065578 | 1066042 | 18 | 8019119 | 8020087 |
| 18 | 1067396 | 1068722 | 18 | 8024261 | 8028305 |
| 18 | 1071395 | 1078482 | 18 | 8032653 | 8035633 |
| 18 | 1095357 | 1095740 | 18 | 8040796 | 8041182 |
| 18 | 1101135 | 1101394 | 18 | 8058089 | 8058632 |
| 18 | 1131206 | 1136211 | 18 | 8059235 | 8059900 |
| 18 | 1138786 | 1139211 | 18 | 8068126 | 8068544 |
| 18 | 1139706 | 1141813 | 18 | 8078201 | 8078928 |
| 18 | 1149064 | 1151157 | 18 | 8082625 | 8083182 |
| 18 | 1153933 | 1155193 | 18 | 8086086 | 8086094 |
| 18 | 1161311 | 1161805 | 18 | 8089010 | 8089797 |
| 18 | 1164142 | 1165380 | 18 | 8092816 | 8094258 |
| 18 | 1172076 | 1172186 | 18 | 8097516 | 8097861 |
| 18 | 1173070 | 1175278 | 18 | 8100042 | 8100724 |
| 18 | 1185804 | 1187280 | 18 | 8101692 | 8102354 |
| 18 | 1191963 | 1192548 | 18 | 8114146 | 8114281 |
| 18 | 1197651 | 1209353 | 18 | 8117637 | 8118039 |
| 18 | 1211072 | 1212286 | 18 | 8119981 | 8123880 |
| 18 | 1215380 | 1216160 | 18 | 8127890 | 8131573 |
| 18 | 1218707 | 1218816 | 18 | 8147237 | 8148216 |
| 18 | 1221318 | 1224021 | 18 | 8157414 | 8157900 |
| 18 | 1226773 | 1228880 | 18 | 8161439 | 8162366 |
| 18 | 1232289 | 1232630 | 18 | 8166533 | 8166869 |
| 18 | 1238493 | 1241033 | 18 | 8167976 | 8170011 |
| 18 | 1244557 | 1244816 | 18 | 8173358 | 8174660 |
| 18 | 1246682 | 1247587 | 18 | 8181595 | 8182142 |
| 18 | 1249506 | 1249699 | 18 | 8183938 | 8184290 |
| 18 | 1256520 | 1257608 | 18 | 8204193 | 8204584 |
| 18 | 1265477 | 1266209 | 18 | 8211853 | 8212359 |
| 18 | 1269785 | 1272468 | 18 | 8219968 | 8220047 |
| 18 | 1277696 | 1277981 | 18 | 8222768 | 8223307 |
| 18 | 1291767 | 1297993 | 18 | 8233540 | 8234569 |
| 18 | 1305503 | 1316668 | 18 | 8241942 | 8242103 |
| 18 | 1324154 | 1324292 | 18 | 8249996 | 8250500 |
| 18 | 1333436 | 1334312 | 18 | 8253727 | 8254225 |
| 18 | 1335342 | 1342023 | 18 | 8255747 | 8256516 |
| 18 | 1342523 | 1342812 | 18 | 8258208 | 8261038 |
| 18 | 1358646 | 1361174 | 18 | 8263763 | 8264480 |
| 18 | 1364034 | 1364734 | 18 | 8268630 | 8269464 |

The chromosomal positon was obtained from UCSC genome browser (http://genome.ucsc.edu/) build 36.

APPENDIX C: Chromosome 18
Page 4 of 72

| Chr | Start | End | Chr | Start | End |
|---|---|---|---|---|---|
| 18 | 1368785 | 1372261 | 18 | 8273264 | 8274551 |
| 18 | 1372417 | 1372715 | 18 | 8275652 | 8276279 |
| 18 | 1378695 | 1379279 | 18 | 8277638 | 8282206 |
| 18 | 1382427 | 1382618 | 18 | 8290803 | 8293329 |
| 18 | 1383086 | 1389079 | 18 | 8294622 | 8296365 |
| 18 | 1391597 | 1392028 | 18 | 8300938 | 8302876 |
| 18 | 1393646 | 1394490 | 18 | 8311505 | 8311946 |
| 18 | 1400731 | 1402358 | 18 | 8317125 | 8317808 |
| 18 | 1406898 | 1408756 | 18 | 8321486 | 8322276 |
| 18 | 1411483 | 1412546 | 18 | 8329857 | 8330762 |
| 18 | 1426113 | 1428786 | 18 | 8333484 | 8333583 |
| 18 | 1431241 | 1431371 | 18 | 8338638 | 8339673 |
| 18 | 1438800 | 1438934 | 18 | 8346105 | 8346428 |
| 18 | 1448850 | 1450507 | 18 | 8348172 | 8348384 |
| 18 | 1464744 | 1465142 | 18 | 8375449 | 8376130 |
| 18 | 1471491 | 1471889 | 18 | 8381442 | 8381914 |
| 18 | 1478110 | 1484182 | 18 | 8384130 | 8384533 |
| 18 | 1488841 | 1489117 | 18 | 8389961 | 8390541 |
| 18 | 1489747 | 1489822 | 18 | 8396759 | 8397298 |
| 18 | 1495147 | 1496316 | 18 | 8400263 | 8401653 |
| 18 | 1504353 | 1505566 | 18 | 8403102 | 8403732 |
| 18 | 1511454 | 1512349 | 18 | 8413560 | 8413735 |
| 18 | 1513164 | 1513770 | 18 | 8415625 | 8416790 |
| 18 | 1517433 | 1529532 | 18 | 8422716 | 8427441 |
| 18 | 1536461 | 1537104 | 18 | 8428912 | 8429391 |
| 18 | 1539159 | 1540086 | 18 | 8445367 | 8446008 |
| 18 | 1540151 | 1541066 | 18 | 8448818 | 8450571 |
| 18 | 1554261 | 1555816 | 18 | 8450633 | 8452367 |
| 18 | 1557375 | 1557841 | 18 | 8459931 | 8460574 |
| 18 | 1560234 | 1571424 | 18 | 8466994 | 8471420 |
| 18 | 1572715 | 1572931 | 18 | 8482727 | 8483557 |
| 18 | 1575740 | 1576286 | 18 | 8485099 | 8486597 |
| 18 | 1600095 | 1601086 | 18 | 8490749 | 8491499 |
| 18 | 1603590 | 1610120 | 18 | 8497148 | 8498572 |
| 18 | 1611357 | 1612388 | 18 | 8498997 | 8499544 |
| 18 | 1614820 | 1615251 | 18 | 8503175 | 8503874 |
| 18 | 1617082 | 1618328 | 18 | 8505129 | 8505333 |
| 18 | 1625181 | 1626567 | 18 | 8512572 | 8513232 |
| 18 | 1628578 | 1629223 | 18 | 8516610 | 8517310 |
| 18 | 1630178 | 1630481 | 18 | 8519416 | 8519666 |
| 18 | 1642517 | 1646969 | 18 | 8526587 | 8528232 |
| 18 | 1652654 | 1653180 | 18 | 8539373 | 8539880 |
| 18 | 1653732 | 1656602 | 18 | 8545028 | 8545729 |
| 18 | 1659592 | 1659995 | 18 | 8555525 | 8556053 |
| 18 | 1660497 | 1660923 | 18 | 8576191 | 8576825 |
| 18 | 1662531 | 1663421 | 18 | 8588192 | 8588282 |
| 18 | 1669758 | 1670063 | 18 | 8592912 | 8593090 |
| 18 | 1670602 | 1671394 | 18 | 8595664 | 8596124 |
| 18 | 1675668 | 1678837 | 18 | 8602008 | 8603479 |
| 18 | 1682152 | 1682979 | 18 | 8613758 | 8614531 |
| 18 | 1706712 | 1708542 | 18 | 8620476 | 8620813 |
| 18 | 1712648 | 1717401 | 18 | 8630687 | 8630945 |
| 18 | 1724663 | 1724828 | 18 | 8635907 | 8635909 |
| 18 | 1731350 | 1732517 | 18 | 8647058 | 8650618 |
| 18 | 1752299 | 1752644 | 18 | 8652640 | 8653464 |

The chromosomal positon was obtained from UCSC genome browser (http://genome.ucsc.edu/) build 36.

APPENDIX C: Chromosome 18
Page 5 of 72

| Chr | Start | End | | Chr | Start | End |
|---|---|---|---|---|---|---|
| 18 | 1760231 | 1760439 | | 18 | 8657125 | 8658614 |
| 18 | 1769587 | 1770183 | | 18 | 8665737 | 8668236 |
| 18 | 1781693 | 1782274 | | 18 | 8696713 | 8697662 |
| 18 | 1784384 | 1784643 | | 18 | 8698065 | 8698314 |
| 18 | 1800918 | 1804095 | | 18 | 8702873 | 8704338 |
| 18 | 1805378 | 1807879 | | 18 | 8711303 | 8712286 |
| 18 | 1808867 | 1809669 | | 18 | 8712487 | 8713417 |
| 18 | 1811663 | 1819356 | | 18 | 8737202 | 8737997 |
| 18 | 1821739 | 1822624 | | 18 | 8741122 | 8742176 |
| 18 | 1837893 | 1838198 | | 18 | 8745168 | 8746827 |
| 18 | 1848233 | 1850842 | | 18 | 8751146 | 8751522 |
| 18 | 1853009 | 1853185 | | 18 | 8752597 | 8753432 |
| 18 | 1853670 | 1853878 | | 18 | 8759735 | 8760244 |
| 18 | 1858880 | 1859695 | | 18 | 8768894 | 8769654 |
| 18 | 1863123 | 1889015 | | 18 | 8770568 | 8771376 |
| 18 | 1890017 | 1890301 | | 18 | 8771711 | 8773222 |
| 18 | 1898088 | 1898983 | | 18 | 8774480 | 8778290 |
| 18 | 1908413 | 1909100 | | 18 | 8786048 | 8786467 |
| 18 | 1910813 | 1911586 | | 18 | 8789722 | 8791495 |
| 18 | 1915789 | 1918649 | | 18 | 8793222 | 8794483 |
| 18 | 1925851 | 1926957 | | 18 | 8795314 | 8795860 |
| 18 | 1935291 | 1935913 | | 18 | 8796469 | 8797929 |
| 18 | 1940545 | 1941145 | | 18 | 8806852 | 8807066 |
| 18 | 1941588 | 1942436 | | 18 | 8808475 | 8809670 |
| 18 | 1950548 | 1955388 | | 18 | 8814712 | 8815357 |
| 18 | 1959025 | 1959359 | | 18 | 8816875 | 8817812 |
| 18 | 1962909 | 1963214 | | 18 | 8819833 | 8821117 |
| 18 | 1965499 | 1965763 | | 18 | 8826201 | 8826509 |
| 18 | 1970709 | 1973406 | | 18 | 8851592 | 8853156 |
| 18 | 1975690 | 1978097 | | 18 | 8853727 | 8853898 |
| 18 | 1983335 | 1984058 | | 18 | 8866152 | 8866513 |
| 18 | 1987528 | 1990376 | | 18 | 8895657 | 8897033 |
| 18 | 1997498 | 1999597 | | 18 | 8902719 | 8902869 |
| 18 | 2005966 | 2015215 | | 18 | 8917117 | 8918467 |
| 18 | 2017176 | 2019197 | | 18 | 8919211 | 8919457 |
| 18 | 2031946 | 2032151 | | 18 | 8927512 | 8928112 |
| 18 | 2034861 | 2035811 | | 18 | 8928598 | 8929971 |
| 18 | 2036935 | 2037297 | | 18 | 8938663 | 8940331 |
| 18 | 2039828 | 2042148 | | 18 | 8941766 | 8942162 |
| 18 | 2043422 | 2044229 | | 18 | 8947373 | 8947983 |
| 18 | 2044875 | 2045726 | | 18 | 8950864 | 8951351 |
| 18 | 2047393 | 2049382 | | 18 | 8956224 | 8957586 |
| 18 | 2057162 | 2061073 | | 18 | 8959565 | 8960146 |
| 18 | 2064880 | 2065166 | | 18 | 8967750 | 8969234 |
| 18 | 2066983 | 2067912 | | 18 | 8972459 | 8973594 |
| 18 | 2073032 | 2074015 | | 18 | 8977697 | 8978256 |
| 18 | 2076610 | 2076842 | | 18 | 8980374 | 8980842 |
| 18 | 2084870 | 2086741 | | 18 | 8983661 | 8984172 |
| 18 | 2086750 | 2088036 | | 18 | 8988444 | 8989604 |
| 18 | 2112501 | 2113482 | | 18 | 9010767 | 9012274 |
| 18 | 2115843 | 2117424 | | 18 | 9036472 | 9037262 |
| 18 | 2122561 | 2123620 | | 18 | 9038311 | 9038956 |
| 18 | 2127488 | 2131688 | | 18 | 9042603 | 9042930 |
| 18 | 2134583 | 2139756 | | 18 | 9043430 | 9044861 |
| 18 | 2143119 | 2144387 | | 18 | 9052188 | 9052981 |

The chromosomal positon was obtained from UCSC genome browser (http://genome.ucsc.edu/) build 36.

APPENDIX C: Chromosome 18
Page 6 of 72

| Chr | Start | End | Chr | Start | End |
|---|---|---|---|---|---|
| 18 | 2149857 | 2149864 | 18 | 9072698 | 9072904 |
| 18 | 2151685 | 2153051 | 18 | 9084004 | 9085756 |
| 18 | 2158731 | 2160136 | 18 | 9085936 | 9086860 |
| 18 | 2160708 | 2162673 | 18 | 9090081 | 9091671 |
| 18 | 2164222 | 2164862 | 18 | 9095013 | 9097773 |
| 18 | 2166668 | 2167832 | 18 | 9106826 | 9107348 |
| 18 | 2181003 | 2181701 | 18 | 9109190 | 9109280 |
| 18 | 2183763 | 2184206 | 18 | 9110897 | 9111904 |
| 18 | 2186144 | 2186891 | 18 | 9112674 | 9113917 |
| 18 | 2188985 | 2189379 | 18 | 9126004 | 9126904 |
| 18 | 2191877 | 2203399 | 18 | 9132356 | 9133023 |
| 18 | 2207972 | 2209109 | 18 | 9141413 | 9141784 |
| 18 | 2211253 | 2212128 | 18 | 9149868 | 9150813 |
| 18 | 2224647 | 2226498 | 18 | 9154766 | 9163521 |
| 18 | 2229329 | 2230673 | 18 | 9167843 | 9168297 |
| 18 | 2235163 | 2235478 | 18 | 9175257 | 9176110 |
| 18 | 2245962 | 2247909 | 18 | 9178505 | 9180190 |
| 18 | 2263202 | 2264063 | 18 | 9195513 | 9195711 |
| 18 | 2265881 | 2268388 | 18 | 9204399 | 9206189 |
| 18 | 2270613 | 2272698 | 18 | 9211867 | 9211967 |
| 18 | 2287865 | 2288202 | 18 | 9217912 | 9223165 |
| 18 | 2291379 | 2292323 | 18 | 9227581 | 9228533 |
| 18 | 2310619 | 2311780 | 18 | 9239211 | 9243220 |
| 18 | 2316549 | 2320330 | 18 | 9245649 | 9246011 |
| 18 | 2320794 | 2321427 | 18 | 9246732 | 9247491 |
| 18 | 2321639 | 2322967 | 18 | 9261034 | 9261925 |
| 18 | 2341116 | 2341721 | 18 | 9292304 | 9293612 |
| 18 | 2347081 | 2348154 | 18 | 9300293 | 9301817 |
| 18 | 2351242 | 2351336 | 18 | 9310507 | 9311538 |
| 18 | 2353044 | 2354659 | 18 | 9320029 | 9320960 |
| 18 | 2355329 | 2356664 | 18 | 9323436 | 9324045 |
| 18 | 2361724 | 2366971 | 18 | 9336402 | 9338631 |
| 18 | 2371763 | 2372134 | 18 | 9344666 | 9345430 |
| 18 | 2381703 | 2382302 | 18 | 9346042 | 9349613 |
| 18 | 2385144 | 2386411 | 18 | 9350504 | 9351160 |
| 18 | 2390662 | 2391680 | 18 | 9373877 | 9374423 |
| 18 | 2393545 | 2395269 | 18 | 9379466 | 9379627 |
| 18 | 2398421 | 2399688 | 18 | 9380772 | 9381366 |
| 18 | 2401889 | 2402458 | 18 | 9390139 | 9391280 |
| 18 | 2414199 | 2418021 | 18 | 9397949 | 9399359 |
| 18 | 2421825 | 2425766 | 18 | 9401459 | 9403937 |
| 18 | 2429919 | 2431695 | 18 | 9411138 | 9412723 |
| 18 | 2433928 | 2434827 | 18 | 9423642 | 9423827 |
| 18 | 2439619 | 2449225 | 18 | 9435568 | 9435971 |
| 18 | 2452808 | 2453072 | 18 | 9437645 | 9437906 |
| 18 | 2455972 | 2456358 | 18 | 9440097 | 9441647 |
| 18 | 2462020 | 2463090 | 18 | 9444044 | 9446933 |
| 18 | 2464113 | 2464304 | 18 | 9463319 | 9463531 |
| 18 | 2471917 | 2472661 | 18 | 9464130 | 9466168 |
| 18 | 2479016 | 2479494 | 18 | 9467437 | 9468653 |
| 18 | 2483613 | 2483798 | 18 | 9478745 | 9478948 |
| 18 | 2498527 | 2499382 | 18 | 9479997 | 9480238 |
| 18 | 2518624 | 2519648 | 18 | 9484309 | 9484782 |
| 18 | 2522853 | 2525455 | 18 | 9496021 | 9496335 |
| 18 | 2531355 | 2531909 | 18 | 9509701 | 9509916 |

The chromosomal positon was obtained from UCSC genome browser (http://genome.ucsc.edu/) build 36.

APPENDIX C: Chromosome 18
Page 7 of 72

| Chr | Start | End | | Chr | Start | End |
|---|---|---|---|---|---|---|
| 18 | 2533256 | 2533898 | | 18 | 9520393 | 9520779 |
| 18 | 2536586 | 2538051 | | 18 | 9523662 | 9526391 |
| 18 | 2546115 | 2547402 | | 18 | 9529427 | 9530613 |
| 18 | 2550194 | 2550993 | | 18 | 9532798 | 9534340 |
| 18 | 2555745 | 2556398 | | 18 | 9548243 | 9549017 |
| 18 | 2559416 | 2559606 | | 18 | 9550551 | 9551293 |
| 18 | 2560362 | 2561081 | | 18 | 9571442 | 9573182 |
| 18 | 2561841 | 2562676 | | 18 | 9575525 | 9575990 |
| 18 | 2569843 | 2570265 | | 18 | 9580984 | 9581545 |
| 18 | 2571961 | 2572961 | | 18 | 9582928 | 9583327 |
| 18 | 2580548 | 2581477 | | 18 | 9593218 | 9593436 |
| 18 | 2594721 | 2595621 | | 18 | 9603998 | 9605427 |
| 18 | 2595836 | 2597020 | | 18 | 9609154 | 9610054 |
| 18 | 2606457 | 2606855 | | 18 | 9617975 | 9618465 |
| 18 | 2607734 | 2607759 | | 18 | 9623655 | 9626321 |
| 18 | 2615247 | 2615528 | | 18 | 9627046 | 9627392 |
| 18 | 2626326 | 2627846 | | 18 | 9628893 | 9629338 |
| 18 | 2632984 | 2633649 | | 18 | 9633135 | 9633558 |
| 18 | 2640998 | 2641950 | | 18 | 9635162 | 9635292 |
| 18 | 2645900 | 2646826 | | 18 | 9640287 | 9641585 |
| 18 | 2663617 | 2663835 | | 18 | 9643057 | 9643262 |
| 18 | 2674110 | 2674527 | | 18 | 9651784 | 9652369 |
| 18 | 2675839 | 2675853 | | 18 | 9654661 | 9659548 |
| 18 | 2694834 | 2697200 | | 18 | 9667589 | 9668109 |
| 18 | 2698027 | 2699030 | | 18 | 9674239 | 9675319 |
| 18 | 2699398 | 2700187 | | 18 | 9679071 | 9681389 |
| 18 | 2711145 | 2712356 | | 18 | 9688078 | 9692456 |
| 18 | 2737981 | 2738742 | | 18 | 9696642 | 9700330 |
| 18 | 2754253 | 2754270 | | 18 | 9703140 | 9703418 |
| 18 | 2759255 | 2759784 | | 18 | 9711753 | 9713370 |
| 18 | 2761299 | 2761619 | | 18 | 9713756 | 9714794 |
| 18 | 2771756 | 2771890 | | 18 | 9715477 | 9716009 |
| 18 | 2777151 | 2778415 | | 18 | 9722879 | 9723161 |
| 18 | 2781617 | 2782373 | | 18 | 9725618 | 9726529 |
| 18 | 2786453 | 2787588 | | 18 | 9731079 | 9733970 |
| 18 | 2787998 | 2789316 | | 18 | 9737035 | 9739146 |
| 18 | 2796324 | 2797280 | | 18 | 9741457 | 9741818 |
| 18 | 2801626 | 2801977 | | 18 | 9745078 | 9746677 |
| 18 | 2813895 | 2814138 | | 18 | 9752535 | 9753251 |
| 18 | 2829316 | 2830370 | | 18 | 9778444 | 9780156 |
| 18 | 2832019 | 2833754 | | 18 | 9787347 | 9787708 |
| 18 | 2844994 | 2847949 | | 18 | 9789258 | 9791759 |
| 18 | 2859387 | 2859894 | | 18 | 9792106 | 9793987 |
| 18 | 2865177 | 2865553 | | 18 | 9797035 | 9799914 |
| 18 | 2868877 | 2871967 | | 18 | 9805253 | 9806162 |
| 18 | 2872312 | 2872442 | | 18 | 9808352 | 9811131 |
| 18 | 2879829 | 2880176 | | 18 | 9821416 | 9827202 |
| 18 | 2882179 | 2883379 | | 18 | 9828418 | 9829000 |
| 18 | 2890517 | 2891770 | | 18 | 9841615 | 9841643 |
| 18 | 2899665 | 2903648 | | 18 | 9842441 | 9844388 |
| 18 | 2931575 | 2933587 | | 18 | 9850441 | 9852811 |
| 18 | 2940206 | 2942019 | | 18 | 9855160 | 9857310 |
| 18 | 2946431 | 2946788 | | 18 | 9876477 | 9877843 |
| 18 | 2949744 | 2952313 | | 18 | 9913832 | 9917857 |
| 18 | 2953672 | 2954747 | | 18 | 9923500 | 9924172 |

The chromosomal positon was obtained from UCSC genome browser (http://genome.ucsc.edu/) build 36.

APPENDIX C: Chromosome 18
Page 8 of 72

| Chr | Start | End | Chr | Start | End |
|---|---|---|---|---|---|
| 18 | 2957965 | 2962662 | 18 | 9930998 | 9932251 |
| 18 | 3004505 | 3005418 | 18 | 9935810 | 9936596 |
| 18 | 3007635 | 3009160 | 18 | 9941916 | 9943984 |
| 18 | 3016839 | 3017054 | 18 | 9948626 | 9948864 |
| 18 | 3045393 | 3045619 | 18 | 9948865 | 9949512 |
| 18 | 3045901 | 3046186 | 18 | 9951084 | 9953716 |
| 18 | 3050540 | 3052313 | 18 | 9955063 | 9955160 |
| 18 | 3058891 | 3061158 | 18 | 9957497 | 9958977 |
| 18 | 3064336 | 3064497 | 18 | 9962838 | 9963466 |
| 18 | 3068390 | 3069769 | 18 | 9981336 | 9984933 |
| 18 | 3076349 | 3077126 | 18 | 9985718 | 9987384 |
| 18 | 3083488 | 3083932 | 18 | 9990082 | 9992594 |
| 18 | 3088605 | 3089905 | 18 | 9996159 | 9997618 |
| 18 | 3102046 | 3102517 | 18 | 9999668 | 10000544 |
| 18 | 3108318 | 3109447 | 18 | 10005363 | 10008448 |
| 18 | 3110382 | 3110798 | 18 | 10010359 | 10013227 |
| 18 | 3112685 | 3113597 | 18 | 10018028 | 10018758 |
| 18 | 3118965 | 3119380 | 18 | 10019848 | 10021488 |
| 18 | 3120800 | 3121440 | 18 | 10022443 | 10023283 |
| 18 | 3122975 | 3123737 | 18 | 10024752 | 10027279 |
| 18 | 3128498 | 3129936 | 18 | 10044436 | 10045124 |
| 18 | 3131089 | 3132598 | 18 | 10058538 | 10059403 |
| 18 | 3142403 | 3143393 | 18 | 10060527 | 10063177 |
| 18 | 3157703 | 3157889 | 18 | 10065904 | 10066844 |
| 18 | 3160970 | 3164766 | 18 | 10073106 | 10073231 |
| 18 | 3176683 | 3177116 | 18 | 10074697 | 10075885 |
| 18 | 3203119 | 3203380 | 18 | 10077709 | 10078910 |
| 18 | 3206347 | 3207631 | 18 | 10084898 | 10087208 |
| 18 | 3210944 | 3211693 | 18 | 10092419 | 10093143 |
| 18 | 3211942 | 3212155 | 18 | 10095753 | 10101379 |
| 18 | 3217140 | 3218245 | 18 | 10101882 | 10102821 |
| 18 | 3219547 | 3221489 | 18 | 10106002 | 10106982 |
| 18 | 3223381 | 3225636 | 18 | 10111290 | 10112998 |
| 18 | 3226728 | 3227007 | 18 | 10119033 | 10119612 |
| 18 | 3234069 | 3237164 | 18 | 10123019 | 10123279 |
| 18 | 3244853 | 3246661 | 18 | 10130925 | 10131435 |
| 18 | 3248429 | 3249384 | 18 | 10135742 | 10135990 |
| 18 | 3250116 | 3251139 | 18 | 10141050 | 10141488 |
| 18 | 3251322 | 3251624 | 18 | 10155420 | 10156730 |
| 18 | 3255450 | 3257255 | 18 | 10170029 | 10171685 |
| 18 | 3264330 | 3265405 | 18 | 10177863 | 10178601 |
| 18 | 3269645 | 3271145 | 18 | 10189752 | 10190803 |
| 18 | 3272312 | 3273973 | 18 | 10197943 | 10198744 |
| 18 | 3278630 | 3279149 | 18 | 10201565 | 10202100 |
| 18 | 3283914 | 3284327 | 18 | 10205734 | 10205823 |
| 18 | 3287155 | 3287645 | 18 | 10208754 | 10209623 |
| 18 | 3300238 | 3300814 | 18 | 10212014 | 10213657 |
| 18 | 3305104 | 3307084 | 18 | 10220785 | 10220792 |
| 18 | 3311308 | 3311961 | 18 | 10226919 | 10227338 |
| 18 | 3313785 | 3314284 | 18 | 10228797 | 10229533 |
| 18 | 3329092 | 3332251 | 18 | 10233704 | 10233871 |
| 18 | 3332700 | 3333566 | 18 | 10237153 | 10237918 |
| 18 | 3334863 | 3336211 | 18 | 10239222 | 10239347 |
| 18 | 3344650 | 3345697 | 18 | 10245839 | 10249847 |
| 18 | 3349969 | 3351554 | 18 | 10250278 | 10251435 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 3368326 | 3369079 | | | 18 | 10252903 | 10254437 |
| 18 | 3375226 | 3375330 | | | 18 | 10257326 | 10257711 |
| 18 | 3382719 | 3383048 | | | 18 | 10258785 | 10259133 |
| 18 | 3394846 | 3395924 | | | 18 | 10264357 | 10264562 |
| 18 | 3396123 | 3396327 | | | 18 | 10266134 | 10272032 |
| 18 | 3399646 | 3400187 | | | 18 | 10273451 | 10273932 |
| 18 | 3401501 | 3402360 | | | 18 | 10274487 | 10274893 |
| 18 | 3404519 | 3405332 | | | 18 | 10276603 | 10277458 |
| 18 | 3408073 | 3408413 | | | 18 | 10285017 | 10285444 |
| 18 | 3423448 | 3423950 | | | 18 | 10291691 | 10294783 |
| 18 | 3427725 | 3430069 | | | 18 | 10305739 | 10305883 |
| 18 | 3437236 | 3437537 | | | 18 | 10310463 | 10310858 |
| 18 | 3439956 | 3445245 | | | 18 | 10314336 | 10315945 |
| 18 | 3447488 | 3447658 | | | 18 | 10326876 | 10327363 |
| 18 | 3471339 | 3472729 | | | 18 | 10329616 | 10330526 |
| 18 | 3484760 | 3485551 | | | 18 | 10331716 | 10335522 |
| 18 | 3516668 | 3517233 | | | 18 | 10338848 | 10339539 |
| 18 | 3523995 | 3524410 | | | 18 | 10345092 | 10347846 |
| 18 | 3542176 | 3542358 | | | 18 | 10349111 | 10350392 |
| 18 | 3553419 | 3554780 | | | 18 | 10355628 | 10356017 |
| 18 | 3564385 | 3565359 | | | 18 | 10359303 | 10359618 |
| 18 | 3585039 | 3585869 | | | 18 | 10359768 | 10360418 |
| 18 | 3592871 | 3593984 | | | 18 | 10367404 | 10368339 |
| 18 | 3613196 | 3614423 | | | 18 | 10376145 | 10377657 |
| 18 | 3620449 | 3621302 | | | 18 | 10381840 | 10382847 |
| 18 | 3645557 | 3645977 | | | 18 | 10396198 | 10396886 |
| 18 | 3651188 | 3652370 | | | 18 | 10402967 | 10404923 |
| 18 | 3671640 | 3673533 | | | 18 | 10407022 | 10407279 |
| 18 | 3676999 | 3677688 | | | 18 | 10415431 | 10415510 |
| 18 | 3699133 | 3699531 | | | 18 | 10431769 | 10433776 |
| 18 | 3706646 | 3706756 | | | 18 | 10434394 | 10435194 |
| 18 | 3718942 | 3719531 | | | 18 | 10439233 | 10439606 |
| 18 | 3730593 | 3731642 | | | 18 | 10443605 | 10446391 |
| 18 | 3737699 | 3739051 | | | 18 | 10453869 | 10455322 |
| 18 | 3739900 | 3740361 | | | 18 | 10456592 | 10457418 |
| 18 | 3747816 | 3750141 | | | 18 | 10457783 | 10458328 |
| 18 | 3762817 | 3762972 | | | 18 | 10458717 | 10459437 |
| 18 | 3764126 | 3764378 | | | 18 | 10465570 | 10473963 |
| 18 | 3768554 | 3769525 | | | 18 | 10476753 | 10477118 |
| 18 | 3780757 | 3781228 | | | 18 | 10477417 | 10478022 |
| 18 | 3782752 | 3783582 | | | 18 | 10480867 | 10484942 |
| 18 | 3796374 | 3796758 | | | 18 | 10492774 | 10493160 |
| 18 | 3797889 | 3799035 | | | 18 | 10500577 | 10503081 |
| 18 | 3806221 | 3806878 | | | 18 | 10507202 | 10507628 |
| 18 | 3808959 | 3809408 | | | 18 | 10509630 | 10510106 |
| 18 | 3814722 | 3817846 | | | 18 | 10512583 | 10514134 |
| 18 | 3822489 | 3825346 | | | 18 | 10515512 | 10516033 |
| 18 | 3826393 | 3828617 | | | 18 | 10516678 | 10516884 |
| 18 | 3833687 | 3834104 | | | 18 | 10520435 | 10521092 |
| 18 | 3844924 | 3845474 | | | 18 | 10522320 | 10522968 |
| 18 | 3862724 | 3864634 | | | 18 | 10523430 | 10525412 |
| 18 | 3868971 | 3870566 | | | 18 | 10525882 | 10526623 |
| 18 | 3887598 | 3888344 | | | 18 | 10539436 | 10539735 |
| 18 | 3899424 | 3899674 | | | 18 | 10544027 | 10544425 |
| 18 | 3912658 | 3915397 | | | 18 | 10549061 | 10549430 |

The chromosomal positon was obtained from UCSC genome browser (http://genome.ucsc.edu/) build 36.

APPENDIX C: Chromosome 18
Page 10 of 72

| Chr | Start | End | | | Chr | Start | End |
|---|---|---|---|---|---|---|---|
| 18 | 3920414 | 3921130 | | | 18 | 10551863 | 10555509 |
| 18 | 3923164 | 3923345 | | | 18 | 10562620 | 10569257 |
| 18 | 3940922 | 3942135 | | | 18 | 10578932 | 10580948 |
| 18 | 3948700 | 3949884 | | | 18 | 10604264 | 10606480 |
| 18 | 3950606 | 3952988 | | | 18 | 10622868 | 10626608 |
| 18 | 3961911 | 3962473 | | | 18 | 10649113 | 10649913 |
| 18 | 3963218 | 3964367 | | | 18 | 10651415 | 10651547 |
| 18 | 3967799 | 3968740 | | | 18 | 10654639 | 10655114 |
| 18 | 3971145 | 3971739 | | | 18 | 10671864 | 10672781 |
| 18 | 3978276 | 3979474 | | | 18 | 10676580 | 10676989 |
| 18 | 3994993 | 3995299 | | | 18 | 10678836 | 10679671 |
| 18 | 3999308 | 3999489 | | | 18 | 10680875 | 10681311 |
| 18 | 4015209 | 4015698 | | | 18 | 10687737 | 10688286 |
| 18 | 4018472 | 4019258 | | | 18 | 10693941 | 10697161 |
| 18 | 4027309 | 4029629 | | | 18 | 10701146 | 10702306 |
| 18 | 4045340 | 4045621 | | | 18 | 10705724 | 10707503 |
| 18 | 4051821 | 4054676 | | | 18 | 10714197 | 10723894 |
| 18 | 4058095 | 4058932 | | | 18 | 10735061 | 10738136 |
| 18 | 4060831 | 4060975 | | | 18 | 10741770 | 10742589 |
| 18 | 4064699 | 4065788 | | | 18 | 10744158 | 10755794 |
| 18 | 4073539 | 4074548 | | | 18 | 10756831 | 10757139 |
| 18 | 4098009 | 4098329 | | | 18 | 10757922 | 10760481 |
| 18 | 4112414 | 4112659 | | | 18 | 10767221 | 10767742 |
| 18 | 4126522 | 4127423 | | | 18 | 10769718 | 10770084 |
| 18 | 4140352 | 4141031 | | | 18 | 10773703 | 10774393 |
| 18 | 4148065 | 4148219 | | | 18 | 10782914 | 10783497 |
| 18 | 4151911 | 4152332 | | | 18 | 10784937 | 10785811 |
| 18 | 4167168 | 4168181 | | | 18 | 10787589 | 10787862 |
| 18 | 4170892 | 4171570 | | | 18 | 10791131 | 10799028 |
| 18 | 4174432 | 4174548 | | | 18 | 10805844 | 10806029 |
| 18 | 4181485 | 4182172 | | | 18 | 10808372 | 10808472 |
| 18 | 4192562 | 4192788 | | | 18 | 10810857 | 10811381 |
| 18 | 4205011 | 4205798 | | | 18 | 10819118 | 10820484 |
| 18 | 4213050 | 4213449 | | | 18 | 10822522 | 10823882 |
| 18 | 4214939 | 4220290 | | | 18 | 10829070 | 10829727 |
| 18 | 4222453 | 4223541 | | | 18 | 10835923 | 10836075 |
| 18 | 4226700 | 4227404 | | | 18 | 10839345 | 10839560 |
| 18 | 4229034 | 4229442 | | | 18 | 10849172 | 10850545 |
| 18 | 4231759 | 4231989 | | | 18 | 10857841 | 10859529 |
| 18 | 4233428 | 4233771 | | | 18 | 10867531 | 10869714 |
| 18 | 4235410 | 4236422 | | | 18 | 10879925 | 10880797 |
| 18 | 4237063 | 4238997 | | | 18 | 10882328 | 10884134 |
| 18 | 4240592 | 4249959 | | | 18 | 10889554 | 10890932 |
| 18 | 4256027 | 4257371 | | | 18 | 10897814 | 10898234 |
| 18 | 4272573 | 4273446 | | | 18 | 10904145 | 10904430 |
| 18 | 4280855 | 4281172 | | | 18 | 10910165 | 10910398 |
| 18 | 4284250 | 4285059 | | | 18 | 10913130 | 10913662 |
| 18 | 4317961 | 4322123 | | | 18 | 10914738 | 10917178 |
| 18 | 4325379 | 4326094 | | | 18 | 10927360 | 10927760 |
| 18 | 4332217 | 4332701 | | | 18 | 10939627 | 10940083 |
| 18 | 4332894 | 4334321 | | | 18 | 10948099 | 10949264 |
| 18 | 4338192 | 4339460 | | | 18 | 10956127 | 10956573 |
| 18 | 4340529 | 4344467 | | | 18 | 10962771 | 10965819 |
| 18 | 4345501 | 4345836 | | | 18 | 10970889 | 10970901 |
| 18 | 4349717 | 4350053 | | | 18 | 10973413 | 10973633 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 4360916 | 4361355 | 18 | 10980452 | 10981034 |
| 18 | 4367469 | 4367478 | 18 | 10991162 | 10991998 |
| 18 | 4368441 | 4369470 | 18 | 10992278 | 10992423 |
| 18 | 4371969 | 4376822 | 18 | 11000205 | 11002029 |
| 18 | 4377540 | 4378513 | 18 | 11003381 | 11006673 |
| 18 | 4378727 | 4379813 | 18 | 11021378 | 11022625 |
| 18 | 4380328 | 4380752 | 18 | 11027958 | 11028794 |
| 18 | 4381743 | 4382844 | 18 | 11032127 | 11032715 |
| 18 | 4389475 | 4389904 | 18 | 11035687 | 11036261 |
| 18 | 4408792 | 4409420 | 18 | 11037058 | 11037876 |
| 18 | 4424700 | 4425016 | 18 | 11040589 | 11041276 |
| 18 | 4430703 | 4431850 | 18 | 11042980 | 11043657 |
| 18 | 4439046 | 4439900 | 18 | 11044628 | 11045589 |
| 18 | 4441450 | 4441618 | 18 | 11048030 | 11053690 |
| 18 | 4449003 | 4449567 | 18 | 11060113 | 11065239 |
| 18 | 4454090 | 4454385 | 18 | 11078250 | 11079450 |
| 18 | 4472420 | 4472942 | 18 | 11084847 | 11088069 |
| 18 | 4490918 | 4491745 | 18 | 11091011 | 11091832 |
| 18 | 4493560 | 4494309 | 18 | 11093144 | 11095738 |
| 18 | 4507382 | 4508630 | 18 | 11100373 | 11102646 |
| 18 | 4510289 | 4510970 | 18 | 11104369 | 11105515 |
| 18 | 4512362 | 4512878 | 18 | 11107889 | 11109649 |
| 18 | 4515115 | 4516112 | 18 | 11111832 | 11116914 |
| 18 | 4521652 | 4521802 | 18 | 11123626 | 11125319 |
| 18 | 4525296 | 4525730 | 18 | 11127052 | 11128962 |
| 18 | 4529127 | 4529702 | 18 | 11131228 | 11137184 |
| 18 | 4534329 | 4535124 | 18 | 11138002 | 11138242 |
| 18 | 4548769 | 4555320 | 18 | 11153641 | 11154163 |
| 18 | 4572076 | 4573502 | 18 | 11156854 | 11158011 |
| 18 | 4579184 | 4579961 | 18 | 11162234 | 11163430 |
| 18 | 4584211 | 4584919 | 18 | 11165703 | 11166667 |
| 18 | 4590421 | 4591462 | 18 | 11170375 | 11173093 |
| 18 | 4594200 | 4600101 | 18 | 11180082 | 11183580 |
| 18 | 4601594 | 4602705 | 18 | 11186456 | 11189211 |
| 18 | 4603490 | 4603500 | 18 | 11192707 | 11196471 |
| 18 | 4612926 | 4615355 | 18 | 11199802 | 11202787 |
| 18 | 4617525 | 4619028 | 18 | 11203025 | 11203215 |
| 18 | 4619660 | 4619903 | 18 | 11204015 | 11205091 |
| 18 | 4621779 | 4622023 | 18 | 11206591 | 11207880 |
| 18 | 4622706 | 4623035 | 18 | 11211603 | 11211865 |
| 18 | 4624975 | 4625542 | 18 | 11213595 | 11213840 |
| 18 | 4626937 | 4627714 | 18 | 11221412 | 11221622 |
| 18 | 4630584 | 4631133 | 18 | 11222860 | 11223519 |
| 18 | 4634365 | 4634611 | 18 | 11233460 | 11233860 |
| 18 | 4638850 | 4642396 | 18 | 11234669 | 11235363 |
| 18 | 4644777 | 4645627 | 18 | 11237621 | 11239265 |
| 18 | 4648103 | 4648953 | 18 | 11242009 | 11243533 |
| 18 | 4652907 | 4653741 | 18 | 11244186 | 11244486 |
| 18 | 4654989 | 4655178 | 18 | 11245456 | 11245690 |
| 18 | 4655379 | 4656073 | 18 | 11247376 | 11248895 |
| 18 | 4658069 | 4658181 | 18 | 11255602 | 11257735 |
| 18 | 4662241 | 4663448 | 18 | 11265900 | 11276406 |
| 18 | 4694081 | 4694664 | 18 | 11281412 | 11281569 |
| 18 | 4711301 | 4715012 | 18 | 11282964 | 11283152 |
| 18 | 4718186 | 4718625 | 18 | 11285446 | 11288700 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 4723891 | 4727180 | | | 18 | 11300716 | 11304537 |
| 18 | 4728971 | 4730911 | | | 18 | 11304684 | 11305060 |
| 18 | 4741235 | 4746931 | | | 18 | 11308260 | 11310203 |
| 18 | 4752767 | 4753158 | | | 18 | 11311407 | 11314255 |
| 18 | 4758222 | 4758990 | | | 18 | 11320018 | 11320900 |
| 18 | 4768968 | 4772741 | | | 18 | 11325352 | 11325894 |
| 18 | 4776252 | 4776869 | | | 18 | 11326845 | 11327135 |
| 18 | 4781981 | 4785197 | | | 18 | 11340192 | 11348340 |
| 18 | 4787515 | 4788229 | | | 18 | 11350549 | 11351172 |
| 18 | 4792780 | 4793160 | | | 18 | 11366754 | 11374181 |
| 18 | 4797562 | 4798161 | | | 18 | 11376635 | 11378031 |
| 18 | 4798461 | 4798753 | | | 18 | 11392003 | 11392785 |
| 18 | 4801878 | 4802189 | | | 18 | 11394811 | 11395840 |
| 18 | 4812911 | 4813171 | | | 18 | 11398212 | 11398496 |
| 18 | 4813402 | 4814905 | | | 18 | 11404469 | 11405110 |
| 18 | 4823057 | 4823481 | | | 18 | 11409122 | 11409492 |
| 18 | 4831569 | 4832013 | | | 18 | 11410993 | 11411092 |
| 18 | 4843240 | 4843678 | | | 18 | 11413949 | 11415422 |
| 18 | 4850809 | 4851380 | | | 18 | 11417250 | 11418465 |
| 18 | 4857390 | 4857773 | | | 18 | 11420111 | 11420701 |
| 18 | 4893279 | 4894970 | | | 18 | 11421791 | 11422980 |
| 18 | 4896618 | 4897761 | | | 18 | 11425921 | 11432539 |
| 18 | 4899043 | 4899759 | | | 18 | 11442487 | 11442949 |
| 18 | 4910689 | 4910699 | | | 18 | 11444827 | 11445395 |
| 18 | 4916644 | 4919365 | | | 18 | 11449374 | 11449567 |
| 18 | 4921140 | 4924573 | | | 18 | 11456312 | 11456613 |
| 18 | 4972072 | 4972750 | | | 18 | 11457271 | 11458602 |
| 18 | 4975940 | 4976760 | | | 18 | 11459000 | 11459994 |
| 18 | 4981746 | 4984156 | | | 18 | 11460324 | 11461024 |
| 18 | 4984986 | 4985235 | | | 18 | 11484633 | 11484854 |
| 18 | 5003865 | 5004668 | | | 18 | 11489601 | 11495685 |
| 18 | 5027408 | 5027564 | | | 18 | 11496560 | 11497132 |
| 18 | 5033970 | 5034550 | | | 18 | 11503359 | 11524354 |
| 18 | 5039773 | 5040435 | | | 18 | 11531971 | 11534328 |
| 18 | 5042415 | 5043524 | | | 18 | 11535534 | 11536164 |
| 18 | 5056147 | 5056343 | | | 18 | 11542085 | 11542634 |
| 18 | 5058781 | 5059711 | | | 18 | 11553918 | 11563502 |
| 18 | 5066219 | 5066688 | | | 18 | 11567529 | 11568185 |
| 18 | 5069201 | 5070151 | | | 18 | 11568953 | 11570497 |
| 18 | 5079430 | 5081939 | | | 18 | 11580946 | 11581292 |
| 18 | 5087211 | 5087765 | | | 18 | 11588289 | 11588997 |
| 18 | 5090356 | 5091518 | | | 18 | 11623716 | 11634149 |
| 18 | 5093672 | 5093916 | | | 18 | 11641033 | 11655573 |
| 18 | 5097836 | 5100259 | | | 18 | 11659557 | 11669143 |
| 18 | 5106104 | 5107086 | | | 18 | 11671958 | 11672256 |
| 18 | 5118576 | 5121276 | | | 18 | 11679899 | 11693348 |
| 18 | 5126858 | 5127361 | | | 18 | 11719685 | 11719933 |
| 18 | 5138352 | 5140274 | | | 18 | 11732359 | 11734234 |
| 18 | 5141824 | 5143505 | | | 18 | 11739667 | 11741557 |
| 18 | 5144727 | 5146152 | | | 18 | 11747638 | 11748285 |
| 18 | 5150489 | 5159577 | | | 18 | 11750024 | 11751259 |
| 18 | 5161130 | 5162872 | | | 18 | 11759505 | 11759793 |
| 18 | 5164406 | 5164905 | | | 18 | 11765374 | 11765564 |
| 18 | 5166832 | 5167090 | | | 18 | 11768235 | 11769791 |
| 18 | 5171383 | 5172153 | | | 18 | 11773476 | 11774421 |

The chromosomal positon was obtained from UCSC genome browser (http://genome.ucsc.edu/) build 36.

APPENDIX C: Chromosome 18
Page 13 of 72

| Chr | Start | End | Chr | Start | End |
|---|---|---|---|---|---|
| 18 | 5187757 | 5188333 | 18 | 11774806 | 11775297 |
| 18 | 5191800 | 5192839 | 18 | 11777261 | 11778491 |
| 18 | 5196630 | 5197247 | 18 | 11790115 | 11791030 |
| 18 | 5197801 | 5198887 | 18 | 11793353 | 11795015 |
| 18 | 5203539 | 5204193 | 18 | 11800560 | 11801500 |
| 18 | 5209169 | 5209446 | 18 | 11807369 | 11809308 |
| 18 | 5213647 | 5214590 | 18 | 11827754 | 11829216 |
| 18 | 5221207 | 5223203 | 18 | 11829832 | 11831346 |
| 18 | 5224099 | 5224918 | 18 | 11841374 | 11842559 |
| 18 | 5228369 | 5228854 | 18 | 11848932 | 11853192 |
| 18 | 5236972 | 5238535 | 18 | 11853461 | 11853816 |
| 18 | 5245953 | 5246597 | 18 | 11867944 | 11871502 |
| 18 | 5254029 | 5257273 | 18 | 11888828 | 11889227 |
| 18 | 5265810 | 5266017 | 18 | 11904014 | 11906006 |
| 18 | 5270669 | 5272304 | 18 | 11911124 | 11912095 |
| 18 | 5274678 | 5275484 | 18 | 11918487 | 11918853 |
| 18 | 5280397 | 5282961 | 18 | 11933984 | 11935394 |
| 18 | 5283289 | 5284614 | 18 | 11944396 | 11945793 |
| 18 | 5290596 | 5290924 | 18 | 11951353 | 11953118 |
| 18 | 5295882 | 5299394 | 18 | 11960644 | 11962862 |
| 18 | 5300527 | 5303164 | 18 | 11969536 | 11974086 |
| 18 | 5308708 | 5308887 | 18 | 11980489 | 11981324 |
| 18 | 5309413 | 5313283 | 18 | 11983484 | 11985349 |
| 18 | 5324616 | 5329673 | 18 | 12004286 | 12004796 |
| 18 | 5329803 | 5330169 | 18 | 12018338 | 12020684 |
| 18 | 5331060 | 5331866 | 18 | 12024741 | 12029353 |
| 18 | 5336856 | 5338626 | 18 | 12037671 | 12038816 |
| 18 | 5341945 | 5343981 | 18 | 12039329 | 12040291 |
| 18 | 5345743 | 5346683 | 18 | 12042944 | 12043519 |
| 18 | 5347610 | 5347865 | 18 | 12044572 | 12044990 |
| 18 | 5352513 | 5355458 | 18 | 12046252 | 12046622 |
| 18 | 5372694 | 5373186 | 18 | 12050180 | 12060216 |
| 18 | 5378593 | 5380601 | 18 | 12063432 | 12063996 |
| 18 | 5384080 | 5385065 | 18 | 12065717 | 12066392 |
| 18 | 5399799 | 5401146 | 18 | 12075094 | 12076883 |
| 18 | 5404936 | 5406786 | 18 | 12080708 | 12085938 |
| 18 | 5407229 | 5409410 | 18 | 12091293 | 12091726 |
| 18 | 5411243 | 5412652 | 18 | 12091797 | 12092738 |
| 18 | 5414721 | 5415580 | 18 | 12104736 | 12106316 |
| 18 | 5418947 | 5419261 | 18 | 12117775 | 12120123 |
| 18 | 5430159 | 5430503 | 18 | 12131465 | 12135773 |
| 18 | 5434747 | 5435501 | 18 | 12149982 | 12153738 |
| 18 | 5439040 | 5439289 | 18 | 12156175 | 12156577 |
| 18 | 5446377 | 5447872 | 18 | 12205080 | 12205340 |
| 18 | 5448290 | 5448772 | 18 | 12215529 | 12242486 |
| 18 | 5450690 | 5453395 | 18 | 12245188 | 12245964 |
| 18 | 5462505 | 5463056 | 18 | 12247403 | 12249563 |
| 18 | 5464726 | 5466087 | 18 | 12250677 | 12251017 |
| 18 | 5471058 | 5472417 | 18 | 12253764 | 12255501 |
| 18 | 5490031 | 5490821 | 18 | 12264863 | 12266683 |
| 18 | 5494842 | 5497116 | 18 | 12268883 | 12270003 |
| 18 | 5499066 | 5499269 | 18 | 12272892 | 12273523 |
| 18 | 5499409 | 5499528 | 18 | 12278370 | 12284549 |
| 18 | 5501560 | 5502857 | 18 | 12297204 | 12297446 |
| 18 | 5505168 | 5506328 | 18 | 12298332 | 12300024 |

The chromosomal positon was obtained from UCSC genome browser (http://genome.ucsc.edu/) build 36.

APPENDIX C: Chromosome 18
Page 14 of 72

| Chr | Start | End | Chr | Start | End |
|---|---|---|---|---|---|
| 18 | 5507759 | 5508395 | 18 | 12307960 | 12311368 |
| 18 | 5516866 | 5517409 | 18 | 12314885 | 12316179 |
| 18 | 5523587 | 5524430 | 18 | 12325028 | 12325332 |
| 18 | 5527154 | 5527639 | 18 | 12348375 | 12348570 |
| 18 | 5539266 | 5539827 | 18 | 12363473 | 12364135 |
| 18 | 5544977 | 5545510 | 18 | 12365194 | 12366604 |
| 18 | 5549370 | 5549544 | 18 | 12384340 | 12398719 |
| 18 | 5559832 | 5560293 | 18 | 12400390 | 12401865 |
| 18 | 5561621 | 5563857 | 18 | 12412911 | 12413811 |
| 18 | 5576146 | 5577981 | 18 | 12418929 | 12425059 |
| 18 | 5585164 | 5585764 | 18 | 12428332 | 12428706 |
| 18 | 5594369 | 5594790 | 18 | 12430320 | 12432306 |
| 18 | 5598136 | 5598874 | 18 | 12438941 | 12441761 |
| 18 | 5614312 | 5617062 | 18 | 12444758 | 12445836 |
| 18 | 5618197 | 5620371 | 18 | 12460321 | 12464491 |
| 18 | 5626672 | 5626910 | 18 | 12502660 | 12503104 |
| 18 | 5628019 | 5629586 | 18 | 12521389 | 12521505 |
| 18 | 5632873 | 5635295 | 18 | 12522966 | 12524632 |
| 18 | 5640643 | 5642042 | 18 | 12528516 | 12529534 |
| 18 | 5645158 | 5645168 | 18 | 12535107 | 12537490 |
| 18 | 5649521 | 5649804 | 18 | 12560925 | 12563003 |
| 18 | 5654436 | 5655460 | 18 | 12569146 | 12570730 |
| 18 | 5660588 | 5660903 | 18 | 12577253 | 12577841 |
| 18 | 5666144 | 5669060 | 18 | 12582703 | 12583601 |
| 18 | 5683173 | 5683651 | 18 | 12590386 | 12590600 |
| 18 | 5687771 | 5687908 | 18 | 12602200 | 12603501 |
| 18 | 5689735 | 5690274 | 18 | 12616100 | 12616720 |
| 18 | 5699328 | 5700726 | 18 | 12620315 | 12623303 |
| 18 | 5713958 | 5715044 | 18 | 12630154 | 12636590 |
| 18 | 5718793 | 5719328 | 18 | 12650837 | 12652859 |
| 18 | 5724436 | 5724722 | 18 | 12662831 | 12663943 |
| 18 | 5729833 | 5730270 | 18 | 12676564 | 12677149 |
| 18 | 5733598 | 5734412 | 18 | 12691816 | 12692932 |
| 18 | 5751441 | 5751701 | 18 | 12693526 | 12696162 |
| 18 | 5756642 | 5758005 | 18 | 12707924 | 12708624 |
| 18 | 5759641 | 5760773 | 18 | 12723421 | 12726436 |
| 18 | 5762387 | 5762921 | 18 | 12731535 | 12733643 |
| 18 | 5769672 | 5770027 | 18 | 12739280 | 12740753 |
| 18 | 5776283 | 5776708 | 18 | 12745556 | 12750343 |
| 18 | 5785996 | 5788087 | 18 | 12756627 | 12757478 |
| 18 | 5792525 | 5793405 | 18 | 12759007 | 12760002 |
| 18 | 5795630 | 5799107 | 18 | 12767510 | 12769800 |
| 18 | 5811877 | 5812614 | 18 | 12782144 | 12783485 |
| 18 | 5816228 | 5817070 | 18 | 12786644 | 12786905 |
| 18 | 5823113 | 5823449 | 18 | 12806364 | 12807580 |
| 18 | 5835637 | 5835836 | 18 | 12810979 | 12811880 |
| 18 | 5838648 | 5839130 | 18 | 12817827 | 12819217 |
| 18 | 5852314 | 5855840 | 18 | 12823422 | 12823987 |
| 18 | 5858555 | 5859467 | 18 | 12835927 | 12837096 |
| 18 | 5861827 | 5862307 | 18 | 12850819 | 12852927 |
| 18 | 5865889 | 5865914 | 18 | 12872649 | 12873084 |
| 18 | 5867989 | 5869282 | 18 | 12877343 | 12877473 |
| 18 | 5870709 | 5870844 | 18 | 12882447 | 12884442 |
| 18 | 5879528 | 5881970 | 18 | 12893905 | 12894209 |
| 18 | 5889982 | 5890516 | 18 | 12901595 | 12902725 |

The chromosomal positon was obtained from UCSC genome browser (http://genome.ucsc.edu/) build 36.

APPENDIX C: Chromosome 18
Page 15 of 72

| Chr | Start | End | Chr | Start | End |
|---|---|---|---|---|---|
| 18 | 5896533 | 5896907 | 18 | 12910998 | 12911170 |
| 18 | 5904424 | 5905764 | 18 | 12929820 | 12930326 |
| 18 | 5907201 | 5907839 | 18 | 12939311 | 12940713 |
| 18 | 5914994 | 5915799 | 18 | 12957504 | 12962623 |
| 18 | 5921605 | 5923080 | 18 | 12981661 | 12983948 |
| 18 | 5925876 | 5926296 | 18 | 12984481 | 12985021 |
| 18 | 5932872 | 5933063 | 18 | 12993671 | 12995120 |
| 18 | 5933329 | 5933582 | 18 | 13002127 | 13002996 |
| 18 | 5940960 | 5941256 | 18 | 13003925 | 13007960 |
| 18 | 5945277 | 5960924 | 18 | 13009697 | 13013329 |
| 18 | 5963849 | 5964619 | 18 | 13020357 | 13020699 |
| 18 | 5966576 | 5969166 | 18 | 13022649 | 13023530 |
| 18 | 5970798 | 5971506 | 18 | 13032948 | 13033277 |
| 18 | 5983379 | 5985129 | 18 | 13034538 | 13035068 |
| 18 | 5987287 | 5987297 | 18 | 13038605 | 13040452 |
| 18 | 6002887 | 6006466 | 18 | 13046047 | 13047825 |
| 18 | 6021059 | 6021134 | 18 | 13051697 | 13052907 |
| 18 | 6031039 | 6032866 | 18 | 13056288 | 13056837 |
| 18 | 6041824 | 6042788 | 18 | 13058597 | 13059697 |
| 18 | 6048969 | 6049298 | 18 | 13079076 | 13079561 |
| 18 | 6051871 | 6052634 | 18 | 13080632 | 13081274 |
| 18 | 6066006 | 6066499 | 18 | 13091626 | 13092911 |
| 18 | 6086982 | 6088088 | 18 | 13098213 | 13099146 |
| 18 | 6095090 | 6096192 | 18 | 13105368 | 13106369 |
| 18 | 6097387 | 6100763 | 18 | 13106477 | 13108402 |
| 18 | 6104648 | 6107286 | 18 | 13110730 | 13111547 |
| 18 | 6120865 | 6124126 | 18 | 13115896 | 13117673 |
| 18 | 6131359 | 6132390 | 18 | 13119759 | 13122170 |
| 18 | 6133787 | 6136757 | 18 | 13123420 | 13134721 |
| 18 | 6141829 | 6141858 | 18 | 13146155 | 13146463 |
| 18 | 6146040 | 6146690 | 18 | 13147374 | 13147541 |
| 18 | 6147196 | 6147548 | 18 | 13151593 | 13152103 |
| 18 | 6149080 | 6150386 | 18 | 13155178 | 13156130 |
| 18 | 6162331 | 6162852 | 18 | 13167043 | 13167282 |
| 18 | 6168648 | 6169280 | 18 | 13171339 | 13179382 |
| 18 | 6176712 | 6177334 | 18 | 13181288 | 13182189 |
| 18 | 6183419 | 6184736 | 18 | 13193127 | 13194119 |
| 18 | 6199065 | 6199538 | 18 | 13201594 | 13205743 |
| 18 | 6203730 | 6204144 | 18 | 13214268 | 13215496 |
| 18 | 6208760 | 6209559 | 18 | 13221168 | 13236532 |
| 18 | 6216864 | 6217489 | 18 | 13241654 | 13245942 |
| 18 | 6221321 | 6221937 | 18 | 13246715 | 13247450 |
| 18 | 6222657 | 6225432 | 18 | 13251261 | 13264578 |
| 18 | 6231408 | 6232906 | 18 | 13270267 | 13278003 |
| 18 | 6234069 | 6234363 | 18 | 13282352 | 13292733 |
| 18 | 6238335 | 6239376 | 18 | 13303860 | 13311344 |
| 18 | 6243706 | 6243791 | 18 | 13316735 | 13318249 |
| 18 | 6245356 | 6266525 | 18 | 13349480 | 13366605 |
| 18 | 6267867 | 6268191 | 18 | 13373196 | 13374227 |
| 18 | 6274247 | 6276540 | 18 | 13377138 | 13383573 |
| 18 | 6293609 | 6294374 | 18 | 13386986 | 13396735 |
| 18 | 6295809 | 6296273 | 18 | 13399804 | 13400436 |
| 18 | 6300512 | 6301564 | 18 | 13400620 | 13401308 |
| 18 | 6305131 | 6306391 | 18 | 13402409 | 13423179 |
| 18 | 6314512 | 6315053 | 18 | 13425838 | 13426232 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 6318895 | 6320688 | 18 | 13428472 | 13428935 |
| 18 | 6321537 | 6321853 | 18 | 13432008 | 13444778 |
| 18 | 6335680 | 6336009 | 18 | 13448976 | 13451413 |
| 18 | 6346326 | 6347410 | 18 | 13452824 | 13454288 |
| 18 | 6352387 | 6353188 | 18 | 13454319 | 13456663 |
| 18 | 6354787 | 6356249 | 18 | 13460592 | 13472483 |
| 18 | 6365227 | 6366777 | 18 | 13482313 | 13482348 |
| 18 | 6380346 | 6380857 | 18 | 13487802 | 13495869 |
| 18 | 6382988 | 6395480 | 18 | 13499392 | 13499989 |
| 18 | 6420491 | 6422078 | 18 | 13510213 | 13510924 |
| 18 | 6424726 | 6424956 | 18 | 13512002 | 13513216 |
| 18 | 6426381 | 6428834 | 18 | 13515489 | 13515914 |
| 18 | 6438435 | 6438747 | 18 | 13517260 | 13518270 |
| 18 | 6444529 | 6444958 | 18 | 13522217 | 13524157 |
| 18 | 6457109 | 6458885 | 18 | 13532221 | 13534345 |
| 18 | 6463211 | 6464467 | 18 | 13536311 | 13536786 |
| 18 | 6466421 | 6467191 | 18 | 13539606 | 13543841 |
| 18 | 6474460 | 6476096 | 18 | 13549980 | 13550560 |
| 18 | 6479128 | 6479893 | 18 | 13551813 | 13552384 |
| 18 | 6485316 | 6487427 | 18 | 13555220 | 13556702 |
| 18 | 6493623 | 6494501 | 18 | 13567180 | 13568138 |
| 18 | 6501886 | 6505881 | 18 | 13569822 | 13582075 |
| 18 | 6511781 | 6512197 | 18 | 13582264 | 13582622 |
| 18 | 6516024 | 6516254 | 18 | 13593668 | 13602208 |
| 18 | 6517804 | 6518541 | 18 | 13604927 | 13605504 |
| 18 | 6523484 | 6523750 | 18 | 13608898 | 13619337 |
| 18 | 6532439 | 6533729 | 18 | 13629478 | 13640922 |
| 18 | 6540509 | 6541134 | 18 | 13644251 | 13644731 |
| 18 | 6545700 | 6548172 | 18 | 13654225 | 13654281 |
| 18 | 6549233 | 6556485 | 18 | 13670605 | 13671426 |
| 18 | 6559288 | 6560518 | 18 | 13686126 | 13686314 |
| 18 | 6565831 | 6566226 | 18 | 13689580 | 13691146 |
| 18 | 6569790 | 6570576 | 18 | 13696139 | 13699168 |
| 18 | 6574385 | 6574846 | 18 | 13713324 | 13713715 |
| 18 | 6578808 | 6579464 | 18 | 13716175 | 13716850 |
| 18 | 6582128 | 6583378 | 18 | 13724890 | 13725369 |
| 18 | 6596288 | 6597327 | 18 | 13727215 | 13728332 |
| 18 | 6598575 | 6599431 | 18 | 13728363 | 13728742 |
| 18 | 6600511 | 6601026 | 18 | 13737393 | 13737674 |
| 18 | 6607786 | 6608435 | 18 | 13746055 | 13747627 |
| 18 | 6611138 | 6611330 | 18 | 13748634 | 13749159 |
| 18 | 6617840 | 6618578 | 18 | 13780758 | 13781744 |
| 18 | 6621320 | 6623688 | 18 | 13786600 | 13787214 |
| 18 | 6629893 | 6635767 | 18 | 13788948 | 13789747 |
| 18 | 6638035 | 6638752 | 18 | 13801549 | 13819511 |
| 18 | 6642193 | 6643444 | 18 | 13822269 | 13823805 |
| 18 | 6647875 | 6647882 | 18 | 13826650 | 13827374 |
| 18 | 6650677 | 6650991 | 18 | 13831958 | 13835494 |
| 18 | 6651868 | 6652728 | 18 | 13842123 | 13842811 |
| 18 | 6656402 | 6656622 | 18 | 13845230 | 13845729 |
| 18 | 6662400 | 6662984 | 18 | 13855257 | 13855553 |
| 18 | 6672566 | 6673942 | 18 | 13857615 | 13862472 |
| 18 | 6676382 | 6676703 | 18 | 13865364 | 13883209 |
| 18 | 6681417 | 6681702 | 18 | 13900503 | 13901278 |
| 18 | 6702993 | 6703754 | 18 | 13903267 | 13903509 |

The chromosomal positon was obtained from UCSC genome browser (http://genome.ucsc.edu/) build 36.

APPENDIX C: Chromosome 18
Page 17 of 72

| Chr | Start | End | | | Chr | Start | End |
|---|---|---|---|---|---|---|---|
| 18 | 6704870 | 6706004 | | | 18 | 13905767 | 13906247 |
| 18 | 6717983 | 6718549 | | | 18 | 13913626 | 13914618 |
| 18 | 6720167 | 6720894 | | | 18 | 13919399 | 13920139 |
| 18 | 6723044 | 6723867 | | | 18 | 13921679 | 13922485 |
| 18 | 6730493 | 6731200 | | | 18 | 13926941 | 13927784 |
| 18 | 6733651 | 6734099 | | | 18 | 13929910 | 13930556 |
| 18 | 6735700 | 6736364 | | | 18 | 13937075 | 13937484 |
| 18 | 6737209 | 6741489 | | | 18 | 13943613 | 13944014 |
| 18 | 6750594 | 6750711 | | | 18 | 13945848 | 13948502 |
| 18 | 6750973 | 6753002 | | | 18 | 13961129 | 13962297 |
| 18 | 6754652 | 6755014 | | | 18 | 13963388 | 13963815 |
| 18 | 6760049 | 6760599 | | | 18 | 13982166 | 13983852 |
| 18 | 6761868 | 6765595 | | | 18 | 13986817 | 13987919 |
| 18 | 6771420 | 6771645 | | | 18 | 13988596 | 13990765 |
| 18 | 6776603 | 6776723 | | | 18 | 13992227 | 13997519 |
| 18 | 6786999 | 6788625 | | | 18 | 14006177 | 14006380 |
| 18 | 6797295 | 6805033 | | | 18 | 14010063 | 14010655 |
| 18 | 6809050 | 6812112 | | | 18 | 14016690 | 14017181 |
| 18 | 6823192 | 6823804 | | | 18 | 14024105 | 14025034 |
| 18 | 6827229 | 6827740 | | | 18 | 14036719 | 14036948 |
| 18 | 6834712 | 6835011 | | | 18 | 14045055 | 14046032 |
| 18 | 6839976 | 6840396 | | | 18 | 14046727 | 14047162 |
| 18 | 6842428 | 6843248 | | | 18 | 14061976 | 14062986 |
| 18 | 6849459 | 6849663 | | | 18 | 14066151 | 14066441 |
| 18 | 6855509 | 6856563 | | | 18 | 14068475 | 14069819 |
| 18 | 6857530 | 6858898 | | | 18 | 14073552 | 14074442 |
| 18 | 6859867 | 6860003 | | | 18 | 14085877 | 14086422 |
| 18 | 6862957 | 6863184 | | | 18 | 14087328 | 14087958 |
| 18 | 6863590 | 6863829 | | | 18 | 14088053 | 14088567 |
| 18 | 6867927 | 6869408 | | | 18 | 14097927 | 14099335 |
| 18 | 6870212 | 6871189 | | | 18 | 14101013 | 14101846 |
| 18 | 6876513 | 6876936 | | | 18 | 14110774 | 14111278 |
| 18 | 6880576 | 6883180 | | | 18 | 14114746 | 14115102 |
| 18 | 6884867 | 6885902 | | | 18 | 14135365 | 14142755 |
| 18 | 6890551 | 6891672 | | | 18 | 14163274 | 14170040 |
| 18 | 6907893 | 6911025 | | | 18 | 14173651 | 14181083 |
| 18 | 6914326 | 6915562 | | | 18 | 14204230 | 14205760 |
| 18 | 6937252 | 6937704 | | | 18 | 14211797 | 14226499 |
| 18 | 6941148 | 6944762 | | | 18 | 14273472 | 14273872 |
| 18 | 6945542 | 6947298 | | | 18 | 14279113 | 14279507 |
| 18 | 6949599 | 6949758 | | | 18 | 14289973 | 14290254 |
| 18 | 6950470 | 6950763 | | | 18 | 14301702 | 14302951 |
| 18 | 6950925 | 6951534 | | | 18 | 14309455 | 14323342 |
| 18 | 6952816 | 6954113 | | | 18 | 14324427 | 14330971 |
| 18 | 6955349 | 6957128 | | | 18 | 14340134 | 14341161 |
| 18 | 6958119 | 6958319 | | | 18 | 14349657 | 14350289 |
| 18 | 6961747 | 6962431 | | | 18 | 14350814 | 14352424 |
| 18 | 6982264 | 6985220 | | | 18 | 14382346 | 14383981 |
| 18 | 6990438 | 6990778 | | | 18 | 14409152 | 14410239 |
| 18 | 6992164 | 6992325 | | | 18 | 14420566 | 14422555 |
| 18 | 6995791 | 6995804 | | | 18 | 14448308 | 14453629 |
| 18 | 6997895 | 6998756 | | | 18 | 14456516 | 14456936 |
| 18 | 7000960 | 7001469 | | | 18 | 14463793 | 14465768 |
| 18 | 7002840 | 7003459 | | | 18 | 14474410 | 14479244 |
| 18 | 7008043 | 7011299 | | | 18 | 14517963 | 14529756 |

The chromosomal positon was obtained from UCSC genome browser (http://genome.ucsc.edu/) build 36.

APPENDIX C: Chromosome 18
Page 18 of 72

| Chr | Start | End | | | Chr | Start | End |
|---|---|---|---|---|---|---|---|
| 18 | 7012972 | 7015438 | | | 18 | 14532639 | 14535398 |
| 18 | 7017199 | 7018216 | | | 18 | 14560616 | 14605831 |
| 18 | 7026820 | 7027453 | | | 18 | 14701140 | 14707134 |
| 18 | 7028158 | 7029069 | | | 18 | 14711998 | 14716353 |
| 18 | 7029554 | 7030405 | | | 18 | 14720823 | 14721389 |
| 18 | 7040811 | 7041239 | | | 18 | 14747256 | 14751272 |
| 18 | 7051883 | 7052478 | | | 18 | 14760736 | 14761627 |
| 18 | 7052914 | 7053283 | | | 18 | 14828921 | 14831240 |
| 18 | 7080586 | 7080790 | | | 18 | 14854671 | 14858527 |
| 18 | 7084508 | 7084740 | | | 18 | 14865819 | 14880221 |
| 18 | 7099146 | 7099870 | | | 18 | 14903594 | 14904389 |
| 18 | 7107547 | 7110146 | | | 18 | 14914557 | 14915842 |
| 18 | 7114213 | 7114524 | | | 18 | 14917721 | 14919350 |
| 18 | 7117515 | 7118020 | | | 18 | 14920535 | 14920615 |
| | | | | | 18 | 14923028 | 14924371 |
| | | | | | 18 | 14925291 | 14926716 |
| | | | | | 18 | 14931329 | 14932004 |
| | | | | | 18 | 14933910 | 14934550 |
| | | | | | 18 | 14938624 | 14938988 |
| | | | | | 18 | 14942173 | 14943977 |
| | | | | | 18 | 14955115 | 14956831 |
| | | | | | 18 | 14970535 | 14971313 |
| | | | | | 18 | 14971416 | 14976797 |
| | | | | | 18 | 14988507 | 14997357 |
| | | | | | 18 | 15008861 | 15016238 |
| | | | | | 18 | 15034636 | 15043117 |
| | | | | | 18 | 15098987 | 15105257 |
| | | | | | 18 | 15109658 | 15114023 |
| | | | | | 18 | 15117038 | 15120351 |
| | | | | | 18 | 15163595 | 15172472 |
| | | | | | 18 | 15189367 | 15192659 |
| | | | | | 18 | 15299011 | 15299822 |
| | | | | | 18 | 15304804 | 15305919 |
| | | | | | 18 | 15315583 | 15318470 |
| | | | | | 18 | 15352744 | 15362152 |
| | | | | | 18 | 15374559 | 15399176 |
| 18 | 16796800 | 16798169 | | | 18 | 44865572 | 44867791 |
| 18 | 16879141 | 16879831 | | | 18 | 44904132 | 44904582 |
| 18 | 17074896 | 17075383 | | | 18 | 44951510 | 44954066 |
| 18 | 17075555 | 17077412 | | | 18 | 44961270 | 44961643 |
| 18 | 17124850 | 17126954 | | | 18 | 45050017 | 45051832 |
| 18 | 17139457 | 17143733 | | | 18 | 45054053 | 45055893 |
| 18 | 17148671 | 17150298 | | | 18 | 45065029 | 45066316 |
| 18 | 17162437 | 17163737 | | | 18 | 45123593 | 45125666 |
| 18 | 17164811 | 17165627 | | | 18 | 45144201 | 45146275 |
| 18 | 17177435 | 17179531 | | | 18 | 45196695 | 45199409 |
| 18 | 17215562 | 17216864 | | | 18 | 45218623 | 45219672 |
| 18 | 17300061 | 17301404 | | | 18 | 45279398 | 45282990 |
| 18 | 17554306 | 17555806 | | | 18 | 45293773 | 45295424 |
| 18 | 17569749 | 17575708 | | | 18 | 45388806 | 45391308 |
| 18 | 17610411 | 17612320 | | | 18 | 45402039 | 45407231 |
| 18 | 17626723 | 17631715 | | | 18 | 45509607 | 45511758 |
| 18 | 17636726 | 17637629 | | | 18 | 45526616 | 45528206 |
| 18 | 17651875 | 17652962 | | | 18 | 45539357 | 45540527 |
| 18 | 17664445 | 17668724 | | | 18 | 45606516 | 45607114 |

The chromosomal positon was obtained from UCSC genome browser (http://genome.ucsc.edu/) build 36.

APPENDIX C: Chromosome 18
Page 19 of 72

| Chr | Start | End | | | Chr | Start | End |
|---|---|---|---|---|---|---|---|
| 18 | 17688929 | 17689534 | | | 18 | 45610714 | 45614197 |
| 18 | 17713717 | 17716517 | | | 18 | 45621808 | 45623776 |
| 18 | 17812426 | 17813230 | | | 18 | 45626526 | 45627831 |
| 18 | 17835874 | 17836870 | | | 18 | 45651873 | 45659545 |
| 18 | 17936829 | 17940734 | | | 18 | 45669812 | 45670703 |
| 18 | 17983830 | 17986449 | | | 18 | 45670838 | 45673013 |
| 18 | 18011024 | 18012925 | | | 18 | 45689729 | 45691647 |
| 18 | 18027107 | 18028080 | | | 18 | 45822239 | 45826100 |
| 18 | 18084389 | 18085725 | | | 18 | 45853545 | 45856125 |
| 18 | 18100459 | 18102560 | | | 18 | 45862987 | 45866512 |
| 18 | 18129422 | 18130607 | | | 18 | 45909888 | 45913915 |
| 18 | 18132517 | 18133781 | | | 18 | 45939525 | 45942053 |
| 18 | 18158541 | 18163191 | | | 18 | 45947846 | 45950242 |
| 18 | 18169758 | 18174805 | | | 18 | 45954449 | 45959157 |
| 18 | 18178386 | 18184599 | | | 18 | 45966891 | 45967522 |
| 18 | 18189078 | 18189892 | | | 18 | 46053359 | 46057634 |
| 18 | 18251760 | 18253080 | | | 18 | 46060261 | 46067421 |
| 18 | 18314918 | 18317652 | | | 18 | 46136293 | 46137324 |
| 18 | 18342783 | 18347171 | | | 18 | 46218683 | 46225057 |
| 18 | 18379112 | 18380243 | | | 18 | 46387334 | 46388039 |
| 18 | 18418194 | 18419322 | | | 18 | 46403481 | 46406182 |
| 18 | 18442443 | 18444555 | | | 18 | 46419586 | 46420423 |
| 18 | 18446906 | 18447621 | | | 18 | 46431145 | 46432430 |
| 18 | 18479838 | 18481216 | | | 18 | 46512072 | 46514742 |
| 18 | 18496965 | 18514392 | | | 18 | 46523574 | 46524745 |
| 18 | 18527097 | 18529506 | | | 18 | 46591986 | 46592581 |
| 18 | 18575287 | 18576758 | | | 18 | 46620133 | 46620338 |
| 18 | 18631552 | 18632988 | | | 18 | 46727486 | 46729635 |
| 18 | 18671303 | 18672731 | | | 18 | 46731653 | 46734413 |
| 18 | 18674942 | 18676886 | | | 18 | 46788413 | 46789503 |
| 18 | 18835504 | 18836311 | | | 18 | 46863542 | 46865455 |
| 18 | 18935875 | 18942163 | | | 18 | 46888207 | 46892888 |
| 18 | 18969045 | 18971985 | | | 18 | 46908491 | 46914025 |
| 18 | 19025533 | 19026857 | | | 18 | 46916056 | 46918552 |
| 18 | 19065633 | 19066133 | | | 18 | 46931791 | 46935396 |
| 18 | 19071118 | 19073283 | | | 18 | 46975066 | 46976328 |
| 18 | 19091254 | 19093999 | | | 18 | 46990841 | 46992086 |
| 18 | 19101001 | 19101896 | | | 18 | 47002671 | 47004699 |
| 18 | 19146790 | 19148234 | | | 18 | 47067797 | 47068656 |
| 18 | 19164675 | 19166593 | | | 18 | 47166911 | 47170145 |
| 18 | 19345478 | 19347611 | | | 18 | 47266882 | 47270395 |
| 18 | 19371784 | 19373087 | | | 18 | 47439310 | 47441837 |
| 18 | 19427160 | 19429059 | | | 18 | 47446094 | 47448574 |
| 18 | 19454352 | 19455247 | | | 18 | 47467188 | 47468208 |
| 18 | 19503753 | 19505504 | | | 18 | 47494121 | 47497820 |
| 18 | 19523400 | 19524000 | | | 18 | 47527227 | 47531284 |
| 18 | 19529308 | 19529490 | | | 18 | 47535642 | 47538959 |
| 18 | 19551060 | 19552656 | | | 18 | 47542338 | 47543451 |
| 18 | 19603352 | 19604000 | | | 18 | 47579495 | 47581244 |
| 18 | 19639675 | 19641870 | | | 18 | 47587539 | 47590008 |
| 18 | 19676536 | 19682581 | | | 18 | 47604402 | 47604937 |
| 18 | 19690964 | 19692259 | | | 18 | 47633447 | 47633649 |
| 18 | 19706439 | 19708305 | | | 18 | 47674403 | 47677603 |
| 18 | 19710815 | 19714258 | | | 18 | 47689373 | 47692389 |
| 18 | 19743134 | 19748788 | | | 18 | 47757967 | 47761756 |

The chromosomal positon was obtained from UCSC genome browser (http://genome.ucsc.edu/) build 36.

APPENDIX C: Chromosome 18
Page 20 of 72

| Chr | Start | End | Chr | Start | End |
|---|---|---|---|---|---|
| 18 | 19761465 | 19762310 | 18 | 47835769 | 47836663 |
| 18 | 19787096 | 19788293 | 18 | 47889046 | 47893222 |
| 18 | 19816205 | 19817245 | 18 | 47955121 | 47960656 |
| 18 | 19845906 | 19846642 | 18 | 47970300 | 47973678 |
| 18 | 19846887 | 19848302 | 18 | 47980994 | 47982699 |
| 18 | 19973359 | 19974217 | 18 | 48011151 | 48011846 |
| 18 | 20002688 | 20003634 | 18 | 48021616 | 48023904 |
| 18 | 20064100 | 20067556 | 18 | 48026744 | 48031780 |
| 18 | 20299383 | 20299888 | 18 | 48034520 | 48036238 |
| 18 | 20393505 | 20395901 | 18 | 48049983 | 48051522 |
| 18 | 20403624 | 20406302 | 18 | 48054163 | 48058057 |
| 18 | 20442126 | 20443416 | 18 | 48086247 | 48087897 |
| 18 | 20466183 | 20467651 | 18 | 48128889 | 48131614 |
| 18 | 20489602 | 20492733 | 18 | 48137651 | 48137970 |
| 18 | 20492835 | 20494689 | 18 | 48167053 | 48169566 |
| 18 | 20495948 | 20497821 | 18 | 48189314 | 48190435 |
| 18 | 20512677 | 20514411 | 18 | 48199007 | 48200852 |
| 18 | 20538812 | 20539945 | 18 | 48209802 | 48211235 |
| 18 | 20560364 | 20561739 | 18 | 48256031 | 48258072 |
| 18 | 20564505 | 20566202 | 18 | 48270762 | 48271583 |
| 18 | 20575064 | 20578457 | 18 | 48274332 | 48278017 |
| 18 | 20590879 | 20591925 | 18 | 48297496 | 48301232 |
| 18 | 20595800 | 20599028 | 18 | 48312786 | 48318817 |
| 18 | 20644421 | 20646504 | 18 | 48326024 | 48332719 |
| 18 | 20651438 | 20653093 | 18 | 48351727 | 48353785 |
| 18 | 20666317 | 20667992 | 18 | 48376825 | 48379482 |
| 18 | 20671177 | 20676314 | 18 | 48384549 | 48390262 |
| 18 | 20690342 | 20691431 | 18 | 48406768 | 48408189 |
| 18 | 20711358 | 20712201 | 18 | 48459881 | 48463202 |
| 18 | 20747540 | 20754358 | 18 | 48465916 | 48472158 |
| 18 | 20764965 | 20770291 | 18 | 48475315 | 48475770 |
| 18 | 20795062 | 20797493 | 18 | 48487928 | 48489083 |
| 18 | 20818858 | 20821801 | 18 | 48513062 | 48514466 |
| 18 | 20826827 | 20826882 | 18 | 48556954 | 48557098 |
| 18 | 20849516 | 20851436 | 18 | 48566014 | 48569506 |
| 18 | 20853692 | 20855327 | 18 | 48597727 | 48598297 |
| 18 | 20877696 | 20879074 | 18 | 48599996 | 48601570 |
| 18 | 20883702 | 20886540 | 18 | 48617715 | 48618507 |
| 18 | 20907787 | 20911419 | 18 | 48671623 | 48674974 |
| 18 | 20913894 | 20915305 | 18 | 48681509 | 48682149 |
| 18 | 20940540 | 20941884 | 18 | 48693476 | 48696011 |
| 18 | 20949790 | 20950473 | 18 | 48720000 | 48721446 |
| 18 | 21058008 | 21058924 | 18 | 48746247 | 48747286 |
| 18 | 21252343 | 21254945 | 18 | 48762462 | 48764184 |
| 18 | 21286810 | 21290967 | 18 | 48778131 | 48784022 |
| 18 | 21306398 | 21307405 | 18 | 48809588 | 48810604 |
| 18 | 21311364 | 21312404 | 18 | 48816890 | 48828801 |
| 18 | 21398567 | 21401332 | 18 | 48856264 | 48862413 |
| 18 | 21420978 | 21423033 | 18 | 48883491 | 48887665 |
| 18 | 21428505 | 21432493 | 18 | 48913116 | 48915369 |
| 18 | 21453634 | 21458045 | 18 | 49026200 | 49029966 |
| 18 | 21473893 | 21476201 | 18 | 49046469 | 49048591 |
| 18 | 21479798 | 21482829 | 18 | 49076525 | 49077975 |
| 18 | 21512139 | 21517441 | 18 | 49151138 | 49153592 |
| 18 | 21528542 | 21529366 | 18 | 49207219 | 49207673 |

The chromosomal positon was obtained from UCSC genome browser (http://genome.ucsc.edu/) build 36.

APPENDIX C: Chromosome 18
Page 21 of 72

| Chr | Start | End | | | Chr | Start | End |
|---|---|---|---|---|---|---|---|
| 18 | 21535498 | 21537766 | | | 18 | 49242727 | 49243720 |
| 18 | 21544924 | 21546761 | | | 18 | 49250299 | 49253075 |
| 18 | 21616207 | 21617701 | | | 18 | 49322398 | 49327358 |
| 18 | 21648047 | 21649193 | | | 18 | 49356459 | 49358603 |
| 18 | 21680061 | 21680942 | | | 18 | 49370280 | 49374512 |
| 18 | 21693940 | 21697769 | | | 18 | 49382725 | 49383879 |
| 18 | 21702058 | 21702462 | | | 18 | 49467815 | 49468749 |
| 18 | 21771984 | 21772889 | | | 18 | 49486264 | 49486547 |
| 18 | 21923930 | 21925664 | | | 18 | 49489808 | 49498681 |
| 18 | 22056999 | 22061998 | | | 18 | 49532765 | 49533944 |
| 18 | 22128869 | 22131273 | | | 18 | 49546565 | 49548266 |
| 18 | 22168439 | 22170142 | | | 18 | 49559972 | 49566786 |
| 18 | 22178757 | 22185464 | | | 18 | 49580756 | 49582624 |
| 18 | 22269607 | 22270557 | | | 18 | 49628547 | 49635684 |
| 18 | 22313048 | 22313917 | | | 18 | 49699489 | 49702687 |
| 18 | 22341737 | 22342480 | | | 18 | 49763641 | 49764014 |
| 18 | 22382723 | 22384588 | | | 18 | 49807105 | 49807640 |
| 18 | 22385158 | 22386123 | | | 18 | 49854324 | 49856949 |
| 18 | 22435977 | 22439570 | | | 18 | 49874849 | 49876541 |
| 18 | 22511787 | 22515045 | | | 18 | 49892719 | 49898070 |
| 18 | 22558097 | 22559288 | | | 18 | 49904220 | 49906417 |
| 18 | 22561890 | 22563499 | | | 18 | 49923717 | 49925001 |
| 18 | 22566881 | 22569222 | | | 18 | 49949168 | 49950739 |
| 18 | 22576290 | 22576938 | | | 18 | 49953613 | 49955272 |
| 18 | 22629732 | 22630996 | | | 18 | 50005294 | 50007072 |
| 18 | 22694791 | 22700365 | | | 18 | 50026841 | 50029698 |
| 18 | 22711852 | 22713908 | | | 18 | 50034497 | 50037045 |
| 18 | 22718115 | 22723588 | | | 18 | 50128117 | 50132815 |
| 18 | 22765726 | 22768993 | | | 18 | 50138790 | 50140280 |
| 18 | 22787474 | 22787689 | | | 18 | 50195616 | 50197931 |
| 18 | 22857929 | 22859783 | | | 18 | 50218077 | 50220367 |
| 18 | 22873932 | 22881947 | | | 18 | 50269945 | 50273138 |
| 18 | 22892415 | 22894737 | | | 18 | 50289048 | 50302182 |
| 18 | 22905455 | 22906985 | | | 18 | 50369697 | 50370886 |
| 18 | 22913780 | 22915496 | | | 18 | 50422871 | 50424466 |
| 18 | 22917687 | 22921267 | | | 18 | 50433927 | 50435920 |
| 18 | 22940776 | 22942949 | | | 18 | 50478494 | 50479796 |
| 18 | 22969968 | 22971016 | | | 18 | 50523533 | 50524129 |
| 18 | 22987956 | 22989213 | | | 18 | 50532291 | 50536782 |
| 18 | 23008667 | 23010905 | | | 18 | 50564280 | 50565743 |
| 18 | 23142042 | 23148776 | | | 18 | 50578893 | 50584292 |
| 18 | 23205922 | 23210829 | | | 18 | 50666732 | 50670252 |
| 18 | 23243999 | 23246252 | | | 18 | 50677327 | 50678827 |
| 18 | 23249175 | 23249598 | | | 18 | 50702454 | 50703433 |
| 18 | 23320588 | 23322231 | | | 18 | 50709375 | 50712574 |
| 18 | 23364249 | 23368275 | | | 18 | 50745936 | 50758908 |
| 18 | 23396043 | 23397214 | | | 18 | 50782340 | 50784828 |
| 18 | 23417361 | 23418004 | | | 18 | 50800978 | 50802331 |
| 18 | 23434063 | 23436248 | | | 18 | 50844627 | 50849026 |
| 18 | 23474030 | 23477013 | | | 18 | 50886167 | 50887537 |
| 18 | 23484752 | 23490549 | | | 18 | 50896519 | 50900003 |
| 18 | 23517844 | 23519503 | | | 18 | 50914614 | 50915798 |
| 18 | 23605726 | 23606188 | | | 18 | 50954291 | 50955768 |
| 18 | 23609792 | 23617492 | | | 18 | 50980192 | 50982227 |
| 18 | 23659339 | 23659612 | | | 18 | 50996607 | 50999436 |

The chromosomal positon was obtained from UCSC genome browser (http://genome.ucsc.edu/) build 36.

APPENDIX C: Chromosome 18
Page 22 of 72

| Chr | Start | End | Chr | Start | End |
|---|---|---|---|---|---|
| 18 | 23666805 | 23669913 | 18 | 51014980 | 51015698 |
| 18 | 23672065 | 23673295 | 18 | 51052720 | 51056713 |
| 18 | 23731474 | 23737066 | 18 | 51077746 | 51077899 |
| 18 | 23784094 | 23789177 | 18 | 51086806 | 51091072 |
| 18 | 23806388 | 23808215 | 18 | 51118709 | 51121532 |
| 18 | 23811776 | 23815435 | 18 | 51132832 | 51133794 |
| 18 | 23864096 | 23868202 | 18 | 51138838 | 51141506 |
| 18 | 23934282 | 23936830 | 18 | 51155430 | 51156320 |
| 18 | 23950085 | 23956161 | 18 | 51168067 | 51169868 |
| 18 | 23971606 | 23978652 | 18 | 51211146 | 51211980 |
| 18 | 24029110 | 24032437 | 18 | 51282474 | 51284246 |
| 18 | 24043881 | 24046578 | 18 | 51327828 | 51329909 |
| 18 | 24148412 | 24150367 | 18 | 51385683 | 51388009 |
| 18 | 24203457 | 24204337 | 18 | 51396084 | 51400634 |
| 18 | 24272680 | 24273440 | 18 | 51411866 | 51412404 |
| 18 | 24335659 | 24340500 | 18 | 51421305 | 51421845 |
| 18 | 24347353 | 24347488 | 18 | 51438031 | 51438907 |
| 18 | 24372683 | 24374627 | 18 | 51479934 | 51480579 |
| 18 | 24390545 | 24396398 | 18 | 51481726 | 51484120 |
| 18 | 24405217 | 24406358 | 18 | 51563667 | 51569029 |
| 18 | 24414256 | 24416392 | 18 | 51600004 | 51600693 |
| 18 | 24449462 | 24454099 | 18 | 51602134 | 51603190 |
| 18 | 24467639 | 24469134 | 18 | 51630614 | 51632261 |
| 18 | 24499985 | 24505644 | 18 | 51635239 | 51645578 |
| 18 | 24518987 | 24519581 | 18 | 51672768 | 51674078 |
| 18 | 24540303 | 24545121 | 18 | 51714851 | 51715822 |
| 18 | 24562143 | 24564039 | 18 | 51732885 | 51736761 |
| 18 | 24595676 | 24602859 | 18 | 51749327 | 51751521 |
| 18 | 24624459 | 24629538 | 18 | 51755663 | 51760055 |
| 18 | 24632375 | 24646047 | 18 | 51781201 | 51784832 |
| 18 | 24711301 | 24711903 | 18 | 51826292 | 51834960 |
| 18 | 24753829 | 24754750 | 18 | 51860973 | 51861283 |
| 18 | 24770634 | 24772036 | 18 | 51907382 | 51908140 |
| 18 | 24891132 | 24891981 | 18 | 51928481 | 51933255 |
| 18 | 24896514 | 24898297 | 18 | 51937515 | 51938856 |
| 18 | 24904606 | 24904715 | 18 | 51942452 | 51947923 |
| 18 | 24904947 | 24905450 | 18 | 51987499 | 51989634 |
| 18 | 24917633 | 24919067 | 18 | 52005954 | 52009787 |
| 18 | 24925702 | 24930091 | 18 | 52063413 | 52066028 |
| 18 | 24932878 | 24936766 | 18 | 52085372 | 52087531 |
| 18 | 25090201 | 25091097 | 18 | 52107144 | 52107709 |
| 18 | 25104637 | 25107898 | 18 | 52259339 | 52260027 |
| 18 | 25110248 | 25113512 | 18 | 52283112 | 52287052 |
| 18 | 25131420 | 25133730 | 18 | 52375219 | 52385902 |
| 18 | 25163632 | 25164776 | 18 | 52426737 | 52428179 |
| 18 | 25171952 | 25174867 | 18 | 52455715 | 52456050 |
| 18 | 25182131 | 25183304 | 18 | 52470041 | 52472199 |
| 18 | 25293357 | 25294198 | 18 | 52527222 | 52529860 |
| 18 | 25346389 | 25349444 | 18 | 52587783 | 52588913 |
| 18 | 25407273 | 25410815 | 18 | 52662643 | 52662906 |
| 18 | 25449150 | 25452126 | 18 | 52695904 | 52698550 |
| 18 | 25467169 | 25470449 | 18 | 52707615 | 52712710 |
| 18 | 25482463 | 25484519 | 18 | 52725590 | 52726316 |
| 18 | 25527563 | 25530067 | 18 | 52785041 | 52787068 |
| 18 | 25578876 | 25583119 | 18 | 52822031 | 52823056 |

The chromosomal positon was obtained from UCSC genome browser (http://genome.ucsc.edu/) build 36.

APPENDIX C: Chromosome 18
Page 23 of 72

| Chr | Start | End | Chr | Start | End |
|---|---|---|---|---|---|
| 18 | 25597588 | 25600254 | 18 | 52857214 | 52858533 |
| 18 | 25614527 | 25616438 | 18 | 52860458 | 52871381 |
| 18 | 25691138 | 25693354 | 18 | 52874071 | 52902218 |
| 18 | 25706892 | 25708593 | 18 | 52905994 | 52909034 |
| 18 | 25759618 | 25760284 | 18 | 52910815 | 52913999 |
| 18 | 25779931 | 25785410 | 18 | 52927911 | 52930694 |
| 18 | 25810848 | 25812387 | 18 | 52931939 | 52933939 |
| 18 | 25825258 | 25827242 | 18 | 52948885 | 52958072 |
| 18 | 25884466 | 25886336 | 18 | 52965142 | 52967432 |
| 18 | 25906330 | 25907031 | 18 | 52968300 | 52972274 |
| 18 | 25927939 | 25929231 | 18 | 52975105 | 52976892 |
| 18 | 25935023 | 25937812 | 18 | 52980155 | 52984008 |
| 18 | 25974033 | 25976408 | 18 | 53013150 | 53016281 |
| 18 | 25990492 | 25993893 | 18 | 53038384 | 53041446 |
| 18 | 26008131 | 26011477 | 18 | 53062047 | 53075643 |
| 18 | 26036717 | 26037425 | 18 | 53086167 | 53086592 |
| 18 | 26043971 | 26050856 | 18 | 53095138 | 53095684 |
| 18 | 26070371 | 26070962 | 18 | 53097135 | 53099616 |
| 18 | 26073825 | 26077900 | 18 | 53123015 | 53123706 |
| 18 | 26081074 | 26085347 | 18 | 53146968 | 53148347 |
| 18 | 26093715 | 26094172 | 18 | 53157644 | 53158919 |
| 18 | 26118581 | 26122398 | 18 | 53170145 | 53171471 |
| 18 | 26176921 | 26177547 | 18 | 53186668 | 53187798 |
| 18 | 26220533 | 26221284 | 18 | 53199585 | 53202311 |
| 18 | 26326712 | 26328067 | 18 | 53203648 | 53204293 |
| 18 | 26330109 | 26330684 | 18 | 53247080 | 53249966 |
| 18 | 26415220 | 26417635 | 18 | 53251634 | 53253194 |
| 18 | 26422450 | 26424406 | 18 | 53256606 | 53259499 |
| 18 | 26429429 | 26430559 | 18 | 53285492 | 53290481 |
| 18 | 26435268 | 26436874 | 18 | 53306851 | 53309517 |
| 18 | 26446038 | 26447773 | 18 | 53316842 | 53322009 |
| 18 | 26478685 | 26479497 | 18 | 53326432 | 53327266 |
| 18 | 26536801 | 26537765 | 18 | 53334950 | 53337345 |
| 18 | 26546029 | 26548553 | 18 | 53346243 | 53348475 |
| 18 | 26555983 | 26558131 | 18 | 53361048 | 53361593 |
| 18 | 26597369 | 26600384 | 18 | 53379079 | 53379358 |
| 18 | 26607455 | 26609112 | 18 | 53515625 | 53517440 |
| 18 | 26639649 | 26640966 | 18 | 53528762 | 53529764 |
| 18 | 26642179 | 26644285 | 18 | 53567115 | 53570090 |
| 18 | 26674517 | 26675315 | 18 | 53683332 | 53683729 |
| 18 | 26711609 | 26713716 | 18 | 53737961 | 53739086 |
| 18 | 26731491 | 26734232 | 18 | 53741940 | 53743780 |
| 18 | 26797265 | 26799300 | 18 | 53766784 | 53769945 |
| 18 | 26807669 | 26810052 | 18 | 53775095 | 53775904 |
| 18 | 26831161 | 26832643 | 18 | 53788926 | 53789918 |
| 18 | 26861904 | 26863575 | 18 | 53801754 | 53802039 |
| 18 | 26880600 | 26883765 | 18 | 53862067 | 53863704 |
| 18 | 26893851 | 26894013 | 18 | 53866202 | 53869180 |
| 18 | 26896174 | 26899742 | 18 | 53915059 | 53921021 |
| 18 | 26924640 | 26925823 | 18 | 53939131 | 53942580 |
| 18 | 26932750 | 26933767 | 18 | 53945018 | 53950417 |
| 18 | 26935636 | 26937746 | 18 | 53961523 | 53962463 |
| 18 | 26942712 | 26942788 | 18 | 53971363 | 53973311 |
| 18 | 26944118 | 26945294 | 18 | 53975931 | 53977389 |
| 18 | 26965741 | 26966518 | 18 | 54013483 | 54014242 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 27015279 | 27023349 | 18 | 54023222 | 54024004 |
| 18 | 27032873 | 27033436 | 18 | 54065477 | 54066165 |
| 18 | 27044751 | 27050600 | 18 | 54073645 | 54074985 |
| 18 | 27103090 | 27104273 | 18 | 54118031 | 54119302 |
| 18 | 27150572 | 27152511 | 18 | 54190815 | 54192478 |
| 18 | 27161889 | 27166203 | 18 | 54192868 | 54194146 |
| 18 | 27295920 | 27297611 | 18 | 54196657 | 54198202 |
| 18 | 27355130 | 27356666 | 18 | 54220513 | 54222268 |
| 18 | 27361471 | 27362143 | 18 | 54270022 | 54270756 |
| 18 | 27366247 | 27367623 | 18 | 54362811 | 54364649 |
| 18 | 27433034 | 27436267 | 18 | 54476128 | 54480661 |
| 18 | 27467187 | 27468884 | 18 | 54532393 | 54533965 |
| 18 | 27510752 | 27515110 | 18 | 54561876 | 54562588 |
| 18 | 27536509 | 27537632 | 18 | 54602477 | 54603788 |
| 18 | 27594296 | 27595086 | 18 | 54664485 | 54667094 |
| 18 | 27608075 | 27609788 | 18 | 54683861 | 54686066 |
| 18 | 27625151 | 27626838 | 18 | 54688427 | 54689891 |
| 18 | 27853840 | 27855452 | 18 | 54704668 | 54707551 |
| 18 | 27868274 | 27870184 | 18 | 54734358 | 54735771 |
| 18 | 27883403 | 27884231 | 18 | 54776733 | 54779724 |
| 18 | 27912140 | 27913154 | 18 | 54783311 | 54785316 |
| 18 | 28046180 | 28048256 | 18 | 54798142 | 54799849 |
| 18 | 28165701 | 28168389 | 18 | 54804738 | 54806202 |
| 18 | 28205428 | 28206325 | 18 | 54874091 | 54876521 |
| 18 | 28217090 | 28218497 | 18 | 54942725 | 54944759 |
| 18 | 28254368 | 28256938 | 18 | 54949739 | 54951334 |
| 18 | 28278370 | 28279341 | 18 | 55084617 | 55090983 |
| 18 | 28282226 | 28284759 | 18 | 55094637 | 55096166 |
| 18 | 28290015 | 28291468 | 18 | 55173157 | 55176340 |
| 18 | 28360306 | 28361392 | 18 | 55276729 | 55278823 |
| 18 | 28381823 | 28383342 | 18 | 55308838 | 55310663 |
| 18 | 28429266 | 28430806 | 18 | 55358499 | 55359297 |
| 18 | 28505616 | 28507173 | 18 | 55379373 | 55379688 |
| 18 | 28529020 | 28529785 | 18 | 55386068 | 55388291 |
| 18 | 28534089 | 28535528 | 18 | 55430893 | 55431998 |
| 18 | 28587452 | 28587667 | 18 | 55435209 | 55437594 |
| 18 | 28636624 | 28638303 | 18 | 55463170 | 55465445 |
| 18 | 28664363 | 28666344 | 18 | 55481597 | 55484198 |
| 18 | 28763956 | 28765234 | 18 | 55523506 | 55527579 |
| 18 | 28780436 | 28781422 | 18 | 55548713 | 55549753 |
| 18 | 28792428 | 28794068 | 18 | 55631312 | 55632221 |
| 18 | 28803371 | 28806727 | 18 | 55703677 | 55704257 |
| 18 | 28865880 | 28867012 | 18 | 55708315 | 55708960 |
| 18 | 28930128 | 28941366 | 18 | 55745715 | 55747576 |
| 18 | 28956499 | 28958873 | 18 | 55828274 | 55829220 |
| 18 | 29018345 | 29022580 | 18 | 55835524 | 55839215 |
| 18 | 29046317 | 29057237 | 18 | 55845773 | 55845777 |
| 18 | 29079285 | 29080923 | 18 | 55862597 | 55865134 |
| 18 | 29081593 | 29084656 | 18 | 55893022 | 55894142 |
| 18 | 29085001 | 29087052 | 18 | 55905042 | 55905692 |
| 18 | 29089072 | 29094280 | 18 | 55961693 | 55962662 |
| 18 | 29097939 | 29100030 | 18 | 56020348 | 56033201 |
| 18 | 29138367 | 29140071 | 18 | 56075070 | 56078070 |
| 18 | 29197391 | 29199952 | 18 | 56133745 | 56138363 |
| 18 | 29213628 | 29215138 | 18 | 56276162 | 56277117 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 29234698 | 29236671 | | | 18 | 56371621 | 56373827 |
| 18 | 29287886 | 29290772 | | | 18 | 56395272 | 56399104 |
| 18 | 29295260 | 29295385 | | | 18 | 56405787 | 56412337 |
| 18 | 29300245 | 29304762 | | | 18 | 56459253 | 56460393 |
| 18 | 29422451 | 29423417 | | | 18 | 56472657 | 56473517 |
| 18 | 29438626 | 29444338 | | | 18 | 56481029 | 56482379 |
| 18 | 29447378 | 29454471 | | | 18 | 56580571 | 56583177 |
| 18 | 29494041 | 29497013 | | | 18 | 56586363 | 56587150 |
| 18 | 29515962 | 29517133 | | | 18 | 56615338 | 56624248 |
| 18 | 29520487 | 29522315 | | | 18 | 56627381 | 56633597 |
| 18 | 29530291 | 29533148 | | | 18 | 56654681 | 56660590 |
| 18 | 29536500 | 29537594 | | | 18 | 56664976 | 56667303 |
| 18 | 29547097 | 29557565 | | | 18 | 56731109 | 56732237 |
| 18 | 29561979 | 29564357 | | | 18 | 56763884 | 56765001 |
| 18 | 29577807 | 29579345 | | | 18 | 56857400 | 56859289 |
| 18 | 29583867 | 29584634 | | | 18 | 56898522 | 56906589 |
| 18 | 29588916 | 29589765 | | | 18 | 56916338 | 56918805 |
| 18 | 29595488 | 29597301 | | | 18 | 56951365 | 56952358 |
| 18 | 29629925 | 29632766 | | | 18 | 56959705 | 56962474 |
| 18 | 29672115 | 29680521 | | | 18 | 56992477 | 57000703 |
| 18 | 29685626 | 29689263 | | | 18 | 57014967 | 57016743 |
| 18 | 29707104 | 29720020 | | | 18 | 57043567 | 57044032 |
| 18 | 29753616 | 29755906 | | | 18 | 57095164 | 57096598 |
| 18 | 29794745 | 29796784 | | | 18 | 57156577 | 57160494 |
| 18 | 29821060 | 29824774 | | | 18 | 57211664 | 57211866 |
| 18 | 29839919 | 29844837 | | | 18 | 57276916 | 57279044 |
| 18 | 29851292 | 29852798 | | | 18 | 57289156 | 57291327 |
| 18 | 29932375 | 29936613 | | | 18 | 57298437 | 57299171 |
| 18 | 29939093 | 29940414 | | | 18 | 57351647 | 57352627 |
| 18 | 29951825 | 29951829 | | | 18 | 57394953 | 57396619 |
| 18 | 29983744 | 29989917 | | | 18 | 57428143 | 57431464 |
| 18 | 30009543 | 30012489 | | | 18 | 57500776 | 57501391 |
| 18 | 30017644 | 30020578 | | | 18 | 57508327 | 57508748 |
| 18 | 30039686 | 30042364 | | | 18 | 57670834 | 57670989 |
| 18 | 30057432 | 30058294 | | | 18 | 57706247 | 57710914 |
| 18 | 30113180 | 30114011 | | | 18 | 57735914 | 57736248 |
| 18 | 30124093 | 30126020 | | | 18 | 57755733 | 57756974 |
| 18 | 30146958 | 30151542 | | | 18 | 57766896 | 57768764 |
| 18 | 30173186 | 30181517 | | | 18 | 57777694 | 57777927 |
| 18 | 30268769 | 30270983 | | | 18 | 57790746 | 57794492 |
| 18 | 30305659 | 30306707 | | | 18 | 57799087 | 57801284 |
| 18 | 30340466 | 30343346 | | | 18 | 57917388 | 57919010 |
| 18 | 30345885 | 30348415 | | | 18 | 57982407 | 57983681 |
| 18 | 30382344 | 30383205 | | | 18 | 58027393 | 58030585 |
| 18 | 30420333 | 30421380 | | | 18 | 58047542 | 58049004 |
| 18 | 30543300 | 30543809 | | | 18 | 58073857 | 58077002 |
| 18 | 30558204 | 30562838 | | | 18 | 58081978 | 58086509 |
| 18 | 30606106 | 30607576 | | | 18 | 58115421 | 58116264 |
| 18 | 30622073 | 30624123 | | | 18 | 58118371 | 58123792 |
| 18 | 30631506 | 30636045 | | | 18 | 58139527 | 58159934 |
| 18 | 30690588 | 30693670 | | | 18 | 58238818 | 58239410 |
| 18 | 30710037 | 30712363 | | | 18 | 58253816 | 58255531 |
| 18 | 30716975 | 30719474 | | | 18 | 58303644 | 58305456 |
| 18 | 30723970 | 30725907 | | | 18 | 58343223 | 58344071 |
| 18 | 30746870 | 30751080 | | | 18 | 58371553 | 58372733 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 30787584 | 30788222 | 18 | 58517785 | 58521411 |
| 18 | 30832022 | 30834826 | 18 | 58590664 | 58592731 |
| 18 | 30838526 | 30840186 | 18 | 58597146 | 58597920 |
| 18 | 30849863 | 30853725 | 18 | 58601947 | 58603060 |
| 18 | 30863963 | 30864965 | 18 | 58617291 | 58617711 |
| 18 | 30893342 | 30895547 | 18 | 58685135 | 58685664 |
| 18 | 30921163 | 30922750 | 18 | 58759624 | 58762153 |
| 18 | 30960733 | 30963928 | 18 | 58771558 | 58772111 |
| 18 | 30965864 | 30966316 | 18 | 58806065 | 58806827 |
| 18 | 30971602 | 30974975 | 18 | 58809778 | 58812258 |
| 18 | 30997526 | 31001296 | 18 | 58880458 | 58881764 |
| 18 | 31016266 | 31018104 | 18 | 58905945 | 58910782 |
| 18 | 31059416 | 31059921 | 18 | 58916171 | 58917803 |
| 18 | 31096177 | 31096982 | 18 | 58919668 | 58923848 |
| 18 | 31114546 | 31115069 | 18 | 58926143 | 58927651 |
| 18 | 31128974 | 31130693 | 18 | 58944217 | 58945931 |
| 18 | 31168236 | 31169477 | 18 | 58954618 | 58956578 |
| 18 | 31182192 | 31184765 | 18 | 58970085 | 58971501 |
| 18 | 31243868 | 31245639 | 18 | 58976024 | 58979156 |
| 18 | 31292952 | 31295635 | 18 | 58983825 | 58984925 |
| 18 | 31330627 | 31333674 | 18 | 59055648 | 59059574 |
| 18 | 31341895 | 31343746 | 18 | 59086535 | 59087582 |
| 18 | 31349476 | 31350456 | 18 | 59110602 | 59110703 |
| 18 | 31368158 | 31371242 | 18 | 59132751 | 59133765 |
| 18 | 31429305 | 31439791 | 18 | 59181899 | 59183338 |
| 18 | 31441175 | 31441727 | 18 | 59285102 | 59287371 |
| 18 | 31450060 | 31450759 | 18 | 59304908 | 59308866 |
| 18 | 31469247 | 31472255 | 18 | 59338731 | 59340446 |
| 18 | 31513334 | 31519144 | 18 | 59350299 | 59352196 |
| 18 | 31524334 | 31525770 | 18 | 59355667 | 59358161 |
| 18 | 31558074 | 31564194 | 18 | 59372860 | 59374727 |
| 18 | 31622538 | 31631814 | 18 | 59435763 | 59437872 |
| 18 | 31643803 | 31644664 | 18 | 59476453 | 59476857 |
| 18 | 31707264 | 31709160 | 18 | 59482209 | 59490815 |
| 18 | 31738274 | 31739696 | 18 | 59515577 | 59520442 |
| 18 | 31865526 | 31866717 | 18 | 59530317 | 59531707 |
| 18 | 31962679 | 31964055 | 18 | 59538957 | 59540085 |
| 18 | 31972385 | 31973087 | 18 | 59558233 | 59559374 |
| 18 | 31976321 | 31978738 | 18 | 59561163 | 59561867 |
| 18 | 31988271 | 31988345 | 18 | 59573832 | 59576147 |
| 18 | 32009710 | 32010216 | 18 | 59593131 | 59595543 |
| 18 | 32020189 | 32023802 | 18 | 59602059 | 59603454 |
| 18 | 32119330 | 32120207 | 18 | 59620589 | 59621421 |
| 18 | 32124133 | 32126290 | 18 | 59680229 | 59684697 |
| 18 | 32129827 | 32131827 | 18 | 59723949 | 59731679 |
| 18 | 32136654 | 32141977 | 18 | 59734351 | 59752051 |
| 18 | 32155284 | 32157074 | 18 | 59788249 | 59789635 |
| 18 | 32171563 | 32172438 | 18 | 59796872 | 59799950 |
| 18 | 32186040 | 32189682 | 18 | 59805888 | 59806385 |
| 18 | 32260656 | 32261798 | 18 | 59819548 | 59821514 |
| 18 | 32265073 | 32266026 | 18 | 60035310 | 60035938 |
| 18 | 32281398 | 32281859 | 18 | 60062446 | 60065712 |
| 18 | 32301400 | 32302834 | 18 | 60124803 | 60128403 |
| 18 | 32316878 | 32319887 | 18 | 60144085 | 60145001 |
| 18 | 32327342 | 32327903 | 18 | 60150584 | 60154363 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 32372061 | 32373234 | 18 | 60216060 | 60225193 |
| 18 | 32375671 | 32380894 | 18 | 60251213 | 60251702 |
| 18 | 32427887 | 32429497 | 18 | 60289751 | 60290755 |
| 18 | 32435057 | 32435698 | 18 | 60330538 | 60333259 |
| 18 | 32467940 | 32469154 | 18 | 60333491 | 60333823 |
| 18 | 32483060 | 32491481 | 18 | 60358940 | 60360338 |
| 18 | 32524252 | 32530524 | 18 | 60365526 | 60368264 |
| 18 | 32543037 | 32552231 | 18 | 60397859 | 60399630 |
| 18 | 32556867 | 32560183 | 18 | 60402000 | 60406574 |
| 18 | 32573863 | 32574638 | 18 | 60464620 | 60465865 |
| 18 | 32590676 | 32591948 | 18 | 60476545 | 60477702 |
| 18 | 32594419 | 32595763 | 18 | 60485983 | 60487083 |
| 18 | 32598067 | 32600959 | 18 | 60528084 | 60532824 |
| 18 | 32615678 | 32618946 | 18 | 60539888 | 60541072 |
| 18 | 32619381 | 32621042 | 18 | 60635753 | 60637692 |
| 18 | 32623459 | 32625344 | 18 | 60760138 | 60764216 |
| 18 | 32637707 | 32640419 | 18 | 60887347 | 60891405 |
| 18 | 32644382 | 32644744 | 18 | 60925616 | 60926457 |
| 18 | 32726401 | 32727595 | 18 | 60939305 | 60940555 |
| 18 | 32736727 | 32736960 | 18 | 60945941 | 60947640 |
| 18 | 32785274 | 32787068 | 18 | 60964770 | 60968858 |
| 18 | 32824032 | 32824872 | 18 | 61008268 | 61014481 |
| 18 | 32849898 | 32851863 | 18 | 61060604 | 61063210 |
| 18 | 32895213 | 32896056 | 18 | 61124872 | 61126701 |
| 18 | 32951716 | 32953324 | 18 | 61198644 | 61199158 |
| 18 | 32957662 | 32960736 | 18 | 61201847 | 61203031 |
| 18 | 33012706 | 33016821 | 18 | 61221520 | 61223719 |
| 18 | 33031426 | 33032637 | 18 | 61233140 | 61234145 |
| 18 | 33088275 | 33123806 | 18 | 61240689 | 61242428 |
| 18 | 33126312 | 33128488 | 18 | 61273922 | 61274345 |
| 18 | 33135458 | 33237862 | 18 | 61275344 | 61278750 |
| 18 | 33242546 | 33247685 | 18 | 61281179 | 61285802 |
| 18 | 33252497 | 33261617 | 18 | 61305906 | 61307621 |
| 18 | 33268360 | 33313879 | 18 | 61330954 | 61331923 |
| 18 | 33319745 | 33391611 | 18 | 61378776 | 61381441 |
| 18 | 33403564 | 33419118 | 18 | 61434521 | 61438212 |
| 18 | 33439197 | 33452132 | 18 | 61445454 | 61450988 |
| 18 | 33463413 | 33466842 | 18 | 61507905 | 61508550 |
| 18 | 33494488 | 33512033 | 18 | 61617053 | 61619884 |
| 18 | 33547160 | 33547645 | 18 | 61655258 | 61657909 |
| 18 | 33553312 | 33554107 | 18 | 61713577 | 61714524 |
| 18 | 33564848 | 33566014 | 18 | 61778479 | 61782071 |
| 18 | 33606815 | 33617373 | 18 | 61849866 | 61850171 |
| 18 | 33640147 | 33640773 | 18 | 61864388 | 61865171 |
| 18 | 33703324 | 33708407 | 18 | 61910050 | 61911703 |
| 18 | 33740282 | 33745727 | 18 | 62069075 | 62071217 |
| 18 | 33747634 | 33749178 | 18 | 62134863 | 62135738 |
| 18 | 33792352 | 33793538 | 18 | 62175521 | 62177851 |
| 18 | 33796374 | 33796986 | 18 | 62221515 | 62223234 |
| 18 | 33800920 | 33801174 | 18 | 62252188 | 62256359 |
| 18 | 33811312 | 33813664 | 18 | 62267387 | 62267980 |
| 18 | 33829751 | 33830571 | 18 | 62268200 | 62268313 |
| 18 | 33845295 | 33847486 | 18 | 62268479 | 62273052 |
| 18 | 33872941 | 33880422 | 18 | 62356796 | 62359404 |
| 18 | 33900146 | 33900871 | 18 | 62367961 | 62369018 |

The chromosomal positon was obtained from UCSC genome browser (http://genome.ucsc.edu/) build 36.

APPENDIX C: Chromosome 18

| Chr | Start | End | | Chr | Start | End |
|---|---|---|---|---|---|---|
| 18 | 33910311 | 33914103 | | 18 | 62378381 | 62380279 |
| 18 | 33930838 | 33934699 | | 18 | 62405239 | 62406694 |
| 18 | 33979946 | 33983264 | | 18 | 62521019 | 62521256 |
| 18 | 33989622 | 33999722 | | 18 | 62594068 | 62596524 |
| 18 | 34053458 | 34054284 | | 18 | 62610760 | 62611499 |
| 18 | 34059465 | 34061722 | | 18 | 62618995 | 62621963 |
| 18 | 34086302 | 34092422 | | 18 | 62627844 | 62631180 |
| 18 | 34097560 | 34118487 | | 18 | 62635199 | 62638623 |
| 18 | 34169857 | 34172330 | | 18 | 62661084 | 62664616 |
| 18 | 34179842 | 34181789 | | 18 | 62667829 | 62668723 |
| 18 | 34278808 | 34280630 | | 18 | 62690379 | 62692467 |
| 18 | 34315928 | 34319589 | | 18 | 62717683 | 62719460 |
| 18 | 34327802 | 34333169 | | 18 | 62758886 | 62762173 |
| 18 | 34336983 | 34358143 | | 18 | 62836291 | 62839468 |
| 18 | 34375624 | 34377344 | | 18 | 62856851 | 62860211 |
| 18 | 34388382 | 34389471 | | 18 | 62880296 | 62882666 |
| 18 | 34427620 | 34438579 | | 18 | 63037968 | 63038798 |
| 18 | 34491227 | 34499038 | | 18 | 63059063 | 63063048 |
| 18 | 34521771 | 34531464 | | 18 | 63072673 | 63074222 |
| 18 | 34568428 | 34574617 | | 18 | 63160966 | 63165174 |
| 18 | 34595338 | 34596337 | | 18 | 63165417 | 63168208 |
| 18 | 34616819 | 34627504 | | 18 | 63259299 | 63260786 |
| 18 | 34635970 | 34645436 | | 18 | 63320331 | 63323430 |
| 18 | 34659746 | 34669834 | | 18 | 63338720 | 63339967 |
| 18 | 34684752 | 34686344 | | 18 | 63347324 | 63351922 |
| 18 | 34714824 | 34716656 | | 18 | 63354812 | 63354895 |
| 18 | 34718035 | 34720180 | | 18 | 63369309 | 63370615 |
| 18 | 34721889 | 34725226 | | 18 | 63391106 | 63394496 |
| 18 | 34799695 | 34803116 | | 18 | 63402693 | 63407535 |
| 18 | 34817180 | 34822661 | | 18 | 63430953 | 63437682 |
| 18 | 34851805 | 34855169 | | 18 | 63468056 | 63470760 |
| 18 | 34862882 | 34864621 | | 18 | 63476019 | 63479173 |
| 18 | 34870408 | 34871999 | | 18 | 63509374 | 63511187 |
| 18 | 34887358 | 34900915 | | 18 | 63592521 | 63597867 |
| 18 | 34904645 | 34908699 | | 18 | 63613976 | 63615311 |
| 18 | 34919879 | 34922791 | | 18 | 63619324 | 63622067 |
| 18 | 34929943 | 34937260 | | 18 | 63741421 | 63742407 |
| 18 | 34996578 | 35008099 | | 18 | 63751995 | 63754115 |
| 18 | 35019634 | 35024936 | | 18 | 63759777 | 63761461 |
| 18 | 35035531 | 35037750 | | 18 | 63787907 | 63788662 |
| 18 | 35048457 | 35057739 | | 18 | 63807976 | 63808766 |
| 18 | 35095062 | 35100511 | | 18 | 63810123 | 63812151 |
| 18 | 35106065 | 35109534 | | 18 | 63878196 | 63880266 |
| 18 | 35113002 | 35114292 | | 18 | 63903118 | 63905758 |
| 18 | 35117532 | 35119308 | | 18 | 63941020 | 63942757 |
| 18 | 35125886 | 35129908 | | 18 | 64013159 | 64014383 |
| 18 | 35147823 | 35148662 | | 18 | 64029898 | 64032047 |
| 18 | 35151804 | 35161186 | | 18 | 64114723 | 64116048 |
| 18 | 35171667 | 35173076 | | 18 | 64174224 | 64175429 |
| 18 | 35246304 | 35247276 | | 18 | 64178874 | 64180832 |
| 18 | 35266831 | 35271923 | | 18 | 64209343 | 64210686 |
| 18 | 35313091 | 35317206 | | 18 | 64263534 | 64274711 |
| 18 | 35318622 | 35322555 | | 18 | 64290367 | 64290994 |
| 18 | 35331429 | 35339894 | | 18 | 64322237 | 64326174 |
| 18 | 35341745 | 35343457 | | 18 | 64379681 | 64380695 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 35384701 | 35387897 | | | 18 | 64449287 | 64456418 |
| 18 | 35393626 | 35394425 | | | 18 | 64495306 | 64495983 |
| 18 | 35434528 | 35435042 | | | 18 | 64576589 | 64579116 |
| 18 | 35466342 | 35467725 | | | 18 | 64612294 | 64614696 |
| 18 | 35488705 | 35491672 | | | 18 | 64667473 | 64668548 |
| 18 | 35534248 | 35535301 | | | 18 | 64675965 | 64679737 |
| 18 | 35553352 | 35578099 | | | 18 | 64691025 | 64691446 |
| 18 | 35603541 | 35622656 | | | 18 | 64694122 | 64694774 |
| 18 | 35625299 | 35626345 | | | 18 | 64709956 | 64711631 |
| 18 | 35668599 | 35673878 | | | 18 | 64742236 | 64746171 |
| 18 | 35705851 | 35707083 | | | 18 | 64762495 | 64763515 |
| 18 | 35741320 | 35743368 | | | 18 | 64766783 | 64768058 |
| 18 | 35799148 | 35801387 | | | 18 | 64775393 | 64778024 |
| 18 | 35803535 | 35807391 | | | 18 | 64784163 | 64785468 |
| 18 | 35885546 | 35887062 | | | 18 | 64800313 | 64800768 |
| 18 | 35925167 | 35932645 | | | 18 | 64832891 | 64833607 |
| 18 | 36076707 | 36080577 | | | 18 | 64875546 | 64878457 |
| 18 | 36087807 | 36091094 | | | 18 | 64888047 | 64890930 |
| 18 | 36138664 | 36139762 | | | 18 | 64917643 | 64919938 |
| 18 | 36176182 | 36177395 | | | 18 | 64932927 | 64935158 |
| 18 | 36190054 | 36195126 | | | 18 | 64996401 | 64999525 |
| 18 | 36222128 | 36224492 | | | 18 | 65012685 | 65013762 |
| 18 | 36235769 | 36238068 | | | 18 | 65017525 | 65019352 |
| 18 | 36280442 | 36285286 | | | 18 | 65041741 | 65042801 |
| 18 | 36295105 | 36298927 | | | 18 | 65176536 | 65177624 |
| 18 | 36307403 | 36308448 | | | 18 | 65218609 | 65219649 |
| 18 | 36323720 | 36324517 | | | 18 | 65254058 | 65258768 |
| 18 | 36330649 | 36331593 | | | 18 | 65287160 | 65290703 |
| 18 | 36336717 | 36338232 | | | 18 | 65293247 | 65293763 |
| 18 | 36387289 | 36388504 | | | 18 | 65340372 | 65341185 |
| 18 | 36392456 | 36393816 | | | 18 | 65371493 | 65372585 |
| 18 | 36399957 | 36404432 | | | 18 | 65422234 | 65422801 |
| 18 | 36406714 | 36412134 | | | 18 | 65426188 | 65429052 |
| 18 | 36470377 | 36473159 | | | 18 | 65439050 | 65439781 |
| 18 | 36476386 | 36477058 | | | 18 | 65470576 | 65472356 |
| 18 | 36480527 | 36489080 | | | 18 | 65474244 | 65475147 |
| 18 | 36499358 | 36502043 | | | 18 | 65599839 | 65604405 |
| 18 | 36520433 | 36522714 | | | 18 | 65635330 | 65638249 |
| 18 | 36531686 | 36536279 | | | 18 | 65656722 | 65661494 |
| 18 | 36540370 | 36547163 | | | 18 | 65720176 | 65722481 |
| 18 | 36583400 | 36583975 | | | 18 | 65730103 | 65731568 |
| 18 | 36621353 | 36624353 | | | 18 | 65750553 | 65752752 |
| 18 | 36632187 | 36633804 | | | 18 | 65766989 | 65771525 |
| 18 | 36639012 | 36645637 | | | 18 | 65939787 | 65943193 |
| 18 | 36651163 | 36653545 | | | 18 | 66015465 | 66018658 |
| 18 | 36707022 | 36710192 | | | 18 | 66023360 | 66028922 |
| 18 | 36739427 | 36746329 | | | 18 | 66066992 | 66069749 |
| 18 | 36757906 | 36758396 | | | 18 | 66089705 | 66091193 |
| 18 | 36790456 | 36790721 | | | 18 | 66094230 | 66095241 |
| 18 | 36836667 | 36836677 | | | 18 | 66105319 | 66109839 |
| 18 | 36843937 | 36845773 | | | 18 | 66156670 | 66157607 |
| 18 | 36855681 | 36857203 | | | 18 | 66233752 | 66234488 |
| 18 | 36864143 | 36865311 | | | 18 | 66256485 | 66258697 |
| 18 | 36903626 | 36906221 | | | 18 | 66274055 | 66281951 |
| 18 | 36928428 | 36935560 | | | 18 | 66317342 | 66318946 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 36960622 | 36963528 | 18 | 66331668 | 66333048 |
| 18 | 36967225 | 36975736 | 18 | 66379804 | 66380823 |
| 18 | 36977323 | 36980433 | 18 | 66392288 | 66397949 |
| 18 | 36982861 | 36984557 | 18 | 66427590 | 66431302 |
| 18 | 36988136 | 36989127 | 18 | 66441301 | 66443196 |
| 18 | 36992501 | 36992956 | 18 | 66452499 | 66453879 |
| 18 | 37022028 | 37025693 | 18 | 66462169 | 66466150 |
| 18 | 37044766 | 37046985 | 18 | 66472835 | 66474399 |
| 18 | 37057890 | 37066599 | 18 | 66487313 | 66488198 |
| 18 | 37076175 | 37078885 | 18 | 66542880 | 66548254 |
| 18 | 37079362 | 37079728 | 18 | 66626939 | 66627582 |
| 18 | 37085485 | 37095013 | 18 | 66642148 | 66642318 |
| 18 | 37119374 | 37121401 | 18 | 66664645 | 66667543 |
| 18 | 37128235 | 37129615 | 18 | 66713507 | 66714757 |
| 18 | 37167306 | 37171718 | 18 | 66783075 | 66783251 |
| 18 | 37184160 | 37189927 | 18 | 66854325 | 66860286 |
| 18 | 37199318 | 37200842 | 18 | 66871400 | 66876259 |
| 18 | 37202682 | 37203171 | 18 | 66882345 | 66885558 |
| 18 | 37238904 | 37240069 | 18 | 66900439 | 66901564 |
| 18 | 37272162 | 37279390 | 18 | 66954743 | 66956531 |
| 18 | 37337242 | 37338609 | 18 | 66980185 | 66981028 |
| 18 | 37346071 | 37350077 | 18 | 67121401 | 67123886 |
| 18 | 37351469 | 37352189 | 18 | 67172584 | 67173885 |
| 18 | 37408692 | 37413688 | 18 | 67359159 | 67360919 |
| 18 | 37417665 | 37419312 | 18 | 67363447 | 67367807 |
| 18 | 37432692 | 37434623 | 18 | 67399508 | 67402252 |
| 18 | 37478398 | 37482820 | 18 | 67447946 | 67450351 |
| 18 | 37521229 | 37532667 | 18 | 67469029 | 67471921 |
| 18 | 37541521 | 37542923 | 18 | 67492170 | 67495458 |
| 18 | 37565231 | 37567408 | 18 | 67504521 | 67506816 |
| 18 | 37606635 | 37608665 | 18 | 67693600 | 67694483 |
| 18 | 37631242 | 37631727 | 18 | 67781015 | 67782158 |
| 18 | 37635406 | 37636681 | 18 | 67793871 | 67794784 |
| 18 | 37654089 | 37655873 | 18 | 67823443 | 67824798 |
| 18 | 37680777 | 37686744 | 18 | 67862260 | 67863948 |
| 18 | 37694670 | 37696562 | 18 | 68031503 | 68033028 |
| 18 | 37710579 | 37712642 | 18 | 68037315 | 68040703 |
| 18 | 37717249 | 37718646 | 18 | 68043437 | 68044352 |
| 18 | 37720031 | 37721201 | 18 | 68125804 | 68129676 |
| 18 | 37752634 | 37753912 | 18 | 68135652 | 68138131 |
| 18 | 37852412 | 37854257 | 18 | 68149160 | 68150151 |
| 18 | 37883357 | 37884876 | 18 | 68256524 | 68257897 |
| 18 | 37910783 | 37914677 | 18 | 68262551 | 68263544 |
| 18 | 37925833 | 37933070 | 18 | 68283266 | 68283682 |
| 18 | 38007424 | 38015699 | 18 | 68286554 | 68288106 |
| 18 | 38095130 | 38098585 | 18 | 68319581 | 68321606 |
| 18 | 38102254 | 38102928 | 18 | 68323391 | 68323766 |
| 18 | 38126062 | 38129115 | 18 | 68365136 | 68365802 |
| 18 | 38148976 | 38150120 | 18 | 68367747 | 68368562 |
| 18 | 38178791 | 38182105 | 18 | 68373986 | 68375153 |
| 18 | 38201179 | 38208737 | 18 | 68380028 | 68384042 |
| 18 | 38226782 | 38229110 | 18 | 68419593 | 68421213 |
| 18 | 38232651 | 38237490 | 18 | 68429548 | 68432206 |
| 18 | 38248845 | 38250375 | 18 | 68492807 | 68499644 |
| 18 | 38256044 | 38257568 | 18 | 68521906 | 68522736 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 38276772 | 38279469 | | | 18 | 68538714 | 68539440 |
| 18 | 38342596 | 38348092 | | | 18 | 68576564 | 68580561 |
| 18 | 38363521 | 38364847 | | | 18 | 68638554 | 68643991 |
| 18 | 38397593 | 38400143 | | | 18 | 68688395 | 68692912 |
| 18 | 38410603 | 38420760 | | | 18 | 68706615 | 68709815 |
| 18 | 38449944 | 38452993 | | | 18 | 68758118 | 68758509 |
| 18 | 38469215 | 38479198 | | | 18 | 68914853 | 68917019 |
| 18 | 38502597 | 38506877 | | | 18 | 68965218 | 68967967 |
| 18 | 38509973 | 38513315 | | | 18 | 68991969 | 68996422 |
| 18 | 38522007 | 38525162 | | | 18 | 68999478 | 69001122 |
| 18 | 38536953 | 38538092 | | | 18 | 69006030 | 69007463 |
| 18 | 38553209 | 38555588 | | | 18 | 69024092 | 69024654 |
| 18 | 38558329 | 38562227 | | | 18 | 69037648 | 69042626 |
| 18 | 38587439 | 38589650 | | | 18 | 69110768 | 69111050 |
| 18 | 38610086 | 38613606 | | | 18 | 69131053 | 69138775 |
| 18 | 38616987 | 38617914 | | | 18 | 69150044 | 69152430 |
| 18 | 38654289 | 38656372 | | | 18 | 69310279 | 69312847 |
| 18 | 38698401 | 38705005 | | | 18 | 69400450 | 69402521 |
| 18 | 38715438 | 38718649 | | | 18 | 69468969 | 69471108 |
| 18 | 38724678 | 38726497 | | | 18 | 69505788 | 69512799 |
| 18 | 38747732 | 38757524 | | | 18 | 69526430 | 69527862 |
| 18 | 38763285 | 38766391 | | | 18 | 69532495 | 69533891 |
| 18 | 38775234 | 38784024 | | | 18 | 69550025 | 69551142 |
| 18 | 38789214 | 38790660 | | | 18 | 69566782 | 69570213 |
| 18 | 38808927 | 38812428 | | | 18 | 69572875 | 69580830 |
| 18 | 38835440 | 38838570 | | | 18 | 69596683 | 69597836 |
| 18 | 38843923 | 38844216 | | | 18 | 69648641 | 69651046 |
| 18 | 38847487 | 38855564 | | | 18 | 69706936 | 69713377 |
| 18 | 38888934 | 38889467 | | | 18 | 69738006 | 69738460 |
| 18 | 38899738 | 38902839 | | | 18 | 69752245 | 69755653 |
| 18 | 38906320 | 38906660 | | | 18 | 69756834 | 69762285 |
| 18 | 39014835 | 39019686 | | | 18 | 69775384 | 69778054 |
| 18 | 39026950 | 39028360 | | | 18 | 69790033 | 69792657 |
| 18 | 39079405 | 39088320 | | | 18 | 69795706 | 69804098 |
| 18 | 39107552 | 39108671 | | | 18 | 69809138 | 69810078 |
| 18 | 39134512 | 39140390 | | | 18 | 69813698 | 69818877 |
| 18 | 39142986 | 39149744 | | | 18 | 69825941 | 69832325 |
| 18 | 39204953 | 39206902 | | | 18 | 69836434 | 69838163 |
| 18 | 39209327 | 39213322 | | | 18 | 69852201 | 69856371 |
| 18 | 39221464 | 39223824 | | | 18 | 69879009 | 69880698 |
| 18 | 39256019 | 39258765 | | | 18 | 69884248 | 69898208 |
| 18 | 39268263 | 39270226 | | | 18 | 69934423 | 69938255 |
| 18 | 39290651 | 39291808 | | | 18 | 69940526 | 69946627 |
| 18 | 39299069 | 39301290 | | | 18 | 69956114 | 69958035 |
| 18 | 39308564 | 39309149 | | | 18 | 69965234 | 69966110 |
| 18 | 39316209 | 39317671 | | | 18 | 69982421 | 70001796 |
| 18 | 39342787 | 39346080 | | | 18 | 70033191 | 70037948 |
| 18 | 39384705 | 39391550 | | | 18 | 70043961 | 70044213 |
| 18 | 39396367 | 39398382 | | | 18 | 70060429 | 70061372 |
| 18 | 39401816 | 39410731 | | | 18 | 70084673 | 70087055 |
| 18 | 39412720 | 39415750 | | | 18 | 70094713 | 70096294 |
| 18 | 39437270 | 39440343 | | | 18 | 70099131 | 70110068 |
| 18 | 39443436 | 39444555 | | | 18 | 70121130 | 70122704 |
| 18 | 39469502 | 39474747 | | | 18 | 70131492 | 70134487 |
| 18 | 39532586 | 39540716 | | | 18 | 70143297 | 70146258 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 39580276 | 39581390 | | | 18 | 70149662 | 70156691 |
| 18 | 39605857 | 39607588 | | | 18 | 70162167 | 70163569 |
| 18 | 39651687 | 39657868 | | | 18 | 70181442 | 70182535 |
| 18 | 39659557 | 39661184 | | | 18 | 70217335 | 70217947 |
| 18 | 39733556 | 39737038 | | | 18 | 70220926 | 70221487 |
| 18 | 39763002 | 39764605 | | | 18 | 70228436 | 70229301 |
| 18 | 39795662 | 39796301 | | | 18 | 70242894 | 70255226 |
| 18 | 39914448 | 39915077 | | | 18 | 70262514 | 70264332 |
| 18 | 39922337 | 39924439 | | | 18 | 70283772 | 70285509 |
| 18 | 39931118 | 39931739 | | | 18 | 70313699 | 70315648 |
| 18 | 40018461 | 40020279 | | | 18 | 70316262 | 70317988 |
| 18 | 40104656 | 40106836 | | | 18 | 70319403 | 70320007 |
| 18 | 40114236 | 40128922 | | | 18 | 70323942 | 70335915 |
| 18 | 40153464 | 40156849 | | | 18 | 70340607 | 70341457 |
| 18 | 40224901 | 40232705 | | | 18 | 70343988 | 70349520 |
| 18 | 40252073 | 40258825 | | | 18 | 70363467 | 70365809 |
| 18 | 40284181 | 40288908 | | | 18 | 70371203 | 70374659 |
| 18 | 40341738 | 40342799 | | | 18 | 70407189 | 70409084 |
| 18 | 40349547 | 40355595 | | | 18 | 70424492 | 70425558 |
| 18 | 40369891 | 40371165 | | | 18 | 70521994 | 70523988 |
| 18 | 40372864 | 40376432 | | | 18 | 70541378 | 70542498 |
| 18 | 40382174 | 40383372 | | | 18 | 70767840 | 70770292 |
| 18 | 40389921 | 40391953 | | | 18 | 70850964 | 70852213 |
| 18 | 40397198 | 40405382 | | | 18 | 70857081 | 70860981 |
| 18 | 40423296 | 40428047 | | | 18 | 70873129 | 70875137 |
| 18 | 40447413 | 40448930 | | | 18 | 70900593 | 70909167 |
| 18 | 40450470 | 40451120 | | | 18 | 70916275 | 70918672 |
| 18 | 40464080 | 40466046 | | | 18 | 70922702 | 70931356 |
| 18 | 40491484 | 40494106 | | | 18 | 70945381 | 70957717 |
| 18 | 40512155 | 40514053 | | | 18 | 70963419 | 70984466 |
| 18 | 40515420 | 40516198 | | | 18 | 70995604 | 71001536 |
| 18 | 40516418 | 40517097 | | | 18 | 71005055 | 71012014 |
| 18 | 40553888 | 40560098 | | | 18 | 71018601 | 71019866 |
| 18 | 40565360 | 40567370 | | | 18 | 71024692 | 71025984 |
| 18 | 40583531 | 40587908 | | | 18 | 71034469 | 71035947 |
| 18 | 40593194 | 40594420 | | | 18 | 71044776 | 71048028 |
| 18 | 40599994 | 40601325 | | | 18 | 71074588 | 71075666 |
| 18 | 40605887 | 40607019 | | | 18 | 71105039 | 71106367 |
| 18 | 40619344 | 40620309 | | | 18 | 71118245 | 71119955 |
| 18 | 40626191 | 40627637 | | | 18 | 71121144 | 71124901 |
| 18 | 40721477 | 40722804 | | | 18 | 71126735 | 71129290 |
| 18 | 40770094 | 40772773 | | | 18 | 71136636 | 71146709 |
| 18 | 40783900 | 40787175 | | | 18 | 71157071 | 71163418 |
| 18 | 40790692 | 40793516 | | | 18 | 71173653 | 71186351 |
| 18 | 40832910 | 40834264 | | | 18 | 71198634 | 71207214 |
| 18 | 40897298 | 40898209 | | | 18 | 71226000 | 71235129 |
| 18 | 40909644 | 40910434 | | | 18 | 71240359 | 71242542 |
| 18 | 40946990 | 40948932 | | | 18 | 71246715 | 71249540 |
| 18 | 40955068 | 40959165 | | | 18 | 71256246 | 71257103 |
| 18 | 41002751 | 41011180 | | | 18 | 71271565 | 71274525 |
| 18 | 41049228 | 41056769 | | | 18 | 71280063 | 71284033 |
| 18 | 41063895 | 41072419 | | | 18 | 71289054 | 71291408 |
| 18 | 41099650 | 41111087 | | | 18 | 71295008 | 71295753 |
| 18 | 41128806 | 41129820 | | | 18 | 71296907 | 71297401 |
| 18 | 41150691 | 41152401 | | | 18 | 71304833 | 71312015 |

The chromosomal positon was obtained from UCSC genome browser (http://genome.ucsc.edu/) build 36.

APPENDIX C: Chromosome 18

| Chr | Start | End | | Chr | Start | End |
|---|---|---|---|---|---|---|
| 18 | 41155085 | 41157110 | | 18 | 71313124 | 71313883 |
| 18 | 41188857 | 41190358 | | 18 | 71354573 | 71375316 |
| 18 | 41233002 | 41235792 | | 18 | 71389742 | 71395972 |
| 18 | 41245423 | 41245848 | | 18 | 71401613 | 71407950 |
| 18 | 41270572 | 41272117 | | 18 | 71426218 | 71431777 |
| 18 | 41293790 | 41295321 | | 18 | 71452554 | 71453184 |
| 18 | 41297467 | 41299056 | | 18 | 71461953 | 71465859 |
| 18 | 41351239 | 41352619 | | 18 | 71467553 | 71473377 |
| 18 | 41355389 | 41357657 | | 18 | 71477735 | 71486815 |
| 18 | 41373324 | 41374842 | | 18 | 71519939 | 71528949 |
| 18 | 41383795 | 41384253 | | 18 | 71534267 | 71535530 |
| 18 | 41398689 | 41400584 | | 18 | 71580500 | 71587074 |
| 18 | 41413024 | 41416680 | | 18 | 71590566 | 71592544 |
| 18 | 41423554 | 41425683 | | 18 | 71594153 | 71595573 |
| 18 | 41430957 | 41434857 | | 18 | 71615434 | 71619180 |
| 18 | 41445771 | 41446448 | | 18 | 71623824 | 71625169 |
| 18 | 41453407 | 41454470 | | 18 | 71647943 | 71654524 |
| 18 | 41456432 | 41460720 | | 18 | 71662892 | 71665470 |
| 18 | 41466153 | 41467603 | | 18 | 71702774 | 71707425 |
| 18 | 41473402 | 41480092 | | 18 | 71710983 | 71715556 |
| 18 | 41495247 | 41499450 | | 18 | 71729482 | 71732039 |
| 18 | 41507324 | 41508943 | | 18 | 71743409 | 71747415 |
| 18 | 41512856 | 41519829 | | 18 | 71757440 | 71759812 |
| 18 | 41520002 | 41522404 | | 18 | 71786214 | 71787392 |
| 18 | 41619010 | 41619824 | | 18 | 71834753 | 71836601 |
| 18 | 41662756 | 41664095 | | 18 | 71845682 | 71849822 |
| 18 | 41670485 | 41677128 | | 18 | 71855957 | 71856718 |
| 18 | 41865767 | 41867147 | | 18 | 71878039 | 71880471 |
| 18 | 41876155 | 41877893 | | 18 | 71888338 | 71899712 |
| 18 | 41925436 | 41926697 | | 18 | 71931265 | 71935844 |
| 18 | 42007497 | 42008923 | | 18 | 71939498 | 71941950 |
| 18 | 42064366 | 42065364 | | 18 | 71966385 | 71972746 |
| 18 | 42102711 | 42106597 | | 18 | 71977811 | 71978883 |
| 18 | 42116911 | 42117883 | | 18 | 71985581 | 71997497 |
| 18 | 42126963 | 42128517 | | 18 | 72009040 | 72011470 |
| 18 | 42134786 | 42139797 | | 18 | 72095423 | 72097673 |
| 18 | 42144014 | 42148135 | | 18 | 72102095 | 72106137 |
| 18 | 42155539 | 42157726 | | 18 | 72112222 | 72116798 |
| 18 | 42166358 | 42167703 | | 18 | 72151334 | 72153158 |
| 18 | 42168985 | 42172045 | | 18 | 72156892 | 72157312 |
| 18 | 42174698 | 42176597 | | 18 | 72178081 | 72179196 |
| 18 | 42181845 | 42185891 | | 18 | 72186389 | 72193309 |
| 18 | 42189546 | 42192601 | | 18 | 72197377 | 72213459 |
| 18 | 42202678 | 42203398 | | 18 | 72216413 | 72224934 |
| 18 | 42212086 | 42215887 | | 18 | 72231449 | 72249496 |
| 18 | 42227217 | 42228511 | | 18 | 72258112 | 72259225 |
| 18 | 42231016 | 42234126 | | 18 | 72262093 | 72267284 |
| 18 | 42238020 | 42247477 | | 18 | 72272601 | 72278883 |
| 18 | 42260604 | 42262449 | | 18 | 72284696 | 72288426 |
| 18 | 42266147 | 42267999 | | 18 | 72291555 | 72292661 |
| 18 | 42283903 | 42284619 | | 18 | 72296147 | 72313228 |
| 18 | 42289500 | 42296927 | | 18 | 72332090 | 72334615 |
| 18 | 42308183 | 42310703 | | 18 | 72347398 | 72350689 |
| 18 | 42317172 | 42326026 | | 18 | 72365300 | 72392874 |
| 18 | 42341080 | 42344480 | | 18 | 72398294 | 72409066 |

The chromosomal positon was obtained from UCSC genome browser (http://genome.ucsc.edu/) build 36.

APPENDIX C: Chromosome 18
Page 34 of 72

| Chr | Start | End | | | Chr | Start | End |
|---|---|---|---|---|---|---|---|
| 18 | 42356015 | 42370412 | | | 18 | 72423784 | 72427458 |
| 18 | 42390622 | 42414225 | | | 18 | 72429192 | 72434559 |
| 18 | 42427733 | 42428608 | | | 18 | 72437057 | 72457193 |
| 18 | 42456217 | 42466169 | | | 18 | 72459272 | 72480396 |
| 18 | 42473494 | 42474244 | | | 18 | 72500606 | 72502095 |
| 18 | 42475519 | 42476958 | | | 18 | 72507695 | 72512010 |
| 18 | 42478950 | 42493441 | | | 18 | 72513985 | 72550288 |
| 18 | 42499101 | 42499881 | | | 18 | 72563594 | 72566994 |
| 18 | 42501870 | 42505615 | | | 18 | 72575580 | 72578380 |
| 18 | 42507773 | 42520425 | | | 18 | 72614330 | 72616712 |
| 18 | 42525669 | 42533732 | | | 18 | 72623444 | 72637435 |
| 18 | 42548885 | 42566575 | | | 18 | 72646354 | 72647763 |
| 18 | 42585853 | 42589433 | | | 18 | 72661002 | 72665462 |
| 18 | 42599628 | 42600793 | | | 18 | 72711006 | 72712326 |
| 18 | 42617327 | 42622318 | | | 18 | 72780541 | 72782657 |
| 18 | 42625340 | 42626066 | | | 18 | 72814053 | 72815319 |
| 18 | 42646383 | 42647808 | | | 18 | 72820056 | 72822737 |
| 18 | 42653269 | 42660621 | | | 18 | 72824024 | 72840336 |
| 18 | 42784063 | 42785410 | | | 18 | 72846590 | 72887509 |
| 18 | 42795923 | 42816848 | | | 18 | 72890539 | 72895165 |
| 18 | 42828791 | 42832047 | | | 18 | 72914866 | 72940294 |
| 18 | 42835367 | 42839069 | | | 18 | 72944356 | 72945613 |
| 18 | 42843182 | 42851263 | | | 18 | 72952236 | 72956341 |
| 18 | 42855357 | 42856047 | | | 18 | 72960215 | 72962344 |
| 18 | 42858894 | 42861891 | | | 18 | 72965161 | 72966193 |
| 18 | 42909589 | 42910110 | | | 18 | 72977351 | 73011542 |
| 18 | 42931128 | 42932153 | | | 18 | 73016572 | 73020326 |
| 18 | 43038470 | 43040180 | | | 18 | 73021842 | 73028776 |
| 18 | 43042632 | 43043217 | | | 18 | 73039616 | 73063041 |
| 18 | 43062847 | 43068111 | | | 18 | 73082087 | 73084210 |
| 18 | 43108667 | 43114699 | | | 18 | 73091832 | 73093342 |
| 18 | 43117638 | 43118265 | | | 18 | 73108160 | 73109845 |
| 18 | 43120563 | 43134800 | | | 18 | 73113197 | 73119595 |
| 18 | 43161337 | 43164021 | | | 18 | 73135959 | 73147645 |
| 18 | 43178986 | 43196011 | | | 18 | 73163537 | 73165274 |
| 18 | 43203758 | 43204582 | | | 18 | 73173734 | 73186287 |
| 18 | 43207434 | 43209914 | | | 18 | 73213011 | 73224427 |
| 18 | 43264431 | 43266627 | | | 18 | 73233369 | 73234817 |
| 18 | 43281853 | 43286872 | | | 18 | 73238855 | 73251589 |
| 18 | 43302601 | 43305260 | | | 18 | 73283408 | 73291885 |
| 18 | 43326159 | 43328280 | | | 18 | 73326321 | 73327563 |
| 18 | 43338750 | 43341087 | | | 18 | 73330603 | 73345566 |
| 18 | 43373579 | 43375529 | | | 18 | 73358681 | 73372292 |
| 18 | 43393701 | 43394802 | | | 18 | 73387526 | 73390448 |
| 18 | 43415454 | 43423992 | | | 18 | 73401803 | 73412946 |
| 18 | 43497100 | 43505233 | | | 18 | 73417684 | 73425206 |
| 18 | 43506229 | 43518486 | | | 18 | 73437710 | 73439430 |
| 18 | 43523934 | 43536631 | | | 18 | 73446611 | 73468730 |
| 18 | 43558179 | 43561472 | | | 18 | 73476299 | 73477071 |
| 18 | 43578466 | 43580415 | | | 18 | 73486936 | 73500956 |
| 18 | 43607428 | 43610218 | | | 18 | 73506461 | 73516985 |
| 18 | 43626797 | 43628567 | | | 18 | 73523249 | 73524662 |
| 18 | 43689121 | 43693059 | | | 18 | 73530947 | 73532749 |
| 18 | 43696737 | 43699402 | | | 18 | 73557481 | 73559469 |
| 18 | 43729394 | 43734375 | | | 18 | 73572658 | 73575078 |

The chromosomal positon was obtained from UCSC genome browser (http://genome.ucsc.edu/) build 36.

APPENDIX C: Chromosome 18
Page 35 of 72

| Chr | Start | End | | | Chr | Start | End |
|---|---|---|---|---|---|---|---|
| 18 | 43759446 | 43760618 | | | 18 | 73588299 | 73592706 |
| 18 | 43778016 | 43780501 | | | 18 | 73600971 | 73602222 |
| 18 | 43794679 | 43794965 | | | 18 | 73613633 | 73614492 |
| 18 | 43800047 | 43804928 | | | 18 | 73617182 | 73620342 |
| 18 | 43829600 | 43830942 | | | 18 | 73625760 | 73630485 |
| 18 | 43919054 | 43921842 | | | 18 | 73677854 | 73685234 |
| 18 | 43954811 | 43956909 | | | 18 | 73693680 | 73722560 |
| 18 | 43981700 | 43983120 | | | 18 | 73745516 | 73756324 |
| 18 | 44046697 | 44048563 | | | 18 | 73759861 | 73762385 |
| 18 | 44093642 | 44096337 | | | 18 | 73772384 | 73779524 |
| 18 | 44110982 | 44115072 | | | 18 | 73789417 | 73799736 |
| 18 | 44116740 | 44117975 | | | 18 | 73808220 | 73813185 |
| 18 | 44128863 | 44129528 | | | 18 | 73816080 | 73827996 |
| 18 | 44140392 | 44141690 | | | 18 | 73831272 | 73833788 |
| 18 | 44164947 | 44168092 | | | 18 | 73843889 | 73845240 |
| 18 | 44168822 | 44169665 | | | 18 | 73876842 | 73886789 |
| 18 | 44176351 | 44178256 | | | 18 | 73888274 | 73897298 |
| 18 | 44188466 | 44191104 | | | 18 | 73905471 | 73917594 |
| 18 | 44232577 | 44235380 | | | 18 | 73931394 | 73935226 |
| 18 | 44239399 | 44243898 | | | 18 | 73940285 | 73963846 |
| 18 | 44270033 | 44270175 | | | 18 | 73968095 | 73975612 |
| 18 | 44325310 | 44329030 | | | 18 | 73984591 | 74002054 |
| 18 | 44360528 | 44361418 | | | 18 | 74005543 | 74008340 |
| 18 | 44368707 | 44370807 | | | 18 | 74011734 | 74042351 |
| 18 | 44396521 | 44402946 | | | 18 | 74052964 | 74063479 |
| 18 | 44437793 | 44440372 | | | 18 | 74067372 | 74068622 |
| 18 | 44441917 | 44444607 | | | 18 | 74072263 | 74082343 |
| 18 | 44448624 | 44449638 | | | 18 | 74087444 | 74094545 |
| 18 | 44493965 | 44494700 | | | 18 | 74098749 | 74113586 |
| 18 | 44515246 | 44523697 | | | 18 | 74127622 | 74130903 |
| 18 | 44535200 | 44536360 | | | 18 | 74140657 | 74142436 |
| 18 | 44546713 | 44548218 | | | 18 | 74154610 | 74206474 |
| 18 | 44560214 | 44562150 | | | 18 | 74210939 | 74237466 |
| 18 | 44592857 | 44595418 | | | 18 | 74247969 | 74267615 |
| 18 | 44597822 | 44609355 | | | 18 | 74269543 | 74300918 |
| 18 | 44614536 | 44615413 | | | 18 | 74304783 | 74318580 |
| 18 | 44621439 | 44622784 | | | 18 | 74333104 | 74390849 |
| 18 | 44633498 | 44634214 | | | 18 | 74400060 | 74567857 |
| 18 | 44639842 | 44644286 | | | 18 | 74570271 | 74570764 |
| 18 | 44653715 | 44659651 | | | 18 | 74572635 | 74582601 |
| 18 | 44665119 | 44670350 | | | 18 | 74586240 | 74604209 |
| 18 | 44696155 | 44702286 | | | 18 | 74611212 | 74694664 |
| 18 | 44706747 | 44710762 | | | 18 | 74698642 | 74702901 |
| 18 | 44719105 | 44728468 | | | 18 | 74716413 | 74741386 |
| 18 | 44742914 | 44744674 | | | 18 | 74756754 | 74833794 |
| 18 | 44754801 | 44760398 | | | 18 | 74842405 | 74843014 |
| 18 | 44767572 | 44778975 | | | 18 | 74850857 | 74884827 |
| 18 | 44783380 | 44789083 | | | 18 | 74890871 | 74893317 |
| 18 | 44791726 | 44808567 | | | 18 | 74902763 | 74909946 |
| 18 | 44851799 | 44852648 | | | 18 | 74913548 | 74915646 |
| | | | | | 18 | 74919288 | 74920901 |
| | | | | | 18 | 74926684 | 74928617 |
| | | | | | 18 | 74970490 | 74971235 |
| | | | | | 18 | 75160842 | 75161681 |
| | | | | | 18 | 75195389 | 75198735 |

The chromosomal positon was obtained from UCSC genome browser (http://genome.ucsc.edu/) build 36.

APPENDIX C: Chromosome 18
Page 36 of 72

| Chr | Start | End | | | Chr | Start | End |
|---|---|---|---|---|---|---|---|
| | | | | | 18 | 75205862 | 75210947 |
| | | | | | 18 | 75223639 | 75228805 |
| | | | | | 18 | 75239035 | 75246975 |
| | | | | | 18 | 75258003 | 75259478 |
| | | | | | 18 | 75262396 | 75266676 |
| | | | | | 18 | 75268266 | 75360592 |
| | | | | | 18 | 75370880 | 75377290 |
| | | | | | 18 | 75379240 | 75383578 |
| | | | | | 18 | 75384202 | 75385409 |
| | | | | | 18 | 75385609 | 75396613 |
| | | | | | 18 | 75399718 | 75503505 |
| | | | | | 18 | 75505765 | 75511733 |
| | | | | | 18 | 75541697 | 75543422 |
| | | | | | 18 | 75553565 | 75559705 |
| | | | | | 18 | 75564720 | 75569785 |
| | | | | | 18 | 75575813 | 75610842 |
| | | | | | 18 | 75620221 | 75684791 |
| | | | | | 18 | 75687416 | 75700825 |
| | | | | | 18 | 75705444 | 75740715 |
| | | | | | 18 | 75744821 | 75751349 |
| | | | | | 18 | 75762622 | 75784446 |
| | | | | | 18 | 75794840 | 75795192 |
| | | | | | 18 | 75822488 | 75823771 |
| | | | | | 18 | 75847728 | 75851371 |
| | | | | | 18 | 75916792 | 75918543 |
| | | | | | 18 | 75927930 | 75933356 |
| | | | | | 18 | 76021565 | 76030439 |
| | | | | | 18 | 76035615 | 76048656 |
| | | | | | 18 | 76055429 | 76060762 |
| | | | | | 18 | 76092345 | 76098627 |
| 18 | 878 | 2585 | | | 18 | 6953418 | 6957125 |
| 18 | 39766 | 40396 | | | 18 | 6960327 | 6960402 |
| 18 | 53539 | 101639 | | | 18 | 6971751 | 6971941 |
| 18 | 129567 | 141066 | | | 18 | 6976366 | 6977166 |
| 18 | 144090 | 144445 | | | 18 | 6997564 | 6997629 |
| 18 | 145460 | 146665 | | | 18 | 7001665 | 7002265 |
| 18 | 160458 | 160558 | | | 18 | 7027959 | 7029156 |
| 18 | 164144 | 165085 | | | 18 | 7035161 | 7038043 |
| 18 | 179076 | 180563 | | | 18 | 7046224 | 7047275 |
| 18 | 207539 | 207819 | | | 18 | 7056632 | 7057362 |
| 18 | 208584 | 208965 | | | 18 | 7077848 | 7079738 |
| 18 | 211167 | 211292 | | | 18 | 7097061 | 7100451 |
| 18 | 224888 | 227737 | | | 18 | 7105471 | 7119956 |
| 18 | 230251 | 231503 | | | 18 | 7123146 | 7123846 |
| 18 | 236554 | 237449 | | | 18 | 7147831 | 7148931 |
| 18 | 251323 | 252158 | | | 18 | 7150439 | 7151507 |
| 18 | 254441 | 254991 | | | 18 | 7162597 | 7163874 |
| 18 | 258483 | 259618 | | | 18 | 7170310 | 7175568 |
| 18 | 266192 | 270161 | | | 18 | 7190410 | 7194566 |
| 18 | 272865 | 275638 | | | 18 | 7200255 | 7201883 |
| 18 | 288863 | 289754 | | | 18 | 7204573 | 7205243 |
| 18 | 309628 | 310439 | | | 18 | 7208712 | 7209202 |
| 18 | 323008 | 323733 | | | 18 | 7221016 | 7224799 |
| 18 | 326331 | 326701 | | | 18 | 7227075 | 7227881 |
| 18 | 328257 | 329617 | | | 18 | 7249585 | 7250090 |

The chromosomal positon was obtained from UCSC genome browser (http://genome.ucsc.edu/) build 36.

APPENDIX C: Chromosome 18
Page 37 of 72

| Chr | Start | End | Chr | Start | End |
|---|---|---|---|---|---|
| 18 | 330927 | 335286 | 18 | 7251945 | 7252170 |
| 18 | 342801 | 346731 | 18 | 7257362 | 7258252 |
| 18 | 351530 | 353105 | 18 | 7269473 | 7271380 |
| 18 | 355958 | 357128 | 18 | 7278028 | 7278043 |
| 18 | 361262 | 362148 | 18 | 7281268 | 7284511 |
| 18 | 368654 | 376524 | 18 | 7298921 | 7299584 |
| 18 | 382371 | 383321 | 18 | 7309904 | 7310669 |
| 18 | 386232 | 387187 | 18 | 7317027 | 7319028 |
| 18 | 389238 | 390008 | 18 | 7335624 | 7335964 |
| 18 | 390673 | 391408 | 18 | 7344688 | 7345344 |
| 18 | 395256 | 396920 | 18 | 7347442 | 7350419 |
| 18 | 397825 | 398230 | 18 | 7353707 | 7356106 |
| 18 | 399823 | 400183 | 18 | 7357016 | 7357346 |
| 18 | 403761 | 404116 | 18 | 7360546 | 7360846 |
| 18 | 424483 | 425933 | 18 | 7369242 | 7369677 |
| 18 | 434882 | 435147 | 18 | 7372037 | 7377558 |
| 18 | 437104 | 438674 | 18 | 7379913 | 7380861 |
| 18 | 442055 | 442690 | 18 | 7395398 | 7403059 |
| 18 | 448247 | 457355 | 18 | 7404164 | 7405297 |
| 18 | 460965 | 461527 | 18 | 7406990 | 7407977 |
| 18 | 475177 | 475957 | 18 | 7411072 | 7412977 |
| 18 | 480933 | 482063 | 18 | 7416098 | 7418900 |
| 18 | 485372 | 486222 | 18 | 7420635 | 7421485 |
| 18 | 487757 | 489386 | 18 | 7423220 | 7425594 |
| 18 | 491269 | 491614 | 18 | 7426419 | 7426802 |
| 18 | 493459 | 494140 | 18 | 7439555 | 7440920 |
| 18 | 504486 | 506046 | 18 | 7457030 | 7458450 |
| 18 | 508730 | 509715 | 18 | 7491237 | 7492455 |
| 18 | 545854 | 546704 | 18 | 7494424 | 7494754 |
| 18 | 565703 | 566128 | 18 | 7495750 | 7496586 |
| 18 | 569701 | 570520 | 18 | 7504570 | 7508109 |
| 18 | 578095 | 579305 | 18 | 7508754 | 7510139 |
| 18 | 585046 | 585376 | 18 | 7514044 | 7515400 |
| 18 | 586543 | 587948 | 18 | 7532849 | 7533391 |
| 18 | 588949 | 590309 | 18 | 7534956 | 7535934 |
| 18 | 592259 | 592529 | 18 | 7545778 | 7546293 |
| 18 | 594710 | 595320 | 18 | 7554907 | 7556197 |
| 18 | 600547 | 600727 | 18 | 7562475 | 7563375 |
| 18 | 614553 | 615208 | 18 | 7564546 | 7565216 |
| 18 | 620519 | 620971 | 18 | 7565401 | 7566031 |
| 18 | 630888 | 632873 | 18 | 7575828 | 7576763 |
| 18 | 652208 | 658081 | 18 | 7581963 | 7585849 |
| 18 | 665121 | 665636 | 18 | 7596619 | 7597764 |
| 18 | 693065 | 695059 | 18 | 7598179 | 7599229 |
| 18 | 699852 | 700032 | 18 | 7607749 | 7608034 |
| 18 | 702058 | 705287 | 18 | 7608600 | 7610310 |
| 18 | 732731 | 732966 | 18 | 7611448 | 7612596 |
| 18 | 752807 | 753187 | 18 | 7616939 | 7617579 |
| 18 | 753822 | 755114 | 18 | 7625357 | 7626057 |
| 18 | 756226 | 756513 | 18 | 7630233 | 7632448 |
| 18 | 764968 | 765433 | 18 | 7632976 | 7634617 |
| 18 | 768243 | 768563 | 18 | 7637681 | 7638496 |
| 18 | 785970 | 786875 | 18 | 7640085 | 7640285 |
| 18 | 787794 | 788604 | 18 | 7648427 | 7648682 |
| 18 | 795456 | 795956 | 18 | 7656661 | 7657007 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 803238 | 804079 | 18 | 7662430 | 7662832 |
| 18 | 813415 | 814646 | 18 | 7665679 | 7666343 |
| 18 | 820348 | 820760 | 18 | 7671349 | 7672451 |
| 18 | 821775 | 823371 | 18 | 7675641 | 7675869 |
| 18 | 831431 | 832403 | 18 | 7678112 | 7678167 |
| 18 | 835526 | 836326 | 18 | 7683112 | 7683957 |
| 18 | 843901 | 845991 | 18 | 7686580 | 7688005 |
| 18 | 859445 | 862545 | 18 | 7690350 | 7690595 |
| 18 | 868985 | 869885 | 18 | 7700738 | 7704942 |
| 18 | 872075 | 872330 | 18 | 7706217 | 7707368 |
| 18 | 882502 | 882812 | 18 | 7707668 | 7710061 |
| 18 | 887377 | 888211 | 18 | 7713354 | 7713874 |
| 18 | 892091 | 893015 | 18 | 7720778 | 7721008 |
| 18 | 894870 | 901739 | 18 | 7733000 | 7733180 |
| 18 | 904489 | 907488 | 18 | 7735215 | 7735810 |
| 18 | 911279 | 911594 | 18 | 7738569 | 7740754 |
| 18 | 912889 | 916749 | 18 | 7744608 | 7745163 |
| 18 | 929165 | 929350 | 18 | 7745518 | 7750642 |
| 18 | 943626 | 943921 | 18 | 7752684 | 7753509 |
| 18 | 948253 | 950866 | 18 | 7759217 | 7761225 |
| 18 | 951651 | 952030 | 18 | 7764085 | 7767754 |
| 18 | 953386 | 953506 | 18 | 7776906 | 7777741 |
| 18 | 956206 | 957021 | 18 | 7781466 | 7783525 |
| 18 | 957236 | 958036 | 18 | 7786470 | 7787340 |
| 18 | 984866 | 985359 | 18 | 7790189 | 7797709 |
| 18 | 988877 | 990109 | 18 | 7808352 | 7812942 |
| 18 | 992835 | 993450 | 18 | 7831787 | 7834717 |
| 18 | 999966 | 1000011 | 18 | 7841481 | 7842260 |
| 18 | 1007647 | 1015449 | 18 | 7847510 | 7848045 |
| 18 | 1018250 | 1018375 | 18 | 7850504 | 7853154 |
| 18 | 1040459 | 1040750 | 18 | 7863651 | 7864356 |
| 18 | 1040952 | 1042112 | 18 | 7867893 | 7869699 |
| 18 | 1051514 | 1051669 | 18 | 7875179 | 7876240 |
| 18 | 1052237 | 1052662 | 18 | 7880561 | 7880693 |
| 18 | 1065123 | 1065858 | 18 | 7885270 | 7890612 |
| 18 | 1072239 | 1072329 | 18 | 7898038 | 7898953 |
| 18 | 1076695 | 1077475 | 18 | 7914113 | 7915908 |
| 18 | 1081213 | 1082382 | 18 | 7919235 | 7919656 |
| 18 | 1084647 | 1084942 | 18 | 7923463 | 7924043 |
| 18 | 1085612 | 1089423 | 18 | 7933799 | 7939436 |
| 18 | 1094457 | 1095888 | 18 | 7946344 | 7949649 |
| 18 | 1101130 | 1101395 | 18 | 7952944 | 7953592 |
| 18 | 1106633 | 1107342 | 18 | 7964271 | 7964951 |
| 18 | 1108932 | 1110048 | 18 | 7971477 | 7973957 |
| 18 | 1110833 | 1110983 | 18 | 7976093 | 7978898 |
| 18 | 1117591 | 1118176 | 18 | 7980620 | 7981515 |
| 18 | 1118491 | 1118721 | 18 | 7984660 | 7985415 |
| 18 | 1121848 | 1122403 | 18 | 7985475 | 7986050 |
| 18 | 1124268 | 1124293 | 18 | 7989906 | 7990141 |
| 18 | 1126047 | 1127008 | 18 | 7993600 | 7993970 |
| 18 | 1131206 | 1132906 | 18 | 7994801 | 7996501 |
| 18 | 1142281 | 1144028 | 18 | 7997406 | 7997756 |
| 18 | 1150996 | 1152223 | 18 | 8000411 | 8001616 |
| 18 | 1157063 | 1157573 | 18 | 8003112 | 8003247 |
| 18 | 1165018 | 1165373 | 18 | 8007231 | 8007857 |

The chromosomal positon was obtained from UCSC genome browser (http://genome.ucsc.edu/) build 36.

APPENDIX C: Chromosome 18
Page 39 of 72

| Chr | Start | End | | | Chr | Start | End |
|---|---|---|---|---|---|---|---|
| 18 | 1168151 | 1170031 | | | 18 | 8009890 | 8010241 |
| 18 | 1173846 | 1175276 | | | 18 | 8012101 | 8012676 |
| 18 | 1176675 | 1177315 | | | 18 | 8019834 | 8020714 |
| 18 | 1179163 | 1180681 | | | 18 | 8023657 | 8028306 |
| 18 | 1181468 | 1182088 | | | 18 | 8029252 | 8029512 |
| 18 | 1183287 | 1183702 | | | 18 | 8030375 | 8036118 |
| 18 | 1204142 | 1205302 | | | 18 | 8040522 | 8041167 |
| 18 | 1208127 | 1212286 | | | 18 | 8042462 | 8043763 |
| 18 | 1216311 | 1217026 | | | 18 | 8056016 | 8056946 |
| 18 | 1227155 | 1228205 | | | 18 | 8070837 | 8071297 |
| 18 | 1233245 | 1233605 | | | 18 | 8075307 | 8076212 |
| 18 | 1238743 | 1240340 | | | 18 | 8078198 | 8078923 |
| 18 | 1241967 | 1242302 | | | 18 | 8084639 | 8085049 |
| 18 | 1243827 | 1244817 | | | 18 | 8093220 | 8093995 |
| 18 | 1250661 | 1250791 | | | 18 | 8101945 | 8102865 |
| 18 | 1256807 | 1257922 | | | 18 | 8119981 | 8123881 |
| 18 | 1265965 | 1266210 | | | 18 | 8133206 | 8133876 |
| 18 | 1279978 | 1280461 | | | 18 | 8150914 | 8151337 |
| 18 | 1285282 | 1295085 | | | 18 | 8151707 | 8152907 |
| 18 | 1297698 | 1299884 | | | 18 | 8157610 | 8158070 |
| 18 | 1301303 | 1301573 | | | 18 | 8160768 | 8163119 |
| 18 | 1303884 | 1304099 | | | 18 | 8182906 | 8183541 |
| 18 | 1305655 | 1319261 | | | 18 | 8189212 | 8189802 |
| 18 | 1323636 | 1324651 | | | 18 | 8192454 | 8193099 |
| 18 | 1335340 | 1336551 | | | 18 | 8207480 | 8207500 |
| 18 | 1338819 | 1338964 | | | 18 | 8214054 | 8215149 |
| 18 | 1339543 | 1342185 | | | 18 | 8219868 | 8221468 |
| 18 | 1356076 | 1357094 | | | 18 | 8222504 | 8223304 |
| 18 | 1361028 | 1362023 | | | 18 | 8233330 | 8234566 |
| 18 | 1374918 | 1376109 | | | 18 | 8241667 | 8241957 |
| 18 | 1383086 | 1384148 | | | 18 | 8243639 | 8244028 |
| 18 | 1387808 | 1388243 | | | 18 | 8250911 | 8251471 |
| 18 | 1388563 | 1389080 | | | 18 | 8257983 | 8258938 |
| 18 | 1391064 | 1392029 | | | 18 | 8261132 | 8261432 |
| 18 | 1393446 | 1394486 | | | 18 | 8263447 | 8264167 |
| 18 | 1394726 | 1397804 | | | 18 | 8279238 | 8283316 |
| 18 | 1400731 | 1403482 | | | 18 | 8301788 | 8302873 |
| 18 | 1407839 | 1408944 | | | 18 | 8304821 | 8306336 |
| 18 | 1411484 | 1414788 | | | 18 | 8310655 | 8318742 |
| 18 | 1414998 | 1415463 | | | 18 | 8329302 | 8329577 |
| 18 | 1415538 | 1415808 | | | 18 | 8331823 | 8332323 |
| 18 | 1418509 | 1419039 | | | 18 | 8333485 | 8334200 |
| 18 | 1419516 | 1420111 | | | 18 | 8336691 | 8337984 |
| 18 | 1426114 | 1428946 | | | 18 | 8338994 | 8339549 |
| 18 | 1448357 | 1449351 | | | 18 | 8343529 | 8344249 |
| 18 | 1451901 | 1452291 | | | 18 | 8345939 | 8347069 |
| 18 | 1456765 | 1457590 | | | 18 | 8349774 | 8351334 |
| 18 | 1459815 | 1461535 | | | 18 | 8353995 | 8356067 |
| 18 | 1470112 | 1470207 | | | 18 | 8358559 | 8358764 |
| 18 | 1479671 | 1480865 | | | 18 | 8361561 | 8362392 |
| 18 | 1489312 | 1489437 | | | 18 | 8379643 | 8380273 |
| 18 | 1498093 | 1499666 | | | 18 | 8384129 | 8384414 |
| 18 | 1503083 | 1504998 | | | 18 | 8392602 | 8393758 |
| 18 | 1505918 | 1512345 | | | 18 | 8399544 | 8399814 |
| 18 | 1513165 | 1514897 | | | 18 | 8400839 | 8401064 |

The chromosomal positon was obtained from UCSC genome browser (http://genome.ucsc.edu/) build 36.

APPENDIX C: Chromosome 18
Page 40 of 72

| Chr | Start | End | | | Chr | Start | End |
|---|---|---|---|---|---|---|---|
| 18 | 1517428 | 1517723 | | | 18 | 8403733 | 8404557 |
| 18 | 1519012 | 1523556 | | | 18 | 8406353 | 8406988 |
| 18 | 1535071 | 1535826 | | | 18 | 8407367 | 8408366 |
| 18 | 1538702 | 1539367 | | | 18 | 8416436 | 8416501 |
| 18 | 1541492 | 1542322 | | | 18 | 8423217 | 8427247 |
| 18 | 1543098 | 1545174 | | | 18 | 8428907 | 8429392 |
| 18 | 1551164 | 1552804 | | | 18 | 8438121 | 8438616 |
| 18 | 1554710 | 1555810 | | | 18 | 8444379 | 8446099 |
| 18 | 1557376 | 1557841 | | | 18 | 8448934 | 8449339 |
| 18 | 1559415 | 1560080 | | | 18 | 8454510 | 8456115 |
| 18 | 1563808 | 1570327 | | | 18 | 8460310 | 8462246 |
| 18 | 1574171 | 1576031 | | | 18 | 8467170 | 8470965 |
| 18 | 1583099 | 1583642 | | | 18 | 8482293 | 8482728 |
| 18 | 1587010 | 1587890 | | | 18 | 8497413 | 8497458 |
| 18 | 1594091 | 1594501 | | | 18 | 8505814 | 8506788 |
| 18 | 1603796 | 1605041 | | | 18 | 8508068 | 8508083 |
| 18 | 1608739 | 1609435 | | | 18 | 8512573 | 8513543 |
| 18 | 1611220 | 1612985 | | | 18 | 8527773 | 8528233 |
| 18 | 1617082 | 1617694 | | | 18 | 8535582 | 8535767 |
| 18 | 1624765 | 1625717 | | | 18 | 8545025 | 8545455 |
| 18 | 1642204 | 1647318 | | | 18 | 8560263 | 8561185 |
| 18 | 1653731 | 1656597 | | | 18 | 8588189 | 8588279 |
| 18 | 1657652 | 1657767 | | | 18 | 8602009 | 8603474 |
| 18 | 1659320 | 1659995 | | | 18 | 8615159 | 8615469 |
| 18 | 1660495 | 1660635 | | | 18 | 8642828 | 8643418 |
| 18 | 1675511 | 1677017 | | | 18 | 8647059 | 8648325 |
| 18 | 1678327 | 1679646 | | | 18 | 8675462 | 8676007 |
| 18 | 1682686 | 1682976 | | | 18 | 8685971 | 8686481 |
| 18 | 1685472 | 1685952 | | | 18 | 8693489 | 8696278 |
| 18 | 1697865 | 1698065 | | | 18 | 8699632 | 8699767 |
| 18 | 1702124 | 1703869 | | | 18 | 8705716 | 8706321 |
| 18 | 1706709 | 1708575 | | | 18 | 8707025 | 8707335 |
| 18 | 1732514 | 1732899 | | | 18 | 8710102 | 8710947 |
| 18 | 1745426 | 1745611 | | | 18 | 8712737 | 8713602 |
| 18 | 1751363 | 1752988 | | | 18 | 8722690 | 8723300 |
| 18 | 1756275 | 1758627 | | | 18 | 8725685 | 8726063 |
| 18 | 1769293 | 1770298 | | | 18 | 8732851 | 8733131 |
| 18 | 1771820 | 1773605 | | | 18 | 8745639 | 8746827 |
| 18 | 1777175 | 1781169 | | | 18 | 8768770 | 8769200 |
| 18 | 1782650 | 1783425 | | | 18 | 8776396 | 8778546 |
| 18 | 1793912 | 1796008 | | | 18 | 8780171 | 8780496 |
| 18 | 1805583 | 1807690 | | | 18 | 8784677 | 8787716 |
| 18 | 1808743 | 1809740 | | | 18 | 8790278 | 8791681 |
| 18 | 1811969 | 1812470 | | | 18 | 8793067 | 8793517 |
| 18 | 1814807 | 1816186 | | | 18 | 8795560 | 8796335 |
| 18 | 1817002 | 1817177 | | | 18 | 8797855 | 8798363 |
| 18 | 1817597 | 1819352 | | | 18 | 8801758 | 8803453 |
| 18 | 1819732 | 1819902 | | | 18 | 8806853 | 8807063 |
| 18 | 1820267 | 1822034 | | | 18 | 8829227 | 8831999 |
| 18 | 1822979 | 1823254 | | | 18 | 8832264 | 8832504 |
| 18 | 1827253 | 1828118 | | | 18 | 8838449 | 8839519 |
| 18 | 1841526 | 1842512 | | | 18 | 8840534 | 8841274 |
| 18 | 1852811 | 1853551 | | | 18 | 8842522 | 8842967 |
| 18 | 1859984 | 1860669 | | | 18 | 8847935 | 8851973 |
| 18 | 1861899 | 1872330 | | | 18 | 8855926 | 8856631 |

The chromosomal positon was obtained from UCSC genome browser (http://genome.ucsc.edu/) build 36.

APPENDIX C: Chromosome 18
Page 41 of 72

| Chr | Start | End | Chr | Start | End |
|---|---|---|---|---|---|
| 18 | 1874141 | 1875959 | 18 | 8859156 | 8860311 |
| 18 | 1877215 | 1878820 | 18 | 8862784 | 8862959 |
| 18 | 1880136 | 1880456 | 18 | 8879807 | 8880212 |
| 18 | 1883972 | 1888725 | 18 | 8900300 | 8901085 |
| 18 | 1896583 | 1896768 | 18 | 8902355 | 8902870 |
| 18 | 1898804 | 1899809 | 18 | 8926993 | 8927638 |
| 18 | 1908264 | 1908941 | 18 | 8934835 | 8935370 |
| 18 | 1918665 | 1919500 | 18 | 8938664 | 8939369 |
| 18 | 1946871 | 1947041 | 18 | 8941407 | 8942162 |
| 18 | 1950549 | 1955264 | 18 | 8967975 | 8969125 |
| 18 | 1959531 | 1960173 | 18 | 8970954 | 8973594 |
| 18 | 1964265 | 1965760 | 18 | 8977696 | 8978248 |
| 18 | 1984708 | 1985153 | 18 | 8980608 | 8981825 |
| 18 | 1986607 | 1990377 | 18 | 8995577 | 8995752 |
| 18 | 1995393 | 1996188 | 18 | 8998799 | 8999259 |
| 18 | 1997821 | 1998723 | 18 | 9007193 | 9007763 |
| 18 | 2005849 | 2006614 | 18 | 9017596 | 9018436 |
| 18 | 2011454 | 2011804 | 18 | 9024934 | 9026796 |
| 18 | 2012946 | 2017732 | 18 | 9038957 | 9039222 |
| 18 | 2019088 | 2019198 | 18 | 9043832 | 9044677 |
| 18 | 2039824 | 2042199 | 18 | 9053816 | 9054390 |
| 18 | 2043917 | 2043967 | 18 | 9059325 | 9059542 |
| 18 | 2053118 | 2053303 | 18 | 9067232 | 9071734 |
| 18 | 2055527 | 2056047 | 18 | 9072524 | 9073369 |
| 18 | 2058075 | 2059939 | 18 | 9081184 | 9081254 |
| 18 | 2064878 | 2065163 | 18 | 9081489 | 9082805 |
| 18 | 2073464 | 2073739 | 18 | 9084392 | 9085932 |
| 18 | 2074724 | 2075108 | 18 | 9088090 | 9088985 |
| 18 | 2084377 | 2085032 | 18 | 9090080 | 9090960 |
| 18 | 2087040 | 2087450 | 18 | 9093814 | 9094389 |
| 18 | 2088695 | 2089534 | 18 | 9095780 | 9097621 |
| 18 | 2092283 | 2093123 | 18 | 9104751 | 9105211 |
| 18 | 2104414 | 2105634 | 18 | 9109581 | 9110402 |
| 18 | 2108693 | 2109309 | 18 | 9111158 | 9111899 |
| 18 | 2117658 | 2117853 | 18 | 9116133 | 9116558 |
| 18 | 2122152 | 2124906 | 18 | 9138057 | 9138177 |
| 18 | 2128009 | 2131688 | 18 | 9141410 | 9141780 |
| 18 | 2133059 | 2133409 | 18 | 9176013 | 9176628 |
| 18 | 2134584 | 2135825 | 18 | 9190091 | 9190575 |
| 18 | 2137452 | 2144971 | 18 | 9191338 | 9192325 |
| 18 | 2150655 | 2151956 | 18 | 9194728 | 9197469 |
| 18 | 2156497 | 2158727 | 18 | 9205625 | 9206189 |
| 18 | 2161031 | 2161415 | 18 | 9209661 | 9210187 |
| 18 | 2163395 | 2164863 | 18 | 9211402 | 9211773 |
| 18 | 2167512 | 2168768 | 18 | 9233531 | 9233561 |
| 18 | 2174520 | 2178932 | 18 | 9242603 | 9244008 |
| 18 | 2179327 | 2179522 | 18 | 9244788 | 9246006 |
| 18 | 2188100 | 2188510 | 18 | 9246891 | 9247971 |
| 18 | 2188985 | 2194133 | 18 | 9250159 | 9251364 |
| 18 | 2197869 | 2202669 | 18 | 9253401 | 9253824 |
| 18 | 2209907 | 2210552 | 18 | 9264083 | 9265557 |
| 18 | 2211249 | 2211879 | 18 | 9275481 | 9276046 |
| 18 | 2213587 | 2214457 | 18 | 9309094 | 9310838 |
| 18 | 2218991 | 2219421 | 18 | 9312703 | 9313468 |
| 18 | 2225405 | 2226775 | 18 | 9320645 | 9321295 |

The chromosomal positon was obtained from UCSC genome browser (http://genome.ucsc.edu/) build 36.

APPENDIX C: Chromosome 18
Page 42 of 72

| Chr | Start | End | Chr | Start | End |
|---|---|---|---|---|---|
| 18 | 2227855 | 2228115 | 18 | 9327943 | 9328243 |
| 18 | 2246775 | 2247905 | 18 | 9330771 | 9332155 |
| 18 | 2254139 | 2255939 | 18 | 9338023 | 9338997 |
| 18 | 2258929 | 2260529 | 18 | 9344660 | 9347013 |
| 18 | 2265577 | 2266262 | 18 | 9348132 | 9348542 |
| 18 | 2291017 | 2292597 | 18 | 9361608 | 9362708 |
| 18 | 2297651 | 2297661 | 18 | 9370026 | 9371101 |
| 18 | 2302166 | 2303314 | 18 | 9374613 | 9375156 |
| 18 | 2307109 | 2307414 | 18 | 9382627 | 9383290 |
| 18 | 2311982 | 2312956 | 18 | 9393999 | 9394718 |
| 18 | 2315904 | 2319138 | 18 | 9398374 | 9399354 |
| 18 | 2321838 | 2322733 | 18 | 9403608 | 9404921 |
| 18 | 2324603 | 2324873 | 18 | 9406563 | 9407513 |
| 18 | 2326204 | 2326484 | 18 | 9412720 | 9414223 |
| 18 | 2328575 | 2329361 | 18 | 9423638 | 9424433 |
| 18 | 2330232 | 2331497 | 18 | 9437782 | 9440752 |
| 18 | 2332672 | 2337425 | 18 | 9446139 | 9447034 |
| 18 | 2340922 | 2341718 | 18 | 9450037 | 9450590 |
| 18 | 2349146 | 2349921 | 18 | 9450860 | 9452195 |
| 18 | 2354655 | 2355870 | 18 | 9464131 | 9465336 |
| 18 | 2378043 | 2378373 | 18 | 9472527 | 9472647 |
| 18 | 2382137 | 2383309 | 18 | 9478745 | 9478945 |
| 18 | 2387720 | 2388305 | 18 | 9479991 | 9480235 |
| 18 | 2398611 | 2399311 | 18 | 9488234 | 9488805 |
| 18 | 2404040 | 2404090 | 18 | 9492094 | 9494067 |
| 18 | 2404855 | 2405585 | 18 | 9497913 | 9499079 |
| 18 | 2411537 | 2413062 | 18 | 9503682 | 9503862 |
| 18 | 2413619 | 2414634 | 18 | 9505106 | 9506830 |
| 18 | 2420479 | 2425457 | 18 | 9510292 | 9510472 |
| 18 | 2433929 | 2435522 | 18 | 9512227 | 9513062 |
| 18 | 2444382 | 2445137 | 18 | 9520774 | 9521515 |
| 18 | 2458651 | 2459121 | 18 | 9522451 | 9523212 |
| 18 | 2483319 | 2484419 | 18 | 9524842 | 9525432 |
| 18 | 2498742 | 2499382 | 18 | 9531478 | 9534976 |
| 18 | 2499392 | 2500137 | 18 | 9552390 | 9553935 |
| 18 | 2503547 | 2504498 | 18 | 9570666 | 9571301 |
| 18 | 2505982 | 2506477 | 18 | 9584918 | 9585764 |
| 18 | 2508701 | 2509730 | 18 | 9598655 | 9598908 |
| 18 | 2519024 | 2520889 | 18 | 9609154 | 9610054 |
| 18 | 2522729 | 2525456 | 18 | 9610525 | 9618083 |
| 18 | 2530616 | 2531355 | 18 | 9626962 | 9627387 |
| 18 | 2536062 | 2537912 | 18 | 9654658 | 9655408 |
| 18 | 2546116 | 2548183 | 18 | 9664926 | 9666005 |
| 18 | 2550195 | 2550464 | 18 | 9671202 | 9672127 |
| 18 | 2551244 | 2551874 | 18 | 9673920 | 9675685 |
| 18 | 2569354 | 2570262 | 18 | 9677893 | 9678493 |
| 18 | 2577931 | 2578896 | 18 | 9683585 | 9686199 |
| 18 | 2580279 | 2581099 | 18 | 9687024 | 9687384 |
| 18 | 2589579 | 2589959 | 18 | 9690389 | 9690536 |
| 18 | 2599682 | 2600307 | 18 | 9694335 | 9694900 |
| 18 | 2603261 | 2603577 | 18 | 9696323 | 9696643 |
| 18 | 2609435 | 2611400 | 18 | 9699459 | 9700464 |
| 18 | 2615248 | 2615633 | 18 | 9712639 | 9713364 |
| 18 | 2617611 | 2618311 | 18 | 9715314 | 9716819 |
| 18 | 2625744 | 2626951 | 18 | 9721286 | 9722043 |

The chromosomal positon was obtained from UCSC genome browser (http://genome.ucsc.edu/) build 36.

APPENDIX C: Chromosome 18
Page 43 of 72

| Chr | Start | End | | Chr | Start | End |
|---|---|---|---|---|---|---|
| 18 | 2630759 | 2630779 | | 18 | 9722793 | 9723343 |
| 18 | 2633839 | 2634304 | | 18 | 9725370 | 9726325 |
| 18 | 2641600 | 2641949 | | 18 | 9733346 | 9733971 |
| 18 | 2663609 | 2663749 | | 18 | 9737308 | 9741818 |
| 18 | 2677453 | 2678418 | | 18 | 9744984 | 9746484 |
| 18 | 2681278 | 2681568 | | 18 | 9748619 | 9748924 |
| 18 | 2700503 | 2701436 | | 18 | 9751253 | 9753248 |
| 18 | 2713305 | 2713865 | | 18 | 9761221 | 9762151 |
| 18 | 2720569 | 2721396 | | 18 | 9766271 | 9767511 |
| 18 | 2723981 | 2724351 | | 18 | 9789738 | 9791709 |
| 18 | 2745274 | 2745948 | | 18 | 9797056 | 9799475 |
| 18 | 2749365 | 2749885 | | 18 | 9800360 | 9801087 |
| 18 | 2765831 | 2766074 | | 18 | 9809038 | 9809668 |
| 18 | 2767199 | 2767659 | | 18 | 9814080 | 9818450 |
| 18 | 2771405 | 2772280 | | 18 | 9821097 | 9822047 |
| 18 | 2788647 | 2789082 | | 18 | 9825517 | 9828671 |
| 18 | 2794442 | 2794696 | | 18 | 9845572 | 9845832 |
| 18 | 2804175 | 2808423 | | 18 | 9847094 | 9850857 |
| 18 | 2815140 | 2816140 | | 18 | 9857241 | 9858752 |
| 18 | 2845203 | 2848120 | | 18 | 9860507 | 9862886 |
| 18 | 2865249 | 2866297 | | 18 | 9880661 | 9881286 |
| 18 | 2879515 | 2880085 | | 18 | 9896179 | 9896704 |
| 18 | 2882750 | 2883580 | | 18 | 9900309 | 9901809 |
| 18 | 2897546 | 2898181 | | 18 | 9902810 | 9903255 |
| 18 | 2902879 | 2903649 | | 18 | 9916630 | 9917145 |
| 18 | 2912497 | 2913542 | | 18 | 9920461 | 9920756 |
| 18 | 2924101 | 2924236 | | 18 | 9928289 | 9928609 |
| 18 | 2924796 | 2926076 | | 18 | 9935807 | 9936642 |
| 18 | 2945608 | 2945997 | | 18 | 9940745 | 9943981 |
| 18 | 2949228 | 2952310 | | 18 | 9948859 | 9949509 |
| 18 | 2958656 | 2963595 | | 18 | 9954623 | 9955603 |
| 18 | 2969777 | 2969842 | | 18 | 9958163 | 9958978 |
| 18 | 2973195 | 2973260 | | 18 | 9959263 | 9959698 |
| 18 | 2981428 | 2983353 | | 18 | 9985229 | 9986549 |
| 18 | 3000154 | 3001149 | | 18 | 10003894 | 10004289 |
| 18 | 3017870 | 3019110 | | 18 | 10005209 | 10005609 |
| 18 | 3033095 | 3033220 | | 18 | 10008449 | 10008984 |
| 18 | 3035035 | 3036670 | | 18 | 10009884 | 10014297 |
| 18 | 3046061 | 3046562 | | 18 | 10018029 | 10019189 |
| 18 | 3050538 | 3052313 | | 18 | 10022249 | 10023284 |
| 18 | 3052908 | 3053468 | | 18 | 10024593 | 10026560 |
| 18 | 3069159 | 3069914 | | 18 | 10038704 | 10039608 |
| 18 | 3090520 | 3091020 | | 18 | 10047180 | 10047395 |
| 18 | 3098468 | 3098898 | | 18 | 10048090 | 10050439 |
| 18 | 3101907 | 3102517 | | 18 | 10061088 | 10061718 |
| 18 | 3108083 | 3109443 | | 18 | 10062453 | 10063178 |
| 18 | 3113594 | 3114923 | | 18 | 10077461 | 10086799 |
| 18 | 3118816 | 3119566 | | 18 | 10088528 | 10090247 |
| 18 | 3121045 | 3121440 | | 18 | 10092211 | 10092761 |
| 18 | 3122631 | 3123256 | | 18 | 10099508 | 10101378 |
| 18 | 3128082 | 3131553 | | 18 | 10101883 | 10103338 |
| 18 | 3142403 | 3143393 | | 18 | 10106328 | 10106744 |
| 18 | 3158256 | 3158757 | | 18 | 10111954 | 10113284 |
| 18 | 3160966 | 3162031 | | 18 | 10115277 | 10117613 |
| 18 | 3193451 | 3193798 | | 18 | 10133898 | 10134978 |

The chromosomal positon was obtained from UCSC genome browser (http://genome.ucsc.edu/) build 36.

APPENDIX C: Chromosome 18
Page 44 of 72

| Chr | Start | End | Chr | Start | End |
|---|---|---|---|---|---|
| 18 | 3197398 | 3197803 | 18 | 10140171 | 10142060 |
| 18 | 3199305 | 3203380 | 18 | 10149417 | 10149682 |
| 18 | 3215663 | 3215913 | 18 | 10153146 | 10153701 |
| 18 | 3223682 | 3223942 | 18 | 10169140 | 10172171 |
| 18 | 3226423 | 3226728 | 18 | 10176284 | 10176889 |
| 18 | 3233209 | 3233569 | 18 | 10186607 | 10187887 |
| 18 | 3235497 | 3237665 | 18 | 10188077 | 10188782 |
| 18 | 3243236 | 3247565 | 18 | 10192752 | 10193052 |
| 18 | 3255449 | 3257251 | 18 | 10205014 | 10206024 |
| 18 | 3259027 | 3259667 | 18 | 10233128 | 10234043 |
| 18 | 3269296 | 3271271 | 18 | 10239223 | 10239723 |
| 18 | 3283914 | 3284204 | 18 | 10242976 | 10249841 |
| 18 | 3287626 | 3290370 | 18 | 10251376 | 10252356 |
| 18 | 3303393 | 3307688 | 18 | 10252902 | 10253572 |
| 18 | 3313781 | 3314281 | 18 | 10256037 | 10256367 |
| 18 | 3319425 | 3321375 | 18 | 10258482 | 10259134 |
| 18 | 3322685 | 3324737 | 18 | 10266126 | 10267898 |
| 18 | 3329817 | 3332247 | 18 | 10272422 | 10274397 |
| 18 | 3339106 | 3340778 | 18 | 10276604 | 10277459 |
| 18 | 3360303 | 3361158 | 18 | 10280801 | 10281276 |
| 18 | 3370346 | 3371294 | 18 | 10284004 | 10284544 |
| 18 | 3375966 | 3377479 | 18 | 10289627 | 10291058 |
| 18 | 3382720 | 3383045 | 18 | 10293265 | 10294120 |
| 18 | 3387122 | 3387597 | 18 | 10297896 | 10298701 |
| 18 | 3389382 | 3389886 | 18 | 10306372 | 10307564 |
| 18 | 3391787 | 3392412 | 18 | 10310204 | 10311264 |
| 18 | 3394052 | 3394843 | 18 | 10311934 | 10312845 |
| 18 | 3395613 | 3395785 | 18 | 10320431 | 10321876 |
| 18 | 3416128 | 3419385 | 18 | 10326562 | 10327092 |
| 18 | 3428194 | 3429040 | 18 | 10342960 | 10346500 |
| 18 | 3438105 | 3439957 | 18 | 10351788 | 10351863 |
| 18 | 3442589 | 3443878 | 18 | 10364020 | 10365075 |
| 18 | 3448611 | 3449164 | 18 | 10365425 | 10366070 |
| 18 | 3452005 | 3452300 | 18 | 10371957 | 10373102 |
| 18 | 3475140 | 3475580 | 18 | 10376291 | 10377057 |
| 18 | 3481903 | 3484067 | 18 | 10380122 | 10380767 |
| 18 | 3487441 | 3488091 | 18 | 10387100 | 10387275 |
| 18 | 3489234 | 3490200 | 18 | 10399529 | 10400069 |
| 18 | 3493542 | 3494162 | 18 | 10405783 | 10406503 |
| 18 | 3511243 | 3511998 | 18 | 10407015 | 10407510 |
| 18 | 3523996 | 3526069 | 18 | 10411416 | 10413001 |
| 18 | 3529926 | 3531401 | 18 | 10425222 | 10425578 |
| 18 | 3543986 | 3544451 | 18 | 10426394 | 10427039 |
| 18 | 3549017 | 3552265 | 18 | 10431860 | 10432435 |
| 18 | 3562374 | 3563595 | 18 | 10436305 | 10437930 |
| 18 | 3568257 | 3569018 | 18 | 10445026 | 10445941 |
| 18 | 3582415 | 3583387 | 18 | 10448127 | 10448567 |
| 18 | 3584465 | 3584530 | 18 | 10456173 | 10458329 |
| 18 | 3593242 | 3593500 | 18 | 10459789 | 10460854 |
| 18 | 3595210 | 3596677 | 18 | 10465001 | 10473584 |
| 18 | 3612038 | 3614424 | 18 | 10476754 | 10477119 |
| 18 | 3615651 | 3617294 | 18 | 10481548 | 10482938 |
| 18 | 3633795 | 3635451 | 18 | 10488752 | 10489839 |
| 18 | 3637891 | 3639111 | 18 | 10492769 | 10493434 |
| 18 | 3639880 | 3640552 | 18 | 10499411 | 10500366 |

The chromosomal positon was obtained from UCSC genome browser (http://genome.ucsc.edu/) build 36.

APPENDIX C: Chromosome 18
Page 45 of 72

| Chr | Start | End | | | Chr | Start | End |
|---|---|---|---|---|---|---|---|
| 18 | 3642803 | 3642813 | | | 18 | 10505034 | 10505919 |
| 18 | 3644378 | 3644893 | | | 18 | 10506334 | 10507289 |
| 18 | 3666551 | 3666856 | | | 18 | 10516454 | 10516884 |
| 18 | 3668533 | 3669356 | | | 18 | 10522965 | 10523273 |
| 18 | 3683518 | 3691199 | | | 18 | 10525885 | 10527261 |
| 18 | 3693605 | 3694811 | | | 18 | 10537992 | 10539090 |
| 18 | 3698949 | 3700217 | | | 18 | 10551786 | 10552271 |
| 18 | 3708493 | 3709174 | | | 18 | 10578228 | 10579977 |
| 18 | 3712096 | 3712711 | | | 18 | 10583469 | 10584154 |
| 18 | 3718943 | 3721940 | | | 18 | 10587063 | 10588309 |
| 18 | 3737318 | 3737323 | | | 18 | 10595685 | 10605421 |
| 18 | 3747459 | 3748267 | | | 18 | 10610325 | 10610820 |
| 18 | 3752472 | 3752787 | | | 18 | 10624974 | 10630991 |
| 18 | 3754881 | 3757114 | | | 18 | 10654935 | 10656385 |
| 18 | 3760038 | 3760548 | | | 18 | 10664320 | 10665120 |
| 18 | 3762818 | 3763217 | | | 18 | 10671918 | 10672458 |
| 18 | 3778404 | 3779184 | | | 18 | 10676570 | 10676990 |
| 18 | 3780184 | 3781623 | | | 18 | 10686476 | 10687867 |
| 18 | 3783053 | 3783838 | | | 18 | 10693266 | 10699189 |
| 18 | 3786223 | 3788459 | | | 18 | 10701907 | 10702162 |
| 18 | 3789824 | 3790300 | | | 18 | 10705719 | 10707789 |
| 18 | 3793816 | 3795596 | | | 18 | 10711655 | 10712196 |
| 18 | 3798716 | 3799181 | | | 18 | 10714693 | 10715283 |
| 18 | 3799909 | 3800504 | | | 18 | 10720276 | 10721853 |
| 18 | 3802334 | 3802795 | | | 18 | 10724475 | 10725417 |
| 18 | 3803942 | 3804202 | | | 18 | 10726022 | 10726402 |
| 18 | 3806232 | 3807322 | | | 18 | 10733102 | 10733927 |
| 18 | 3814888 | 3817123 | | | 18 | 10735062 | 10737672 |
| 18 | 3819706 | 3819836 | | | 18 | 10741771 | 10743086 |
| 18 | 3820786 | 3822181 | | | 18 | 10745035 | 10750635 |
| 18 | 3822486 | 3826587 | | | 18 | 10755080 | 10755710 |
| 18 | 3832445 | 3832960 | | | 18 | 10757923 | 10759023 |
| 18 | 3835505 | 3835960 | | | 18 | 10764150 | 10764415 |
| 18 | 3837378 | 3839463 | | | 18 | 10772649 | 10774594 |
| 18 | 3849765 | 3850210 | | | 18 | 10775404 | 10776394 |
| 18 | 3862994 | 3864264 | | | 18 | 10777342 | 10777432 |
| 18 | 3873530 | 3874130 | | | 18 | 10780607 | 10781504 |
| 18 | 3874965 | 3875795 | | | 18 | 10791398 | 10793045 |
| 18 | 3881467 | 3884431 | | | 18 | 10800691 | 10806030 |
| 18 | 3887491 | 3888335 | | | 18 | 10810858 | 10811376 |
| 18 | 3890799 | 3891474 | | | 18 | 10816093 | 10817263 |
| 18 | 3904275 | 3906029 | | | 18 | 10822283 | 10824409 |
| 18 | 3909911 | 3911078 | | | 18 | 10831376 | 10831791 |
| 18 | 3913478 | 3915398 | | | 18 | 10834036 | 10834901 |
| 18 | 3916966 | 3918301 | | | 18 | 10837196 | 10837831 |
| 18 | 3927586 | 3929656 | | | 18 | 10839346 | 10839841 |
| 18 | 3929781 | 3930151 | | | 18 | 10844022 | 10844207 |
| 18 | 3931511 | 3932694 | | | 18 | 10846866 | 10850631 |
| 18 | 3945411 | 3946962 | | | 18 | 10852430 | 10853710 |
| 18 | 3949141 | 3952000 | | | 18 | 10856991 | 10859266 |
| 18 | 3954357 | 3954557 | | | 18 | 10859528 | 10861112 |
| 18 | 3956013 | 3957183 | | | 18 | 10864574 | 10864789 |
| 18 | 3957828 | 3958213 | | | 18 | 10866994 | 10868494 |
| 18 | 3965498 | 3968930 | | | 18 | 10871403 | 10878981 |
| 18 | 3994444 | 3995599 | | | 18 | 10881995 | 10882720 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 3996963 | 3997773 | 18 | 10892707 | 10893772 |
| 18 | 4001224 | 4002075 | 18 | 10895694 | 10895869 |
| 18 | 4008009 | 4008154 | 18 | 10900204 | 10901065 |
| 18 | 4013213 | 4014234 | 18 | 10910166 | 10910396 |
| 18 | 4019651 | 4021131 | 18 | 10914019 | 10914594 |
| 18 | 4022377 | 4022880 | 18 | 10915529 | 10916481 |
| 18 | 4023465 | 4024463 | 18 | 10927046 | 10929188 |
| 18 | 4030660 | 4031095 | 18 | 10930530 | 10931015 |
| 18 | 4036829 | 4036959 | 18 | 10940081 | 10941511 |
| 18 | 4038902 | 4040561 | 18 | 10942026 | 10943714 |
| 18 | 4045216 | 4047356 | 18 | 10954646 | 10955596 |
| 18 | 4049792 | 4050955 | 18 | 10960292 | 10960787 |
| 18 | 4054002 | 4054212 | 18 | 10963017 | 10965702 |
| 18 | 4058247 | 4058707 | 18 | 10973414 | 10974029 |
| 18 | 4082305 | 4083020 | 18 | 10978112 | 10978367 |
| 18 | 4085710 | 4087137 | 18 | 10981027 | 10983978 |
| 18 | 4094374 | 4096901 | 18 | 10990694 | 10991999 |
| 18 | 4098124 | 4099004 | 18 | 10992279 | 10992484 |
| 18 | 4101251 | 4102096 | 18 | 10995904 | 10996169 |
| 18 | 4112829 | 4114059 | 18 | 11003552 | 11006668 |
| 18 | 4115995 | 4116315 | 18 | 11008266 | 11009666 |
| 18 | 4119360 | 4119570 | 18 | 11011222 | 11017120 |
| 18 | 4121995 | 4122945 | 18 | 11018806 | 11019776 |
| 18 | 4128166 | 4128555 | 18 | 11021912 | 11025150 |
| 18 | 4137653 | 4138183 | 18 | 11027530 | 11028956 |
| 18 | 4149411 | 4150021 | 18 | 11036732 | 11037877 |
| 18 | 4153021 | 4153906 | 18 | 11043371 | 11045341 |
| 18 | 4163425 | 4167434 | 18 | 11046621 | 11047376 |
| 18 | 4169828 | 4170893 | 18 | 11057507 | 11058483 |
| 18 | 4181480 | 4182170 | 18 | 11060553 | 11066197 |
| 18 | 4187493 | 4188505 | 18 | 11066207 | 11066836 |
| 18 | 4213051 | 4213660 | 18 | 11067766 | 11077796 |
| 18 | 4231985 | 4232410 | 18 | 11083227 | 11087694 |
| 18 | 4234483 | 4236683 | 18 | 11093643 | 11101933 |
| 18 | 4236783 | 4238993 | 18 | 11106381 | 11107210 |
| 18 | 4247185 | 4247420 | 18 | 11109991 | 11110411 |
| 18 | 4256218 | 4257013 | 18 | 11115246 | 11120041 |
| 18 | 4260405 | 4260410 | 18 | 11128091 | 11137600 |
| 18 | 4262619 | 4263419 | 18 | 11138003 | 11139406 |
| 18 | 4265636 | 4266263 | 18 | 11140351 | 11141204 |
| 18 | 4268030 | 4269370 | 18 | 11143434 | 11144145 |
| 18 | 4271171 | 4272436 | 18 | 11147363 | 11154160 |
| 18 | 4273181 | 4273446 | 18 | 11165683 | 11170042 |
| 18 | 4276292 | 4276977 | 18 | 11173090 | 11173682 |
| 18 | 4278759 | 4278984 | 18 | 11174452 | 11174987 |
| 18 | 4287905 | 4289510 | 18 | 11181806 | 11183566 |
| 18 | 4295008 | 4296239 | 18 | 11185333 | 11185518 |
| 18 | 4306309 | 4307054 | 18 | 11186743 | 11187568 |
| 18 | 4313599 | 4316378 | 18 | 11193117 | 11195832 |
| 18 | 4324580 | 4326095 | 18 | 11198425 | 11200356 |
| 18 | 4329383 | 4329708 | 18 | 11203591 | 11205085 |
| 18 | 4330248 | 4330793 | 18 | 11208676 | 11210646 |
| 18 | 4349922 | 4350127 | 18 | 11212331 | 11213071 |
| 18 | 4364762 | 4365183 | 18 | 11213836 | 11216882 |
| 18 | 4367683 | 4367803 | 18 | 11219197 | 11219492 |

The chromosomal positon was obtained from UCSC genome browser (http://genome.ucsc.edu/) build 36.

APPENDIX C: Chromosome 18
Page 47 of 72

| Chr | Start | End | Chr | Start | End |
|---|---|---|---|---|---|
| 18 | 4368438 | 4369468 | 18 | 11222134 | 11222731 |
| 18 | 4372783 | 4375849 | 18 | 11223930 | 11224555 |
| 18 | 4377314 | 4378724 | 18 | 11226190 | 11226390 |
| 18 | 4382845 | 4383565 | 18 | 11227613 | 11227878 |
| 18 | 4391195 | 4392160 | 18 | 11230855 | 11231305 |
| 18 | 4394576 | 4395238 | 18 | 11232832 | 11233976 |
| 18 | 4401388 | 4402458 | 18 | 11236295 | 11239071 |
| 18 | 4413139 | 4413314 | 18 | 11242010 | 11242501 |
| 18 | 4419635 | 4419640 | 18 | 11244816 | 11245311 |
| 18 | 4421892 | 4423194 | 18 | 11256661 | 11257736 |
| 18 | 4425212 | 4425604 | 18 | 11259394 | 11259454 |
| 18 | 4428224 | 4428975 | 18 | 11261166 | 11261848 |
| 18 | 4431536 | 4431851 | 18 | 11263389 | 11263924 |
| 18 | 4434166 | 4434721 | 18 | 11268681 | 11276403 |
| 18 | 4438452 | 4441617 | 18 | 11284257 | 11286218 |
| 18 | 4443860 | 4444295 | 18 | 11286705 | 11286850 |
| 18 | 4447773 | 4448658 | 18 | 11287028 | 11289044 |
| 18 | 4449003 | 4450578 | 18 | 11303103 | 11303998 |
| 18 | 4451438 | 4451653 | 18 | 11309006 | 11313862 |
| 18 | 4453321 | 4454441 | 18 | 11316618 | 11316848 |
| 18 | 4460097 | 4460702 | 18 | 11321837 | 11322042 |
| 18 | 4473441 | 4473896 | 18 | 11342157 | 11342757 |
| 18 | 4478930 | 4479770 | 18 | 11344142 | 11345315 |
| 18 | 4490915 | 4491520 | 18 | 11347444 | 11348483 |
| 18 | 4497230 | 4501605 | 18 | 11350968 | 11351792 |
| 18 | 4512528 | 4512878 | 18 | 11360108 | 11360573 |
| 18 | 4517780 | 4521907 | 18 | 11362134 | 11362908 |
| 18 | 4533860 | 4534905 | 18 | 11365739 | 11366620 |
| 18 | 4538726 | 4539126 | 18 | 11367746 | 11370981 |
| 18 | 4546549 | 4547646 | 18 | 11376776 | 11377366 |
| 18 | 4549256 | 4552881 | 18 | 11388937 | 11389652 |
| 18 | 4553976 | 4555317 | 18 | 11390297 | 11391177 |
| 18 | 4562107 | 4563542 | 18 | 11394695 | 11394805 |
| 18 | 4566105 | 4567203 | 18 | 11402795 | 11408334 |
| 18 | 4569347 | 4570977 | 18 | 11413948 | 11415151 |
| 18 | 4577443 | 4577899 | 18 | 11416409 | 11418021 |
| 18 | 4584451 | 4585261 | 18 | 11419537 | 11424532 |
| 18 | 4588471 | 4589648 | 18 | 11431232 | 11432267 |
| 18 | 4594365 | 4595496 | 18 | 11436528 | 11437214 |
| 18 | 4598827 | 4599802 | 18 | 11437399 | 11438439 |
| 18 | 4609402 | 4612926 | 18 | 11460334 | 11460855 |
| 18 | 4613361 | 4615896 | 18 | 11476178 | 11477378 |
| 18 | 4627260 | 4628345 | 18 | 11479532 | 11480847 |
| 18 | 4638678 | 4642108 | 18 | 11488982 | 11489922 |
| 18 | 4643542 | 4645122 | 18 | 11491791 | 11492021 |
| 18 | 4668540 | 4671304 | 18 | 11494176 | 11497328 |
| 18 | 4695121 | 4695516 | 18 | 11505226 | 11521041 |
| 18 | 4700761 | 4701875 | 18 | 11531969 | 11532064 |
| 18 | 4711297 | 4712497 | 18 | 11534559 | 11536380 |
| 18 | 4716728 | 4717396 | 18 | 11539105 | 11543400 |
| 18 | 4718987 | 4719382 | 18 | 11548344 | 11548754 |
| 18 | 4722604 | 4723014 | 18 | 11549515 | 11552274 |
| 18 | 4726163 | 4727397 | 18 | 11554154 | 11555414 |
| 18 | 4727832 | 4728407 | 18 | 11556509 | 11563499 |
| 18 | 4728802 | 4729751 | 18 | 11568953 | 11569943 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 4738876 | 4739661 | 18 | 11573513 | 11576571 |
| 18 | 4741051 | 4741921 | 18 | 11590408 | 11590813 |
| 18 | 4748158 | 4749943 | 18 | 11623817 | 11635231 |
| 18 | 4753918 | 4754464 | 18 | 11640288 | 11657448 |
| 18 | 4759937 | 4760793 | 18 | 11659557 | 11660527 |
| 18 | 4766759 | 4768239 | 18 | 11663392 | 11668894 |
| 18 | 4769473 | 4770461 | 18 | 11675687 | 11675982 |
| 18 | 4776573 | 4777223 | 18 | 11677707 | 11678390 |
| 18 | 4777788 | 4778033 | 18 | 11680385 | 11682563 |
| 18 | 4779770 | 4780455 | 18 | 11684197 | 11695419 |
| 18 | 4782060 | 4783712 | 18 | 11698304 | 11698819 |
| 18 | 4786997 | 4787512 | 18 | 11702194 | 11702709 |
| 18 | 4794791 | 4794961 | 18 | 11717598 | 11717930 |
| 18 | 4797387 | 4798157 | 18 | 11719175 | 11741328 |
| 18 | 4802190 | 4803621 | 18 | 11742223 | 11742818 |
| 18 | 4812912 | 4814377 | 18 | 11744808 | 11746919 |
| 18 | 4821527 | 4823482 | 18 | 11750630 | 11751984 |
| 18 | 4826588 | 4827288 | 18 | 11765564 | 11766394 |
| 18 | 4840149 | 4841185 | 18 | 11768547 | 11770246 |
| 18 | 4845160 | 4845602 | 18 | 11780282 | 11782822 |
| 18 | 4847802 | 4850272 | 18 | 11785837 | 11786654 |
| 18 | 4866175 | 4866255 | 18 | 11792620 | 11794040 |
| 18 | 4877806 | 4879099 | 18 | 11802376 | 11802466 |
| 18 | 4886372 | 4889614 | 18 | 11807363 | 11808480 |
| 18 | 4893471 | 4894966 | 18 | 11821380 | 11822250 |
| 18 | 4897315 | 4898630 | 18 | 11830363 | 11831920 |
| 18 | 4902301 | 4904932 | 18 | 11837231 | 11839166 |
| 18 | 4923222 | 4923888 | 18 | 11841545 | 11842110 |
| 18 | 4929686 | 4931011 | 18 | 11848933 | 11850923 |
| 18 | 4931774 | 4932109 | 18 | 11851928 | 11853193 |
| 18 | 4935324 | 4935654 | 18 | 11859519 | 11860627 |
| 18 | 4936869 | 4939064 | 18 | 11863625 | 11865545 |
| 18 | 4943112 | 4943527 | 18 | 11868173 | 11868913 |
| 18 | 4966174 | 4968514 | 18 | 11874368 | 11874848 |
| 18 | 4982177 | 4982832 | 18 | 11901755 | 11902400 |
| 18 | 4984157 | 4984457 | 18 | 11909599 | 11911615 |
| 18 | 4989030 | 4989415 | 18 | 11915896 | 11919833 |
| 18 | 4992931 | 4994031 | 18 | 11935570 | 11937653 |
| 18 | 5008319 | 5010305 | 18 | 11944132 | 11947380 |
| 18 | 5012653 | 5012998 | 18 | 11952439 | 11953324 |
| 18 | 5018096 | 5018566 | 18 | 11960513 | 11962863 |
| 18 | 5037870 | 5038815 | 18 | 11967772 | 11967802 |
| 18 | 5039395 | 5040430 | 18 | 11973437 | 11974087 |
| 18 | 5052368 | 5052578 | 18 | 11983905 | 11985340 |
| 18 | 5053273 | 5055575 | 18 | 11996544 | 11999316 |
| 18 | 5056147 | 5057143 | 18 | 12012587 | 12012747 |
| 18 | 5059296 | 5059876 | 18 | 12023360 | 12023840 |
| 18 | 5066216 | 5069547 | 18 | 12025572 | 12026012 |
| 18 | 5071825 | 5072175 | 18 | 12032946 | 12033667 |
| 18 | 5074005 | 5075204 | 18 | 12050181 | 12051551 |
| 18 | 5077924 | 5081670 | 18 | 12058256 | 12059146 |
| 18 | 5083699 | 5085746 | 18 | 12066088 | 12067139 |
| 18 | 5095692 | 5098603 | 18 | 12068915 | 12069693 |
| 18 | 5109812 | 5110422 | 18 | 12073258 | 12074378 |
| 18 | 5111332 | 5111662 | 18 | 12080199 | 12083256 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 5122168 | 5123834 | 18 | 12087452 | 12088062 |
| 18 | 5132684 | 5133363 | 18 | 12091269 | 12091724 |
| 18 | 5139014 | 5140760 | 18 | 12105301 | 12106176 |
| 18 | 5142210 | 5146306 | 18 | 12135229 | 12136344 |
| 18 | 5148162 | 5148682 | 18 | 12141662 | 12142262 |
| 18 | 5153182 | 5153997 | 18 | 12149710 | 12152534 |
| 18 | 5155082 | 5158370 | 18 | 12165031 | 12167903 |
| 18 | 5169660 | 5172475 | 18 | 12182410 | 12182415 |
| 18 | 5179966 | 5181146 | 18 | 12210256 | 12214255 |
| 18 | 5186088 | 5186933 | 18 | 12221422 | 12229588 |
| 18 | 5188573 | 5189060 | 18 | 12237049 | 12242483 |
| 18 | 5189610 | 5189965 | 18 | 12243428 | 12244463 |
| 18 | 5194542 | 5195267 | 18 | 12247404 | 12247944 |
| 18 | 5198283 | 5199158 | 18 | 12249324 | 12250019 |
| 18 | 5203027 | 5204558 | 18 | 12254159 | 12255502 |
| 18 | 5205217 | 5207462 | 18 | 12268593 | 12269569 |
| 18 | 5208562 | 5209257 | 18 | 12272513 | 12274273 |
| 18 | 5227120 | 5228855 | 18 | 12283866 | 12284356 |
| 18 | 5230706 | 5231236 | 18 | 12293659 | 12294244 |
| 18 | 5234521 | 5236386 | 18 | 12296273 | 12297447 |
| 18 | 5237626 | 5238536 | 18 | 12298783 | 12302195 |
| 18 | 5239741 | 5240781 | 18 | 12303432 | 12304432 |
| 18 | 5265806 | 5266016 | 18 | 12308026 | 12308411 |
| 18 | 5269042 | 5269147 | 18 | 12334184 | 12335138 |
| 18 | 5272636 | 5272991 | 18 | 12340499 | 12340997 |
| 18 | 5275005 | 5275485 | 18 | 12344901 | 12347122 |
| 18 | 5275915 | 5278920 | 18 | 12363469 | 12364419 |
| 18 | 5280098 | 5280655 | 18 | 12366020 | 12366605 |
| 18 | 5283236 | 5284190 | 18 | 12384340 | 12385592 |
| 18 | 5290595 | 5290980 | 18 | 12386417 | 12401546 |
| 18 | 5293190 | 5294510 | 18 | 12416904 | 12418005 |
| 18 | 5295878 | 5301759 | 18 | 12422813 | 12423348 |
| 18 | 5307362 | 5307702 | 18 | 12427937 | 12432547 |
| 18 | 5308709 | 5309579 | 18 | 12440656 | 12441508 |
| 18 | 5311893 | 5313139 | 18 | 12448160 | 12449076 |
| 18 | 5314701 | 5315041 | 18 | 12453338 | 12453408 |
| 18 | 5317470 | 5320166 | 18 | 12463790 | 12465330 |
| 18 | 5321621 | 5321921 | 18 | 12478154 | 12478439 |
| 18 | 5326342 | 5327662 | 18 | 12478661 | 12479834 |
| 18 | 5331385 | 5331865 | 18 | 12490537 | 12490767 |
| 18 | 5342191 | 5343341 | 18 | 12492708 | 12494202 |
| 18 | 5345177 | 5346077 | 18 | 12509388 | 12510043 |
| 18 | 5352940 | 5355459 | 18 | 12510978 | 12511866 |
| 18 | 5363741 | 5365229 | 18 | 12516656 | 12520006 |
| 18 | 5368982 | 5369787 | 18 | 12527032 | 12528122 |
| 18 | 5371925 | 5372420 | 18 | 12536946 | 12542335 |
| 18 | 5378530 | 5378875 | 18 | 12555132 | 12555723 |
| 18 | 5399076 | 5399166 | 18 | 12557513 | 12558306 |
| 18 | 5399361 | 5400810 | 18 | 12577563 | 12579772 |
| 18 | 5403657 | 5404452 | 18 | 12580660 | 12583602 |
| 18 | 5407601 | 5408281 | 18 | 12590070 | 12591040 |
| 18 | 5418948 | 5419546 | 18 | 12599160 | 12601410 |
| 18 | 5420156 | 5420456 | 18 | 12615611 | 12616266 |
| 18 | 5433957 | 5436307 | 18 | 12622768 | 12623163 |
| 18 | 5438686 | 5438786 | 18 | 12624633 | 12626570 |

The chromosomal positon was obtained from UCSC genome browser (http://genome.ucsc.edu/) build 36.

APPENDIX C: Chromosome 18
Page 50 of 72

| Chr | Start | End | Chr | Start | End |
|---|---|---|---|---|---|
| 18 | 5440919 | 5441709 | 18 | 12635601 | 12636586 |
| 18 | 5443738 | 5445870 | 18 | 12643573 | 12645389 |
| 18 | 5447993 | 5456667 | 18 | 12649245 | 12649790 |
| 18 | 5462272 | 5463217 | 18 | 12656400 | 12664128 |
| 18 | 5463782 | 5464722 | 18 | 12666220 | 12666632 |
| 18 | 5464917 | 5467551 | 18 | 12672092 | 12675542 |
| 18 | 5475546 | 5476406 | 18 | 12676359 | 12677189 |
| 18 | 5490028 | 5492228 | 18 | 12702969 | 12703249 |
| 18 | 5493277 | 5493717 | 18 | 12710247 | 12710859 |
| 18 | 5495133 | 5497028 | 18 | 12716075 | 12716245 |
| 18 | 5500995 | 5506179 | 18 | 12720923 | 12721203 |
| 18 | 5526301 | 5527640 | 18 | 12726147 | 12726922 |
| 18 | 5531338 | 5531558 | 18 | 12731110 | 12731594 |
| 18 | 5537535 | 5537985 | 18 | 12734030 | 12734185 |
| 18 | 5539617 | 5543163 | 18 | 12756858 | 12757533 |
| 18 | 5548496 | 5549006 | 18 | 12759748 | 12760003 |
| 18 | 5559598 | 5563609 | 18 | 12768291 | 12768621 |
| 18 | 5566488 | 5566848 | 18 | 12773271 | 12774271 |
| 18 | 5568783 | 5569896 | 18 | 12811471 | 12812456 |
| 18 | 5577606 | 5577771 | 18 | 12828511 | 12830922 |
| 18 | 5585591 | 5586574 | 18 | 12832208 | 12833554 |
| 18 | 5594962 | 5599086 | 18 | 12835925 | 12836847 |
| 18 | 5600061 | 5600166 | 18 | 12847609 | 12847929 |
| 18 | 5603122 | 5606071 | 18 | 12849167 | 12850885 |
| 18 | 5609213 | 5609541 | 18 | 12869605 | 12870140 |
| 18 | 5613196 | 5617808 | 18 | 12872645 | 12873665 |
| 18 | 5620377 | 5621333 | 18 | 12876060 | 12876595 |
| 18 | 5628491 | 5629246 | 18 | 12882444 | 12884438 |
| 18 | 5632321 | 5637884 | 18 | 12897695 | 12898414 |
| 18 | 5641714 | 5642039 | 18 | 12925755 | 12926165 |
| 18 | 5652625 | 5654680 | 18 | 12941754 | 12941879 |
| 18 | 5658314 | 5659024 | 18 | 12964223 | 12964773 |
| 18 | 5660164 | 5660899 | 18 | 12973220 | 12973585 |
| 18 | 5664715 | 5665620 | 18 | 12975370 | 12976045 |
| 18 | 5667015 | 5667340 | 18 | 13000897 | 13001987 |
| 18 | 5668185 | 5670935 | 18 | 13002597 | 13004398 |
| 18 | 5683647 | 5684337 | 18 | 13006369 | 13006744 |
| 18 | 5684822 | 5687452 | 18 | 13023811 | 13024061 |
| 18 | 5687672 | 5689034 | 18 | 13037201 | 13039251 |
| 18 | 5694925 | 5700903 | 18 | 13046548 | 13047825 |
| 18 | 5702413 | 5702873 | 18 | 13049420 | 13050062 |
| 18 | 5708721 | 5709131 | 18 | 13056283 | 13058908 |
| 18 | 5714724 | 5715664 | 18 | 13061154 | 13061634 |
| 18 | 5717669 | 5718194 | 18 | 13063655 | 13063895 |
| 18 | 5724433 | 5724718 | 18 | 13080629 | 13081279 |
| 18 | 5730378 | 5731264 | 18 | 13096163 | 13096888 |
| 18 | 5747807 | 5749022 | 18 | 13107673 | 13108598 |
| 18 | 5756643 | 5763428 | 18 | 13110405 | 13111520 |
| 18 | 5765038 | 5765228 | 18 | 13122970 | 13125290 |
| 18 | 5767430 | 5767990 | 18 | 13126170 | 13128048 |
| 18 | 5768065 | 5768250 | 18 | 13130122 | 13131348 |
| 18 | 5770683 | 5772793 | 18 | 13134728 | 13134938 |
| 18 | 5775927 | 5776707 | 18 | 13140315 | 13141220 |
| 18 | 5785992 | 5786977 | 18 | 13141816 | 13142601 |
| 18 | 5788148 | 5789176 | 18 | 13143591 | 13145904 |

The chromosomal positon was obtained from UCSC genome browser (http://genome.ucsc.edu/) build 36.

APPENDIX C: Chromosome 18

| Chr | Start | End | | Chr | Start | End |
|---|---|---|---|---|---|---|
| 18 | 5794646 | 5795283 | | 18 | 13154869 | 13160807 |
| 18 | 5803113 | 5803918 | | 18 | 13171214 | 13173295 |
| 18 | 5811878 | 5814378 | | 18 | 13177080 | 13178561 |
| 18 | 5823109 | 5823577 | | 18 | 13181289 | 13183157 |
| 18 | 5824772 | 5825380 | | 18 | 13184617 | 13186291 |
| 18 | 5826358 | 5826978 | | 18 | 13193128 | 13206513 |
| 18 | 5827633 | 5827858 | | 18 | 13209194 | 13209923 |
| 18 | 5835837 | 5836862 | | 18 | 13213758 | 13214268 |
| 18 | 5838525 | 5841720 | | 18 | 13218566 | 13219594 |
| 18 | 5856509 | 5857424 | | 18 | 13221484 | 13236838 |
| 18 | 5858554 | 5859729 | | 18 | 13241655 | 13246891 |
| 18 | 5861129 | 5865308 | | 18 | 13251122 | 13277566 |
| 18 | 5868288 | 5868823 | | 18 | 13281847 | 13292180 |
| 18 | 5871505 | 5872278 | | 18 | 13298133 | 13298413 |
| 18 | 5875144 | 5876071 | | 18 | 13299118 | 13302875 |
| 18 | 5878933 | 5879293 | | 18 | 13303435 | 13303652 |
| 18 | 5879526 | 5881971 | | 18 | 13304118 | 13317905 |
| 18 | 5886014 | 5887359 | | 18 | 13326880 | 13328361 |
| 18 | 5894653 | 5896168 | | 18 | 13339276 | 13339566 |
| 18 | 5907195 | 5907840 | | 18 | 13342459 | 13343059 |
| 18 | 5913812 | 5914237 | | 18 | 13348700 | 13349480 |
| 18 | 5915006 | 5915796 | | 18 | 13350570 | 13363436 |
| 18 | 5920492 | 5923077 | | 18 | 13364586 | 13365141 |
| 18 | 5924017 | 5928933 | | 18 | 13368121 | 13369061 |
| 18 | 5933763 | 5933938 | | 18 | 13369791 | 13371452 |
| 18 | 5937558 | 5937883 | | 18 | 13376070 | 13384004 |
| 18 | 5939111 | 5940155 | | 18 | 13386372 | 13387062 |
| 18 | 5945749 | 5945804 | | 18 | 13388331 | 13389997 |
| 18 | 5947522 | 5960310 | | 18 | 13393876 | 13396031 |
| 18 | 5962500 | 5964620 | | 18 | 13402558 | 13405701 |
| 18 | 5966502 | 5966842 | | 18 | 13407362 | 13408793 |
| 18 | 5968492 | 5969167 | | 18 | 13411746 | 13423180 |
| 18 | 5976888 | 5977638 | | 18 | 13427003 | 13428068 |
| 18 | 5983595 | 5986829 | | 18 | 13432683 | 13444779 |
| 18 | 5990978 | 5991802 | | 18 | 13448975 | 13451420 |
| 18 | 6011859 | 6012264 | | 18 | 13453575 | 13454315 |
| 18 | 6014378 | 6014733 | | 18 | 13454575 | 13456015 |
| 18 | 6031094 | 6033976 | | 18 | 13458185 | 13460132 |
| 18 | 6034036 | 6035334 | | 18 | 13463762 | 13466233 |
| 18 | 6036475 | 6039698 | | 18 | 13480204 | 13481179 |
| 18 | 6040885 | 6042035 | | 18 | 13486594 | 13486840 |
| 18 | 6048310 | 6048599 | | 18 | 13489853 | 13493730 |
| 18 | 6052336 | 6052351 | | 18 | 13495294 | 13496554 |
| 18 | 6069476 | 6070156 | | 18 | 13510214 | 13511389 |
| 18 | 6076114 | 6076744 | | 18 | 13512471 | 13513213 |
| 18 | 6082042 | 6084553 | | 18 | 13532291 | 13534650 |
| 18 | 6087594 | 6088959 | | 18 | 13539687 | 13543727 |
| 18 | 6092314 | 6092839 | | 18 | 13549941 | 13552015 |
| 18 | 6097388 | 6100919 | | 18 | 13553300 | 13553630 |
| 18 | 6104870 | 6108597 | | 18 | 13555901 | 13556316 |
| 18 | 6109152 | 6110533 | | 18 | 13557191 | 13559163 |
| 18 | 6118536 | 6119815 | | 18 | 13561151 | 13567170 |
| 18 | 6122657 | 6124127 | | 18 | 13567180 | 13567900 |
| 18 | 6128485 | 6132110 | | 18 | 13569822 | 13570927 |
| 18 | 6133787 | 6134365 | | 18 | 13580217 | 13580647 |

The chromosomal positon was obtained from UCSC genome browser (http://genome.ucsc.edu/) build 36.

APPENDIX C: Chromosome 18
Page 52 of 72

| Chr | Start | End | | | Chr | Start | End |
|---|---|---|---|---|---|---|---|
| 18 | 6139930 | 6140635 | | | 18 | 13581242 | 13581482 |
| 18 | 6146026 | 6147006 | | | 18 | 13584165 | 13586091 |
| 18 | 6149441 | 6151168 | | | 18 | 13593759 | 13596344 |
| 18 | 6153101 | 6160492 | | | 18 | 13600051 | 13601679 |
| 18 | 6164569 | 6165177 | | | 18 | 13605168 | 13605503 |
| 18 | 6174702 | 6175773 | | | 18 | 13606456 | 13607249 |
| 18 | 6180505 | 6184737 | | | 18 | 13610579 | 13623116 |
| 18 | 6192064 | 6192744 | | | 18 | 13625721 | 13640916 |
| 18 | 6195130 | 6195360 | | | 18 | 13641122 | 13641327 |
| 18 | 6200238 | 6200818 | | | 18 | 13643977 | 13648329 |
| 18 | 6201458 | 6202243 | | | 18 | 13670531 | 13670601 |
| 18 | 6204423 | 6205703 | | | 18 | 13671236 | 13672046 |
| 18 | 6206873 | 6207643 | | | 18 | 13692522 | 13692902 |
| 18 | 6209031 | 6210106 | | | 18 | 13724676 | 13725251 |
| 18 | 6215789 | 6217283 | | | 18 | 13747093 | 13747628 |
| 18 | 6228194 | 6232714 | | | 18 | 13750575 | 13751320 |
| 18 | 6247085 | 6254452 | | | 18 | 13756471 | 13756701 |
| 18 | 6257519 | 6257684 | | | 18 | 13757621 | 13758216 |
| 18 | 6257849 | 6265667 | | | 18 | 13779244 | 13781589 |
| 18 | 6267864 | 6268189 | | | 18 | 13786601 | 13786921 |
| 18 | 6273065 | 6273325 | | | 18 | 13802032 | 13802642 |
| 18 | 6273983 | 6274998 | | | 18 | 13808059 | 13817610 |
| 18 | 6275608 | 6276540 | | | 18 | 13821639 | 13827900 |
| 18 | 6283354 | 6283685 | | | 18 | 13831959 | 13832019 |
| 18 | 6288350 | 6290404 | | | 18 | 13835234 | 13835890 |
| 18 | 6292556 | 6294298 | | | 18 | 13839384 | 13839999 |
| 18 | 6296600 | 6297110 | | | 18 | 13856811 | 13863740 |
| 18 | 6300157 | 6300432 | | | 18 | 13866154 | 13867234 |
| 18 | 6302005 | 6302215 | | | 18 | 13868434 | 13870490 |
| 18 | 6304897 | 6305132 | | | 18 | 13875302 | 13883221 |
| 18 | 6305997 | 6306392 | | | 18 | 13894533 | 13896646 |
| 18 | 6315538 | 6316143 | | | 18 | 13899323 | 13899528 |
| 18 | 6318892 | 6319072 | | | 18 | 13908652 | 13916031 |
| 18 | 6319834 | 6320909 | | | 18 | 13920705 | 13924646 |
| 18 | 6331492 | 6331780 | | | 18 | 13929907 | 13931847 |
| 18 | 6339065 | 6339775 | | | 18 | 13943289 | 13944079 |
| 18 | 6345515 | 6345565 | | | 18 | 13950469 | 13950904 |
| 18 | 6351492 | 6354372 | | | 18 | 13959779 | 13962449 |
| 18 | 6357753 | 6361510 | | | 18 | 13973118 | 13974508 |
| 18 | 6363415 | 6367203 | | | 18 | 13977238 | 13977433 |
| 18 | 6374048 | 6374228 | | | 18 | 13977858 | 13978473 |
| 18 | 6379448 | 6385915 | | | 18 | 13982068 | 13982163 |
| 18 | 6387948 | 6392012 | | | 18 | 13982573 | 13983068 |
| 18 | 6393144 | 6394316 | | | 18 | 13985068 | 13985573 |
| 18 | 6394516 | 6396986 | | | 18 | 13987328 | 13997513 |
| 18 | 6401226 | 6401801 | | | 18 | 14002562 | 14003002 |
| 18 | 6403586 | 6404371 | | | 18 | 14013601 | 14014211 |
| 18 | 6413216 | 6413321 | | | 18 | 14017091 | 14017176 |
| 18 | 6419342 | 6422342 | | | 18 | 14018131 | 14019294 |
| 18 | 6423421 | 6423681 | | | 18 | 14034263 | 14035230 |
| 18 | 6427832 | 6428605 | | | 18 | 14040753 | 14043051 |
| 18 | 6431966 | 6432386 | | | 18 | 14052949 | 14053711 |
| 18 | 6442155 | 6442455 | | | 18 | 14069650 | 14069815 |
| 18 | 6462497 | 6465672 | | | 18 | 14086878 | 14088053 |
| 18 | 6471464 | 6471789 | | | 18 | 14088568 | 14088818 |

The chromosomal positon was obtained from UCSC genome browser (http://genome.ucsc.edu/) build 36.

APPENDIX C: Chromosome 18
Page 53 of 72

| Chr | Start | End | Chr | Start | End |
|---|---|---|---|---|---|
| 18 | 6472859 | 6478508 | 18 | 14090419 | 14091559 |
| 18 | 6484291 | 6485316 | 18 | 14114412 | 14117006 |
| 18 | 6488478 | 6488884 | 18 | 14121376 | 14123831 |
| 18 | 6493617 | 6495242 | 18 | 14149727 | 14150170 |
| 18 | 6496332 | 6503611 | 18 | 14167477 | 14170041 |
| 18 | 6511777 | 6512077 | 18 | 14177242 | 14178972 |
| 18 | 6531223 | 6531878 | 18 | 14180119 | 14189645 |
| 18 | 6547083 | 6553312 | 18 | 14204518 | 14205761 |
| 18 | 6555937 | 6557147 | 18 | 14229300 | 14231473 |
| 18 | 6557857 | 6558097 | 18 | 14251980 | 14252290 |
| 18 | 6560515 | 6561135 | 18 | 14273223 | 14273873 |
| 18 | 6568661 | 6569313 | 18 | 14284036 | 14285213 |
| 18 | 6578804 | 6580214 | 18 | 14293129 | 14294678 |
| 18 | 6587797 | 6591114 | 18 | 14304519 | 14307780 |
| 18 | 6593934 | 6594567 | 18 | 14336166 | 14338051 |
| 18 | 6603299 | 6603854 | 18 | 14342669 | 14342849 |
| 18 | 6607783 | 6608789 | 18 | 14358487 | 14362376 |
| 18 | 6615829 | 6616024 | 18 | 14381021 | 14383982 |
| 18 | 6618475 | 6619984 | 18 | 14396093 | 14396648 |
| 18 | 6621736 | 6621956 | 18 | 14420563 | 14422556 |
| 18 | 6623329 | 6623689 | 18 | 14445343 | 14449514 |
| 18 | 6628635 | 6635766 | 18 | 14453909 | 14462879 |
| 18 | 6637416 | 6638658 | 18 | 14532640 | 14533573 |
| 18 | 6640738 | 6641368 | 18 | 14542684 | 14546536 |
| 18 | 6642999 | 6644664 | 18 | 14560617 | 14561002 |
| 18 | 6649420 | 6650136 | 18 | 14572579 | 14573789 |
| 18 | 6654971 | 6656097 | 18 | 14580391 | 14588881 |
| 18 | 6662985 | 6664000 | 18 | 14630293 | 14632535 |
| 18 | 6670216 | 6671756 | 18 | 14644051 | 14655518 |
| 18 | 6672686 | 6674158 | 18 | 14665047 | 14670838 |
| 18 | 6675218 | 6680549 | 18 | 14681223 | 14683258 |
| 18 | 6683432 | 6684162 | 18 | 14720641 | 14721675 |
| 18 | 6700585 | 6701870 | 18 | 14723966 | 14724256 |
| 18 | 6703925 | 6705450 | 18 | 14724396 | 14724496 |
| 18 | 6706902 | 6711901 | 18 | 14728749 | 14729385 |
| 18 | 6713296 | 6713471 | 18 | 14742915 | 14743420 |
| 18 | 6718810 | 6719105 | 18 | 14747563 | 14749642 |
| 18 | 6728848 | 6731494 | 18 | 14757953 | 14758733 |
| 18 | 6733413 | 6733994 | 18 | 14760733 | 14762180 |
| 18 | 6735940 | 6736360 | 18 | 14777847 | 14781414 |
| 18 | 6739168 | 6741659 | 18 | 14868236 | 14880218 |
| 18 | 6748722 | 6749136 | 18 | 14896002 | 14896272 |
| 18 | 6753818 | 6754543 | 18 | 14899839 | 14904389 |
| 18 | 6775386 | 6775401 | 18 | 14905364 | 14905794 |
| 18 | 6777628 | 6778168 | 18 | 14907179 | 14909089 |
| 18 | 6797290 | 6801566 | 18 | 14911359 | 14913083 |
| 18 | 6804354 | 6804624 | 18 | 14914558 | 14915383 |
| 18 | 6808448 | 6808839 | 18 | 14917601 | 14918571 |
| 18 | 6810445 | 6811824 | 18 | 14920536 | 14920616 |
| 18 | 6812999 | 6815070 | 18 | 14924542 | 14925127 |
| 18 | 6819096 | 6819701 | 18 | 14932005 | 14935149 |
| 18 | 6825177 | 6828770 | 18 | 14938829 | 14939601 |
| 18 | 6829978 | 6830798 | 18 | 14941036 | 14942168 |
| 18 | 6833436 | 6833626 | 18 | 14943156 | 14943581 |
| 18 | 6840548 | 6841238 | 18 | 14950579 | 14951131 |

The chromosomal positon was obtained from UCSC genome browser (http://genome.ucsc.edu/) build 36.

APPENDIX C: Chromosome 18
Page 54 of 72

| Chr | Start | End | | | Chr | Start | End |
|---|---|---|---|---|---|---|---|
| 18 | 6842739 | 6842854 | | | 18 | 14954396 | 14957431 |
| 18 | 6855384 | 6856559 | | | 18 | 14963145 | 14963845 |
| 18 | 6868766 | 6868958 | | | 18 | 14969676 | 14970266 |
| 18 | 6875409 | 6875857 | | | 18 | 15039812 | 15040257 |
| 18 | 6878422 | 6879157 | | | 18 | 15043531 | 15044829 |
| 18 | 6882651 | 6883576 | | | 18 | 15065184 | 15077232 |
| 18 | 6902080 | 6903580 | | | 18 | 15114021 | 15120838 |
| 18 | 6908310 | 6910196 | | | 18 | 15157338 | 15158453 |
| 18 | 6935004 | 6935319 | | | 18 | 15190129 | 15194110 |
| 18 | 6937253 | 6937643 | | | 18 | 15195205 | 15235779 |
| 18 | 6949078 | 6950004 | | | 18 | 15239360 | 15239910 |
| | | | | | 18 | 15304314 | 15306100 |
| | | | | | 18 | 15350407 | 15367800 |
| 18 | 16909002 | 16911253 | | | 18 | 46556088 | 46557132 |
| 18 | 17017851 | 17018911 | | | 18 | 46600667 | 46602597 |
| 18 | 17063928 | 17066345 | | | 18 | 46731648 | 46734918 |
| 18 | 17074314 | 17075384 | | | 18 | 46887989 | 46893609 |
| 18 | 17080884 | 17083229 | | | 18 | 46902231 | 46903336 |
| 18 | 17119787 | 17120287 | | | 18 | 46918198 | 46918553 |
| 18 | 17131205 | 17131770 | | | 18 | 46931957 | 46935572 |
| 18 | 17134899 | 17135529 | | | 18 | 46962439 | 46963663 |
| 18 | 17139728 | 17144869 | | | 18 | 46970102 | 46976557 |
| 18 | 17149693 | 17150073 | | | 18 | 46986267 | 46989277 |
| 18 | 17152462 | 17153912 | | | 18 | 47035642 | 47036979 |
| 18 | 17282908 | 17284380 | | | 18 | 47132519 | 47136509 |
| 18 | 17300347 | 17301408 | | | 18 | 47227749 | 47228964 |
| 18 | 17381158 | 17385433 | | | 18 | 47242548 | 47246198 |
| 18 | 17407540 | 17407745 | | | 18 | 47258822 | 47269246 |
| 18 | 17432186 | 17433861 | | | 18 | 47284968 | 47286304 |
| 18 | 17664442 | 17668167 | | | 18 | 47320744 | 47322919 |
| 18 | 17743976 | 17744941 | | | 18 | 47331938 | 47335449 |
| 18 | 17780454 | 17781321 | | | 18 | 47344045 | 47345221 |
| 18 | 17815064 | 17821529 | | | 18 | 47363925 | 47367822 |
| 18 | 17824883 | 17826123 | | | 18 | 47393911 | 47397797 |
| 18 | 17854403 | 17856088 | | | 18 | 47401890 | 47404255 |
| 18 | 17897720 | 17900665 | | | 18 | 47430076 | 47432541 |
| 18 | 17936708 | 17937773 | | | 18 | 47439402 | 47448260 |
| 18 | 17960868 | 17965012 | | | 18 | 47480067 | 47490684 |
| 18 | 17983827 | 17986480 | | | 18 | 47542738 | 47543552 |
| 18 | 18010774 | 18012435 | | | 18 | 47544827 | 47545642 |
| 18 | 18018336 | 18019071 | | | 18 | 47553831 | 47555726 |
| 18 | 18035574 | 18037887 | | | 18 | 47592802 | 47594097 |
| 18 | 18069813 | 18070874 | | | 18 | 47624558 | 47625038 |
| 18 | 18096820 | 18098325 | | | 18 | 47645712 | 47646212 |
| 18 | 18101331 | 18102560 | | | 18 | 47658477 | 47663233 |
| 18 | 18120602 | 18122545 | | | 18 | 47674254 | 47674654 |
| 18 | 18151490 | 18152845 | | | 18 | 47688054 | 47690414 |
| 18 | 18158150 | 18163027 | | | 18 | 47724897 | 47729392 |
| 18 | 18169759 | 18173801 | | | 18 | 47735872 | 47736571 |
| 18 | 18183483 | 18186491 | | | 18 | 47813413 | 47815428 |
| 18 | 18188914 | 18191678 | | | 18 | 47825723 | 47826933 |
| 18 | 18195922 | 18197602 | | | 18 | 47858670 | 47859475 |
| 18 | 18245307 | 18246777 | | | 18 | 47862693 | 47865103 |
| 18 | 18251471 | 18252366 | | | 18 | 47867126 | 47870121 |
| 18 | 18323788 | 18326566 | | | 18 | 47880941 | 47882744 |

The chromosomal positon was obtained from UCSC genome browser (http://genome.ucsc.edu/) build 36.

APPENDIX C: Chromosome 18
Page 55 of 72

| Chr | Start | End | | | Chr | Start | End |
|---|---|---|---|---|---|---|---|
| 18 | 18335879 | 18337729 | | | 18 | 47933860 | 47936380 |
| 18 | 18354640 | 18356867 | | | 18 | 47960187 | 47963788 |
| 18 | 18375723 | 18377783 | | | 18 | 48005333 | 48008160 |
| 18 | 18392408 | 18393901 | | | 18 | 48033725 | 48036333 |
| 18 | 18394371 | 18398169 | | | 18 | 48049513 | 48057454 |
| 18 | 18446957 | 18448032 | | | 18 | 48120482 | 48122480 |
| 18 | 18473485 | 18474301 | | | 18 | 48159470 | 48162030 |
| 18 | 18513392 | 18515792 | | | 18 | 48183710 | 48187646 |
| 18 | 18527097 | 18529503 | | | 18 | 48215274 | 48216969 |
| 18 | 18532656 | 18533961 | | | 18 | 48231740 | 48232115 |
| 18 | 18536393 | 18537983 | | | 18 | 48242129 | 48242634 |
| 18 | 18575562 | 18576758 | | | 18 | 48257192 | 48258218 |
| 18 | 18619466 | 18622530 | | | 18 | 48268973 | 48270378 |
| 18 | 18663763 | 18665752 | | | 18 | 48272140 | 48273265 |
| 18 | 18935166 | 18941922 | | | 18 | 48297497 | 48299892 |
| 18 | 18977089 | 18977579 | | | 18 | 48311401 | 48316959 |
| 18 | 19025948 | 19026858 | | | 18 | 48356697 | 48357562 |
| 18 | 19065319 | 19066439 | | | 18 | 48362422 | 48363562 |
| 18 | 19070699 | 19071669 | | | 18 | 48441537 | 48442142 |
| 18 | 19091215 | 19094000 | | | 18 | 48459882 | 48464218 |
| 18 | 19138577 | 19142291 | | | 18 | 48470190 | 48475767 |
| 18 | 19164496 | 19166670 | | | 18 | 48478577 | 48479720 |
| 18 | 19185775 | 19190058 | | | 18 | 48521162 | 48523067 |
| 18 | 19330523 | 19334263 | | | 18 | 48534021 | 48536751 |
| 18 | 19338357 | 19338912 | | | 18 | 48611389 | 48611889 |
| 18 | 19349221 | 19355323 | | | 18 | 48619717 | 48620547 |
| 18 | 19371988 | 19373088 | | | 18 | 48629367 | 48630632 |
| 18 | 19375036 | 19376590 | | | 18 | 48650202 | 48651747 |
| 18 | 19436890 | 19438830 | | | 18 | 48693477 | 48695180 |
| 18 | 19453303 | 19453908 | | | 18 | 48762398 | 48764185 |
| 18 | 19465071 | 19466263 | | | 18 | 48856265 | 48858317 |
| 18 | 19491759 | 19499292 | | | 18 | 48903180 | 48906830 |
| 18 | 19626696 | 19628336 | | | 18 | 48934439 | 48935209 |
| 18 | 19658400 | 19662197 | | | 18 | 48977722 | 48977977 |
| 18 | 19705380 | 19705855 | | | 18 | 48982465 | 48986051 |
| 18 | 19706435 | 19709166 | | | 18 | 49001986 | 49003464 |
| 18 | 19712570 | 19714024 | | | 18 | 49090766 | 49100807 |
| 18 | 19742826 | 19749271 | | | 18 | 49126905 | 49128275 |
| 18 | 19788616 | 19789888 | | | 18 | 49154480 | 49155665 |
| 18 | 19816206 | 19817161 | | | 18 | 49189130 | 49190035 |
| 18 | 19845903 | 19846373 | | | 18 | 49192225 | 49194210 |
| 18 | 19850792 | 19854356 | | | 18 | 49250511 | 49252726 |
| 18 | 19887511 | 19888570 | | | 18 | 49259814 | 49261999 |
| 18 | 19973500 | 19973850 | | | 18 | 49406012 | 49407824 |
| 18 | 20104480 | 20105469 | | | 18 | 49505887 | 49506367 |
| 18 | 20150351 | 20151556 | | | 18 | 49561852 | 49564637 |
| 18 | 20303456 | 20304441 | | | 18 | 49570131 | 49570724 |
| 18 | 20321740 | 20323884 | | | 18 | 49595577 | 49598703 |
| 18 | 20327556 | 20328841 | | | 18 | 49628368 | 49629973 |
| 18 | 20391541 | 20392286 | | | 18 | 49656144 | 49657249 |
| 18 | 20394438 | 20396978 | | | 18 | 49699807 | 49703143 |
| 18 | 20402480 | 20404313 | | | 18 | 49744969 | 49745974 |
| 18 | 20423360 | 20427196 | | | 18 | 49764015 | 49764290 |
| 18 | 20441632 | 20443983 | | | 18 | 49796338 | 49798368 |
| 18 | 20464072 | 20469021 | | | 18 | 49874845 | 49876542 |

The chromosomal positon was obtained from UCSC genome browser (http://genome.ucsc.edu/) build 36.

APPENDIX C: Chromosome 18
Page 56 of 72

| Chr | Start | End | | | Chr | Start | End |
|---|---|---|---|---|---|---|---|
| 18 | 20491314 | 20492169 | | | 18 | 49891178 | 49898373 |
| 18 | 20494011 | 20495436 | | | 18 | 49938095 | 49938900 |
| 18 | 20496376 | 20498977 | | | 18 | 49953977 | 49955262 |
| 18 | 20505307 | 20506302 | | | 18 | 49986378 | 49989728 |
| 18 | 20511017 | 20512457 | | | 18 | 50024371 | 50028054 |
| 18 | 20512672 | 20515677 | | | 18 | 50034491 | 50035166 |
| 18 | 20538453 | 20539483 | | | 18 | 50195120 | 50202745 |
| 18 | 20560365 | 20571081 | | | 18 | 50245831 | 50249056 |
| 18 | 20575064 | 20579218 | | | 18 | 50293943 | 50302177 |
| 18 | 20602614 | 20604058 | | | 18 | 50387621 | 50395361 |
| 18 | 20623528 | 20625362 | | | 18 | 50408807 | 50409555 |
| 18 | 20645277 | 20647612 | | | 18 | 50412299 | 50413334 |
| 18 | 20650454 | 20653546 | | | 18 | 50424908 | 50425818 |
| 18 | 20674330 | 20676780 | | | 18 | 50434881 | 50437156 |
| 18 | 20683945 | 20686867 | | | 18 | 50439550 | 50441605 |
| 18 | 20709736 | 20711611 | | | 18 | 50476761 | 50479796 |
| 18 | 20717619 | 20719077 | | | 18 | 50523532 | 50523958 |
| 18 | 20723283 | 20725608 | | | 18 | 50536022 | 50536782 |
| 18 | 20750151 | 20753731 | | | 18 | 50558839 | 50561695 |
| 18 | 20758245 | 20760490 | | | 18 | 50565116 | 50567931 |
| 18 | 20768257 | 20770628 | | | 18 | 50581036 | 50583834 |
| 18 | 20771435 | 20771645 | | | 18 | 50595357 | 50595887 |
| 18 | 20774631 | 20777385 | | | 18 | 50702280 | 50704455 |
| 18 | 20779654 | 20785304 | | | 18 | 50706121 | 50712095 |
| 18 | 20797819 | 20800680 | | | 18 | 50745933 | 50750170 |
| 18 | 20821347 | 20822802 | | | 18 | 50752862 | 50755457 |
| 18 | 20837023 | 20838528 | | | 18 | 50782124 | 50785158 |
| 18 | 20875156 | 20878664 | | | 18 | 50848737 | 50849652 |
| 18 | 20886041 | 20886566 | | | 18 | 50880529 | 50881749 |
| 18 | 20889761 | 20891681 | | | 18 | 50894933 | 50899259 |
| 18 | 20910709 | 20911570 | | | 18 | 50914353 | 50915755 |
| 18 | 20913895 | 20914670 | | | 18 | 50995486 | 50996812 |
| 18 | 20956845 | 20958564 | | | 18 | 51000477 | 51000912 |
| 18 | 21053178 | 21054713 | | | 18 | 51032810 | 51038046 |
| 18 | 21058249 | 21061719 | | | 18 | 51039795 | 51041479 |
| 18 | 21080533 | 21082338 | | | 18 | 51053091 | 51053236 |
| 18 | 21082828 | 21083834 | | | 18 | 51068607 | 51069952 |
| 18 | 21205397 | 21206683 | | | 18 | 51092941 | 51097959 |
| 18 | 21223398 | 21224820 | | | 18 | 51107926 | 51109007 |
| 18 | 21253931 | 21254666 | | | 18 | 51112581 | 51114206 |
| 18 | 21277077 | 21279027 | | | 18 | 51114730 | 51115795 |
| 18 | 21285270 | 21286295 | | | 18 | 51118285 | 51121713 |
| 18 | 21306399 | 21307422 | | | 18 | 51133128 | 51135210 |
| 18 | 21339441 | 21340928 | | | 18 | 51173654 | 51174381 |
| 18 | 21378245 | 21379045 | | | 18 | 51177570 | 51180749 |
| 18 | 21389202 | 21389688 | | | 18 | 51206644 | 51209381 |
| 18 | 21400593 | 21404008 | | | 18 | 51219555 | 51220538 |
| 18 | 21471224 | 21474748 | | | 18 | 51224816 | 51225742 |
| 18 | 21480905 | 21482830 | | | 18 | 51248799 | 51250150 |
| 18 | 21495651 | 21497096 | | | 18 | 51256473 | 51258541 |
| 18 | 21535116 | 21538030 | | | 18 | 51280273 | 51282309 |
| 18 | 21590005 | 21590795 | | | 18 | 51285879 | 51286889 |
| 18 | 21676538 | 21678653 | | | 18 | 51309532 | 51310257 |
| 18 | 21709986 | 21711156 | | | 18 | 51328110 | 51329450 |
| 18 | 21771983 | 21772885 | | | 18 | 51369087 | 51369977 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 21804062 | 21804667 | 18 | 51395842 | 51399599 |
| 18 | 21966692 | 21969319 | 18 | 51438028 | 51439228 |
| 18 | 21994846 | 21995868 | 18 | 51449655 | 51455787 |
| 18 | 22037701 | 22039989 | 18 | 51468293 | 51470388 |
| 18 | 22067155 | 22069045 | 18 | 51477915 | 51479180 |
| 18 | 22207950 | 22210275 | 18 | 51482321 | 51485247 |
| 18 | 22315056 | 22315906 | 18 | 51489226 | 51489836 |
| 18 | 22330993 | 22332820 | 18 | 51505858 | 51507351 |
| 18 | 22374770 | 22378432 | 18 | 51514755 | 51516580 |
| 18 | 22385159 | 22386634 | 18 | 51532260 | 51532815 |
| 18 | 22454181 | 22455416 | 18 | 51564306 | 51567132 |
| 18 | 22469339 | 22471536 | 18 | 51568183 | 51569649 |
| 18 | 22494437 | 22496669 | 18 | 51624954 | 51626034 |
| 18 | 22554151 | 22555931 | 18 | 51629425 | 51632523 |
| 18 | 22645402 | 22646773 | 18 | 51635779 | 51640687 |
| 18 | 22661005 | 22665931 | 18 | 51661985 | 51663633 |
| 18 | 22690751 | 22692377 | 18 | 51675790 | 51677345 |
| 18 | 22698895 | 22699781 | 18 | 51681199 | 51682419 |
| 18 | 22750788 | 22752367 | 18 | 51748781 | 51751857 |
| 18 | 22767802 | 22769134 | 18 | 51755382 | 51759602 |
| 18 | 22787475 | 22788530 | 18 | 51788669 | 51789892 |
| 18 | 22793525 | 22796763 | 18 | 51881934 | 51883389 |
| 18 | 22857710 | 22858625 | 18 | 51912315 | 51912955 |
| 18 | 22880386 | 22882241 | 18 | 51953967 | 51956337 |
| 18 | 22901711 | 22911060 | 18 | 51956582 | 51959297 |
| 18 | 22914831 | 22921711 | 18 | 51988035 | 51989735 |
| 18 | 22936405 | 22942228 | 18 | 52005950 | 52008328 |
| 18 | 22954239 | 22957937 | 18 | 52047263 | 52050926 |
| 18 | 22961003 | 22962602 | 18 | 52062933 | 52066993 |
| 18 | 23022047 | 23023032 | 18 | 52105833 | 52109044 |
| 18 | 23026007 | 23026408 | 18 | 52131833 | 52132668 |
| 18 | 23048075 | 23048625 | 18 | 52139746 | 52141006 |
| 18 | 23187244 | 23188284 | 18 | 52146495 | 52147901 |
| 18 | 23247934 | 23248914 | 18 | 52174001 | 52175401 |
| 18 | 23278634 | 23281715 | 18 | 52207470 | 52207938 |
| 18 | 23314430 | 23316453 | 18 | 52219083 | 52222684 |
| 18 | 23320585 | 23321750 | 18 | 52276976 | 52278021 |
| 18 | 23379168 | 23380448 | 18 | 52288573 | 52291708 |
| 18 | 23391587 | 23392727 | 18 | 52306784 | 52307479 |
| 18 | 23395154 | 23397029 | 18 | 52309944 | 52310869 |
| 18 | 23420623 | 23423191 | 18 | 52379924 | 52381916 |
| 18 | 23464053 | 23465714 | 18 | 52396828 | 52398929 |
| 18 | 23486114 | 23490605 | 18 | 52481633 | 52483090 |
| 18 | 23510259 | 23512884 | 18 | 52485704 | 52487094 |
| 18 | 23516270 | 23519875 | 18 | 52501313 | 52502011 |
| 18 | 23605262 | 23606187 | 18 | 52564923 | 52566049 |
| 18 | 23701756 | 23702798 | 18 | 52695616 | 52696168 |
| 18 | 23733804 | 23738292 | 18 | 52707213 | 52712762 |
| 18 | 23755402 | 23756472 | 18 | 52737415 | 52738545 |
| 18 | 23767826 | 23769583 | 18 | 52789904 | 52790859 |
| 18 | 23785746 | 23789062 | 18 | 52837646 | 52838111 |
| 18 | 23820746 | 23824533 | 18 | 52861622 | 52895130 |
| 18 | 23932488 | 23932823 | 18 | 52896925 | 52898910 |
| 18 | 23934283 | 23936153 | 18 | 52902048 | 52914321 |
| 18 | 23950787 | 23956160 | 18 | 52927653 | 52928533 |

The chromosomal positon was obtained from UCSC genome browser (http://genome.ucsc.edu/) build 36.

APPENDIX C: Chromosome 18
Page 58 of 72

| Chr | Start | End | Chr | Start | End |
|---|---|---|---|---|---|
| 18 | 23976969 | 23979379 | 18 | 52944875 | 52947097 |
| 18 | 24029107 | 24030971 | 18 | 52955060 | 52960548 |
| 18 | 24043457 | 24046824 | 18 | 52965768 | 52966918 |
| 18 | 24146716 | 24150692 | 18 | 52970155 | 52973535 |
| 18 | 24184320 | 24185881 | 18 | 52975590 | 52976890 |
| 18 | 24230131 | 24231641 | 18 | 53035220 | 53035904 |
| 18 | 24282849 | 24285000 | 18 | 53038857 | 53049526 |
| 18 | 24328289 | 24329189 | 18 | 53058842 | 53060547 |
| 18 | 24335716 | 24337780 | 18 | 53061607 | 53073309 |
| 18 | 24339687 | 24340845 | 18 | 53101647 | 53106728 |
| 18 | 24364309 | 24366769 | 18 | 53116616 | 53118066 |
| 18 | 24405380 | 24406660 | 18 | 53144564 | 53148935 |
| 18 | 24482911 | 24484426 | 18 | 53152566 | 53154197 |
| 18 | 24485868 | 24487658 | 18 | 53157644 | 53158914 |
| 18 | 24519506 | 24519576 | 18 | 53165860 | 53166750 |
| 18 | 24540300 | 24541526 | 18 | 53170676 | 53172658 |
| 18 | 24581601 | 24582606 | 18 | 53189658 | 53191018 |
| 18 | 24625282 | 24628457 | 18 | 53203640 | 53204135 |
| 18 | 24636726 | 24639617 | 18 | 53245375 | 53259500 |
| 18 | 24642954 | 24643519 | 18 | 53264200 | 53265690 |
| 18 | 24658551 | 24659331 | 18 | 53283478 | 53297046 |
| 18 | 24708175 | 24708410 | 18 | 53304072 | 53305729 |
| 18 | 24720440 | 24724227 | 18 | 53311623 | 53312428 |
| 18 | 24805162 | 24807927 | 18 | 53318955 | 53322572 |
| 18 | 24838127 | 24839222 | 18 | 53334765 | 53337405 |
| 18 | 24901854 | 24904605 | 18 | 53347044 | 53348474 |
| 18 | 24914452 | 24917704 | 18 | 53360843 | 53361433 |
| 18 | 24929906 | 24931206 | 18 | 53371462 | 53372067 |
| 18 | 24935849 | 24936562 | 18 | 53516166 | 53517276 |
| 18 | 24997208 | 24999277 | 18 | 53545614 | 53548238 |
| 18 | 25012812 | 25014445 | 18 | 53589943 | 53591514 |
| 18 | 25019531 | 25019786 | 18 | 53598830 | 53599855 |
| 18 | 25068747 | 25070797 | 18 | 53733997 | 53735157 |
| 18 | 25087527 | 25087532 | 18 | 53743101 | 53743781 |
| 18 | 25105541 | 25107749 | 18 | 53776006 | 53778335 |
| 18 | 25157271 | 25159160 | 18 | 53788503 | 53789918 |
| 18 | 25172885 | 25174861 | 18 | 53793088 | 53794848 |
| 18 | 25357303 | 25357693 | 18 | 53898628 | 53901070 |
| 18 | 25391560 | 25394297 | 18 | 53946582 | 53950417 |
| 18 | 25407277 | 25410814 | 18 | 53957918 | 53958572 |
| 18 | 25482459 | 25485869 | 18 | 53961524 | 53962309 |
| 18 | 25598705 | 25600636 | 18 | 53970887 | 53973312 |
| 18 | 25614935 | 25616435 | 18 | 53993386 | 53997011 |
| 18 | 25652997 | 25654912 | 18 | 54013273 | 54014243 |
| 18 | 25656502 | 25657882 | 18 | 54041498 | 54043261 |
| 18 | 25691728 | 25692409 | 18 | 54112269 | 54112707 |
| 18 | 25706603 | 25707863 | 18 | 54116888 | 54119693 |
| 18 | 25721794 | 25722469 | 18 | 54219677 | 54221099 |
| 18 | 25779139 | 25781422 | 18 | 54236486 | 54239048 |
| 18 | 25791507 | 25792522 | 18 | 54305443 | 54305743 |
| 18 | 25796057 | 25797032 | 18 | 54352981 | 54354931 |
| 18 | 25818622 | 25819787 | 18 | 54363387 | 54364925 |
| 18 | 25985183 | 25985708 | 18 | 54367409 | 54369234 |
| 18 | 25988692 | 25989768 | 18 | 54370524 | 54371669 |
| 18 | 25990318 | 25991433 | 18 | 54374492 | 54376207 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 26006378 | 26011189 | | | 18 | 54484148 | 54485642 |
| 18 | 26067522 | 26070959 | | | 18 | 54577361 | 54579148 |
| 18 | 26073771 | 26077895 | | | 18 | 54582002 | 54584353 |
| 18 | 26106315 | 26107085 | | | 18 | 54587138 | 54588205 |
| 18 | 26114128 | 26121811 | | | 18 | 54610594 | 54612680 |
| 18 | 26136442 | 26138774 | | | 18 | 54664486 | 54669573 |
| 18 | 26252672 | 26254518 | | | 18 | 54705504 | 54707714 |
| 18 | 26326934 | 26327634 | | | 18 | 54775971 | 54777056 |
| 18 | 26359977 | 26361717 | | | 18 | 54929155 | 54932586 |
| 18 | 26365824 | 26366084 | | | 18 | 54970347 | 54971058 |
| 18 | 26379807 | 26381782 | | | 18 | 54974618 | 54975963 |
| 18 | 26476579 | 26479497 | | | 18 | 54995594 | 54999632 |
| 18 | 26597099 | 26599903 | | | 18 | 55030790 | 55037055 |
| 18 | 26650954 | 26652869 | | | 18 | 55038600 | 55039559 |
| 18 | 26674464 | 26674514 | | | 18 | 55049200 | 55051578 |
| 18 | 26692599 | 26693294 | | | 18 | 55084184 | 55086730 |
| 18 | 26722639 | 26724099 | | | 18 | 55090304 | 55093168 |
| 18 | 26797411 | 26801781 | | | 18 | 55097978 | 55103180 |
| 18 | 26808121 | 26810776 | | | 18 | 55114638 | 55118896 |
| 18 | 26841871 | 26842697 | | | 18 | 55122366 | 55127629 |
| 18 | 26907633 | 26908983 | | | 18 | 55173151 | 55176983 |
| 18 | 26924641 | 26925822 | | | 18 | 55211782 | 55212731 |
| 18 | 26934535 | 26936277 | | | 18 | 55411720 | 55413769 |
| 18 | 26944115 | 26945295 | | | 18 | 55470658 | 55471496 |
| 18 | 27015276 | 27023349 | | | 18 | 55481772 | 55483542 |
| 18 | 27025831 | 27027747 | | | 18 | 55515960 | 55516767 |
| 18 | 27040773 | 27041888 | | | 18 | 55522777 | 55528575 |
| 18 | 27051011 | 27052061 | | | 18 | 55548866 | 55549968 |
| 18 | 27059115 | 27059811 | | | 18 | 55596279 | 55597951 |
| 18 | 27061273 | 27063987 | | | 18 | 55661874 | 55668730 |
| 18 | 27090043 | 27092943 | | | 18 | 55708549 | 55709647 |
| 18 | 27103357 | 27106020 | | | 18 | 55723207 | 55725650 |
| 18 | 27154309 | 27156535 | | | 18 | 55726599 | 55727730 |
| 18 | 27304882 | 27305738 | | | 18 | 55744807 | 55747577 |
| 18 | 27345193 | 27346848 | | | 18 | 55806051 | 55808658 |
| 18 | 27410788 | 27416072 | | | 18 | 55835525 | 55838751 |
| 18 | 27466925 | 27468684 | | | 18 | 55845547 | 55845777 |
| 18 | 27511351 | 27513956 | | | 18 | 55864049 | 55866177 |
| 18 | 27594767 | 27595112 | | | 18 | 55922117 | 55925828 |
| 18 | 27623114 | 27624552 | | | 18 | 55993087 | 55994109 |
| 18 | 27624807 | 27627897 | | | 18 | 56023353 | 56023925 |
| 18 | 27826937 | 27827312 | | | 18 | 56025639 | 56028719 |
| 18 | 27866545 | 27870330 | | | 18 | 56125692 | 56127707 |
| 18 | 27884656 | 27886838 | | | 18 | 56133896 | 56135156 |
| 18 | 28084425 | 28086498 | | | 18 | 56185800 | 56188910 |
| 18 | 28151972 | 28153852 | | | 18 | 56209534 | 56210744 |
| 18 | 28183964 | 28185500 | | | 18 | 56243584 | 56244494 |
| 18 | 28224723 | 28226878 | | | 18 | 56330478 | 56332977 |
| 18 | 28253943 | 28257649 | | | 18 | 56352195 | 56354222 |
| 18 | 28272876 | 28273927 | | | 18 | 56368390 | 56368800 |
| 18 | 28360482 | 28361389 | | | 18 | 56405787 | 56412336 |
| 18 | 28389501 | 28390767 | | | 18 | 56564921 | 56565396 |
| 18 | 28518631 | 28519745 | | | 18 | 56572715 | 56577121 |
| 18 | 28523119 | 28525704 | | | 18 | 56586824 | 56588864 |
| 18 | 28529014 | 28530344 | | | 18 | 56620723 | 56624075 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 28534607 | 28535197 | 18 | 56627540 | 56629048 |
| 18 | 28604777 | 28605433 | 18 | 56654841 | 56658817 |
| 18 | 28629135 | 28632958 | 18 | 56731103 | 56731563 |
| 18 | 28649868 | 28650498 | 18 | 56785848 | 56787423 |
| 18 | 28664360 | 28667404 | 18 | 56900629 | 56904306 |
| 18 | 28701964 | 28702689 | 18 | 56961807 | 56962472 |
| 18 | 28713632 | 28717435 | 18 | 56974666 | 56978205 |
| 18 | 28725491 | 28726931 | 18 | 57016304 | 57020671 |
| 18 | 28735525 | 28738365 | 18 | 57029245 | 57032988 |
| 18 | 28740913 | 28741813 | 18 | 57117516 | 57119285 |
| 18 | 28780430 | 28781638 | 18 | 57149560 | 57150790 |
| 18 | 28797212 | 28799008 | 18 | 57217012 | 57219277 |
| 18 | 28803367 | 28808965 | 18 | 57387616 | 57388517 |
| 18 | 28834618 | 28837768 | 18 | 57436181 | 57438993 |
| 18 | 28840743 | 28842323 | 18 | 57473497 | 57475752 |
| 18 | 28930126 | 28938510 | 18 | 57578934 | 57582824 |
| 18 | 28940097 | 28941366 | 18 | 57697802 | 57699063 |
| 18 | 28947587 | 28948977 | 18 | 57707369 | 57711630 |
| 18 | 28956616 | 28957727 | 18 | 57714362 | 57715520 |
| 18 | 29020766 | 29023046 | 18 | 57767686 | 57771815 |
| 18 | 29035616 | 29037409 | 18 | 57790743 | 57791973 |
| 18 | 29046317 | 29047852 | 18 | 57885678 | 57887194 |
| 18 | 29050328 | 29054997 | 18 | 57959946 | 57960996 |
| 18 | 29062543 | 29065558 | 18 | 58004618 | 58005178 |
| 18 | 29079282 | 29080922 | 18 | 58021186 | 58023561 |
| 18 | 29137721 | 29140066 | 18 | 58068880 | 58069571 |
| 18 | 29147585 | 29149560 | 18 | 58073478 | 58076998 |
| 18 | 29197392 | 29199320 | 18 | 58122622 | 58123793 |
| 18 | 29255342 | 29256771 | 18 | 58125855 | 58128252 |
| 18 | 29287788 | 29290768 | 18 | 58131062 | 58134325 |
| 18 | 29303231 | 29304771 | 18 | 58144367 | 58145333 |
| 18 | 29410941 | 29413481 | 18 | 58146769 | 58147079 |
| 18 | 29459198 | 29459958 | 18 | 58149044 | 58160313 |
| 18 | 29484556 | 29488920 | 18 | 58162731 | 58164178 |
| 18 | 29494042 | 29495788 | 18 | 58238254 | 58239971 |
| 18 | 29524643 | 29526413 | 18 | 58251232 | 58255087 |
| 18 | 29530288 | 29531553 | 18 | 58343379 | 58344069 |
| 18 | 29551613 | 29554171 | 18 | 58439102 | 58440453 |
| 18 | 29574871 | 29575431 | 18 | 58452252 | 58453602 |
| 18 | 29578092 | 29579342 | 18 | 58563411 | 58563776 |
| 18 | 29595702 | 29597297 | 18 | 58602100 | 58603060 |
| 18 | 29629926 | 29632891 | 18 | 58645982 | 58647362 |
| 18 | 29677764 | 29679851 | 18 | 58771557 | 58772112 |
| 18 | 29688183 | 29689554 | 18 | 58809234 | 58812369 |
| 18 | 29714189 | 29718169 | 18 | 58825722 | 58826936 |
| 18 | 29795242 | 29796357 | 18 | 58897619 | 58899134 |
| 18 | 29840401 | 29843708 | 18 | 58904408 | 58910478 |
| 18 | 29858950 | 29861049 | 18 | 58916522 | 58918139 |
| 18 | 29876100 | 29877040 | 18 | 58926144 | 58931618 |
| 18 | 29890409 | 29891419 | 18 | 58955494 | 58957866 |
| 18 | 29915977 | 29919751 | 18 | 58971090 | 58971695 |
| 18 | 29932046 | 29932516 | 18 | 58975755 | 58978774 |
| 18 | 29934759 | 29935954 | 18 | 58983521 | 58985001 |
| 18 | 29965147 | 29965837 | 18 | 59055590 | 59057582 |
| 18 | 29987813 | 29989913 | 18 | 59076814 | 59081008 |

The chromosomal positon was obtained from UCSC genome browser (http://genome.ucsc.edu/) build 36.

APPENDIX C: Chromosome 18
Page 61 of 72

| Chr | Start | End | | | Chr | Start | End |
|---|---|---|---|---|---|---|---|
| 18 | 30018151 | 30019291 | | | 18 | 59105134 | 59106075 |
| 18 | 30033275 | 30034873 | | | 18 | 59109071 | 59112089 |
| 18 | 30057078 | 30058294 | | | 18 | 59121047 | 59121492 |
| 18 | 30113035 | 30114535 | | | 18 | 59195702 | 59199228 |
| 18 | 30124901 | 30127031 | | | 18 | 59294822 | 59295797 |
| 18 | 30141865 | 30143455 | | | 18 | 59350141 | 59353729 |
| 18 | 30340587 | 30343051 | | | 18 | 59372860 | 59378574 |
| 18 | 30345635 | 30347489 | | | 18 | 59406385 | 59407185 |
| 18 | 30358796 | 30362866 | | | 18 | 59529298 | 59531123 |
| 18 | 30486360 | 30486920 | | | 18 | 59574633 | 59576147 |
| 18 | 30528679 | 30530760 | | | 18 | 59592701 | 59595544 |
| 18 | 30534675 | 30536475 | | | 18 | 59613307 | 59615093 |
| 18 | 30593600 | 30594230 | | | 18 | 59615379 | 59617345 |
| 18 | 30595635 | 30596666 | | | 18 | 59645332 | 59649923 |
| 18 | 30609504 | 30611294 | | | 18 | 59665961 | 59666986 |
| 18 | 30614985 | 30616750 | | | 18 | 59680223 | 59688053 |
| 18 | 30620290 | 30622550 | | | 18 | 59713286 | 59713766 |
| 18 | 30638108 | 30638828 | | | 18 | 59742438 | 59744046 |
| 18 | 30690759 | 30692432 | | | 18 | 59748505 | 59753357 |
| 18 | 30696828 | 30698741 | | | 18 | 59767357 | 59768057 |
| 18 | 30723970 | 30724904 | | | 18 | 59796872 | 59799947 |
| 18 | 30745926 | 30749034 | | | 18 | 59819255 | 59820708 |
| 18 | 30762929 | 30767493 | | | 18 | 59823239 | 59824374 |
| 18 | 30888190 | 30891405 | | | 18 | 59858301 | 59864013 |
| 18 | 30893602 | 30896242 | | | 18 | 59945505 | 59947858 |
| 18 | 30950630 | 30951520 | | | 18 | 59956855 | 59959238 |
| 18 | 30960641 | 30974280 | | | 18 | 59972849 | 59973529 |
| 18 | 30997847 | 31001484 | | | 18 | 59983067 | 59983611 |
| 18 | 31015933 | 31017635 | | | 18 | 60028294 | 60029359 |
| 18 | 31038234 | 31038334 | | | 18 | 60144790 | 60145325 |
| 18 | 31071960 | 31073509 | | | 18 | 60147024 | 60149404 |
| 18 | 31113002 | 31113277 | | | 18 | 60150425 | 60150915 |
| 18 | 31127180 | 31130390 | | | 18 | 60151380 | 60151695 |
| 18 | 31211601 | 31213173 | | | 18 | 60156566 | 60157606 |
| 18 | 31246349 | 31247454 | | | 18 | 60184025 | 60184610 |
| 18 | 31266001 | 31267596 | | | 18 | 60216554 | 60221004 |
| 18 | 31292628 | 31295425 | | | 18 | 60263611 | 60263776 |
| 18 | 31306571 | 31307726 | | | 18 | 60330539 | 60333260 |
| 18 | 31331910 | 31335135 | | | 18 | 60358333 | 60368496 |
| 18 | 31341143 | 31343553 | | | 18 | 60404082 | 60406570 |
| 18 | 31369342 | 31370037 | | | 18 | 60432257 | 60433060 |
| 18 | 31436565 | 31437765 | | | 18 | 60484520 | 60487084 |
| 18 | 31450055 | 31451690 | | | 18 | 60490249 | 60492893 |
| 18 | 31459453 | 31460763 | | | 18 | 60531358 | 60532288 |
| 18 | 31487172 | 31488112 | | | 18 | 60631361 | 60633096 |
| 18 | 31517425 | 31519138 | | | 18 | 60636971 | 60638221 |
| 18 | 31618093 | 31619219 | | | 18 | 60727141 | 60727956 |
| 18 | 31619714 | 31622842 | | | 18 | 60783094 | 60785655 |
| 18 | 31738274 | 31739760 | | | 18 | 60790155 | 60791280 |
| 18 | 31784588 | 31787295 | | | 18 | 60807776 | 60808381 |
| 18 | 31834494 | 31835645 | | | 18 | 60811176 | 60812457 |
| 18 | 31852024 | 31854124 | | | 18 | 60867578 | 60869959 |
| 18 | 31880490 | 31881831 | | | 18 | 60887753 | 60891406 |
| 18 | 31995495 | 31997485 | | | 18 | 60903495 | 60904195 |
| 18 | 32014088 | 32016175 | | | 18 | 60925615 | 60926760 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 32105104 | 32105499 | | | 18 | 60931080 | 60931605 |
| 18 | 32137205 | 32137620 | | | 18 | 60941571 | 60944108 |
| 18 | 32140031 | 32141499 | | | 18 | 60984525 | 60993164 |
| 18 | 32142864 | 32146178 | | | 18 | 61013487 | 61015451 |
| 18 | 32155480 | 32156790 | | | 18 | 61060410 | 61063120 |
| 18 | 32205031 | 32208215 | | | 18 | 61144521 | 61145901 |
| 18 | 32265072 | 32268006 | | | 18 | 61220167 | 61223234 |
| 18 | 32280479 | 32281859 | | | 18 | 61231232 | 61234144 |
| 18 | 32292226 | 32293979 | | | 18 | 61240687 | 61241402 |
| 18 | 32303705 | 32305315 | | | 18 | 61269983 | 61270448 |
| 18 | 32308276 | 32310606 | | | 18 | 61275550 | 61277356 |
| 18 | 32313755 | 32319328 | | | 18 | 61286804 | 61288158 |
| 18 | 32324199 | 32327897 | | | 18 | 61305585 | 61307100 |
| 18 | 32341702 | 32342787 | | | 18 | 61313305 | 61313958 |
| 18 | 32343445 | 32344400 | | | 18 | 61316785 | 61317445 |
| 18 | 32366638 | 32367250 | | | 18 | 61429081 | 61430209 |
| 18 | 32380501 | 32382459 | | | 18 | 61517138 | 61517368 |
| 18 | 32406405 | 32407158 | | | 18 | 61545402 | 61547206 |
| 18 | 32427888 | 32432175 | | | 18 | 61547961 | 61548716 |
| 18 | 32463525 | 32464305 | | | 18 | 61618755 | 61620385 |
| 18 | 32468435 | 32469380 | | | 18 | 61703444 | 61703974 |
| 18 | 32469565 | 32470560 | | | 18 | 61754356 | 61758287 |
| 18 | 32472835 | 32474322 | | | 18 | 61778480 | 61781301 |
| 18 | 32475022 | 32476788 | | | 18 | 61795772 | 61796978 |
| 18 | 32480022 | 32483384 | | | 18 | 61843818 | 61845353 |
| 18 | 32500213 | 32501415 | | | 18 | 61864388 | 61866961 |
| 18 | 32525944 | 32528789 | | | 18 | 61885657 | 61886318 |
| 18 | 32533463 | 32534788 | | | 18 | 61886448 | 61886643 |
| 18 | 32538853 | 32543807 | | | 18 | 61889238 | 61890371 |
| 18 | 32549539 | 32551877 | | | 18 | 61945451 | 61947422 |
| 18 | 32557984 | 32559404 | | | 18 | 61967301 | 61969022 |
| 18 | 32602965 | 32604586 | | | 18 | 62067675 | 62071130 |
| 18 | 32619382 | 32621037 | | | 18 | 62134359 | 62136029 |
| 18 | 32652617 | 32655487 | | | 18 | 62138455 | 62139030 |
| 18 | 32663612 | 32664487 | | | 18 | 62214750 | 62216660 |
| 18 | 32713743 | 32715324 | | | 18 | 62216824 | 62217224 |
| 18 | 32732374 | 32737560 | | | 18 | 62221968 | 62222558 |
| 18 | 32742922 | 32745011 | | | 18 | 62250850 | 62256760 |
| 18 | 32812471 | 32815287 | | | 18 | 62266924 | 62273052 |
| 18 | 32988867 | 32989718 | | | 18 | 62340111 | 62342025 |
| 18 | 33072278 | 33073373 | | | 18 | 62367760 | 62369015 |
| 18 | 33080990 | 33081939 | | | 18 | 62405233 | 62406693 |
| 18 | 33088881 | 33123061 | | | 18 | 62453379 | 62457241 |
| 18 | 33134949 | 33148964 | | | 18 | 62465419 | 62468709 |
| 18 | 33154919 | 33179263 | | | 18 | 62502597 | 62505685 |
| 18 | 33183583 | 33188227 | | | 18 | 62524920 | 62527027 |
| 18 | 33200764 | 33234699 | | | 18 | 62589249 | 62590355 |
| 18 | 33242545 | 33256537 | | | 18 | 62594064 | 62597676 |
| 18 | 33265023 | 33269558 | | | 18 | 62635193 | 62638624 |
| 18 | 33272393 | 33342531 | | | 18 | 62663073 | 62664956 |
| 18 | 33344476 | 33357792 | | | 18 | 62690353 | 62692468 |
| 18 | 33359288 | 33392161 | | | 18 | 62718211 | 62720708 |
| 18 | 33399109 | 33401980 | | | 18 | 62787835 | 62790030 |
| 18 | 33403235 | 33414967 | | | 18 | 62795666 | 62796306 |
| 18 | 33417688 | 33422180 | | | 18 | 62853100 | 62854450 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 33432881 | 33434092 | 18 | 62873965 | 62876587 |
| 18 | 33436090 | 33437474 | 18 | 62881537 | 62882662 |
| 18 | 33439194 | 33451674 | 18 | 63030236 | 63031031 |
| 18 | 33465443 | 33466441 | 18 | 63040382 | 63041137 |
| 18 | 33495979 | 33508159 | 18 | 63072669 | 63073464 |
| 18 | 33518205 | 33518855 | 18 | 63083613 | 63084033 |
| 18 | 33521291 | 33522409 | 18 | 63105385 | 63106260 |
| 18 | 33530840 | 33535445 | 18 | 63160759 | 63161944 |
| 18 | 33539040 | 33540926 | 18 | 63223219 | 63228041 |
| 18 | 33547031 | 33547646 | 18 | 63243799 | 63245045 |
| 18 | 33555648 | 33558588 | 18 | 63249640 | 63250707 |
| 18 | 33563855 | 33567470 | 18 | 63331124 | 63332729 |
| 18 | 33602014 | 33603351 | 18 | 63336290 | 63342306 |
| 18 | 33608685 | 33615628 | 18 | 63347426 | 63349431 |
| 18 | 33632257 | 33633067 | 18 | 63369302 | 63370137 |
| 18 | 33647620 | 33649420 | 18 | 63380446 | 63380676 |
| 18 | 33678702 | 33681091 | 18 | 63396022 | 63396314 |
| 18 | 33694120 | 33694848 | 18 | 63431932 | 63433811 |
| 18 | 33703970 | 33708254 | 18 | 63438593 | 63439983 |
| 18 | 33805831 | 33807716 | 18 | 63446275 | 63447662 |
| 18 | 33808546 | 33813010 | 18 | 63467374 | 63470759 |
| 18 | 33843558 | 33846043 | 18 | 63476168 | 63480340 |
| 18 | 33857211 | 33859247 | 18 | 63548647 | 63550872 |
| 18 | 33861332 | 33864227 | 18 | 63592522 | 63594867 |
| 18 | 33873867 | 33879252 | 18 | 63601624 | 63601989 |
| 18 | 33917509 | 33919859 | 18 | 63606172 | 63608212 |
| 18 | 33992153 | 33995213 | 18 | 63613972 | 63615587 |
| 18 | 33996883 | 33999718 | 18 | 63690000 | 63691045 |
| 18 | 34008369 | 34009708 | 18 | 63775064 | 63775724 |
| 18 | 34036063 | 34036440 | 18 | 63917561 | 63919316 |
| 18 | 34071120 | 34072635 | 18 | 63999784 | 64002179 |
| 18 | 34090491 | 34092173 | 18 | 64013155 | 64014384 |
| 18 | 34097558 | 34098603 | 18 | 64030201 | 64032047 |
| 18 | 34203617 | 34206682 | 18 | 64112039 | 64112309 |
| 18 | 34225516 | 34228116 | 18 | 64209465 | 64210295 |
| 18 | 34276106 | 34284868 | 18 | 64217383 | 64220302 |
| 18 | 34290116 | 34290776 | 18 | 64244999 | 64245769 |
| 18 | 34295805 | 34301173 | 18 | 64257528 | 64259338 |
| 18 | 34335320 | 34335875 | 18 | 64265443 | 64269729 |
| 18 | 34383771 | 34385198 | 18 | 64273156 | 64274711 |
| 18 | 34385918 | 34386658 | 18 | 64284971 | 64286546 |
| 18 | 34396712 | 34398912 | 18 | 64376671 | 64378431 |
| 18 | 34434240 | 34438185 | 18 | 64386260 | 64387245 |
| 18 | 34497628 | 34499478 | 18 | 64441563 | 64443120 |
| 18 | 34511999 | 34513827 | 18 | 64495303 | 64495978 |
| 18 | 34521769 | 34525583 | 18 | 64572422 | 64572612 |
| 18 | 34569940 | 34574617 | 18 | 64576584 | 64578252 |
| 18 | 34583435 | 34584476 | 18 | 64598653 | 64601863 |
| 18 | 34595150 | 34596330 | 18 | 64676757 | 64680009 |
| 18 | 34625651 | 34627501 | 18 | 64691022 | 64692998 |
| 18 | 34643389 | 34645148 | 18 | 64694183 | 64694768 |
| 18 | 34662484 | 34663864 | 18 | 64709767 | 64712462 |
| 18 | 34682329 | 34686389 | 18 | 64720033 | 64720923 |
| 18 | 34705367 | 34707779 | 18 | 64762494 | 64763744 |
| 18 | 34729124 | 34729759 | 18 | 64766783 | 64767763 |

The chromosomal positon was obtained from UCSC genome browser (http://genome.ucsc.edu/) build 36.

APPENDIX C: Chromosome 18
Page 64 of 72

| Chr | Start | End | Chr | Start | End |
|---|---|---|---|---|---|
| 18 | 34761049 | 34763234 | 18 | 64784239 | 64785714 |
| 18 | 34787085 | 34788140 | 18 | 64874646 | 64876909 |
| 18 | 34822047 | 34824513 | 18 | 64977010 | 64977625 |
| 18 | 34852022 | 34853473 | 18 | 64985340 | 64985930 |
| 18 | 34876284 | 34877395 | 18 | 64997728 | 64999526 |
| 18 | 34887643 | 34889699 | 18 | 65010720 | 65015138 |
| 18 | 34894687 | 34900912 | 18 | 65018662 | 65019349 |
| 18 | 34904918 | 34906128 | 18 | 65159474 | 65162044 |
| 18 | 34929511 | 34934989 | 18 | 65195513 | 65195893 |
| 18 | 34945857 | 34949888 | 18 | 65219830 | 65220495 |
| 18 | 35019632 | 35030206 | 18 | 65287968 | 65289593 |
| 18 | 35051168 | 35056601 | 18 | 65339573 | 65340639 |
| 18 | 35077315 | 35079170 | 18 | 65369504 | 65369894 |
| 18 | 35136414 | 35140106 | 18 | 65395031 | 65395951 |
| 18 | 35148032 | 35149227 | 18 | 65500115 | 65501440 |
| 18 | 35164481 | 35167831 | 18 | 65525843 | 65528872 |
| 18 | 35265470 | 35272607 | 18 | 65543554 | 65544615 |
| 18 | 35286352 | 35290255 | 18 | 65636018 | 65636793 |
| 18 | 35312099 | 35317202 | 18 | 65648531 | 65650836 |
| 18 | 35331426 | 35339895 | 18 | 65657273 | 65661268 |
| 18 | 35347844 | 35349294 | 18 | 65681763 | 65682608 |
| 18 | 35365156 | 35368221 | 18 | 65719416 | 65726023 |
| 18 | 35392302 | 35394425 | 18 | 65736804 | 65746023 |
| 18 | 35414954 | 35417615 | 18 | 65750463 | 65752568 |
| 18 | 35424612 | 35429385 | 18 | 65753532 | 65755896 |
| 18 | 35481210 | 35483655 | 18 | 65767136 | 65768521 |
| 18 | 35505633 | 35506623 | 18 | 65788696 | 65789996 |
| 18 | 35513188 | 35515175 | 18 | 65798391 | 65801076 |
| 18 | 35553708 | 35556250 | 18 | 65846523 | 65846988 |
| 18 | 35559242 | 35563351 | 18 | 65869841 | 65871589 |
| 18 | 35568790 | 35577209 | 18 | 66023361 | 66029154 |
| 18 | 35579530 | 35580825 | 18 | 66049602 | 66050964 |
| 18 | 35617428 | 35622777 | 18 | 66066434 | 66069292 |
| 18 | 35624768 | 35626228 | 18 | 66102655 | 66103715 |
| 18 | 35704305 | 35713231 | 18 | 66108398 | 66109225 |
| 18 | 35717970 | 35720010 | 18 | 66198788 | 66200207 |
| 18 | 35800050 | 35802111 | 18 | 66278177 | 66282760 |
| 18 | 35804751 | 35809946 | 18 | 66316693 | 66318153 |
| 18 | 35828517 | 35828992 | 18 | 66325569 | 66333049 |
| 18 | 35841196 | 35845386 | 18 | 66379805 | 66380820 |
| 18 | 35859309 | 35861738 | 18 | 66393743 | 66397806 |
| 18 | 35868681 | 35870217 | 18 | 66405317 | 66407090 |
| 18 | 35882965 | 35883935 | 18 | 66426596 | 66428051 |
| 18 | 35909110 | 35911287 | 18 | 66436356 | 66438101 |
| 18 | 35938617 | 35940358 | 18 | 66441301 | 66442136 |
| 18 | 35942625 | 35944673 | 18 | 66453642 | 66454531 |
| 18 | 35973358 | 35974493 | 18 | 66461754 | 66462546 |
| 18 | 35984284 | 35984819 | 18 | 66467432 | 66470136 |
| 18 | 35986094 | 35986992 | 18 | 66473026 | 66474394 |
| 18 | 36035279 | 36038242 | 18 | 66498982 | 66500072 |
| 18 | 36083366 | 36092388 | 18 | 66544004 | 66545084 |
| 18 | 36117987 | 36119157 | 18 | 66550625 | 66551106 |
| 18 | 36176566 | 36177875 | 18 | 66574500 | 66575050 |
| 18 | 36189615 | 36195272 | 18 | 66626748 | 66628493 |
| 18 | 36207347 | 36209393 | 18 | 66645073 | 66646157 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 36236083 | 36237238 | 18 | 66659048 | 66662158 |
| 18 | 36279312 | 36285285 | 18 | 66666323 | 66667543 |
| 18 | 36307779 | 36308449 | 18 | 66854321 | 66855441 |
| 18 | 36330623 | 36332003 | 18 | 66873049 | 66873799 |
| 18 | 36336987 | 36338457 | 18 | 66880175 | 66880840 |
| 18 | 36354671 | 36356211 | 18 | 66895138 | 66896522 |
| 18 | 36384480 | 36389120 | 18 | 66924180 | 66926279 |
| 18 | 36401798 | 36403868 | 18 | 66931750 | 66934421 |
| 18 | 36407354 | 36408994 | 18 | 66948258 | 66950244 |
| 18 | 36460199 | 36461610 | 18 | 66954740 | 66956551 |
| 18 | 36470377 | 36482468 | 18 | 67019377 | 67020927 |
| 18 | 36500672 | 36502043 | 18 | 67052181 | 67055638 |
| 18 | 36539967 | 36543326 | 18 | 67068770 | 67071326 |
| 18 | 36589768 | 36592108 | 18 | 67080490 | 67081549 |
| 18 | 36639009 | 36653874 | 18 | 67096130 | 67097110 |
| 18 | 36668457 | 36669208 | 18 | 67100357 | 67102472 |
| 18 | 36703914 | 36705688 | 18 | 67121166 | 67123363 |
| 18 | 36708653 | 36712644 | 18 | 67190985 | 67192873 |
| 18 | 36718810 | 36719300 | 18 | 67311645 | 67315439 |
| 18 | 36745091 | 36745861 | 18 | 67344656 | 67346633 |
| 18 | 36746496 | 36746696 | 18 | 67363122 | 67367489 |
| 18 | 36755150 | 36755540 | 18 | 67368980 | 67370102 |
| 18 | 36813689 | 36814874 | 18 | 67392542 | 67394277 |
| 18 | 36836438 | 36836662 | 18 | 67399363 | 67402106 |
| 18 | 36855339 | 36856545 | 18 | 67425227 | 67426290 |
| 18 | 36859034 | 36859874 | 18 | 67550987 | 67551662 |
| 18 | 36864143 | 36865342 | 18 | 67582356 | 67583671 |
| 18 | 36916441 | 36925284 | 18 | 67615844 | 67616779 |
| 18 | 36929074 | 36933637 | 18 | 67748254 | 67749532 |
| 18 | 36967224 | 36968505 | 18 | 67862258 | 67864256 |
| 18 | 37044761 | 37048862 | 18 | 67872986 | 67873916 |
| 18 | 37064646 | 37065391 | 18 | 67877460 | 67879222 |
| 18 | 37089473 | 37090978 | 18 | 67983564 | 67985054 |
| 18 | 37093394 | 37095424 | 18 | 68016811 | 68018705 |
| 18 | 37187883 | 37189928 | 18 | 68031078 | 68032704 |
| 18 | 37239269 | 37240534 | 18 | 68125974 | 68129672 |
| 18 | 37254427 | 37255402 | 18 | 68184982 | 68187755 |
| 18 | 37263214 | 37264874 | 18 | 68192836 | 68193381 |
| 18 | 37336075 | 37337550 | 18 | 68212823 | 68214279 |
| 18 | 37347352 | 37349214 | 18 | 68282313 | 68291608 |
| 18 | 37371299 | 37371754 | 18 | 68319577 | 68323767 |
| 18 | 37409407 | 37413832 | 18 | 68325677 | 68326270 |
| 18 | 37481790 | 37483870 | 18 | 68333736 | 68335676 |
| 18 | 37489196 | 37491621 | 18 | 68337987 | 68339263 |
| 18 | 37496798 | 37500163 | 18 | 68356320 | 68357511 |
| 18 | 37508029 | 37509104 | 18 | 68392533 | 68394343 |
| 18 | 37521354 | 37522054 | 18 | 68417843 | 68421064 |
| 18 | 37530148 | 37531698 | 18 | 68430907 | 68432203 |
| 18 | 37538886 | 37543623 | 18 | 68467678 | 68469383 |
| 18 | 37580481 | 37581778 | 18 | 68490704 | 68497087 |
| 18 | 37588761 | 37591022 | 18 | 68514504 | 68515986 |
| 18 | 37639887 | 37640632 | 18 | 68537974 | 68540607 |
| 18 | 37652230 | 37652770 | 18 | 68555754 | 68556839 |
| 18 | 37654060 | 37654891 | 18 | 68568375 | 68570534 |
| 18 | 37670187 | 37670882 | 18 | 68576562 | 68577755 |

The chromosomal positon was obtained from UCSC genome browser (http://genome.ucsc.edu/) build 36.

APPENDIX C: Chromosome 18

| Chr | Start | End | | | Chr | Start | End |
|---|---|---|---|---|---|---|---|
| 18 | 37680775 | 37686741 | | | 18 | 68586247 | 68586723 |
| 18 | 37716542 | 37717527 | | | 18 | 68595181 | 68596999 |
| 18 | 37719782 | 37721202 | | | 18 | 68608059 | 68609807 |
| 18 | 37734564 | 37736979 | | | 18 | 68615782 | 68616297 |
| 18 | 37778620 | 37781390 | | | 18 | 68628919 | 68635842 |
| 18 | 37803136 | 37804731 | | | 18 | 68638548 | 68646584 |
| 18 | 37850774 | 37853354 | | | 18 | 68657379 | 68658714 |
| 18 | 37912813 | 37914833 | | | 18 | 68706440 | 68707504 |
| 18 | 37928403 | 37930189 | | | 18 | 68783434 | 68784082 |
| 18 | 37939637 | 37940940 | | | 18 | 68815127 | 68818142 |
| 18 | 37951309 | 37954166 | | | 18 | 68828932 | 68831093 |
| 18 | 37971457 | 37973972 | | | 18 | 68841740 | 68842500 |
| 18 | 37990221 | 37994899 | | | 18 | 68846500 | 68848783 |
| 18 | 38008993 | 38011534 | | | 18 | 68863236 | 68864411 |
| 18 | 38019847 | 38021632 | | | 18 | 68876144 | 68877454 |
| 18 | 38074321 | 38076316 | | | 18 | 68965022 | 68969597 |
| 18 | 38102250 | 38102929 | | | 18 | 68990567 | 68995448 |
| 18 | 38114505 | 38115815 | | | 18 | 69018488 | 69018734 |
| 18 | 38132822 | 38133872 | | | 18 | 69024093 | 69024509 |
| 18 | 38197193 | 38202980 | | | 18 | 69037649 | 69038534 |
| 18 | 38245408 | 38247189 | | | 18 | 69101706 | 69103352 |
| 18 | 38261172 | 38263912 | | | 18 | 69131050 | 69139542 |
| 18 | 38277868 | 38279043 | | | 18 | 69180497 | 69181850 |
| 18 | 38306046 | 38307153 | | | 18 | 69216774 | 69217954 |
| 18 | 38314095 | 38314975 | | | 18 | 69234310 | 69236221 |
| 18 | 38341262 | 38343882 | | | 18 | 69274547 | 69277568 |
| 18 | 38354514 | 38359149 | | | 18 | 69303915 | 69304725 |
| 18 | 38368306 | 38369696 | | | 18 | 69337418 | 69338566 |
| 18 | 38413006 | 38422364 | | | 18 | 69351864 | 69353821 |
| 18 | 38448184 | 38453109 | | | 18 | 69400336 | 69402021 |
| 18 | 38479005 | 38481743 | | | 18 | 69469428 | 69471384 |
| 18 | 38502598 | 38504536 | | | 18 | 69481012 | 69482807 |
| 18 | 38522885 | 38525724 | | | 18 | 69497732 | 69498812 |
| 18 | 38537105 | 38538085 | | | 18 | 69505787 | 69510202 |
| 18 | 38553460 | 38555585 | | | 18 | 69533277 | 69533892 |
| 18 | 38584261 | 38587439 | | | 18 | 69538730 | 69539470 |
| 18 | 38640955 | 38642407 | | | 18 | 69553687 | 69554987 |
| 18 | 38644124 | 38644518 | | | 18 | 69572436 | 69582295 |
| 18 | 38649900 | 38650845 | | | 18 | 69644491 | 69653787 |
| 18 | 38653832 | 38657552 | | | 18 | 69664030 | 69665440 |
| 18 | 38662329 | 38663566 | | | 18 | 69669349 | 69689430 |
| 18 | 38681661 | 38683406 | | | 18 | 69706877 | 69713374 |
| 18 | 38694718 | 38695608 | | | 18 | 69718926 | 69719911 |
| 18 | 38698473 | 38699383 | | | 18 | 69732009 | 69732875 |
| 18 | 38708757 | 38709496 | | | 18 | 69740367 | 69743268 |
| 18 | 38725671 | 38726492 | | | 18 | 69752241 | 69754539 |
| 18 | 38750305 | 38755839 | | | 18 | 69756834 | 69762651 |
| 18 | 38779445 | 38783063 | | | 18 | 69766051 | 69767366 |
| 18 | 38803399 | 38804966 | | | 18 | 69776405 | 69777885 |
| 18 | 38813733 | 38815223 | | | 18 | 69789349 | 69793118 |
| 18 | 38846732 | 38848353 | | | 18 | 69795704 | 69803839 |
| 18 | 38875814 | 38880334 | | | 18 | 69809139 | 69810604 |
| 18 | 38886015 | 38890475 | | | 18 | 69824343 | 69830929 |
| 18 | 38950275 | 38953172 | | | 18 | 69852202 | 69857347 |
| 18 | 38960574 | 38963164 | | | 18 | 69889964 | 69897241 |

The chromosomal positon was obtained from UCSC genome browser (http://genome.ucsc.edu/) build 36.

APPENDIX C: Chromosome 18
Page 67 of 72

| Chr | Start | End | | | Chr | Start | End |
|---|---|---|---|---|---|---|---|
| 18 | 38971685 | 38972625 | | | 18 | 69934653 | 69936171 |
| 18 | 39014830 | 39019681 | | | 18 | 69940867 | 69943809 |
| 18 | 39030819 | 39031859 | | | 18 | 69984656 | 69986311 |
| 18 | 39034652 | 39036068 | | | 18 | 69989852 | 69995894 |
| 18 | 39086278 | 39088315 | | | 18 | 70033397 | 70038369 |
| 18 | 39102408 | 39108663 | | | 18 | 70060428 | 70061365 |
| 18 | 39117139 | 39119206 | | | 18 | 70084904 | 70086701 |
| 18 | 39148034 | 39149119 | | | 18 | 70099882 | 70103729 |
| 18 | 39218970 | 39223544 | | | 18 | 70106724 | 70109459 |
| 18 | 39260032 | 39260900 | | | 18 | 70139280 | 70139970 |
| 18 | 39268264 | 39270224 | | | 18 | 70143675 | 70146255 |
| 18 | 39290861 | 39291650 | | | 18 | 70149639 | 70156690 |
| 18 | 39315865 | 39317350 | | | 18 | 70162164 | 70163491 |
| 18 | 39375814 | 39376699 | | | 18 | 70165417 | 70165872 |
| 18 | 39401628 | 39405829 | | | 18 | 70181353 | 70182533 |
| 18 | 39436817 | 39440340 | | | 18 | 70203136 | 70206211 |
| 18 | 39443122 | 39447595 | | | 18 | 70217336 | 70218651 |
| 18 | 39472982 | 39474107 | | | 18 | 70219886 | 70221482 |
| 18 | 39505814 | 39506854 | | | 18 | 70246749 | 70248559 |
| 18 | 39533497 | 39538870 | | | 18 | 70262706 | 70263941 |
| 18 | 39541358 | 39542893 | | | 18 | 70317293 | 70318204 |
| 18 | 39605854 | 39608269 | | | 18 | 70319404 | 70320004 |
| 18 | 39652203 | 39657532 | | | 18 | 70328593 | 70329478 |
| 18 | 39659944 | 39661004 | | | 18 | 70344189 | 70345109 |
| 18 | 39695806 | 39701040 | | | 18 | 70360567 | 70365305 |
| 18 | 39713356 | 39715206 | | | 18 | 70373814 | 70378652 |
| 18 | 39733553 | 39736541 | | | 18 | 70389732 | 70392443 |
| 18 | 39762443 | 39765578 | | | 18 | 70397735 | 70400190 |
| 18 | 39864822 | 39866540 | | | 18 | 70406990 | 70407420 |
| 18 | 39883283 | 39883891 | | | 18 | 70653083 | 70654344 |
| 18 | 39910218 | 39915078 | | | 18 | 70710411 | 70711039 |
| 18 | 39921399 | 39923497 | | | 18 | 70835614 | 70836914 |
| 18 | 40014706 | 40016134 | | | 18 | 70850962 | 70852212 |
| 18 | 40028118 | 40030914 | | | 18 | 70857076 | 70859111 |
| 18 | 40032684 | 40034615 | | | 18 | 70919401 | 70923783 |
| 18 | 40054661 | 40055056 | | | 18 | 70950177 | 70957397 |
| 18 | 40068725 | 40073721 | | | 18 | 70967277 | 70981164 |
| 18 | 40116714 | 40119114 | | | 18 | 71006076 | 71010718 |
| 18 | 40123866 | 40125671 | | | 18 | 71019637 | 71022721 |
| 18 | 40158913 | 40160393 | | | 18 | 71024653 | 71025983 |
| 18 | 40226653 | 40231253 | | | 18 | 71087202 | 71089453 |
| 18 | 40244500 | 40245413 | | | 18 | 71137561 | 71147095 |
| 18 | 40251716 | 40258097 | | | 18 | 71158382 | 71162129 |
| 18 | 40271280 | 40272340 | | | 18 | 71176177 | 71185986 |
| 18 | 40329445 | 40329755 | | | 18 | 71187602 | 71192761 |
| 18 | 40340020 | 40343419 | | | 18 | 71198115 | 71212879 |
| 18 | 40379069 | 40386625 | | | 18 | 71222354 | 71225194 |
| 18 | 40389627 | 40392252 | | | 18 | 71230816 | 71234366 |
| 18 | 40399115 | 40405018 | | | 18 | 71240828 | 71254237 |
| 18 | 40422450 | 40427835 | | | 18 | 71270803 | 71272326 |
| 18 | 40468968 | 40471933 | | | 18 | 71279023 | 71284030 |
| 18 | 40515234 | 40515849 | | | 18 | 71295274 | 71295754 |
| 18 | 40526140 | 40527970 | | | 18 | 71296404 | 71297402 |
| 18 | 40531005 | 40531896 | | | 18 | 71303204 | 71314406 |
| 18 | 40555390 | 40565081 | | | 18 | 71335602 | 71337555 |

The chromosomal positon was obtained from UCSC genome browser (http://genome.ucsc.edu/) build 36.

APPENDIX C: Chromosome 18

| Chr | Start | End | | Chr | Start | End |
|---|---|---|---|---|---|---|
| 18 | 40565361 | 40567346 | | 18 | 71345321 | 71348161 |
| 18 | 40581861 | 40588779 | | 18 | 71351846 | 71356084 |
| 18 | 40592960 | 40594420 | | 18 | 71362429 | 71373044 |
| 18 | 40604218 | 40605887 | | 18 | 71388220 | 71394233 |
| 18 | 40619340 | 40619885 | | 18 | 71396876 | 71397316 |
| 18 | 40626190 | 40627075 | | 18 | 71402379 | 71415648 |
| 18 | 40628640 | 40633551 | | 18 | 71424164 | 71428506 |
| 18 | 40657915 | 40659591 | | 18 | 71452555 | 71453185 |
| 18 | 40664223 | 40668255 | | 18 | 71461426 | 71466744 |
| 18 | 40673164 | 40674229 | | 18 | 71472883 | 71475485 |
| 18 | 40706755 | 40707590 | | 18 | 71477425 | 71486636 |
| 18 | 40721133 | 40724095 | | 18 | 71491109 | 71493329 |
| 18 | 40738290 | 40739942 | | 18 | 71519910 | 71526737 |
| 18 | 40770774 | 40771787 | | 18 | 71534268 | 71535931 |
| 18 | 40776248 | 40780898 | | 18 | 71543695 | 71546069 |
| 18 | 40791593 | 40793359 | | 18 | 71561403 | 71561984 |
| 18 | 40799730 | 40802740 | | 18 | 71563160 | 71568394 |
| 18 | 40810727 | 40813362 | | 18 | 71584482 | 71586830 |
| 18 | 40851440 | 40853120 | | 18 | 71594154 | 71595014 |
| 18 | 40865636 | 40868737 | | 18 | 71606543 | 71610164 |
| 18 | 40939055 | 40939590 | | 18 | 71612161 | 71616101 |
| 18 | 40947569 | 40949824 | | 18 | 71618321 | 71625035 |
| 18 | 40995782 | 40999579 | | 18 | 71648168 | 71652018 |
| 18 | 41066450 | 41072420 | | 18 | 71658732 | 71664726 |
| 18 | 41103810 | 41109123 | | 18 | 71700850 | 71707701 |
| 18 | 41149182 | 41152462 | | 18 | 71710984 | 71712745 |
| 18 | 41155086 | 41155991 | | 18 | 71729576 | 71732441 |
| 18 | 41175182 | 41176685 | | 18 | 71742730 | 71749652 |
| 18 | 41183751 | 41185636 | | 18 | 71755135 | 71756033 |
| 18 | 41192479 | 41193516 | | 18 | 71763072 | 71765487 |
| 18 | 41265715 | 41266420 | | 18 | 71775187 | 71777414 |
| 18 | 41276046 | 41277431 | | 18 | 71786359 | 71787386 |
| 18 | 41291210 | 41293502 | | 18 | 71823994 | 71830740 |
| 18 | 41296182 | 41303682 | | 18 | 71834988 | 71836676 |
| 18 | 41328723 | 41331397 | | 18 | 71846149 | 71849436 |
| 18 | 41333967 | 41335071 | | 18 | 71874643 | 71879536 |
| 18 | 41343855 | 41344715 | | 18 | 71888730 | 71900958 |
| 18 | 41355910 | 41357968 | | 18 | 71904157 | 71909559 |
| 18 | 41359003 | 41361263 | | 18 | 71919541 | 71925710 |
| 18 | 41387752 | 41388162 | | 18 | 71926930 | 71930316 |
| 18 | 41392637 | 41400435 | | 18 | 71933836 | 71935986 |
| 18 | 41420291 | 41434503 | | 18 | 71939989 | 71941949 |
| 18 | 41464944 | 41467004 | | 18 | 71943944 | 71945450 |
| 18 | 41471797 | 41473948 | | 18 | 71949599 | 71950611 |
| 18 | 41476770 | 41478315 | | 18 | 71955714 | 71957434 |
| 18 | 41483845 | 41489854 | | 18 | 71969367 | 71974408 |
| 18 | 41508046 | 41509119 | | 18 | 71976963 | 71978740 |
| 18 | 41515772 | 41519659 | | 18 | 71982419 | 71997498 |
| 18 | 41520169 | 41523005 | | 18 | 72008506 | 72010611 |
| 18 | 41544025 | 41545235 | | 18 | 72018060 | 72018792 |
| 18 | 41554216 | 41555671 | | 18 | 72044096 | 72047365 |
| 18 | 41593511 | 41594611 | | 18 | 72058152 | 72067805 |
| 18 | 41608200 | 41610236 | | 18 | 72071109 | 72073092 |
| 18 | 41640907 | 41641117 | | 18 | 72085424 | 72088683 |
| 18 | 41663236 | 41664096 | | 18 | 72091788 | 72093203 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 41669881 | 41674694 | 18 | 72095303 | 72097674 |
| 18 | 41826629 | 41827927 | 18 | 72102096 | 72106069 |
| 18 | 41883548 | 41884626 | 18 | 72122171 | 72126675 |
| 18 | 41894775 | 41897277 | 18 | 72151335 | 72153155 |
| 18 | 41932262 | 41933363 | 18 | 72159148 | 72159623 |
| 18 | 41988327 | 41992761 | 18 | 72160693 | 72166266 |
| 18 | 42056923 | 42057415 | 18 | 72173966 | 72180319 |
| 18 | 42082312 | 42084138 | 18 | 72183570 | 72208943 |
| 18 | 42133100 | 42141130 | 18 | 72209873 | 72211692 |
| 18 | 42142098 | 42142903 | 18 | 72217623 | 72224179 |
| 18 | 42156070 | 42157727 | 18 | 72231645 | 72254801 |
| 18 | 42172683 | 42173533 | 18 | 72257948 | 72266795 |
| 18 | 42202679 | 42204857 | 18 | 72269471 | 72279850 |
| 18 | 42212086 | 42214548 | 18 | 72284437 | 72288737 |
| 18 | 42231297 | 42233067 | 18 | 72291556 | 72292822 |
| 18 | 42238249 | 42248513 | 18 | 72295822 | 72307088 |
| 18 | 42283979 | 42297390 | 18 | 72311396 | 72313344 |
| 18 | 42316832 | 42325948 | 18 | 72323024 | 72325882 |
| 18 | 42337972 | 42346181 | 18 | 72328667 | 72329412 |
| 18 | 42349361 | 42372368 | 18 | 72332001 | 72334460 |
| 18 | 42386267 | 42407190 | 18 | 72347399 | 72350703 |
| 18 | 42410843 | 42412106 | 18 | 72356646 | 72358959 |
| 18 | 42427463 | 42428863 | 18 | 72365581 | 72366471 |
| 18 | 42436612 | 42438302 | 18 | 72367622 | 72391266 |
| 18 | 42441504 | 42442635 | 18 | 72397731 | 72400954 |
| 18 | 42458234 | 42467398 | 18 | 72406266 | 72408697 |
| 18 | 42469583 | 42470744 | 18 | 72423781 | 72446852 |
| 18 | 42478740 | 42519721 | 18 | 72451674 | 72467417 |
| 18 | 42525850 | 42528142 | 18 | 72478872 | 72481417 |
| 18 | 42530347 | 42540214 | 18 | 72489257 | 72492987 |
| 18 | 42549121 | 42573815 | 18 | 72502332 | 72549178 |
| 18 | 42584278 | 42588139 | 18 | 72556561 | 72557315 |
| 18 | 42647480 | 42648766 | 18 | 72576071 | 72577951 |
| 18 | 42701379 | 42702704 | 18 | 72602486 | 72606515 |
| 18 | 42778051 | 42816574 | 18 | 72611406 | 72616614 |
| 18 | 42829016 | 42831500 | 18 | 72623445 | 72624861 |
| 18 | 42834992 | 42836262 | 18 | 72660052 | 72665727 |
| 18 | 42844000 | 42845380 | 18 | 72820632 | 72843921 |
| 18 | 42848920 | 42849558 | 18 | 72845266 | 72846326 |
| 18 | 42854063 | 42856698 | 18 | 72846471 | 72891813 |
| 18 | 42859456 | 42861605 | 18 | 72903375 | 72904285 |
| 18 | 42884915 | 42886470 | 18 | 72914862 | 72936570 |
| 18 | 42954509 | 42958892 | 18 | 72953717 | 72962341 |
| 18 | 42991172 | 42992597 | 18 | 72965159 | 72966464 |
| 18 | 43005488 | 43008411 | 18 | 72975975 | 72988012 |
| 18 | 43028869 | 43031234 | 18 | 72992480 | 72998199 |
| 18 | 43039561 | 43040181 | 18 | 73000242 | 73012030 |
| 18 | 43042180 | 43044510 | 18 | 73021923 | 73028119 |
| 18 | 43088954 | 43090184 | 18 | 73039926 | 73049305 |
| 18 | 43105078 | 43118554 | 18 | 73053589 | 73057224 |
| 18 | 43153426 | 43154226 | 18 | 73074659 | 73076789 |
| 18 | 43156132 | 43159773 | 18 | 73089718 | 73093208 |
| 18 | 43161903 | 43163475 | 18 | 73094810 | 73109841 |
| 18 | 43180112 | 43186692 | 18 | 73113927 | 73116667 |
| 18 | 43191348 | 43193700 | 18 | 73134434 | 73147636 |

The chromosomal positon was obtained from UCSC genome browser (http://genome.ucsc.edu/) build 36.

APPENDIX C: Chromosome 18
Page 70 of 72

| Chr | Start | End | Chr | Start | End |
|---|---|---|---|---|---|
| 18 | 43208470 | 43209440 | 18 | 73162798 | 73165073 |
| 18 | 43230290 | 43232010 | 18 | 73175367 | 73191521 |
| 18 | 43269193 | 43270879 | 18 | 73203910 | 73205725 |
| 18 | 43276500 | 43278210 | 18 | 73207525 | 73224438 |
| 18 | 43280975 | 43283139 | 18 | 73237876 | 73251934 |
| 18 | 43325525 | 43328584 | 18 | 73284609 | 73289141 |
| 18 | 43333903 | 43341087 | 18 | 73325041 | 73327397 |
| 18 | 43353265 | 43354444 | 18 | 73330602 | 73341127 |
| 18 | 43373689 | 43376190 | 18 | 73343348 | 73346315 |
| 18 | 43380517 | 43381617 | 18 | 73358148 | 73363473 |
| 18 | 43394298 | 43395868 | 18 | 73366486 | 73369401 |
| 18 | 43430239 | 43438147 | 18 | 73384836 | 73385756 |
| 18 | 43452490 | 43453285 | 18 | 73387166 | 73390609 |
| 18 | 43459884 | 43464791 | 18 | 73407438 | 73413322 |
| 18 | 43475526 | 43482463 | 18 | 73430687 | 73431483 |
| 18 | 43492518 | 43518482 | 18 | 73438567 | 73439431 |
| 18 | 43524453 | 43538040 | 18 | 73444223 | 73450064 |
| 18 | 43559383 | 43561473 | 18 | 73456600 | 73471162 |
| 18 | 43618846 | 43620291 | 18 | 73487997 | 73502637 |
| 18 | 43692344 | 43693054 | 18 | 73506462 | 73517431 |
| 18 | 43705733 | 43707775 | 18 | 73530812 | 73532467 |
| 18 | 43728514 | 43734376 | 18 | 73557481 | 73559951 |
| 18 | 43750583 | 43754222 | 18 | 73571894 | 73575660 |
| 18 | 43827568 | 43829128 | 18 | 73577945 | 73579115 |
| 18 | 43838432 | 43841787 | 18 | 73586179 | 73601823 |
| 18 | 43856680 | 43858074 | 18 | 73609627 | 73611127 |
| 18 | 43878380 | 43886560 | 18 | 73613068 | 73614493 |
| 18 | 43913936 | 43918878 | 18 | 73617743 | 73622083 |
| 18 | 43923848 | 43924258 | 18 | 73625761 | 73631555 |
| 18 | 43955653 | 43957367 | 18 | 73643335 | 73645157 |
| 18 | 43998842 | 44000382 | 18 | 73648297 | 73648537 |
| 18 | 44013091 | 44014411 | 18 | 73674119 | 73674849 |
| 18 | 44032692 | 44033859 | 18 | 73678136 | 73682217 |
| 18 | 44059433 | 44060473 | 18 | 73689983 | 73691014 |
| 18 | 44093772 | 44096337 | 18 | 73693678 | 73718508 |
| 18 | 44109643 | 44115071 | 18 | 73720774 | 73721719 |
| 18 | 44116740 | 44117735 | 18 | 73745905 | 73756325 |
| 18 | 44166018 | 44167813 | 18 | 73760497 | 73761537 |
| 18 | 44176223 | 44180588 | 18 | 73771285 | 73774975 |
| 18 | 44204328 | 44205323 | 18 | 73777580 | 73778810 |
| 18 | 44239485 | 44244896 | 18 | 73791326 | 73795180 |
| 18 | 44313538 | 44316818 | 18 | 73802314 | 73835199 |
| 18 | 44327936 | 44329746 | 18 | 73850765 | 73881609 |
| 18 | 44333307 | 44334342 | 18 | 73883309 | 73884855 |
| 18 | 44360529 | 44361414 | 18 | 73887280 | 73888811 |
| 18 | 44396522 | 44397407 | 18 | 73892415 | 73896609 |
| 18 | 44442468 | 44443643 | 18 | 73909284 | 73916636 |
| 18 | 44495266 | 44496666 | 18 | 73928272 | 73935812 |
| 18 | 44534746 | 44535836 | 18 | 73938801 | 73975606 |
| 18 | 44614622 | 44615614 | 18 | 73981520 | 74007615 |
| 18 | 44648665 | 44649710 | 18 | 74011214 | 74026783 |
| 18 | 44658427 | 44659857 | 18 | 74030545 | 74039801 |
| 18 | 44698381 | 44701652 | 18 | 74053450 | 74064055 |
| 18 | 44709985 | 44710643 | 18 | 74067528 | 74081524 |
| 18 | 44712693 | 44715683 | 18 | 74085839 | 74094541 |

The chromosomal positon was obtained from UCSC genome browser (http://genome.ucsc.edu/) build 36.

APPENDIX C: Chromosome 18

| Chr | Start | End | Chr | Start | End |
|---|---|---|---|---|---|
| 18 | 44716970 | 44720081 | 18 | 74099955 | 74110466 |
| 18 | 44722428 | 44723919 | 18 | 74116276 | 74117061 |
| 18 | 44726969 | 44728888 | 18 | 74128274 | 74130814 |
| 18 | 44734692 | 44735811 | 18 | 74136463 | 74138018 |
| 18 | 44742915 | 44744405 | 18 | 74138593 | 74142136 |
| 18 | 44753815 | 44757008 | 18 | 74145774 | 74160123 |
| 18 | 44777827 | 44778662 | 18 | 74162879 | 74198826 |
| 18 | 44785708 | 44788639 | 18 | 74205305 | 74206220 |
| 18 | 44792573 | 44802411 | 18 | 74208754 | 74239274 |
| 18 | 44832940 | 44834540 | 18 | 74248740 | 74318580 |
| 18 | 44851794 | 44852969 | 18 | 74331650 | 74395886 |
| 18 | 44865273 | 44865568 | 18 | 74399405 | 74411289 |
| 18 | 44942376 | 44943376 | 18 | 74415799 | 74502594 |
| 18 | 45008132 | 45009392 | 18 | 74504734 | 74561739 |
| 18 | 45029582 | 45030717 | 18 | 74564550 | 74604210 |
| 18 | 45083303 | 45084063 | 18 | 74611302 | 74620186 |
| 18 | 45122159 | 45125666 | 18 | 74624268 | 74703805 |
| 18 | 45137527 | 45138607 | 18 | 74708344 | 74722706 |
| 18 | 45161717 | 45164161 | 18 | 74735262 | 74744431 |
| 18 | 45278237 | 45283990 | 18 | 74752487 | 74833795 |
| 18 | 45388952 | 45391402 | 18 | 74838778 | 74843366 |
| 18 | 45399910 | 45402575 | 18 | 74852778 | 74862764 |
| 18 | 45509608 | 45513013 | 18 | 74864769 | 74866359 |
| 18 | 45564637 | 45565607 | 18 | 74871864 | 74872762 |
| 18 | 45612166 | 45614348 | 18 | 74874713 | 74903509 |
| 18 | 45634828 | 45636458 | 18 | 74908871 | 74920902 |
| 18 | 45651668 | 45659545 | 18 | 74923568 | 74928946 |
| 18 | 45669662 | 45670702 | 18 | 75048509 | 75049965 |
| 18 | 45672182 | 45673007 | 18 | 75206828 | 75207968 |
| 18 | 45673772 | 45678183 | 18 | 75242205 | 75250721 |
| 18 | 45684638 | 45687885 | 18 | 75256340 | 75258667 |
| 18 | 45820301 | 45825133 | 18 | 75265227 | 75265892 |
| 18 | 45845242 | 45849327 | 18 | 75268957 | 75307878 |
| 18 | 45858650 | 45864164 | 18 | 75319021 | 75353021 |
| 18 | 45910941 | 45913750 | 18 | 75357262 | 75362309 |
| 18 | 45917333 | 45923789 | 18 | 75364020 | 75367210 |
| 18 | 45939281 | 45944012 | 18 | 75370881 | 75377441 |
| 18 | 45954631 | 45959902 | 18 | 75378941 | 75383579 |
| 18 | 45970634 | 45972704 | 18 | 75384199 | 75385410 |
| 18 | 45990129 | 45992986 | 18 | 75386864 | 75452512 |
| 18 | 46295238 | 46296309 | 18 | 75456852 | 75503776 |
| 18 | 46308618 | 46310379 | 18 | 75510954 | 75513001 |
| 18 | 46327115 | 46329125 | 18 | 75586637 | 75589685 |
| 18 | 46349918 | 46352249 | 18 | 75622721 | 75648873 |
| 18 | 46371148 | 46373323 | 18 | 75656706 | 75684788 |
| 18 | 46376333 | 46382000 | 18 | 75687637 | 75696669 |
| 18 | 46387105 | 46388335 | 18 | 75705714 | 75738611 |
| 18 | 46398018 | 46404657 | 18 | 75744377 | 75756801 |
| 18 | 46415192 | 46421958 | 18 | 75819562 | 75829791 |
| 18 | 46425871 | 46429386 | 18 | 75849639 | 75862163 |
| 18 | 46429756 | 46432356 | 18 | 75870133 | 75872649 |
| 18 | 46436247 | 46437477 | 18 | 75928591 | 75931156 |
| 18 | 46507284 | 46508274 | 18 | 76001324 | 76005569 |
|  |  |  | 18 | 76029567 | 76033886 |
|  |  |  | 18 | 76035341 | 76039838 |

The chromosomal positon was obtained from UCSC genome browser (http://genome.ucsc.edu/) build 36.

APPENDIX C: Chromosome 18
Page 72 of 72

| Chr | Start | End | | | Chr | Start | End |
|---|---|---|---|---|---|---|---|
| | | | | | 18 | 76044074 | 76046397 |
| | | | | | 18 | 76092345 | 76093435 |
| | | | | | 18 | 76112396 | 76116328 |

The chromosomal positon was obtained from UCSC genome browser (http://genome.ucsc.edu/) build 36.

APPENDIX D: Chromosome X
Page 1 of 73

| Chr | Start | End | | | Chr | Start | End |
|---|---|---|---|---|---|---|---|
| X | 866 | 449316 | | | X | 29045073 | 29048123 |
| X | 463402 | 499553 | | | X | 29152042 | 29153350 |
| X | 512825 | 520397 | | | X | 29193394 | 29200739 |
| X | 527786 | 757850 | | | X | 29355330 | 29360064 |
| X | 762378 | 769971 | | | X | 29363141 | 29363384 |
| X | 778821 | 1607960 | | | X | 29457705 | 29458651 |
| X | 1620006 | 1870433 | | | X | 29474574 | 29477454 |
| X | 1649170 | 1649735 | | | X | 29498480 | 29500704 |
| X | 1888762 | 2334434 | | | X | 29744436 | 29746984 |
| X | 2351721 | 2441982 | | | X | 29759232 | 29761632 |
| X | 2446319 | 2449301 | | | X | 29785659 | 29787490 |
| X | 2459629 | 2462225 | | | X | 29803460 | 29805709 |
| X | 2465369 | 2468821 | | | X | 29836613 | 29839466 |
| X | 2476594 | 2535204 | | | X | 29891164 | 29892762 |
| X | 2568200 | 2623039 | | | X | 29903412 | 29916268 |
| X | 2624129 | 2626123 | | | X | 29943728 | 29945326 |
| X | 2626946 | 2697216 | | | X | 29963711 | 29964745 |
| X | 2714807 | 2733346 | | | X | 29976967 | 29980838 |
| X | 2751351 | 2796541 | | | X | 30031551 | 30037517 |
| X | 2800552 | 2801625 | | | X | 30044642 | 30048860 |
| X | 2804179 | 2813162 | | | X | 30101303 | 30102051 |
| X | 2822945 | 2827784 | | | X | 30107004 | 30114893 |
| X | 2834502 | 2874884 | | | X | 30142998 | 30151031 |
| X | 2877287 | 2877814 | | | X | 30158779 | 30162179 |
| X | 2887330 | 2898166 | | | X | 30165764 | 30166065 |
| X | 2938523 | 2944594 | | | X | 30169837 | 30171663 |
| X | 2959363 | 2961246 | | | X | 30175115 | 30179514 |
| X | 2981594 | 2985458 | | | X | 30201195 | 30216684 |
| X | 2999884 | 3017172 | | | X | 30233782 | 30235730 |
| X | 3033025 | 3048507 | | | X | 30300716 | 30304013 |
| X | 3056109 | 3062257 | | | X | 30330590 | 30337366 |
| X | 3070156 | 3074956 | | | X | 30385726 | 30389850 |
| X | 3086848 | 3091739 | | | X | 30404216 | 30405809 |
| X | 3102060 | 3103921 | | | X | 30442101 | 30442819 |
| X | 3133793 | 3152573 | | | X | 30499876 | 30504271 |
| X | 3166336 | 3168466 | | | X | 30580058 | 30581883 |
| X | 3193785 | 3196569 | | | X | 30588781 | 30598121 |
| X | 3208211 | 3209310 | | | X | 30715356 | 30735240 |
| X | 3213286 | 3214996 | | | X | 30757519 | 30760595 |
| X | 3221247 | 3222932 | | | X | 30790132 | 30804387 |
| X | 3237779 | 3239590 | | | X | 30815751 | 30818246 |
| X | 3244075 | 3261659 | | | X | 30820298 | 30843943 |
| X | 3275796 | 3278975 | | | X | 30854132 | 30862727 |
| X | 3294991 | 3296376 | | | X | 30895142 | 30900046 |
| X | 3322516 | 3327357 | | | X | 30903886 | 30904624 |
| X | 3348499 | 3349254 | | | X | 30999822 | 31000777 |
| X | 3354444 | 3371650 | | | X | 31013371 | 31014788 |
| X | 3387798 | 3389364 | | | X | 31025244 | 31026400 |
| X | 3409645 | 3420436 | | | X | 31043393 | 31059725 |
| X | 3441367 | 3454976 | | | X | 31063480 | 31067431 |
| X | 3463212 | 3488555 | | | X | 31093500 | 31095095 |
| X | 3491985 | 3497184 | | | X | 31106693 | 31118127 |
| X | 3510912 | 3511833 | | | X | 31147233 | 31149144 |
| X | 3528356 | 3535258 | | | X | 31152330 | 31155503 |
| X | 3538655 | 3542573 | | | X | 31190680 | 31191159 |

The chromosomal positon was obtained from UCSC genome browser (http://genome.ucsc.edu/) build 36.

APPENDIX D: Chromosome X
Page 2 of 73

| Chr | Start | End | | | Chr | Start | End |
|---|---|---|---|---|---|---|---|
| X | 3549097 | 3554132 | | | X | 31194357 | 31195419 |
| X | 3559986 | 3561937 | | | X | 31198607 | 31206694 |
| X | 3567825 | 3664713 | | | X | 31225350 | 31225811 |
| X | 3684638 | 3687682 | | | X | 31246831 | 31247193 |
| X | 4001885 | 4003581 | | | X | 31297582 | 31298947 |
| X | 4019972 | 4025488 | | | X | 31327829 | 31330253 |
| X | 4025793 | 4031935 | | | X | 31401791 | 31402842 |
| X | 4045050 | 4050317 | | | X | 31410864 | 31412806 |
| X | 4087787 | 4090258 | | | X | 31412996 | 31416544 |
| X | 4112313 | 4115666 | | | X | 31425327 | 31425693 |
| X | 4138607 | 4140376 | | | X | 31471843 | 31472515 |
| X | 4164879 | 4166240 | | | X | 31493266 | 31494550 |
| X | 4176432 | 4177494 | | | X | 31528786 | 31536357 |
| X | 4179212 | 4181213 | | | X | 31563696 | 31564653 |
| X | 4241604 | 4243345 | | | X | 31578658 | 31584927 |
| X | 4265156 | 4269080 | | | X | 31638864 | 31641299 |
| X | 4294822 | 4299564 | | | X | 31675114 | 31680389 |
| X | 4366140 | 4366505 | | | X | 31727141 | 31731172 |
| X | 4411382 | 4413826 | | | X | 31736138 | 31740139 |
| X | 4437804 | 4440369 | | | X | 31774398 | 31775966 |
| X | 4460159 | 4465192 | | | X | 31811659 | 31816401 |
| X | 4465997 | 4474520 | | | X | 31818539 | 31819731 |
| X | 4489189 | 4490723 | | | X | 31841712 | 31842230 |
| X | 4494171 | 4494500 | | | X | 31863208 | 31865066 |
| X | 4539929 | 4545812 | | | X | 31891626 | 31892542 |
| X | 4612564 | 4614626 | | | X | 31903982 | 31905599 |
| X | 4646423 | 4647721 | | | X | 31915380 | 31916161 |
| X | 4692664 | 4702837 | | | X | 31989015 | 31990827 |
| X | 4772537 | 4773793 | | | X | 31994120 | 31997044 |
| X | 4792197 | 4794220 | | | X | 32026477 | 32030122 |
| X | 4845311 | 4846394 | | | X | 32032507 | 32035893 |
| X | 4881590 | 4886464 | | | X | 32108185 | 32109316 |
| X | 4910290 | 4916910 | | | X | 32113306 | 32115610 |
| X | 4944907 | 4948423 | | | X | 32130715 | 32133199 |
| X | 4964052 | 4965445 | | | X | 32146457 | 32150148 |
| X | 5040510 | 5041826 | | | X | 32166636 | 32168175 |
| X | 5072661 | 5078620 | | | X | 32176241 | 32188970 |
| X | 5111180 | 5113392 | | | X | 32191780 | 32196148 |
| X | 5163450 | 5164838 | | | X | 32202781 | 32204364 |
| X | 5175202 | 5187256 | | | X | 32209293 | 32212589 |
| X | 5191249 | 5193652 | | | X | 32235017 | 32239326 |
| X | 5221405 | 5222214 | | | X | 32324064 | 32327811 |
| X | 5235915 | 5236998 | | | X | 32332665 | 32337043 |
| X | 5273605 | 5276581 | | | X | 32348190 | 32349240 |
| X | 5292340 | 5297431 | | | X | 32370524 | 32372676 |
| X | 5318809 | 5319040 | | | X | 32393537 | 32393969 |
| X | 5332172 | 5332660 | | | X | 32395065 | 32396384 |
| X | 5460100 | 5465701 | | | X | 32412632 | 32413114 |
| X | 5476896 | 5478807 | | | X | 32493404 | 32495830 |
| X | 5483695 | 5486101 | | | X | 32512841 | 32513442 |
| X | 5540139 | 5543338 | | | X | 32586849 | 32588425 |
| X | 5587855 | 5589088 | | | X | 32596624 | 32597472 |
| X | 5670180 | 5673164 | | | X | 32610831 | 32613783 |
| X | 5753114 | 5756493 | | | X | 32712962 | 32713530 |
| X | 5766590 | 5771593 | | | X | 32748054 | 32750826 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 5794099 | 5797279 | X | 32820274 | 32823511 |
| X | 5820576 | 5832011 | X | 32827920 | 32829644 |
| X | 5848427 | 5848683 | X | 32862776 | 32864832 |
| X | 5934674 | 5936645 | X | 32882495 | 32886209 |
| X | 6044003 | 6046825 | X | 32891762 | 32898175 |
| X | 6063921 | 6065654 | X | 32914611 | 32914914 |
| X | 6079041 | 6082282 | X | 32979592 | 32984905 |
| X | 6114163 | 6115536 | X | 33004783 | 33007908 |
| X | 6132271 | 6132695 | X | 33034397 | 33038862 |
| X | 6199571 | 6206951 | X | 33083141 | 33083682 |
| X | 6301457 | 6303111 | X | 33115762 | 33117785 |
| X | 6308732 | 6315787 | X | 33122757 | 33124391 |
| X | 6345236 | 6346362 | X | 33243532 | 33244230 |
| X | 6350200 | 6350470 | X | 33263539 | 33265485 |
| X | 6366188 | 6367335 | X | 33318139 | 33325368 |
| X | 6402867 | 6405986 | X | 33328457 | 33329493 |
| X | 6411962 | 6412408 | X | 33484271 | 33486659 |
| X | 6486674 | 6490425 | X | 33537064 | 33540031 |
| X | 6505332 | 6508675 | X | 33558799 | 33559709 |
| X | 6550966 | 6552615 | X | 33564685 | 33572565 |
| X | 6598931 | 6599810 | X | 33594933 | 33595597 |
| X | 6615302 | 6616872 | X | 33644391 | 33648547 |
| X | 6617290 | 6619287 | X | 33654001 | 33654561 |
| X | 6656827 | 6657925 | X | 33720444 | 33725512 |
| X | 6661030 | 6661776 | X | 33770556 | 33773860 |
| X | 6687303 | 6688857 | X | 33794647 | 33795444 |
| X | 6813127 | 6814535 | X | 33823463 | 33826871 |
| X | 6818078 | 6819455 | X | 33840248 | 33841278 |
| X | 6871260 | 6872059 | X | 33872264 | 33878939 |
| X | 6873058 | 6874273 | X | 33910598 | 33916574 |
| X | 6894918 | 6897250 | X | 33923499 | 33926607 |
| X | 6938148 | 6940700 | X | 33958830 | 33959722 |
| X | 6955396 | 6957868 | X | 33964431 | 33965116 |
| X | 6982662 | 6983639 | X | 33974764 | 33975090 |
| X | 6997435 | 7005634 | X | 34001516 | 34005916 |
| X | 7016007 | 7017583 | X | 34040517 | 34042152 |
| X | 7019106 | 7024074 | X | 34053351 | 34060494 |
| X | 7063840 | 7066801 | X | 34074431 | 34077910 |
| X | 7081619 | 7082373 | X | 34085891 | 34086431 |
| X | 7082957 | 7086335 | X | 34135518 | 34137079 |
| X | 7133010 | 7134011 | X | 34137640 | 34143139 |
| X | 7135860 | 7136820 | X | 34146264 | 34150174 |
| X | 7142478 | 7144613 | X | 34194802 | 34197572 |
| X | 7146817 | 7149170 | X | 34216969 | 34217955 |
| X | 7151295 | 7154623 | X | 34227072 | 34228805 |
| X | 7187750 | 7188325 | X | 34259499 | 34260471 |
| X | 7208591 | 7209690 | X | 34269864 | 34276695 |
| X | 7223652 | 7230244 | X | 34281058 | 34291946 |
| X | 7268887 | 7274629 | X | 34315775 | 34316585 |
| X | 7287172 | 7289745 | X | 34378076 | 34384445 |
| X | 7297264 | 7300352 | X | 34414292 | 34421232 |
| X | 7317153 | 7318263 | X | 34482677 | 34487023 |
| X | 7321326 | 7322503 | X | 34491786 | 34494220 |
| X | 7334561 | 7342038 | X | 34513036 | 34514895 |
| X | 7346953 | 7349802 | X | 34516957 | 34517432 |

The chromosomal positon was obtained from UCSC genome browser (http://genome.ucsc.edu/) build 36.

APPENDIX D: Chromosome X
Page 4 of 73

| Chr | Start | End | | | Chr | Start | End |
|---|---|---|---|---|---|---|---|
| X | 7356000 | 7357728 | | | X | 34570249 | 34579488 |
| X | 7374244 | 7376368 | | | X | 34584990 | 34589799 |
| X | 7589291 | 7592734 | | | X | 34591865 | 34595445 |
| X | 7599701 | 7601030 | | | X | 34637318 | 34638002 |
| X | 7620437 | 7622215 | | | X | 34688525 | 34700436 |
| X | 7647726 | 7650078 | | | X | 34711958 | 34712964 |
| X | 7652699 | 7655225 | | | X | 34741818 | 34746614 |
| X | 7673018 | 7675287 | | | X | 34760932 | 34762584 |
| X | 7691660 | 7694141 | | | X | 34772355 | 34776176 |
| X | 7701733 | 7706398 | | | X | 34793883 | 34803351 |
| X | 7745435 | 7746973 | | | X | 34813139 | 34816340 |
| X | 7761303 | 7763007 | | | X | 34870167 | 34877901 |
| X | 7769414 | 7773543 | | | X | 34882788 | 34885639 |
| X | 7792845 | 7799168 | | | X | 34919113 | 34932965 |
| X | 7801349 | 7802359 | | | X | 34939263 | 34947006 |
| X | 7814433 | 7816208 | | | X | 35065221 | 35072546 |
| X | 7833300 | 7835549 | | | X | 35077734 | 35079281 |
| X | 7866473 | 7867642 | | | X | 35082788 | 35085927 |
| X | 7867982 | 7871823 | | | X | 35127878 | 35138624 |
| X | 7925452 | 7927141 | | | X | 35163959 | 35167665 |
| X | 7927438 | 7932688 | | | X | 35199933 | 35200839 |
| X | 7934236 | 7936756 | | | X | 35219128 | 35221932 |
| X | 7953629 | 7958504 | | | X | 35249991 | 35252635 |
| X | 7976307 | 7983059 | | | X | 35301738 | 35304539 |
| X | 8049982 | 8051372 | | | X | 35314634 | 35318987 |
| X | 8057075 | 8058863 | | | X | 35328996 | 35332320 |
| X | 8071966 | 8073273 | | | X | 35337916 | 35339861 |
| X | 8118309 | 8118959 | | | X | 35384219 | 35386385 |
| X | 8154299 | 8156315 | | | X | 35426829 | 35430649 |
| X | 8160488 | 8164540 | | | X | 35469371 | 35470658 |
| X | 8167954 | 8168314 | | | X | 35480194 | 35484949 |
| X | 8193051 | 8201269 | | | X | 35490516 | 35494165 |
| X | 8208528 | 8216913 | | | X | 35523744 | 35525995 |
| X | 8240944 | 8243545 | | | X | 35537830 | 35540586 |
| X | 8305219 | 8311371 | | | X | 35553801 | 35554846 |
| X | 8314614 | 8317758 | | | X | 35587313 | 35593174 |
| X | 8359457 | 8360652 | | | X | 35606527 | 35607658 |
| X | 8392981 | 8397305 | | | X | 35664627 | 35665810 |
| X | 8397985 | 8399490 | | | X | 35666801 | 35673079 |
| X | 8402671 | 8407160 | | | X | 35678448 | 35680586 |
| X | 8414248 | 8416053 | | | X | 35701071 | 35703556 |
| X | 8449497 | 8452146 | | | X | 35759878 | 35761378 |
| X | 8473489 | 8475650 | | | X | 35846017 | 35848557 |
| X | 8496228 | 8497315 | | | X | 35953113 | 35954678 |
| X | 8526943 | 8527208 | | | X | 36023639 | 36033072 |
| X | 8548433 | 8550898 | | | X | 36121962 | 36129973 |
| X | 8560681 | 8561679 | | | X | 36141719 | 36147161 |
| X | 8578432 | 8580468 | | | X | 36182402 | 36185788 |
| X | 8583115 | 8583595 | | | X | 36235429 | 36241380 |
| X | 8598266 | 8599539 | | | X | 36248951 | 36252563 |
| X | 8600523 | 8603652 | | | X | 36291938 | 36296215 |
| X | 8612760 | 8614307 | | | X | 36304422 | 36306454 |
| X | 8643994 | 8645140 | | | X | 36317617 | 36328348 |
| X | 8660179 | 8662726 | | | X | 36334141 | 36337837 |
| X | 8669576 | 8677101 | | | X | 36349385 | 36350662 |

The chromosomal positon was obtained from UCSC genome browser (http://genome.ucsc.edu/) build 36.

APPENDIX D: Chromosome X
Page 5 of 73

| Chr | Start | End | Chr | Start | End |
|---|---|---|---|---|---|
| X | 8709931 | 8711989 | X | 36367545 | 36369025 |
| X | 8722086 | 8723844 | X | 36388897 | 36389287 |
| X | 8735770 | 8738414 | X | 36400184 | 36403747 |
| X | 8757257 | 8758638 | X | 36436748 | 36443566 |
| X | 8772806 | 8775910 | X | 36450691 | 36452876 |
| X | 8803779 | 8832669 | X | 36458173 | 36459380 |
| X | 8868757 | 8869166 | X | 36486742 | 36487477 |
| X | 8888987 | 8894228 | X | 36567088 | 36568598 |
| X | 8956643 | 8957421 | X | 36574615 | 36579083 |
| X | 8983146 | 8996541 | X | 36648188 | 36649198 |
| X | 9001444 | 9002160 | X | 36653966 | 36656325 |
| X | 9039055 | 9040595 | X | 36657597 | 36659912 |
| X | 9072280 | 9073586 | X | 36665192 | 36672742 |
| X | 9155514 | 9160899 | X | 36690459 | 36698092 |
| X | 9163356 | 9164472 | X | 36708996 | 36712095 |
| X | 9169141 | 9170631 | X | 36745182 | 36751864 |
| X | 9194962 | 9204098 | X | 36791637 | 36799679 |
| X | 9212891 | 9214166 | X | 36872887 | 36874472 |
| X | 9243113 | 9245559 | X | 36881370 | 36884707 |
| X | 9266603 | 9267908 | X | 36885430 | 36886870 |
| X | 9272013 | 9276851 | X | 36889503 | 36892298 |
| X | 9283880 | 9284841 | X | 36895586 | 36907101 |
| X | 9291079 | 9293643 | X | 36912197 | 36914512 |
| X | 9298532 | 9312579 | X | 36928813 | 36932117 |
| X | 9325817 | 9349098 | X | 36936355 | 36940118 |
| X | 9358738 | 9361555 | X | 36946570 | 36953259 |
| X | 9370290 | 9374196 | X | 36962195 | 36968792 |
| X | 9395338 | 9401857 | X | 37002240 | 37006636 |
| X | 9414127 | 9414607 | X | 37042424 | 37045248 |
| X | 9416177 | 9417519 | X | 37052552 | 37053200 |
| X | 9420820 | 9424878 | X | 37073666 | 37076314 |
| X | 9446371 | 9462407 | X | 37093023 | 37094681 |
| X | 9485344 | 9486704 | X | 37109976 | 37110811 |
| X | 9488641 | 9488981 | X | 37136221 | 37151729 |
| X | 9492331 | 9498146 | X | 37179650 | 37181748 |
| X | 9504258 | 9506614 | X | 37185616 | 37186422 |
| X | 9525885 | 9526895 | X | 37187268 | 37191048 |
| X | 9548528 | 9549286 | X | 37209000 | 37212822 |
| X | 9578719 | 9592041 | X | 37223255 | 37229413 |
| X | 9607577 | 9648346 | X | 37235513 | 37237808 |
| X | 9659509 | 9668305 | X | 37249156 | 37250931 |
| X | 9687380 | 9693517 | X | 37285438 | 37290297 |
| X | 9706845 | 9707822 | X | 37315618 | 37317092 |
| X | 9717064 | 9719512 | X | 37343900 | 37346609 |
| X | 9726345 | 9730772 | X | 37353967 | 37372106 |
| X | 9750967 | 9834103 | X | 37405787 | 37409644 |
| X | 9860003 | 9875458 | X | 37430155 | 37434840 |
| X | 9886758 | 9889584 | X | 37466121 | 37470776 |
| X | 9919848 | 9933794 | X | 37480685 | 37485187 |
| X | 9940435 | 9947810 | X | 37489363 | 37491588 |
| X | 9965227 | 9966609 | X | 37497264 | 37503547 |
| X | 9971457 | 9971931 | X | 37520203 | 37521119 |
| X | 9990210 | 9995011 | X | 37537920 | 37544186 |
| X | 10007099 | 10011263 | X | 37553885 | 37556421 |
| X | 10029820 | 10068009 | X | 37566873 | 37574336 |

The chromosomal positon was obtained from UCSC genome browser (http://genome.ucsc.edu/) build 36.

APPENDIX D: Chromosome X
Page 6 of 73

| Chr | Start | End | Chr | Start | End |
|---|---|---|---|---|---|
| X | 10074462 | 10074944 | X | 37587475 | 37592016 |
| X | 10088808 | 10105633 | X | 37619038 | 37620022 |
| X | 10113646 | 10114642 | X | 37636638 | 37640429 |
| X | 10118631 | 10122507 | X | 37662853 | 37667522 |
| X | 10141453 | 10142124 | X | 37672665 | 37676980 |
| X | 10148164 | 10149254 | X | 37691942 | 37693602 |
| X | 10174116 | 10177171 | X | 37730132 | 37733010 |
| X | 10195887 | 10196827 | X | 37745684 | 37750878 |
| X | 10200993 | 10205874 | X | 37757931 | 37761685 |
| X | 10237477 | 10238498 | X | 37770590 | 37771651 |
| X | 10267664 | 10272158 | X | 37781184 | 37783164 |
| X | 10300773 | 10307581 | X | 37819655 | 37820260 |
| X | 10325890 | 10326393 | X | 37825272 | 37835188 |
| X | 10343289 | 10347898 | X | 37846373 | 37856034 |
| X | 10381513 | 10382306 | X | 37881748 | 37894542 |
| X | 10425824 | 10427274 | X | 37897722 | 37898968 |
| X | 10431339 | 10437908 | X | 37916192 | 37918390 |
| X | 10510186 | 10518396 | X | 37923691 | 37934014 |
| X | 10521605 | 10527098 | X | 37951749 | 37954538 |
| X | 10537614 | 10539211 | X | 37963117 | 37965622 |
| X | 10548010 | 10548520 | X | 37975915 | 37984539 |
| X | 10549311 | 10550366 | X | 38000248 | 38001622 |
| X | 10590998 | 10591960 | X | 38035382 | 38036993 |
| X | 10602381 | 10606033 | X | 38055866 | 38065066 |
| X | 10651293 | 10652469 | X | 38070716 | 38072005 |
| X | 10691069 | 10693877 | X | 38074539 | 38078703 |
| X | 10741713 | 10743963 | X | 38132356 | 38133466 |
| X | 10752589 | 10755709 | X | 38139037 | 38141495 |
| X | 10775162 | 10777116 | X | 38161543 | 38165395 |
| X | 10779637 | 10790005 | X | 38192527 | 38196856 |
| X | 10803175 | 10814220 | X | 38211175 | 38213190 |
| X | 10837440 | 10838707 | X | 38227872 | 38229535 |
| X | 10847632 | 10851336 | X | 38233696 | 38235736 |
| X | 10867002 | 10871439 | X | 38299671 | 38303919 |
| X | 10914059 | 10914907 | X | 38304636 | 38307297 |
| X | 10921224 | 10924813 | X | 38315436 | 38321637 |
| X | 11003896 | 11005651 | X | 38340599 | 38344798 |
| X | 11012062 | 11013332 | X | 38391437 | 38393356 |
| X | 11032431 | 11033810 | X | 38459751 | 38466517 |
| X | 11036754 | 11040001 | X | 38469411 | 38471385 |
| X | 11103961 | 11110263 | X | 38479570 | 38481491 |
| X | 11142428 | 11144324 | X | 38537842 | 38539089 |
| X | 11152967 | 11156194 | X | 38545227 | 38550434 |
| X | 11157596 | 11165620 | X | 38576961 | 38591748 |
| X | 11225374 | 11227104 | X | 38603427 | 38605712 |
| X | 11244086 | 11246263 | X | 38615768 | 38617210 |
| X | 11255099 | 11264339 | X | 38623515 | 38626446 |
| X | 11267310 | 11268471 | X | 38679540 | 38694664 |
| X | 11295979 | 11297982 | X | 38699174 | 38701405 |
| X | 11326144 | 11332353 | X | 38719425 | 38722656 |
| X | 11348965 | 11352806 | X | 38742887 | 38747294 |
| X | 11363499 | 11364165 | X | 38776026 | 38777411 |
| X | 11385430 | 11387934 | X | 38805259 | 38805865 |
| X | 11400059 | 11402344 | X | 38826511 | 38828925 |
| X | 11404664 | 11408267 | X | 38861255 | 38861881 |

The chromosomal positon was obtained from UCSC genome browser (http://genome.ucsc.edu/) build 36.

APPENDIX D: Chromosome X
Page 7 of 73

| Chr | Start | End | | Chr | Start | End |
|---|---|---|---|---|---|---|
| X | 11417333 | 11421481 | | X | 38896815 | 38899150 |
| X | 11435668 | 11436768 | | X | 38903208 | 38908205 |
| X | 11451674 | 11461356 | | X | 38942729 | 38949055 |
| X | 11472312 | 11475819 | | X | 38963091 | 38967285 |
| X | 11488592 | 11489527 | | X | 38986920 | 38990099 |
| X | 11507958 | 11524997 | | X | 39048645 | 39052332 |
| X | 11538834 | 11542777 | | X | 39140912 | 39144522 |
| X | 11568086 | 11568985 | | X | 39159979 | 39166280 |
| X | 11577213 | 11590395 | | X | 39175399 | 39177860 |
| X | 11592519 | 11594590 | | X | 39183022 | 39190799 |
| X | 11613520 | 11615993 | | X | 39220037 | 39222258 |
| X | 11632064 | 11635015 | | X | 39228397 | 39229851 |
| X | 11642368 | 11644072 | | X | 39238681 | 39240777 |
| X | 11652871 | 11664975 | | X | 39252154 | 39257758 |
| X | 11673862 | 11680766 | | X | 39258252 | 39264015 |
| X | 11683650 | 11689476 | | X | 39279379 | 39295052 |
| X | 11753575 | 11758966 | | X | 39320126 | 39326165 |
| X | 11778611 | 11779541 | | X | 39352671 | 39357909 |
| X | 11811416 | 11814581 | | X | 39374629 | 39377980 |
| X | 11894614 | 11903969 | | X | 39385520 | 39390204 |
| X | 11920152 | 11927380 | | X | 39391028 | 39393740 |
| X | 11948115 | 11958947 | | X | 39422228 | 39423462 |
| X | 11972335 | 11975011 | | X | 39434776 | 39440397 |
| X | 12068311 | 12072084 | | X | 39461179 | 39463433 |
| X | 12090027 | 12091247 | | X | 39474477 | 39476249 |
| X | 12109610 | 12110777 | | X | 39497321 | 39511883 |
| X | 12114775 | 12117451 | | X | 39522711 | 39524554 |
| X | 12170240 | 12171241 | | X | 39537027 | 39539470 |
| X | 12215296 | 12217961 | | X | 39544349 | 39553684 |
| X | 12248197 | 12253350 | | X | 39557202 | 39566698 |
| X | 12287898 | 12291773 | | X | 39574493 | 39575230 |
| X | 12327053 | 12336834 | | X | 39576445 | 39578040 |
| X | 12343634 | 12350685 | | X | 39584246 | 39585826 |
| X | 12381274 | 12394875 | | X | 39595986 | 39604333 |
| X | 12395597 | 12395848 | | X | 39609192 | 39617509 |
| X | 12397917 | 12398933 | | X | 39639734 | 39654988 |
| X | 12412521 | 12413210 | | X | 39659438 | 39660373 |
| X | 12452813 | 12453781 | | X | 39661772 | 39664333 |
| X | 12510972 | 12512421 | | X | 39672211 | 39675041 |
| X | 12541423 | 12543131 | | X | 39710901 | 39715553 |
| X | 12607135 | 12610466 | | X | 39720958 | 39721481 |
| X | 12615605 | 12616985 | | X | 39723654 | 39729495 |
| X | 12635618 | 12647294 | | X | 39775384 | 39778582 |
| X | 12659806 | 12663452 | | X | 39805415 | 39819461 |
| X | 12694500 | 12701462 | | X | 39835493 | 39842756 |
| X | 12712140 | 12713146 | | X | 39844653 | 39845720 |
| X | 12718944 | 12720999 | | X | 39852357 | 39902950 |
| X | 12743169 | 12747914 | | X | 39910335 | 39912417 |
| X | 12754201 | 12754886 | | X | 39930057 | 39934783 |
| X | 12759815 | 12767165 | | X | 39946790 | 39956374 |
| X | 12774915 | 12785208 | | X | 39976153 | 39979131 |
| X | 12829678 | 12831843 | | X | 40003737 | 40008020 |
| X | 12839439 | 12841821 | | X | 40025742 | 40026572 |
| X | 12851952 | 12853916 | | X | 40037250 | 40057742 |
| X | 12868769 | 12872344 | | X | 40067683 | 40069615 |

The chromosomal positon was obtained from UCSC genome browser (http://genome.ucsc.edu/) build 36.

APPENDIX D: Chromosome X

Page 8 of 73

| Chr | Start | End | Chr | Start | End |
|---|---|---|---|---|---|
| X | 12884440 | 12887168 | X | 40070959 | 40073495 |
| X | 12887552 | 12892583 | X | 40081611 | 40088215 |
| X | 12901027 | 12904826 | X | 40101861 | 40108093 |
| X | 12967621 | 12973158 | X | 40243013 | 40245253 |
| X | 13002887 | 13004104 | X | 40261995 | 40265842 |
| X | 13029876 | 13030059 | X | 40304177 | 40307091 |
| X | 13043783 | 13049623 | X | 40320204 | 40328224 |
| X | 13121302 | 13122576 | X | 40366309 | 40368565 |
| X | 13129787 | 13134129 | X | 40375284 | 40377886 |
| X | 13149283 | 13151626 | X | 40386011 | 40386741 |
| X | 13173620 | 13174494 | X | 40474258 | 40474453 |
| X | 13202062 | 13203656 | X | 40480619 | 40482764 |
| X | 13204459 | 13207731 | X | 40539376 | 40546122 |
| X | 13229433 | 13233285 | X | 40569784 | 40570085 |
| X | 13239969 | 13243980 | X | 40574450 | 40581205 |
| X | 13246753 | 13254123 | X | 40584371 | 40585662 |
| X | 13305795 | 13307861 | X | 40599935 | 40600482 |
| X | 13343227 | 13344280 | X | 40608663 | 40611064 |
| X | 13367285 | 13370883 | X | 40614456 | 40614964 |
| X | 13392462 | 13394746 | X | 40674686 | 40683133 |
| X | 13473544 | 13475085 | X | 40756704 | 40758440 |
| X | 13497978 | 13499004 | X | 40771621 | 40776914 |
| X | 13552938 | 13555912 | X | 40779978 | 40781057 |
| X | 13617328 | 13620398 | X | 40820670 | 40821341 |
| X | 13683462 | 13688312 | X | 40830295 | 40835272 |
| X | 13694465 | 13694945 | X | 40840018 | 40840603 |
| X | 13707868 | 13727517 | X | 40950800 | 40952624 |
| X | 13745129 | 13755042 | X | 40981737 | 41000049 |
| X | 13762890 | 13763622 | X | 41010669 | 41014085 |
| X | 13773790 | 13775230 | X | 41019107 | 41030803 |
| X | 13803734 | 13815184 | X | 41046089 | 41048560 |
| X | 13831129 | 13832743 | X | 41055102 | 41056603 |
| X | 13865126 | 13865854 | X | 41065694 | 41074909 |
| X | 13877105 | 13885565 | X | 41095348 | 41111864 |
| X | 13891211 | 13895737 | X | 41124806 | 41141080 |
| X | 13909742 | 13913349 | X | 41151142 | 41156434 |
| X | 13961666 | 13962091 | X | 41186935 | 41193547 |
| X | 13966520 | 13977451 | X | 41196127 | 41200660 |
| X | 14009095 | 14018619 | X | 41214977 | 41226152 |
| X | 14045718 | 14049307 | X | 41236344 | 41240475 |
| X | 14091950 | 14096123 | X | 41251807 | 41253206 |
| X | 14143023 | 14168309 | X | 41334320 | 41337098 |
| X | 14172698 | 14174583 | X | 41384296 | 41390277 |
| X | 14184590 | 14189219 | X | 41452938 | 41454654 |
| X | 14193476 | 14194618 | X | 41464376 | 41469266 |
| X | 14202073 | 14212495 | X | 41552632 | 41553067 |
| X | 14245949 | 14248136 | X | 41609072 | 41612992 |
| X | 14254572 | 14258515 | X | 41622037 | 41623365 |
| X | 14263956 | 14266436 | X | 41626069 | 41644446 |
| X | 14270163 | 14272292 | X | 41666540 | 41669210 |
| X | 14278488 | 14284621 | X | 41690054 | 41695943 |
| X | 14309139 | 14325049 | X | 41721920 | 41728005 |
| X | 14354487 | 14356914 | X | 41729139 | 41729964 |
| X | 14360078 | 14363478 | X | 41764797 | 41766899 |
| X | 14380588 | 14383359 | X | 41774879 | 41778161 |

The chromosomal positon was obtained from UCSC genome browser (http://genome.ucsc.edu/) build 36.

APPENDIX D: Chromosome X
Page 9 of 73

| Chr | Start | End | | | Chr | Start | End |
|---|---|---|---|---|---|---|---|
| X | 14394873 | 14428363 | | | X | 41815357 | 41818652 |
| X | 14464095 | 14465519 | | | X | 41847579 | 41856344 |
| X | 14468864 | 14469139 | | | X | 41869474 | 41873655 |
| X | 14474819 | 14476706 | | | X | 41909881 | 41910146 |
| X | 14480124 | 14483179 | | | X | 41959579 | 41965635 |
| X | 14506814 | 14508606 | | | X | 42004681 | 42009266 |
| X | 14522726 | 14603708 | | | X | 42020698 | 42022284 |
| X | 14610550 | 14617396 | | | X | 42042954 | 42047297 |
| X | 14620505 | 14624071 | | | X | 42062622 | 42064567 |
| X | 14629384 | 14656705 | | | X | 42073028 | 42074810 |
| X | 14666174 | 14680162 | | | X | 42097471 | 42098035 |
| X | 14709585 | 14720230 | | | X | 42121111 | 42123425 |
| X | 14722457 | 14728142 | | | X | 42146295 | 42151158 |
| X | 14734402 | 14747180 | | | X | 42185623 | 42193371 |
| X | 14800893 | 14802049 | | | X | 42220975 | 42221884 |
| X | 14847756 | 14849055 | | | X | 42236207 | 42241230 |
| X | 14869136 | 14875368 | | | X | 42267709 | 42269071 |
| X | 14906995 | 14909238 | | | X | 42272528 | 42278644 |
| X | 14947801 | 14948796 | | | X | 42322677 | 42326305 |
| X | 14971415 | 14973098 | | | X | 42346384 | 42348639 |
| X | 15023248 | 15026279 | | | X | 42363824 | 42365933 |
| X | 15048157 | 15050720 | | | X | 42371040 | 42373227 |
| X | 15070600 | 15071508 | | | X | 42436555 | 42437867 |
| X | 15090521 | 15091066 | | | X | 42454474 | 42458967 |
| X | 15093918 | 15103544 | | | X | 42484240 | 42493996 |
| X | 15114905 | 15116340 | | | X | 42500458 | 42503896 |
| X | 15152636 | 15153581 | | | X | 42506796 | 42512663 |
| X | 15162246 | 15166312 | | | X | 42522101 | 42523277 |
| X | 15193256 | 15197693 | | | X | 42539312 | 42543013 |
| X | 15250751 | 15253053 | | | X | 42600093 | 42627995 |
| X | 15261352 | 15265734 | | | X | 42664414 | 42664654 |
| X | 15281186 | 15282449 | | | X | 42684869 | 42688212 |
| X | 15364805 | 15372300 | | | X | 42705802 | 42706796 |
| X | 15410160 | 15413799 | | | X | 42716308 | 42725097 |
| X | 15441239 | 15448694 | | | X | 42725954 | 42728154 |
| X | 15460788 | 15469054 | | | X | 42729524 | 42733239 |
| X | 15471184 | 15472754 | | | X | 42738305 | 42741120 |
| X | 15479643 | 15482008 | | | X | 42785439 | 42786641 |
| X | 15517766 | 15520319 | | | X | 42851868 | 42868783 |
| X | 15527379 | 15531983 | | | X | 42881797 | 42887652 |
| X | 15563392 | 15567411 | | | X | 42902806 | 42909920 |
| X | 15574351 | 15574956 | | | X | 42921841 | 42926879 |
| X | 15581298 | 15583573 | | | X | 42972497 | 42976854 |
| X | 15606414 | 15607335 | | | X | 43022364 | 43023719 |
| X | 15615274 | 15616475 | | | X | 43045298 | 43064205 |
| X | 15630786 | 15631326 | | | X | 43104395 | 43109776 |
| X | 15646318 | 15652098 | | | X | 43156936 | 43162261 |
| X | 15667639 | 15678762 | | | X | 43168374 | 43172823 |
| X | 15708204 | 15709419 | | | X | 43206637 | 43211260 |
| X | 15744368 | 15745734 | | | X | 43224226 | 43225771 |
| X | 15766615 | 15767319 | | | X | 43229712 | 43231439 |
| X | 15777697 | 15778698 | | | X | 43249204 | 43252369 |
| X | 15847526 | 15849394 | | | X | 43263567 | 43266414 |
| X | 15890296 | 15892636 | | | X | 43271600 | 43274755 |
| X | 15912256 | 15914093 | | | X | 43298077 | 43305135 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 15935537 | 15939605 | X | 43329506 | 43330929 |
| X | 15970001 | 15980220 | X | 43375025 | 43378123 |
| X | 16007259 | 16009251 | X | 43396591 | 43401001 |
| X | 16016670 | 16019113 | X | 43405295 | 43409840 |
| X | 16058315 | 16066118 | X | 43459779 | 43465049 |
| X | 16069430 | 16070193 | X | 43490256 | 43491028 |
| X | 16074418 | 16076381 | X | 43501173 | 43505575 |
| X | 16095406 | 16101147 | X | 43520652 | 43521690 |
| X | 16146255 | 16149813 | X | 43541919 | 43543788 |
| X | 16180629 | 16181679 | X | 43557194 | 43557794 |
| X | 16232509 | 16233362 | X | 43563749 | 43564276 |
| X | 16234769 | 16236158 | X | 43576421 | 43584314 |
| X | 16302847 | 16304640 | X | 43674554 | 43680219 |
| X | 16390304 | 16391635 | X | 43707931 | 43708821 |
| X | 16564600 | 16569028 | X | 43778541 | 43780149 |
| X | 16581816 | 16585504 | X | 43840378 | 43841768 |
| X | 16612246 | 16614126 | X | 43849040 | 43851643 |
| X | 16625360 | 16633360 | X | 43854880 | 43859416 |
| X | 16639737 | 16650692 | X | 43865060 | 43866627 |
| X | 16664413 | 16671883 | X | 43901320 | 43904259 |
| X | 16675280 | 16679650 | X | 43911273 | 43912765 |
| X | 16707866 | 16712770 | X | 43915250 | 43916126 |
| X | 16726444 | 16729930 | X | 43947073 | 43949094 |
| X | 16749124 | 16755448 | X | 43992565 | 43994606 |
| X | 16766040 | 16770128 | X | 44030100 | 44034295 |
| X | 16794708 | 16799993 | X | 44058977 | 44059829 |
| X | 16807182 | 16811470 | X | 44088355 | 44089267 |
| X | 16815408 | 16818828 | X | 44171783 | 44182018 |
| X | 16834293 | 16834742 | X | 44219203 | 44222406 |
| X | 16841966 | 16843292 | X | 44246312 | 44249908 |
| X | 16941918 | 16944857 | X | 44253745 | 44262443 |
| X | 16960851 | 16963632 | X | 44288336 | 44290162 |
| X | 16978635 | 16981309 | X | 44299056 | 44300142 |
| X | 16997713 | 17003358 | X | 44310891 | 44318407 |
| X | 17011033 | 17013530 | X | 44342678 | 44344955 |
| X | 17032180 | 17033904 | X | 44355922 | 44358557 |
| X | 17077260 | 17079693 | X | 44377681 | 44379836 |
| X | 17080058 | 17090114 | X | 44388957 | 44391981 |
| X | 17103665 | 17106644 | X | 44418308 | 44425470 |
| X | 17111927 | 17113658 | X | 44460072 | 44464906 |
| X | 17162803 | 17163141 | X | 44492731 | 44495246 |
| X | 17204461 | 17205936 | X | 44519720 | 44556046 |
| X | 17214429 | 17220448 | X | 44574436 | 44594873 |
| X | 17237627 | 17239792 | X | 44617114 | 44618079 |
| X | 17278188 | 17282477 | X | 44618710 | 44619040 |
| X | 17287433 | 17288819 | X | 44664396 | 44664997 |
| X | 17290137 | 17291046 | X | 44684096 | 44687368 |
| X | 17302935 | 17309380 | X | 44714834 | 44717803 |
| X | 17317108 | 17320168 | X | 44744008 | 44750297 |
| X | 17322664 | 17323592 | X | 44766471 | 44769223 |
| X | 17334045 | 17339512 | X | 44788561 | 44790024 |
| X | 17349236 | 17352894 | X | 44842627 | 44847331 |
| X | 17363776 | 17366109 | X | 44888980 | 44896657 |
| X | 17388155 | 17390116 | X | 44907132 | 44908568 |
| X | 17404190 | 17415218 | X | 44910250 | 44916052 |

The chromosomal positon was obtained from UCSC genome browser (http://genome.ucsc.edu/) build 36.

APPENDIX D: Chromosome X
Page 11 of 73

| Chr | Start | End | | | Chr | Start | End |
|---|---|---|---|---|---|---|---|
| X | 17431934 | 17441684 | | | X | 44932116 | 44933996 |
| X | 17444754 | 17445514 | | | X | 44975072 | 44976302 |
| X | 17453302 | 17455944 | | | X | 45054657 | 45056524 |
| X | 17515985 | 17521193 | | | X | 45058879 | 45063793 |
| X | 17539469 | 17542515 | | | X | 45122222 | 45125929 |
| X | 17558326 | 17569256 | | | X | 45178511 | 45181457 |
| X | 17583607 | 17585027 | | | X | 45190672 | 45195356 |
| X | 17589088 | 17590349 | | | X | 45214758 | 45216117 |
| X | 17594856 | 17600135 | | | X | 45253429 | 45257808 |
| X | 17617390 | 17619271 | | | X | 45285714 | 45286292 |
| X | 17624116 | 17629366 | | | X | 45286691 | 45300445 |
| X | 17654221 | 17655837 | | | X | 45306012 | 45306407 |
| X | 17657031 | 17659074 | | | X | 45365674 | 45367297 |
| X | 17663740 | 17665925 | | | X | 45376128 | 45377600 |
| X | 17693194 | 17706000 | | | X | 45393020 | 45394934 |
| X | 17719349 | 17722639 | | | X | 45412233 | 45413517 |
| X | 17729174 | 17734171 | | | X | 45440694 | 45445606 |
| X | 17764968 | 17768593 | | | X | 45472035 | 45472843 |
| X | 17782325 | 17789348 | | | X | 45507029 | 45511339 |
| X | 17810860 | 17812270 | | | X | 45589272 | 45597323 |
| X | 17825266 | 17826616 | | | X | 45616100 | 45618464 |
| X | 17832413 | 17836301 | | | X | 45626330 | 45630403 |
| X | 17858433 | 17860300 | | | X | 45644037 | 45644791 |
| X | 17879545 | 17881198 | | | X | 45680879 | 45683388 |
| X | 17883781 | 17885403 | | | X | 45842909 | 45848048 |
| X | 17891158 | 17894325 | | | X | 45863300 | 45865606 |
| X | 17927398 | 17935174 | | | X | 45883121 | 45886297 |
| X | 17952701 | 17958245 | | | X | 45898931 | 45907510 |
| X | 17960986 | 17973945 | | | X | 45927494 | 45928931 |
| X | 17988767 | 17994092 | | | X | 45936031 | 45939890 |
| X | 18049452 | 18051252 | | | X | 45951350 | 45951894 |
| X | 18092936 | 18094552 | | | X | 45960140 | 45965330 |
| X | 18103426 | 18106946 | | | X | 45978775 | 45980343 |
| X | 18133265 | 18134909 | | | X | 46000249 | 46001311 |
| X | 18143107 | 18162744 | | | X | 46032377 | 46033242 |
| X | 18173486 | 18174121 | | | X | 46037237 | 46040983 |
| X | 18187016 | 18189448 | | | X | 46051424 | 46052819 |
| X | 18230911 | 18232351 | | | X | 46070739 | 46071935 |
| X | 18277239 | 18279007 | | | X | 46088268 | 46090036 |
| X | 18281826 | 18283127 | | | X | 46183352 | 46186357 |
| X | 18288837 | 18293625 | | | X | 46191487 | 46192012 |
| X | 18321485 | 18327945 | | | X | 46200475 | 46201155 |
| X | 18349315 | 18354393 | | | X | 46230235 | 46234682 |
| X | 18363944 | 18366485 | | | X | 46272807 | 46273743 |
| X | 18427158 | 18435217 | | | X | 46288593 | 46293027 |
| X | 18456252 | 18459674 | | | X | 46305315 | 46306466 |
| X | 18477649 | 18478893 | | | X | 46317812 | 46321836 |
| X | 18506035 | 18513582 | | | X | 46332235 | 46334461 |
| X | 18559423 | 18561203 | | | X | 46351717 | 46353404 |
| X | 18569097 | 18574638 | | | X | 46367529 | 46368281 |
| X | 18593494 | 18606875 | | | X | 46390090 | 46393276 |
| X | 18652771 | 18653752 | | | X | 46397861 | 46399683 |
| X | 18656794 | 18659593 | | | X | 46491550 | 46494605 |
| X | 18671312 | 18672562 | | | X | 46502426 | 46503901 |
| X | 18689445 | 18690407 | | | X | 46534160 | 46536224 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 18691947 | 18693717 | X | 46540577 | 46542267 |
| X | 18697878 | 18698116 | X | 46549595 | 46550228 |
| X | 18708219 | 18709437 | X | 46580986 | 46581992 |
| X | 18743514 | 18744494 | X | 46656279 | 46658509 |
| X | 18758236 | 18761457 | X | 46700458 | 46709415 |
| X | 18786682 | 18836030 | X | 46716377 | 46718785 |
| X | 18883595 | 18888341 | X | 46728572 | 46732092 |
| X | 18889959 | 18892055 | X | 46738407 | 46738858 |
| X | 18892643 | 18895446 | X | 46744283 | 46750230 |
| X | 18908311 | 18908562 | X | 46751741 | 46753052 |
| X | 18911772 | 18913216 | X | 46765002 | 46767280 |
| X | 18930462 | 18932797 | X | 46773168 | 46773809 |
| X | 18958604 | 18967708 | X | 46785162 | 46788317 |
| X | 18972118 | 18972715 | X | 46822477 | 46823652 |
| X | 18998391 | 19000903 | X | 46835633 | 46836662 |
| X | 19023035 | 19025912 | X | 46869366 | 46874563 |
| X | 19034206 | 19047136 | X | 46888097 | 46890103 |
| X | 19049871 | 19051926 | X | 46892424 | 46893306 |
| X | 19079426 | 19079714 | X | 46899174 | 46995350 |
| X | 19087620 | 19089324 | X | 47017741 | 47067656 |
| X | 19101510 | 19104259 | X | 47081433 | 47084915 |
| X | 19123093 | 19125232 | X | 47095389 | 47131916 |
| X | 19164454 | 19168411 | X | 47154503 | 47156943 |
| X | 19253233 | 19256882 | X | 47192248 | 47193682 |
| X | 19258282 | 19261017 | X | 47206804 | 47212119 |
| X | 19263306 | 19263850 | X | 47226024 | 47228770 |
| X | 19272527 | 19273679 | X | 47247688 | 47250114 |
| X | 19296102 | 19316787 | X | 47267782 | 47271040 |
| X | 19325774 | 19327113 | X | 47304479 | 47335199 |
| X | 19339431 | 19341777 | X | 47349664 | 47361198 |
| X | 19370503 | 19376254 | X | 47362852 | 47396145 |
| X | 19418365 | 19425101 | X | 47402649 | 47407123 |
| X | 19433297 | 19443887 | X | 47426660 | 47428049 |
| X | 19457644 | 19462216 | X | 47432062 | 47433704 |
| X | 19469997 | 19475237 | X | 47462676 | 47471344 |
| X | 19480698 | 19481094 | X | 47484552 | 47485256 |
| X | 19482894 | 19485401 | X | 47547913 | 47552492 |
| X | 19492547 | 19493046 | X | 47580826 | 47581690 |
| X | 19510220 | 19510551 | X | 47606472 | 47607012 |
| X | 19516040 | 19518567 | X | 47621021 | 47626460 |
| X | 19519108 | 19522874 | X | 47634750 | 47637594 |
| X | 19530949 | 19533744 | X | 47678410 | 47678847 |
| X | 19567221 | 19567919 | X | 47698168 | 47704765 |
| X | 19572079 | 19573863 | X | 47736714 | 47737053 |
| X | 19610790 | 19614123 | X | 47748055 | 47776801 |
| X | 19627078 | 19628003 | X | 47788290 | 47792019 |
| X | 19649529 | 19651373 | X | 47813895 | 47819388 |
| X | 19670900 | 19681472 | X | 47823150 | 47826931 |
| X | 19687435 | 19689014 | X | 47833719 | 47835473 |
| X | 19695949 | 19699152 | X | 47847404 | 47933383 |
| X | 19764020 | 19765276 | X | 47939714 | 47943232 |
| X | 19779457 | 19783383 | X | 47957921 | 47958875 |
| X | 19796960 | 19797462 | X | 47961200 | 47963609 |
| X | 19812554 | 19814033 | X | 47979537 | 48259626 |
| X | 19814617 | 19817927 | X | 48264772 | 48267354 |

The chromosomal positon was obtained from UCSC genome browser (http://genome.ucsc.edu/) build 36.

APPENDIX D: Chromosome X
Page 13 of 73

| Chr | Start | End | Chr | Start | End |
|---|---|---|---|---|---|
| X | 19878209 | 19882098 | X | 48276708 | 48357220 |
| X | 19892563 | 19895051 | X | 48372268 | 48376133 |
| X | 19928241 | 19935143 | X | 48385715 | 48389613 |
| X | 19983088 | 19985022 | X | 48399206 | 48404109 |
| X | 19991283 | 19994244 | X | 48411337 | 48451761 |
| X | 20025073 | 20026003 | X | 48475007 | 48482555 |
| X | 20031662 | 20034042 | X | 48485318 | 48487072 |
| X | 20043483 | 20050861 | X | 48502180 | 48506726 |
| X | 20068577 | 20073706 | X | 48515171 | 48521095 |
| X | 20078786 | 20084169 | X | 48528868 | 48578289 |
| X | 20193357 | 20197330 | X | 48589015 | 48594864 |
| X | 20224727 | 20225777 | X | 48625977 | 48668217 |
| X | 20233551 | 20234620 | X | 48679237 | 48682596 |
| X | 20248497 | 20252922 | X | 48698973 | 49258958 |
| X | 20267246 | 20270367 | X | 49270960 | 49279364 |
| X | 20278506 | 20280458 | X | 49344999 | 49347469 |
| X | 20290131 | 20290775 | X | 49399388 | 49405443 |
| X | 20355501 | 20360287 | X | 49414414 | 49419493 |
| X | 20386725 | 20388229 | X | 49473005 | 49474572 |
| X | 20425982 | 20429716 | X | 49479520 | 49481099 |
| X | 20441045 | 20443085 | X | 49496555 | 49498500 |
| X | 20452167 | 20454254 | X | 49529436 | 49533015 |
| X | 20464780 | 20465426 | X | 49573364 | 49576412 |
| X | 20503627 | 20508206 | X | 49581582 | 49601462 |
| X | 20531417 | 20534549 | X | 49612528 | 49628118 |
| X | 20553616 | 20557630 | X | 49636035 | 49637024 |
| X | 20565975 | 20584519 | X | 49643709 | 49644957 |
| X | 20586710 | 20593966 | X | 49666223 | 49667064 |
| X | 20606087 | 20645381 | X | 49680410 | 49688921 |
| X | 20659998 | 20695550 | X | 49694283 | 49694740 |
| X | 20699955 | 20706454 | X | 49705598 | 49709108 |
| X | 20734542 | 20750631 | X | 49720486 | 49722674 |
| X | 20753270 | 20753975 | X | 49731260 | 49732662 |
| X | 20781742 | 20783191 | X | 49735409 | 49735740 |
| X | 20820953 | 20826974 | X | 49748311 | 49754841 |
| X | 20843250 | 20844573 | X | 49817574 | 49819395 |
| X | 20847651 | 20878254 | X | 49833053 | 49836989 |
| X | 20902964 | 20918557 | X | 49850991 | 49854147 |
| X | 20947184 | 20948545 | X | 49856351 | 49858349 |
| X | 20998762 | 21010833 | X | 50095888 | 50098092 |
| X | 21028694 | 21052065 | X | 50098505 | 50100083 |
| X | 21071563 | 21077099 | X | 50103988 | 50105950 |
| X | 21095191 | 21096076 | X | 50132001 | 50138345 |
| X | 21106669 | 21124188 | X | 50145615 | 50163120 |
| X | 21132067 | 21134043 | X | 50178555 | 50215296 |
| X | 21152893 | 21190503 | X | 50228070 | 50230640 |
| X | 21198513 | 21202974 | X | 50254104 | 50255255 |
| X | 21216841 | 21219383 | X | 50262669 | 50266226 |
| X | 21276582 | 21292347 | X | 50279029 | 50279809 |
| X | 21300963 | 21303334 | X | 50283376 | 50285855 |
| X | 21362144 | 21362768 | X | 50308137 | 50311204 |
| X | 21436457 | 21444017 | X | 50315739 | 50317679 |
| X | 21489086 | 21489938 | X | 50336204 | 50336561 |
| X | 21498051 | 21504122 | X | 50359089 | 50359797 |
| X | 21525744 | 21527833 | X | 50362791 | 50364505 |

The chromosomal positon was obtained from UCSC genome browser (http://genome.ucsc.edu/) build 36.

APPENDIX D: Chromosome X
Page 14 of 73

| Chr | Start | End | Chr | Start | End |
|---|---|---|---|---|---|
| X | 21550018 | 21552301 | X | 50401246 | 50404190 |
| X | 21576649 | 21581090 | X | 50406810 | 50438410 |
| X | 21583834 | 21589228 | X | 50441789 | 50444881 |
| X | 21660646 | 21662294 | X | 50450920 | 50471211 |
| X | 21669755 | 21684835 | X | 50506903 | 50509252 |
| X | 21728292 | 21732013 | X | 50513066 | 50530654 |
| X | 21745417 | 21746672 | X | 50550786 | 50555862 |
| X | 21766863 | 21769137 | X | 50557613 | 50558524 |
| X | 21771032 | 21775316 | X | 50567995 | 50571465 |
| X | 21783947 | 21785520 | X | 50572668 | 50574274 |
| X | 21830526 | 21834227 | X | 50574999 | 50576639 |
| X | 21861020 | 21875307 | X | 50582992 | 50590520 |
| X | 21885057 | 21887049 | X | 50599236 | 50601052 |
| X | 21899459 | 21901947 | X | 50630449 | 50632700 |
| X | 21912537 | 21913776 | X | 50638360 | 50647042 |
| X | 21948651 | 21951060 | X | 50665096 | 50665196 |
| X | 21962323 | 21969013 | X | 50686846 | 50688208 |
| X | 21984902 | 21988841 | X | 50707775 | 50709788 |
| X | 21997997 | 21999063 | X | 50748436 | 50753632 |
| X | 22013866 | 22014553 | X | 50785167 | 50786013 |
| X | 22062901 | 22064672 | X | 50786332 | 50788853 |
| X | 22089505 | 22092535 | X | 50814889 | 50817369 |
| X | 22121807 | 22123013 | X | 50837205 | 50842480 |
| X | 22124879 | 22125385 | X | 50845405 | 50846821 |
| X | 22137129 | 22137421 | X | 50853858 | 50854883 |
| X | 22154414 | 22156336 | X | 50864165 | 50868119 |
| X | 22219554 | 22219779 | X | 50894658 | 50902795 |
| X | 22234433 | 22236392 | X | 50919012 | 50920702 |
| X | 22244235 | 22247509 | X | 50924442 | 50924985 |
| X | 22255781 | 22260167 | X | 50944820 | 50946713 |
| X | 22267318 | 22270429 | X | 50978052 | 50981635 |
| X | 22276968 | 22279462 | X | 50992621 | 50994769 |
| X | 22290461 | 22292665 | X | 51015129 | 51033370 |
| X | 22300468 | 22302236 | X | 51038561 | 51044728 |
| X | 22326223 | 22328086 | X | 51050669 | 51057763 |
| X | 22372849 | 22374719 | X | 51079953 | 51089354 |
| X | 22383575 | 22383681 | X | 51091017 | 51093272 |
| X | 22397541 | 22400438 | X | 51106800 | 51116638 |
| X | 22423077 | 22427509 | X | 51164811 | 51168021 |
| X | 22441098 | 22447052 | X | 51172179 | 51172831 |
| X | 22454787 | 22464508 | X | 51177585 | 51181471 |
| X | 22483676 | 22488000 | X | 51228960 | 51230056 |
| X | 22506308 | 22508913 | X | 51254689 | 51258862 |
| X | 22518645 | 22520365 | X | 51277772 | 51278462 |
| X | 22545213 | 22546280 | X | 51363286 | 51370609 |
| X | 22555439 | 22555541 | X | 51376983 | 51378896 |
| X | 22561091 | 22562079 | X | 51400285 | 51401873 |
| X | 22569239 | 22569907 | X | 51402897 | 51410758 |
| X | 22586452 | 22591042 | X | 51455594 | 51459232 |
| X | 22603050 | 22603572 | X | 51508434 | 51512898 |
| X | 22611145 | 22612240 | X | 51568712 | 51569562 |
| X | 22673653 | 22677135 | X | 51589071 | 51589661 |
| X | 22699688 | 22701782 | X | 51592830 | 51594533 |
| X | 22770937 | 22773052 | X | 51623976 | 51624698 |
| X | 22785232 | 22786024 | X | 51637945 | 51639988 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 22806911 | 22808518 | X | 51652992 | 51657582 |
| X | 22817006 | 22818998 | X | 51680438 | 51683404 |
| X | 22822194 | 22825447 | X | 51734900 | 51735633 |
| X | 22859545 | 22864870 | X | 51776826 | 51777426 |
| X | 22903870 | 22904979 | X | 51777701 | 51794462 |
| X | 22926559 | 22928569 | X | 51900939 | 51903078 |
| X | 22965888 | 22969745 | X | 51992260 | 51993749 |
| X | 22990124 | 22991990 | X | 52005233 | 52005993 |
| X | 23008861 | 23011676 | X | 52010426 | 52014527 |
| X | 23042220 | 23047870 | X | 52069645 | 52081206 |
| X | 23065344 | 23066175 | X | 52089497 | 52090953 |
| X | 23072397 | 23072613 | X | 52608009 | 52609180 |
| X | 23077687 | 23080355 | X | 52622445 | 52623829 |
| X | 23118194 | 23118860 | X | 52628241 | 52629587 |
| X | 23211828 | 23212158 | X | 52629994 | 52631186 |
| X | 23228419 | 23231292 | X | 52639688 | 52639864 |
| X | 23237034 | 23239054 | X | 52658580 | 52670741 |
| X | 23242190 | 23243637 | X | 52679083 | 52690738 |
| X | 23261304 | 23263950 | X | 52698954 | 52840714 |
| X | 23277071 | 23283271 | X | 52851605 | 52855231 |
| X | 23294661 | 23296598 | X | 52912869 | 52913485 |
| X | 23298631 | 23303001 | X | 52915981 | 52919984 |
| X | 23335112 | 23337845 | X | 52920617 | 52968503 |
| X | 23391022 | 23394602 | X | 52980115 | 53022466 |
| X | 23479845 | 23480837 | X | 53027040 | 53029467 |
| X | 23483136 | 23483935 | X | 53034648 | 53041710 |
| X | 23501487 | 23506088 | X | 53045328 | 53046913 |
| X | 23544344 | 23544565 | X | 53067595 | 53070400 |
| X | 23595785 | 23598035 | X | 53072325 | 53075544 |
| X | 23653096 | 23656604 | X | 53094037 | 53103980 |
| X | 23670091 | 23673281 | X | 53117350 | 53140594 |
| X | 23688147 | 23690385 | X | 53160313 | 53161043 |
| X | 23693002 | 23696457 | X | 53163243 | 53165510 |
| X | 23723564 | 23726382 | X | 53189184 | 53189809 |
| X | 23731972 | 23737490 | X | 53202307 | 53209532 |
| X | 23747189 | 23750937 | X | 53217103 | 53219987 |
| X | 23768682 | 23772059 | X | 53239126 | 53244999 |
| X | 23834367 | 23836483 | X | 53248549 | 53251171 |
| X | 23844470 | 23854592 | X | 53262970 | 53264892 |
| X | 23859639 | 23865825 | X | 53278164 | 53283388 |
| X | 23868532 | 23871816 | X | 53296218 | 53297063 |
| X | 23881851 | 23883607 | X | 53300374 | 53317295 |
| X | 23891081 | 23907838 | X | 53325221 | 53343146 |
| X | 23931654 | 23940241 | X | 53355156 | 53387903 |
| X | 23952457 | 23981956 | X | 53407449 | 53413578 |
| X | 24035515 | 24041580 | X | 53424345 | 53428877 |
| X | 24048749 | 24050836 | X | 53438458 | 53441344 |
| X | 24052941 | 24064968 | X | 53447285 | 53449914 |
| X | 24130513 | 24139321 | X | 53469418 | 53478508 |
| X | 24186022 | 24186774 | X | 53482205 | 53489783 |
| X | 24197610 | 24198541 | X | 53502772 | 53517703 |
| X | 24201243 | 24205951 | X | 53577040 | 53577850 |
| X | 24239218 | 24247922 | X | 53587808 | 53593864 |
| X | 24255913 | 24257523 | X | 53608569 | 53608976 |
| X | 24288354 | 24291640 | X | 53638855 | 53644055 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 24325353 | 24328241 | X | 53651430 | 53654600 |
| X | 24352997 | 24355081 | X | 53671345 | 53671903 |
| X | 24371132 | 24373413 | X | 53675934 | 53678230 |
| X | 24373786 | 24376741 | X | 53688542 | 53689126 |
| X | 24392820 | 24394453 | X | 53692508 | 53694657 |
| X | 24395548 | 24396658 | X | 53726612 | 53733882 |
| X | 24445591 | 24451755 | X | 53739792 | 53740562 |
| X | 24490573 | 24491758 | X | 53750674 | 53752556 |
| X | 24555220 | 24556291 | X | 53754473 | 53757585 |
| X | 24575382 | 24576127 | X | 53759970 | 53761109 |
| X | 24621413 | 24622874 | X | 53764012 | 53766517 |
| X | 24694576 | 24699538 | X | 53799632 | 53806320 |
| X | 24748306 | 24750036 | X | 53844632 | 53852604 |
| X | 24751801 | 24754590 | X | 53856060 | 53858247 |
| X | 24754922 | 24756903 | X | 53939235 | 53941152 |
| X | 24764305 | 24769229 | X | 53962638 | 53963911 |
| X | 24788451 | 24791335 | X | 54042161 | 54045641 |
| X | 24799461 | 24806867 | X | 54086788 | 54089801 |
| X | 24824305 | 24831317 | X | 54111359 | 54116275 |
| X | 24860455 | 24863967 | X | 54152826 | 54153520 |
| X | 24888403 | 24893567 | X | 54203718 | 54206284 |
| X | 24904896 | 24911821 | X | 54256421 | 54259522 |
| X | 24927779 | 24929774 | X | 54336116 | 54336400 |
| X | 24930171 | 24935806 | X | 54400393 | 54402930 |
| X | 24936351 | 24937654 | X | 54410811 | 54411786 |
| X | 24941118 | 24949553 | X | 54423779 | 54424567 |
| X | 24956437 | 24959371 | X | 54454783 | 54459055 |
| X | 24967159 | 24970789 | X | 54481271 | 54514593 |
| X | 25003653 | 25004842 | X | 54524996 | 54548817 |
| X | 25034496 | 25034792 | X | 54564724 | 54566258 |
| X | 25080838 | 25081963 | X | 54572402 | 54574261 |
| X | 25082303 | 25082648 | X | 54590122 | 54595536 |
| X | 25098388 | 25100711 | X | 54603306 | 54608832 |
| X | 25128957 | 25131194 | X | 54612244 | 54614797 |
| X | 25134969 | 25135459 | X | 54625719 | 54630329 |
| X | 25146260 | 25148329 | X | 54681350 | 54684266 |
| X | 25152951 | 25159091 | X | 54701813 | 54704307 |
| X | 25159846 | 25162876 | X | 54735393 | 54739426 |
| X | 25250853 | 25255617 | X | 54800174 | 54801981 |
| X | 25304670 | 25320094 | X | 54828868 | 54829698 |
| X | 25362547 | 25371821 | X | 54850745 | 54870522 |
| X | 25373966 | 25376271 | X | 54913615 | 54920811 |
| X | 25424117 | 25425797 | X | 54942517 | 54943057 |
| X | 25454055 | 25456375 | X | 54963535 | 54965041 |
| X | 25471441 | 25471920 | X | 54993897 | 54995232 |
| X | 25522310 | 25524404 | X | 54999907 | 55029312 |
| X | 25585833 | 25586577 | X | 55042745 | 55044561 |
| X | 25608696 | 25615714 | X | 55049771 | 55051958 |
| X | 25640388 | 25644729 | X | 55075725 | 55077211 |
| X | 25693372 | 25696076 | X | 55099248 | 55100130 |
| X | 25720188 | 25721857 | X | 55118144 | 55118754 |
| X | 25733098 | 25736182 | X | 55131796 | 55133189 |
| X | 25753987 | 25757706 | X | 55142470 | 55143235 |
| X | 25771265 | 25773349 | X | 55155887 | 55158961 |
| X | 25792915 | 25796442 | X | 55161216 | 55161992 |

The chromosomal positon was obtained from UCSC genome browser (http://genome.ucsc.edu/) build 36.

APPENDIX D: Chromosome X
Page 17 of 73

| Chr | Start | End | Chr | Start | End |
|---|---|---|---|---|---|
| X | 25803463 | 25806029 | X | 55175578 | 55178174 |
| X | 25815274 | 25818659 | X | 55188685 | 55192081 |
| X | 25842196 | 25843159 | X | 55203714 | 55207097 |
| X | 25894127 | 25894875 | X | 55214388 | 55215538 |
| X | 25951728 | 25953502 | X | 55218962 | 55220451 |
| X | 25992105 | 25995718 | X | 55223343 | 55227527 |
| X | 26006947 | 26007812 | X | 55263565 | 55265222 |
| X | 26017346 | 26020097 | X | 55269111 | 55270203 |
| X | 26030850 | 26035859 | X | 55320563 | 55323896 |
| X | 26051732 | 26054126 | X | 55370109 | 55372603 |
| X | 26063505 | 26069024 | X | 55384493 | 55387323 |
| X | 26087848 | 26094007 | X | 55448304 | 55451931 |
| X | 26099267 | 26102035 | X | 55457846 | 55461010 |
| X | 26119763 | 26124655 | X | 55486664 | 55496092 |
| X | 26149661 | 26150376 | X | 55531396 | 55534161 |
| X | 26156881 | 26157206 | X | 55565519 | 55566664 |
| X | 26233479 | 26234275 | X | 55570961 | 55571664 |
| X | 26312671 | 26318525 | X | 55571979 | 55574647 |
| X | 26334315 | 26335184 | X | 55589356 | 55605004 |
| X | 26340019 | 26342942 | X | 55635896 | 55637881 |
| X | 26355908 | 26356929 | X | 55759154 | 55762328 |
| X | 26360974 | 26377554 | X | 55764623 | 55765844 |
| X | 26407374 | 26408222 | X | 55784992 | 55788306 |
| X | 26461575 | 26477170 | X | 55802137 | 55805485 |
| X | 26485920 | 26487996 | X | 55821086 | 55829937 |
| X | 26490297 | 26491610 | X | 55831669 | 55836572 |
| X | 26519462 | 26520722 | X | 55895146 | 55898942 |
| X | 26549619 | 26552305 | X | 55902576 | 55905951 |
| X | 26563541 | 26564626 | X | 55944521 | 55947458 |
| X | 26573904 | 26576581 | X | 55955234 | 55956693 |
| X | 26655585 | 26656684 | X | 55958694 | 55962181 |
| X | 26662607 | 26664191 | X | 56020437 | 56025463 |
| X | 26676237 | 26677123 | X | 56039269 | 56040694 |
| X | 26679189 | 26681839 | X | 56048051 | 56049981 |
| X | 26713435 | 26716329 | X | 56065987 | 56075221 |
| X | 26718487 | 26721846 | X | 56098601 | 56099515 |
| X | 26742648 | 26744893 | X | 56126307 | 56133158 |
| X | 26772614 | 26778697 | X | 56226016 | 56233237 |
| X | 26783228 | 26787438 | X | 56236239 | 56237213 |
| X | 26793110 | 26793494 | X | 56259263 | 56261432 |
| X | 26865793 | 26872575 | X | 56275102 | 56277199 |
| X | 26938336 | 26940221 | X | 56304023 | 56308647 |
| X | 26942808 | 26948831 | X | 56333834 | 56335126 |
| X | 26964683 | 26966419 | X | 56352068 | 56353242 |
| X | 26975016 | 26976171 | X | 56355664 | 56360144 |
| X | 27077497 | 27082348 | X | 56553357 | 56563430 |
| X | 27128425 | 27129096 | X | 56606878 | 56608783 |
| X | 27133687 | 27142275 | X | 56615439 | 56615843 |
| X | 27185890 | 27188775 | X | 56650867 | 56653470 |
| X | 27204730 | 27209899 | X | 56661493 | 56664475 |
| X | 27214534 | 27222918 | X | 56769916 | 56771815 |
| X | 27243524 | 27245137 | X | 56801088 | 56855453 |
| X | 27326971 | 27327698 | X | 56875729 | 56876329 |
| X | 27379867 | 27384136 | X | 56927536 | 56927746 |
| X | 27397411 | 27400275 | X | 57005725 | 57008026 |

The chromosomal positon was obtained from UCSC genome browser (http://genome.ucsc.edu/) build 36.

APPENDIX D: Chromosome X
Page 18 of 73

| Chr | Start | End | | | Chr | Start | End |
|---|---|---|---|---|---|---|---|
| X | 27568335 | 27572665 | | | X | 57029969 | 57032180 |
| X | 27620392 | 27621776 | | | X | 57037770 | 57039106 |
| X | 27622280 | 27623140 | | | X | 57080648 | 57082017 |
| X | 27625198 | 27626638 | | | X | 57113131 | 57115473 |
| X | 27669868 | 27676618 | | | X | 57126176 | 57126611 |
| X | 27682848 | 27692858 | | | X | 57164226 | 57165053 |
| X | 27700206 | 27710768 | | | X | 57180210 | 57181126 |
| X | 27720897 | 27724255 | | | X | 57257852 | 57267885 |
| X | 27735755 | 27741034 | | | X | 57305678 | 57306647 |
| X | 27747529 | 27748841 | | | X | 57326609 | 57327353 |
| X | 27757996 | 27760190 | | | X | 57346200 | 57354204 |
| X | 27792184 | 27792319 | | | X | 57445212 | 57445658 |
| X | 27832612 | 27833691 | | | X | 57468395 | 57474516 |
| X | 27835809 | 27836878 | | | X | 57555790 | 57557571 |
| X | 27849231 | 27861326 | | | X | 57570868 | 57571849 |
| X | 27867801 | 27871572 | | | X | 57633668 | 57637757 |
| X | 27898483 | 27899758 | | | X | 57639234 | 57641383 |
| X | 27907744 | 27909599 | | | X | 57650823 | 57651728 |
| X | 27923057 | 27930826 | | | X | 57692085 | 57692604 |
| X | 27965113 | 27973746 | | | X | 57697394 | 57705920 |
| X | 27982056 | 27982776 | | | X | 57776397 | 57778953 |
| X | 27988210 | 27991678 | | | X | 57794025 | 57800139 |
| X | 27998078 | 27998513 | | | X | 57808689 | 57809518 |
| X | 27998811 | 27999971 | | | X | 57917098 | 57920218 |
| X | 28031047 | 28045359 | | | X | 57952496 | 57954412 |
| X | 28094545 | 28095474 | | | X | 57960680 | 57963178 |
| X | 28108696 | 28109746 | | | X | 57965774 | 57966524 |
| X | 28150838 | 28155525 | | | X | 57969548 | 57970907 |
| X | 28181400 | 28182977 | | | X | 57976422 | 57977794 |
| X | 28193509 | 28193958 | | | X | 58012408 | 58015338 |
| X | 28194379 | 28195319 | | | X | 58021135 | 58021505 |
| X | 28261132 | 28266880 | | | X | 58028262 | 58029252 |
| X | 28271478 | 28274216 | | | X | 58069220 | 58071783 |
| X | 28307009 | 28310274 | | | X | 58105418 | 58107689 |
| X | 28377545 | 28380583 | | | X | 58197694 | 58209940 |
| X | 28383620 | 28395242 | | | X | 58238851 | 58240116 |
| X | 28396965 | 28401350 | | | X | 58246806 | 58257409 |
| X | 28428809 | 28436013 | | | X | 58278667 | 58288471 |
| X | 28466882 | 28467960 | | | X | 58296755 | 58335702 |
| X | 28572887 | 28575179 | | | X | 58339739 | 58437367 |
| X | 28583074 | 28588077 | | | X | 58453833 | 58456308 |
| X | 28694382 | 28698107 | | | X | 58474235 | 58487530 |
| X | 28732594 | 28737081 | | | | | |
| X | 28740850 | 28742650 | | | | | |
| X | 28748408 | 28750558 | | | | | |
| X | 28778611 | 28782551 | | | | | |
| X | 28817002 | 28826268 | | | | | |
| X | 28844537 | 28850323 | | | | | |
| X | 28866604 | 28867907 | | | | | |
| X | 28874425 | 28876538 | | | | | |
| X | 28895763 | 28898563 | | | | | |
| X | 28905650 | 28907287 | | | | | |
| X | 28916343 | 28917208 | | | | | |
| X | 29000997 | 29002163 | | | | | |
| X | 61602284 | 61643992 | | | X | 111522195 | 111523437 |

The chromosomal positon was obtained from UCSC genome browser (http://genome.ucsc.edu/) build 36.

APPENDIX D: Chromosome X
Page 19 of 73

| Chr | Start | End | Chr | Start | End |
|---|---|---|---|---|---|
| X | 61837030 | 61847694 | X | 111598249 | 111607622 |
| X | 61858349 | 61876117 | X | 111628214 | 111631311 |
| X | 61923654 | 61932231 | X | 111651422 | 111658281 |
| X | 61944805 | 61964343 | X | 111668514 | 111677897 |
| X | 61978385 | 61981676 | X | 111706655 | 111709260 |
| X | 61983035 | 61988627 | X | 111733555 | 111752537 |
| X | 62321840 | 62327124 | X | 111801199 | 111818966 |
| X | 62487140 | 62488075 | X | 111828040 | 111829310 |
| X | 62488520 | 62491277 | X | 111890879 | 111894160 |
| X | 62499729 | 62501691 | X | 111902785 | 111908175 |
| X | 62523462 | 62528573 | X | 111969962 | 111971875 |
| X | 62533736 | 62534414 | X | 111989106 | 111990884 |
| X | 62563163 | 62571562 | X | 112008027 | 112010495 |
| X | 62641783 | 62651976 | X | 112018038 | 112019641 |
| X | 62722611 | 62723540 | X | 112029027 | 112029237 |
| X | 62801080 | 62803889 | X | 112075023 | 112080297 |
| X | 62809002 | 62814028 | X | 112146934 | 112149119 |
| X | 62827865 | 62839332 | X | 112239694 | 112243859 |
| X | 62890918 | 62892230 | X | 112266151 | 112267509 |
| X | 63102807 | 63114008 | X | 112311792 | 112321064 |
| X | 63179743 | 63181217 | X | 112395988 | 112397040 |
| X | 63300077 | 63307551 | X | 112402644 | 112405365 |
| X | 63341213 | 63343818 | X | 112412641 | 112417728 |
| X | 63428305 | 63432608 | X | 112439879 | 112442809 |
| X | 63442408 | 63445302 | X | 112464414 | 112477631 |
| X | 63479235 | 63494481 | X | 112570106 | 112571725 |
| X | 63506461 | 63506740 | X | 112625965 | 112628813 |
| X | 63521639 | 63522663 | X | 112658565 | 112659987 |
| X | 63531022 | 63532108 | X | 112733319 | 112742785 |
| X | 63553377 | 63561645 | X | 112784650 | 112786039 |
| X | 63657112 | 63665920 | X | 112873536 | 112876678 |
| X | 63834260 | 63840160 | X | 112922616 | 112926237 |
| X | 63856494 | 63857985 | X | 113004563 | 113007202 |
| X | 63921335 | 63923487 | X | 113129507 | 113131671 |
| X | 63925163 | 63927823 | X | 113152250 | 113156796 |
| X | 63978957 | 63987696 | X | 113169509 | 113178210 |
| X | 64028961 | 64031125 | X | 113229896 | 113236494 |
| X | 64092454 | 64093642 | X | 113245608 | 113245871 |
| X | 64104940 | 64105916 | X | 113261221 | 113263218 |
| X | 64130916 | 64131602 | X | 113271925 | 113274435 |
| X | 64169918 | 64172986 | X | 113280060 | 113284198 |
| X | 64217848 | 64219989 | X | 113365928 | 113372531 |
| X | 64246102 | 64249445 | X | 113512181 | 113513554 |
| X | 64267738 | 64271788 | X | 113526852 | 113532097 |
| X | 64308531 | 64311332 | X | 113541048 | 113541622 |
| X | 64415233 | 64417316 | X | 113606916 | 113616467 |
| X | 64497476 | 64502037 | X | 113680728 | 113681888 |
| X | 64543278 | 64545198 | X | 113758937 | 113760867 |
| X | 64603969 | 64607262 | X | 113786386 | 113787855 |
| X | 64637433 | 64639415 | X | 113955296 | 113956198 |
| X | 64650140 | 64666965 | X | 113958452 | 113966737 |
| X | 64670555 | 64730648 | X | 114018865 | 114024408 |
| X | 64741263 | 64746093 | X | 114125471 | 114129670 |
| X | 64768026 | 64779087 | X | 114202154 | 114207452 |
| X | 64802243 | 64805361 | X | 114208815 | 114212996 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 64832871 | 64834233 | | X | 114320827 | 114335177 |
| X | 64839461 | 64842606 | | X | 114359121 | 114363672 |
| X | 64909775 | 64911315 | | X | 114429062 | 114432354 |
| X | 64923458 | 64932619 | | X | 114468032 | 114470704 |
| X | 64955133 | 64959041 | | X | 114473182 | 114475231 |
| X | 65007069 | 65014631 | | X | 114497299 | 114499081 |
| X | 65022057 | 65024011 | | X | 114518754 | 114525704 |
| X | 65065152 | 65069470 | | X | 114592332 | 114597251 |
| X | 65128965 | 65132424 | | X | 114624206 | 114628803 |
| X | 65140583 | 65143009 | | X | 114671273 | 114672182 |
| X | 65212046 | 65213391 | | X | 114678268 | 114691690 |
| X | 65250059 | 65254250 | | X | 114711014 | 114713269 |
| X | 65293211 | 65294144 | | X | 114743810 | 114744669 |
| X | 65398605 | 65399860 | | X | 114781754 | 114783698 |
| X | 65522331 | 65528538 | | X | 114794585 | 114827845 |
| X | 65568029 | 65571741 | | X | 114831438 | 114834258 |
| X | 65578303 | 65580058 | | X | 114842084 | 114847350 |
| X | 65608986 | 65609886 | | X | 114906815 | 114932607 |
| X | 65634628 | 65636573 | | X | 114981393 | 114983824 |
| X | 65650410 | 65657533 | | X | 114998287 | 114999343 |
| X | 65667262 | 65669535 | | X | 115040731 | 115046835 |
| X | 65758357 | 65760745 | | X | 115054156 | 115057505 |
| X | 65769738 | 65771532 | | X | 115105728 | 115107186 |
| X | 65805178 | 65813719 | | X | 115211634 | 115214794 |
| X | 65833743 | 65839047 | | X | 115245278 | 115248451 |
| X | 65847032 | 65852416 | | X | 115272924 | 115281307 |
| X | 65862819 | 65865922 | | X | 115309821 | 115343986 |
| X | 66006090 | 66015247 | | X | 115416998 | 115421484 |
| X | 66035296 | 66040941 | | X | 115427556 | 115436376 |
| X | 66067915 | 66078381 | | X | 115457616 | 115459343 |
| X | 66095830 | 66098562 | | X | 115628915 | 115640621 |
| X | 66178063 | 66189360 | | X | 115653290 | 115656481 |
| X | 66234551 | 66235679 | | X | 115710998 | 115713111 |
| X | 66244112 | 66247702 | | X | 115910792 | 115912856 |
| X | 66272021 | 66276667 | | X | 115925585 | 115926469 |
| X | 66294070 | 66296395 | | X | 115948375 | 115949590 |
| X | 66317294 | 66321556 | | X | 115979460 | 115981425 |
| X | 66340149 | 66345594 | | X | 116004584 | 116018605 |
| X | 66349236 | 66350492 | | X | 116018874 | 116020872 |
| X | 66441437 | 66443766 | | X | 116021188 | 116022888 |
| X | 66470367 | 66471674 | | X | 116048588 | 116050983 |
| X | 66487439 | 66490324 | | X | 116071203 | 116084061 |
| X | 66502737 | 66508585 | | X | 116247178 | 116250158 |
| X | 66575676 | 66584364 | | X | 116343564 | 116357864 |
| X | 66618609 | 66622994 | | X | 116384025 | 116401177 |
| X | 66659633 | 66661420 | | X | 116403728 | 116405013 |
| X | 66664271 | 66665261 | | X | 116433408 | 116441109 |
| X | 66681090 | 66683258 | | X | 116441763 | 116448031 |
| X | 66707566 | 66712903 | | X | 116470114 | 116474281 |
| X | 66719121 | 66723265 | | X | 116531942 | 116542983 |
| X | 66756662 | 66759443 | | X | 116572846 | 116573541 |
| X | 66791299 | 66793764 | | X | 116611293 | 116620731 |
| X | 66820699 | 66829472 | | X | 116645766 | 116647854 |
| X | 66834194 | 66836999 | | X | 116735867 | 116739414 |
| X | 66935360 | 66942601 | | X | 116772629 | 116774374 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 67000831 | 67001071 | X | 116908679 | 116912319 |
| X | 67009002 | 67009449 | X | 116935335 | 116939812 |
| X | 67028926 | 67037405 | X | 117003921 | 117008178 |
| X | 67176023 | 67180802 | X | 117033493 | 117034751 |
| X | 67193094 | 67197010 | X | 117123588 | 117124801 |
| X | 67206750 | 67218041 | X | 117142132 | 117146869 |
| X | 67221520 | 67225406 | X | 117206533 | 117207635 |
| X | 67232072 | 67236493 | X | 117215447 | 117218907 |
| X | 67301447 | 67302354 | X | 117234668 | 117237154 |
| X | 67411859 | 67413392 | X | 117311759 | 117313940 |
| X | 67419460 | 67420020 | X | 117349356 | 117352641 |
| X | 67460643 | 67466568 | X | 117361600 | 117367860 |
| X | 67483048 | 67484776 | X | 117598209 | 117601980 |
| X | 67501907 | 67502127 | X | 117606871 | 117611395 |
| X | 67545794 | 67546862 | X | 117615159 | 117617966 |
| X | 67569146 | 67570822 | X | 117652154 | 117652683 |
| X | 67625651 | 67636080 | X | 117788153 | 117790875 |
| X | 67657428 | 67660001 | X | 117841748 | 117863362 |
| X | 67777094 | 67780071 | X | 117870182 | 117874314 |
| X | 67783678 | 67790959 | X | 117895551 | 117897471 |
| X | 67794174 | 67799036 | X | 117903314 | 117906266 |
| X | 67819836 | 67824137 | X | 117992562 | 117996047 |
| X | 67829104 | 67831096 | X | 118043298 | 118050995 |
| X | 67834736 | 67836671 | X | 118070970 | 118073437 |
| X | 67840656 | 67841501 | X | 118090709 | 118092314 |
| X | 67844048 | 67847120 | X | 118162023 | 118163148 |
| X | 67855355 | 67861636 | X | 118186092 | 118188612 |
| X | 67918948 | 67922338 | X | 118226920 | 118231566 |
| X | 67948873 | 67953983 | X | 118253586 | 118255787 |
| X | 67958027 | 67979211 | X | 118289897 | 118293547 |
| X | 68003185 | 68005077 | X | 118313093 | 118319646 |
| X | 68008130 | 68035804 | X | 118334460 | 118343504 |
| X | 68048631 | 68050517 | X | 118388275 | 118392348 |
| X | 68062729 | 68066163 | X | 118402917 | 118406304 |
| X | 68076642 | 68080496 | X | 118416802 | 118429122 |
| X | 68105585 | 68116953 | X | 118437926 | 118444922 |
| X | 68126593 | 68136087 | X | 118464912 | 118476407 |
| X | 68137473 | 68139571 | X | 118485625 | 118520082 |
| X | 68149001 | 68150663 | X | 118542889 | 118596137 |
| X | 68173645 | 68175148 | X | 118604665 | 118608572 |
| X | 68217418 | 68234840 | X | 118612998 | 118625475 |
| X | 68238378 | 68239778 | X | 118630151 | 118632563 |
| X | 68244077 | 68245223 | X | 118634439 | 118637284 |
| X | 68256174 | 68256469 | X | 118650581 | 118653617 |
| X | 68257422 | 68259112 | X | 118670696 | 118685878 |
| X | 68273110 | 68274406 | X | 118699405 | 118701414 |
| X | 68283347 | 68286465 | X | 118709856 | 118818470 |
| X | 68286965 | 68288058 | X | 118853004 | 118856738 |
| X | 68297478 | 68303162 | X | 118868485 | 118871368 |
| X | 68364991 | 68367185 | X | 118886766 | 118913996 |
| X | 68391158 | 68392754 | X | 118958714 | 118962903 |
| X | 68416307 | 68422912 | X | 119007218 | 119019903 |
| X | 68438642 | 68442927 | X | 119031048 | 119035719 |
| X | 68495555 | 68497480 | X | 119063654 | 119106194 |
| X | 68503361 | 68504723 | X | 119113767 | 119117656 |

The chromosomal positon was obtained from UCSC genome browser (http://genome.ucsc.edu/) build 36.

APPENDIX D: Chromosome X
Page 22 of 73

| Chr | Start | End | | | Chr | Start | End |
|---|---|---|---|---|---|---|---|
| X | 68534089 | 68536049 | | | X | 119128372 | 119128966 |
| X | 68554507 | 68565192 | | | X | 119133053 | 119133917 |
| X | 68584626 | 68591848 | | | X | 119160692 | 119167403 |
| X | 68608437 | 68613164 | | | X | 119224012 | 119225052 |
| X | 68634940 | 68675617 | | | X | 119262373 | 119264215 |
| X | 68774158 | 68777407 | | | X | 119268054 | 119270572 |
| X | 68810387 | 68812286 | | | X | 119301499 | 119303514 |
| X | 68832429 | 68841213 | | | X | 119313819 | 119320440 |
| X | 68911027 | 68911839 | | | X | 119326094 | 119329877 |
| X | 68942328 | 68943498 | | | X | 119383986 | 119384801 |
| X | 69064703 | 69068405 | | | X | 119387807 | 119389047 |
| X | 69188702 | 69189513 | | | X | 119393486 | 119398859 |
| X | 69195986 | 69204924 | | | X | 119446748 | 119449272 |
| X | 69269706 | 69272659 | | | X | 119485980 | 119494306 |
| X | 69368114 | 69373268 | | | X | 119577552 | 119579574 |
| X | 69395354 | 69396554 | | | X | 119592065 | 119593633 |
| X | 69404355 | 69404997 | | | X | 119598123 | 119599476 |
| X | 69417821 | 69418876 | | | X | 119621048 | 119622703 |
| X | 69423046 | 69424820 | | | X | 119647603 | 119650337 |
| X | 69425742 | 69427527 | | | X | 119735687 | 119737575 |
| X | 69457879 | 69459746 | | | X | 119892494 | 119893129 |
| X | 69483796 | 69487368 | | | X | 119957141 | 119958425 |
| X | 69560561 | 69592817 | | | X | 119994599 | 120001479 |
| X | 69628637 | 69632043 | | | X | 120008284 | 120010268 |
| X | 69642918 | 69650313 | | | X | 120016119 | 120021512 |
| X | 69662410 | 69663338 | | | X | 120062189 | 120069673 |
| X | 69668536 | 69675012 | | | X | 120115035 | 120118540 |
| X | 69696471 | 69698604 | | | X | 120182304 | 120184747 |
| X | 69770834 | 69772151 | | | X | 120187751 | 120196436 |
| X | 70044686 | 70045630 | | | X | 120204785 | 120208035 |
| X | 70063890 | 70082121 | | | X | 120216586 | 120222797 |
| X | 70092638 | 70102471 | | | X | 120272519 | 120280172 |
| X | 70166593 | 70168065 | | | X | 120385643 | 120388540 |
| X | 70178461 | 70181569 | | | X | 120420899 | 120425229 |
| X | 70189398 | 70193057 | | | X | 120471133 | 120477909 |
| X | 70195240 | 70201165 | | | X | 120498116 | 120498963 |
| X | 70201577 | 70207324 | | | X | 120559125 | 120565198 |
| X | 70217399 | 70220434 | | | X | 120644908 | 120647549 |
| X | 70232170 | 70239684 | | | X | 120686939 | 120689301 |
| X | 70250273 | 70298019 | | | X | 121164818 | 121165806 |
| X | 70304171 | 70307829 | | | X | 121181972 | 121189696 |
| X | 70312890 | 70421434 | | | X | 121239791 | 121245115 |
| X | 70447510 | 70452371 | | | X | 121332765 | 121337976 |
| X | 70482735 | 70491374 | | | X | 121463198 | 121467932 |
| X | 70499940 | 70504782 | | | X | 121492363 | 121502246 |
| X | 70533918 | 70535425 | | | X | 121543095 | 121553160 |
| X | 70541449 | 70545661 | | | X | 121619326 | 121623421 |
| X | 70580255 | 70583108 | | | X | 121682576 | 121683966 |
| X | 70609703 | 70612350 | | | X | 121698319 | 121700789 |
| X | 70628600 | 70640752 | | | X | 121821753 | 121823191 |
| X | 70649088 | 70656953 | | | X | 121842977 | 121848208 |
| X | 70668775 | 70671657 | | | X | 121916453 | 121916831 |
| X | 70703331 | 70709417 | | | X | 121941995 | 121956638 |
| X | 70714871 | 70716311 | | | X | 121985653 | 121991520 |
| X | 70724690 | 70726807 | | | X | 122009830 | 122011689 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 70737102 | 70741815 | X | 122028418 | 122032069 |
| X | 70748944 | 70754718 | X | 122037520 | 122041889 |
| X | 70768602 | 70769766 | X | 122188813 | 122196009 |
| X | 70794091 | 70817155 | X | 122203179 | 122204187 |
| X | 70949396 | 70961604 | X | 122209875 | 122213330 |
| X | 70997575 | 71014374 | X | 122213892 | 122216752 |
| X | 71042261 | 71048687 | X | 122222648 | 122226384 |
| X | 71077418 | 71087825 | X | 122233170 | 122234045 |
| X | 71133125 | 71133890 | X | 122251348 | 122268225 |
| X | 71142943 | 71144328 | X | 122293187 | 122332006 |
| X | 71163799 | 71164379 | X | 122371830 | 122375268 |
| X | 71187995 | 71194730 | X | 122411327 | 122420071 |
| X | 71202046 | 71218428 | X | 122452959 | 122455082 |
| X | 71239511 | 71247883 | X | 122517265 | 122519286 |
| X | 71258895 | 71278471 | X | 122523302 | 122525082 |
| X | 71292988 | 71337333 | X | 122572485 | 122574740 |
| X | 71356475 | 71403164 | X | 122693690 | 122697555 |
| X | 71411546 | 71423389 | X | 122737513 | 122810710 |
| X | 71434927 | 71442626 | X | 122825019 | 122826839 |
| X | 71493108 | 71497234 | X | 122841161 | 122842592 |
| X | 71557742 | 71563689 | X | 122849215 | 122852636 |
| X | 71610284 | 71614394 | X | 122859655 | 122866089 |
| X | 71632271 | 71634198 | X | 122874625 | 122877972 |
| X | 71680761 | 71682326 | X | 122890792 | 122900909 |
| X | 71707322 | 71711666 | X | 122918273 | 122924847 |
| X | 71721624 | 71722277 | X | 122941738 | 122945235 |
| X | 71737742 | 71741894 | X | 123030163 | 123033449 |
| X | 71843258 | 71849649 | X | 123115634 | 123116182 |
| X | 71850973 | 71853910 | X | 123133785 | 123136229 |
| X | 71876327 | 72052867 | X | 123195288 | 123199272 |
| X | 72149572 | 72153730 | X | 123231721 | 123234513 |
| X | 72263113 | 72264757 | X | 123293683 | 123295317 |
| X | 72271014 | 72276230 | X | 123364527 | 123367921 |
| X | 72350460 | 72351733 | X | 123381865 | 123384183 |
| X | 72394683 | 72401055 | X | 123462885 | 123471038 |
| X | 72412573 | 72416368 | X | 123494936 | 123503513 |
| X | 72489591 | 72494519 | X | 123509261 | 123512624 |
| X | 72551573 | 72559184 | X | 123563649 | 123567925 |
| X | 72664994 | 72672338 | X | 123596705 | 123597979 |
| X | 72705733 | 72710041 | X | 123635957 | 123639646 |
| X | 72844667 | 72850980 | X | 123654798 | 123655917 |
| X | 72870580 | 72880066 | X | 123697828 | 123699969 |
| X | 72939569 | 72946074 | X | 123746893 | 123747489 |
| X | 73011742 | 73014788 | X | 123781017 | 123782137 |
| X | 73099589 | 73101070 | X | 123801128 | 123803719 |
| X | 73130323 | 73133823 | X | 123811531 | 123812795 |
| X | 73175974 | 73176514 | X | 123813540 | 123815525 |
| X | 73202465 | 73203210 | X | 123852278 | 123854668 |
| X | 73243629 | 73244991 | X | 123951680 | 123954577 |
| X | 73253771 | 73255464 | X | 123960548 | 123962557 |
| X | 73258176 | 73266759 | X | 124039084 | 124046542 |
| X | 73289925 | 73291778 | X | 124098820 | 124099957 |
| X | 73297740 | 73300513 | X | 124135060 | 124141541 |
| X | 73314614 | 73318763 | X | 124164540 | 124167913 |
| X | 73351158 | 73358070 | X | 124177314 | 124182474 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 73406937 | 73409244 | X | 124269756 | 124273022 |
| X | 73427626 | 73431947 | X | 124279527 | 124282112 |
| X | 73440722 | 73443396 | X | 124287838 | 124290775 |
| X | 73499520 | 73508831 | X | 124312932 | 124314977 |
| X | 73556355 | 73559154 | X | 124364314 | 124368746 |
| X | 73638095 | 73639700 | X | 124391731 | 124392943 |
| X | 73660938 | 73661293 | X | 124429583 | 124431989 |
| X | 73672474 | 73674910 | X | 124435979 | 124440021 |
| X | 73676221 | 73678620 | X | 124465326 | 124466390 |
| X | 73686887 | 73690131 | X | 124581566 | 124585994 |
| X | 73730285 | 73732767 | X | 124603502 | 124604593 |
| X | 73749505 | 73751556 | X | 124795583 | 124806816 |
| X | 73761799 | 73764194 | X | 124908754 | 124909441 |
| X | 73882834 | 73883648 | X | 124988324 | 124992565 |
| X | 73923931 | 73931976 | X | 125027047 | 125027867 |
| X | 73981230 | 73984239 | X | 125061399 | 125065755 |
| X | 74061114 | 74062340 | X | 125075964 | 125077598 |
| X | 74062906 | 74064735 | X | 125096627 | 125099648 |
| X | 74217816 | 74222994 | X | 125120888 | 125128308 |
| X | 74259732 | 74262290 | X | 125131472 | 125131790 |
| X | 74292169 | 74294558 | X | 125251414 | 125253712 |
| X | 74309199 | 74317115 | X | 125309345 | 125315325 |
| X | 74340189 | 74346370 | X | 125356599 | 125359539 |
| X | 74410375 | 74411180 | X | 125365648 | 125367445 |
| X | 74469994 | 74472359 | X | 125496269 | 125501076 |
| X | 74512519 | 74513640 | X | 125512862 | 125515736 |
| X | 74515410 | 74519016 | X | 125601406 | 125611998 |
| X | 74562641 | 74565684 | X | 125777629 | 125782126 |
| X | 74646719 | 74660894 | X | 125843539 | 125844049 |
| X | 74761381 | 74764016 | X | 125962009 | 125965606 |
| X | 74768336 | 74775243 | X | 126039379 | 126044423 |
| X | 74992805 | 74997340 | X | 126101734 | 126103218 |
| X | 75038113 | 75041266 | X | 126115305 | 126117581 |
| X | 75057413 | 75057703 | X | 126210941 | 126218173 |
| X | 75101511 | 75105732 | X | 126247576 | 126251210 |
| X | 75121585 | 75123811 | X | 126267429 | 126273942 |
| X | 75161619 | 75167690 | X | 126281975 | 126283932 |
| X | 75273588 | 75278108 | X | 126295039 | 126296048 |
| X | 75309157 | 75310044 | X | 126346279 | 126348234 |
| X | 75390496 | 75391449 | X | 126371302 | 126372483 |
| X | 75414158 | 75419443 | X | 126464808 | 126469606 |
| X | 75541261 | 75546780 | X | 126512270 | 126518039 |
| X | 75564004 | 75567378 | X | 126579524 | 126582243 |
| X | 75569045 | 75574838 | X | 126619547 | 126625582 |
| X | 75594436 | 75598375 | X | 126629919 | 126641162 |
| X | 75656102 | 75657783 | X | 126650974 | 126657424 |
| X | 75675525 | 75676580 | X | 126962702 | 126963827 |
| X | 75792814 | 75795887 | X | 126983352 | 126990157 |
| X | 75844903 | 75851674 | X | 126998433 | 127001192 |
| X | 75853665 | 75854284 | X | 127022816 | 127030923 |
| X | 75924660 | 75925509 | X | 127101095 | 127102618 |
| X | 76033000 | 76035868 | X | 127126734 | 127133394 |
| X | 76206967 | 76252729 | X | 127204181 | 127208920 |
| X | 76495184 | 76497113 | X | 127212826 | 127217464 |
| X | 77441791 | 77452103 | X | 127302553 | 127303008 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 77475451 | 77477577 | X | 127322193 | 127324683 |
| X | 77508927 | 77509377 | X | 127331764 | 127336380 |
| X | 77550995 | 77557348 | X | 127355929 | 127357938 |
| X | 77565772 | 77567449 | X | 127492204 | 127496973 |
| X | 77669654 | 77672118 | X | 127562228 | 127566687 |
| X | 77704720 | 77706098 | X | 127592226 | 127595785 |
| X | 77796859 | 77800951 | X | 127626121 | 127628478 |
| X | 77812164 | 77823306 | X | 127701057 | 127704507 |
| X | 77841150 | 77845306 | X | 127724025 | 127732237 |
| X | 77869300 | 77873522 | X | 127742493 | 127743838 |
| X | 77879079 | 77882732 | X | 127810745 | 127813899 |
| X | 77907144 | 77908423 | X | 127828110 | 127829655 |
| X | 78016478 | 78018137 | X | 127837779 | 127842360 |
| X | 78064392 | 78065678 | X | 127857925 | 127860145 |
| X | 78114094 | 78115680 | X | 127872336 | 127874456 |
| X | 78162099 | 78168099 | X | 127897750 | 127899546 |
| X | 78192055 | 78196176 | X | 127922710 | 127929996 |
| X | 78237629 | 78242741 | X | 127954654 | 127963138 |
| X | 78309518 | 78316918 | X | 127965034 | 127965730 |
| X | 78405157 | 78406862 | X | 127994894 | 127998288 |
| X | 78466236 | 78469134 | X | 127998672 | 128005858 |
| X | 78475347 | 78487138 | X | 128036705 | 128040195 |
| X | 78493655 | 78494531 | X | 128048696 | 128049497 |
| X | 78529071 | 78531356 | X | 128072039 | 128082858 |
| X | 78671643 | 78674040 | X | 128100839 | 128105744 |
| X | 78698711 | 78702092 | X | 128173414 | 128184291 |
| X | 78918811 | 78920933 | X | 128235381 | 128240891 |
| X | 79018955 | 79021082 | X | 128280845 | 128283346 |
| X | 79094387 | 79100437 | X | 128287400 | 128288154 |
| X | 79163696 | 79168393 | X | 128288540 | 128288694 |
| X | 79195693 | 79197572 | X | 128333679 | 128336253 |
| X | 79321028 | 79323831 | X | 128348600 | 128356207 |
| X | 79455024 | 79456475 | X | 128390176 | 128400040 |
| X | 79476946 | 79478503 | X | 128406749 | 128408016 |
| X | 79564774 | 79566011 | X | 128505836 | 128507022 |
| X | 79714484 | 79717184 | X | 128543941 | 128547166 |
| X | 79765187 | 79767099 | X | 128554775 | 128567786 |
| X | 79948226 | 79952698 | X | 128583623 | 128590613 |
| X | 80071460 | 80072040 | X | 128610644 | 128617749 |
| X | 80095930 | 80100650 | X | 128660857 | 128663921 |
| X | 80154151 | 80159339 | X | 128700078 | 128704632 |
| X | 80178152 | 80182878 | X | 128709024 | 128716238 |
| X | 80225906 | 80229657 | X | 128729956 | 128736824 |
| X | 80272498 | 80274915 | X | 128749294 | 128755375 |
| X | 80302996 | 80311431 | X | 128804343 | 128807716 |
| X | 80398856 | 80405183 | X | 128857251 | 128868081 |
| X | 80514246 | 80517865 | X | 128886284 | 128896075 |
| X | 80530792 | 80534813 | X | 128917713 | 128927751 |
| X | 80600903 | 80602452 | X | 128940819 | 128948720 |
| X | 80627145 | 80629942 | X | 128960837 | 128978171 |
| X | 80668587 | 80670720 | X | 128998992 | 129088753 |
| X | 80842160 | 80844762 | X | 129125022 | 129134374 |
| X | 80881989 | 80895106 | X | 129148235 | 129150113 |
| X | 80947571 | 80954656 | X | 129225859 | 129235834 |
| X | 81006363 | 81008494 | X | 129283376 | 129288566 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 81041179 | 81047001 | | X | 129297897 | 129302281 |
| X | 81160033 | 81165179 | | X | 129342692 | 129352786 |
| X | 81255882 | 81256697 | | X | 129360637 | 129366232 |
| X | 81282139 | 81287361 | | X | 129388071 | 129392567 |
| X | 81416797 | 81420602 | | X | 129460296 | 129471888 |
| X | 81460791 | 81464752 | | X | 129488016 | 129493198 |
| X | 81497008 | 81497842 | | X | 129518480 | 129519241 |
| X | 81613820 | 81621350 | | X | 129549697 | 129550857 |
| X | 81799879 | 81807818 | | X | 129593533 | 129597053 |
| X | 81850123 | 81854997 | | X | 129621303 | 129623218 |
| X | 81869773 | 81871864 | | X | 129656821 | 129658795 |
| X | 82210457 | 82212442 | | X | 129698427 | 129700216 |
| X | 82283670 | 82284183 | | X | 129711327 | 129714545 |
| X | 82414502 | 82418783 | | X | 129717860 | 129720284 |
| X | 82467812 | 82468756 | | X | 129729375 | 129744594 |
| X | 82621095 | 82625883 | | X | 129787181 | 129795330 |
| X | 82649779 | 82656288 | | X | 129864335 | 129865545 |
| X | 82736649 | 82742212 | | X | 129869340 | 129871375 |
| X | 82755394 | 82757635 | | X | 129933157 | 129941105 |
| X | 82775180 | 82777422 | | X | 130005539 | 130012719 |
| X | 82844574 | 82850429 | | X | 130019324 | 130020749 |
| X | 82946077 | 82947138 | | X | 130042883 | 130045549 |
| X | 82959040 | 82961673 | | X | 130059652 | 130060537 |
| X | 83048148 | 83049610 | | X | 130127368 | 130142871 |
| X | 83201106 | 83202077 | | X | 130147971 | 130148900 |
| X | 83293312 | 83303852 | | X | 130186113 | 130189233 |
| X | 83329540 | 83331776 | | X | 130219477 | 130221856 |
| X | 83344062 | 83348325 | | X | 130227496 | 130230951 |
| X | 83397503 | 83402508 | | X | 130281045 | 130286443 |
| X | 83464292 | 83467045 | | X | 130304513 | 130309497 |
| X | 83478681 | 83481819 | | X | 130319936 | 130320650 |
| X | 83642328 | 83645136 | | X | 130325941 | 130329077 |
| X | 83646291 | 83654681 | | X | 130355845 | 130357769 |
| X | 83831155 | 83835228 | | X | 130370312 | 130371747 |
| X | 83859059 | 83859940 | | X | 130415342 | 130417360 |
| X | 83880473 | 83886165 | | X | 130438218 | 130439515 |
| X | 83985140 | 83990799 | | X | 130505817 | 130508598 |
| X | 83994861 | 83998903 | | X | 130573797 | 130578169 |
| X | 84074731 | 84076430 | | X | 130644153 | 130646434 |
| X | 84144346 | 84146665 | | X | 130665372 | 130682037 |
| X | 84186319 | 84186605 | | X | 130701222 | 130704215 |
| X | 84217367 | 84227818 | | X | 130714039 | 130728302 |
| X | 84383910 | 84388391 | | X | 130735158 | 130736509 |
| X | 84401249 | 84407395 | | X | 130756878 | 130763785 |
| X | 84420550 | 84422434 | | X | 130774823 | 130775145 |
| X | 84468040 | 84471117 | | X | 130800523 | 130804713 |
| X | 84511623 | 84512062 | | X | 130812793 | 130814198 |
| X | 84524186 | 84531159 | | X | 130851501 | 130863779 |
| X | 84551124 | 84554199 | | X | 130868829 | 130870319 |
| X | 84602353 | 84618560 | | X | 130904629 | 130906561 |
| X | 84636510 | 84648723 | | X | 130913876 | 130919902 |
| X | 84723900 | 84732054 | | X | 130942286 | 130945020 |
| X | 84750586 | 84758828 | | X | 130967105 | 130971294 |
| X | 84809360 | 84811544 | | X | 130978248 | 130979816 |
| X | 84852309 | 84860723 | | X | 131023584 | 131029482 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 84969957 | 84971368 | | X | 131032568 | 131035935 |
| X | 85054310 | 85056486 | | X | 131039239 | 131045054 |
| X | 85073767 | 85075177 | | X | 131070149 | 131072240 |
| X | 85133906 | 85138498 | | X | 131080501 | 131082025 |
| X | 85168143 | 85170654 | | X | 131083369 | 131093472 |
| X | 85188821 | 85190511 | | X | 131112124 | 131115292 |
| X | 85222565 | 85227815 | | X | 131140034 | 131143434 |
| X | 85236494 | 85238635 | | X | 131177941 | 131180411 |
| X | 85287741 | 85291688 | | X | 131202237 | 131202957 |
| X | 85357373 | 85358324 | | X | 131253205 | 131255580 |
| X | 85506145 | 85509346 | | X | 131277918 | 131295519 |
| X | 85578132 | 85581184 | | X | 131307828 | 131313345 |
| X | 85617647 | 85621291 | | X | 131329011 | 131339845 |
| X | 85651156 | 85652923 | | X | 131353866 | 131366167 |
| X | 85655066 | 85656371 | | X | 131373433 | 131374250 |
| X | 85662073 | 85663826 | | X | 131390505 | 131397937 |
| X | 85725849 | 85730702 | | X | 131418819 | 131422132 |
| X | 85735399 | 85738338 | | X | 131436314 | 131440531 |
| X | 85817182 | 85820965 | | X | 131450165 | 131452851 |
| X | 85866234 | 85868097 | | X | 131456953 | 131464290 |
| X | 85969472 | 85978663 | | X | 131492505 | 131498435 |
| X | 86020441 | 86028408 | | X | 131512152 | 131516390 |
| X | 86029417 | 86030555 | | X | 131523392 | 131528040 |
| X | 86071000 | 86073396 | | X | 131548942 | 131556705 |
| X | 86095852 | 86098001 | | X | 131580134 | 131594444 |
| X | 86167749 | 86170669 | | X | 131598428 | 131601030 |
| X | 86282046 | 86282600 | | X | 131603715 | 131607052 |
| X | 86297105 | 86300213 | | X | 131618847 | 131622338 |
| X | 86304060 | 86304414 | | X | 131633219 | 131639304 |
| X | 86336265 | 86342873 | | X | 131656003 | 131656854 |
| X | 86383850 | 86387891 | | X | 131659395 | 131669480 |
| X | 86433059 | 86435239 | | X | 131681598 | 131682063 |
| X | 86568049 | 86574088 | | X | 131702778 | 131704580 |
| X | 86618444 | 86622668 | | X | 131785827 | 131787410 |
| X | 86675662 | 86679953 | | X | 131792096 | 131810471 |
| X | 86757940 | 86759437 | | X | 131880848 | 131883436 |
| X | 86822450 | 86835122 | | X | 131910876 | 131912880 |
| X | 86857249 | 86859010 | | X | 131917501 | 131920459 |
| X | 86860429 | 86863495 | | X | 131925302 | 131928287 |
| X | 86868426 | 86871074 | | X | 131943734 | 131948039 |
| X | 86925737 | 86946709 | | X | 132005766 | 132007762 |
| X | 87174017 | 87179436 | | X | 132031779 | 132032190 |
| X | 87289758 | 87291277 | | X | 132055931 | 132059176 |
| X | 87346536 | 87348095 | | X | 132068456 | 132081838 |
| X | 87359178 | 87364488 | | X | 132135702 | 132138153 |
| X | 87410505 | 87412047 | | X | 132178348 | 132180231 |
| X | 87440440 | 87442408 | | X | 132202871 | 132209857 |
| X | 87588994 | 87593356 | | X | 132295452 | 132297621 |
| X | 87682111 | 87684428 | | X | 132314039 | 132315328 |
| X | 87708386 | 87712138 | | X | 132374895 | 132378811 |
| X | 87933581 | 87936040 | | X | 132487139 | 132491429 |
| X | 87964666 | 87966545 | | X | 132496050 | 132498043 |
| X | 87987249 | 87992347 | | X | 132511212 | 132512033 |
| X | 88004193 | 88006452 | | X | 132526141 | 132529772 |
| X | 88050080 | 88051925 | | X | 132568996 | 132572673 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 88133262 | 88134863 | X | 132614815 | 132616068 |
| X | 88172300 | 88174310 | X | 132637406 | 132640551 |
| X | 88295692 | 88296042 | X | 132676595 | 132677515 |
| X | 88320619 | 88322809 | X | 132704412 | 132711975 |
| X | 88329973 | 88330989 | X | 132742599 | 132747004 |
| X | 88342991 | 88364418 | X | 132747461 | 132750307 |
| X | 88686850 | 88738395 | X | 132774350 | 132782237 |
| X | 88902440 | 88904585 | X | 132834454 | 132836722 |
| X | 89159858 | 89162885 | X | 132844958 | 132845366 |
| X | 89358832 | 89368608 | X | 132882010 | 132882369 |
| X | 89637449 | 89675388 | X | 132891283 | 132893426 |
| X | 89675972 | 89683792 | X | 132908005 | 132912647 |
| X | 89755733 | 89770635 | X | 132945655 | 132949299 |
| X | 89785411 | 89786682 | X | 133033686 | 133039744 |
| X | 90204160 | 90208154 | X | 133049530 | 133053129 |
| X | 90229179 | 90234423 | X | 133078541 | 133085405 |
| X | 90239148 | 90240226 | X | 133101560 | 133103062 |
| X | 90497913 | 90499369 | X | 133133357 | 133135768 |
| X | 90575690 | 90578423 | X | 133142779 | 133150488 |
| X | 91335854 | 91337505 | X | 133192038 | 133200611 |
| X | 91356397 | 91368135 | X | 133332803 | 133333924 |
| X | 91370018 | 91371194 | X | 133334661 | 133336601 |
| X | 91417541 | 91421799 | X | 133399710 | 133400343 |
| X | 91457959 | 91460795 | X | 133418758 | 133423157 |
| X | 91963583 | 91974107 | X | 133454078 | 133456821 |
| X | 92257460 | 92269619 | X | 133467548 | 133470620 |
| X | 92372148 | 92373763 | X | 133491120 | 133514138 |
| X | 92403886 | 92404263 | X | 133542931 | 133545369 |
| X | 92442837 | 92445423 | X | 133597965 | 133603537 |
| X | 92467259 | 92470660 | X | 133608593 | 133609338 |
| X | 92476668 | 92477732 | X | 133636797 | 133639775 |
| X | 92487483 | 92489373 | X | 133641807 | 133646902 |
| X | 92513982 | 92518325 | X | 133665761 | 133668972 |
| X | 92571634 | 92576639 | X | 133698914 | 133701709 |
| X | 92586344 | 92588135 | X | 133706326 | 133708161 |
| X | 92603161 | 92604192 | X | 133757329 | 133758823 |
| X | 92719962 | 92723984 | X | 133829376 | 133832861 |
| X | 92730168 | 92731622 | X | 133847154 | 133848011 |
| X | 92740862 | 92742035 | X | 133865076 | 133878071 |
| X | 92753097 | 92754826 | X | 133921178 | 133929304 |
| X | 92811155 | 92813121 | X | 133948641 | 133950235 |
| X | 92852001 | 92855042 | X | 133965462 | 133966422 |
| X | 92907121 | 92908141 | X | 133972605 | 133974444 |
| X | 92951056 | 92953955 | X | 133983364 | 133984154 |
| X | 93040822 | 93041774 | X | 133992415 | 133995092 |
| X | 93117244 | 93119365 | X | 133997706 | 134001075 |
| X | 93316224 | 93317787 | X | 134013046 | 134015423 |
| X | 93451605 | 93455193 | X | 134024455 | 134024997 |
| X | 93487284 | 93490170 | X | 134056840 | 134060992 |
| X | 93529348 | 93530716 | X | 134132343 | 134135798 |
| X | 93586894 | 93593059 | X | 134235491 | 134236982 |
| X | 93617632 | 93619458 | X | 134292540 | 134296875 |
| X | 93785988 | 93795864 | X | 134303613 | 134307806 |
| X | 94022831 | 94024988 | X | 134318496 | 134322281 |
| X | 94283369 | 94284681 | X | 134382592 | 134388165 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 94337868 | 94339347 | X | 134393965 | 134402002 |
| X | 94428825 | 94434243 | X | 134430431 | 134432349 |
| X | 94473898 | 94474688 | X | 134442920 | 134448274 |
| X | 94579540 | 94585008 | X | 134466094 | 134467284 |
| X | 94608665 | 94612953 | X | 134481852 | 134484672 |
| X | 94626953 | 94630124 | X | 134494072 | 134495633 |
| X | 94639905 | 94641547 | X | 134508957 | 134510613 |
| X | 94815514 | 94820510 | X | 134608341 | 134610347 |
| X | 94887420 | 94890867 | X | 134639325 | 134642189 |
| X | 94906807 | 94907403 | X | 134669017 | 134803775 |
| X | 94921747 | 94922819 | X | 134844482 | 134856694 |
| X | 94962059 | 94965834 | X | 134877582 | 134883709 |
| X | 95005702 | 95006724 | X | 134892146 | 134907746 |
| X | 95090523 | 95092978 | X | 134986076 | 134993165 |
| X | 95108047 | 95108869 | X | 135002793 | 135012793 |
| X | 95137822 | 95146383 | X | 135040145 | 135045379 |
| X | 95172854 | 95177306 | X | 135114290 | 135124586 |
| X | 95177795 | 95179100 | X | 135165818 | 135166697 |
| X | 95230459 | 95235934 | X | 135172164 | 135174146 |
| X | 95247063 | 95249945 | X | 135182657 | 135183773 |
| X | 95284183 | 95285574 | X | 135231366 | 135231606 |
| X | 95292463 | 95295088 | X | 135262450 | 135264647 |
| X | 95351391 | 95354095 | X | 135332491 | 135335972 |
| X | 95376555 | 95377404 | X | 135374135 | 135376855 |
| X | 95511517 | 95515140 | X | 135405876 | 135413076 |
| X | 95522677 | 95525792 | X | 135423168 | 135426707 |
| X | 95609653 | 95616668 | X | 135438362 | 135450438 |
| X | 95646254 | 95648231 | X | 135480078 | 135481582 |
| X | 95736490 | 95739001 | X | 135484192 | 135488132 |
| X | 95765480 | 95772591 | X | 135490522 | 135493074 |
| X | 95930096 | 95930964 | X | 135494566 | 135496328 |
| X | 96025629 | 96026432 | X | 135551175 | 135553469 |
| X | 96078975 | 96080134 | X | 135562908 | 135566870 |
| X | 96193395 | 96196607 | X | 135580735 | 135581941 |
| X | 96220609 | 96221469 | X | 135653936 | 135658124 |
| X | 96311858 | 96314031 | X | 135676431 | 135678893 |
| X | 96437777 | 96440650 | X | 135789856 | 135851546 |
| X | 96449643 | 96457141 | X | 135858235 | 135863565 |
| X | 96558287 | 96560894 | X | 135873896 | 135875835 |
| X | 96676753 | 96683753 | X | 135885048 | 135895494 |
| X | 96712003 | 96717815 | X | 135938508 | 135944967 |
| X | 96731756 | 96735195 | X | 135959389 | 135962948 |
| X | 96861568 | 96862513 | X | 136095173 | 136097665 |
| X | 96956708 | 96958066 | X | 136145506 | 136146753 |
| X | 96963059 | 96963803 | X | 136159100 | 136162194 |
| X | 96969041 | 96970077 | X | 136176826 | 136177652 |
| X | 96974989 | 96977315 | X | 136228236 | 136231340 |
| X | 96982376 | 96992108 | X | 136312384 | 136315894 |
| X | 97167828 | 97168995 | X | 136350064 | 136352085 |
| X | 97177392 | 97180372 | X | 136455169 | 136467681 |
| X | 97190812 | 97191711 | X | 136475560 | 136479261 |
| X | 97220539 | 97229671 | X | 136488584 | 136500200 |
| X | 97235695 | 97243694 | X | 136648270 | 136654438 |
| X | 97341072 | 97343003 | X | 136690769 | 136692315 |
| X | 97390552 | 97390793 | X | 136747842 | 136750083 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 97429214 | 97436454 | X | 136755994 | 136764367 |
| X | 97469433 | 97474702 | X | 136778272 | 136781439 |
| X | 97479766 | 97482951 | X | 136865127 | 136867585 |
| X | 97499402 | 97499673 | X | 136892732 | 136894206 |
| X | 97540041 | 97548008 | X | 136949854 | 136950280 |
| X | 97625032 | 97629469 | X | 137035324 | 137038082 |
| X | 97753073 | 97756952 | X | 137054527 | 137054984 |
| X | 97910264 | 97911087 | X | 137061466 | 137062445 |
| X | 98086303 | 98091155 | X | 137154519 | 137154829 |
| X | 98212389 | 98214366 | X | 137157859 | 137161307 |
| X | 98302262 | 98306894 | X | 137168443 | 137179456 |
| X | 98307924 | 98312720 | X | 137210359 | 137217789 |
| X | 98323605 | 98325699 | X | 137382913 | 137384215 |
| X | 98330388 | 98332444 | X | 137388308 | 137390607 |
| X | 98436977 | 98448237 | X | 137426625 | 137432270 |
| X | 98608527 | 98611460 | X | 137457599 | 137466569 |
| X | 98798310 | 98798884 | X | 137494107 | 137500199 |
| X | 98839381 | 98840860 | X | 137620016 | 137622220 |
| X | 98846863 | 98849836 | X | 137642220 | 137655112 |
| X | 98999391 | 99009156 | X | 137753057 | 137757116 |
| X | 99080295 | 99082528 | X | 137820767 | 137823313 |
| X | 99097072 | 99098973 | X | 137824858 | 137831344 |
| X | 99109717 | 99110134 | X | 137848685 | 137858863 |
| X | 99127290 | 99129375 | X | 137878444 | 137880179 |
| X | 99140935 | 99142721 | X | 137887973 | 137888619 |
| X | 99215895 | 99226664 | X | 137940119 | 137944855 |
| X | 99245664 | 99247165 | X | 138110163 | 138117718 |
| X | 99293821 | 99295766 | X | 138161195 | 138161980 |
| X | 99334922 | 99336616 | X | 138244958 | 138249931 |
| X | 99427565 | 99431235 | X | 138273982 | 138275555 |
| X | 99437937 | 99438497 | X | 138334392 | 138339824 |
| X | 99460494 | 99461383 | X | 138448970 | 138455608 |
| X | 99480735 | 99486338 | X | 138463147 | 138470829 |
| X | 99505715 | 99509916 | X | 138514784 | 138517685 |
| X | 99518392 | 99519526 | X | 138591679 | 138602810 |
| X | 99547563 | 99553664 | X | 138639518 | 138650177 |
| X | 99602514 | 99604698 | X | 138656580 | 138657740 |
| X | 99630401 | 99632500 | X | 138762455 | 138769439 |
| X | 99648843 | 99651207 | X | 138802288 | 138803413 |
| X | 99682452 | 99687620 | X | 138840958 | 138844014 |
| X | 99748643 | 99749438 | X | 138891082 | 138895506 |
| X | 99774182 | 99779401 | X | 138935883 | 138946665 |
| X | 99802649 | 99806976 | X | 139000804 | 139005963 |
| X | 99814476 | 99816230 | X | 139075793 | 139076921 |
| X | 99873674 | 99877798 | X | 139112065 | 139115052 |
| X | 99878386 | 99882992 | X | 139171854 | 139174480 |
| X | 99926958 | 99934188 | X | 139301210 | 139312885 |
| X | 99960408 | 99964176 | X | 139325642 | 139328058 |
| X | 100059580 | 100060543 | X | 139331134 | 139338280 |
| X | 100191466 | 100195644 | X | 139390558 | 139393108 |
| X | 100210080 | 100210680 | X | 139414293 | 139424767 |
| X | 100238711 | 100240117 | X | 139483684 | 139484602 |
| X | 100267535 | 100271497 | X | 139531732 | 139532794 |
| X | 100431195 | 100438314 | X | 139581566 | 139583656 |
| X | 100477141 | 100497699 | X | 139592176 | 139594167 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 100503014 | 100505759 | X | 139601071 | 139609623 |
| X | 100532255 | 100534227 | X | 139616499 | 139644333 |
| X | 100546529 | 100554616 | X | 139693059 | 139694814 |
| X | 100558427 | 100565324 | X | 139725859 | 139730149 |
| X | 100600107 | 100603618 | X | 139819256 | 139824287 |
| X | 100627091 | 100628775 | X | 139874520 | 139881405 |
| X | 100633555 | 100635209 | X | 139894781 | 139896191 |
| X | 100674393 | 100675926 | X | 140046120 | 140053698 |
| X | 100679716 | 100694697 | X | 140066061 | 140070869 |
| X | 100752890 | 100757908 | X | 140097517 | 140100840 |
| X | 100764628 | 100767140 | X | 140164189 | 140168416 |
| X | 100796259 | 100801456 | X | 140181953 | 140189831 |
| X | 100874691 | 100875681 | X | 140278333 | 140280169 |
| X | 100891585 | 100893401 | X | 140326109 | 140330361 |
| X | 100896412 | 100897986 | X | 140375584 | 140376698 |
| X | 100947214 | 100965122 | X | 140550266 | 140552145 |
| X | 100978248 | 100986896 | X | 140585012 | 140586716 |
| X | 101025639 | 101031023 | X | 140591778 | 140616391 |
| X | 101072745 | 101075661 | X | 140794781 | 140798142 |
| X | 101087609 | 101090851 | X | 140810854 | 140825238 |
| X | 101112066 | 101114323 | X | 140847646 | 140851280 |
| X | 101129244 | 101134205 | X | 140887845 | 140889114 |
| X | 101266437 | 101268618 | X | 140927916 | 140931968 |
| X | 101272306 | 101274773 | X | 140974017 | 140974967 |
| X | 101294936 | 101298722 | X | 141085472 | 141091536 |
| X | 101338935 | 101483262 | X | 141108845 | 141126920 |
| X | 101635367 | 101636382 | X | 141144493 | 141148629 |
| X | 101685387 | 101690081 | X | 141157694 | 141162976 |
| X | 101705199 | 101714534 | X | 141181111 | 141190203 |
| X | 101740762 | 101741813 | X | 141215509 | 141217691 |
| X | 101785931 | 101791612 | X | 141242371 | 141244352 |
| X | 101792072 | 101794350 | X | 141300014 | 141308476 |
| X | 101801282 | 101801906 | X | 141334676 | 141335408 |
| X | 101852573 | 101856056 | X | 141340147 | 141343582 |
| X | 101865495 | 101868203 | X | 141399998 | 141407760 |
| X | 101909489 | 101911117 | X | 141420533 | 141426800 |
| X | 102107081 | 102110550 | X | 141614604 | 141618566 |
| X | 102130689 | 102144076 | X | 141694229 | 141696022 |
| X | 102199792 | 102225206 | X | 141769616 | 141770262 |
| X | 102231255 | 102238988 | X | 141794233 | 141798038 |
| X | 102266600 | 102285741 | X | 141839377 | 141845165 |
| X | 102292508 | 102295096 | X | 141941420 | 141950243 |
| X | 102311949 | 102323732 | X | 142009491 | 142011206 |
| X | 102354865 | 102362968 | X | 142036422 | 142039604 |
| X | 102395231 | 102396921 | X | 142201329 | 142203717 |
| X | 102415905 | 102418202 | X | 142277688 | 142279624 |
| X | 102433225 | 102435677 | X | 142334918 | 142335392 |
| X | 102451527 | 102453087 | X | 142341783 | 142344021 |
| X | 102471402 | 102472503 | X | 142377055 | 142378985 |
| X | 102498102 | 102506367 | X | 142424394 | 142435120 |
| X | 102515645 | 102520233 | X | 142497993 | 142500642 |
| X | 102538717 | 102539792 | X | 142533062 | 142534373 |
| X | 102543209 | 102543980 | X | 142548854 | 142555053 |
| X | 102552769 | 102554207 | X | 142622471 | 142640819 |
| X | 102570621 | 102579969 | X | 142693825 | 142695260 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 102585414 | 102588912 | X | 142737533 | 142743730 |
| X | 102619327 | 102623012 | X | 142804481 | 142806813 |
| X | 102627789 | 102629325 | X | 142837707 | 142839811 |
| X | 102633432 | 102640993 | X | 142933118 | 142933788 |
| X | 102653628 | 102655151 | X | 142959996 | 142960701 |
| X | 102657676 | 102662755 | X | 142983533 | 143019277 |
| X | 102698722 | 102707625 | X | 143123787 | 143125304 |
| X | 102713039 | 102717123 | X | 143146661 | 143148438 |
| X | 102726834 | 102728280 | X | 143161733 | 143163206 |
| X | 102766836 | 102771124 | X | 143206628 | 143208269 |
| X | 102775419 | 102780199 | X | 143220333 | 143222258 |
| X | 102800921 | 102805030 | X | 143240981 | 143246955 |
| X | 102815769 | 102816371 | X | 143327134 | 143333700 |
| X | 102827628 | 102831664 | X | 143398895 | 143401788 |
| X | 102832396 | 102834042 | X | 143448311 | 143458067 |
| X | 102840601 | 102842911 | X | 143501162 | 143510431 |
| X | 102848642 | 102855687 | X | 143527681 | 143529102 |
| X | 102903946 | 102912537 | X | 143561780 | 143562486 |
| X | 102927048 | 102928628 | X | 143650658 | 143652930 |
| X | 102972051 | 102974992 | X | 143681367 | 143690093 |
| X | 102980913 | 102984452 | X | 143717758 | 143724355 |
| X | 102991904 | 102997537 | X | 143732958 | 143735668 |
| X | 103046069 | 103060959 | X | 143811118 | 143811825 |
| X | 103066842 | 103068482 | X | 143873464 | 143878463 |
| X | 103102198 | 103104357 | X | 143897344 | 143898744 |
| X | 103145765 | 103189714 | X | 143945448 | 143949048 |
| X | 103235877 | 103245665 | X | 143958957 | 143965597 |
| X | 103248138 | 103248853 | X | 144018697 | 144022992 |
| X | 103296574 | 103298944 | X | 144122008 | 144122823 |
| X | 103383271 | 103393210 | X | 144136754 | 144144077 |
| X | 103427112 | 103430655 | X | 144251658 | 144256201 |
| X | 103463810 | 103466138 | X | 144387805 | 144394578 |
| X | 103496831 | 103498455 | X | 144450366 | 144455388 |
| X | 103527695 | 103529287 | X | 144484563 | 144485269 |
| X | 103572927 | 103573725 | X | 144516698 | 144520787 |
| X | 103656517 | 103660227 | X | 144564157 | 144564622 |
| X | 103695641 | 103699874 | X | 144605798 | 144615620 |
| X | 103718207 | 103721350 | X | 144622555 | 144624018 |
| X | 103752546 | 103760824 | X | 144711034 | 144714120 |
| X | 103779542 | 103796000 | X | 144737782 | 144743020 |
| X | 103802262 | 103810993 | X | 144766283 | 144770606 |
| X | 103835599 | 103858202 | X | 144788187 | 144788502 |
| X | 103865617 | 103886318 | X | 144796766 | 144799863 |
| X | 103894071 | 103903369 | X | 144858730 | 144865422 |
| X | 103915232 | 103926977 | X | 144884237 | 144888506 |
| X | 103942253 | 103947759 | X | 144930993 | 144935948 |
| X | 104002532 | 104007354 | X | 144955334 | 144960040 |
| X | 104014507 | 104027538 | X | 145032840 | 145036543 |
| X | 104118379 | 104133773 | X | 145059954 | 145061225 |
| X | 104141966 | 104142825 | X | 145070084 | 145072677 |
| X | 104196279 | 104200032 | X | 145098480 | 145105292 |
| X | 104223524 | 104240257 | X | 145147175 | 145149352 |
| X | 104247858 | 104278811 | X | 145156121 | 145164623 |
| X | 104294508 | 104298005 | X | 145217557 | 145222671 |
| X | 104327912 | 104328635 | X | 145244904 | 145247176 |

The chromosomal positon was obtained from UCSC genome browser (http://genome.ucsc.edu/) build 36.

APPENDIX D: Chromosome X
Page 33 of 73

| Chr | Start | End | Chr | Start | End |
| --- | --- | --- | --- | --- | --- |
| X | 104335046 | 104336190 | X | 145274439 | 145277744 |
| X | 104350360 | 104352060 | X | 145337146 | 145342178 |
| X | 104396912 | 104397216 | X | 145352143 | 145352464 |
| X | 104415837 | 104420463 | X | 145365507 | 145367508 |
| X | 104444886 | 104446027 | X | 145470305 | 145475000 |
| X | 104461969 | 104478015 | X | 145622657 | 145623183 |
| X | 104486910 | 104491769 | X | 145664880 | 145666653 |
| X | 104537128 | 104538265 | X | 145681500 | 145682054 |
| X | 104560571 | 104565599 | X | 145738810 | 145746170 |
| X | 104595413 | 104602749 | X | 145848385 | 145852255 |
| X | 104632437 | 104650782 | X | 145975140 | 145976982 |
| X | 104684677 | 104700533 | X | 146062983 | 146064528 |
| X | 104708998 | 104712410 | X | 146156586 | 146160980 |
| X | 104727416 | 104729746 | X | 146169847 | 146176059 |
| X | 104743983 | 104750237 | X | 146277020 | 146279167 |
| X | 104763915 | 104768846 | X | 146310285 | 146311183 |
| X | 104802180 | 104803762 | X | 146356154 | 146362091 |
| X | 104833613 | 104840966 | X | 146367343 | 146369297 |
| X | 104853906 | 104857820 | X | 146454464 | 146455793 |
| X | 104883231 | 104886944 | X | 146515313 | 146520543 |
| X | 104935740 | 104942865 | X | 146577602 | 146578684 |
| X | 104951668 | 104954037 | X | 146592143 | 146592424 |
| X | 104958743 | 104968814 | X | 146667234 | 146668813 |
| X | 104978804 | 104983975 | X | 146751198 | 146754690 |
| X | 104999835 | 105014537 | X | 146800202 | 146803039 |
| X | 105024505 | 105025765 | X | 146841655 | 146848984 |
| X | 105031995 | 105034329 | X | 146852703 | 146853520 |
| X | 105048974 | 105053867 | X | 146854330 | 146859043 |
| X | 105114278 | 105116176 | X | 146878872 | 146883236 |
| X | 105122307 | 105126402 | X | 146912765 | 146919833 |
| X | 105146379 | 105154523 | X | 146923302 | 146928123 |
| X | 105165652 | 105176604 | X | 146964545 | 146977311 |
| X | 105219532 | 105224196 | X | 147010343 | 147048288 |
| X | 105276795 | 105277786 | X | 147074753 | 147090266 |
| X | 105431554 | 105432840 | X | 147104930 | 147110190 |
| X | 105451193 | 105454743 | X | 147177299 | 147186264 |
| X | 105462144 | 105463739 | X | 147254641 | 147255659 |
| X | 105516469 | 105521309 | X | 147269238 | 147271385 |
| X | 105529292 | 105530628 | X | 147285282 | 147290049 |
| X | 105550324 | 105556088 | X | 147294410 | 147297550 |
| X | 105570171 | 105572585 | X | 147299526 | 147300472 |
| X | 105589417 | 105595271 | X | 147357051 | 147361143 |
| X | 105614117 | 105614715 | X | 147377219 | 147378771 |
| X | 105616092 | 105624115 | X | 147388801 | 147394102 |
| X | 105639366 | 105642591 | X | 147419757 | 147420021 |
| X | 105714706 | 105718267 | X | 147430467 | 147438885 |
| X | 105741311 | 105746672 | X | 147460460 | 147464301 |
| X | 105760298 | 105762365 | X | 147494048 | 147498643 |
| X | 105817077 | 105818232 | X | 147511819 | 147514084 |
| X | 105858062 | 105866948 | X | 147530807 | 147533812 |
| X | 105921942 | 105924126 | X | 147591901 | 147601265 |
| X | 105931743 | 105934172 | X | 147601726 | 147602471 |
| X | 105936565 | 105937020 | X | 147660444 | 147661126 |
| X | 105962391 | 105969225 | X | 147686450 | 147690162 |
| X | 105996758 | 105998200 | X | 147725943 | 147730785 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 106000378 | 106009500 | X | 147742718 | 147746466 |
| X | 106062983 | 106065144 | X | 147750149 | 147752162 |
| X | 106126389 | 106130370 | X | 147778454 | 147784768 |
| X | 106151624 | 106152763 | X | 147790824 | 147793099 |
| X | 106180208 | 106183899 | X | 147800629 | 147803866 |
| X | 106322827 | 106325034 | X | 147814050 | 147816502 |
| X | 106335237 | 106338886 | X | 147887834 | 147889041 |
| X | 106401506 | 106403670 | X | 147895992 | 147897018 |
| X | 106428424 | 106431226 | X | 147916085 | 147922187 |
| X | 106442279 | 106445839 | X | 147949301 | 147956287 |
| X | 106453310 | 106457200 | X | 147963170 | 147965000 |
| X | 106470057 | 106470838 | X | 148025483 | 148029405 |
| X | 106477317 | 106480311 | X | 148092415 | 148098414 |
| X | 106514411 | 106515571 | X | 148112331 | 148112778 |
| X | 106578845 | 106593734 | X | 148118770 | 148119575 |
| X | 106648171 | 106653201 | X | 148296609 | 148299487 |
| X | 106658234 | 106660855 | X | 148303377 | 148306123 |
| X | 106671530 | 106680612 | X | 148312761 | 148323556 |
| X | 106688447 | 106693258 | X | 148344831 | 148351220 |
| X | 106726853 | 106760574 | X | 148381439 | 148384144 |
| X | 106801477 | 106852279 | X | 148389530 | 148391539 |
| X | 106868486 | 106906398 | X | 148392564 | 148395164 |
| X | 106915366 | 106917166 | X | 148398571 | 148401978 |
| X | 106956852 | 106959116 | X | 148413191 | 148414417 |
| X | 107066080 | 107068467 | X | 148422098 | 148436484 |
| X | 107111629 | 107113275 | X | 148493979 | 148496887 |
| X | 107125618 | 107130538 | X | 148519650 | 148521715 |
| X | 107178590 | 107181538 | X | 148536878 | 148572260 |
| X | 107220779 | 107221664 | X | 148579618 | 148581133 |
| X | 107269600 | 107271565 | X | 148594229 | 148596287 |
| X | 107344836 | 107352488 | X | 148598628 | 148601136 |
| X | 107363966 | 107365711 | X | 148647317 | 148652492 |
| X | 107372750 | 107375402 | X | 148690980 | 148698877 |
| X | 107383252 | 107388764 | X | 148747292 | 148752675 |
| X | 107432418 | 107436553 | X | 148754546 | 148757328 |
| X | 107464616 | 107475493 | X | 148765574 | 148765750 |
| X | 107499577 | 107503597 | X | 148770010 | 148774313 |
| X | 107525747 | 107529190 | X | 148852280 | 148866745 |
| X | 107533836 | 107541933 | X | 148921398 | 148936324 |
| X | 107559888 | 107561620 | X | 148947098 | 148950836 |
| X | 107645255 | 107648010 | X | 149014948 | 149019061 |
| X | 107663986 | 107665917 | X | 149048494 | 149049923 |
| X | 107670929 | 107671130 | X | 149084496 | 149085176 |
| X | 107731365 | 107732165 | X | 149120700 | 149122116 |
| X | 107754350 | 107755799 | X | 149140423 | 149142113 |
| X | 107864418 | 107867018 | X | 149177235 | 149177895 |
| X | 107915005 | 107916125 | X | 149219242 | 149222201 |
| X | 108105028 | 108106336 | X | 149231784 | 149233414 |
| X | 108158373 | 108159619 | X | 149233913 | 149234365 |
| X | 108250148 | 108260072 | X | 149240923 | 149241344 |
| X | 108286115 | 108288020 | X | 149245659 | 149248686 |
| X | 108308217 | 108312712 | X | 149255548 | 149257954 |
| X | 108366488 | 108378737 | X | 149265422 | 149266231 |
| X | 108385119 | 108393262 | X | 149279672 | 149285744 |
| X | 108399127 | 108403212 | X | 149371938 | 149373957 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 108475981 | 108476750 | | X | 149387976 | 149390040 |
| X | 108494755 | 108495208 | | X | 149419544 | 149439555 |
| X | 108533834 | 108541291 | | X | 149453223 | 149468495 |
| X | 108570898 | 108586771 | | X | 149517388 | 149519842 |
| X | 108612507 | 108637610 | | X | 149521838 | 149524434 |
| X | 108663330 | 108668612 | | X | 149539026 | 149543840 |
| X | 108693463 | 108694592 | | X | 149592556 | 149593811 |
| X | 108742712 | 108745299 | | X | 149611990 | 149615027 |
| X | 108747276 | 108751832 | | X | 149675388 | 149697901 |
| X | 108752525 | 108755341 | | X | 149726129 | 149727311 |
| X | 108758857 | 108763908 | | X | 149805131 | 149806000 |
| X | 108772661 | 108774484 | | X | 149810891 | 149819017 |
| X | 108810659 | 108810933 | | X | 149822644 | 149825197 |
| X | 108862028 | 108863890 | | X | 149857614 | 149864304 |
| X | 108913103 | 108914475 | | X | 149871987 | 149873219 |
| X | 108941133 | 108946757 | | X | 149876719 | 149878438 |
| X | 108975068 | 108975789 | | X | 149884747 | 149922054 |
| X | 108986094 | 108993586 | | X | 149937840 | 149938762 |
| X | 108994595 | 108995691 | | X | 149939684 | 149941133 |
| X | 109034430 | 109041007 | | X | 149988780 | 149990979 |
| X | 109088139 | 109096997 | | X | 149999054 | 150001967 |
| X | 109131234 | 109134185 | | X | 150030975 | 150035231 |
| X | 109134795 | 109141869 | | X | 150092404 | 150100702 |
| X | 109147159 | 109149379 | | X | 150166433 | 150168042 |
| X | 109161629 | 109164464 | | X | 150276356 | 150279401 |
| X | 109173347 | 109181094 | | X | 150291378 | 150297619 |
| X | 109215822 | 109219829 | | X | 150310787 | 150317217 |
| X | 109240830 | 109245409 | | X | 150351286 | 150354116 |
| X | 109257077 | 109263526 | | X | 150383638 | 150384908 |
| X | 109276865 | 109277731 | | X | 150416704 | 150422352 |
| X | 109294991 | 109296211 | | X | 150434725 | 150436900 |
| X | 109302265 | 109305709 | | X | 150480155 | 150483622 |
| X | 109330662 | 109336521 | | X | 150594599 | 150601058 |
| X | 109354380 | 109356546 | | X | 150609342 | 150630165 |
| X | 109397829 | 109400943 | | X | 150640123 | 150665027 |
| X | 109411668 | 109417300 | | X | 150674456 | 150675851 |
| X | 109438986 | 109440616 | | X | 150677706 | 150686508 |
| X | 109447233 | 109448813 | | X | 150719416 | 150720439 |
| X | 109492620 | 109496210 | | X | 150788044 | 150790735 |
| X | 109508656 | 109508851 | | X | 150818168 | 150818927 |
| X | 109548371 | 109550936 | | X | 150820041 | 150844786 |
| X | 109578640 | 109588570 | | X | 150873504 | 150875729 |
| X | 109642755 | 109646656 | | X | 150891080 | 150896907 |
| X | 109707464 | 109711232 | | X | 150911055 | 150913729 |
| X | 109723513 | 109726907 | | X | 150958910 | 150960484 |
| X | 109764455 | 109768439 | | X | 150989630 | 150995275 |
| X | 109776165 | 109777155 | | X | 151002921 | 151004702 |
| X | 109821646 | 109823925 | | X | 151036438 | 151039779 |
| X | 109832121 | 109836519 | | X | 151054297 | 151059641 |
| X | 109966449 | 109969675 | | X | 151130478 | 151133324 |
| X | 109995712 | 109996382 | | X | 151147264 | 151148840 |
| X | 110073824 | 110074638 | | X | 151162740 | 151166378 |
| X | 110130045 | 110131790 | | X | 151176168 | 151177716 |
| X | 110224031 | 110227482 | | X | 151196794 | 151203360 |
| X | 110244575 | 110264241 | | X | 151303959 | 151315868 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 110264639 | 110265661 | X | 151356301 | 151362247 |
| X | 110266550 | 110277529 | X | 151364974 | 151367301 |
| X | 110300691 | 110307641 | X | 151399242 | 151405166 |
| X | 110317988 | 110339987 | X | 151556503 | 151575221 |
| X | 110353226 | 110359006 | X | 151585921 | 151586430 |
| X | 110361430 | 110362221 | X | 151589896 | 151686493 |
| X | 110390401 | 110391111 | X | 151738448 | 151744529 |
| X | 110401088 | 110414961 | X | 151749435 | 151762183 |
| X | 110420182 | 110422488 | X | 151769300 | 151774571 |
| X | 110427688 | 110428913 | X | 151786958 | 151794770 |
| X | 110502493 | 110532313 | X | 151809480 | 151848664 |
| X | 110539576 | 110540655 | X | 151864814 | 151867602 |
| X | 110547928 | 110548233 | X | 151877539 | 151878660 |
| X | 110553928 | 110554828 | X | 151907059 | 151917092 |
| X | 110617199 | 110618600 | X | 151918098 | 151921028 |
| X | 110623869 | 110625462 | X | 151946928 | 151959486 |
| X | 110630868 | 110632405 | X | 151973312 | 151981270 |
| X | 110648629 | 110651508 | X | 151993509 | 152003671 |
| X | 110749280 | 110754939 | X | 152013858 | 152021051 |
| X | 110804458 | 110805580 | X | 152077492 | 152083536 |
| X | 110806142 | 110813701 | X | 152090813 | 152092793 |
| X | 110887777 | 110892512 | X | 152096954 | 152103381 |
| X | 110898843 | 110901366 | X | 152110906 | 152114433 |
| X | 110929052 | 110930237 | X | 152127827 | 152142899 |
| X | 110995751 | 110998652 | X | 152157626 | 152214598 |
| X | 111029534 | 111032837 | X | 152218762 | 152253206 |
| X | 111048332 | 111049800 | X | 152264553 | 152275047 |
| X | 111052076 | 111063379 | X | 152297917 | 152353769 |
| X | 111111375 | 111116171 | X | 152358641 | 152531934 |
| X | 111150290 | 111152256 | X | 152539514 | 152760921 |
| X | 111164781 | 111198564 | X | 152776394 | 152958716 |
| X | 111210417 | 111213591 | X | 152966381 | 152982955 |
| X | 111284590 | 111285871 | X | 153014749 | 153541555 |
| X | 111314894 | 111317473 | X | 153552850 | 153554659 |
| X | 111398564 | 111406104 | X | 153575098 | 153582331 |
| X | 111441996 | 111444936 | X | 153596252 | 153597941 |
| X | 111484550 | 111499869 | X | 153631770 | 153633224 |
| X | 111510400 | 111512826 | X | 153640447 | 153642978 |
| | | | X | 153643973 | 153666188 |
| | | | X | 153672786 | 153679298 |
| | | | X | 153686176 | 153687857 |
| | | | X | 153688498 | 153689524 |
| | | | X | 153698990 | 153702034 |
| | | | X | 153810681 | 153816720 |
| | | | X | 153906354 | 153909377 |
| | | | X | 153924361 | 153933971 |
| | | | X | 153934810 | 153939691 |
| | | | X | 153947897 | 153948890 |
| | | | X | 153951553 | 153955393 |
| | | | X | 153967573 | 153970751 |
| | | | X | 154017178 | 154019921 |
| | | | X | 154069928 | 154077399 |
| | | | X | 154094940 | 154098631 |
| | | | X | 154129394 | 154134220 |
| | | | X | 154173832 | 154176159 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| | | | | | X | 154418285 | 154418939 |
| | | | | | X | 154447710 | 154449322 |
| | | | | | X | 154529021 | 154535990 |
| | | | | | X | 154628261 | 154632846 |
| | | | | | X | 154648770 | 154651670 |
| | | | | | X | 154683664 | 154702912 |
| | | | | | X | 154744789 | 154749412 |
| | | | | | X | 154757028 | 154765794 |
| | | | | | X | 154827805 | 154830356 |
| | | | | | X | 154832460 | 154912255 |
| X | 867 | 456833 | | | X | 29279956 | 29283974 |
| X | 462433 | 499554 | | | X | 29320057 | 29322541 |
| X | 512821 | 515110 | | | X | 29322591 | 29324128 |
| X | 518167 | 520398 | | | X | 29332848 | 29334799 |
| X | 523683 | 769972 | | | X | 29366860 | 29369145 |
| X | 779175 | 1612055 | | | X | 29393529 | 29395451 |
| X | 1618152 | 1641141 | | | X | 29425077 | 29427557 |
| X | 1651530 | 2453176 | | | X | 29448681 | 29453638 |
| X | 2465075 | 2469755 | | | X | 29489047 | 29491138 |
| X | 2476595 | 2540166 | | | X | 29533548 | 29535619 |
| X | 2557259 | 2562164 | | | X | 29621781 | 29624696 |
| X | 2567795 | 2620253 | | | X | 29626057 | 29626952 |
| X | 2626757 | 2696912 | | | X | 29668372 | 29668922 |
| X | 2704192 | 2706776 | | | X | 29759413 | 29761632 |
| X | 2714808 | 2733346 | | | X | 29796320 | 29798375 |
| X | 2762305 | 2777427 | | | X | 29851233 | 29852898 |
| X | 2788417 | 2798067 | | | X | 29855230 | 29855300 |
| X | 2807911 | 2828692 | | | X | 29868593 | 29870232 |
| X | 2834141 | 2874881 | | | X | 29879032 | 29880152 |
| X | 2882251 | 2898167 | | | X | 29884928 | 29886305 |
| X | 2940274 | 2943838 | | | X | 29904546 | 29915599 |
| X | 2954753 | 2958448 | | | X | 29924279 | 29926758 |
| X | 2983087 | 3013145 | | | X | 29945797 | 29948809 |
| X | 3033912 | 3034262 | | | X | 29974867 | 29979384 |
| X | 3037742 | 3044144 | | | X | 29996128 | 29998906 |
| X | 3056645 | 3061646 | | | X | 30031548 | 30038379 |
| X | 3065628 | 3067430 | | | X | 30040390 | 30045875 |
| X | 3070040 | 3074953 | | | X | 30101298 | 30102971 |
| X | 3136849 | 3152968 | | | X | 30108453 | 30114888 |
| X | 3167782 | 3172716 | | | X | 30142199 | 30144994 |
| X | 3181396 | 3186936 | | | X | 30165585 | 30166330 |
| X | 3187781 | 3188781 | | | X | 30180800 | 30182740 |
| X | 3192060 | 3195578 | | | X | 30200355 | 30207149 |
| X | 3207892 | 3209632 | | | X | 30213926 | 30218237 |
| X | 3214322 | 3214997 | | | X | 30226241 | 30228914 |
| X | 3221033 | 3222930 | | | X | 30236949 | 30239091 |
| X | 3233391 | 3239591 | | | X | 30245488 | 30249374 |
| X | 3244072 | 3260180 | | | X | 30262967 | 30263392 |
| X | 3272426 | 3277006 | | | X | 30267940 | 30269930 |
| X | 3287518 | 3289938 | | | X | 30282797 | 30283952 |
| X | 3295677 | 3296377 | | | X | 30297280 | 30298277 |
| X | 3344481 | 3345556 | | | X | 30300717 | 30301382 |
| X | 3354199 | 3356159 | | | X | 30316992 | 30318024 |
| X | 3361465 | 3366954 | | | X | 30354970 | 30356650 |
| X | 3395754 | 3396599 | | | X | 30385282 | 30386422 |

The chromosomal positon was obtained from UCSC genome browser (http://genome.ucsc.edu/) build 36.

APPENDIX D: Chromosome X
Page 38 of 73

| Chr | Start | End | | | Chr | Start | End |
|---|---|---|---|---|---|---|---|
| X | 3417097 | 3420437 | | | X | 30398044 | 30398724 |
| X | 3424777 | 3426668 | | | X | 30403578 | 30405802 |
| X | 3428995 | 3433106 | | | X | 30435423 | 30437685 |
| X | 3443594 | 3453995 | | | X | 30441292 | 30442820 |
| X | 3463209 | 3468842 | | | X | 30487839 | 30489345 |
| X | 3477239 | 3478594 | | | X | 30536540 | 30537944 |
| X | 3493127 | 3497667 | | | X | 30557764 | 30558964 |
| X | 3516709 | 3965659 | | | X | 30580859 | 30582319 |
| X | 4046992 | 4048028 | | | X | 30594504 | 30600906 |
| X | 4051237 | 4053648 | | | X | 30612173 | 30613951 |
| X | 4087786 | 4090113 | | | X | 30660129 | 30660928 |
| X | 4121429 | 4122636 | | | X | 30775626 | 30776866 |
| X | 4176433 | 4177569 | | | X | 30798483 | 30800464 |
| X | 4241601 | 4243586 | | | X | 30816538 | 30819428 |
| X | 4265157 | 4271735 | | | X | 30838918 | 30841773 |
| X | 4295538 | 4297179 | | | X | 30846719 | 30848357 |
| X | 4305087 | 4308926 | | | X | 30871189 | 30872934 |
| X | 4385344 | 4386764 | | | X | 30885579 | 30886079 |
| X | 4436434 | 4438595 | | | X | 30887439 | 30890639 |
| X | 4460156 | 4465384 | | | X | 30903332 | 30904712 |
| X | 4466478 | 4475351 | | | X | 30908201 | 30909352 |
| X | 4487805 | 4488285 | | | X | 30932940 | 30934630 |
| X | 4512571 | 4518108 | | | X | 30959727 | 30963028 |
| X | 4545038 | 4545813 | | | X | 30978338 | 30979634 |
| X | 4558004 | 4559826 | | | X | 30985219 | 30988137 |
| X | 4566098 | 4567098 | | | X | 30999268 | 31000808 |
| X | 4583659 | 4585583 | | | X | 31034983 | 31036683 |
| X | 4622995 | 4626740 | | | X | 31041214 | 31041889 |
| X | 4646424 | 4647721 | | | X | 31045817 | 31048871 |
| X | 4660969 | 4661699 | | | X | 31106690 | 31107515 |
| X | 4662930 | 4665387 | | | X | 31115593 | 31117083 |
| X | 4683466 | 4686166 | | | X | 31122396 | 31124947 |
| X | 4699912 | 4701912 | | | X | 31141217 | 31142392 |
| X | 4712049 | 4715882 | | | X | 31147234 | 31149788 |
| X | 4843460 | 4846759 | | | X | 31194105 | 31196055 |
| X | 4857451 | 4858972 | | | X | 31296086 | 31298488 |
| X | 4888901 | 4890482 | | | X | 31350921 | 31352016 |
| X | 4915318 | 4917743 | | | X | 31410325 | 31412992 |
| X | 4923918 | 4926531 | | | X | 31417670 | 31419476 |
| X | 5095746 | 5100527 | | | X | 31434620 | 31437170 |
| X | 5108230 | 5113937 | | | X | 31487268 | 31489125 |
| X | 5123742 | 5128143 | | | X | 31528787 | 31531567 |
| X | 5162677 | 5164836 | | | X | 31559886 | 31564453 |
| X | 5172214 | 5174149 | | | X | 31645676 | 31648442 |
| X | 5183832 | 5185637 | | | X | 31693124 | 31693464 |
| X | 5195788 | 5197830 | | | X | 31723236 | 31731172 |
| X | 5211120 | 5212685 | | | X | 31733787 | 31734562 |
| X | 5273351 | 5274916 | | | X | 31738899 | 31740910 |
| X | 5290269 | 5297431 | | | X | 31774395 | 31776625 |
| X | 5318809 | 5319525 | | | X | 31919094 | 31919973 |
| X | 5324089 | 5326174 | | | X | 31938694 | 31939849 |
| X | 5332948 | 5334373 | | | X | 31950841 | 31952798 |
| X | 5357299 | 5358597 | | | X | 31963909 | 31965669 |
| X | 5482296 | 5486094 | | | X | 32033825 | 32034720 |
| X | 5557090 | 5558648 | | | X | 32041197 | 32044097 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 5586965 | 5589722 | X | 32060729 | 32062930 |
| X | 5599441 | 5602028 | X | 32068043 | 32069995 |
| X | 5629599 | 5630949 | X | 32079306 | 32081078 |
| X | 5670180 | 5673363 | X | 32113107 | 32115606 |
| X | 5681181 | 5682353 | X | 32187764 | 32188964 |
| X | 5711803 | 5713518 | X | 32209288 | 32212589 |
| X | 5725691 | 5729769 | X | 32285239 | 32286369 |
| X | 5753114 | 5756494 | X | 32370327 | 32372677 |
| X | 5814993 | 5832012 | X | 32384554 | 32385685 |
| X | 5835229 | 5838485 | X | 32411083 | 32412816 |
| X | 5933363 | 5936281 | X | 32440735 | 32443508 |
| X | 5966559 | 5967644 | X | 32463271 | 32466696 |
| X | 5988371 | 5990550 | X | 32490999 | 32495134 |
| X | 6032629 | 6034910 | X | 32591935 | 32592872 |
| X | 6044001 | 6046826 | X | 32615867 | 32616151 |
| X | 6060327 | 6061412 | X | 32712937 | 32714062 |
| X | 6064620 | 6066315 | X | 32751652 | 32753242 |
| X | 6079042 | 6080302 | X | 32862265 | 32864541 |
| X | 6131996 | 6132696 | X | 32880094 | 32880594 |
| X | 6141934 | 6144207 | X | 32890297 | 32891002 |
| X | 6155591 | 6156644 | X | 32891762 | 32897164 |
| X | 6172945 | 6174547 | X | 32902787 | 32904709 |
| X | 6188869 | 6191250 | X | 32935257 | 32936142 |
| X | 6200021 | 6206948 | X | 32981860 | 32984905 |
| X | 6210601 | 6212551 | X | 33040679 | 33044740 |
| X | 6227831 | 6228236 | X | 33179646 | 33181111 |
| X | 6271364 | 6273046 | X | 33284408 | 33285698 |
| X | 6286067 | 6288433 | X | 33328454 | 33329494 |
| X | 6350201 | 6351336 | X | 33408959 | 33410779 |
| X | 6368942 | 6370264 | X | 33455630 | 33457960 |
| X | 6378875 | 6382670 | X | 33558800 | 33559910 |
| X | 6466012 | 6469207 | X | 33623804 | 33625379 |
| X | 6494961 | 6496370 | X | 33629296 | 33632900 |
| X | 6505329 | 6508930 | X | 33661549 | 33664359 |
| X | 6550962 | 6555368 | X | 33772283 | 33774318 |
| X | 6617291 | 6619286 | X | 33840248 | 33842318 |
| X | 6659448 | 6661777 | X | 33868316 | 33869431 |
| X | 6668787 | 6669704 | X | 33875152 | 33878939 |
| X | 6671980 | 6672475 | X | 33923498 | 33926994 |
| X | 6771028 | 6773568 | X | 33964431 | 33966346 |
| X | 6813128 | 6814093 | X | 33974756 | 33979966 |
| X | 6816758 | 6817153 | X | 34000517 | 34005912 |
| X | 6850855 | 6853025 | X | 34040953 | 34042153 |
| X | 6859082 | 6860514 | X | 34053350 | 34060834 |
| X | 6894919 | 6897250 | X | 34074231 | 34076891 |
| X | 6904776 | 6907733 | X | 34111791 | 34112886 |
| X | 6918091 | 6920220 | X | 34167422 | 34168397 |
| X | 6965489 | 6968704 | X | 34211657 | 34217955 |
| X | 6992090 | 6994690 | X | 34225840 | 34229357 |
| X | 7002959 | 7005634 | X | 34270875 | 34274805 |
| X | 7021483 | 7023494 | X | 34283304 | 34286272 |
| X | 7054025 | 7056049 | X | 34315776 | 34316581 |
| X | 7058259 | 7061529 | X | 34383678 | 34384439 |
| X | 7080700 | 7082370 | X | 34418585 | 34421232 |
| X | 7115581 | 7116838 | X | 34439706 | 34442461 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 7146818 | 7149170 | | | X | 34489030 | 34492313 |
| X | 7161789 | 7163104 | | | X | 34504178 | 34508366 |
| X | 7185398 | 7188777 | | | X | 34540246 | 34543906 |
| X | 7258027 | 7258684 | | | X | 34555506 | 34558367 |
| X | 7286774 | 7288854 | | | X | 34558487 | 34560583 |
| X | 7310148 | 7318257 | | | X | 34571017 | 34576733 |
| X | 7339177 | 7342039 | | | X | 34583750 | 34586091 |
| X | 7346719 | 7349965 | | | X | 34588118 | 34589796 |
| X | 7356000 | 7359028 | | | X | 34592107 | 34595004 |
| X | 7441089 | 7441769 | | | X | 34616269 | 34619687 |
| X | 7468278 | 7468958 | | | X | 34659066 | 34666109 |
| X | 7482321 | 7483701 | | | X | 34681144 | 34684079 |
| X | 7486391 | 7487453 | | | X | 34692963 | 34699668 |
| X | 7554705 | 7557205 | | | X | 34741818 | 34746425 |
| X | 7591034 | 7592129 | | | X | 34772790 | 34776177 |
| X | 7599976 | 7601031 | | | X | 34824637 | 34826051 |
| X | 7628213 | 7631640 | | | X | 34830549 | 34832244 |
| X | 7702394 | 7710023 | | | X | 34869768 | 34872723 |
| X | 7724280 | 7725060 | | | X | 34895900 | 34898521 |
| X | 7750860 | 7753122 | | | X | 34911397 | 34917467 |
| X | 7762373 | 7764163 | | | X | 34934995 | 34937279 |
| X | 7765803 | 7769308 | | | X | 34939934 | 34941305 |
| X | 7770038 | 7772861 | | | X | 34942746 | 34947006 |
| X | 7814354 | 7816209 | | | X | 34974873 | 34977869 |
| X | 7818672 | 7820131 | | | X | 35038804 | 35046351 |
| X | 7855678 | 7861535 | | | X | 35078522 | 35079282 |
| X | 7869141 | 7870576 | | | X | 35080593 | 35085618 |
| X | 7878776 | 7879331 | | | X | 35101222 | 35103001 |
| X | 7934551 | 7935769 | | | X | 35200840 | 35203938 |
| X | 7976308 | 7983059 | | | X | 35217889 | 35221599 |
| X | 8049443 | 8052970 | | | X | 35255616 | 35257291 |
| X | 8072319 | 8074184 | | | X | 35283327 | 35285647 |
| X | 8111402 | 8112217 | | | X | 35315650 | 35318629 |
| X | 8118310 | 8120100 | | | X | 35324962 | 35332315 |
| X | 8139924 | 8140887 | | | X | 35338518 | 35339866 |
| X | 8155359 | 8155988 | | | X | 35388336 | 35390226 |
| X | 8160486 | 8164536 | | | X | 35394853 | 35395538 |
| X | 8167631 | 8168311 | | | X | 35395784 | 35397364 |
| X | 8204092 | 8205477 | | | X | 35425086 | 35428298 |
| X | 8208026 | 8211052 | | | X | 35437552 | 35439697 |
| X | 8217189 | 8218284 | | | X | 35496009 | 35496954 |
| X | 8237023 | 8239476 | | | X | 35523708 | 35525993 |
| X | 8241706 | 8243543 | | | X | 35537831 | 35540587 |
| X | 8255782 | 8258418 | | | X | 35671626 | 35673076 |
| X | 8314615 | 8317700 | | | X | 35698469 | 35703554 |
| X | 8379130 | 8381942 | | | X | 35726442 | 35727737 |
| X | 8397982 | 8399487 | | | X | 35745270 | 35746566 |
| X | 8403461 | 8407002 | | | X | 35817664 | 35819515 |
| X | 8492099 | 8499301 | | | X | 36021843 | 36031836 |
| X | 8543639 | 8547262 | | | X | 36141715 | 36147156 |
| X | 8569169 | 8570398 | | | X | 36193349 | 36195890 |
| X | 8583116 | 8585371 | | | X | 36199390 | 36202042 |
| X | 8598491 | 8599536 | | | X | 36241076 | 36244311 |
| X | 8610278 | 8614302 | | | X | 36284760 | 36285320 |
| X | 8643659 | 8645140 | | | X | 36291779 | 36298076 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 8660180 | 8662723 | X | 36319063 | 36320938 |
| X | 8665539 | 8666252 | X | 36348501 | 36350663 |
| X | 8669014 | 8677102 | X | 36390441 | 36403744 |
| X | 8681693 | 8682883 | X | 36455670 | 36459380 |
| X | 8709930 | 8712255 | X | 36471535 | 36473315 |
| X | 8722537 | 8723422 | X | 36501521 | 36502707 |
| X | 8726715 | 8730168 | X | 36506639 | 36511239 |
| X | 8756559 | 8758639 | X | 36529341 | 36536353 |
| X | 8762819 | 8764514 | X | 36561308 | 36570341 |
| X | 8772806 | 8774788 | X | 36615940 | 36618270 |
| X | 8868597 | 8869492 | X | 36640577 | 36646397 |
| X | 8873762 | 8877186 | X | 36652286 | 36653391 |
| X | 8888988 | 8893399 | X | 36653966 | 36656646 |
| X | 8897250 | 8898323 | X | 36657176 | 36663438 |
| X | 8956089 | 8957414 | X | 36671426 | 36674558 |
| X | 9039815 | 9044588 | X | 36676763 | 36713763 |
| X | 9045306 | 9047201 | X | 36725413 | 36726218 |
| X | 9053238 | 9054431 | X | 36731847 | 36735424 |
| X | 9065557 | 9068434 | X | 36750670 | 36751860 |
| X | 9072281 | 9072828 | X | 36759701 | 36762543 |
| X | 9078860 | 9083478 | X | 36795848 | 36799058 |
| X | 9144914 | 9148743 | X | 36838451 | 36839521 |
| X | 9155508 | 9156013 | X | 36850028 | 36851738 |
| X | 9168012 | 9170227 | X | 36881364 | 36884703 |
| X | 9195971 | 9204099 | X | 36884883 | 36893255 |
| X | 9222503 | 9225309 | X | 36898940 | 36904587 |
| X | 9248969 | 9250206 | X | 36921748 | 36924068 |
| X | 9260538 | 9267619 | X | 36935996 | 36940116 |
| X | 9268384 | 9269904 | X | 36940676 | 36941876 |
| X | 9275235 | 9293185 | X | 36946568 | 36953256 |
| X | 9298198 | 9302822 | X | 36961930 | 36963500 |
| X | 9309919 | 9314304 | X | 36972599 | 36974811 |
| X | 9325711 | 9349095 | X | 36988940 | 36990076 |
| X | 9357376 | 9361211 | X | 37003760 | 37006977 |
| X | 9370994 | 9374190 | X | 37046524 | 37047809 |
| X | 9379929 | 9382182 | X | 37063453 | 37066193 |
| X | 9395339 | 9403804 | X | 37093024 | 37094682 |
| X | 9419561 | 9425151 | X | 37106209 | 37108912 |
| X | 9443367 | 9476124 | X | 37122821 | 37124962 |
| X | 9492815 | 9497551 | X | 37180430 | 37181345 |
| X | 9517963 | 9537691 | X | 37185292 | 37186712 |
| X | 9570439 | 9592153 | X | 37208056 | 37212823 |
| X | 9607578 | 9648532 | X | 37248877 | 37251343 |
| X | 9659509 | 9668306 | X | 37283104 | 37284585 |
| X | 9672279 | 9672986 | X | 37285430 | 37289761 |
| X | 9687661 | 9693518 | X | 37302268 | 37304228 |
| X | 9705070 | 9714725 | X | 37315619 | 37317089 |
| X | 9719125 | 9728988 | X | 37343562 | 37347837 |
| X | 9756395 | 9803367 | X | 37369642 | 37372527 |
| X | 9816465 | 9835714 | X | 37383517 | 37388609 |
| X | 9849591 | 9875455 | X | 37500493 | 37508751 |
| X | 9884832 | 9893150 | X | 37537095 | 37547872 |
| X | 9895456 | 9900016 | X | 37590609 | 37592017 |
| X | 9919649 | 9921659 | X | 37594387 | 37595142 |
| X | 9924658 | 9934350 | X | 37643694 | 37645679 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 9938921 | 9939846 | | X | 37664319 | 37668484 |
| X | 9940816 | 9944971 | | X | 37730129 | 37733005 |
| X | 9949014 | 9953515 | | X | 37759297 | 37761682 |
| X | 9964664 | 9966610 | | X | 37768985 | 37772696 |
| X | 9970228 | 9975752 | | X | 37781185 | 37782885 |
| X | 9993217 | 9995012 | | X | 37813675 | 37829187 |
| X | 10017498 | 10023425 | | X | 37837039 | 37838984 |
| X | 10029821 | 10031956 | | X | 37846374 | 37855634 |
| X | 10037208 | 10074715 | | X | 37885178 | 37886643 |
| X | 10091360 | 10095356 | | X | 37889843 | 37894898 |
| X | 10097704 | 10104079 | | X | 37898097 | 37900148 |
| X | 10111757 | 10123052 | | X | 37906433 | 37915753 |
| X | 10198408 | 10203343 | | X | 37929594 | 37932565 |
| X | 10211682 | 10214000 | | X | 37950705 | 37952185 |
| X | 10225119 | 10226811 | | X | 37963818 | 37967263 |
| X | 10236893 | 10238498 | | X | 37983600 | 37984540 |
| X | 10267662 | 10274719 | | X | 38000249 | 38001249 |
| X | 10298151 | 10299217 | | X | 38059740 | 38061893 |
| X | 10300042 | 10305679 | | X | 38070713 | 38072004 |
| X | 10320139 | 10321438 | | X | 38079365 | 38080222 |
| X | 10325663 | 10327813 | | X | 38087364 | 38088059 |
| X | 10359453 | 10359468 | | X | 38099842 | 38101015 |
| X | 10381507 | 10384969 | | X | 38120304 | 38122414 |
| X | 10431334 | 10437613 | | X | 38139034 | 38141492 |
| X | 10445589 | 10446379 | | X | 38161541 | 38163346 |
| X | 10453026 | 10455070 | | X | 38168936 | 38170831 |
| X | 10472804 | 10474645 | | X | 38174143 | 38175987 |
| X | 10516908 | 10517728 | | X | 38211176 | 38214227 |
| X | 10536398 | 10539049 | | X | 38232476 | 38239393 |
| X | 10544203 | 10545863 | | X | 38257234 | 38258284 |
| X | 10547366 | 10548521 | | X | 38304197 | 38307448 |
| X | 10549056 | 10550501 | | X | 38315437 | 38317225 |
| X | 10617644 | 10618815 | | X | 38340594 | 38345962 |
| X | 10746904 | 10749114 | | X | 38351301 | 38352136 |
| X | 10829213 | 10830663 | | X | 38366008 | 38369384 |
| X | 10837947 | 10839167 | | X | 38371739 | 38379083 |
| X | 10843818 | 10852819 | | X | 38463160 | 38465506 |
| X | 10866999 | 10873388 | | X | 38479568 | 38481490 |
| X | 10898562 | 10903413 | | X | 38502224 | 38504839 |
| X | 10983722 | 10985001 | | X | 38505089 | 38507422 |
| X | 10988317 | 10992254 | | X | 38544388 | 38550289 |
| X | 11011782 | 11013332 | | X | 38551409 | 38556208 |
| X | 11022512 | 11024227 | | X | 38576005 | 38583662 |
| X | 11036505 | 11040744 | | X | 38603428 | 38605283 |
| X | 11093902 | 11096702 | | X | 38612847 | 38617206 |
| X | 11101959 | 11103152 | | X | 38623511 | 38627757 |
| X | 11136717 | 11138092 | | X | 38666637 | 38669232 |
| X | 11141895 | 11144325 | | X | 38679157 | 38694663 |
| X | 11154710 | 11155567 | | X | 38712123 | 38720659 |
| X | 11165024 | 11168693 | | X | 38728952 | 38736387 |
| X | 11210576 | 11214707 | | X | 38775291 | 38776872 |
| X | 11219536 | 11220316 | | X | 38788541 | 38790731 |
| X | 11245021 | 11247317 | | X | 38804830 | 38805950 |
| X | 11266861 | 11268471 | | X | 38849122 | 38850102 |
| X | 11269951 | 11271426 | | X | 38878527 | 38878657 |

The chromosomal positon was obtained from UCSC genome browser (http://genome.ucsc.edu/) build 36.

APPENDIX D: Chromosome X
Page 43 of 73

| Chr | Start | End | Chr | Start | End |
|---|---|---|---|---|---|
| X | 11280170 | 11281876 | X | 38879622 | 38884452 |
| X | 11295555 | 11298112 | X | 38896880 | 38899147 |
| X | 11302134 | 11303889 | X | 38902403 | 38907351 |
| X | 11322791 | 11332107 | X | 38909047 | 38910814 |
| X | 11345755 | 11349531 | X | 38942120 | 38944287 |
| X | 11362017 | 11364164 | X | 38957595 | 38969816 |
| X | 11372663 | 11375285 | X | 38986920 | 38994411 |
| X | 11383418 | 11387288 | X | 39002943 | 39004233 |
| X | 11397271 | 11402940 | X | 39061615 | 39063713 |
| X | 11458165 | 11461354 | X | 39102210 | 39105366 |
| X | 11471259 | 11476014 | X | 39117548 | 39118843 |
| X | 11492454 | 11494789 | X | 39121764 | 39123605 |
| X | 11535328 | 11541962 | X | 39140912 | 39143431 |
| X | 11577212 | 11581027 | X | 39159244 | 39167574 |
| X | 11592520 | 11594591 | X | 39186933 | 39191551 |
| X | 11652872 | 11669115 | X | 39208622 | 39209507 |
| X | 11683647 | 11687005 | X | 39257073 | 39257758 |
| X | 11730094 | 11732489 | X | 39258253 | 39264296 |
| X | 11753572 | 11757948 | X | 39272968 | 39274625 |
| X | 11778515 | 11780577 | X | 39279180 | 39287492 |
| X | 11832440 | 11833643 | X | 39319712 | 39322142 |
| X | 11873153 | 11875486 | X | 39334462 | 39335052 |
| X | 11920484 | 11921426 | X | 39366195 | 39367165 |
| X | 11948113 | 11952095 | X | 39385661 | 39387556 |
| X | 11960377 | 11962069 | X | 39415677 | 39418352 |
| X | 12014938 | 12019855 | X | 39419832 | 39421673 |
| X | 12043556 | 12045948 | X | 39422228 | 39423093 |
| X | 12049981 | 12050756 | X | 39450711 | 39451711 |
| X | 12056543 | 12059238 | X | 39461964 | 39463434 |
| X | 12060810 | 12062235 | X | 39465585 | 39466375 |
| X | 12064072 | 12067534 | X | 39474138 | 39475264 |
| X | 12082826 | 12087006 | X | 39496347 | 39510398 |
| X | 12090508 | 12090943 | X | 39522712 | 39526770 |
| X | 12097516 | 12102380 | X | 39537804 | 39539281 |
| X | 12171242 | 12173060 | X | 39547849 | 39553684 |
| X | 12194682 | 12196933 | X | 39563655 | 39566864 |
| X | 12210871 | 12211967 | X | 39584947 | 39588237 |
| X | 12215707 | 12218760 | X | 39609193 | 39617510 |
| X | 12247546 | 12249279 | X | 39638785 | 39655324 |
| X | 12252914 | 12262686 | X | 39658709 | 39659439 |
| X | 12295237 | 12295747 | X | 39672562 | 39675687 |
| X | 12327548 | 12330369 | X | 39698075 | 39702129 |
| X | 12334624 | 12337264 | X | 39707189 | 39708274 |
| X | 12344064 | 12348804 | X | 39711523 | 39716172 |
| X | 12359324 | 12361669 | X | 39722937 | 39729790 |
| X | 12388813 | 12391392 | X | 39751223 | 39752763 |
| X | 12414536 | 12418151 | X | 39766347 | 39769603 |
| X | 12435528 | 12440871 | X | 39774258 | 39779576 |
| X | 12456294 | 12458140 | X | 39789013 | 39793800 |
| X | 12510002 | 12512422 | X | 39816628 | 39820044 |
| X | 12537790 | 12538450 | X | 39828146 | 39828701 |
| X | 12585989 | 12589101 | X | 39831707 | 39835009 |
| X | 12606431 | 12607521 | X | 39838505 | 39843307 |
| X | 12635359 | 12637097 | X | 39860785 | 39884304 |
| X | 12644287 | 12650792 | X | 39899951 | 39902234 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 12651687 | 12657524 | X | 39910931 | 39913523 |
| X | 12659802 | 12663652 | X | 39924412 | 39933212 |
| X | 12682912 | 12685982 | X | 39948297 | 39950217 |
| X | 12691230 | 12704837 | X | 39964158 | 39968484 |
| X | 12709301 | 12709922 | X | 39976154 | 39981538 |
| X | 12718938 | 12720996 | X | 39986306 | 39990261 |
| X | 12725524 | 12731654 | X | 40003737 | 40008021 |
| X | 12734397 | 12741649 | X | 40037181 | 40055223 |
| X | 12743437 | 12744172 | X | 40068164 | 40069146 |
| X | 12752453 | 12758921 | X | 40102709 | 40108094 |
| X | 12793989 | 12795709 | X | 40116671 | 40118742 |
| X | 12799836 | 12801291 | X | 40242574 | 40244969 |
| X | 12809825 | 12811774 | X | 40252148 | 40256243 |
| X | 12813832 | 12815202 | X | 40298262 | 40307092 |
| X | 12827947 | 12832023 | X | 40309707 | 40311032 |
| X | 12868770 | 12872345 | X | 40314412 | 40319510 |
| X | 12881239 | 12883716 | X | 40321788 | 40330133 |
| X | 12887552 | 12892578 | X | 40366310 | 40368907 |
| X | 12908193 | 12911734 | X | 40374983 | 40377887 |
| X | 12955154 | 12958204 | X | 40411505 | 40414423 |
| X | 12970499 | 12974179 | X | 40431152 | 40432612 |
| X | 13002374 | 13004599 | X | 40473955 | 40474453 |
| X | 13026871 | 13028500 | X | 40487929 | 40489629 |
| X | 13043783 | 13044603 | X | 40515375 | 40516538 |
| X | 13076018 | 13080121 | X | 40534900 | 40536105 |
| X | 13083036 | 13085579 | X | 40543203 | 40548373 |
| X | 13101668 | 13102713 | X | 40571988 | 40573638 |
| X | 13121837 | 13122965 | X | 40574151 | 40581309 |
| X | 13138033 | 13139398 | X | 40677388 | 40677855 |
| X | 13169063 | 13170539 | X | 40681485 | 40684052 |
| X | 13191927 | 13193539 | X | 40708189 | 40710748 |
| X | 13201838 | 13204109 | X | 40751137 | 40764606 |
| X | 13238870 | 13246750 | X | 40793389 | 40794126 |
| X | 13247741 | 13248801 | X | 40821018 | 40821338 |
| X | 13305796 | 13307861 | X | 40836369 | 40840599 |
| X | 13324689 | 13325744 | X | 40866893 | 40869792 |
| X | 13347553 | 13349238 | X | 40937033 | 40939561 |
| X | 13367282 | 13371194 | X | 40965565 | 40967155 |
| X | 13373611 | 13374311 | X | 40982008 | 41048916 |
| X | 13391048 | 13394975 | X | 41069578 | 41072692 |
| X | 13426371 | 13427626 | X | 41095754 | 41112673 |
| X | 13436511 | 13440105 | X | 41119143 | 41139937 |
| X | 13445343 | 13446348 | X | 41150763 | 41154669 |
| X | 13452661 | 13459722 | X | 41186936 | 41200660 |
| X | 13462967 | 13464577 | X | 41214972 | 41229418 |
| X | 13480164 | 13484918 | X | 41236344 | 41240476 |
| X | 13491002 | 13494908 | X | 41252157 | 41253207 |
| X | 13497979 | 13499004 | X | 41315144 | 41318564 |
| X | 13499314 | 13503079 | X | 41346347 | 41347295 |
| X | 13512489 | 13513679 | X | 41389343 | 41390278 |
| X | 13554063 | 13556438 | X | 41415285 | 41419634 |
| X | 13563873 | 13566578 | X | 41453785 | 41455075 |
| X | 13579561 | 13580386 | X | 41486334 | 41487399 |
| X | 13593198 | 13600218 | X | 41652622 | 41652922 |
| X | 13629892 | 13632237 | X | 41666537 | 41668172 |

The chromosomal positon was obtained from UCSC genome browser (http://genome.ucsc.edu/) build 36.

APPENDIX D: Chromosome X
Page 45 of 73

| Chr | Start | End | Chr | Start | End |
|---|---|---|---|---|---|
| X | 13683462 | 13688189 | X | 41683487 | 41687401 |
| X | 13693651 | 13694946 | X | 41703180 | 41705455 |
| X | 13712105 | 13716004 | X | 41706697 | 41708836 |
| X | 13724425 | 13727517 | X | 41793464 | 41795962 |
| X | 13736824 | 13741193 | X | 41798191 | 41799561 |
| X | 13747707 | 13756185 | X | 41815354 | 41818384 |
| X | 13767716 | 13771118 | X | 41826630 | 41831712 |
| X | 13773791 | 13775231 | X | 41833908 | 41835793 |
| X | 13792348 | 13794432 | X | 41852867 | 41854068 |
| X | 13796533 | 13798615 | X | 41889726 | 41895516 |
| X | 13799643 | 13801229 | X | 41909882 | 41912352 |
| X | 13827674 | 13828844 | X | 41922452 | 41930377 |
| X | 13830529 | 13833537 | X | 41933444 | 41934194 |
| X | 13858352 | 13860178 | X | 41955448 | 41958371 |
| X | 13871044 | 13872345 | X | 41961761 | 41966201 |
| X | 13878140 | 13882151 | X | 41983705 | 41986945 |
| X | 13909558 | 13910345 | X | 42005771 | 42008018 |
| X | 13934053 | 13937366 | X | 42061988 | 42065578 |
| X | 13971362 | 13974883 | X | 42142419 | 42144106 |
| X | 13992082 | 13994502 | X | 42176898 | 42178559 |
| X | 14001418 | 14002282 | X | 42185620 | 42189453 |
| X | 14045718 | 14046593 | X | 42204017 | 42205908 |
| X | 14058183 | 14059596 | X | 42216066 | 42221331 |
| X | 14065651 | 14066441 | X | 42231668 | 42232543 |
| X | 14091950 | 14101882 | X | 42236203 | 42238795 |
| X | 14141715 | 14144455 | X | 42282679 | 42286319 |
| X | 14152202 | 14155719 | X | 42292147 | 42305308 |
| X | 14160792 | 14163570 | X | 42314944 | 42316344 |
| X | 14174254 | 14174584 | X | 42346381 | 42348404 |
| X | 14176394 | 14177469 | X | 42362898 | 42365934 |
| X | 14184361 | 14185156 | X | 42385528 | 42389666 |
| X | 14187244 | 14189759 | X | 42429753 | 42430933 |
| X | 14201883 | 14205040 | X | 42453698 | 42460122 |
| X | 14225817 | 14229545 | X | 42482838 | 42494795 |
| X | 14245950 | 14252679 | X | 42506793 | 42515240 |
| X | 14260177 | 14261659 | X | 42535991 | 42536926 |
| X | 14278485 | 14284618 | X | 42543689 | 42545302 |
| X | 14292579 | 14294254 | X | 42575440 | 42580495 |
| X | 14310510 | 14313970 | X | 42587293 | 42591446 |
| X | 14355463 | 14362185 | X | 42684155 | 42686970 |
| X | 14366935 | 14369589 | X | 42718258 | 42719850 |
| X | 14403495 | 14417013 | X | 42723502 | 42725091 |
| X | 14473747 | 14476887 | X | 42729524 | 42733240 |
| X | 14505658 | 14508600 | X | 42738817 | 42740097 |
| X | 14512771 | 14513681 | X | 42752046 | 42754102 |
| X | 14522723 | 14524104 | X | 42785433 | 42786877 |
| X | 14525129 | 14526449 | X | 42805252 | 42808553 |
| X | 14532066 | 14535195 | X | 42849174 | 42852024 |
| X | 14559556 | 14560760 | X | 42859285 | 42860785 |
| X | 14568961 | 14574040 | X | 42863617 | 42869497 |
| X | 14582683 | 14585738 | X | 42886428 | 42888618 |
| X | 14589304 | 14600918 | X | 42956591 | 42957764 |
| X | 14631510 | 14634385 | X | 42995005 | 42996993 |
| X | 14643605 | 14651172 | X | 43022365 | 43023720 |
| X | 14654993 | 14656704 | X | 43046562 | 43047932 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 14671983 | 14673406 | | | X | 43060020 | 43063221 |
| X | 14674947 | 14680737 | | | X | 43072108 | 43073772 |
| X | 14709586 | 14715478 | | | X | 43091379 | 43096452 |
| X | 14731498 | 14733852 | | | X | 43136776 | 43137511 |
| X | 14768509 | 14774736 | | | X | 43223160 | 43223400 |
| X | 14777083 | 14779349 | | | X | 43223845 | 43226730 |
| X | 14800878 | 14802048 | | | X | 43235581 | 43238205 |
| X | 14810407 | 14811314 | | | X | 43249793 | 43251708 |
| X | 14847457 | 14849053 | | | X | 43294957 | 43301886 |
| X | 14856548 | 14856643 | | | X | 43317950 | 43321491 |
| X | 14868041 | 14872840 | | | X | 43328000 | 43334800 |
| X | 14880691 | 14886743 | | | X | 43382826 | 43386153 |
| X | 14971380 | 14973097 | | | X | 43396062 | 43401002 |
| X | 14981559 | 14985573 | | | X | 43457909 | 43465584 |
| X | 14988925 | 14992776 | | | X | 43500809 | 43504295 |
| X | 15010466 | 15014176 | | | X | 43570156 | 43576876 |
| X | 15048486 | 15051771 | | | X | 43606203 | 43609228 |
| X | 15069704 | 15073250 | | | X | 43639481 | 43639620 |
| X | 15076199 | 15077521 | | | X | 43707477 | 43710442 |
| X | 15089719 | 15091065 | | | X | 43747626 | 43751791 |
| X | 15097424 | 15104295 | | | X | 43764066 | 43772191 |
| X | 15164301 | 15165643 | | | X | 43772891 | 43774499 |
| X | 15193257 | 15197694 | | | X | 43793972 | 43795017 |
| X | 15211562 | 15215728 | | | X | 43805566 | 43807731 |
| X | 15261071 | 15264180 | | | X | 43849626 | 43851644 |
| X | 15299308 | 15302113 | | | X | 43854881 | 43858239 |
| X | 15304941 | 15307540 | | | X | 43863202 | 43864566 |
| X | 15360949 | 15362716 | | | X | 43887893 | 43888263 |
| X | 15363506 | 15365991 | | | X | 43897737 | 43900790 |
| X | 15380271 | 15382186 | | | X | 43901821 | 43903315 |
| X | 15420896 | 15421526 | | | X | 43911270 | 43912766 |
| X | 15434628 | 15448691 | | | X | 43915250 | 43916125 |
| X | 15451581 | 15452816 | | | X | 43981827 | 43982902 |
| X | 15457500 | 15462988 | | | X | 43989674 | 43991059 |
| X | 15472075 | 15472755 | | | X | 44026398 | 44028736 |
| X | 15514475 | 15520314 | | | X | 44033687 | 44034296 |
| X | 15523179 | 15527799 | | | X | 44111362 | 44115727 |
| X | 15528841 | 15531984 | | | X | 44124877 | 44127148 |
| X | 15540310 | 15541590 | | | X | 44177337 | 44182015 |
| X | 15564997 | 15570364 | | | X | 44193943 | 44195378 |
| X | 15574602 | 15576440 | | | X | 44204492 | 44205899 |
| X | 15604710 | 15605680 | | | X | 44219200 | 44221208 |
| X | 15618586 | 15622784 | | | X | 44234373 | 44238682 |
| X | 15630972 | 15633783 | | | X | 44243938 | 44247921 |
| X | 15668798 | 15676531 | | | X | 44256913 | 44261586 |
| X | 15733537 | 15736119 | | | X | 44308813 | 44318951 |
| X | 15744368 | 15745734 | | | X | 44355922 | 44360551 |
| X | 15753708 | 15755882 | | | X | 44388091 | 44392517 |
| X | 15777698 | 15779401 | | | X | 44417404 | 44422514 |
| X | 15793779 | 15795589 | | | X | 44460013 | 44463732 |
| X | 15855209 | 15856528 | | | X | 44479048 | 44481063 |
| X | 15890956 | 15892817 | | | X | 44493369 | 44495716 |
| X | 15924656 | 15927406 | | | X | 44500838 | 44536006 |
| X | 15940784 | 15943539 | | | X | 44548056 | 44550843 |
| X | 15990271 | 15991848 | | | X | 44574608 | 44594869 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 16006421 | 16008421 | X | 44616790 | 44618080 |
| X | 16015231 | 16025994 | X | 44624569 | 44628370 |
| X | 16046709 | 16047659 | X | 44642768 | 44643821 |
| X | 16057336 | 16060291 | X | 44659024 | 44659689 |
| X | 16075814 | 16076378 | X | 44700916 | 44701551 |
| X | 16082262 | 16084092 | X | 44723387 | 44724671 |
| X | 16089004 | 16101328 | X | 44744009 | 44750827 |
| X | 16107248 | 16113815 | X | 44764320 | 44769219 |
| X | 16143816 | 16150444 | X | 44886202 | 44901793 |
| X | 16179324 | 16181679 | X | 44907129 | 44908565 |
| X | 16281342 | 16282447 | X | 44931782 | 44934150 |
| X | 16343457 | 16345484 | X | 44945229 | 44946134 |
| X | 16351340 | 16352329 | X | 45007405 | 45010108 |
| X | 16362138 | 16364866 | X | 45014585 | 45017050 |
| X | 16380040 | 16386565 | X | 45024170 | 45025040 |
| X | 16474430 | 16475455 | X | 45125060 | 45127698 |
| X | 16506032 | 16510754 | X | 45128263 | 45129223 |
| X | 16582987 | 16585505 | X | 45135136 | 45138351 |
| X | 16603898 | 16605424 | X | 45152967 | 45154483 |
| X | 16612242 | 16618803 | X | 45220308 | 45221914 |
| X | 16640376 | 16650693 | X | 45257143 | 45257463 |
| X | 16661995 | 16679651 | X | 45281435 | 45283837 |
| X | 16694042 | 16705597 | X | 45286685 | 45292538 |
| X | 16722986 | 16731254 | X | 45297134 | 45300484 |
| X | 16748785 | 16755598 | X | 45326610 | 45328704 |
| X | 16758855 | 16764901 | X | 45347679 | 45348135 |
| X | 16766470 | 16770462 | X | 45376516 | 45377601 |
| X | 16771183 | 16772278 | X | 45393020 | 45394930 |
| X | 16799571 | 16801580 | X | 45395395 | 45396015 |
| X | 16815174 | 16818169 | X | 45412227 | 45413012 |
| X | 16841961 | 16844441 | X | 45431343 | 45432005 |
| X | 16873409 | 16875774 | X | 45457916 | 45458361 |
| X | 16919124 | 16921673 | X | 45462621 | 45464971 |
| X | 16944307 | 16946161 | X | 45475518 | 45476628 |
| X | 16960852 | 16962166 | X | 45501034 | 45503192 |
| X | 17050917 | 17051737 | X | 45506230 | 45511052 |
| X | 17084698 | 17098230 | X | 45538919 | 45541732 |
| X | 17114153 | 17116409 | X | 45546374 | 45549627 |
| X | 17162799 | 17163739 | X | 45578891 | 45584892 |
| X | 17204461 | 17210670 | X | 45591980 | 45596641 |
| X | 17220448 | 17221478 | X | 45612911 | 45618461 |
| X | 17225206 | 17227716 | X | 45641727 | 45643622 |
| X | 17250669 | 17253373 | X | 45680556 | 45682196 |
| X | 17253748 | 17264271 | X | 45770603 | 45775585 |
| X | 17289803 | 17291043 | X | 45780637 | 45783737 |
| X | 17295907 | 17297875 | X | 45825684 | 45831788 |
| X | 17302333 | 17309380 | X | 45863736 | 45869997 |
| X | 17351112 | 17352027 | X | 45897082 | 45903437 |
| X | 17359351 | 17360341 | X | 45921764 | 45924033 |
| X | 17371399 | 17373408 | X | 45936222 | 45940271 |
| X | 17387580 | 17391237 | X | 45950915 | 45951895 |
| X | 17410065 | 17413082 | X | 45961921 | 45963581 |
| X | 17421151 | 17424723 | X | 45999858 | 46001414 |
| X | 17435136 | 17442738 | X | 46005973 | 46007628 |
| X | 17515986 | 17521759 | X | 46011708 | 46016901 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 17555926 | 17560956 | X | 46032378 | 46033493 |
| X | 17566933 | 17569388 | X | 46037213 | 46040488 |
| X | 17586433 | 17589248 | X | 46050990 | 46052820 |
| X | 17596763 | 17600344 | X | 46100636 | 46102677 |
| X | 17606889 | 17613964 | X | 46162616 | 46163831 |
| X | 17616259 | 17619495 | X | 46181534 | 46182787 |
| X | 17657028 | 17658268 | X | 46190528 | 46192083 |
| X | 17664116 | 17668040 | X | 46250690 | 46251389 |
| X | 17688838 | 17704821 | X | 46288484 | 46290003 |
| X | 17718965 | 17720469 | X | 46317813 | 46320636 |
| X | 17731674 | 17734686 | X | 46342293 | 46345247 |
| X | 17743262 | 17744952 | X | 46351473 | 46353778 |
| X | 17766629 | 17767364 | X | 46440805 | 46443985 |
| X | 17787309 | 17789931 | X | 46460187 | 46461102 |
| X | 17810441 | 17811861 | X | 46478471 | 46481773 |
| X | 17821750 | 17822055 | X | 46502427 | 46503902 |
| X | 17875718 | 17877119 | X | 46549594 | 46550384 |
| X | 17879301 | 17881266 | X | 46556459 | 46557744 |
| X | 17883782 | 17884690 | X | 46571500 | 46572949 |
| X | 17889859 | 17891514 | X | 46580983 | 46581993 |
| X | 17925260 | 17935980 | X | 46588151 | 46589906 |
| X | 17955296 | 17958246 | X | 46620116 | 46621453 |
| X | 17959456 | 17960261 | X | 46655964 | 46659313 |
| X | 17960980 | 17974882 | X | 46698345 | 46701943 |
| X | 18007888 | 18009373 | X | 46704526 | 46708081 |
| X | 18134155 | 18134910 | X | 46737040 | 46738854 |
| X | 18146491 | 18156381 | X | 46744280 | 46750231 |
| X | 18222532 | 18229512 | X | 46785162 | 46787438 |
| X | 18281827 | 18283128 | X | 46800047 | 46800787 |
| X | 18288456 | 18296208 | X | 46828324 | 46829897 |
| X | 18321478 | 18335438 | X | 46871723 | 46890639 |
| X | 18352990 | 18354393 | X | 46892424 | 46893298 |
| X | 18358852 | 18366064 | X | 46899774 | 46903132 |
| X | 18427154 | 18429904 | X | 46913085 | 46977871 |
| X | 18452856 | 18456563 | X | 46984595 | 46995346 |
| X | 18560332 | 18561433 | X | 47001592 | 47007429 |
| X | 18572527 | 18608293 | X | 47018871 | 47066849 |
| X | 18644676 | 18646697 | X | 47081329 | 47085712 |
| X | 18671103 | 18672563 | X | 47089857 | 47131947 |
| X | 18692258 | 18695262 | X | 47153495 | 47157280 |
| X | 18697875 | 18698385 | X | 47159370 | 47165371 |
| X | 18715628 | 18717664 | X | 47169629 | 47186343 |
| X | 18765362 | 18766612 | X | 47213023 | 47216280 |
| X | 18787864 | 18836031 | X | 47226022 | 47227917 |
| X | 18838096 | 18851543 | X | 47257138 | 47259663 |
| X | 18873739 | 18882076 | X | 47267378 | 47292709 |
| X | 18893059 | 18898337 | X | 47303731 | 47334028 |
| X | 18910348 | 18913216 | X | 47342392 | 47345596 |
| X | 18932796 | 18933266 | X | 47348565 | 47353283 |
| X | 18966688 | 18967709 | X | 47356874 | 47396146 |
| X | 18990834 | 18991747 | X | 47402865 | 47406118 |
| X | 18998812 | 19000900 | X | 47423254 | 47428340 |
| X | 19005951 | 19012300 | X | 47463055 | 47471815 |
| X | 19034207 | 19035628 | X | 47480301 | 47481626 |
| X | 19040604 | 19045447 | X | 47538819 | 47544805 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 19057447 | 19058129 | X | 47547854 | 47553110 |
| X | 19084626 | 19088680 | X | 47554050 | 47556391 |
| X | 19101506 | 19104260 | X | 47579377 | 47580312 |
| X | 19113122 | 19114291 | X | 47580827 | 47581399 |
| X | 19167413 | 19171634 | X | 47611625 | 47625051 |
| X | 19174602 | 19182240 | X | 47634747 | 47636687 |
| X | 19182657 | 19184289 | X | 47663959 | 47668534 |
| X | 19230928 | 19232083 | X | 47685805 | 47687573 |
| X | 19239374 | 19240904 | X | 47698169 | 47702906 |
| X | 19253028 | 19255048 | X | 47745971 | 47746687 |
| X | 19258282 | 19274283 | X | 47748056 | 47767055 |
| X | 19279730 | 19326314 | X | 47770709 | 47777547 |
| X | 19338646 | 19342661 | X | 47789185 | 47792291 |
| X | 19356241 | 19359461 | X | 47793716 | 47795536 |
| X | 19370098 | 19388552 | X | 47812778 | 47817396 |
| X | 19418121 | 19421230 | X | 47824948 | 47826931 |
| X | 19428762 | 19429722 | X | 47845907 | 47904121 |
| X | 19433696 | 19444543 | X | 47909300 | 47955636 |
| X | 19457054 | 19472383 | X | 47959697 | 47960632 |
| X | 19474008 | 19475633 | X | 47961200 | 47963610 |
| X | 19506697 | 19511501 | X | 47986042 | 47990006 |
| X | 19529225 | 19532555 | X | 47998502 | 48002458 |
| X | 19611439 | 19614369 | X | 48011041 | 48042122 |
| X | 19617099 | 19617859 | X | 48048124 | 48053524 |
| X | 19673181 | 19677726 | X | 48070983 | 48259627 |
| X | 19687435 | 19689578 | X | 48264770 | 48266930 |
| X | 19716105 | 19718192 | X | 48276243 | 48360913 |
| X | 19756984 | 19761884 | X | 48387674 | 48389611 |
| X | 19777254 | 19783384 | X | 48397443 | 48404110 |
| X | 19792866 | 19794316 | X | 48410501 | 48462642 |
| X | 19799991 | 19804024 | X | 48472486 | 48482496 |
| X | 19810716 | 19812131 | X | 48484789 | 48489462 |
| X | 19812551 | 19814239 | X | 48503472 | 48506253 |
| X | 19814614 | 19817059 | X | 48511819 | 48548848 |
| X | 19908517 | 19914068 | X | 48553296 | 48594864 |
| X | 19917035 | 19925422 | X | 48607857 | 48617569 |
| X | 19928242 | 19932352 | X | 48625978 | 48668482 |
| X | 19945966 | 19954732 | X | 48679237 | 48682037 |
| X | 19981832 | 19985023 | X | 48690228 | 48693885 |
| X | 19987533 | 19987880 | X | 48698659 | 49258112 |
| X | 19992629 | 19994241 | X | 49266916 | 49279630 |
| X | 20037153 | 20046187 | X | 49285034 | 49289780 |
| X | 20152926 | 20156348 | X | 49291160 | 49293195 |
| X | 20193228 | 20197722 | X | 49310771 | 49311906 |
| X | 20198641 | 20199931 | X | 49316454 | 49319739 |
| X | 20215187 | 20216773 | X | 49345000 | 49348405 |
| X | 20224728 | 20225778 | X | 49361398 | 49364829 |
| X | 20233047 | 20234616 | X | 49380950 | 49393541 |
| X | 20249483 | 20252582 | X | 49403809 | 49409189 |
| X | 20278507 | 20279957 | X | 49438984 | 49446338 |
| X | 20290470 | 20296077 | X | 49467430 | 49467922 |
| X | 20298457 | 20299243 | X | 49476512 | 49477587 |
| X | 20301396 | 20303970 | X | 49479521 | 49481770 |
| X | 20329184 | 20329779 | X | 49482535 | 49485046 |
| X | 20353280 | 20355865 | X | 49496141 | 49500701 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 20376558 | 20379883 | X | 49529062 | 49533348 |
| X | 20380198 | 20382286 | X | 49539444 | 49541346 |
| X | 20391965 | 20395012 | X | 49558369 | 49562803 |
| X | 20399066 | 20403071 | X | 49573743 | 49575848 |
| X | 20414892 | 20417272 | X | 49580837 | 49592042 |
| X | 20426092 | 20428632 | X | 49612524 | 49614019 |
| X | 20461987 | 20464471 | X | 49623264 | 49629743 |
| X | 20490314 | 20491649 | X | 49643706 | 49644252 |
| X | 20532156 | 20541518 | X | 49700178 | 49701210 |
| X | 20547937 | 20549973 | X | 49705229 | 49708714 |
| X | 20568930 | 20572891 | X | 49744916 | 49746192 |
| X | 20590203 | 20593963 | X | 49749407 | 49754842 |
| X | 20637587 | 20646347 | X | 49776882 | 49781755 |
| X | 20659256 | 20663917 | X | 49807549 | 49807809 |
| X | 20671414 | 20673863 | X | 49847865 | 49853194 |
| X | 20692882 | 20694017 | X | 49855785 | 50041454 |
| X | 20699546 | 20707026 | X | 50054173 | 50055527 |
| X | 20716892 | 20718942 | X | 50086451 | 50089468 |
| X | 20723327 | 20731997 | X | 50089743 | 50098093 |
| X | 20732172 | 20733912 | X | 50104476 | 50105331 |
| X | 20739758 | 20744594 | X | 50123637 | 50126062 |
| X | 20812967 | 20816265 | X | 50130666 | 50133211 |
| X | 20847646 | 20849710 | X | 50158762 | 50163687 |
| X | 20859728 | 20878253 | X | 50178786 | 50186302 |
| X | 20881512 | 20882659 | X | 50198068 | 50199183 |
| X | 20888446 | 20889926 | X | 50228581 | 50232124 |
| X | 20895151 | 20908457 | X | 50232794 | 50234479 |
| X | 20916358 | 20918553 | X | 50242936 | 50244266 |
| X | 20964325 | 20966950 | X | 50251736 | 50253611 |
| X | 20998757 | 21004248 | X | 50279029 | 50280374 |
| X | 21007496 | 21010869 | X | 50315740 | 50319466 |
| X | 21037500 | 21047832 | X | 50339511 | 50340171 |
| X | 21061209 | 21065636 | X | 50346362 | 50349102 |
| X | 21095449 | 21096359 | X | 50359417 | 50366127 |
| X | 21101515 | 21103135 | X | 50377303 | 50378675 |
| X | 21122040 | 21123850 | X | 50401247 | 50404191 |
| X | 21153074 | 21163749 | X | 50409741 | 50418346 |
| X | 21214651 | 21219383 | X | 50424239 | 50431082 |
| X | 21291759 | 21292344 | X | 50434645 | 50437936 |
| X | 21301655 | 21303335 | X | 50446762 | 50471827 |
| X | 21313017 | 21314511 | X | 50506900 | 50516666 |
| X | 21318122 | 21321207 | X | 50526880 | 50528251 |
| X | 21416074 | 21418174 | X | 50553432 | 50555859 |
| X | 21515546 | 21516161 | X | 50566548 | 50571464 |
| X | 21526675 | 21527249 | X | 50571634 | 50574275 |
| X | 21583555 | 21587318 | X | 50642944 | 50646575 |
| X | 21605585 | 21606875 | X | 50657295 | 50663736 |
| X | 21625655 | 21638038 | X | 50663856 | 50666002 |
| X | 21660545 | 21666179 | X | 50676562 | 50679258 |
| X | 21668969 | 21685375 | X | 50693062 | 50696700 |
| X | 21689680 | 21692545 | X | 50707774 | 50709143 |
| X | 21725951 | 21726626 | X | 50781739 | 50784528 |
| X | 21730446 | 21732008 | X | 50807252 | 50808352 |
| X | 21767503 | 21768248 | X | 50826400 | 50827905 |
| X | 21783941 | 21785913 | X | 50837641 | 50841336 |

The chromosomal positon was obtained from UCSC genome browser (http://genome.ucsc.edu/) build 36.

APPENDIX D: Chromosome X
Page 51 of 73

| Chr | Start | End | | | Chr | Start | End |
|---|---|---|---|---|---|---|---|
| X | 21830520 | 21834226 | | | X | 50850806 | 50853219 |
| X | 21855211 | 21857614 | | | X | 50858320 | 50860351 |
| X | 21859634 | 21875798 | | | X | 50894655 | 50902490 |
| X | 21884216 | 21890045 | | | X | 50907871 | 50909531 |
| X | 21893378 | 21901197 | | | X | 50944819 | 50946709 |
| X | 21909639 | 21910573 | | | X | 50982261 | 50983337 |
| X | 21947952 | 21949978 | | | X | 50992976 | 50995436 |
| X | 21961534 | 21969378 | | | X | 51015126 | 51033666 |
| X | 21997809 | 21999064 | | | X | 51034156 | 51034746 |
| X | 22029419 | 22031239 | | | X | 51050670 | 51053162 |
| X | 22037645 | 22040104 | | | X | 51082814 | 51088690 |
| X | 22062142 | 22063427 | | | X | 51091517 | 51093272 |
| X | 22089677 | 22092532 | | | X | 51106797 | 51113127 |
| X | 22121808 | 22123014 | | | X | 51155294 | 51156154 |
| X | 22139161 | 22142511 | | | X | 51159425 | 51161530 |
| X | 22148731 | 22150628 | | | X | 51165627 | 51169110 |
| X | 22198073 | 22201936 | | | X | 51170354 | 51173457 |
| X | 22238894 | 22241890 | | | X | 51177131 | 51181471 |
| X | 22244570 | 22247304 | | | X | 51195270 | 51196290 |
| X | 22255782 | 22256542 | | | X | 51204328 | 51205597 |
| X | 22267315 | 22268900 | | | X | 51235122 | 51235632 |
| X | 22302755 | 22305383 | | | X | 51255127 | 51260392 |
| X | 22326223 | 22327198 | | | X | 51261632 | 51266557 |
| X | 22351964 | 22357117 | | | X | 51328001 | 51328611 |
| X | 22487268 | 22494833 | | | X | 51333633 | 51335328 |
| X | 22552582 | 22553532 | | | X | 51365006 | 51368215 |
| X | 22569236 | 22569906 | | | X | 51456580 | 51458238 |
| X | 22586096 | 22590401 | | | X | 51496732 | 51499032 |
| X | 22601546 | 22602476 | | | X | 51518740 | 51521687 |
| X | 22716480 | 22718449 | | | X | 51589071 | 51590134 |
| X | 22816670 | 22818995 | | | X | 51623974 | 51626138 |
| X | 22844314 | 22845539 | | | X | 51634928 | 51640374 |
| X | 22880727 | 22881437 | | | X | 51652668 | 51655104 |
| X | 22911175 | 22913264 | | | X | 51662355 | 51662695 |
| X | 22926559 | 22928070 | | | X | 51665656 | 51669619 |
| X | 22975047 | 22976770 | | | X | 51676695 | 51680004 |
| X | 23008862 | 23011672 | | | X | 51718503 | 51725031 |
| X | 23042220 | 23043791 | | | X | 51759339 | 51762057 |
| X | 23046866 | 23048171 | | | X | 51778864 | 51794328 |
| X | 23054349 | 23057988 | | | X | 51846100 | 51849345 |
| X | 23084695 | 23088545 | | | X | 51857406 | 51860266 |
| X | 23242190 | 23243638 | | | X | 51900936 | 51913310 |
| X | 23259261 | 23263947 | | | X | 51992255 | 51993743 |
| X | 23268303 | 23271357 | | | X | 52010902 | 52014285 |
| X | 23278704 | 23283006 | | | X | 52041542 | 52043783 |
| X | 23294662 | 23296599 | | | X | 52070344 | 52072249 |
| X | 23300348 | 23300438 | | | X | 52080143 | 52085133 |
| X | 23321162 | 23323817 | | | X | 52115278 | 52117513 |
| X | 23335106 | 23337845 | | | X | 52589812 | 52590532 |
| X | 23390338 | 23394601 | | | X | 52608291 | 52609426 |
| X | 23433478 | 23439878 | | | X | 52623020 | 52624530 |
| X | 23446900 | 23450814 | | | X | 52628242 | 52629607 |
| X | 23462465 | 23468156 | | | X | 52635760 | 52640089 |
| X | 23479839 | 23482038 | | | X | 52649276 | 52650036 |
| X | 23482633 | 23483936 | | | X | 52656379 | 52670742 |

The chromosomal positon was obtained from UCSC genome browser (http://genome.ucsc.edu/) build 36.

APPENDIX D: Chromosome X
Page 52 of 73

| Chr | Start | End | | | Chr | Start | End |
|---|---|---|---|---|---|---|---|
| X | 23497601 | 23506089 | | | X | 52679084 | 52690739 |
| X | 23507941 | 23513493 | | | X | 52699220 | 52702454 |
| X | 23531155 | 23532164 | | | X | 52710119 | 52713673 |
| X | 23556065 | 23557906 | | | X | 52851197 | 52854007 |
| X | 23584371 | 23585723 | | | X | 52899224 | 52901188 |
| X | 23644568 | 23655311 | | | X | 52912270 | 52914341 |
| X | 23670726 | 23676524 | | | X | 52920614 | 52966617 |
| X | 23693842 | 23701221 | | | X | 52980115 | 53022466 |
| X | 23723444 | 23725633 | | | X | 53029790 | 53030450 |
| X | 23731263 | 23745706 | | | X | 53035024 | 53042306 |
| X | 23768968 | 23772059 | | | X | 53068062 | 53072256 |
| X | 23777384 | 23780914 | | | X | 53072326 | 53075794 |
| X | 23834902 | 23836480 | | | X | 53089960 | 53103980 |
| X | 23861402 | 23865822 | | | X | 53116181 | 53135253 |
| X | 23868958 | 23871875 | | | X | 53149206 | 53149916 |
| X | 23874442 | 23876067 | | | X | 53159106 | 53161044 |
| X | 23882576 | 23884876 | | | X | 53189185 | 53190012 |
| X | 23891680 | 23907262 | | | X | 53239127 | 53245095 |
| X | 23926857 | 23939888 | | | X | 53262971 | 53264886 |
| X | 23953129 | 23982813 | | | X | 53275979 | 53290617 |
| X | 23994360 | 24001835 | | | X | 53313911 | 53317935 |
| X | 24014477 | 24020827 | | | X | 53325222 | 53327311 |
| X | 24028641 | 24030860 | | | X | 53331791 | 53331891 |
| X | 24045350 | 24064158 | | | X | 53332546 | 53344110 |
| X | 24079078 | 24080989 | | | X | 53355153 | 53356650 |
| X | 24085777 | 24088180 | | | X | 53360405 | 53387413 |
| X | 24097375 | 24099791 | | | X | 53399569 | 53405109 |
| X | 24109783 | 24111604 | | | X | 53423801 | 53427796 |
| X | 24127024 | 24128529 | | | X | 53433443 | 53463747 |
| X | 24130074 | 24138352 | | | X | 53468444 | 53478509 |
| X | 24165273 | 24167288 | | | X | 53482596 | 53485586 |
| X | 24201243 | 24205986 | | | X | 53501588 | 53525512 |
| X | 24239644 | 24246110 | | | X | 53527734 | 53528739 |
| X | 24288355 | 24292970 | | | X | 53572660 | 53596049 |
| X | 24352998 | 24355082 | | | X | 53616778 | 53618243 |
| X | 24391492 | 24394452 | | | X | 53630447 | 53632092 |
| X | 24427640 | 24429067 | | | X | 53671345 | 53672539 |
| X | 24485894 | 24493070 | | | X | 53688082 | 53689122 |
| X | 24520461 | 24522306 | | | X | 53695930 | 53697233 |
| X | 24558686 | 24559702 | | | X | 53726577 | 53734864 |
| X | 24574853 | 24576583 | | | X | 53750255 | 53752992 |
| X | 24583887 | 24584472 | | | X | 53764013 | 53768152 |
| X | 24621409 | 24622391 | | | X | 53794063 | 53795787 |
| X | 24633835 | 24635243 | | | X | 53802039 | 53804559 |
| X | 24678562 | 24679346 | | | X | 53856061 | 53858424 |
| X | 24689349 | 24691660 | | | X | 53879121 | 53880680 |
| X | 24693848 | 24698796 | | | X | 53887405 | 53888765 |
| X | 24709390 | 24710635 | | | X | 53915708 | 53923187 |
| X | 24774965 | 24775620 | | | X | 53939136 | 53941433 |
| X | 24791682 | 24792596 | | | X | 54045641 | 54046116 |
| X | 24805442 | 24806861 | | | X | 54067864 | 54070167 |
| X | 24830264 | 24830649 | | | X | 54072834 | 54079321 |
| X | 24904255 | 24906897 | | | X | 54083978 | 54089399 |
| X | 24915240 | 24916585 | | | X | 54116519 | 54117494 |
| X | 24932596 | 24935807 | | | X | 54141637 | 54145033 |

The chromosomal positon was obtained from UCSC genome browser (http://genome.ucsc.edu/) build 36.

APPENDIX D: Chromosome X
Page 53 of 73

| Chr | Start | End | Chr | Start | End |
|---|---|---|---|---|---|
| X | 24935942 | 24937655 | X | 54203714 | 54204554 |
| X | 24956994 | 24959372 | X | 54219786 | 54220841 |
| X | 24970200 | 24974037 | X | 54225383 | 54227576 |
| X | 25030758 | 25032158 | X | 54250608 | 54258318 |
| X | 25055307 | 25057167 | X | 54363536 | 54365358 |
| X | 25099437 | 25103392 | X | 54399733 | 54402929 |
| X | 25111957 | 25113394 | X | 54456042 | 54462316 |
| X | 25124378 | 25127954 | X | 54477345 | 54490371 |
| X | 25128954 | 25131638 | X | 54501790 | 54513959 |
| X | 25146718 | 25159087 | X | 54536649 | 54552655 |
| X | 25191327 | 25193117 | X | 54563782 | 54568020 |
| X | 25295098 | 25297835 | X | 54571728 | 54575710 |
| X | 25304671 | 25308182 | X | 54583562 | 54584987 |
| X | 25309962 | 25311617 | X | 54605743 | 54608200 |
| X | 25315387 | 25320092 | X | 54681351 | 54684264 |
| X | 25357438 | 25368499 | X | 54703917 | 54704307 |
| X | 25382264 | 25383407 | X | 54798745 | 54801982 |
| X | 25388343 | 25392200 | X | 54850746 | 54852516 |
| X | 25427818 | 25428483 | X | 54857916 | 54860973 |
| X | 25462625 | 25464680 | X | 54862818 | 54874118 |
| X | 25473669 | 25476419 | X | 54891673 | 54892093 |
| X | 25481725 | 25489121 | X | 54963027 | 54965077 |
| X | 25505156 | 25506321 | X | 54998688 | 55002759 |
| X | 25567038 | 25571663 | X | 55026435 | 55029918 |
| X | 25574197 | 25574547 | X | 55034575 | 55036535 |
| X | 25594202 | 25598142 | X | 55043241 | 55044766 |
| X | 25608873 | 25621253 | X | 55049247 | 55051959 |
| X | 25670673 | 25671999 | X | 55060270 | 55061310 |
| X | 25689238 | 25690863 | X | 55061815 | 55063331 |
| X | 25780424 | 25782176 | X | 55098908 | 55102858 |
| X | 25787553 | 25788783 | X | 55105829 | 55114989 |
| X | 25831373 | 25832638 | X | 55117794 | 55120005 |
| X | 25841798 | 25843787 | X | 55132275 | 55132735 |
| X | 25868248 | 25868598 | X | 55148000 | 55151238 |
| X | 25891077 | 25892677 | X | 55161213 | 55165927 |
| X | 25936670 | 25938010 | X | 55188682 | 55189387 |
| X | 25991507 | 25995121 | X | 55204354 | 55206859 |
| X | 26018627 | 26026483 | X | 55213819 | 55215539 |
| X | 26066456 | 26069618 | X | 55221479 | 55227528 |
| X | 26079686 | 26085392 | X | 55268137 | 55276153 |
| X | 26087517 | 26089787 | X | 55297659 | 55299182 |
| X | 26098728 | 26102031 | X | 55322849 | 55324334 |
| X | 26119363 | 26123033 | X | 55370110 | 55372418 |
| X | 26156881 | 26157206 | X | 55376809 | 55380716 |
| X | 26232440 | 26234365 | X | 55385917 | 55387324 |
| X | 26309980 | 26318821 | X | 55400813 | 55406016 |
| X | 26330288 | 26336247 | X | 55419297 | 55422212 |
| X | 26360969 | 26363851 | X | 55432559 | 55433529 |
| X | 26373546 | 26376209 | X | 55448074 | 55449753 |
| X | 26401005 | 26403463 | X | 55469674 | 55471779 |
| X | 26420673 | 26422732 | X | 55531900 | 55534162 |
| X | 26432321 | 26434074 | X | 55563375 | 55564415 |
| X | 26440930 | 26441380 | X | 55591473 | 55602118 |
| X | 26465736 | 26472734 | X | 55635981 | 55638896 |
| X | 26485591 | 26487198 | X | 55663639 | 55666504 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 26519722 | 26521397 | X | 55678260 | 55681444 |
| X | 26580218 | 26580944 | X | 55760619 | 55762329 |
| X | 26662602 | 26664622 | X | 55795913 | 55796183 |
| X | 26684784 | 26686904 | X | 55803212 | 55805486 |
| X | 26707063 | 26716561 | X | 55819837 | 55827333 |
| X | 26718487 | 26721569 | X | 55831668 | 55836568 |
| X | 26730931 | 26732245 | X | 55951480 | 55952445 |
| X | 26783989 | 26787435 | X | 56070130 | 56075222 |
| X | 26938337 | 26938937 | X | 56126304 | 56133452 |
| X | 27023029 | 27029797 | X | 56158542 | 56161506 |
| X | 27055576 | 27058055 | X | 56254873 | 56256811 |
| X | 27099407 | 27101532 | X | 56288181 | 56290585 |
| X | 27187815 | 27188775 | X | 56341091 | 56343373 |
| X | 27206647 | 27207343 | X | 56355660 | 56357115 |
| X | 27214103 | 27222919 | X | 56488018 | 56488973 |
| X | 27326972 | 27327955 | X | 56606504 | 56608664 |
| X | 27379867 | 27385038 | X | 56678410 | 56681218 |
| X | 27471227 | 27474134 | X | 56773012 | 56774954 |
| X | 27505432 | 27508182 | X | 56777294 | 56778624 |
| X | 27519330 | 27521349 | X | 56808425 | 56846803 |
| X | 27577722 | 27579860 | X | 56906663 | 56907378 |
| X | 27582275 | 27585826 | X | 56947118 | 56949101 |
| X | 27666742 | 27668627 | X | 56990048 | 56996502 |
| X | 27673908 | 27676618 | X | 57021266 | 57022461 |
| X | 27734950 | 27738831 | X | 57025601 | 57027081 |
| X | 27752424 | 27755796 | X | 57030607 | 57032642 |
| X | 27757747 | 27761086 | X | 57037764 | 57039106 |
| X | 27791920 | 27792802 | X | 57087733 | 57089138 |
| X | 27795667 | 27796727 | X | 57113132 | 57115153 |
| X | 27836323 | 27836873 | X | 57158247 | 57159622 |
| X | 27898606 | 27900506 | X | 57162677 | 57165052 |
| X | 27906985 | 27909765 | X | 57216629 | 57218656 |
| X | 27928014 | 27931872 | X | 57247354 | 57248479 |
| X | 27965685 | 27971356 | X | 57253753 | 57256915 |
| X | 27991233 | 27991679 | X | 57262684 | 57267884 |
| X | 28002051 | 28003011 | X | 57403955 | 57411208 |
| X | 28030849 | 28034977 | X | 57414320 | 57415769 |
| X | 28041293 | 28042593 | X | 57490208 | 57495519 |
| X | 28144527 | 28147761 | X | 57551186 | 57559045 |
| X | 28152238 | 28155523 | X | 57559560 | 57560300 |
| X | 28159454 | 28160969 | X | 57634184 | 57637754 |
| X | 28213356 | 28215173 | X | 57721621 | 57724136 |
| X | 28260778 | 28266880 | X | 57784984 | 57786724 |
| X | 28302146 | 28303614 | X | 57808898 | 57811173 |
| X | 28340196 | 28346873 | X | 57816484 | 57824645 |
| X | 28352282 | 28352942 | X | 57893291 | 57894238 |
| X | 28375241 | 28378626 | X | 57952497 | 57955123 |
| X | 28396966 | 28399101 | X | 57967380 | 57968040 |
| X | 28428806 | 28438440 | X | 58007452 | 58010782 |
| X | 28526981 | 28528770 | X | 58027650 | 58029253 |
| X | 28540638 | 28542193 | X | 58041301 | 58043531 |
| X | 28564708 | 28565588 | X | 58103398 | 58108941 |
| X | 28586169 | 28588729 | X | 58114307 | 58121562 |
| X | 28598366 | 28604019 | X | 58122162 | 58123607 |
| X | 28705210 | 28707105 | X | 58147048 | 58150303 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 28749788 | 28755097 | | | X | 58160019 | 58160759 |
| X | 28778612 | 28781352 | | | X | 58191058 | 58193259 |
| X | 28821068 | 28826266 | | | X | 58194144 | 58195857 |
| X | 28843663 | 28844538 | | | X | 58204808 | 58209939 |
| X | 28855288 | 28856594 | | | X | 58215398 | 58221642 |
| X | 28896263 | 28898559 | | | X | 58278021 | 58287001 |
| X | 28901626 | 28903256 | | | X | 58296756 | 58335703 |
| X | 28905647 | 28907287 | | | X | 58341231 | 58377055 |
| X | 28948632 | 28950361 | | | X | 58386826 | 58434136 |
| X | 28953162 | 28954175 | | | X | 58453830 | 58466114 |
| X | 29045723 | 29048739 | | | X | 58483406 | 58486326 |
| X | 29058655 | 29062901 | | | X | 58510517 | 58541323 |
| X | 29113938 | 29115543 | | | X | 58580201 | 58581711 |
| X | 29137705 | 29139025 | | | | | |
| X | 29191095 | 29196220 | | | | | |
| X | 29207172 | 29209575 | | | | | |
| X | 29230177 | 29231187 | | | | | |
| X | 29241708 | 29243878 | | | | | |
| X | 29252742 | 29256290 | | | | | |
| X | 61602283 | 61640618 | | | X | 111957999 | 111959010 |
| X | 61825789 | 61830538 | | | X | 111969651 | 111970965 |
| X | 61858676 | 61872734 | | | X | 111987038 | 111988248 |
| X | 61886108 | 61889372 | | | X | 111988884 | 111991190 |
| X | 61923939 | 61961993 | | | X | 112007521 | 112009276 |
| X | 62019118 | 62021083 | | | X | 112028425 | 112030236 |
| X | 62148980 | 62152337 | | | X | 112073624 | 112076038 |
| X | 62211991 | 62212792 | | | X | 112230903 | 112232633 |
| X | 62217984 | 62222463 | | | X | 112239695 | 112244775 |
| X | 62238248 | 62239978 | | | X | 112313667 | 112317490 |
| X | 62394996 | 62399834 | | | X | 112323461 | 112329762 |
| X | 62415692 | 62417852 | | | X | 112368769 | 112371519 |
| X | 62458869 | 62463756 | | | X | 112402638 | 112405366 |
| X | 62483919 | 62487601 | | | X | 112416631 | 112417726 |
| X | 62489109 | 62491274 | | | X | 112431833 | 112434565 |
| X | 62546156 | 62550765 | | | X | 112440262 | 112443564 |
| X | 62563163 | 62572508 | | | X | 112570106 | 112571506 |
| X | 62606225 | 62608347 | | | X | 112657963 | 112660508 |
| X | 62702021 | 62703001 | | | X | 112733103 | 112734245 |
| X | 62764408 | 62768413 | | | X | 112738305 | 112742017 |
| X | 62789273 | 62790073 | | | X | 112865037 | 112866034 |
| X | 62808948 | 62811178 | | | X | 113112924 | 113114894 |
| X | 62851559 | 62855492 | | | X | 113167800 | 113178205 |
| X | 62872908 | 62878206 | | | X | 113234990 | 113236610 |
| X | 62890918 | 62892231 | | | X | 113280061 | 113283842 |
| X | 62903845 | 62905202 | | | X | 113480232 | 113482723 |
| X | 62925641 | 62928971 | | | X | 113509124 | 113513309 |
| X | 62982470 | 62983805 | | | X | 113529983 | 113532303 |
| X | 62985331 | 62990652 | | | X | 113759586 | 113760756 |
| X | 63214737 | 63214962 | | | X | 113944892 | 113945532 |
| X | 63229494 | 63234082 | | | X | 113950799 | 113952585 |
| X | 63395933 | 63399338 | | | X | 114073664 | 114075504 |
| X | 63474046 | 63477725 | | | X | 114099751 | 114102861 |
| X | 63485014 | 63488644 | | | X | 114125468 | 114129110 |
| X | 63530253 | 63535631 | | | X | 114160762 | 114161709 |
| X | 63553378 | 63563095 | | | X | 114209648 | 114213303 |

The chromosomal positon was obtained from UCSC genome browser (http://genome.ucsc.edu/) build 36.

APPENDIX D: Chromosome X
Page 56 of 73

| Chr | Start | End | Chr | Start | End |
|---|---|---|---|---|---|
| X | 63592240 | 63599121 | X | 114231406 | 114234553 |
| X | 63639528 | 63640274 | X | 114329159 | 114333537 |
| X | 63662201 | 63665914 | X | 114408983 | 114410343 |
| X | 63699733 | 63704053 | X | 114419046 | 114426807 |
| X | 63727681 | 63736857 | X | 114426852 | 114436688 |
| X | 63787886 | 63794694 | X | 114464176 | 114466378 |
| X | 63837536 | 63838850 | X | 114497976 | 114499754 |
| X | 63880851 | 63883407 | X | 114538369 | 114541867 |
| X | 63885093 | 63886068 | X | 114554263 | 114559824 |
| X | 63925159 | 63930040 | X | 114594213 | 114596722 |
| X | 63959357 | 63961842 | X | 114677472 | 114685738 |
| X | 63979894 | 63987694 | X | 114710470 | 114717263 |
| X | 64029437 | 64031456 | X | 114777432 | 114778242 |
| X | 64102786 | 64106357 | X | 114781749 | 114784019 |
| X | 64112198 | 64114548 | X | 114805446 | 114821384 |
| X | 64130316 | 64131861 | X | 114842085 | 114846136 |
| X | 64162699 | 64166269 | X | 114865599 | 114935214 |
| X | 64170397 | 64172360 | X | 114936959 | 114941018 |
| X | 64265452 | 64271647 | X | 114980044 | 114983821 |
| X | 64474807 | 64478802 | X | 115007050 | 115008775 |
| X | 64498131 | 64502656 | X | 115040732 | 115046304 |
| X | 64554201 | 64557746 | X | 115105726 | 115107006 |
| X | 64603340 | 64607263 | X | 115130322 | 115131846 |
| X | 64638321 | 64639546 | X | 115211469 | 115212261 |
| X | 64651081 | 64688683 | X | 115247947 | 115250785 |
| X | 64718841 | 64731099 | X | 115275963 | 115281308 |
| X | 64770879 | 64778276 | X | 115293855 | 115294877 |
| X | 64802499 | 64804697 | X | 115317844 | 115322129 |
| X | 64815026 | 64818806 | X | 115331120 | 115333601 |
| X | 64854938 | 64856619 | X | 115341675 | 115343985 |
| X | 64883177 | 64885411 | X | 115430693 | 115433829 |
| X | 64923379 | 64928019 | X | 115451765 | 115452745 |
| X | 64933881 | 64939676 | X | 115520970 | 115525315 |
| X | 65008453 | 65016261 | X | 115649462 | 115652566 |
| X | 65067835 | 65069471 | X | 115710998 | 115713942 |
| X | 65131690 | 65138323 | X | 115776240 | 115777170 |
| X | 65149195 | 65151350 | X | 115854839 | 115857535 |
| X | 65160650 | 65164711 | X | 115899164 | 115902324 |
| X | 65166031 | 65168096 | X | 115958667 | 115967792 |
| X | 65180511 | 65183301 | X | 115979457 | 115981783 |
| X | 65205532 | 65209821 | X | 116083377 | 116084062 |
| X | 65211877 | 65214986 | X | 116093863 | 116097369 |
| X | 65254244 | 65256229 | X | 116200473 | 116200653 |
| X | 65293208 | 65294138 | X | 116343564 | 116348535 |
| X | 65324609 | 65325550 | X | 116388902 | 116393957 |
| X | 65438123 | 65447522 | X | 116403673 | 116405889 |
| X | 65463205 | 65464900 | X | 116409967 | 116414418 |
| X | 65522235 | 65530804 | X | 116436298 | 116439473 |
| X | 65547943 | 65558506 | X | 116504412 | 116507992 |
| X | 65574034 | 65576364 | X | 116531943 | 116533718 |
| X | 65579273 | 65580058 | X | 116561907 | 116565071 |
| X | 65598498 | 65602807 | X | 116611292 | 116621647 |
| X | 65608987 | 65611252 | X | 116726643 | 116727258 |
| X | 65770118 | 65773579 | X | 116735248 | 116740353 |
| X | 65808800 | 65813720 | X | 116786314 | 116788534 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 65833495 | 65839048 | | X | 116805286 | 116808979 |
| X | 65870529 | 65871179 | | X | 116819542 | 116821612 |
| X | 65896728 | 65906156 | | X | 116853086 | 116857681 |
| X | 66002067 | 66007356 | | X | 116868202 | 116871107 |
| X | 66030242 | 66039779 | | X | 117025790 | 117026991 |
| X | 66141384 | 66142984 | | X | 117087314 | 117088280 |
| X | 66154550 | 66157417 | | X | 117105219 | 117105878 |
| X | 66229314 | 66233365 | | X | 117149411 | 117153485 |
| X | 66272018 | 66277747 | | X | 117181545 | 117182270 |
| X | 66317294 | 66320178 | | X | 117206176 | 117207631 |
| X | 66340450 | 66344386 | | X | 117215448 | 117218029 |
| X | 66349236 | 66350844 | | X | 117227281 | 117237153 |
| X | 66423570 | 66425210 | | X | 117267306 | 117269213 |
| X | 66469351 | 66471673 | | X | 117326468 | 117327608 |
| X | 66474228 | 66477673 | | X | 117360819 | 117364508 |
| X | 66482223 | 66489450 | | X | 117436687 | 117441595 |
| X | 66580355 | 66582772 | | X | 117492652 | 117515054 |
| X | 66622751 | 66625087 | | X | 117515660 | 117516657 |
| X | 66637427 | 66640772 | | X | 117573888 | 117576286 |
| X | 66663250 | 66665255 | | X | 117598206 | 117601981 |
| X | 66679748 | 66683779 | | X | 117607510 | 117611395 |
| X | 66702159 | 66704224 | | X | 117614630 | 117617685 |
| X | 66719118 | 66721869 | | X | 117724268 | 117735508 |
| X | 66820370 | 66828464 | | X | 117821724 | 117825312 |
| X | 66832885 | 66852115 | | X | 117840804 | 117848760 |
| X | 66865806 | 66871113 | | X | 117857225 | 117858984 |
| X | 66919530 | 66921845 | | X | 117870176 | 117874311 |
| X | 66938274 | 66942595 | | X | 117883605 | 117884065 |
| X | 67032945 | 67035621 | | X | 117885375 | 117887676 |
| X | 67045356 | 67047246 | | X | 117955331 | 117962905 |
| X | 67176783 | 67180803 | | X | 117982701 | 117995123 |
| X | 67194951 | 67197010 | | X | 118043299 | 118054185 |
| X | 67233163 | 67236788 | | X | 118083529 | 118092315 |
| X | 67447397 | 67454565 | | X | 118191668 | 118195151 |
| X | 67460639 | 67465458 | | X | 118214374 | 118220868 |
| X | 67529503 | 67539200 | | X | 118236399 | 118237634 |
| X | 67550547 | 67551757 | | X | 118239380 | 118255788 |
| X | 67562702 | 67570823 | | X | 118265222 | 118271286 |
| X | 67591433 | 67595555 | | X | 118288978 | 118292513 |
| X | 67609777 | 67613721 | | X | 118342639 | 118343504 |
| X | 67631028 | 67637227 | | X | 118383964 | 118392608 |
| X | 67649360 | 67652956 | | X | 118411856 | 118430241 |
| X | 67783773 | 67790960 | | X | 118473633 | 118477402 |
| X | 67797944 | 67799037 | | X | 118485626 | 118595557 |
| X | 67821316 | 67826401 | | X | 118604666 | 118632564 |
| X | 67848761 | 67858212 | | X | 118645625 | 118688628 |
| X | 67912297 | 67921417 | | X | 118700256 | 118700831 |
| X | 67959608 | 67996556 | | X | 118710232 | 118730670 |
| X | 67997296 | 67999631 | | X | 118738957 | 118847362 |
| X | 68002441 | 68005078 | | X | 118866827 | 118891448 |
| X | 68010506 | 68036055 | | X | 118894760 | 118934384 |
| X | 68048632 | 68051092 | | X | 118940207 | 118945108 |
| X | 68054638 | 68056089 | | X | 118959195 | 118964837 |
| X | 68072542 | 68079667 | | X | 119007219 | 119009862 |
| X | 68101799 | 68104511 | | X | 119016255 | 119019315 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 68126594 | 68136088 | | | X | 119027378 | 119035720 |
| X | 68156879 | 68158549 | | | X | 119043269 | 119045064 |
| X | 68162709 | 68165450 | | | X | 119113768 | 119118221 |
| X | 68195983 | 68198308 | | | X | 119133047 | 119136595 |
| X | 68217934 | 68226875 | | | X | 119162246 | 119220270 |
| X | 68229675 | 68234841 | | | X | 119237915 | 119239950 |
| X | 68244078 | 68246048 | | | X | 119262374 | 119263359 |
| X | 68270070 | 68274072 | | | X | 119268390 | 119270089 |
| X | 68286355 | 68288059 | | | X | 119301065 | 119304690 |
| X | 68296938 | 68303160 | | | X | 119313409 | 119316677 |
| X | 68414128 | 68442928 | | | X | 119325815 | 119330408 |
| X | 68484975 | 68487220 | | | X | 119370590 | 119372210 |
| X | 68495556 | 68505733 | | | X | 119418178 | 119420178 |
| X | 68537913 | 68540483 | | | X | 119423884 | 119426639 |
| X | 68546007 | 68549193 | | | X | 119484641 | 119495347 |
| X | 68550138 | 68557866 | | | X | 119578043 | 119579575 |
| X | 68601481 | 68603977 | | | X | 119592063 | 119593958 |
| X | 68634940 | 68646564 | | | X | 119598473 | 119600363 |
| X | 68656835 | 68675943 | | | X | 119602798 | 119609587 |
| X | 68677303 | 68678388 | | | X | 119621044 | 119622704 |
| X | 68681433 | 68683199 | | | X | 119631723 | 119632448 |
| X | 68720313 | 68727170 | | | X | 119637550 | 119650337 |
| X | 68753068 | 68754023 | | | X | 119681618 | 119686166 |
| X | 68768528 | 68768813 | | | X | 119743359 | 119746376 |
| X | 68787400 | 68789220 | | | X | 119750313 | 119753371 |
| X | 68796625 | 68799830 | | | X | 119755834 | 119757589 |
| X | 68833664 | 68840034 | | | X | 119774203 | 119776718 |
| X | 68844131 | 68848845 | | | X | 119886087 | 119949137 |
| X | 68877082 | 68880714 | | | X | 119957138 | 119958418 |
| X | 68915215 | 68916115 | | | X | 119994600 | 120001131 |
| X | 69016837 | 69017317 | | | X | 120008951 | 120010938 |
| X | 69106288 | 69109098 | | | X | 120016071 | 120022447 |
| X | 69137533 | 69143758 | | | X | 120038189 | 120040616 |
| X | 69147476 | 69150141 | | | X | 120063348 | 120069668 |
| X | 69187644 | 69205723 | | | X | 120182461 | 120184746 |
| X | 69208614 | 69211701 | | | X | 120204779 | 120208031 |
| X | 69227240 | 69227580 | | | X | 120222113 | 120223423 |
| X | 69228060 | 69241185 | | | X | 120251311 | 120255702 |
| X | 69256099 | 69290527 | | | X | 120262819 | 120265253 |
| X | 69302666 | 69312791 | | | X | 120277254 | 120284230 |
| X | 69339090 | 69341106 | | | X | 120306392 | 120310970 |
| X | 69370442 | 69374616 | | | X | 120429803 | 120430163 |
| X | 69425743 | 69427365 | | | X | 120431490 | 120436781 |
| X | 69457682 | 69460807 | | | X | 120471428 | 120477275 |
| X | 69481556 | 69487674 | | | X | 120492364 | 120498964 |
| X | 69496925 | 69509296 | | | X | 120506366 | 120508665 |
| X | 69514125 | 69516917 | | | X | 120560850 | 120565194 |
| X | 69560562 | 69564162 | | | X | 120600627 | 120605823 |
| X | 69569641 | 69592813 | | | X | 120815403 | 120816413 |
| X | 69607844 | 69609862 | | | X | 120865823 | 120868361 |
| X | 69629228 | 69634489 | | | X | 120925141 | 120927365 |
| X | 69643264 | 69648767 | | | X | 120985267 | 120985682 |
| X | 69668705 | 69670762 | | | X | 120990987 | 120994464 |
| X | 69673721 | 69674649 | | | X | 121016186 | 121018071 |
| X | 69805286 | 69805671 | | | X | 121022526 | 121027002 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 70002700 | 70012451 | X | 121134183 | 121136158 |
| X | 70027178 | 70037050 | X | 121181973 | 121189326 |
| X | 70044687 | 70046867 | X | 121251903 | 121253143 |
| X | 70049783 | 70053430 | X | 121395059 | 121396250 |
| X | 70063891 | 70067604 | X | 121415436 | 121418306 |
| X | 70092634 | 70097475 | X | 121551100 | 121552335 |
| X | 70115808 | 70116831 | X | 121585386 | 121587547 |
| X | 70139950 | 70143273 | X | 121682137 | 121683963 |
| X | 70167672 | 70168706 | X | 121709977 | 121710552 |
| X | 70187201 | 70193055 | X | 121827093 | 121829468 |
| X | 70201577 | 70209077 | X | 121887394 | 121892096 |
| X | 70209857 | 70211834 | X | 121920567 | 121921667 |
| X | 70218928 | 70221817 | X | 121951074 | 121956369 |
| X | 70230332 | 70243384 | X | 121962722 | 121971113 |
| X | 70250225 | 70308202 | X | 121995202 | 121998505 |
| X | 70312743 | 70421080 | X | 122036076 | 122039358 |
| X | 70423601 | 70437328 | X | 122069624 | 122072066 |
| X | 70448127 | 70569029 | X | 122074022 | 122075309 |
| X | 70585245 | 70590533 | X | 122092755 | 122094267 |
| X | 70599958 | 70611776 | X | 122102300 | 122104760 |
| X | 70623620 | 70671156 | X | 122138981 | 122143534 |
| X | 70687812 | 70690023 | X | 122155622 | 122157807 |
| X | 70691824 | 70696558 | X | 122169485 | 122170730 |
| X | 70705548 | 70726808 | X | 122189513 | 122196009 |
| X | 70734292 | 70742750 | X | 122211698 | 122213326 |
| X | 70747868 | 70770262 | X | 122235151 | 122240183 |
| X | 70793501 | 70814660 | X | 122242533 | 122243688 |
| X | 70948742 | 70962688 | X | 122263687 | 122268222 |
| X | 70965901 | 70979673 | X | 122281388 | 122284518 |
| X | 71001425 | 71014371 | X | 122301368 | 122304941 |
| X | 71046489 | 71050628 | X | 122308291 | 122313091 |
| X | 71052745 | 71053507 | X | 122323366 | 122326336 |
| X | 71075029 | 71077419 | X | 122330030 | 122332007 |
| X | 71081783 | 71086955 | X | 122396768 | 122411918 |
| X | 71124642 | 71128519 | X | 122452351 | 122455083 |
| X | 71131331 | 71133891 | X | 122523303 | 122527487 |
| X | 71140824 | 71147744 | X | 122640295 | 122642556 |
| X | 71185357 | 71210503 | X | 122693690 | 122700366 |
| X | 71216623 | 71219028 | X | 122710977 | 122825922 |
| X | 71223575 | 71228346 | X | 122841160 | 122844143 |
| X | 71239512 | 71245968 | X | 122858431 | 122866090 |
| X | 71258896 | 71261656 | X | 122880967 | 122924539 |
| X | 71265906 | 71277792 | X | 122932143 | 122935683 |
| X | 71290503 | 71332787 | X | 123135240 | 123136230 |
| X | 71354392 | 71430564 | X | 123148674 | 123151555 |
| X | 71441067 | 71445676 | X | 123188027 | 123191087 |
| X | 71559982 | 71562505 | X | 123216782 | 123218248 |
| X | 71601165 | 71601860 | X | 123254377 | 123255202 |
| X | 71661805 | 71663664 | X | 123293683 | 123298610 |
| X | 71707322 | 71711662 | X | 123364757 | 123366772 |
| X | 71850018 | 71855122 | X | 123377561 | 123385024 |
| X | 71869472 | 71871658 | X | 123391633 | 123395074 |
| X | 72153027 | 72153727 | X | 123406528 | 123408153 |
| X | 72202927 | 72206622 | X | 123431566 | 123435417 |
| X | 72263114 | 72264934 | X | 123451793 | 123454515 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 72307509 | 72311522 | | X | 123462883 | 123465919 |
| X | 72350067 | 72351732 | | X | 123500794 | 123504314 |
| X | 72456791 | 72458738 | | X | 123522217 | 123523807 |
| X | 72591117 | 72593004 | | X | 123568256 | 123569176 |
| X | 72654610 | 72655780 | | X | 123639441 | 123644172 |
| X | 72664995 | 72669598 | | X | 123781227 | 123781739 |
| X | 72697708 | 72704105 | | X | 123813810 | 123815670 |
| X | 72770762 | 72771932 | | X | 123950712 | 123953512 |
| X | 72838429 | 72851366 | | X | 123963973 | 123965963 |
| X | 72875993 | 72880680 | | X | 124026867 | 124029099 |
| X | 72904779 | 72909694 | | X | 124034774 | 124036377 |
| X | 72920760 | 72921831 | | X | 124060325 | 124066377 |
| X | 72938273 | 72947440 | | X | 124095395 | 124097480 |
| X | 72984551 | 72985126 | | X | 124109182 | 124110632 |
| X | 72991708 | 72992758 | | X | 124164541 | 124167390 |
| X | 73028737 | 73040089 | | X | 124195469 | 124197584 |
| X | 73065934 | 73080808 | | X | 124219411 | 124220181 |
| X | 73083114 | 73086961 | | X | 124253516 | 124256927 |
| X | 73099586 | 73101206 | | X | 124269259 | 124276247 |
| X | 73202466 | 73203211 | | X | 124287839 | 124289729 |
| X | 73254400 | 73267130 | | X | 124422883 | 124424789 |
| X | 73297515 | 73300512 | | X | 124443165 | 124445211 |
| X | 73375888 | 73379043 | | X | 124690264 | 124691874 |
| X | 73427623 | 73435513 | | X | 124731297 | 124733127 |
| X | 73500737 | 73501432 | | X | 124798369 | 124798974 |
| X | 73519489 | 73520699 | | X | 124891408 | 124895743 |
| X | 73545485 | 73550212 | | X | 124996890 | 125000261 |
| X | 73553327 | 73559154 | | X | 125015706 | 125017134 |
| X | 73575224 | 73579080 | | X | 125027023 | 125028862 |
| X | 73662541 | 73664741 | | X | 125076559 | 125077594 |
| X | 73672065 | 73675606 | | X | 125126064 | 125128529 |
| X | 73686958 | 73690180 | | X | 125251017 | 125252957 |
| X | 73750650 | 73756453 | | X | 125306938 | 125315320 |
| X | 73770828 | 73773640 | | X | 125506559 | 125507951 |
| X | 73918565 | 73922119 | | X | 125512703 | 125515733 |
| X | 73964120 | 73965828 | | X | 125541134 | 125543143 |
| X | 73993520 | 73996948 | | X | 125570831 | 125575679 |
| X | 74061115 | 74062667 | | X | 125679952 | 125683195 |
| X | 74254643 | 74260617 | | X | 125690762 | 125693962 |
| X | 74292170 | 74295140 | | X | 125774262 | 125780534 |
| X | 74340190 | 74348726 | | X | 125827427 | 125829344 |
| X | 74410376 | 74411181 | | X | 125852916 | 125855806 |
| X | 74429758 | 74433233 | | X | 125901652 | 125908362 |
| X | 74469993 | 74473044 | | X | 125927493 | 125928768 |
| X | 74515144 | 74517506 | | X | 126246443 | 126251886 |
| X | 74552223 | 74563725 | | X | 126267430 | 126274304 |
| X | 74657725 | 74661553 | | X | 126356198 | 126358133 |
| X | 74767562 | 74775244 | | X | 126402064 | 126406592 |
| X | 74913628 | 74917448 | | X | 126490425 | 126490737 |
| X | 74917948 | 74922843 | | X | 126586934 | 126589880 |
| X | 74992806 | 74995842 | | X | 126631369 | 126637604 |
| X | 75055784 | 75057859 | | X | 126705549 | 126706279 |
| X | 75075607 | 75080170 | | X | 126858259 | 126859169 |
| X | 75100620 | 75106163 | | X | 126863445 | 126864195 |
| X | 75119011 | 75123812 | | X | 126960320 | 126963828 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 75124192 | 75125977 | X | 126989761 | 126991483 |
| X | 75272728 | 75276488 | X | 126998687 | 127001189 |
| X | 75308648 | 75310145 | X | 127111390 | 127116340 |
| X | 75390497 | 75391712 | X | 127126728 | 127129305 |
| X | 75545240 | 75546777 | X | 127212820 | 127214235 |
| X | 75563699 | 75567379 | X | 127331765 | 127332180 |
| X | 75578431 | 75581888 | X | 127370001 | 127372840 |
| X | 75656508 | 75658119 | X | 127531581 | 127533856 |
| X | 75886419 | 75889989 | X | 127539217 | 127540817 |
| X | 75940291 | 75943477 | X | 127567547 | 127571185 |
| X | 76056028 | 76059512 | X | 127584445 | 127584825 |
| X | 76094406 | 76095081 | X | 127591540 | 127596086 |
| X | 76109833 | 76111981 | X | 127616889 | 127618421 |
| X | 76495179 | 76496444 | X | 127627094 | 127629079 |
| X | 76509284 | 76511329 | X | 127687184 | 127688654 |
| X | 76549352 | 76550532 | X | 127729643 | 127732112 |
| X | 76554409 | 76555214 | X | 127758842 | 127764954 |
| X | 77379138 | 77382278 | X | 127800332 | 127803167 |
| X | 77444522 | 77452388 | X | 127810737 | 127813899 |
| X | 77509374 | 77509760 | X | 127822191 | 127824424 |
| X | 77660099 | 77667095 | X | 127837780 | 127839946 |
| X | 77668345 | 77672355 | X | 127847426 | 127849683 |
| X | 77704938 | 77706293 | X | 127853212 | 127855137 |
| X | 77716288 | 77722299 | X | 127856204 | 127863886 |
| X | 77796859 | 77798902 | X | 127927241 | 127930081 |
| X | 77841007 | 77844022 | X | 127966863 | 127969199 |
| X | 77938925 | 77943234 | X | 127972244 | 127976145 |
| X | 77956525 | 77960272 | X | 127994461 | 127996172 |
| X | 78015808 | 78018172 | X | 127998673 | 128015148 |
| X | 78034535 | 78039179 | X | 128036704 | 128044081 |
| X | 78064392 | 78065677 | X | 128048092 | 128049962 |
| X | 78095021 | 78096621 | X | 128051957 | 128055102 |
| X | 78184073 | 78187349 | X | 128094298 | 128095633 |
| X | 78193991 | 78196176 | X | 128102656 | 128107146 |
| X | 78237628 | 78242807 | X | 128157762 | 128163260 |
| X | 78296873 | 78297328 | X | 128179592 | 128184292 |
| X | 78315233 | 78316918 | X | 128234852 | 128240890 |
| X | 78622885 | 78623538 | X | 128262795 | 128264607 |
| X | 78655636 | 78656831 | X | 128276110 | 128288155 |
| X | 78698181 | 78702153 | X | 128333679 | 128335914 |
| X | 78782551 | 78783556 | X | 128390174 | 128398411 |
| X | 78926723 | 78928044 | X | 128406280 | 128408017 |
| X | 79006870 | 79007415 | X | 128462798 | 128466031 |
| X | 79098388 | 79100671 | X | 128498249 | 128502765 |
| X | 79163952 | 79168394 | X | 128507022 | 128507955 |
| X | 79186668 | 79189544 | X | 128513650 | 128516751 |
| X | 79244945 | 79250501 | X | 128543937 | 128548478 |
| X | 79271085 | 79274002 | X | 128555546 | 128569582 |
| X | 79276482 | 79277537 | X | 128583304 | 128590614 |
| X | 79319744 | 79323831 | X | 128608305 | 128618120 |
| X | 79400228 | 79402843 | X | 128700079 | 128701903 |
| X | 79455025 | 79456205 | X | 128711146 | 128716694 |
| X | 79476946 | 79478504 | X | 128730822 | 128737234 |
| X | 79563657 | 79566492 | X | 128748327 | 128756066 |
| X | 79592894 | 79593374 | X | 128804344 | 128806987 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 79701209 | 79703933 | X | 128857674 | 128896076 |
| X | 79713580 | 79717275 | X | 128910519 | 128914583 |
| X | 80014234 | 80015556 | X | 128915834 | 128916584 |
| X | 80178149 | 80182879 | X | 128916974 | 128927258 |
| X | 80303461 | 80311430 | X | 128940816 | 129088263 |
| X | 80369055 | 80369470 | X | 129103331 | 129106721 |
| X | 80460884 | 80464162 | X | 129125022 | 129134375 |
| X | 80490725 | 80492879 | X | 129144023 | 129159356 |
| X | 80513772 | 80514682 | X | 129167990 | 129170099 |
| X | 80532221 | 80534923 | X | 129225858 | 129235831 |
| X | 80667460 | 80671076 | X | 129298448 | 129302778 |
| X | 80910673 | 80911090 | X | 129348621 | 129352787 |
| X | 80945483 | 80954297 | X | 129363150 | 129366232 |
| X | 81003727 | 81004645 | X | 129387715 | 129395589 |
| X | 81113327 | 81120458 | X | 129460292 | 129469106 |
| X | 81131775 | 81133859 | X | 129478641 | 129492719 |
| X | 81159545 | 81165175 | X | 129503672 | 129506915 |
| X | 81171297 | 81174795 | X | 129518475 | 129519605 |
| X | 81283760 | 81288103 | X | 129549524 | 129552649 |
| X | 81304483 | 81305923 | X | 129575954 | 129579290 |
| X | 81462815 | 81466063 | X | 129594057 | 129596417 |
| X | 81514146 | 81516196 | X | 129621916 | 129622656 |
| X | 81521518 | 81524765 | X | 129641610 | 129646197 |
| X | 81533914 | 81542751 | X | 129674796 | 129679230 |
| X | 81552316 | 81553106 | X | 129732509 | 129736494 |
| X | 81564173 | 81566023 | X | 129794464 | 129795940 |
| X | 81604405 | 81608005 | X | 129810672 | 129811809 |
| X | 81799104 | 81803429 | X | 129814042 | 129816073 |
| X | 81868599 | 81872294 | X | 129864336 | 129865539 |
| X | 81894995 | 81898732 | X | 129878917 | 129879942 |
| X | 81972717 | 81974347 | X | 129979152 | 129980692 |
| X | 82061583 | 82067834 | X | 130005371 | 130012720 |
| X | 82153650 | 82155976 | X | 130042883 | 130054698 |
| X | 82268915 | 82270705 | X | 130127164 | 130132939 |
| X | 82293301 | 82293971 | X | 130192028 | 130193968 |
| X | 82417998 | 82419083 | X | 130280376 | 130286444 |
| X | 82611455 | 82612597 | X | 130305944 | 130307529 |
| X | 82649780 | 82653230 | X | 130355619 | 130357371 |
| X | 82959033 | 82961024 | X | 130396810 | 130401569 |
| X | 83048145 | 83050004 | X | 130416246 | 130417361 |
| X | 83088402 | 83090863 | X | 130475757 | 130476652 |
| X | 83146176 | 83147577 | X | 130500126 | 130501665 |
| X | 83155347 | 83158258 | X | 130625326 | 130635911 |
| X | 83179617 | 83181343 | X | 130665366 | 130682648 |
| X | 83292163 | 83293828 | X | 130762247 | 130764990 |
| X | 83329039 | 83331995 | X | 130774689 | 130776009 |
| X | 83351921 | 83353887 | X | 130800520 | 130804710 |
| X | 83364550 | 83365826 | X | 130811394 | 130814199 |
| X | 83378472 | 83381357 | X | 130853696 | 130857857 |
| X | 83397192 | 83402504 | X | 130872365 | 130877134 |
| X | 83420457 | 83422495 | X | 130895939 | 130899259 |
| X | 83435645 | 83441153 | X | 130904627 | 130905942 |
| X | 83641429 | 83644356 | X | 130936100 | 130937158 |
| X | 83679979 | 83680778 | X | 130941625 | 130945021 |
| X | 83846025 | 83849557 | X | 130984375 | 130985965 |

The chromosomal positon was obtained from UCSC genome browser (http://genome.ucsc.edu/) build 36.

APPENDIX D: Chromosome X
Page 63 of 73

| Chr | Start | End | Chr | Start | End |
|---|---|---|---|---|---|
| X | 83858634 | 83859934 | X | 130995946 | 130998416 |
| X | 83877833 | 83878863 | X | 131086203 | 131087873 |
| X | 83880473 | 83887423 | X | 131112119 | 131116421 |
| X | 83893303 | 83893653 | X | 131137258 | 131138345 |
| X | 83936382 | 83938018 | X | 131178642 | 131180410 |
| X | 83999823 | 84001040 | X | 131259806 | 131266430 |
| X | 84075590 | 84077186 | X | 131270491 | 131273581 |
| X | 84144348 | 84147219 | X | 131283173 | 131294371 |
| X | 84209610 | 84210525 | X | 131330301 | 131333003 |
| X | 84231941 | 84234166 | X | 131355993 | 131357340 |
| X | 84249249 | 84251344 | X | 131362992 | 131364981 |
| X | 84384521 | 84386868 | X | 131388786 | 131391037 |
| X | 84395687 | 84397220 | X | 131442212 | 131446769 |
| X | 84467561 | 84470317 | X | 131450166 | 131452852 |
| X | 84533681 | 84535224 | X | 131548943 | 131553913 |
| X | 84589745 | 84590812 | X | 131598099 | 131599234 |
| X | 84709353 | 84710598 | X | 131614838 | 131617103 |
| X | 84750581 | 84758492 | X | 131634050 | 131636105 |
| X | 84790047 | 84791713 | X | 131660086 | 131660816 |
| X | 84815776 | 84819240 | X | 131675209 | 131682684 |
| X | 84954920 | 84960650 | X | 131735221 | 131737171 |
| X | 85039117 | 85040427 | X | 131772974 | 131778070 |
| X | 85054310 | 85056768 | X | 131880319 | 131883437 |
| X | 85188822 | 85190507 | X | 131917502 | 131920460 |
| X | 85206781 | 85211836 | X | 131943732 | 131945362 |
| X | 85218492 | 85219972 | X | 132010167 | 132010602 |
| X | 85225039 | 85229521 | X | 132015770 | 132018381 |
| X | 85287740 | 85291470 | X | 132054845 | 132060469 |
| X | 85351411 | 85352592 | X | 132080978 | 132081838 |
| X | 85448993 | 85451713 | X | 132092252 | 132093138 |
| X | 85616292 | 85617374 | X | 132133216 | 132136903 |
| X | 85852138 | 85853215 | X | 132178349 | 132180907 |
| X | 85899418 | 85902142 | X | 132194211 | 132196296 |
| X | 85935123 | 85937212 | X | 132208490 | 132210128 |
| X | 85970863 | 85974954 | X | 132223760 | 132228828 |
| X | 85987981 | 85988253 | X | 132251026 | 132253133 |
| X | 86004487 | 86005507 | X | 132277348 | 132278319 |
| X | 86010004 | 86011034 | X | 132299106 | 132302373 |
| X | 86014604 | 86026261 | X | 132374895 | 132377917 |
| X | 86133286 | 86133756 | X | 132404900 | 132408619 |
| X | 86219257 | 86224798 | X | 132430568 | 132436036 |
| X | 86242124 | 86244435 | X | 132452980 | 132454084 |
| X | 86341630 | 86342870 | X | 132457315 | 132461206 |
| X | 86365683 | 86367553 | X | 132466672 | 132472288 |
| X | 86480573 | 86481743 | X | 132495966 | 132498044 |
| X | 86575972 | 86579379 | X | 132511213 | 132517216 |
| X | 86635306 | 86638597 | X | 132526142 | 132529773 |
| X | 86741707 | 86743532 | X | 132741390 | 132747040 |
| X | 86822451 | 86835123 | X | 132774351 | 132783599 |
| X | 86950671 | 86952830 | X | 132813740 | 132814530 |
| X | 87079634 | 87082314 | X | 132840667 | 132844643 |
| X | 87100751 | 87102877 | X | 132854524 | 132857542 |
| X | 87174317 | 87179436 | X | 132870207 | 132873243 |
| X | 87255719 | 87256444 | X | 132946591 | 132950230 |
| X | 87346533 | 87348094 | X | 132956830 | 132959882 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 87355816 | 87364485 | | | X | 132974052 | 132975167 |
| X | 87440672 | 87442709 | | | X | 132983508 | 132986619 |
| X | 87557388 | 87558415 | | | X | 133056265 | 133062079 |
| X | 87588990 | 87591551 | | | X | 133098111 | 133102703 |
| X | 87707997 | 87712137 | | | X | 133133203 | 133136054 |
| X | 87986005 | 87987080 | | | X | 133141511 | 133143902 |
| X | 88192324 | 88194386 | | | X | 133191585 | 133200386 |
| X | 88219188 | 88220948 | | | X | 133334662 | 133336126 |
| X | 88342480 | 88349970 | | | X | 133349187 | 133351201 |
| X | 88716885 | 88733913 | | | X | 133420792 | 133422603 |
| X | 88899110 | 88902145 | | | X | 133450653 | 133453291 |
| X | 89178190 | 89180555 | | | X | 133466430 | 133478420 |
| X | 89358832 | 89368609 | | | X | 133489391 | 133501176 |
| X | 89479991 | 89498418 | | | X | 133506291 | 133513464 |
| X | 90233059 | 90235349 | | | X | 133574087 | 133574470 |
| X | 90239149 | 90240852 | | | X | 133584095 | 133586852 |
| X | 90347750 | 90352549 | | | X | 133607959 | 133611296 |
| X | 90443276 | 90444286 | | | X | 133642405 | 133643992 |
| X | 90575690 | 90578038 | | | X | 133698366 | 133702691 |
| X | 91335847 | 91337558 | | | X | 133706324 | 133708162 |
| X | 91789676 | 91801319 | | | X | 133757031 | 133764678 |
| X | 92304532 | 92306859 | | | X | 133768387 | 133770556 |
| X | 92429779 | 92432375 | | | X | 133830627 | 133832612 |
| X | 92471042 | 92472658 | | | X | 133841068 | 133841723 |
| X | 92502739 | 92505226 | | | X | 133866094 | 133878584 |
| X | 92568570 | 92570118 | | | X | 133887101 | 133894109 |
| X | 92571635 | 92576705 | | | X | 133916067 | 133928146 |
| X | 92719558 | 92722437 | | | X | 133948641 | 133957636 |
| X | 92746381 | 92749305 | | | X | 133965658 | 133966423 |
| X | 92811155 | 92812444 | | | X | 133992416 | 133995327 |
| X | 92851106 | 92851497 | | | X | 134012201 | 134014322 |
| X | 92861586 | 92864132 | | | X | 134023424 | 134027209 |
| X | 93038328 | 93042435 | | | X | 134029079 | 134029969 |
| X | 93155593 | 93161098 | | | X | 134057286 | 134061467 |
| X | 93268636 | 93272965 | | | X | 134131433 | 134136859 |
| X | 93488851 | 93491121 | | | X | 134154463 | 134160329 |
| X | 93497159 | 93500370 | | | X | 134171096 | 134172081 |
| X | 93586895 | 93590728 | | | X | 134246170 | 134254213 |
| X | 93618892 | 93619452 | | | X | 134292541 | 134295161 |
| X | 93635928 | 93640712 | | | X | 134303614 | 134307166 |
| X | 93668572 | 93671732 | | | X | 134309385 | 134311092 |
| X | 93754641 | 93755572 | | | X | 134335125 | 134337465 |
| X | 93768268 | 93771637 | | | X | 134363911 | 134366416 |
| X | 93777563 | 93779050 | | | X | 134382458 | 134401287 |
| X | 93962180 | 93965680 | | | X | 134416730 | 134418241 |
| X | 94059169 | 94062574 | | | X | 134481853 | 134485231 |
| X | 94219232 | 94220487 | | | X | 134498126 | 134501421 |
| X | 94283264 | 94285075 | | | X | 134575916 | 134576876 |
| X | 94286903 | 94291815 | | | X | 134597671 | 134598836 |
| X | 94443980 | 94445047 | | | X | 134640846 | 134642186 |
| X | 94652618 | 94658771 | | | X | 134669012 | 134678058 |
| X | 94817141 | 94818086 | | | X | 134736119 | 134740518 |
| X | 94835327 | 94836592 | | | X | 134799568 | 134813181 |
| X | 94857677 | 94858272 | | | X | 134820716 | 134822766 |
| X | 94901847 | 94902427 | | | X | 134832043 | 134835033 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 94906807 | 94908049 | | | X | 134860797 | 134862592 |
| X | 95034900 | 95035985 | | | X | 134877276 | 134907762 |
| X | 95108048 | 95109412 | | | X | 134937674 | 134938524 |
| X | 95122057 | 95125629 | | | X | 134978113 | 134993166 |
| X | 95144440 | 95146380 | | | X | 135002794 | 135009990 |
| X | 95177306 | 95178345 | | | X | 135034032 | 135058701 |
| X | 95337230 | 95339429 | | | X | 135076611 | 135079791 |
| X | 95373980 | 95377405 | | | X | 135114290 | 135124882 |
| X | 95522671 | 95525163 | | | X | 135172165 | 135175509 |
| X | 95574813 | 95574933 | | | X | 135200190 | 135206455 |
| X | 95614584 | 95616171 | | | X | 135334114 | 135336975 |
| X | 95664781 | 95666086 | | | X | 135392530 | 135394465 |
| X | 95717003 | 95718762 | | | X | 135406095 | 135407568 |
| X | 95736484 | 95739002 | | | X | 135435768 | 135436353 |
| X | 95739272 | 95747608 | | | X | 135436833 | 135439886 |
| X | 95755775 | 95756759 | | | X | 135445271 | 135450654 |
| X | 95766868 | 95772585 | | | X | 135480078 | 135480851 |
| X | 95784631 | 95785818 | | | X | 135484188 | 135488133 |
| X | 96016295 | 96019224 | | | X | 135489458 | 135491578 |
| X | 96025628 | 96032199 | | | X | 135537104 | 135538762 |
| X | 96045294 | 96047486 | | | X | 135676551 | 135679884 |
| X | 96090693 | 96093282 | | | X | 135749140 | 135758950 |
| X | 96186388 | 96188129 | | | X | 135761563 | 135770652 |
| X | 96312843 | 96314028 | | | X | 135785094 | 135862851 |
| X | 96380861 | 96386440 | | | X | 135867090 | 135869547 |
| X | 96415385 | 96428695 | | | X | 135873397 | 135895184 |
| X | 96436828 | 96439355 | | | X | 135919020 | 135928223 |
| X | 96449639 | 96466042 | | | X | 135939945 | 135945973 |
| X | 96474833 | 96478315 | | | X | 135948538 | 135950961 |
| X | 96493120 | 96496647 | | | X | 135953697 | 135955032 |
| X | 96513907 | 96515847 | | | X | 135959389 | 135964004 |
| X | 96560334 | 96560894 | | | X | 135974602 | 135976092 |
| X | 96623798 | 96625347 | | | X | 136051428 | 136052065 |
| X | 96731751 | 96735190 | | | X | 136053860 | 136055048 |
| X | 96754606 | 96757149 | | | X | 136055863 | 136057778 |
| X | 96775443 | 96779897 | | | X | 136060386 | 136064781 |
| X | 96861569 | 96862789 | | | X | 136094709 | 136097479 |
| X | 96980670 | 96982020 | | | X | 136106418 | 136107443 |
| X | 96982376 | 96994086 | | | X | 136156533 | 136157329 |
| X | 97042828 | 97043843 | | | X | 136176822 | 136177652 |
| X | 97105779 | 97110677 | | | X | 136195351 | 136196151 |
| X | 97169874 | 97171789 | | | X | 136227286 | 136231339 |
| X | 97177393 | 97180673 | | | X | 136267206 | 136269466 |
| X | 97210205 | 97212844 | | | X | 136297491 | 136298306 |
| X | 97220528 | 97230412 | | | X | 136314149 | 136316410 |
| X | 97428942 | 97431530 | | | X | 136333627 | 136342214 |
| X | 97479765 | 97480805 | | | X | 136383801 | 136385611 |
| X | 97487852 | 97493362 | | | X | 136428418 | 136429978 |
| X | 97499402 | 97499671 | | | X | 136434681 | 136436077 |
| X | 97504424 | 97507049 | | | X | 136455170 | 136470333 |
| X | 97624166 | 97625031 | | | X | 136475106 | 136476866 |
| X | 97655379 | 97656424 | | | X | 136498305 | 136500201 |
| X | 97744665 | 97745180 | | | X | 136558671 | 136563450 |
| X | 97753067 | 97754850 | | | X | 136651363 | 136654438 |
| X | 97779996 | 97782041 | | | X | 136681461 | 136681901 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 97909339 | 97911406 | X | 136776343 | 136781438 |
| X | 97994441 | 97995976 | X | 136832813 | 136835237 |
| X | 98031655 | 98033926 | X | 136848215 | 136850532 |
| X | 98063799 | 98065014 | X | 136864030 | 136867965 |
| X | 98148211 | 98149031 | X | 136896720 | 136897740 |
| X | 98191198 | 98197707 | X | 137015350 | 137018656 |
| X | 98211030 | 98213765 | X | 137049476 | 137053508 |
| X | 98270859 | 98272529 | X | 137053823 | 137054980 |
| X | 98300281 | 98307435 | X | 137055210 | 137059257 |
| X | 98436632 | 98449449 | X | 137124296 | 137127845 |
| X | 98454636 | 98458321 | X | 137137557 | 137139512 |
| X | 98469233 | 98471385 | X | 137156195 | 137161503 |
| X | 98497854 | 98501815 | X | 137166509 | 137179457 |
| X | 98563250 | 98563355 | X | 137233894 | 137241751 |
| X | 98638942 | 98639882 | X | 137344136 | 137345141 |
| X | 98641557 | 98643369 | X | 137391168 | 137392443 |
| X | 98783615 | 98784260 | X | 137409295 | 137411413 |
| X | 98838471 | 98844363 | X | 137426621 | 137432266 |
| X | 98858461 | 98866012 | X | 137451268 | 137453013 |
| X | 98923268 | 98925658 | X | 137578420 | 137588387 |
| X | 99134309 | 99142721 | X | 137620013 | 137622576 |
| X | 99150877 | 99152624 | X | 137636796 | 137638793 |
| X | 99164438 | 99166910 | X | 137653747 | 137655112 |
| X | 99216628 | 99217793 | X | 137687592 | 137695873 |
| X | 99218263 | 99218898 | X | 137701147 | 137703452 |
| X | 99292627 | 99298421 | X | 137749238 | 137750833 |
| X | 99358684 | 99361089 | X | 137792530 | 137794250 |
| X | 99442108 | 99443844 | X | 137813152 | 137815787 |
| X | 99481301 | 99486798 | X | 137824704 | 137828779 |
| X | 99512237 | 99513472 | X | 137836343 | 137837623 |
| X | 99547091 | 99554380 | X | 137853132 | 137856169 |
| X | 99629603 | 99632646 | X | 137869061 | 137873029 |
| X | 99713385 | 99715424 | X | 137887974 | 137888619 |
| X | 99731916 | 99736286 | X | 137929865 | 137931290 |
| X | 99761725 | 99764412 | X | 137934165 | 137935566 |
| X | 99776074 | 99778509 | X | 137989523 | 137994181 |
| X | 99806492 | 99812525 | X | 138031188 | 138034323 |
| X | 99827339 | 99829604 | X | 138043316 | 138044461 |
| X | 99924143 | 99925818 | X | 138052310 | 138053115 |
| X | 99928222 | 99933850 | X | 138057981 | 138060691 |
| X | 99961210 | 99962560 | X | 138104310 | 138106143 |
| X | 99986001 | 99990364 | X | 138112463 | 138115268 |
| X | 100004814 | 100006693 | X | 138122265 | 138124457 |
| X | 100115250 | 100118857 | X | 138193843 | 138196278 |
| X | 100123724 | 100127242 | X | 138208327 | 138213971 |
| X | 100185442 | 100198689 | X | 138273982 | 138275552 |
| X | 100207852 | 100210673 | X | 138336099 | 138338999 |
| X | 100223668 | 100232857 | X | 138359970 | 138361411 |
| X | 100238712 | 100246826 | X | 138440806 | 138443387 |
| X | 100275055 | 100283351 | X | 138448970 | 138456233 |
| X | 100376454 | 100378739 | X | 138598600 | 138603231 |
| X | 100431556 | 100436537 | X | 138608805 | 138610025 |
| X | 100477140 | 100497700 | X | 138628992 | 138632316 |
| X | 100502392 | 100506934 | X | 138660306 | 138661026 |
| X | 100532256 | 100533496 | X | 138757689 | 138763554 |

The chromosomal positon was obtained from UCSC genome browser (http://genome.ucsc.edu/) build 36.

APPENDIX D: Chromosome X
Page 67 of 73

| Chr | Start | End | | Chr | Start | End |
|---|---|---|---|---|---|---|
| X | 100546080 | 100554862 | | X | 138816698 | 138822852 |
| X | 100562185 | 100567912 | | X | 138840959 | 138844750 |
| X | 100679722 | 100697233 | | X | 138883370 | 138885618 |
| X | 100752019 | 100759640 | | X | 138892151 | 138911347 |
| X | 100764625 | 100766841 | | X | 138920005 | 138925007 |
| X | 100797965 | 100801457 | | X | 138935884 | 138944948 |
| X | 100835883 | 100837985 | | X | 138966699 | 138977771 |
| X | 100874626 | 100875681 | | X | 139000682 | 139005297 |
| X | 100891582 | 100893402 | | X | 139012581 | 139015322 |
| X | 100963933 | 100965558 | | X | 139038156 | 139041239 |
| X | 100972394 | 100973019 | | X | 139053170 | 139056786 |
| X | 100977654 | 100985950 | | X | 139204665 | 139208752 |
| X | 100988666 | 100990786 | | X | 139236389 | 139238749 |
| X | 101025603 | 101031259 | | X | 139246788 | 139247958 |
| X | 101032769 | 101033474 | | X | 139261184 | 139263868 |
| X | 101071481 | 101072286 | | X | 139296194 | 139300380 |
| X | 101072746 | 101075240 | | X | 139344495 | 139347566 |
| X | 101112514 | 101116256 | | X | 139390559 | 139391579 |
| X | 101121099 | 101122164 | | X | 139401836 | 139402392 |
| X | 101203748 | 101208168 | | X | 139414294 | 139421361 |
| X | 101218541 | 101220681 | | X | 139427515 | 139428819 |
| X | 101264126 | 101265546 | | X | 139446645 | 139449717 |
| X | 101266006 | 101268918 | | X | 139459236 | 139459821 |
| X | 101282221 | 101286038 | | X | 139506404 | 139507429 |
| X | 101294936 | 101298828 | | X | 139598383 | 139642978 |
| X | 101484428 | 101485658 | | X | 139664625 | 139666408 |
| X | 101639449 | 101644699 | | X | 139692390 | 139694440 |
| X | 101656983 | 101663592 | | X | 139765816 | 139768944 |
| X | 101687904 | 101691562 | | X | 139811146 | 139816194 |
| X | 101705198 | 101707140 | | X | 139821104 | 139823114 |
| X | 101740518 | 101742048 | | X | 139856480 | 139857785 |
| X | 101742613 | 101747327 | | X | 139874308 | 139880716 |
| X | 101791828 | 101794351 | | X | 139885547 | 139886588 |
| X | 101801277 | 101802142 | | X | 139894778 | 139896823 |
| X | 101852787 | 101855602 | | X | 140051528 | 140054153 |
| X | 101862400 | 101862930 | | X | 140066997 | 140071390 |
| X | 101878094 | 101879927 | | X | 140097076 | 140103303 |
| X | 101902545 | 101905255 | | X | 140178461 | 140180403 |
| X | 101909335 | 101910722 | | X | 140214052 | 140214718 |
| X | 101913949 | 101914968 | | X | 140276506 | 140280163 |
| X | 101954121 | 101956401 | | X | 140326106 | 140331147 |
| X | 102107082 | 102108607 | | X | 140372684 | 140374813 |
| X | 102129639 | 102132536 | | X | 140375581 | 140376177 |
| X | 102204839 | 102228351 | | X | 140574645 | 140578859 |
| X | 102245256 | 102261680 | | X | 140591484 | 140613498 |
| X | 102272466 | 102281382 | | X | 140736304 | 140737506 |
| X | 102302534 | 102304269 | | X | 140786687 | 140788591 |
| X | 102312125 | 102315711 | | X | 140794782 | 140798601 |
| X | 102322443 | 102325119 | | X | 140808229 | 140830774 |
| X | 102354866 | 102363429 | | X | 140852350 | 140855708 |
| X | 102383134 | 102385140 | | X | 140870548 | 140872974 |
| X | 102395502 | 102397091 | | X | 140889821 | 140891818 |
| X | 102409326 | 102411131 | | X | 140965023 | 140967344 |
| X | 102415439 | 102418373 | | X | 140973953 | 140975378 |
| X | 102433223 | 102435968 | | X | 141031512 | 141033381 |

The chromosomal positon was obtained from UCSC genome browser (http://genome.ucsc.edu/) build 36.

APPENDIX D: Chromosome X

| Chr | Start | End | | Chr | Start | End |
|---|---|---|---|---|---|---|
| X | 102447016 | 102450403 | | X | 141076329 | 141077814 |
| X | 102451528 | 102453088 | | X | 141089368 | 141092733 |
| X | 102471443 | 102473018 | | X | 141103491 | 141113410 |
| X | 102497733 | 102500692 | | X | 141118325 | 141127829 |
| X | 102515640 | 102519494 | | X | 141142369 | 141148625 |
| X | 102538718 | 102539968 | | X | 141166750 | 141168771 |
| X | 102543210 | 102548873 | | X | 141181112 | 141189265 |
| X | 102552575 | 102554203 | | X | 141265050 | 141268260 |
| X | 102570621 | 102579970 | | X | 141299695 | 141307470 |
| X | 102619324 | 102623009 | | X | 141329107 | 141334432 |
| X | 102627286 | 102629319 | | X | 141335177 | 141335402 |
| X | 102632874 | 102637066 | | X | 141340148 | 141343583 |
| X | 102653734 | 102659417 | | X | 141419935 | 141421000 |
| X | 102696828 | 102700745 | | X | 141456196 | 141456917 |
| X | 102713896 | 102717317 | | X | 141482832 | 141483577 |
| X | 102769844 | 102772810 | | X | 141545807 | 141549956 |
| X | 102827628 | 102831658 | | X | 141794769 | 141797214 |
| X | 102832393 | 102833789 | | X | 141842078 | 141845165 |
| X | 102840602 | 102843977 | | X | 141850503 | 141850919 |
| X | 102847943 | 102852717 | | X | 141940271 | 141950244 |
| X | 102868974 | 102871924 | | X | 141956865 | 141958570 |
| X | 102880858 | 102886386 | | X | 142036415 | 142039596 |
| X | 102902637 | 102908590 | | X | 142067322 | 142068587 |
| X | 102926559 | 102928629 | | X | 142150865 | 142152857 |
| X | 102964094 | 102965964 | | X | 142154768 | 142165914 |
| X | 102972052 | 102975188 | | X | 142176200 | 142178062 |
| X | 103001994 | 103004841 | | X | 142190459 | 142192589 |
| X | 103045665 | 103047397 | | X | 142201327 | 142204437 |
| X | 103053119 | 103060790 | | X | 142327273 | 142328478 |
| X | 103090288 | 103095773 | | X | 142374209 | 142378162 |
| X | 103103197 | 103104828 | | X | 142417486 | 142419211 |
| X | 103145766 | 103221960 | | X | 142423137 | 142433399 |
| X | 103243036 | 103249264 | | X | 142471023 | 142474922 |
| X | 103286781 | 103288630 | | X | 142483043 | 142487603 |
| X | 103296574 | 103298715 | | X | 142497993 | 142500643 |
| X | 103361918 | 103365918 | | X | 142531579 | 142534755 |
| X | 103384567 | 103393207 | | X | 142535525 | 142536887 |
| X | 103437284 | 103446159 | | X | 142545452 | 142555074 |
| X | 103455569 | 103458448 | | X | 142622039 | 142640805 |
| X | 103463810 | 103472841 | | X | 142644175 | 142645531 |
| X | 103515489 | 103520235 | | X | 142666795 | 142670430 |
| X | 103549618 | 103551493 | | X | 142693986 | 142700469 |
| X | 103554243 | 103556591 | | X | 142715351 | 142717756 |
| X | 103561541 | 103564037 | | X | 142749285 | 142750444 |
| X | 103599482 | 103601073 | | X | 142804972 | 142806427 |
| X | 103603733 | 103611868 | | X | 143239982 | 143247496 |
| X | 103678462 | 103684834 | | X | 143291657 | 143294532 |
| X | 103695641 | 103700835 | | X | 143424025 | 143424910 |
| X | 103711339 | 103712174 | | X | 143500753 | 143506543 |
| X | 103784432 | 103795557 | | X | 143512778 | 143514173 |
| X | 103798039 | 103798899 | | X | 143584190 | 143591457 |
| X | 103810635 | 103816164 | | X | 143821682 | 143827455 |
| X | 103819466 | 103823071 | | X | 143897030 | 143898744 |
| X | 103831112 | 103832162 | | X | 143921840 | 143923930 |
| X | 103835823 | 103837128 | | X | 143945019 | 143949049 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 103881014 | 103885493 | X | 143950249 | 143953002 |
| X | 103894977 | 103903916 | X | 143958668 | 143961650 |
| X | 103922962 | 103927715 | X | 144068458 | 144072382 |
| X | 104003626 | 104006581 | X | 144076044 | 144084151 |
| X | 104019068 | 104027539 | X | 144136754 | 144145678 |
| X | 104043671 | 104049432 | X | 144209921 | 144215388 |
| X | 104124574 | 104127890 | X | 144251659 | 144256198 |
| X | 104141640 | 104142822 | X | 144323506 | 144328240 |
| X | 104175667 | 104176802 | X | 144388141 | 144389026 |
| X | 104195819 | 104199792 | X | 144393219 | 144396694 |
| X | 104220188 | 104225620 | X | 144516510 | 144520853 |
| X | 104233427 | 104239269 | X | 144544571 | 144544976 |
| X | 104243842 | 104245807 | X | 144577896 | 144583680 |
| X | 104248567 | 104255503 | X | 144609225 | 144613529 |
| X | 104267402 | 104272692 | X | 144681152 | 144686140 |
| X | 104302851 | 104303886 | X | 144700508 | 144704475 |
| X | 104335046 | 104336191 | X | 144705520 | 144714206 |
| X | 104363138 | 104375140 | X | 144737782 | 144743256 |
| X | 104393143 | 104397213 | X | 144767099 | 144769916 |
| X | 104444883 | 104446028 | X | 144787123 | 144789023 |
| X | 104600755 | 104606530 | X | 144860211 | 144866747 |
| X | 104638534 | 104640314 | X | 144881498 | 144886195 |
| X | 104684549 | 104686741 | X | 144930843 | 144935944 |
| X | 104763515 | 104765371 | X | 144955608 | 144957984 |
| X | 104834158 | 104836265 | X | 144971915 | 144974457 |
| X | 104845543 | 104848276 | X | 145032606 | 145036718 |
| X | 104893036 | 104896982 | X | 145059618 | 145061225 |
| X | 104924135 | 104926195 | X | 145062420 | 145064429 |
| X | 104951667 | 104954332 | X | 145094615 | 145097931 |
| X | 104964759 | 104969168 | X | 145099956 | 145104245 |
| X | 104981846 | 104983976 | X | 145147835 | 145149348 |
| X | 104999832 | 105000967 | X | 145218149 | 145221125 |
| X | 105146201 | 105154964 | X | 145226868 | 145227985 |
| X | 105169081 | 105177282 | X | 145229297 | 145237752 |
| X | 105189771 | 105193533 | X | 145263073 | 145265239 |
| X | 105222453 | 105224193 | X | 145267843 | 145269702 |
| X | 105257858 | 105261889 | X | 145274438 | 145277318 |
| X | 105297335 | 105299139 | X | 145311302 | 145314029 |
| X | 105485086 | 105486591 | X | 145323388 | 145325758 |
| X | 105494679 | 105501262 | X | 145337146 | 145342378 |
| X | 105507742 | 105512072 | X | 145387637 | 145388572 |
| X | 105516470 | 105521775 | X | 145398156 | 145400646 |
| X | 105552457 | 105556627 | X | 145430565 | 145435141 |
| X | 105570586 | 105571546 | X | 145742060 | 145744340 |
| X | 105597078 | 105599138 | X | 145799428 | 145803386 |
| X | 105691654 | 105695629 | X | 145977398 | 145978109 |
| X | 105714701 | 105718913 | X | 146021191 | 146024064 |
| X | 105726234 | 105731509 | X | 146058352 | 146059575 |
| X | 105741311 | 105744894 | X | 146113896 | 146116721 |
| X | 105833676 | 105834466 | X | 146121207 | 146124707 |
| X | 105853070 | 105857625 | X | 146149411 | 146153706 |
| X | 105931744 | 105934173 | X | 146169848 | 146176056 |
| X | 105967962 | 105969219 | X | 146272842 | 146273949 |
| X | 106006734 | 106008569 | X | 146316074 | 146316849 |
| X | 106126593 | 106132514 | X | 146368285 | 146368965 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 106181615 | 106186275 | | | X | 146519459 | 146521014 |
| X | 106213870 | 106216404 | | | X | 146532753 | 146537221 |
| X | 106322826 | 106323211 | | | X | 146716906 | 146718241 |
| X | 106335102 | 106337048 | | | X | 146753877 | 146754687 |
| X | 106401503 | 106403669 | | | X | 146797623 | 146802205 |
| X | 106415681 | 106416681 | | | X | 146827257 | 146828142 |
| X | 106471546 | 106475918 | | | X | 146879450 | 146883426 |
| X | 106477318 | 106480208 | | | X | 146908369 | 146909629 |
| X | 106515127 | 106515943 | | | X | 146925825 | 146928121 |
| X | 106578286 | 106592961 | | | X | 146930525 | 146932454 |
| X | 106626535 | 106629119 | | | X | 146970035 | 146976652 |
| X | 106634559 | 106636484 | | | X | 146985487 | 146987832 |
| X | 106640910 | 106652847 | | | X | 147011151 | 147012196 |
| X | 106658230 | 106661421 | | | X | 147033757 | 147044024 |
| X | 106676095 | 106679537 | | | X | 147084627 | 147085176 |
| X | 106682636 | 106683776 | | | X | 147157706 | 147159191 |
| X | 106701867 | 106702917 | | | X | 147260877 | 147264981 |
| X | 106722970 | 106759181 | | | X | 147352079 | 147353364 |
| X | 106766755 | 106767155 | | | X | 147357046 | 147357476 |
| X | 106785361 | 106812002 | | | X | 147389392 | 147391147 |
| X | 106818577 | 106823069 | | | X | 147434492 | 147435917 |
| X | 106832317 | 106850790 | | | X | 147438293 | 147438878 |
| X | 106862064 | 106909281 | | | X | 147500320 | 147502510 |
| X | 106915367 | 106917751 | | | X | 147530808 | 147535374 |
| X | 106918066 | 106920397 | | | X | 147542292 | 147546823 |
| X | 106922055 | 106923330 | | | X | 147567031 | 147570254 |
| X | 106933318 | 106939812 | | | X | 147640554 | 147643284 |
| X | 106955373 | 106958614 | | | X | 147714336 | 147718475 |
| X | 106993897 | 106996520 | | | X | 147763825 | 147774555 |
| X | 107002478 | 107006473 | | | X | 147777915 | 147783324 |
| X | 107035757 | 107037469 | | | X | 147802183 | 147803865 |
| X | 107065003 | 107070936 | | | X | 147814046 | 147815093 |
| X | 107107445 | 107113335 | | | X | 147844076 | 147847387 |
| X | 107137719 | 107145991 | | | X | 147895712 | 147899284 |
| X | 107219282 | 107221665 | | | X | 147924794 | 147933441 |
| X | 107234258 | 107238173 | | | X | 147982930 | 147984175 |
| X | 107269601 | 107274716 | | | X | 148100762 | 148109146 |
| X | 107283269 | 107285788 | | | X | 148180235 | 148180933 |
| X | 107314335 | 107323143 | | | X | 148211106 | 148215203 |
| X | 107328835 | 107331010 | | | X | 148242839 | 148244764 |
| X | 107335773 | 107346419 | | | X | 148260016 | 148261101 |
| X | 107383248 | 107395049 | | | X | 148275080 | 148276650 |
| X | 107397874 | 107399897 | | | X | 148293184 | 148296029 |
| X | 107429456 | 107434674 | | | X | 148321779 | 148324537 |
| X | 107458391 | 107460040 | | | X | 148344205 | 148358910 |
| X | 107464617 | 107468377 | | | X | 148375706 | 148384145 |
| X | 107470302 | 107472506 | | | X | 148393000 | 148395678 |
| X | 107612178 | 107615378 | | | X | 148421689 | 148454856 |
| X | 107666520 | 107671129 | | | X | 148494258 | 148496888 |
| X | 107754346 | 107755446 | | | X | 148500483 | 148502840 |
| X | 107859221 | 107860425 | | | X | 148519651 | 148521716 |
| X | 107864419 | 107867394 | | | X | 148603337 | 148606067 |
| X | 108174691 | 108175902 | | | X | 148647318 | 148661706 |
| X | 108221150 | 108225488 | | | X | 148692930 | 148699762 |
| X | 108235669 | 108237545 | | | X | 148709349 | 148726315 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 108307511 | 108314322 | X | 148765570 | 148765750 |
| X | 108317166 | 108318296 | X | 148770624 | 148774764 |
| X | 108369863 | 108371755 | X | 148835474 | 148867080 |
| X | 108385009 | 108386586 | X | 148879797 | 148882806 |
| X | 108424822 | 108434003 | X | 148921815 | 148932199 |
| X | 108489665 | 108495205 | X | 148963902 | 148966422 |
| X | 108519039 | 108521262 | X | 149064222 | 149065292 |
| X | 108530762 | 108531567 | X | 149099034 | 149100953 |
| X | 108571260 | 108575311 | X | 149130592 | 149136910 |
| X | 108586966 | 108589536 | X | 149152664 | 149158020 |
| X | 108593248 | 108594021 | X | 149163725 | 149164675 |
| X | 108622524 | 108629551 | X | 149183470 | 149185249 |
| X | 108633227 | 108637609 | X | 149246696 | 149248311 |
| X | 108663600 | 108667424 | X | 149255775 | 149258830 |
| X | 108683721 | 108684472 | X | 149278947 | 149285434 |
| X | 108693074 | 108694589 | X | 149332098 | 149340673 |
| X | 108744940 | 108746120 | X | 149366583 | 149367353 |
| X | 108748195 | 108751832 | X | 149372204 | 149374288 |
| X | 108754150 | 108755342 | X | 149388317 | 149390752 |
| X | 108810654 | 108810930 | X | 149423634 | 149439551 |
| X | 108817170 | 108819780 | X | 149452824 | 149471605 |
| X | 108841078 | 108841638 | X | 149482239 | 149488546 |
| X | 108862025 | 108863971 | X | 149522139 | 149527296 |
| X | 108913104 | 108914485 | X | 149597644 | 149599363 |
| X | 108943189 | 108944676 | X | 149611991 | 149617571 |
| X | 108987317 | 108991547 | X | 149668960 | 149697393 |
| X | 108994592 | 109000764 | X | 149764864 | 149768205 |
| X | 109041618 | 109047098 | X | 149805131 | 149828399 |
| X | 109072206 | 109074951 | X | 149858409 | 149864304 |
| X | 109093614 | 109097112 | X | 149871988 | 149916226 |
| X | 109109946 | 109111721 | X | 149928929 | 149934749 |
| X | 109130774 | 109134486 | X | 149943277 | 149949145 |
| X | 109136921 | 109137816 | X | 149961111 | 149962440 |
| X | 109161626 | 109164114 | X | 149995313 | 150001968 |
| X | 109167754 | 109168440 | X | 150005998 | 150008603 |
| X | 109173343 | 109179173 | X | 150030976 | 150035232 |
| X | 109268749 | 109270854 | X | 150046543 | 150052979 |
| X | 109297706 | 109299676 | X | 150072292 | 150081197 |
| X | 109302266 | 109306975 | X | 150091732 | 150103745 |
| X | 109345587 | 109347287 | X | 150145576 | 150150228 |
| X | 109390375 | 109391427 | X | 150166433 | 150169128 |
| X | 109446841 | 109448810 | X | 150198788 | 150204016 |
| X | 109514680 | 109516975 | X | 150227248 | 150229229 |
| X | 109546602 | 109550655 | X | 150310548 | 150317214 |
| X | 109553718 | 109554393 | X | 150331753 | 150337515 |
| X | 109580960 | 109585635 | X | 150351285 | 150353027 |
| X | 109642956 | 109647671 | X | 150401163 | 150402543 |
| X | 109650304 | 109653167 | X | 150434726 | 150436901 |
| X | 109660429 | 109663766 | X | 150441628 | 150442453 |
| X | 109710103 | 109711233 | X | 150451914 | 150457261 |
| X | 109766046 | 109768937 | X | 150464290 | 150471004 |
| X | 109776070 | 109779421 | X | 150479795 | 150486735 |
| X | 109850563 | 109852738 | X | 150537370 | 150539844 |
| X | 109853438 | 109856814 | X | 150571305 | 150576609 |
| X | 109869379 | 109871674 | X | 150597214 | 150601459 |

The chromosomal positon was obtained from UCSC genome browser (http://genome.ucsc.edu/) build 36.

APPENDIX D: Chromosome X

| Chr | Start | End | Chr | Start | End |
|---|---|---|---|---|---|
| X | 109932721 | 109938590 | X | 150609077 | 150630606 |
| X | 109975980 | 109980105 | X | 150640124 | 150651208 |
| X | 109994795 | 109996383 | X | 150653528 | 150665028 |
| X | 110018027 | 110018892 | X | 150674452 | 150687138 |
| X | 110043633 | 110048264 | X | 150711553 | 150720440 |
| X | 110049769 | 110051289 | X | 150722535 | 150726287 |
| X | 110086884 | 110087434 | X | 150730805 | 150732145 |
| X | 110115416 | 110118776 | X | 150787838 | 150790378 |
| X | 110137356 | 110139816 | X | 150809071 | 150810523 |
| X | 110177924 | 110178864 | X | 150823849 | 150825148 |
| X | 110213178 | 110216433 | X | 150829640 | 150845327 |
| X | 110234900 | 110236870 | X | 150857488 | 150858311 |
| X | 110254459 | 110257621 | X | 150872705 | 150881723 |
| X | 110274513 | 110278145 | X | 150890007 | 150896901 |
| X | 110312627 | 110313782 | X | 150902296 | 150903666 |
| X | 110357487 | 110359007 | X | 150934335 | 150937690 |
| X | 110364707 | 110366853 | X | 150945380 | 150947694 |
| X | 110400988 | 110411132 | X | 150987333 | 150988053 |
| X | 110413022 | 110414422 | X | 150990942 | 150991962 |
| X | 110419777 | 110421937 | X | 151001614 | 151011006 |
| X | 110437601 | 110442517 | X | 151036634 | 151040050 |
| X | 110461368 | 110462847 | X | 151054297 | 151058362 |
| X | 110477783 | 110485168 | X | 151075328 | 151077359 |
| X | 110498284 | 110500519 | X | 151095256 | 151096566 |
| X | 110513029 | 110517786 | X | 151163370 | 151165693 |
| X | 110524240 | 110529730 | X | 151176039 | 151177189 |
| X | 110539573 | 110540652 | X | 151197021 | 151203136 |
| X | 110553929 | 110554824 | X | 151221993 | 151233063 |
| X | 110615139 | 110618266 | X | 151284539 | 151286464 |
| X | 110623867 | 110625462 | X | 151290135 | 151292200 |
| X | 110630244 | 110631168 | X | 151296354 | 151300156 |
| X | 110645810 | 110649530 | X | 151398292 | 151401025 |
| X | 110707802 | 110711837 | X | 151439646 | 151440636 |
| X | 110749281 | 110754494 | X | 151548887 | 151549737 |
| X | 110810777 | 110811921 | X | 151557449 | 151577166 |
| X | 110887777 | 110890145 | X | 151578521 | 151579216 |
| X | 110900627 | 110901562 | X | 151620293 | 151655671 |
| X | 110914166 | 110921102 | X | 151740854 | 151744530 |
| X | 110940578 | 110944226 | X | 151749434 | 151774572 |
| X | 110953400 | 110955592 | X | 151781925 | 151844194 |
| X | 110961055 | 110962740 | X | 151855836 | 151857156 |
| X | 111004284 | 111006456 | X | 151860629 | 151867603 |
| X | 111009396 | 111010421 | X | 151876984 | 151878676 |
| X | 111023436 | 111024418 | X | 151902865 | 151917093 |
| X | 111048065 | 111049800 | X | 151918693 | 151921855 |
| X | 111051720 | 111056716 | X | 151928410 | 151931520 |
| X | 111092872 | 111101023 | X | 151938237 | 151941809 |
| X | 111114456 | 111116576 | X | 151946929 | 151952644 |
| X | 111145617 | 111149681 | X | 151957405 | 151958942 |
| X | 111169184 | 111171218 | X | 151974759 | 152004117 |
| X | 111187031 | 111191300 | X | 152013279 | 152021052 |
| X | 111196385 | 111198320 | X | 152088592 | 152093088 |
| X | 111210767 | 111212582 | X | 152098395 | 152102127 |
| X | 111273575 | 111275205 | X | 152110905 | 152114427 |
| X | 111285291 | 111285871 | X | 152121549 | 152140604 |

The chromosomal positon was obtained from UCSC genome browser (http://genome.ucsc.edu/) build 36.

APPENDIX D: Chromosome X

| Chr | Start | End | | | Chr | Start | End |
|---|---|---|---|---|---|---|---|
| X | 111314449 | 111317274 | | | X | 152157967 | 152214383 |
| X | 111319741 | 111321670 | | | X | 152219651 | 152240836 |
| X | 111346403 | 111348574 | | | X | 152263559 | 152275843 |
| X | 111404067 | 111408882 | | | X | 152291889 | 152761396 |
| X | 111484547 | 111485622 | | | X | 152768870 | 152973306 |
| X | 111493406 | 111500106 | | | X | 152993081 | 152999296 |
| X | 111522196 | 111523438 | | | X | 153014749 | 153541731 |
| X | 111654063 | 111658281 | | | X | 153598428 | 153599373 |
| X | 111670243 | 111673183 | | | X | 153638007 | 153639528 |
| X | 111691715 | 111698851 | | | X | 153640998 | 153642978 |
| X | 111742911 | 111745488 | | | X | 153643478 | 153663775 |
| X | 111749703 | 111750573 | | | X | 153686177 | 153688030 |
| X | 111796620 | 111797370 | | | X | 153698991 | 153700828 |
| X | 111806563 | 111819156 | | | X | 153876739 | 153878356 |
| X | 111826990 | 111831296 | | | X | 153937171 | 153939692 |
| X | 111871113 | 111871633 | | | X | 153950521 | 153959272 |
| X | 111902786 | 111904556 | | | X | 153967574 | 153970752 |
| | | | | | X | 154015994 | 154019150 |
| | | | | | X | 154092066 | 154094166 |
| | | | | | X | 154097122 | 154098874 |
| | | | | | X | 154103149 | 154108185 |
| | | | | | X | 154109797 | 154110567 |
| | | | | | X | 154129359 | 154130684 |
| | | | | | X | 154173833 | 154176155 |
| | | | | | X | 154447014 | 154448624 |
| | | | | | X | 154559375 | 154561380 |
| | | | | | X | 154570498 | 154572288 |
| | | | | | X | 154682705 | 154686790 |
| | | | | | X | 154763009 | 154764905 |
| | | | | | X | 154830874 | 154841760 |
| | | | | | X | 154853082 | 154912256 |

The chromosomal positon was obtained from UCSC genome browser (http://genome.ucsc.edu/) build 36.

APPENDIX E: Chromosome Y
Page 1 of 58

| Chr | Start | End | | | Chr | Start | End |
|---|---|---|---|---|---|---|---|
| Y | 108587 | 110217 | | | Y | 14361290 | 14361643 |
| Y | 114944 | 116849 | | | Y | 14370946 | 14371421 |
| Y | 133133 | 133523 | | | Y | 14372876 | 14374236 |
| Y | 214868 | 218845 | | | Y | 14376130 | 14376565 |
| Y | 236161 | 237694 | | | Y | 14381487 | 14382077 |
| Y | 241906 | 244930 | | | Y | 14384030 | 14385299 |
| Y | 248643 | 250943 | | | Y | 14387278 | 14387476 |
| Y | 260569 | 261139 | | | Y | 14405794 | 14406529 |
| Y | 262080 | 263436 | | | Y | 14410625 | 14411937 |
| Y | 286687 | 287052 | | | Y | 14416283 | 14418226 |
| Y | 295843 | 297903 | | | Y | 14423060 | 14423336 |
| Y | 304869 | 307899 | | | Y | 14427689 | 14430456 |
| Y | 312972 | 313842 | | | Y | 14436720 | 14436894 |
| Y | 318564 | 319664 | | | Y | 14440030 | 14440770 |
| Y | 324226 | 324791 | | | Y | 14447319 | 14447535 |
| Y | 337236 | 338353 | | | Y | 14449131 | 14450810 |
| Y | 340261 | 343681 | | | Y | 14454027 | 14454829 |
| Y | 356718 | 359466 | | | Y | 14458961 | 14460160 |
| Y | 363338 | 363981 | | | Y | 14462509 | 14462723 |
| Y | 369636 | 380222 | | | Y | 14477714 | 14478019 |
| Y | 380307 | 380838 | | | Y | 14483546 | 14483707 |
| Y | 381367 | 382403 | | | Y | 14488432 | 14488757 |
| Y | 387332 | 387608 | | | Y | 14489226 | 14490082 |
| Y | 389319 | 391525 | | | Y | 14505479 | 14505784 |
| Y | 425699 | 426257 | | | Y | 14540006 | 14541986 |
| Y | 433368 | 438139 | | | Y | 14565401 | 14565501 |
| Y | 444684 | 445165 | | | Y | 14566510 | 14567727 |
| Y | 449238 | 453261 | | | Y | 14570087 | 14570910 |
| Y | 456098 | 462697 | | | Y | 14581547 | 14582451 |
| Y | 474453 | 475065 | | | Y | 14587236 | 14587641 |
| Y | 492701 | 493237 | | | Y | 14597551 | 14597803 |
| Y | 498081 | 499028 | | | Y | 14680602 | 14682002 |
| Y | 501088 | 502877 | | | Y | 14688259 | 14688724 |
| Y | 508062 | 508496 | | | Y | 14688923 | 14690280 |
| Y | 513655 | 521376 | | | Y | 14694861 | 14695193 |
| Y | 526099 | 527653 | | | Y | 14697660 | 14698470 |
| Y | 538042 | 538448 | | | Y | 14699916 | 14704820 |
| Y | 551387 | 551918 | | | Y | 14710304 | 14710781 |
| Y | 552831 | 554392 | | | Y | 14714279 | 14720561 |
| Y | 564376 | 564691 | | | Y | 14727105 | 14727739 |
| Y | 585656 | 586200 | | | Y | 14733364 | 14735673 |
| Y | 604553 | 604925 | | | Y | 14762074 | 14762252 |
| Y | 610049 | 610519 | | | Y | 14771192 | 14771285 |
| Y | 626666 | 627798 | | | Y | 14773472 | 14777367 |
| Y | 629679 | 631113 | | | Y | 14777932 | 14778295 |
| Y | 657411 | 658228 | | | Y | 14783782 | 14784112 |
| Y | 662619 | 662964 | | | Y | 14786262 | 14787289 |
| Y | 670915 | 672667 | | | Y | 14790461 | 14790693 |
| Y | 673999 | 674693 | | | Y | 14801147 | 14802539 |
| Y | 676328 | 676680 | | | Y | 14812608 | 14813413 |
| Y | 678407 | 679279 | | | Y | 14814741 | 14815024 |
| Y | 685826 | 686504 | | | Y | 14817139 | 14817970 |
| Y | 702918 | 709077 | | | Y | 14823183 | 14824667 |
| Y | 713710 | 714404 | | | Y | 14833994 | 14834249 |
| Y | 728927 | 729642 | | | Y | 14838539 | 14842762 |

The chromosomal positon was obtained from UCSC genome browser (http://genome.ucsc.edu/) build 36.

APPENDIX E: Chromosome Y
Page 2 of 58

| Chr | Start | End | Chr | Start | End |
|---|---|---|---|---|---|
| Y | 739305 | 741119 | Y | 14855813 | 14856471 |
| Y | 764593 | 766084 | Y | 14861207 | 14868535 |
| Y | 770995 | 771617 | Y | 14871971 | 14872524 |
| Y | 776031 | 776602 | Y | 14878001 | 14878307 |
| Y | 796433 | 801498 | Y | 14892837 | 14893482 |
| Y | 811906 | 814617 | Y | 14896246 | 14896560 |
| Y | 837256 | 838010 | Y | 14899642 | 14899985 |
| Y | 883037 | 884006 | Y | 14910871 | 14911688 |
| Y | 905310 | 907589 | Y | 14913263 | 14915295 |
| Y | 912408 | 913283 | Y | 14917437 | 14917942 |
| Y | 915757 | 918102 | Y | 14918706 | 14921896 |
| Y | 929769 | 930152 | Y | 14929587 | 14929889 |
| Y | 938730 | 939574 | Y | 14951717 | 14951770 |
| Y | 1141661 | 1141781 | Y | 14952919 | 14954518 |
| Y | 1145920 | 1145995 | Y | 14958222 | 14958608 |
| Y | 1165276 | 1168199 | Y | 14964073 | 14964768 |
| Y | 1327991 | 1328388 | Y | 14969107 | 14970309 |
| Y | 1342096 | 1342706 | Y | 14973065 | 14973290 |
| Y | 1362792 | 1364120 | Y | 14975195 | 14975513 |
| Y | 1374747 | 1377939 | Y | 14981905 | 14983309 |
| Y | 1393032 | 1394111 | Y | 14983637 | 14983797 |
| Y | 1394799 | 1395809 | Y | 14992865 | 14993431 |
| Y | 1418764 | 1418954 | Y | 14994516 | 14995067 |
| Y | 1431029 | 1432799 | Y | 14998762 | 14999057 |
| Y | 1459876 | 1470501 | Y | 15002313 | 15004002 |
| Y | 1480522 | 1481072 | Y | 15005180 | 15006439 |
| Y | 1497056 | 1498234 | Y | 15013944 | 15014009 |
| Y | 1500506 | 1500850 | Y | 15017134 | 15019127 |
| Y | 1521891 | 1522721 | Y | 15020467 | 15022067 |
| Y | 1534880 | 1535820 | Y | 15026475 | 15027377 |
| Y | 1543808 | 1545428 | Y | 15031447 | 15031497 |
| Y | 1545914 | 1546259 | Y | 15033468 | 15033692 |
| Y | 1551017 | 1554612 | Y | 15037736 | 15038497 |
| Y | 1585948 | 1586663 | Y | 15041315 | 15042140 |
| Y | 1600552 | 1601247 | Y | 15056160 | 15057229 |
| Y | 1614052 | 1619216 | Y | 15065549 | 15066158 |
| Y | 1632081 | 1632818 | Y | 15075206 | 15075529 |
| Y | 1633971 | 1634326 | Y | 15076164 | 15076322 |
| Y | 1640921 | 1641144 | Y | 15079977 | 15082011 |
| Y | 1645316 | 1646160 | Y | 15085124 | 15085399 |
| Y | 1649720 | 1650134 | Y | 15092086 | 15093561 |
| Y | 1661880 | 1662298 | Y | 15095246 | 15095414 |
| Y | 1665744 | 1666314 | Y | 15097009 | 15097480 |
| Y | 1671751 | 1671835 | Y | 15099804 | 15100953 |
| Y | 1672560 | 1674270 | Y | 15103722 | 15104390 |
| Y | 1676096 | 1677991 | Y | 15111132 | 15112001 |
| Y | 1708134 | 1708679 | Y | 15116498 | 15117677 |
| Y | 1720730 | 1721869 | Y | 15136429 | 15137236 |
| Y | 1727637 | 1729441 | Y | 15139896 | 15140532 |
| Y | 1736187 | 1736560 | Y | 15141259 | 15141972 |
| Y | 1747484 | 1748437 | Y | 15144054 | 15144289 |
| Y | 1780450 | 1781770 | Y | 15158389 | 15158804 |
| Y | 1789262 | 1791414 | Y | 15168785 | 15169221 |
| Y | 1799991 | 1803168 | Y | 15171385 | 15175386 |
| Y | 1824686 | 1824982 | Y | 15180660 | 15180800 |

The chromosomal positon was obtained from UCSC genome browser (http://genome.ucsc.edu/) build 36.

APPENDIX E: Chromosome Y
Page 3 of 58

| Chr | Start | End | Chr | Start | End |
| --- | --- | --- | --- | --- | --- |
| Y | 1827447 | 1827514 | Y | 15181504 | 15185504 |
| Y | 1829227 | 1829658 | Y | 15190557 | 15190991 |
| Y | 1842455 | 1844461 | Y | 15202794 | 15203218 |
| Y | 1860462 | 1861777 | Y | 15208748 | 15209263 |
| Y | 1883595 | 1887639 | Y | 15225181 | 15225750 |
| Y | 1902674 | 1907779 | Y | 15229084 | 15234099 |
| Y | 1939976 | 1940411 | Y | 15242318 | 15243699 |
| Y | 1947141 | 1947462 | Y | 15244157 | 15244468 |
| Y | 1949469 | 1949785 | Y | 15245035 | 15245673 |
| Y | 1966342 | 1967506 | Y | 15251196 | 15253137 |
| Y | 1981923 | 1982879 | Y | 15258537 | 15259238 |
| Y | 1993885 | 1994065 | Y | 15260899 | 15262499 |
| Y | 2021139 | 2024753 | Y | 15262690 | 15263290 |
| Y | 2027580 | 2027799 | Y | 15265225 | 15266048 |
| Y | 2134916 | 2136459 | Y | 15270848 | 15272174 |
| Y | 2152113 | 2152238 | Y | 15272857 | 15273643 |
| Y | 2161355 | 2161599 | Y | 15291657 | 15292055 |
| Y | 2179184 | 2180375 | Y | 15296406 | 15296763 |
| Y | 2186694 | 2186987 | Y | 15305014 | 15305276 |
| Y | 2192260 | 2194690 | Y | 15309783 | 15310631 |
| Y | 2212979 | 2213144 | Y | 15313813 | 15313924 |
| Y | 2214814 | 2215255 | Y | 15316923 | 15317193 |
| Y | 2218217 | 2221518 | Y | 15327574 | 15328537 |
| Y | 2227589 | 2228217 | Y | 15329413 | 15329813 |
| Y | 2236732 | 2237233 | Y | 15330331 | 15331154 |
| Y | 2249713 | 2252211 | Y | 15332293 | 15332775 |
| Y | 2253464 | 2254109 | Y | 15333588 | 15334074 |
| Y | 2259273 | 2261056 | Y | 15340044 | 15341266 |
| Y | 2265417 | 2265956 | Y | 15348498 | 15349354 |
| Y | 2292598 | 2293039 | Y | 15350873 | 15351987 |
| Y | 2298930 | 2300542 | Y | 15355186 | 15355861 |
| Y | 2301868 | 2302059 | Y | 15362866 | 15363445 |
| Y | 2341833 | 2342356 | Y | 15367490 | 15367570 |
| Y | 2344609 | 2347012 | Y | 15380528 | 15382565 |
| Y | 2355730 | 2358382 | Y | 15384001 | 15384367 |
| Y | 2373636 | 2375386 | Y | 15385325 | 15385438 |
| Y | 2379394 | 2380579 | Y | 15387073 | 15389273 |
| Y | 2385056 | 2386131 | Y | 15390403 | 15390593 |
| Y | 2396285 | 2397855 | Y | 15397353 | 15397930 |
| Y | 2401925 | 2403724 | Y | 15404803 | 15405488 |
| Y | 2406463 | 2407896 | Y | 15415386 | 15415981 |
| Y | 2415995 | 2419004 | Y | 15423255 | 15424713 |
| Y | 2424767 | 2426645 | Y | 15438847 | 15439056 |
| Y | 2430108 | 2431135 | Y | 15453312 | 15453466 |
| Y | 2443388 | 2445220 | Y | 15462231 | 15462629 |
| Y | 2450209 | 2454406 | Y | 15465480 | 15465741 |
| Y | 2463807 | 2465114 | Y | 15466356 | 15467281 |
| Y | 2469693 | 2469829 | Y | 15469508 | 15469729 |
| Y | 2471631 | 2472533 | Y | 15472845 | 15474240 |
| Y | 2477794 | 2478934 | Y | 15477138 | 15477668 |
| Y | 2489573 | 2489743 | Y | 15481752 | 15482338 |
| Y | 2496027 | 2498332 | Y | 15496220 | 15497482 |
| Y | 2510980 | 2511227 | Y | 15499852 | 15501958 |
| Y | 2515088 | 2516325 | Y | 15508384 | 15512449 |
| Y | 2519082 | 2519314 | Y | 15514331 | 15514480 |

The chromosomal positon was obtained from UCSC genome browser (http://genome.ucsc.edu/) build 36.

APPENDIX E: Chromosome Y
Page 4 of 58

| Chr | Start | End | | | Chr | Start | End |
|---|---|---|---|---|---|---|---|
| Y | 2525444 | 2526102 | | | Y | 15516345 | 15517134 |
| Y | 2534725 | 2535755 | | | Y | 15517434 | 15517705 |
| Y | 2544914 | 2546917 | | | Y | 15519637 | 15519881 |
| Y | 2550549 | 2551092 | | | Y | 15521423 | 15522486 |
| Y | 2556623 | 2561208 | | | Y | 15524682 | 15525155 |
| Y | 2562718 | 2563642 | | | Y | 15525826 | 15526364 |
| Y | 2567067 | 2567466 | | | Y | 15527053 | 15529463 |
| Y | 2575556 | 2576745 | | | Y | 15549761 | 15553884 |
| Y | 2585727 | 2586050 | | | Y | 15563573 | 15564448 |
| Y | 2586235 | 2586279 | | | Y | 15586751 | 15591925 |
| Y | 2598337 | 2600092 | | | Y | 15599092 | 15599237 |
| Y | 2615434 | 2615744 | | | Y | 15600011 | 15600619 |
| Y | 2618146 | 2620077 | | | Y | 15602258 | 15602507 |
| Y | 2623987 | 2626123 | | | Y | 15608737 | 15608751 |
| Y | 2629593 | 2630484 | | | Y | 15622339 | 15622748 |
| Y | 2636229 | 2637134 | | | Y | 15625936 | 15626171 |
| Y | 2641919 | 2643006 | | | Y | 15640644 | 15641594 |
| Y | 2645078 | 2645645 | | | Y | 15651772 | 15652532 |
| Y | 2647249 | 2648337 | | | Y | 15657391 | 15658058 |
| Y | 2674129 | 2675099 | | | Y | 15662095 | 15662518 |
| Y | 2695412 | 2696407 | | | Y | 15665680 | 15666524 |
| Y | 2700921 | 2702141 | | | Y | 15668334 | 15670318 |
| Y | 2708862 | 2709892 | | | Y | 15678227 | 15678998 |
| Y | 2713155 | 2713767 | | | Y | 15683516 | 15683791 |
| Y | 2717283 | 2717496 | | | Y | 15684090 | 15686290 |
| Y | 2721711 | 2722163 | | | Y | 15689140 | 15689610 |
| Y | 2724296 | 2727061 | | | Y | 15694791 | 15695502 |
| Y | 2730911 | 2732588 | | | Y | 15705023 | 15705275 |
| Y | 2751025 | 2751511 | | | Y | 15710736 | 15710973 |
| Y | 2763855 | 2765142 | | | Y | 15713400 | 15714637 |
| Y | 2769034 | 2770124 | | | Y | 15726263 | 15726607 |
| Y | 2773733 | 2774223 | | | Y | 15734769 | 15741005 |
| Y | 2777520 | 2777829 | | | Y | 15743286 | 15748513 |
| Y | 2779644 | 2780985 | | | Y | 15751714 | 15752582 |
| Y | 2783164 | 2783548 | | | Y | 15754603 | 15757942 |
| Y | 2787014 | 2787365 | | | Y | 15781930 | 15782696 |
| Y | 2797185 | 2798128 | | | Y | 15789390 | 15789947 |
| Y | 2803773 | 2804383 | | | Y | 15792417 | 15792545 |
| Y | 2808865 | 2810143 | | | Y | 15794811 | 15794918 |
| Y | 2816491 | 2816697 | | | Y | 15797645 | 15799687 |
| Y | 2824335 | 2824556 | | | Y | 15804137 | 15804501 |
| Y | 2825966 | 2827207 | | | Y | 15805330 | 15805932 |
| Y | 2828352 | 2831102 | | | Y | 15807866 | 15808864 |
| Y | 2835692 | 2836604 | | | Y | 15813598 | 15814042 |
| Y | 2841541 | 2844677 | | | Y | 15819599 | 15819960 |
| Y | 2863720 | 2864647 | | | Y | 15822771 | 15823519 |
| Y | 2871919 | 2872057 | | | Y | 15828502 | 15828953 |
| Y | 2875972 | 2876616 | | | Y | 15835730 | 15836142 |
| Y | 2879675 | 2880344 | | | Y | 15837338 | 15837864 |
| Y | 2884694 | 2884876 | | | Y | 15841106 | 15841817 |
| Y | 2893155 | 2893870 | | | Y | 15854065 | 15854396 |
| Y | 2915829 | 2915945 | | | Y | 15859137 | 15859587 |
| Y | 2930121 | 2932912 | | | Y | 15861137 | 15861198 |
| Y | 2934101 | 2936481 | | | Y | 15868458 | 15868647 |
| Y | 2937932 | 2938605 | | | Y | 15875103 | 15875918 |

The chromosomal positon was obtained from UCSC genome browser (http://genome.ucsc.edu/) build 36.

APPENDIX E: Chromosome Y
Page 5 of 58

| Chr | Start | End | Chr | Start | End |
|---|---|---|---|---|---|
| Y | 2941920 | 2942274 | Y | 15885771 | 15886271 |
| Y | 2949218 | 2949683 | Y | 15892810 | 15893880 |
| Y | 2962997 | 2964009 | Y | 15897700 | 15898268 |
| Y | 2965279 | 2966356 | Y | 15899674 | 15900753 |
| Y | 2977953 | 3024999 | Y | 15908485 | 15909383 |
| Y | 3045267 | 3082715 | Y | 15913887 | 15914367 |
| Y | 3134559 | 3134778 | Y | 15918212 | 15919124 |
| Y | 3221372 | 3221622 | Y | 15927722 | 15928083 |
| Y | 3240755 | 3280734 | Y | 15928718 | 15929038 |
| Y | 3354462 | 3371145 | Y | 15932836 | 15933322 |
| Y | 3383613 | 3392824 | Y | 15945368 | 15945412 |
| Y | 3403600 | 3405624 | Y | 15948458 | 15949032 |
| Y | 3466322 | 3489950 | Y | 15952416 | 15953166 |
| Y | 3575835 | 3606685 | Y | 15954921 | 15955751 |
| Y | 3632519 | 3682075 | Y | 15959358 | 15964308 |
| Y | 3740416 | 3758778 | Y | 15966962 | 15969161 |
| Y | 3772048 | 3772740 | Y | 15977180 | 15982831 |
| Y | 3773953 | 3774247 | Y | 15986449 | 15988626 |
| Y | 3774340 | 3776353 | Y | 15990026 | 15990630 |
| Y | 3776757 | 3777476 | Y | 15998061 | 15998254 |
| Y | 3779689 | 3780874 | Y | 16002828 | 16008322 |
| Y | 3783044 | 3786386 | Y | 16016420 | 16022086 |
| Y | 3790823 | 3793517 | Y | 16035394 | 16036071 |
| Y | 3803644 | 3889738 | Y | 16041877 | 16042338 |
| Y | 3987493 | 3996161 | Y | 16042962 | 16043855 |
| Y | 4047297 | 4066133 | Y | 16046137 | 16046718 |
| Y | 4070776 | 4080865 | Y | 16059472 | 16059897 |
| Y | 4130413 | 4130613 | Y | 16061841 | 16063358 |
| Y | 4140624 | 4173558 | Y | 16065296 | 16072696 |
| Y | 4210079 | 4221801 | Y | 16086750 | 16088316 |
| Y | 4228307 | 4230528 | Y | 16091523 | 16092591 |
| Y | 4259601 | 4266962 | Y | 16095724 | 16096230 |
| Y | 4291692 | 4307883 | Y | 16099662 | 16101232 |
| Y | 4337529 | 4356687 | Y | 16110795 | 16111278 |
| Y | 4412529 | 4412918 | Y | 16115519 | 16115629 |
| Y | 4431345 | 4431625 | Y | 16117239 | 16117455 |
| Y | 4505000 | 4518230 | Y | 16118630 | 16118941 |
| Y | 4524764 | 4531352 | Y | 16121254 | 16121364 |
| Y | 4619528 | 4626801 | Y | 16123757 | 16125413 |
| Y | 4666168 | 4687563 | Y | 16126285 | 16131905 |
| Y | 4755746 | 4775553 | Y | 16154537 | 16155359 |
| Y | 4802596 | 4818250 | Y | 16160341 | 16160574 |
| Y | 4835995 | 4847136 | Y | 16162906 | 16165106 |
| Y | 4888563 | 4919824 | Y | 16165807 | 16166388 |
| Y | 5066658 | 5081480 | Y | 16169749 | 16170256 |
| Y | 5202311 | 5242509 | Y | 16172974 | 16173579 |
| Y | 5284186 | 5406949 | Y | 16178487 | 16178772 |
| Y | 5443216 | 5475018 | Y | 16182518 | 16182589 |
| Y | 5495963 | 5498293 | Y | 16184295 | 16184622 |
| Y | 5531498 | 5579563 | Y | 16214374 | 16214894 |
| Y | 5619037 | 5661285 | Y | 16222109 | 16222286 |
| Y | 5750571 | 5760634 | Y | 16226006 | 16226356 |
| Y | 5890065 | 5899117 | Y | 16229331 | 16230637 |
| Y | 5903006 | 5914199 | Y | 16239238 | 16244983 |
| Y | 5942679 | 5956916 | Y | 16247986 | 16248204 |

The chromosomal positon was obtained from UCSC genome browser (http://genome.ucsc.edu/) build 36.

APPENDIX E: Chromosome Y
Page 6 of 58

| Chr | Start | End | Chr | Start | End |
|---|---|---|---|---|---|
| Y | 5994560 | 6017430 | Y | 16252003 | 16252617 |
| Y | 6038699 | 6047496 | Y | 16252945 | 16253083 |
| Y | 6066830 | 6086265 | Y | 16258551 | 16259988 |
| Y | 6087219 | 6093488 | Y | 16260675 | 16260871 |
| Y | 6108292 | 6120923 | Y | 16264752 | 16265687 |
| Y | 6134469 | 6147086 | Y | 16273106 | 16274001 |
| Y | 6410502 | 6411597 | Y | 16286642 | 16288334 |
| Y | 6431885 | 6438547 | Y | 16292043 | 16297957 |
| Y | 6485561 | 6486419 | Y | 16300884 | 16300961 |
| Y | 6486870 | 6487024 | Y | 16304467 | 16309019 |
| Y | 6487554 | 6493407 | Y | 16311465 | 16312185 |
| Y | 6527217 | 6529107 | Y | 16315140 | 16316656 |
| Y | 6562463 | 6590364 | Y | 16319158 | 16320277 |
| Y | 6649500 | 6655323 | Y | 16320934 | 16321239 |
| Y | 6659566 | 6679519 | Y | 16324674 | 16325790 |
| Y | 6689546 | 6691513 | Y | 16341678 | 16342361 |
| Y | 6705432 | 6706489 | Y | 16351009 | 16351444 |
| Y | 6724778 | 6726617 | Y | 16353737 | 16354497 |
| Y | 6728945 | 6729533 | Y | 16361397 | 16361797 |
| Y | 6730100 | 6730774 | Y | 16370054 | 16372445 |
| Y | 6739373 | 6740610 | Y | 16376586 | 16377376 |
| Y | 6751771 | 6754939 | Y | 16379013 | 16379869 |
| Y | 6755609 | 6756026 | Y | 16380645 | 16381144 |
| Y | 6762480 | 6763091 | Y | 16384457 | 16384756 |
| Y | 6768471 | 6774198 | Y | 16400332 | 16400759 |
| Y | 6775405 | 6776393 | Y | 16405238 | 16405965 |
| Y | 6776960 | 6777354 | Y | 16413268 | 16414029 |
| Y | 6778231 | 6778912 | Y | 16415036 | 16415104 |
| Y | 6780158 | 6788105 | Y | 16419538 | 16419800 |
| Y | 6791550 | 6792465 | Y | 16421650 | 16422145 |
| Y | 6800096 | 6800576 | Y | 16425149 | 16426011 |
| Y | 6804452 | 6804473 | Y | 16427826 | 16428478 |
| Y | 6806080 | 6806543 | Y | 16433345 | 16433504 |
| Y | 6819839 | 6820523 | Y | 16450413 | 16450450 |
| Y | 6836547 | 6841380 | Y | 16450998 | 16455737 |
| Y | 6842996 | 6843679 | Y | 16461055 | 16461725 |
| Y | 6847533 | 6849665 | Y | 16466183 | 16466303 |
| Y | 6857875 | 6857976 | Y | 16470235 | 16471969 |
| Y | 6858168 | 6858508 | Y | 16481262 | 16481442 |
| Y | 6862314 | 6864271 | Y | 16483827 | 16484187 |
| Y | 6865656 | 6866587 | Y | 16488183 | 16488320 |
| Y | 6875288 | 6875918 | Y | 16489713 | 16489820 |
| Y | 6892839 | 6893388 | Y | 16495708 | 16496148 |
| Y | 6893734 | 6894073 | Y | 16513306 | 16513481 |
| Y | 6896517 | 6899360 | Y | 16514884 | 16514995 |
| Y | 6901005 | 6902431 | Y | 16526306 | 16527446 |
| Y | 6903926 | 6905621 | Y | 16537272 | 16537758 |
| Y | 6909396 | 6909437 | Y | 16584586 | 16584849 |
| Y | 6912649 | 6914608 | Y | 16596442 | 16599167 |
| Y | 6915663 | 6916131 | Y | 16600002 | 16601251 |
| Y | 6917286 | 6917858 | Y | 16604669 | 16605339 |
| Y | 6919348 | 6919878 | Y | 16614939 | 16615665 |
| Y | 6923076 | 6927413 | Y | 16616601 | 16617054 |
| Y | 6930984 | 6931877 | Y | 16619300 | 16619832 |
| Y | 6933509 | 6933648 | Y | 16620526 | 16620986 |

The chromosomal positon was obtained from UCSC genome browser (http://genome.ucsc.edu/) build 36.

APPENDIX E: Chromosome Y
Page 7 of 58

| Chr | Start | End | Chr | Start | End |
|---|---|---|---|---|---|
| Y | 6936236 | 6937304 | Y | 16621842 | 16622477 |
| Y | 6941839 | 6943010 | Y | 16626362 | 16627077 |
| Y | 6943195 | 6943603 | Y | 16630358 | 16631560 |
| Y | 6946623 | 6946940 | Y | 16632366 | 16632467 |
| Y | 6957092 | 6958674 | Y | 16635462 | 16635605 |
| Y | 6966138 | 6970242 | Y | 16637959 | 16646035 |
| Y | 6971669 | 6972132 | Y | 16664021 | 16664756 |
| Y | 6975396 | 6978749 | Y | 16665013 | 16671110 |
| Y | 6981157 | 6981933 | Y | 16673338 | 16673532 |
| Y | 6987902 | 6990093 | Y | 16674430 | 16674756 |
| Y | 6992282 | 6995797 | Y | 16675978 | 16676544 |
| Y | 6996792 | 6997213 | Y | 16678392 | 16679258 |
| Y | 7000452 | 7001370 | Y | 16682144 | 16683270 |
| Y | 7006487 | 7010335 | Y | 16701209 | 16701384 |
| Y | 7020764 | 7023719 | Y | 16703032 | 16705328 |
| Y | 7029371 | 7029743 | Y | 16707532 | 16708455 |
| Y | 7031511 | 7035069 | Y | 16708738 | 16708959 |
| Y | 7045630 | 7048591 | Y | 16717699 | 16717965 |
| Y | 7049062 | 7049598 | Y | 16723103 | 16723365 |
| Y | 7050153 | 7050528 | Y | 16724500 | 16725753 |
| Y | 7051467 | 7052202 | Y | 16730212 | 16730288 |
| Y | 7053238 | 7054989 | Y | 16745380 | 16746468 |
| Y | 7056429 | 7057563 | Y | 16747076 | 16747551 |
| Y | 7094757 | 7096766 | Y | 16751711 | 16752433 |
| Y | 7103391 | 7103876 | Y | 16759158 | 16760017 |
| Y | 7111720 | 7112101 | Y | 16764819 | 16766181 |
| Y | 7114025 | 7115365 | Y | 16777780 | 16778840 |
| Y | 7124213 | 7128893 | Y | 16894911 | 16895450 |
| Y | 7130302 | 7133032 | Y | 16904435 | 16905506 |
| Y | 7134177 | 7135513 | Y | 16908098 | 16908862 |
| Y | 7148932 | 7149818 | Y | 16909765 | 16911269 |
| Y | 7149934 | 7150325 | Y | 16917686 | 16924623 |
| Y | 7161888 | 7162052 | Y | 16927545 | 16927764 |
| Y | 7188570 | 7188801 | Y | 16933844 | 16934308 |
| Y | 7193671 | 7195994 | Y | 16936166 | 16936624 |
| Y | 7200718 | 7203781 | Y | 17049575 | 17055139 |
| Y | 7207847 | 7208609 | Y | 17064526 | 17064779 |
| Y | 7211224 | 7211924 | Y | 17071978 | 17073280 |
| Y | 7213209 | 7213659 | Y | 17076933 | 17077958 |
| Y | 7219386 | 7219863 | Y | 17080654 | 17080814 |
| Y | 7237686 | 7238337 | Y | 17084108 | 17085240 |
| Y | 7248818 | 7251773 | Y | 17086565 | 17087427 |
| Y | 7252895 | 7253437 | Y | 17090569 | 17090823 |
| Y | 7259762 | 7260318 | Y | 17105387 | 17105980 |
| Y | 7286351 | 7287276 | Y | 17109760 | 17110853 |
| Y | 7304928 | 7305694 | Y | 17115131 | 17115485 |
| Y | 7321911 | 7322715 | Y | 17122830 | 17123702 |
| Y | 7331684 | 7332014 | Y | 17124663 | 17125004 |
| Y | 7337885 | 7338481 | Y | 17128799 | 17129094 |
| Y | 7338971 | 7340061 | Y | 17144471 | 17145741 |
| Y | 7351210 | 7351633 | Y | 17149838 | 17151498 |
| Y | 7353637 | 7354919 | Y | 17152932 | 17153751 |
| Y | 7377454 | 7377959 | Y | 17155143 | 17155922 |
| Y | 7386091 | 7386380 | Y | 17158479 | 17158660 |
| Y | 7391611 | 7393696 | Y | 17166347 | 17170192 |

The chromosomal positon was obtained from UCSC genome browser (http://genome.ucsc.edu/) build 36.

APPENDIX E: Chromosome Y
Page 8 of 58

| Chr | Start | End | | | Chr | Start | End |
|---|---|---|---|---|---|---|---|
| Y | 7393928 | 7399197 | | | Y | 17173947 | 17175340 |
| Y | 7422932 | 7425529 | | | Y | 17186397 | 17187072 |
| Y | 7427836 | 7427910 | | | Y | 17188102 | 17189173 |
| Y | 7436880 | 7437182 | | | Y | 17195681 | 17196178 |
| Y | 7442923 | 7443101 | | | Y | 17196658 | 17199326 |
| Y | 7450562 | 7452737 | | | Y | 17203754 | 17204749 |
| Y | 7455798 | 7458002 | | | Y | 17213862 | 17214029 |
| Y | 7459527 | 7462362 | | | Y | 17218935 | 17221173 |
| Y | 7465274 | 7465693 | | | Y | 17232086 | 17232218 |
| Y | 7468259 | 7470809 | | | Y | 17238425 | 17238587 |
| Y | 7472579 | 7473163 | | | Y | 17246168 | 17248299 |
| Y | 7475868 | 7476148 | | | Y | 17251511 | 17251977 |
| Y | 7478487 | 7479032 | | | Y | 17257262 | 17257472 |
| Y | 7481548 | 7481767 | | | Y | 17259926 | 17260606 |
| Y | 7483673 | 7485083 | | | Y | 17264406 | 17264621 |
| Y | 7492871 | 7493507 | | | Y | 17267235 | 17267938 |
| Y | 7576765 | 7577510 | | | Y | 17279875 | 17280093 |
| Y | 7578093 | 7580033 | | | Y | 17294625 | 17294689 |
| Y | 7589070 | 7591115 | | | Y | 17316006 | 17317134 |
| Y | 7592757 | 7594911 | | | Y | 17321024 | 17322017 |
| Y | 7608782 | 7611305 | | | Y | 17331078 | 17331394 |
| Y | 7614603 | 7616615 | | | Y | 17336690 | 17337125 |
| Y | 7617775 | 7618120 | | | Y | 17345850 | 17346106 |
| Y | 7620377 | 7625597 | | | Y | 17349055 | 17350346 |
| Y | 7626021 | 7626432 | | | Y | 17350911 | 17351316 |
| Y | 7626544 | 7629289 | | | Y | 17356079 | 17358558 |
| Y | 7630499 | 7631979 | | | Y | 17360312 | 17361234 |
| Y | 7645273 | 7647687 | | | Y | 17368452 | 17370665 |
| Y | 7649089 | 7649460 | | | Y | 17375616 | 17376189 |
| Y | 7651549 | 7652705 | | | Y | 17390653 | 17390696 |
| Y | 7653815 | 7654461 | | | Y | 17393752 | 17394597 |
| Y | 7665510 | 7667768 | | | Y | 17403185 | 17403327 |
| Y | 7671811 | 7672076 | | | Y | 17406314 | 17406625 |
| Y | 7673546 | 7673589 | | | Y | 17407135 | 17407491 |
| Y | 7678629 | 7678949 | | | Y | 17408382 | 17408883 |
| Y | 7699148 | 7699189 | | | Y | 17419498 | 17420125 |
| Y | 7725327 | 7725676 | | | Y | 17422543 | 17424120 |
| Y | 7728167 | 7728443 | | | Y | 17429811 | 17430271 |
| Y | 7729508 | 7730022 | | | Y | 17434283 | 17434608 |
| Y | 7732142 | 7732697 | | | Y | 17441817 | 17444393 |
| Y | 7737616 | 7738369 | | | Y | 17449833 | 17450511 |
| Y | 7741542 | 7741994 | | | Y | 17454195 | 17455651 |
| Y | 7744162 | 7744629 | | | Y | 17457641 | 17457913 |
| Y | 7753990 | 7755024 | | | Y | 17458212 | 17458816 |
| Y | 7756023 | 7756600 | | | Y | 17469442 | 17469775 |
| Y | 7762547 | 7763050 | | | Y | 17472120 | 17472431 |
| Y | 7778335 | 7779555 | | | Y | 17472554 | 17474710 |
| Y | 7788152 | 7788747 | | | Y | 17483658 | 17486486 |
| Y | 7791499 | 7791868 | | | Y | 17497532 | 17498539 |
| Y | 7794184 | 7794545 | | | Y | 17505210 | 17505480 |
| Y | 7796870 | 7797869 | | | Y | 17507805 | 17508273 |
| Y | 7799438 | 7799576 | | | Y | 17520695 | 17521280 |
| Y | 7800291 | 7800376 | | | Y | 17529928 | 17530465 |
| Y | 7803659 | 7803928 | | | Y | 17532338 | 17533504 |
| Y | 7804734 | 7804798 | | | Y | 17544286 | 17544772 |

The chromosomal positon was obtained from UCSC genome browser (http://genome.ucsc.edu/) build 36.

APPENDIX E: Chromosome Y
Page 9 of 58

| Chr | Start | End | | | Chr | Start | End |
|---|---|---|---|---|---|---|---|
| Y | 7805828 | 7806099 | | | Y | 17545786 | 17546896 |
| Y | 7808846 | 7810076 | | | Y | 17551307 | 17553428 |
| Y | 7823879 | 7824939 | | | Y | 17568605 | 17568914 |
| Y | 7831060 | 7831121 | | | Y | 17571919 | 17574908 |
| Y | 7835801 | 7836221 | | | Y | 17581174 | 17582179 |
| Y | 7837222 | 7838415 | | | Y | 17585525 | 17585913 |
| Y | 7840050 | 7844343 | | | Y | 17586936 | 17587286 |
| Y | 7845779 | 7846061 | | | Y | 17599346 | 17599557 |
| Y | 7853536 | 7853779 | | | Y | 17604465 | 17604749 |
| Y | 7868789 | 7868982 | | | Y | 17615224 | 17615311 |
| Y | 7870211 | 7870275 | | | Y | 17615776 | 17615971 |
| Y | 7881589 | 7882548 | | | Y | 17621078 | 17621235 |
| Y | 7890267 | 7891503 | | | Y | 17622434 | 17622521 |
| Y | 7894062 | 7895067 | | | Y | 17624385 | 17624567 |
| Y | 7895927 | 7896408 | | | Y | 17629890 | 17632056 |
| Y | 7899637 | 7899738 | | | Y | 17635187 | 17635321 |
| Y | 7907069 | 7907110 | | | Y | 17642153 | 17642745 |
| Y | 7907463 | 7908017 | | | Y | 17657364 | 17657773 |
| Y | 7914833 | 7915117 | | | Y | 17666151 | 17668880 |
| Y | 7915706 | 7916278 | | | Y | 17672429 | 17673818 |
| Y | 7917793 | 7919485 | | | Y | 17676350 | 17677209 |
| Y | 7923102 | 7923928 | | | Y | 17682171 | 17688634 |
| Y | 7932350 | 7932734 | | | Y | 17691335 | 17693642 |
| Y | 7943035 | 7943709 | | | Y | 17694142 | 17696719 |
| Y | 7943727 | 7944053 | | | Y | 17700012 | 17700546 |
| Y | 7947890 | 7948876 | | | Y | 17702787 | 17704752 |
| Y | 7949950 | 7950574 | | | Y | 17706441 | 17706714 |
| Y | 7954154 | 7954544 | | | Y | 17708426 | 17709744 |
| Y | 7962080 | 7962181 | | | Y | 17712534 | 17712772 |
| Y | 7962826 | 7962993 | | | Y | 17716543 | 17717225 |
| Y | 7970092 | 7970191 | | | Y | 17739459 | 17739719 |
| Y | 7976337 | 7976573 | | | Y | 17742512 | 17742832 |
| Y | 7976850 | 7978931 | | | Y | 17745622 | 17746892 |
| Y | 7982434 | 7986212 | | | Y | 17749225 | 17749241 |
| Y | 7993383 | 7993719 | | | Y | 17757994 | 17758075 |
| Y | 7996165 | 7996953 | | | Y | 17768893 | 17771429 |
| Y | 7997570 | 7998356 | | | Y | 17776448 | 17776784 |
| Y | 8000735 | 8001564 | | | Y | 17783069 | 17783892 |
| Y | 8002497 | 8003638 | | | Y | 17785367 | 17786528 |
| Y | 8006135 | 8006736 | | | Y | 17788280 | 17789292 |
| Y | 8010841 | 8011405 | | | Y | 17791297 | 17791530 |
| Y | 8020280 | 8021900 | | | Y | 17801484 | 17801775 |
| Y | 8024274 | 8027793 | | | Y | 17805547 | 17806343 |
| Y | 8030977 | 8032124 | | | Y | 17822691 | 17822921 |
| Y | 8033972 | 8035658 | | | Y | 17825704 | 17826008 |
| Y | 8039033 | 8041210 | | | Y | 17828739 | 17831271 |
| Y | 8047231 | 8047490 | | | Y | 17843756 | 17843815 |
| Y | 8054162 | 8055037 | | | Y | 17850364 | 17851441 |
| Y | 8058448 | 8058762 | | | Y | 17852543 | 17852652 |
| Y | 8070682 | 8070976 | | | Y | 17852873 | 17853012 |
| Y | 8074102 | 8076867 | | | Y | 17855255 | 17855670 |
| Y | 8077881 | 8078491 | | | Y | 17859688 | 17866056 |
| Y | 8081776 | 8081997 | | | Y | 17868147 | 17868858 |
| Y | 8083016 | 8084420 | | | Y | 17871063 | 17872025 |
| Y | 8089000 | 8089290 | | | Y | 17889422 | 17889590 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 8093022 | 8093822 | Y | 17890104 | 17890305 |
| Y | 8097535 | 8099763 | Y | 17890656 | 17891286 |
| Y | 8102759 | 8104919 | Y | 17892447 | 17894162 |
| Y | 8110328 | 8111613 | Y | 17906278 | 17906640 |
| Y | 8129186 | 8129654 | Y | 17907717 | 17908379 |
| Y | 8130674 | 8131266 | Y | 17915149 | 17918651 |
| Y | 8134500 | 8136454 | Y | 17919926 | 17922240 |
| Y | 8168979 | 8169657 | Y | 17925606 | 17925775 |
| Y | 8172768 | 8174631 | Y | 17926533 | 17926970 |
| Y | 8182832 | 8188930 | Y | 17929235 | 17930115 |
| Y | 8193977 | 8194120 | Y | 17935758 | 17939506 |
| Y | 8199075 | 8199233 | Y | 17941161 | 17941712 |
| Y | 8204312 | 8205376 | Y | 17949799 | 17950069 |
| Y | 8209447 | 8210787 | Y | 17952014 | 17952145 |
| Y | 8212323 | 8212598 | Y | 17952949 | 17953972 |
| Y | 8214873 | 8215314 | Y | 17959032 | 17959181 |
| Y | 8217904 | 8218405 | Y | 17961613 | 17961654 |
| Y | 8220689 | 8221288 | Y | 17964242 | 17964405 |
| Y | 8224074 | 8225738 | Y | 17972280 | 17972565 |
| Y | 8233209 | 8233539 | Y | 17976369 | 17980016 |
| Y | 8248202 | 8248397 | Y | 17980890 | 17984845 |
| Y | 8252174 | 8252403 | Y | 17993348 | 17995180 |
| Y | 8258813 | 8260753 | Y | 18004009 | 18004247 |
| Y | 8261560 | 8261644 | Y | 18005148 | 18005897 |
| Y | 8263357 | 8267783 | Y | 18006380 | 18006829 |
| Y | 8268386 | 8269402 | Y | 18008139 | 18014000 |
| Y | 8275974 | 8277188 | Y | 18017291 | 18017879 |
| Y | 8278714 | 8280111 | Y | 18020365 | 18020401 |
| Y | 8282421 | 8283251 | Y | 18021010 | 18024458 |
| Y | 8284220 | 8284599 | Y | 18036077 | 18036475 |
| Y | 8286190 | 8286987 | Y | 18043295 | 18044164 |
| Y | 8292017 | 8292346 | Y | 18060948 | 18064968 |
| Y | 8294656 | 8294771 | Y | 18572675 | 18574729 |
| Y | 8297721 | 8297953 | Y | 19261775 | 19262861 |
| Y | 8308092 | 8308217 | Y | 19264135 | 19264812 |
| Y | 8309368 | 8309717 | Y | 19277917 | 19278877 |
| Y | 8310917 | 8311391 | Y | 19281675 | 19282839 |
| Y | 8312114 | 8312447 | Y | 19286805 | 19287195 |
| Y | 8314601 | 8314847 | Y | 19292112 | 19292264 |
| Y | 8325324 | 8325347 | Y | 19504575 | 19507101 |
| Y | 8328825 | 8330530 | Y | 19522494 | 19525971 |
| Y | 8331004 | 8331202 | Y | 19528512 | 19529472 |
| Y | 8342286 | 8343714 | Y | 19530538 | 19533318 |
| Y | 8344845 | 8346030 | Y | 19535637 | 19539586 |
| Y | 8347360 | 8348139 | Y | 19544254 | 19544859 |
| Y | 8348488 | 8350477 | Y | 19546458 | 19546859 |
| Y | 8352799 | 8354168 | Y | 19554571 | 19556593 |
| Y | 8358676 | 8359072 | Y | 19561190 | 19561564 |
| Y | 8371752 | 8372941 | Y | 19571401 | 19571700 |
| Y | 8375642 | 8376476 | Y | 19572940 | 19573318 |
| Y | 8378146 | 8379427 | Y | 19588649 | 19589179 |
| Y | 8388115 | 8388909 | Y | 19591277 | 19591902 |
| Y | 8388969 | 8389164 | Y | 19605583 | 19606010 |
| Y | 8390580 | 8390719 | Y | 19620638 | 19621141 |
| Y | 8399825 | 8400050 | Y | 19628142 | 19629439 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 8400805 | 8400841 | Y | 19643337 | 19643714 |
| Y | 8407797 | 8409431 | Y | 19650357 | 19650504 |
| Y | 8410294 | 8411389 | Y | 19660878 | 19661273 |
| Y | 8415662 | 8416123 | Y | 19673257 | 19674189 |
| Y | 8433765 | 8434180 | Y | 19683539 | 19683969 |
| Y | 8435988 | 8437398 | Y | 19690310 | 19690485 |
| Y | 8439907 | 8442127 | Y | 19712049 | 19714077 |
| Y | 8443197 | 8443443 | Y | 19716430 | 19716714 |
| Y | 8448853 | 8494700 | Y | 19718627 | 19718850 |
| Y | 8496094 | 8535156 | Y | 19722846 | 19724190 |
| Y | 8536146 | 8538041 | Y | 19726719 | 19726789 |
| Y | 8542019 | 8560719 | Y | 19740979 | 19742152 |
| Y | 8561008 | 8561033 | Y | 19745196 | 19746998 |
| Y | 8561333 | 8561934 | Y | 19748912 | 19749200 |
| Y | 8562190 | 8615950 | Y | 19756544 | 19756955 |
| Y | 8617449 | 8669208 | Y | 19761412 | 19761726 |
| Y | 8670143 | 8704389 | Y | 19764442 | 19764679 |
| Y | 8708764 | 8709440 | Y | 19777542 | 19778676 |
| Y | 8711046 | 8714782 | Y | 19781085 | 19785588 |
| Y | 8717297 | 8717588 | Y | 19789167 | 19789770 |
| Y | 8719583 | 8721118 | Y | 19791369 | 19793142 |
| Y | 8727970 | 8728307 | Y | 19804423 | 19804780 |
| Y | 8734133 | 8734303 | Y | 19806021 | 19811549 |
| Y | 8741358 | 8744085 | Y | 19823043 | 19823515 |
| Y | 8749965 | 8750835 | Y | 19825100 | 19826456 |
| Y | 8757278 | 8757658 | Y | 19827330 | 19828006 |
| Y | 8768452 | 8770485 | Y | 19833703 | 19834266 |
| Y | 8771711 | 8774027 | Y | 19840449 | 19841523 |
| Y | 8781246 | 8782835 | Y | 19847193 | 19847828 |
| Y | 8791318 | 8791664 | Y | 19854491 | 19854691 |
| Y | 8794767 | 8796241 | Y | 19858711 | 19859626 |
| Y | 8803758 | 8805824 | Y | 19863158 | 19863436 |
| Y | 8807198 | 8807619 | Y | 19867435 | 19871054 |
| Y | 8810558 | 8810600 | Y | 19872019 | 19872656 |
| Y | 8814898 | 8815056 | Y | 19882813 | 19883083 |
| Y | 8815937 | 8817165 | Y | 19884543 | 19885071 |
| Y | 8819885 | 8820184 | Y | 19887710 | 19887942 |
| Y | 8822813 | 8823330 | Y | 19889299 | 19890171 |
| Y | 8824922 | 8825407 | Y | 19901953 | 19903805 |
| Y | 8827308 | 8830208 | Y | 19906490 | 19911403 |
| Y | 8839998 | 8840760 | Y | 19929836 | 19930240 |
| Y | 8842361 | 8842978 | Y | 19931009 | 19931788 |
| Y | 8844974 | 8845363 | Y | 19936033 | 19937588 |
| Y | 8848394 | 8851692 | Y | 19938008 | 19939039 |
| Y | 8853891 | 8859009 | Y | 19941013 | 19941089 |
| Y | 8864565 | 8866119 | Y | 19945034 | 19947039 |
| Y | 8879206 | 8881103 | Y | 19966225 | 19966409 |
| Y | 8889422 | 8889531 | Y | 19968339 | 19969636 |
| Y | 8891540 | 8891910 | Y | 19975846 | 19976158 |
| Y | 8893558 | 8894109 | Y | 19977426 | 19977964 |
| Y | 8896059 | 8898019 | Y | 19983595 | 19988059 |
| Y | 8899169 | 8900269 | Y | 19989388 | 19989848 |
| Y | 8909920 | 8910658 | Y | 20003681 | 20004502 |
| Y | 8912779 | 8913285 | Y | 20010405 | 20014381 |
| Y | 8917343 | 8923073 | Y | 20018797 | 20020468 |

The chromosomal positon was obtained from UCSC genome browser (http://genome.ucsc.edu/) build 36.

APPENDIX E: Chromosome Y
Page 12 of 58

| Chr | Start | End | Chr | Start | End |
|---|---|---|---|---|---|
| Y | 8923918 | 8924098 | Y | 20021589 | 20021884 |
| Y | 8924418 | 8925193 | Y | 20027298 | 20028188 |
| Y | 8928444 | 8956372 | Y | 20032413 | 20033096 |
| Y | 8957735 | 8958273 | Y | 20065524 | 20066570 |
| Y | 8968672 | 8969616 | Y | 20067513 | 20067876 |
| Y | 9055593 | 9062461 | Y | 20075570 | 20076366 |
| Y | 9065350 | 9067402 | Y | 20082224 | 20082519 |
| Y | 9069840 | 9073336 | Y | 20085298 | 20085707 |
| Y | 9095847 | 9096947 | Y | 20086859 | 20096751 |
| Y | 9113403 | 9115976 | Y | 20099449 | 20100666 |
| Y | 9121622 | 9122968 | Y | 20102699 | 20105229 |
| Y | 9124342 | 9124759 | Y | 20106124 | 20106345 |
| Y | 9125538 | 9128387 | Y | 20110819 | 20113437 |
| Y | 9128422 | 9128707 | Y | 20123937 | 20124138 |
| Y | 9132973 | 9133869 | Y | 20135727 | 20136693 |
| Y | 9144417 | 9146795 | Y | 20141364 | 20142280 |
| Y | 9147981 | 9148611 | Y | 20143950 | 20144920 |
| Y | 9155475 | 9195831 | Y | 20146452 | 20147030 |
| Y | 9201482 | 9214501 | Y | 20148639 | 20149099 |
| Y | 9224983 | 9226083 | Y | 20152271 | 20152358 |
| Y | 9228908 | 9230471 | Y | 20158848 | 20159451 |
| Y | 9231765 | 9988375 | Y | 20162747 | 20164347 |
| Y | 9989841 | 9990040 | Y | 20167371 | 20168499 |
| Y | 9992086 | 9993786 | Y | 20170388 | 20171331 |
| Y | 9996546 | 9999640 | Y | 20174279 | 20174752 |
| Y | 10002551 | 10008672 | Y | 20176487 | 20178179 |
| Y | 10024842 | 10025252 | Y | 20200416 | 20201306 |
| Y | 10030058 | 10030420 | Y | 20224430 | 20224816 |
| Y | 10032092 | 10032460 | Y | 20236142 | 20237107 |
| Y | 10035780 | 10037028 | Y | 20240862 | 20241718 |
| Y | 10046400 | 10047737 | Y | 20242371 | 20242699 |
| Y | 10051897 | 10053182 | Y | 20244268 | 20250373 |
| Y | 10059141 | 10060189 | Y | 20252140 | 20253668 |
| Y | 10061208 | 10062774 | Y | 20259575 | 20259758 |
| Y | 10065737 | 10067449 | Y | 20260179 | 20260994 |
| Y | 10073511 | 10075227 | Y | 20268480 | 20268699 |
| Y | 10095064 | 10105819 | Y | 20272293 | 20273327 |
| Y | 10126063 | 10131852 | Y | 20273349 | 20273690 |
| Y | 10133519 | 10259040 | Y | 20278684 | 20280735 |
| Y | 10368554 | 10370434 | Y | 20282894 | 20284303 |
| Y | 10371762 | 10373155 | Y | 20285270 | 20285724 |
| Y | 10379500 | 10380788 | Y | 20286628 | 20294216 |
| Y | 10385869 | 10386391 | Y | 20297586 | 20298569 |
| Y | 10421784 | 10422949 | Y | 20300953 | 20304481 |
| Y | 10426184 | 10426856 | Y | 20309865 | 20310582 |
| Y | 10428887 | 10429023 | Y | 20312659 | 20313419 |
| Y | 10432418 | 10433194 | Y | 20314804 | 20315473 |
| Y | 10439790 | 10440065 | Y | 20330481 | 20330573 |
| Y | 10443631 | 10445918 | Y | 20333728 | 20333918 |
| Y | 10449920 | 10451810 | Y | 20335850 | 20336369 |
| Y | 10453958 | 10454363 | Y | 20337235 | 20337621 |
| Y | 10458119 | 10461997 | Y | 20338861 | 20340709 |
| Y | 10464065 | 10468812 | Y | 20343001 | 20344459 |
| Y | 10471405 | 10472059 | Y | 20349347 | 20350748 |
| Y | 10472979 | 10474149 | Y | 20357442 | 20357890 |

The chromosomal positon was obtained from UCSC genome browser (http://genome.ucsc.edu/) build 36.

APPENDIX E: Chromosome Y
Page 13 of 58

| Chr | Start | End | Chr | Start | End |
|---|---|---|---|---|---|
| Y | 10483170 | 10483640 | Y | 20365275 | 20366370 |
| Y | 10485165 | 10487622 | Y | 20367480 | 20367745 |
| Y | 10493237 | 10494787 | Y | 20368545 | 20370090 |
| Y | 10506730 | 10509069 | Y | 20370587 | 20370936 |
| Y | 10513003 | 10515933 | Y | 20376069 | 20376359 |
| Y | 10520280 | 10534724 | Y | 20378530 | 20379894 |
| Y | 10537633 | 10538445 | Y | 20384576 | 20384670 |
| Y | 10540332 | 10541422 | Y | 20385879 | 20386125 |
| Y | 10560977 | 10562315 | Y | 20390167 | 20390502 |
| Y | 10563687 | 10563883 | Y | 20392416 | 20392700 |
| Y | 10568273 | 10568731 | Y | 20393692 | 20393820 |
| Y | 10576454 | 10576753 | Y | 20394966 | 20396281 |
| Y | 10579606 | 10583139 | Y | 20398905 | 20405966 |
| Y | 10584173 | 10584566 | Y | 20408485 | 20410518 |
| Y | 10585074 | 10588280 | Y | 20412880 | 20419599 |
| Y | 10589868 | 10590193 | Y | 20421333 | 20422663 |
| Y | 10597469 | 10597904 | Y | 20429026 | 20429739 |
| Y | 10601971 | 10602463 | Y | 20431920 | 20433961 |
| Y | 10603264 | 10603829 | Y | 20440009 | 20440593 |
| Y | 10612522 | 10613817 | Y | 20443043 | 20445504 |
| Y | 10615786 | 10621295 | Y | 20446238 | 20449180 |
| Y | 10622241 | 10623481 | Y | 20462921 | 20463085 |
| Y | 10634875 | 10648372 | Y | 20463562 | 20464137 |
| Y | 10650225 | 10655500 | Y | 20465033 | 20465431 |
| Y | 10658282 | 11246906 | Y | 20465947 | 20466137 |
| Y | 11660698 | 11663073 | Y | 20467512 | 20468049 |
| Y | 11670286 | 11673062 | Y | 20468138 | 20468533 |
| Y | 11677756 | 11678627 | Y | 20479027 | 20479062 |
| Y | 11681057 | 11684165 | Y | 20482382 | 20483894 |
| Y | 11687595 | 11688985 | Y | 20493688 | 20493853 |
| Y | 11689800 | 11691165 | Y | 20494718 | 20497986 |
| Y | 11692261 | 11694244 | Y | 20499949 | 20500815 |
| Y | 11697078 | 11729984 | Y | 20501591 | 20502508 |
| Y | 11741040 | 11742894 | Y | 20505908 | 20510316 |
| Y | 11765360 | 11774431 | Y | 20513028 | 20514650 |
| Y | 11793418 | 11794578 | Y | 20517507 | 20519195 |
| Y | 11803478 | 11810305 | Y | 20521054 | 20521732 |
| Y | 11858857 | 11860882 | Y | 20522263 | 20522988 |
| Y | 11865365 | 11883173 | Y | 20523730 | 20525123 |
| Y | 11898098 | 11906096 | Y | 20529955 | 20530213 |
| Y | 11919930 | 11941274 | Y | 20531088 | 20533223 |
| Y | 11943799 | 11951507 | Y | 20535013 | 20535177 |
| Y | 11980971 | 11985195 | Y | 20536194 | 20537130 |
| Y | 11988191 | 11988366 | Y | 20537460 | 20537471 |
| Y | 11990879 | 11997561 | Y | 20538799 | 20540159 |
| Y | 12016484 | 12016506 | Y | 20545716 | 20546623 |
| Y | 12044473 | 12046829 | Y | 20553875 | 20554992 |
| Y | 12056181 | 12057361 | Y | 20557908 | 20562481 |
| Y | 12062800 | 12063834 | Y | 20564523 | 20564809 |
| Y | 12097904 | 12101669 | Y | 20567208 | 20568588 |
| Y | 12109190 | 12111157 | Y | 20578628 | 20581714 |
| Y | 12112013 | 12112664 | Y | 20590032 | 20590903 |
| Y | 12117199 | 12118074 | Y | 20599084 | 20599199 |
| Y | 12154278 | 12173862 | Y | 20601343 | 20601707 |
| Y | 12331638 | 12332817 | Y | 20603050 | 20603730 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 12366204 | 12366892 | | | Y | 20607031 | 20607311 |
| Y | 12381378 | 12381852 | | | Y | 20608005 | 20608802 |
| Y | 12409404 | 12413175 | | | Y | 20616669 | 20616702 |
| Y | 12418609 | 12421792 | | | Y | 20618082 | 20618579 |
| Y | 12431295 | 12435356 | | | Y | 20621690 | 20622520 |
| Y | 12439592 | 12441419 | | | Y | 20638017 | 20638290 |
| Y | 12451482 | 12452808 | | | Y | 20639690 | 20640399 |
| Y | 12465071 | 12465461 | | | Y | 20650419 | 20651335 |
| Y | 12483210 | 12485429 | | | Y | 20670404 | 20672132 |
| Y | 12498180 | 12499828 | | | Y | 20672595 | 20672942 |
| Y | 12511597 | 12511714 | | | Y | 20688494 | 20896615 |
| Y | 12512350 | 12512470 | | | Y | 20922834 | 20928621 |
| Y | 12528027 | 12528477 | | | Y | 20934267 | 20934505 |
| Y | 12531290 | 12531716 | | | Y | 20935280 | 20948138 |
| Y | 12538622 | 12538922 | | | Y | 20961274 | 20961984 |
| Y | 12553481 | 12553871 | | | Y | 20963567 | 20965400 |
| Y | 12573802 | 12576093 | | | Y | 20965925 | 20966072 |
| Y | 12578167 | 12580692 | | | Y | 20971069 | 20972570 |
| Y | 12593912 | 12594756 | | | Y | 20981243 | 20981319 |
| Y | 12595202 | 12595457 | | | Y | 20982779 | 20983024 |
| Y | 12596297 | 12598710 | | | Y | 20983737 | 20984366 |
| Y | 12603082 | 12604818 | | | Y | 20988393 | 20990762 |
| Y | 12606914 | 12608070 | | | Y | 20992005 | 20992346 |
| Y | 12613142 | 12613650 | | | Y | 20995402 | 20995641 |
| Y | 12615498 | 12617908 | | | Y | 21004333 | 21004558 |
| Y | 12626014 | 12626582 | | | Y | 21008848 | 21011251 |
| Y | 12634706 | 12636523 | | | Y | 21018306 | 21018645 |
| Y | 12646278 | 12646701 | | | Y | 21019722 | 21020262 |
| Y | 12672515 | 12678764 | | | Y | 21021132 | 21021590 |
| Y | 12679452 | 12680204 | | | Y | 21022596 | 21022925 |
| Y | 12681490 | 12682328 | | | Y | 21028437 | 21033064 |
| Y | 12683587 | 12685297 | | | Y | 21035098 | 21035663 |
| Y | 12703297 | 12703527 | | | Y | 21036826 | 21037104 |
| Y | 12708443 | 12709473 | | | Y | 21038145 | 21038421 |
| Y | 12716790 | 12717688 | | | Y | 21041970 | 21044092 |
| Y | 12720618 | 12721095 | | | Y | 21048252 | 21048420 |
| Y | 12725330 | 12725654 | | | Y | 21058701 | 21059796 |
| Y | 12726720 | 12727201 | | | Y | 21061095 | 21061445 |
| Y | 12753102 | 12753540 | | | Y | 21063757 | 21064788 |
| Y | 12760398 | 12762830 | | | Y | 21068377 | 21071776 |
| Y | 12775845 | 12778099 | | | Y | 21082751 | 21083114 |
| Y | 12784305 | 12784619 | | | Y | 21092177 | 21092456 |
| Y | 12807504 | 12808420 | | | Y | 21109594 | 21110111 |
| Y | 12809512 | 12809722 | | | Y | 21111704 | 21111740 |
| Y | 12810986 | 12811186 | | | Y | 21113658 | 21115632 |
| Y | 12821327 | 12821707 | | | Y | 21118691 | 21118967 |
| Y | 12827852 | 12828141 | | | Y | 21121977 | 21125523 |
| Y | 12828587 | 12830472 | | | Y | 21130179 | 21130999 |
| Y | 12831517 | 12832542 | | | Y | 21132416 | 21133282 |
| Y | 12844068 | 12846167 | | | Y | 21137468 | 21137654 |
| Y | 12855552 | 12855826 | | | Y | 21137986 | 21139970 |
| Y | 12856526 | 12857142 | | | Y | 21146372 | 21148041 |
| Y | 12858775 | 12861870 | | | Y | 21155772 | 21155968 |
| Y | 12874365 | 12876808 | | | Y | 21158880 | 21159452 |
| Y | 12888930 | 12891320 | | | Y | 21167176 | 21167796 |

The chromosomal positon was obtained from UCSC genome browser (http://genome.ucsc.edu/) build 36.

APPENDIX E: Chromosome Y
Page 15 of 58

| Chr | Start | End | Chr | Start | End |
|---|---|---|---|---|---|
| Y | 12908098 | 12909247 | Y | 21168982 | 21170369 |
| Y | 12913786 | 12914625 | Y | 21172403 | 21172704 |
| Y | 12917001 | 12917066 | Y | 21178010 | 21179682 |
| Y | 12920905 | 12921246 | Y | 21181007 | 21181778 |
| Y | 12929465 | 12929936 | Y | 21182166 | 21182837 |
| Y | 12947797 | 12947829 | Y | 21185752 | 21191033 |
| Y | 12948679 | 12948982 | Y | 21194478 | 21194937 |
| Y | 12954127 | 12954276 | Y | 21202089 | 21203653 |
| Y | 12975100 | 12975998 | Y | 21209124 | 21211895 |
| Y | 12979048 | 12981216 | Y | 21213766 | 21214219 |
| Y | 12990036 | 12990511 | Y | 21215378 | 21217794 |
| Y | 12996169 | 12996592 | Y | 21219001 | 21220076 |
| Y | 13000219 | 13001761 | Y | 21223563 | 21225867 |
| Y | 13014066 | 13014481 | Y | 21226037 | 21226602 |
| Y | 13046440 | 13046878 | Y | 21227487 | 21228073 |
| Y | 13051391 | 13051469 | Y | 21231901 | 21232138 |
| Y | 13058601 | 13058906 | Y | 21237498 | 21237511 |
| Y | 13064071 | 13064384 | Y | 21243980 | 21244836 |
| Y | 13083755 | 13084100 | Y | 21245525 | 21245675 |
| Y | 13089439 | 13089924 | Y | 21268195 | 21271499 |
| Y | 13110730 | 13111345 | Y | 21274120 | 21283203 |
| Y | 13112465 | 13113774 | Y | 21284777 | 21284811 |
| Y | 13121832 | 13123408 | Y | 21286065 | 21290107 |
| Y | 13136421 | 13136623 | Y | 21291247 | 21295542 |
| Y | 13146601 | 13148344 | Y | 21298534 | 21298874 |
| Y | 13151276 | 13151485 | Y | 21300650 | 21303489 |
| Y | 13152530 | 13153499 | Y | 21306220 | 21306433 |
| Y | 13154135 | 13155378 | Y | 21307423 | 21307707 |
| Y | 13158415 | 13161808 | Y | 21310703 | 21310913 |
| Y | 13173842 | 13176990 | Y | 21314111 | 21319869 |
| Y | 13179871 | 13181090 | Y | 21322410 | 21323286 |
| Y | 13190904 | 13198837 | Y | 21329358 | 21329829 |
| Y | 13202064 | 13205659 | Y | 21333149 | 21333536 |
| Y | 13209720 | 13212746 | Y | 21334645 | 21335236 |
| Y | 13216796 | 13218111 | Y | 21340138 | 21341234 |
| Y | 13226418 | 13227003 | Y | 21346100 | 21347337 |
| Y | 13233102 | 13233721 | Y | 21351928 | 21352448 |
| Y | 13260801 | 13261813 | Y | 21353789 | 21355322 |
| Y | 13264144 | 13265254 | Y | 21362372 | 21367853 |
| Y | 13266727 | 13270224 | Y | 21367868 | 21368144 |
| Y | 13273514 | 13275046 | Y | 21368608 | 21370023 |
| Y | 13282729 | 13284859 | Y | 21373562 | 21373996 |
| Y | 13296272 | 13296602 | Y | 21378620 | 21379104 |
| Y | 13306380 | 13307762 | Y | 21382261 | 21382827 |
| Y | 13310986 | 13311198 | Y | 21384890 | 21386409 |
| Y | 13315708 | 13317246 | Y | 21407602 | 21410171 |
| Y | 13323348 | 13323957 | Y | 21412311 | 21415340 |
| Y | 13326322 | 13326627 | Y | 21421419 | 21421995 |
| Y | 13330768 | 13331497 | Y | 21422957 | 21428121 |
| Y | 13346991 | 13347641 | Y | 21429651 | 21429803 |
| Y | 13349425 | 13350185 | Y | 21430708 | 21433176 |
| Y | 13357663 | 13358208 | Y | 21435160 | 21435568 |
| Y | 13362110 | 13362575 | Y | 21439702 | 21441398 |
| Y | 13371601 | 13372111 | Y | 21444307 | 21444554 |
| Y | 13377327 | 13377739 | Y | 21444614 | 21444742 |

The chromosomal positon was obtained from UCSC genome browser (http://genome.ucsc.edu/) build 36.

APPENDIX E: Chromosome Y
Page 16 of 58

| Chr | Start | End | | Chr | Start | End |
|---|---|---|---|---|---|---|
| Y | 13378541 | 13379790 | | Y | 21446893 | 21449369 |
| Y | 13384009 | 13384164 | | Y | 21451291 | 21451612 |
| Y | 13396815 | 13396923 | | Y | 21456697 | 21462264 |
| Y | 13400667 | 13400751 | | Y | 21463619 | 21463888 |
| Y | 13403783 | 13404652 | | Y | 21464787 | 21465604 |
| Y | 13416008 | 13416743 | | Y | 21499280 | 21499375 |
| Y | 13420751 | 13420923 | | Y | 21523883 | 21524613 |
| Y | 13424772 | 13425969 | | Y | 21527365 | 21527550 |
| Y | 13432721 | 13433704 | | Y | 21531412 | 21531782 |
| Y | 13445364 | 13445713 | | Y | 21533668 | 21534489 |
| Y | 13453737 | 13453803 | | Y | 21534928 | 21538127 |
| Y | 13475497 | 13476094 | | Y | 21552751 | 21555338 |
| Y | 13483305 | 13483616 | | Y | 21558534 | 21560153 |
| Y | 13487788 | 13488514 | | Y | 21562457 | 21562616 |
| Y | 13491676 | 13492089 | | Y | 21564401 | 21564747 |
| Y | 13496967 | 13497191 | | Y | 21568053 | 21568223 |
| Y | 13505276 | 13505642 | | Y | 21576009 | 21576093 |
| Y | 13513235 | 13520159 | | Y | 21593060 | 21593322 |
| Y | 13526026 | 13527802 | | Y | 21600280 | 21603474 |
| Y | 13533170 | 13533626 | | Y | 21641482 | 21641645 |
| Y | 13540522 | 13540931 | | Y | 21647380 | 21647780 |
| Y | 13544460 | 13544725 | | Y | 21649015 | 21649378 |
| Y | 13544792 | 13544892 | | Y | 21650456 | 21651031 |
| Y | 13548615 | 13549762 | | Y | 21652950 | 21657385 |
| Y | 13558104 | 13559004 | | Y | 21663361 | 21664034 |
| Y | 13561333 | 13561918 | | Y | 21665320 | 21665499 |
| Y | 13563331 | 13564132 | | Y | 21669048 | 21669640 |
| Y | 13568014 | 13568191 | | Y | 21671242 | 21671631 |
| Y | 13571708 | 13574916 | | Y | 21674622 | 21676142 |
| Y | 13578770 | 13579406 | | Y | 21678789 | 21679011 |
| Y | 13580536 | 13581898 | | Y | 21679436 | 21679653 |
| Y | 13587887 | 13589758 | | Y | 21689698 | 21690981 |
| Y | 13591027 | 13592064 | | Y | 21703163 | 21704265 |
| Y | 13597977 | 13598212 | | Y | 21714706 | 21716312 |
| Y | 13600948 | 13601358 | | Y | 21719566 | 21721002 |
| Y | 13604047 | 13604443 | | Y | 21723864 | 21723963 |
| Y | 13606018 | 13606814 | | Y | 21738802 | 21739285 |
| Y | 13617155 | 13617741 | | Y | 21751956 | 21752566 |
| Y | 13624524 | 13625440 | | Y | 21763302 | 21764413 |
| Y | 13627354 | 13633088 | | Y | 21769731 | 21774049 |
| Y | 13644486 | 13645176 | | Y | 21775302 | 21776187 |
| Y | 13646785 | 13647207 | | Y | 21778861 | 21779316 |
| Y | 13648423 | 13649735 | | Y | 21783227 | 21783868 |
| Y | 13662681 | 13663742 | | Y | 21787137 | 21787956 |
| Y | 13665768 | 13668456 | | Y | 21789061 | 21790825 |
| Y | 13671224 | 13671693 | | Y | 21792158 | 21792698 |
| Y | 13675149 | 13675613 | | Y | 21793787 | 21794247 |
| Y | 13676338 | 13676565 | | Y | 21799359 | 21800258 |
| Y | 13682095 | 13683276 | | Y | 21804117 | 21810736 |
| Y | 13683781 | 13686125 | | Y | 21815483 | 21815840 |
| Y | 13689826 | 13691419 | | Y | 21816955 | 21817428 |
| Y | 13700171 | 13701113 | | Y | 21837109 | 21838033 |
| Y | 13703874 | 13704129 | | Y | 21838359 | 21839016 |
| Y | 13707091 | 13709224 | | Y | 21839869 | 21841027 |
| Y | 13713905 | 13714581 | | Y | 21844660 | 21845422 |

The chromosomal positon was obtained from UCSC genome browser (http://genome.ucsc.edu/) build 36.

APPENDIX E: Chromosome Y

| Chr | Start | End | | Chr | Start | End |
|---|---|---|---|---|---|---|
| Y | 13721480 | 13722017 | | Y | 21853634 | 21854019 |
| Y | 13728727 | 13728844 | | Y | 21855327 | 21855485 |
| Y | 13729208 | 13730018 | | Y | 21859811 | 21860010 |
| Y | 13736268 | 13738103 | | Y | 21861435 | 21862776 |
| Y | 13747615 | 13748930 | | Y | 21876230 | 21878944 |
| Y | 13757839 | 13758971 | | Y | 21892695 | 21893541 |
| Y | 13763221 | 13764495 | | Y | 21895291 | 21896503 |
| Y | 13766618 | 13767382 | | Y | 21900747 | 21902347 |
| Y | 13774168 | 13774618 | | Y | 21915956 | 21916261 |
| Y | 13786035 | 13787742 | | Y | 21920498 | 21924005 |
| Y | 13790175 | 13791013 | | Y | 21943195 | 21943450 |
| Y | 13792830 | 13799968 | | Y | 21944395 | 21944429 |
| Y | 13832101 | 13832646 | | Y | 21946697 | 21949149 |
| Y | 13836281 | 13837560 | | Y | 21950442 | 21951751 |
| Y | 13848504 | 13849741 | | Y | 21957508 | 21963722 |
| Y | 13852417 | 13853068 | | Y | 21980472 | 21981483 |
| Y | 13858500 | 13859965 | | Y | 21991911 | 21993150 |
| Y | 13862702 | 13863046 | | Y | 21998730 | 22001136 |
| Y | 13888469 | 13890359 | | Y | 22003546 | 22003682 |
| Y | 13898908 | 13899134 | | Y | 22005101 | 22006466 |
| Y | 13907847 | 13908427 | | Y | 22009388 | 22013052 |
| Y | 13913320 | 13915300 | | Y | 22015417 | 22016069 |
| Y | 13925000 | 13925899 | | Y | 22017334 | 22017420 |
| Y | 13928234 | 13929731 | | Y | 22021738 | 22022230 |
| Y | 13935726 | 13936064 | | Y | 22023384 | 22026988 |
| Y | 13936239 | 13936946 | | Y | 22028054 | 22028772 |
| Y | 13941733 | 13942111 | | Y | 22029368 | 22029602 |
| Y | 13943214 | 13944011 | | Y | 22031396 | 22032081 |
| Y | 13946633 | 13947054 | | Y | 22033844 | 22034294 |
| Y | 13949643 | 13951030 | | Y | 22035803 | 22036603 |
| Y | 13956768 | 13957410 | | Y | 22040478 | 22041050 |
| Y | 13957776 | 13958583 | | Y | 22041385 | 22042337 |
| Y | 13961850 | 13963374 | | Y | 22044641 | 22045703 |
| Y | 13965300 | 13965625 | | Y | 22047157 | 22049277 |
| Y | 13967329 | 13967964 | | Y | 22050474 | 22051067 |
| Y | 13971233 | 13971638 | | Y | 22056205 | 22057188 |
| Y | 13985477 | 13986452 | | Y | 22060059 | 22061676 |
| Y | 13986975 | 13987630 | | Y | 22063544 | 22171488 |
| Y | 13991041 | 13991959 | | Y | 22171968 | 22176134 |
| Y | 13993676 | 13994602 | | Y | 22176988 | 22178184 |
| Y | 13997924 | 13998175 | | Y | 22179185 | 22179570 |
| Y | 14001664 | 14002265 | | Y | 22182431 | 22183681 |
| Y | 14012506 | 14012646 | | Y | 22188048 | 22190312 |
| Y | 14015181 | 14015685 | | Y | 22192483 | 22193667 |
| Y | 14017502 | 14019290 | | Y | 22214384 | 22215258 |
| Y | 14020971 | 14022374 | | Y | 22216336 | 22217812 |
| Y | 14028701 | 14029348 | | Y | 22221166 | 22223873 |
| Y | 14038039 | 14038229 | | Y | 22223966 | 22224429 |
| Y | 14039968 | 14040385 | | Y | 22231179 | 22232416 |
| Y | 14041380 | 14041556 | | Y | 22255533 | 22256863 |
| Y | 14044283 | 14044653 | | Y | 22257213 | 22257318 |
| Y | 14046470 | 14047101 | | Y | 22263121 | 22267595 |
| Y | 14047757 | 14048148 | | Y | 22271236 | 22274975 |
| Y | 14056579 | 14060255 | | Y | 22294528 | 22295925 |
| Y | 14061186 | 14062102 | | Y | 22305977 | 22307184 |

The chromosomal positon was obtained from UCSC genome browser (http://genome.ucsc.edu/) build 36.

APPENDIX E: Chromosome Y

| Chr | Start | End | | Chr | Start | End |
|---|---|---|---|---|---|---|
| Y | 14071053 | 14071530 | | Y | 22366886 | 22367016 |
| Y | 14072407 | 14073132 | | Y | 22373691 | 22374482 |
| Y | 14091072 | 14092013 | | Y | 22376211 | 22401859 |
| Y | 14096547 | 14096825 | | Y | 22404890 | 22416366 |
| Y | 14099525 | 14101852 | | Y | 22769432 | 22769436 |
| Y | 14104470 | 14106756 | | Y | 22779294 | 22780761 |
| Y | 14111413 | 14112307 | | Y | 22789016 | 22789128 |
| Y | 14118799 | 14119965 | | Y | 22793682 | 22798683 |
| Y | 14125921 | 14127059 | | Y | 22801155 | 22801243 |
| Y | 14128590 | 14130157 | | Y | 22803099 | 22803570 |
| Y | 14133603 | 14133918 | | Y | 22806165 | 22806253 |
| Y | 14141882 | 14141948 | | Y | 22809680 | 22811137 |
| Y | 14160632 | 14161462 | | Y | 22828120 | 22828640 |
| Y | 14165315 | 14165924 | | Y | 22834843 | 22835403 |
| Y | 14173684 | 14174489 | | Y | 22843795 | 22843980 |
| Y | 14176033 | 14176277 | | Y | 22845751 | 22847602 |
| Y | 14178426 | 14179910 | | Y | 22850148 | 22855607 |
| Y | 14192716 | 14194165 | | Y | 22858118 | 22859543 |
| Y | 14201812 | 14202192 | | Y | 22860276 | 22862273 |
| Y | 14206830 | 14210774 | | Y | 22866898 | 22867504 |
| Y | 14215555 | 14216240 | | Y | 22870988 | 22871717 |
| Y | 14216973 | 14217373 | | Y | 22874780 | 22877227 |
| Y | 14223138 | 14224092 | | Y | 22879316 | 22892914 |
| Y | 14225934 | 14226270 | | Y | 22903122 | 22905378 |
| Y | 14229827 | 14230179 | | Y | 22907701 | 22908313 |
| Y | 14237332 | 14237971 | | Y | 22914654 | 22915496 |
| Y | 14239509 | 14239750 | | Y | 22915931 | 22916296 |
| Y | 14247369 | 14247513 | | Y | 22919638 | 22921404 |
| Y | 14262925 | 14263319 | | Y | 22929175 | 22929730 |
| Y | 14266330 | 14267711 | | Y | 23360362 | 23370487 |
| Y | 14269850 | 14271743 | | Y | 26871433 | 26872466 |
| Y | 14273231 | 14276396 | | Y | 26888425 | 26890331 |
| Y | 14286672 | 14287750 | | Y | 26911071 | 26913248 |
| Y | 14290614 | 14290938 | | Y | 26960538 | 26961868 |
| Y | 14292415 | 14292765 | | Y | 26964081 | 26964931 |
| Y | 14296217 | 14296331 | | Y | 26965911 | 26998844 |
| Y | 14297330 | 14308047 | | Y | 27041345 | 27041638 |
| Y | 14311911 | 14312295 | | Y | 27050841 | 27051930 |
| Y | 14319851 | 14320108 | | Y | 27085896 | 27089439 |
| Y | 14325198 | 14326683 | | Y | 27097775 | 27101863 |
| Y | 14337130 | 14337640 | | Y | 27109581 | 27116038 |
| Y | 14342595 | 14343115 | | Y | 27148286 | 27156224 |
| Y | 14356751 | 14357326 | | Y | 27168463 | 27168877 |
| Y | 14359769 | 14360089 | | Y | 27180405 | 27180908 |
| | | | | Y | 27200977 | 27204362 |
| | | | | Y | 27214312 | 27220961 |
| Y | 57266313 | 57320348 | | Y | 57574656 | 57575014 |
| Y | 57377268 | 57378128 | | Y | 57579562 | 57580080 |
| Y | 57378959 | 57379150 | | Y | 57581250 | 57583274 |
| Y | 57387188 | 57387284 | | Y | 57583443 | 57583491 |
| Y | 57392613 | 57392738 | | Y | 57586453 | 57586702 |
| Y | 57392798 | 57392808 | | Y | 57587218 | 57587253 |
| Y | 57392883 | 57411609 | | Y | 57588114 | 57588228 |
| Y | 57411730 | 57411754 | | Y | 57588879 | 57588902 |
| Y | 57412143 | 57412168 | | Y | 57589118 | 57589170 |

The chromosomal positon was obtained from UCSC genome browser (http://genome.ucsc.edu/) build 36.

APPENDIX E: Chromosome Y
Page 19 of 58

| Chr | Start | End | | | Chr | Start | End |
|---|---|---|---|---|---|---|---|
| Y | 57413036 | 57413048 | | | Y | 57589485 | 57589734 |
| Y | 57413415 | 57414092 | | | Y | 57590170 | 57590397 |
| Y | 57414804 | 57415095 | | | Y | 57591223 | 57591279 |
| Y | 57415229 | 57415373 | | | Y | 57591773 | 57592132 |
| Y | 57416174 | 57418552 | | | Y | 57592330 | 57592485 |
| Y | 57423761 | 57423877 | | | Y | 57592615 | 57593526 |
| Y | 57423928 | 57423933 | | | Y | 57598323 | 57598565 |
| Y | 57424219 | 57430857 | | | Y | 57598856 | 57598986 |
| Y | 57431389 | 57431442 | | | Y | 57599035 | 57599477 |
| Y | 57436427 | 57438196 | | | Y | 57599522 | 57599571 |
| Y | 57439441 | 57439921 | | | Y | 57600626 | 57601471 |
| Y | 57440845 | 57442136 | | | Y | 57604381 | 57604508 |
| Y | 57445905 | 57445917 | | | Y | 57604697 | 57604738 |
| Y | 57446005 | 57446133 | | | Y | 57605063 | 57605167 |
| Y | 57446898 | 57447026 | | | Y | 57606274 | 57606488 |
| Y | 57447457 | 57447843 | | | Y | 57607296 | 57607951 |
| Y | 57448393 | 57448699 | | | Y | 57608391 | 57608418 |
| Y | 57448789 | 57448816 | | | Y | 57608900 | 57609001 |
| Y | 57449294 | 57449481 | | | Y | 57609206 | 57609278 |
| Y | 57449906 | 57450045 | | | Y | 57609867 | 57609933 |
| Y | 57450336 | 57450526 | | | Y | 57610994 | 57611076 |
| Y | 57451004 | 57451483 | | | Y | 57611253 | 57611345 |
| Y | 57455766 | 57456266 | | | Y | 57611572 | 57611892 |
| Y | 57456350 | 57456361 | | | Y | 57612589 | 57612773 |
| Y | 57457391 | 57457486 | | | Y | 57613029 | 57613106 |
| Y | 57457591 | 57457596 | | | Y | 57613755 | 57614044 |
| Y | 57458200 | 57458280 | | | Y | 57614502 | 57614794 |
| Y | 57462317 | 57462517 | | | Y | 57616233 | 57617066 |
| Y | 57462691 | 57463883 | | | Y | 57617671 | 57617808 |
| Y | 57471041 | 57472689 | | | Y | 57618013 | 57618046 |
| Y | 57473973 | 57474364 | | | Y | 57618891 | 57618896 |
| Y | 57475558 | 57475611 | | | Y | 57619130 | 57619285 |
| Y | 57475987 | 57476066 | | | Y | 57619493 | 57619531 |
| Y | 57477405 | 57477550 | | | Y | 57620011 | 57620019 |
| Y | 57477662 | 57477706 | | | Y | 57620332 | 57620378 |
| Y | 57477725 | 57477869 | | | Y | 57621118 | 57621124 |
| Y | 57478114 | 57478144 | | | Y | 57621385 | 57621713 |
| Y | 57478347 | 57478508 | | | Y | 57621821 | 57621835 |
| Y | 57478618 | 57478772 | | | Y | 57622804 | 57623014 |
| Y | 57479449 | 57479705 | | | Y | 57623089 | 57624330 |
| Y | 57480201 | 57480296 | | | Y | 57624639 | 57624666 |
| Y | 57480718 | 57480723 | | | Y | 57624915 | 57625018 |
| Y | 57480848 | 57481198 | | | Y | 57625146 | 57625155 |
| Y | 57481633 | 57481658 | | | Y | 57625219 | 57625355 |
| Y | 57482045 | 57483748 | | | Y | 57626704 | 57626837 |
| Y | 57485486 | 57485511 | | | Y | 57626894 | 57627001 |
| Y | 57487296 | 57492104 | | | Y | 57627436 | 57628308 |
| Y | 57492850 | 57493000 | | | Y | 57630155 | 57630346 |
| Y | 57493123 | 57493305 | | | Y | 57630481 | 57630650 |
| Y | 57493511 | 57494142 | | | Y | 57630752 | 57630863 |
| Y | 57494423 | 57494463 | | | Y | 57631778 | 57632154 |
| Y | 57495362 | 57495484 | | | Y | 57632832 | 57632930 |
| Y | 57495861 | 57496199 | | | Y | 57633341 | 57633407 |
| Y | 57496449 | 57496506 | | | Y | 57633528 | 57633572 |
| Y | 57497220 | 57498885 | | | Y | 57633830 | 57633876 |

The chromosomal positon was obtained from UCSC genome browser (http://genome.ucsc.edu/) build 36.

APPENDIX E: Chromosome Y
Page 20 of 58

| Chr | Start | End | Chr | Start | End |
|---|---|---|---|---|---|
| Y | 57499692 | 57499827 | Y | 57634236 | 57634453 |
| Y | 57499910 | 57500267 | Y | 57634556 | 57634600 |
| Y | 57500475 | 57500560 | Y | 57634727 | 57634742 |
| Y | 57500885 | 57500907 | Y | 57635377 | 57635382 |
| Y | 57501726 | 57501794 | Y | 57636278 | 57638284 |
| Y | 57502016 | 57502025 | Y | 57638514 | 57638694 |
| Y | 57502594 | 57502710 | Y | 57638982 | 57639114 |
| Y | 57502975 | 57503259 | Y | 57639257 | 57639421 |
| Y | 57504002 | 57504031 | Y | 57639972 | 57640039 |
| Y | 57504386 | 57504450 | Y | 57640278 | 57640774 |
| Y | 57504597 | 57504660 | Y | 57640999 | 57642422 |
| Y | 57505316 | 57505630 | Y | 57642577 | 57642606 |
| Y | 57505963 | 57506045 | Y | 57642653 | 57642720 |
| Y | 57506409 | 57506438 | Y | 57643127 | 57643141 |
| Y | 57506720 | 57506854 | Y | 57646606 | 57646797 |
| Y | 57507317 | 57507565 | Y | 57648255 | 57648380 |
| Y | 57507849 | 57507925 | Y | 57648544 | 57648678 |
| Y | 57507970 | 57508134 | Y | 57648728 | 57648805 |
| Y | 57508243 | 57508291 | Y | 57652480 | 57661597 |
| Y | 57508684 | 57508719 | Y | 57661952 | 57661968 |
| Y | 57508758 | 57508840 | Y | 57662498 | 57663406 |
| Y | 57509194 | 57509919 | Y | 57663987 | 57664193 |
| Y | 57510634 | 57510669 | Y | 57664444 | 57664463 |
| Y | 57510870 | 57510940 | Y | 57664659 | 57664690 |
| Y | 57511341 | 57511385 | Y | 57664863 | 57664974 |
| Y | 57511545 | 57511629 | Y | 57665135 | 57665156 |
| Y | 57511678 | 57511836 | Y | 57666042 | 57666149 |
| Y | 57511999 | 57512036 | Y | 57666742 | 57666957 |
| Y | 57512978 | 57513016 | Y | 57667692 | 57669084 |
| Y | 57513225 | 57513272 | Y | 57670307 | 57670467 |
| Y | 57513832 | 57513931 | Y | 57670557 | 57670638 |
| Y | 57514602 | 57514759 | Y | 57671253 | 57671317 |
| Y | 57516082 | 57516662 | Y | 57671732 | 57671785 |
| Y | 57517508 | 57517522 | Y | 57679734 | 57679805 |
| Y | 57517865 | 57518138 | Y | 57680150 | 57680291 |
| Y | 57519047 | 57519086 | Y | 57680560 | 57680606 |
| Y | 57519323 | 57519404 | Y | 57681268 | 57681354 |
| Y | 57519638 | 57519668 | Y | 57682061 | 57682266 |
| Y | 57520526 | 57520817 | Y | 57682717 | 57682760 |
| Y | 57520897 | 57520989 | Y | 57683067 | 57683588 |
| Y | 57521123 | 57521232 | Y | 57684946 | 57684956 |
| Y | 57521252 | 57521299 | Y | 57685115 | 57685185 |
| Y | 57521483 | 57521502 | Y | 57685776 | 57685870 |
| Y | 57521900 | 57521938 | Y | 57686639 | 57686699 |
| Y | 57521964 | 57522124 | Y | 57686950 | 57687752 |
| Y | 57522526 | 57522602 | Y | 57688200 | 57688340 |
| Y | 57522828 | 57522996 | Y | 57688506 | 57688565 |
| Y | 57523036 | 57523069 | Y | 57688640 | 57688679 |
| Y | 57523275 | 57523397 | Y | 57688796 | 57688845 |
| Y | 57523629 | 57523904 | Y | 57689025 | 57689055 |
| Y | 57524183 | 57524304 | Y | 57689345 | 57689389 |
| Y | 57524342 | 57524414 | Y | 57689504 | 57689540 |
| Y | 57524567 | 57524712 | Y | 57689965 | 57690499 |
| Y | 57525209 | 57525382 | Y | 57691040 | 57691105 |
| Y | 57525923 | 57525979 | Y | 57691581 | 57691660 |

The chromosomal positon was obtained from UCSC genome browser (http://genome.ucsc.edu/) build 36.

APPENDIX E: Chromosome Y
Page 21 of 58

| Chr | Start | End | | | Chr | Start | End |
|---|---|---|---|---|---|---|---|
| Y | 57526203 | 57526620 | | | Y | 57691732 | 57691775 |
| Y | 57527023 | 57527093 | | | Y | 57691941 | 57691985 |
| Y | 57527228 | 57527292 | | | Y | 57692812 | 57692847 |
| Y | 57527571 | 57527607 | | | Y | 57693207 | 57693264 |
| Y | 57527755 | 57528179 | | | Y | 57693367 | 57693533 |
| Y | 57530070 | 57530505 | | | Y | 57693910 | 57693973 |
| Y | 57531216 | 57531291 | | | Y | 57694740 | 57694930 |
| Y | 57532688 | 57532890 | | | Y | 57695181 | 57695236 |
| Y | 57533783 | 57534152 | | | Y | 57695767 | 57695780 |
| Y | 57534869 | 57535158 | | | Y | 57696169 | 57696225 |
| Y | 57535197 | 57535281 | | | Y | 57697792 | 57697907 |
| Y | 57535313 | 57535359 | | | Y | 57698027 | 57698477 |
| Y | 57535542 | 57535657 | | | Y | 57698943 | 57699023 |
| Y | 57536412 | 57536910 | | | Y | 57699034 | 57699141 |
| Y | 57537631 | 57537650 | | | Y | 57699196 | 57699285 |
| Y | 57537865 | 57537896 | | | Y | 57699893 | 57700893 |
| Y | 57538588 | 57538797 | | | Y | 57701299 | 57701319 |
| Y | 57539650 | 57539664 | | | Y | 57701524 | 57701545 |
| Y | 57539841 | 57540069 | | | Y | 57703251 | 57703334 |
| Y | 57540293 | 57540517 | | | Y | 57703444 | 57703651 |
| Y | 57540841 | 57540988 | | | Y | 57703720 | 57703752 |
| Y | 57541108 | 57541242 | | | Y | 57704492 | 57704530 |
| Y | 57541403 | 57541457 | | | Y | 57704673 | 57704761 |
| Y | 57541657 | 57541678 | | | Y | 57704978 | 57705106 |
| Y | 57541981 | 57542293 | | | Y | 57705616 | 57705694 |
| Y | 57542929 | 57543119 | | | Y | 57707136 | 57707183 |
| Y | 57543660 | 57543747 | | | Y | 57707365 | 57707405 |
| Y | 57544337 | 57544668 | | | Y | 57707736 | 57707756 |
| Y | 57544698 | 57544771 | | | Y | 57707798 | 57707839 |
| Y | 57544877 | 57544952 | | | Y | 57708820 | 57708833 |
| Y | 57545131 | 57545478 | | | Y | 57709111 | 57709911 |
| Y | 57545891 | 57545923 | | | Y | 57710700 | 57710740 |
| Y | 57545972 | 57546219 | | | Y | 57713756 | 57717297 |
| Y | 57546321 | 57546365 | | | Y | 57718533 | 57718623 |
| Y | 57546589 | 57548776 | | | Y | 57720946 | 57721005 |
| Y | 57546791 | 57546881 | | | Y | 57721315 | 57722185 |
| Y | 57550493 | 57550687 | | | Y | 57722820 | 57722837 |
| Y | 57551119 | 57551358 | | | Y | 57723027 | 57723110 |
| Y | 57558411 | 57558735 | | | Y | 57724157 | 57724677 |
| Y | 57559289 | 57559398 | | | Y | 57726566 | 57726743 |
| Y | 57559562 | 57559612 | | | Y | 57726846 | 57726916 |
| Y | 57560089 | 57560245 | | | Y | 57727384 | 57727486 |
| Y | 57560521 | 57560695 | | | Y | 57727616 | 57727750 |
| Y | 57561642 | 57561762 | | | Y | 57727921 | 57728031 |
| Y | 57562127 | 57562337 | | | Y | 57728481 | 57728562 |
| Y | 57563410 | 57563568 | | | Y | 57730503 | 57731006 |
| Y | 57563817 | 57567412 | | | Y | 57731298 | 57731452 |
| Y | 57564867 | 57564958 | | | Y | 57731643 | 57731693 |
| Y | 57568686 | 57568838 | | | Y | 57733381 | 57733490 |
| Y | 57569044 | 57569465 | | | Y | 57734006 | 57734185 |
| Y | 57569723 | 57570247 | | | Y | 57734763 | 57734778 |
| Y | 57571167 | 57571257 | | | Y | 57736998 | 57737019 |
| Y | 57571980 | 57572187 | | | Y | 57737358 | 57738402 |
| Y | 57573735 | 57573933 | | | Y | 57739206 | 57739373 |
| | | | | | Y | 57739503 | 57739533 |

The chromosomal positon was obtained from UCSC genome browser (http://genome.ucsc.edu/) build 36.

APPENDIX E: Chromosome Y
Page 22 of 58

| Chr | Start | End | | | Chr | Start | End |
|---|---|---|---|---|---|---|---|
| | | | | | Y | 57739838 | 57771455 |
| | | | | | Y | 57745735 | 57745745 |
| Y | 1382 | 2261 | | | Y | 7261735 | 7262719 |
| Y | 10511 | 10706 | | | Y | 7263504 | 7264082 |
| Y | 89688 | 107818 | | | Y | 7267268 | 7267328 |
| Y | 108823 | 109658 | | | Y | 7274009 | 7274764 |
| Y | 116495 | 116740 | | | Y | 7278098 | 7279113 |
| Y | 138748 | 139449 | | | Y | 7279368 | 7279748 |
| Y | 143359 | 144638 | | | Y | 7285970 | 7286010 |
| Y | 162761 | 163141 | | | Y | 7286600 | 7286805 |
| Y | 163821 | 164141 | | | Y | 7289523 | 7289648 |
| Y | 217035 | 217485 | | | Y | 7292300 | 7293412 |
| Y | 219090 | 219170 | | | Y | 7297457 | 7297497 |
| Y | 221101 | 222905 | | | Y | 7299642 | 7301148 |
| Y | 226336 | 226481 | | | Y | 7304860 | 7305760 |
| Y | 231162 | 231277 | | | Y | 7308838 | 7309198 |
| Y | 231397 | 231827 | | | Y | 7311007 | 7311442 |
| Y | 233187 | 233557 | | | Y | 7314291 | 7314716 |
| Y | 237450 | 237520 | | | Y | 7315166 | 7316026 |
| Y | 237955 | 240581 | | | Y | 7318209 | 7318249 |
| Y | 242211 | 242441 | | | Y | 7320736 | 7322716 |
| Y | 251229 | 251319 | | | Y | 7323432 | 7326122 |
| Y | 252090 | 253178 | | | Y | 7326836 | 7328347 |
| Y | 254015 | 254045 | | | Y | 7328972 | 7329102 |
| Y | 255230 | 255341 | | | Y | 7330846 | 7331001 |
| Y | 255471 | 256381 | | | Y | 7331660 | 7332020 |
| Y | 258996 | 259366 | | | Y | 7333143 | 7334321 |
| Y | 263347 | 264087 | | | Y | 7338017 | 7338462 |
| Y | 268022 | 268217 | | | Y | 7338662 | 7338697 |
| Y | 273254 | 273484 | | | Y | 7339232 | 7339402 |
| Y | 278503 | 278653 | | | Y | 7340192 | 7340452 |
| Y | 285537 | 285802 | | | Y | 7341498 | 7341858 |
| Y | 294038 | 294834 | | | Y | 7342565 | 7342650 |
| Y | 295869 | 296144 | | | Y | 7343752 | 7346526 |
| Y | 303112 | 305235 | | | Y | 7347301 | 7348431 |
| Y | 307480 | 308565 | | | Y | 7348951 | 7349941 |
| Y | 311097 | 312218 | | | Y | 7351138 | 7351638 |
| Y | 312973 | 313713 | | | Y | 7352248 | 7352860 |
| Y | 316493 | 318415 | | | Y | 7353253 | 7353438 |
| Y | 324112 | 325152 | | | Y | 7353599 | 7355094 |
| Y | 326966 | 327301 | | | Y | 7362697 | 7362942 |
| Y | 340192 | 343712 | | | Y | 7364210 | 7365507 |
| Y | 345048 | 345248 | | | Y | 7367815 | 7368085 |
| Y | 356719 | 357744 | | | Y | 7369206 | 7369331 |
| Y | 360587 | 361994 | | | Y | 7372207 | 7373041 |
| Y | 363434 | 363777 | | | Y | 7373843 | 7377923 |
| Y | 367152 | 367467 | | | Y | 7378293 | 7378443 |
| Y | 368986 | 369427 | | | Y | 7381639 | 7382354 |
| Y | 369637 | 375867 | | | Y | 7383029 | 7383114 |
| Y | 377872 | 378023 | | | Y | 7383329 | 7383484 |
| Y | 378853 | 380248 | | | Y | 7383984 | 7386399 |
| Y | 380313 | 380854 | | | Y | 7386899 | 7387034 |
| Y | 381749 | 382489 | | | Y | 7390657 | 7390872 |
| Y | 385848 | 387603 | | | Y | 7391552 | 7392427 |
| Y | 388940 | 399148 | | | Y | 7393472 | 7393627 |

The chromosomal positon was obtained from UCSC genome browser (http://genome.ucsc.edu/) build 36.

APPENDIX E: Chromosome Y
Page 23 of 58

| Chr | Start | End | | | Chr | Start | End |
|---|---|---|---|---|---|---|---|
| Y | 404503 | 404993 | | | Y | 7393707 | 7400077 |
| Y | 406939 | 407419 | | | Y | 7410217 | 7410482 |
| Y | 416707 | 417789 | | | Y | 7411973 | 7412656 |
| Y | 419209 | 419464 | | | Y | 7414181 | 7414526 |
| Y | 421334 | 421589 | | | Y | 7416011 | 7416446 |
| Y | 426193 | 426378 | | | Y | 7417576 | 7418166 |
| Y | 429292 | 429492 | | | Y | 7418601 | 7419021 |
| Y | 432544 | 437475 | | | Y | 7420936 | 7421156 |
| Y | 441833 | 442223 | | | Y | 7421801 | 7422419 |
| Y | 442498 | 442553 | | | Y | 7422924 | 7425762 |
| Y | 442988 | 443788 | | | Y | 7427867 | 7427907 |
| Y | 444576 | 445151 | | | Y | 7435573 | 7435763 |
| Y | 449007 | 453266 | | | Y | 7439338 | 7439398 |
| Y | 454774 | 455008 | | | Y | 7442191 | 7442826 |
| Y | 456098 | 459198 | | | Y | 7444619 | 7445549 |
| Y | 459723 | 462633 | | | Y | 7446159 | 7446679 |
| Y | 462743 | 464157 | | | Y | 7448391 | 7448902 |
| Y | 470283 | 470568 | | | Y | 7450700 | 7452059 |
| Y | 474425 | 475407 | | | Y | 7455795 | 7458016 |
| Y | 476237 | 476382 | | | Y | 7459478 | 7459858 |
| Y | 481872 | 481992 | | | Y | 7461416 | 7462773 |
| Y | 485927 | 487158 | | | Y | 7463718 | 7465074 |
| Y | 487978 | 488028 | | | Y | 7465269 | 7466049 |
| Y | 488553 | 490737 | | | Y | 7469050 | 7470335 |
| Y | 491012 | 491232 | | | Y | 7470505 | 7470820 |
| Y | 492699 | 493248 | | | Y | 7471360 | 7474779 |
| Y | 494715 | 498754 | | | Y | 7475949 | 7476524 |
| Y | 500549 | 500589 | | | Y | 7478173 | 7478388 |
| Y | 501004 | 502610 | | | Y | 7480088 | 7480288 |
| Y | 508017 | 511877 | | | Y | 7481619 | 7481779 |
| Y | 512806 | 521382 | | | Y | 7481985 | 7482030 |
| Y | 521797 | 521902 | | | Y | 7484199 | 7485239 |
| Y | 522935 | 523415 | | | Y | 7485608 | 7487028 |
| Y | 526099 | 527650 | | | Y | 7489478 | 7492458 |
| Y | 530881 | 531016 | | | Y | 7493034 | 7493059 |
| Y | 535388 | 536578 | | | Y | 7493224 | 7493503 |
| Y | 541503 | 541628 | | | Y | 7494698 | 7495108 |
| Y | 546542 | 546707 | | | Y | 7495299 | 7495499 |
| Y | 547832 | 547972 | | | Y | 7530263 | 7534247 |
| Y | 553037 | 553922 | | | Y | 7568057 | 7568237 |
| Y | 556509 | 557518 | | | Y | 7569275 | 7569315 |
| Y | 559879 | 560201 | | | Y | 7570030 | 7570782 |
| Y | 564447 | 564707 | | | Y | 7571325 | 7577813 |
| Y | 565836 | 567095 | | | Y | 7578856 | 7579856 |
| Y | 581319 | 582309 | | | Y | 7582276 | 7584446 |
| Y | 584502 | 584627 | | | Y | 7585267 | 7586141 |
| Y | 585677 | 586647 | | | Y | 7586476 | 7586606 |
| Y | 586812 | 587367 | | | Y | 7587461 | 7587786 |
| Y | 588213 | 588378 | | | Y | 7588066 | 7588411 |
| Y | 593130 | 593260 | | | Y | 7589896 | 7590991 |
| Y | 594949 | 594964 | | | Y | 7591952 | 7592077 |
| Y | 595842 | 596437 | | | Y | 7592757 | 7596893 |
| Y | 602508 | 604830 | | | Y | 7596928 | 7597083 |
| Y | 606215 | 608430 | | | Y | 7598326 | 7598401 |
| Y | 612384 | 612554 | | | Y | 7600280 | 7600705 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 629525 | 631107 | Y | 7600750 | 7600917 |
| Y | 632309 | 632334 | Y | 7603963 | 7604073 |
| Y | 635409 | 635771 | Y | 7604803 | 7604883 |
| Y | 638225 | 638615 | Y | 7605348 | 7605478 |
| Y | 639588 | 639813 | Y | 7606173 | 7607503 |
| Y | 643160 | 643996 | Y | 7609723 | 7610918 |
| Y | 649756 | 650525 | Y | 7612488 | 7612728 |
| Y | 656766 | 656971 | Y | 7614061 | 7616206 |
| Y | 657493 | 658013 | Y | 7616711 | 7619493 |
| Y | 659540 | 662015 | Y | 7620343 | 7620468 |
| Y | 665733 | 665848 | Y | 7620903 | 7621323 |
| Y | 667120 | 667215 | Y | 7622669 | 7622714 |
| Y | 667410 | 667555 | Y | 7622879 | 7623014 |
| Y | 670705 | 672653 | Y | 7623596 | 7623891 |
| Y | 674135 | 674740 | Y | 7625163 | 7625648 |
| Y | 676289 | 676790 | Y | 7626010 | 7626430 |
| Y | 686057 | 686885 | Y | 7627485 | 7627670 |
| Y | 689301 | 689536 | Y | 7629430 | 7629775 |
| Y | 690846 | 691256 | Y | 7630030 | 7630160 |
| Y | 691326 | 692556 | Y | 7630635 | 7630650 |
| Y | 696775 | 697030 | Y | 7630945 | 7631630 |
| Y | 702460 | 703629 | Y | 7641007 | 7641082 |
| Y | 704835 | 710663 | Y | 7642897 | 7644484 |
| Y | 718422 | 722837 | Y | 7644669 | 7644699 |
| Y | 723577 | 723898 | Y | 7645129 | 7645244 |
| Y | 724522 | 726437 | Y | 7645269 | 7645839 |
| Y | 727573 | 728987 | Y | 7647249 | 7647509 |
| Y | 729507 | 729582 | Y | 7648595 | 7649575 |
| Y | 737465 | 738265 | Y | 7651491 | 7652656 |
| Y | 738813 | 739263 | Y | 7652991 | 7653126 |
| Y | 739303 | 739944 | Y | 7653816 | 7654206 |
| Y | 742405 | 743295 | Y | 7654851 | 7654896 |
| Y | 746005 | 746435 | Y | 7655096 | 7655296 |
| Y | 747185 | 747415 | Y | 7658841 | 7658906 |
| Y | 748607 | 748846 | Y | 7659911 | 7660191 |
| Y | 749271 | 749351 | Y | 7660931 | 7661308 |
| Y | 751790 | 753365 | Y | 7662818 | 7663200 |
| Y | 755274 | 755354 | Y | 7665482 | 7666887 |
| Y | 756100 | 760239 | Y | 7668716 | 7668861 |
| Y | 762203 | 766533 | Y | 7669288 | 7669513 |
| Y | 771002 | 771642 | Y | 7669633 | 7669708 |
| Y | 772167 | 772677 | Y | 7669958 | 7670686 |
| Y | 773452 | 773612 | Y | 7671056 | 7672887 |
| Y | 773787 | 775077 | Y | 7678435 | 7678480 |
| Y | 777172 | 777522 | Y | 7679185 | 7680212 |
| Y | 781347 | 781447 | Y | 7680317 | 7681157 |
| Y | 783021 | 783811 | Y | 7683995 | 7684195 |
| Y | 789115 | 789777 | Y | 7685015 | 7685475 |
| Y | 790602 | 790807 | Y | 7690509 | 7692276 |
| Y | 792318 | 793864 | Y | 7694156 | 7694221 |
| Y | 794274 | 795484 | Y | 7694721 | 7694981 |
| Y | 796584 | 801499 | Y | 7696116 | 7696511 |
| Y | 805523 | 805563 | Y | 7697451 | 7697901 |
| Y | 808683 | 809153 | Y | 7698326 | 7698486 |
| Y | 811903 | 813968 | Y | 7699562 | 7700062 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 817653 | 819248 | Y | 7701704 | 7701974 |
| Y | 821593 | 822043 | Y | 7702104 | 7702264 |
| Y | 825001 | 825171 | Y | 7703374 | 7703650 |
| Y | 826971 | 827346 | Y | 7704693 | 7704798 |
| Y | 828611 | 828696 | Y | 7705830 | 7708234 |
| Y | 830132 | 832957 | Y | 7708304 | 7708349 |
| Y | 833592 | 843691 | Y | 7708424 | 7708534 |
| Y | 847379 | 847916 | Y | 7709602 | 7709737 |
| Y | 849607 | 849972 | Y | 7711599 | 7711729 |
| Y | 851061 | 853091 | Y | 7712894 | 7713164 |
| Y | 856469 | 856727 | Y | 7715962 | 7716607 |
| Y | 858407 | 859427 | Y | 7717927 | 7718237 |
| Y | 860467 | 860735 | Y | 7719328 | 7719458 |
| Y | 862555 | 862775 | Y | 7720578 | 7720833 |
| Y | 863364 | 864064 | Y | 7722258 | 7723143 |
| Y | 869979 | 870324 | Y | 7724058 | 7725692 |
| Y | 874735 | 875060 | Y | 7726312 | 7726527 |
| Y | 878210 | 878740 | Y | 7726852 | 7727103 |
| Y | 882048 | 884023 | Y | 7728033 | 7728053 |
| Y | 889670 | 890975 | Y | 7728463 | 7728593 |
| Y | 892556 | 893631 | Y | 7728663 | 7728973 |
| Y | 904627 | 904937 | Y | 7729779 | 7730089 |
| Y | 907206 | 907442 | Y | 7732137 | 7732272 |
| Y | 909097 | 909372 | Y | 7732817 | 7732957 |
| Y | 912999 | 913279 | Y | 7734582 | 7734762 |
| Y | 915758 | 918043 | Y | 7736322 | 7736452 |
| Y | 916426 | 916446 | Y | 7737022 | 7737107 |
| Y | 919025 | 919125 | Y | 7737577 | 7738232 |
| Y | 922223 | 923283 | Y | 7739955 | 7740060 |
| Y | 924749 | 931583 | Y | 7740365 | 7740610 |
| Y | 932011 | 934756 | Y | 7740695 | 7740940 |
| Y | 935241 | 935843 | Y | 7741520 | 7742035 |
| Y | 938871 | 940460 | Y | 7742060 | 7742400 |
| Y | 943495 | 943610 | Y | 7742735 | 7744635 |
| Y | 949683 | 950353 | Y | 7744875 | 7744995 |
| Y | 955169 | 955214 | Y | 7745475 | 7745805 |
| Y | 1022565 | 1028514 | Y | 7746430 | 7746540 |
| Y | 1132082 | 1132208 | Y | 7746705 | 7746820 |
| Y | 1132738 | 1137135 | Y | 7746985 | 7747155 |
| Y | 1140362 | 1140437 | Y | 7747705 | 7747905 |
| Y | 1141057 | 1141867 | Y | 7748700 | 7748775 |
| Y | 1144560 | 1144950 | Y | 7749790 | 7750755 |
| Y | 1145875 | 1146530 | Y | 7751025 | 7751251 |
| Y | 1146765 | 1149640 | Y | 7751446 | 7751456 |
| Y | 1150315 | 1150690 | Y | 7751566 | 7751606 |
| Y | 1152421 | 1154546 | Y | 7752041 | 7752601 |
| Y | 1160272 | 1168155 | Y | 7753711 | 7754846 |
| Y | 1174318 | 1174373 | Y | 7755471 | 7755586 |
| Y | 1179076 | 1179635 | Y | 7756121 | 7756226 |
| Y | 1295029 | 1295184 | Y | 7756741 | 7756746 |
| Y | 1295914 | 1297379 | Y | 7757986 | 7758962 |
| Y | 1300254 | 1301004 | Y | 7761266 | 7761341 |
| Y | 1304070 | 1304490 | Y | 7762456 | 7763051 |
| Y | 1327505 | 1327722 | Y | 7765786 | 7765976 |
| Y | 1329504 | 1330589 | Y | 7766371 | 7767166 |

The chromosomal positon was obtained from UCSC genome browser (http://genome.ucsc.edu/) build 36.

APPENDIX E: Chromosome Y
Page 26 of 58

| Chr | Start | End | Chr | Start | End |
|---|---|---|---|---|---|
| Y | 1336414 | 1338692 | Y | 7773820 | 7776216 |
| Y | 1341917 | 1342732 | Y | 7778251 | 7779201 |
| Y | 1343747 | 1344237 | Y | 7781031 | 7785693 |
| Y | 1346588 | 1349613 | Y | 7786448 | 7786753 |
| Y | 1358627 | 1358637 | Y | 7787073 | 7787203 |
| Y | 1373262 | 1373312 | Y | 7788113 | 7789083 |
| Y | 1386399 | 1387334 | Y | 7790164 | 7790214 |
| Y | 1391460 | 1391605 | Y | 7790794 | 7790839 |
| Y | 1394788 | 1395803 | Y | 7791189 | 7791364 |
| Y | 1400571 | 1400706 | Y | 7792339 | 7792534 |
| Y | 1404586 | 1404781 | Y | 7794061 | 7794526 |
| Y | 1406799 | 1406864 | Y | 7796705 | 7796935 |
| Y | 1413797 | 1413982 | Y | 7797590 | 7797870 |
| Y | 1415705 | 1415730 | Y | 7798090 | 7798245 |
| Y | 1418745 | 1418955 | Y | 7798485 | 7798590 |
| Y | 1424166 | 1424907 | Y | 7798845 | 7799060 |
| Y | 1435109 | 1435224 | Y | 7799265 | 7799370 |
| Y | 1437587 | 1437737 | Y | 7800285 | 7800390 |
| Y | 1459802 | 1463230 | Y | 7800855 | 7800980 |
| Y | 1469897 | 1470372 | Y | 7801150 | 7801525 |
| Y | 1470908 | 1470953 | Y | 7801575 | 7801675 |
| Y | 1477527 | 1477922 | Y | 7802695 | 7803960 |
| Y | 1496302 | 1496652 | Y | 7804760 | 7804820 |
| Y | 1506198 | 1506323 | Y | 7804875 | 7805395 |
| Y | 1509249 | 1510334 | Y | 7805785 | 7805905 |
| Y | 1514021 | 1514316 | Y | 7806005 | 7806565 |
| Y | 1517208 | 1517338 | Y | 7807630 | 7807690 |
| Y | 1518348 | 1518803 | Y | 7807960 | 7808025 |
| Y | 1519712 | 1521422 | Y | 7809045 | 7809245 |
| Y | 1534144 | 1535821 | Y | 7809940 | 7810080 |
| Y | 1541844 | 1543224 | Y | 7810950 | 7811185 |
| Y | 1544549 | 1544724 | Y | 7812710 | 7813995 |
| Y | 1546145 | 1546280 | Y | 7818065 | 7818825 |
| Y | 1551098 | 1551213 | Y | 7820625 | 7820900 |
| Y | 1556696 | 1557876 | Y | 7822717 | 7825776 |
| Y | 1558261 | 1559056 | Y | 7827994 | 7829912 |
| Y | 1563815 | 1564780 | Y | 7831032 | 7831122 |
| Y | 1566103 | 1566503 | Y | 7831982 | 7832490 |
| Y | 1567954 | 1568514 | Y | 7832830 | 7836938 |
| Y | 1571029 | 1571664 | Y | 7837442 | 7839287 |
| Y | 1573355 | 1573528 | Y | 7840047 | 7844658 |
| Y | 1580232 | 1581789 | Y | 7845220 | 7845325 |
| Y | 1585213 | 1586344 | Y | 7845770 | 7845775 |
| Y | 1588979 | 1589069 | Y | 7846135 | 7846255 |
| Y | 1589294 | 1589419 | Y | 7846440 | 7846675 |
| Y | 1590650 | 1591105 | Y | 7846990 | 7847945 |
| Y | 1602146 | 1604491 | Y | 7849355 | 7849445 |
| Y | 1607271 | 1608071 | Y | 7849855 | 7849915 |
| Y | 1612100 | 1613244 | Y | 7850570 | 7850735 |
| Y | 1614054 | 1616754 | Y | 7851555 | 7851645 |
| Y | 1619771 | 1620026 | Y | 7852090 | 7852510 |
| Y | 1624491 | 1626481 | Y | 7852760 | 7853120 |
| Y | 1632649 | 1633437 | Y | 7853930 | 7854460 |
| Y | 1633567 | 1634482 | Y | 7854695 | 7854885 |
| Y | 1640686 | 1641141 | Y | 7857630 | 7857965 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 1641480 | 1641485 | Y | 7858130 | 7858275 |
| Y | 1643926 | 1644036 | Y | 7858625 | 7859065 |
| Y | 1645500 | 1646715 | Y | 7859260 | 7859380 |
| Y | 1649556 | 1650261 | Y | 7861130 | 7861190 |
| Y | 1652871 | 1652956 | Y | 7862860 | 7862930 |
| Y | 1655257 | 1655792 | Y | 7863465 | 7863525 |
| Y | 1657182 | 1657327 | Y | 7864045 | 7864135 |
| Y | 1661839 | 1662324 | Y | 7864875 | 7865380 |
| Y | 1668642 | 1668907 | Y | 7865480 | 7865530 |
| Y | 1669768 | 1670243 | Y | 7865860 | 7866810 |
| Y | 1672126 | 1673181 | Y | 7867735 | 7868105 |
| Y | 1675877 | 1676092 | Y | 7868831 | 7869296 |
| Y | 1679027 | 1679207 | Y | 7869946 | 7870161 |
| Y | 1680592 | 1680882 | Y | 7870211 | 7870291 |
| Y | 1687476 | 1687651 | Y | 7871096 | 7871536 |
| Y | 1708710 | 1708900 | Y | 7871756 | 7871821 |
| Y | 1716266 | 1722406 | Y | 7871841 | 7871913 |
| Y | 1723081 | 1723456 | Y | 7872308 | 7872328 |
| Y | 1723671 | 1724251 | Y | 7872703 | 7872758 |
| Y | 1726458 | 1729292 | Y | 7873758 | 7874163 |
| Y | 1736281 | 1736576 | Y | 7874613 | 7874758 |
| Y | 1740531 | 1740951 | Y | 7875097 | 7875201 |
| Y | 1742648 | 1742733 | Y | 7876566 | 7876686 |
| Y | 1743599 | 1744622 | Y | 7877311 | 7877486 |
| Y | 1748183 | 1749113 | Y | 7878296 | 7878456 |
| Y | 1753601 | 1755371 | Y | 7878591 | 7878681 |
| Y | 1757541 | 1759709 | Y | 7879181 | 7879516 |
| Y | 1764330 | 1764570 | Y | 7879611 | 7879651 |
| Y | 1765666 | 1766926 | Y | 7879916 | 7880001 |
| Y | 1770240 | 1770380 | Y | 7881586 | 7885520 |
| Y | 1775564 | 1778789 | Y | 7886210 | 7886425 |
| Y | 1779688 | 1781781 | Y | 7886827 | 7886932 |
| Y | 1782046 | 1789944 | Y | 7887527 | 7887772 |
| Y | 1792339 | 1793154 | Y | 7890232 | 7891857 |
| Y | 1795276 | 1796031 | Y | 7892858 | 7893358 |
| Y | 1798121 | 1799636 | Y | 7893433 | 7893608 |
| Y | 1802041 | 1803231 | Y | 7894153 | 7895143 |
| Y | 1806555 | 1806755 | Y | 7895518 | 7895763 |
| Y | 1808715 | 1811556 | Y | 7895868 | 7895948 |
| Y | 1813249 | 1813831 | Y | 7896188 | 7896193 |
| Y | 1824542 | 1826298 | Y | 7896388 | 7896548 |
| Y | 1828553 | 1828748 | Y | 7897358 | 7897548 |
| Y | 1830058 | 1831546 | Y | 7898188 | 7898338 |
| Y | 1833709 | 1833887 | Y | 7899933 | 7900043 |
| Y | 1834242 | 1834372 | Y | 7900403 | 7900423 |
| Y | 1834652 | 1836975 | Y | 7900483 | 7900568 |
| Y | 1842481 | 1844261 | Y | 7902453 | 7902933 |
| Y | 1845767 | 1845922 | Y | 7903213 | 7903338 |
| Y | 1850115 | 1850510 | Y | 7905968 | 7906033 |
| Y | 1850873 | 1851951 | Y | 7906493 | 7906698 |
| Y | 1853541 | 1855292 | Y | 7907063 | 7907103 |
| Y | 1856081 | 1857846 | Y | 7907523 | 7907698 |
| Y | 1858916 | 1858971 | Y | 7908398 | 7910109 |
| Y | 1860463 | 1861108 | Y | 7912622 | 7914708 |
| Y | 1861933 | 1862023 | Y | 7916068 | 7917464 |

The chromosomal positon was obtained from UCSC genome browser (http://genome.ucsc.edu/) build 36.

APPENDIX E: Chromosome Y
Page 28 of 58

| Chr | Start | End | | | Chr | Start | End |
|---|---|---|---|---|---|---|---|
| Y | 1862678 | 1863318 | | | Y | 7917789 | 7919864 |
| Y | 1865558 | 1866158 | | | Y | 7923204 | 7924430 |
| Y | 1866558 | 1866893 | | | Y | 7926897 | 7929460 |
| Y | 1869019 | 1869039 | | | Y | 7930946 | 7930991 |
| Y | 1869829 | 1872051 | | | Y | 7933521 | 7934246 |
| Y | 1874786 | 1875591 | | | Y | 7935746 | 7936106 |
| Y | 1877127 | 1877277 | | | Y | 7940241 | 7940436 |
| Y | 1878132 | 1878945 | | | Y | 7940686 | 7940746 |
| Y | 1879756 | 1879931 | | | Y | 7940921 | 7941221 |
| Y | 1882396 | 1882631 | | | Y | 7941791 | 7942096 |
| Y | 1886693 | 1888368 | | | Y | 7942846 | 7942906 |
| Y | 1890318 | 1891323 | | | Y | 7943446 | 7943526 |
| Y | 1892760 | 1893016 | | | Y | 7943656 | 7944076 |
| Y | 1895335 | 1899675 | | | Y | 7946785 | 7946880 |
| Y | 1902450 | 1907915 | | | Y | 7947885 | 7948310 |
| Y | 1912493 | 1912773 | | | Y | 7948710 | 7948755 |
| Y | 1913802 | 1913892 | | | Y | 7949325 | 7949470 |
| Y | 1918596 | 1918791 | | | Y | 7949635 | 7949715 |
| Y | 1931693 | 1931923 | | | Y | 7950225 | 7950750 |
| Y | 1935236 | 1935969 | | | Y | 7951165 | 7951285 |
| Y | 1938187 | 1938302 | | | Y | 7952275 | 7952470 |
| Y | 1939967 | 1940477 | | | Y | 7953490 | 7954545 |
| Y | 1942399 | 1942634 | | | Y | 7959681 | 7959841 |
| Y | 1947107 | 1947457 | | | Y | 7960361 | 7960436 |
| Y | 1948525 | 1948810 | | | Y | 7960726 | 7961301 |
| Y | 1953173 | 1953548 | | | Y | 7961671 | 7961876 |
| Y | 1956685 | 1956950 | | | Y | 7961981 | 7962151 |
| Y | 1961627 | 1961872 | | | Y | 7962536 | 7962687 |
| Y | 1962696 | 1962841 | | | Y | 7962777 | 7962937 |
| Y | 1963751 | 1964102 | | | Y | 7963252 | 7963387 |
| Y | 1965912 | 1967422 | | | Y | 7963427 | 7963947 |
| Y | 1969112 | 1969602 | | | Y | 7965402 | 7965617 |
| Y | 1972392 | 1972752 | | | Y | 7965802 | 7966577 |
| Y | 1973842 | 1974342 | | | Y | 7967677 | 7967832 |
| Y | 1976107 | 1976227 | | | Y | 7968232 | 7968327 |
| Y | 1976547 | 1977320 | | | Y | 7968957 | 7969342 |
| Y | 1981849 | 1983244 | | | Y | 7969942 | 7970217 |
| Y | 1984505 | 1985000 | | | Y | 7970692 | 7971437 |
| Y | 1991834 | 1993476 | | | Y | 7971923 | 7972103 |
| Y | 1993886 | 1994136 | | | Y | 7972888 | 7973698 |
| Y | 1999031 | 2000472 | | | Y | 7974413 | 7975138 |
| Y | 2005390 | 2005535 | | | Y | 7976393 | 7976723 |
| Y | 2011492 | 2011717 | | | Y | 7976848 | 7978916 |
| Y | 2014242 | 2014337 | | | Y | 7979406 | 7979556 |
| Y | 2019562 | 2020302 | | | Y | 7979936 | 7980216 |
| Y | 2021347 | 2021498 | | | Y | 7981636 | 7985900 |
| Y | 2026325 | 2026470 | | | Y | 7986280 | 7986335 |
| Y | 2027545 | 2027971 | | | Y | 7986470 | 7986700 |
| Y | 2147287 | 2147417 | | | Y | 7986790 | 7986985 |
| Y | 2151894 | 2152679 | | | Y | 7987350 | 7987615 |
| Y | 2161010 | 2161185 | | | Y | 7987925 | 7988355 |
| Y | 2161355 | 2161650 | | | Y | 7990295 | 7990705 |
| Y | 2179540 | 2180550 | | | Y | 7990725 | 7991200 |
| Y | 2182419 | 2182649 | | | Y | 7991830 | 7991860 |
| Y | 2186875 | 2187985 | | | Y | 7992040 | 7992125 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 2194741 | 2195161 | Y | 7992850 | 7992980 |
| Y | 2196353 | 2197518 | Y | 7993520 | 7993690 |
| Y | 2200691 | 2200741 | Y | 7993910 | 7994000 |
| Y | 2204215 | 2204295 | Y | 7994215 | 7994425 |
| Y | 2211835 | 2213145 | Y | 7994740 | 7994865 |
| Y | 2215050 | 2215290 | Y | 7995225 | 7995385 |
| Y | 2216580 | 2217070 | Y | 7995470 | 7996058 |
| Y | 2217640 | 2217680 | Y | 7996163 | 7996848 |
| Y | 2218660 | 2218980 | Y | 7997023 | 7997153 |
| Y | 2223944 | 2224249 | Y | 7997773 | 7998123 |
| Y | 2230114 | 2231354 | Y | 7998323 | 7998353 |
| Y | 2236079 | 2237584 | Y | 7999120 | 8000607 |
| Y | 2242044 | 2242823 | Y | 8000857 | 8001459 |
| Y | 2243651 | 2244228 | Y | 8002518 | 8004028 |
| Y | 2248695 | 2248985 | Y | 8004478 | 8004748 |
| Y | 2249710 | 2250816 | Y | 8005293 | 8005503 |
| Y | 2252306 | 2252506 | Y | 8006980 | 8007030 |
| Y | 2253280 | 2254025 | Y | 8008141 | 8008856 |
| Y | 2256955 | 2257235 | Y | 8009111 | 8009706 |
| Y | 2258888 | 2259093 | Y | 8010106 | 8011446 |
| Y | 2260698 | 2261475 | Y | 8012046 | 8012366 |
| Y | 2265262 | 2265437 | Y | 8012631 | 8012731 |
| Y | 2268707 | 2269022 | Y | 8013646 | 8013741 |
| Y | 2271717 | 2273032 | Y | 8013941 | 8014001 |
| Y | 2284530 | 2286786 | Y | 8014166 | 8014326 |
| Y | 2289558 | 2290018 | Y | 8014536 | 8014616 |
| Y | 2292775 | 2293025 | Y | 8015696 | 8015781 |
| Y | 2297339 | 2297459 | Y | 8016806 | 8016976 |
| Y | 2301684 | 2302029 | Y | 8018331 | 8018821 |
| Y | 2309766 | 2311675 | Y | 8020221 | 8021671 |
| Y | 2313284 | 2314824 | Y | 8023091 | 8023151 |
| Y | 2317035 | 2317435 | Y | 8023376 | 8023526 |
| Y | 2318626 | 2319185 | Y | 8024081 | 8024151 |
| Y | 2320302 | 2321322 | Y | 8030980 | 8032197 |
| Y | 2328778 | 2328973 | Y | 8033024 | 8033159 |
| Y | 2336947 | 2337167 | Y | 8033659 | 8038734 |
| Y | 2340438 | 2341770 | Y | 8039034 | 8039389 |
| Y | 2342020 | 2342545 | Y | 8041126 | 8041296 |
| Y | 2344545 | 2345498 | Y | 8042166 | 8047814 |
| Y | 2346558 | 2347013 | Y | 8048714 | 8048764 |
| Y | 2348876 | 2349101 | Y | 8049349 | 8049354 |
| Y | 2349821 | 2350256 | Y | 8050667 | 8051152 |
| Y | 2352696 | 2352736 | Y | 8052866 | 8053866 |
| Y | 2362882 | 2363057 | Y | 8054188 | 8054523 |
| Y | 2376431 | 2376766 | Y | 8055433 | 8055664 |
| Y | 2379395 | 2380080 | Y | 8057134 | 8057274 |
| Y | 2386622 | 2387693 | Y | 8057499 | 8057869 |
| Y | 2418415 | 2418580 | Y | 8058034 | 8058169 |
| Y | 2420905 | 2421455 | Y | 8058444 | 8061159 |
| Y | 2422540 | 2423500 | Y | 8062219 | 8062244 |
| Y | 2424736 | 2426284 | Y | 8069567 | 8069587 |
| Y | 2430029 | 2430249 | Y | 8070332 | 8070487 |
| Y | 2430824 | 2431204 | Y | 8070947 | 8070972 |
| Y | 2434728 | 2434818 | Y | 8073172 | 8074084 |
| Y | 2443366 | 2443941 | Y | 8075185 | 8075540 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 2445107 | 2445297 | Y | 8077258 | 8078523 |
| Y | 2453356 | 2454231 | Y | 8079055 | 8079200 |
| Y | 2454868 | 2455193 | Y | 8080115 | 8080397 |
| Y | 2456764 | 2456894 | Y | 8081292 | 8081387 |
| Y | 2461794 | 2464278 | Y | 8081817 | 8081997 |
| Y | 2465671 | 2466093 | Y | 8082312 | 8082352 |
| Y | 2469690 | 2471496 | Y | 8083032 | 8084467 |
| Y | 2474073 | 2474393 | Y | 8084727 | 8085376 |
| Y | 2476720 | 2476880 | Y | 8085736 | 8088181 |
| Y | 2477695 | 2478940 | Y | 8089011 | 8089276 |
| Y | 2480703 | 2480753 | Y | 8089921 | 8090558 |
| Y | 2484804 | 2485139 | Y | 8090793 | 8090823 |
| Y | 2485739 | 2485894 | Y | 8092576 | 8093036 |
| Y | 2487004 | 2487599 | Y | 8096700 | 8097126 |
| Y | 2488699 | 2488864 | Y | 8097809 | 8098184 |
| Y | 2496783 | 2499618 | Y | 8098534 | 8098674 |
| Y | 2503399 | 2504438 | Y | 8098894 | 8099544 |
| Y | 2506383 | 2506708 | Y | 8101197 | 8101447 |
| Y | 2507782 | 2508711 | Y | 8102572 | 8107058 |
| Y | 2509876 | 2511593 | Y | 8109598 | 8110119 |
| Y | 2514234 | 2515569 | Y | 8113794 | 8118170 |
| Y | 2517346 | 2517521 | Y | 8118870 | 8118920 |
| Y | 2518268 | 2518338 | Y | 8119285 | 8119648 |
| Y | 2521169 | 2521464 | Y | 8120278 | 8120949 |
| Y | 2524480 | 2524785 | Y | 8127675 | 8128090 |
| Y | 2526942 | 2527912 | Y | 8129180 | 8129655 |
| Y | 2529731 | 2531385 | Y | 8130591 | 8131321 |
| Y | 2532076 | 2532371 | Y | 8131611 | 8131776 |
| Y | 2533480 | 2533555 | Y | 8132626 | 8132796 |
| Y | 2534695 | 2534875 | Y | 8136500 | 8136795 |
| Y | 2537735 | 2537870 | Y | 8137140 | 8137335 |
| Y | 2539876 | 2541121 | Y | 8137840 | 8137895 |
| Y | 2543520 | 2546894 | Y | 8140650 | 8142754 |
| Y | 2547355 | 2547815 | Y | 8143634 | 8144156 |
| Y | 2548480 | 2554204 | Y | 8146524 | 8147210 |
| Y | 2554809 | 2554904 | Y | 8148209 | 8159007 |
| Y | 2556769 | 2562274 | Y | 8159457 | 8159692 |
| Y | 2563599 | 2563639 | Y | 8161293 | 8167748 |
| Y | 2564885 | 2565755 | Y | 8169238 | 8170348 |
| Y | 2566375 | 2567440 | Y | 8173318 | 8174474 |
| Y | 2573700 | 2573915 | Y | 8176096 | 8176291 |
| Y | 2574706 | 2574816 | Y | 8176811 | 8178885 |
| Y | 2577006 | 2577424 | Y | 8179703 | 8180468 |
| Y | 2583582 | 2583667 | Y | 8181203 | 8182178 |
| Y | 2584062 | 2584307 | Y | 8182903 | 8184313 |
| Y | 2585857 | 2586827 | Y | 8185225 | 8185395 |
| Y | 2587050 | 2587115 | Y | 8186672 | 8189643 |
| Y | 2597973 | 2598033 | Y | 8192161 | 8192296 |
| Y | 2598473 | 2599372 | Y | 8192946 | 8193336 |
| Y | 2599532 | 2600332 | Y | 8193636 | 8193836 |
| Y | 2606478 | 2607723 | Y | 8194061 | 8194121 |
| Y | 2607928 | 2607993 | Y | 8195113 | 8195298 |
| Y | 2613960 | 2614260 | Y | 8199426 | 8200101 |
| Y | 2615220 | 2615325 | Y | 8201830 | 8202260 |
| Y | 2615560 | 2615675 | Y | 8203920 | 8204735 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 2620328 | 2620463 | Y | 8207443 | 8208763 |
| Y | 2620813 | 2626179 | Y | 8209508 | 8209718 |
| Y | 2629469 | 2630743 | Y | 8210608 | 8210813 |
| Y | 2633142 | 2633332 | Y | 8212885 | 8213206 |
| Y | 2641831 | 2642852 | Y | 8214602 | 8214727 |
| Y | 2645552 | 2645897 | Y | 8214967 | 8215317 |
| Y | 2647125 | 2647305 | Y | 8215422 | 8219903 |
| Y | 2648983 | 2649989 | Y | 8220685 | 8220950 |
| Y | 2651032 | 2651897 | Y | 8221150 | 8223663 |
| Y | 2654527 | 2655217 | Y | 8224098 | 8225638 |
| Y | 2659834 | 2660186 | Y | 8225868 | 8226073 |
| Y | 2663234 | 2663629 | Y | 8228158 | 8231718 |
| Y | 2667431 | 2668228 | Y | 8232378 | 8233042 |
| Y | 2668598 | 2671296 | Y | 8233205 | 8233420 |
| Y | 2672466 | 2673201 | Y | 8240077 | 8240227 |
| Y | 2676316 | 2676930 | Y | 8240552 | 8240642 |
| Y | 2679470 | 2680985 | Y | 8241540 | 8241640 |
| Y | 2684779 | 2685104 | Y | 8242346 | 8242911 |
| Y | 2690212 | 2690337 | Y | 8244229 | 8244859 |
| Y | 2695823 | 2696408 | Y | 8245584 | 8245664 |
| Y | 2697587 | 2697722 | Y | 8245799 | 8246049 |
| Y | 2698132 | 2698137 | Y | 8246594 | 8246619 |
| Y | 2698167 | 2698367 | Y | 8247769 | 8247879 |
| Y | 2698832 | 2699572 | Y | 8249149 | 8249409 |
| Y | 2708416 | 2709888 | Y | 8251539 | 8252559 |
| Y | 2710228 | 2710698 | Y | 8253244 | 8253404 |
| Y | 2711508 | 2713735 | Y | 8253459 | 8253849 |
| Y | 2713960 | 2714566 | Y | 8255724 | 8255924 |
| Y | 2715016 | 2715036 | Y | 8256124 | 8256189 |
| Y | 2715256 | 2717122 | Y | 8256349 | 8256979 |
| Y | 2717552 | 2717737 | Y | 8258099 | 8258604 |
| Y | 2719192 | 2721174 | Y | 8259499 | 8259639 |
| Y | 2721804 | 2722207 | Y | 8260094 | 8260754 |
| Y | 2722897 | 2722922 | Y | 8261044 | 8261639 |
| Y | 2724013 | 2727793 | Y | 8262397 | 8262717 |
| Y | 2728586 | 2728671 | Y | 8263002 | 8263077 |
| Y | 2729241 | 2732586 | Y | 8263572 | 8264352 |
| Y | 2733322 | 2733452 | Y | 8264777 | 8265062 |
| Y | 2745992 | 2746217 | Y | 8265502 | 8265957 |
| Y | 2748261 | 2749103 | Y | 8266702 | 8267517 |
| Y | 2753101 | 2754179 | Y | 8268352 | 8268427 |
| Y | 2757064 | 2762862 | Y | 8272053 | 8272173 |
| Y | 2763392 | 2764068 | Y | 8272618 | 8272733 |
| Y | 2764752 | 2765219 | Y | 8272888 | 8273278 |
| Y | 2766322 | 2766392 | Y | 8276724 | 8280107 |
| Y | 2768366 | 2770114 | Y | 8280277 | 8280362 |
| Y | 2770759 | 2771319 | Y | 8282187 | 8282222 |
| Y | 2772054 | 2772284 | Y | 8282482 | 8283007 |
| Y | 2773095 | 2774269 | Y | 8283847 | 8283932 |
| Y | 2775659 | 2775944 | Y | 8284486 | 8284581 |
| Y | 2776624 | 2777880 | Y | 8285841 | 8286708 |
| Y | 2778785 | 2779284 | Y | 8287538 | 8288173 |
| Y | 2779634 | 2783699 | Y | 8288308 | 8288403 |
| Y | 2786286 | 2786591 | Y | 8289503 | 8289763 |
| Y | 2788826 | 2789051 | Y | 8290578 | 8290893 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 2789391 | 2789511 | Y | 8290988 | 8291133 |
| Y | 2790369 | 2790659 | Y | 8291583 | 8291906 |
| Y | 2790834 | 2790874 | Y | 8293417 | 8293812 |
| Y | 2792162 | 2792202 | Y | 8294577 | 8294722 |
| Y | 2792684 | 2793204 | Y | 8295217 | 8297598 |
| Y | 2793859 | 2794468 | Y | 8297933 | 8299428 |
| Y | 2794663 | 2795268 | Y | 8299928 | 8300453 |
| Y | 2797118 | 2798213 | Y | 8301278 | 8301458 |
| Y | 2799148 | 2799208 | Y | 8302758 | 8302913 |
| Y | 2800013 | 2801053 | Y | 8304643 | 8304758 |
| Y | 2802622 | 2803719 | Y | 8304913 | 8304933 |
| Y | 2803959 | 2804339 | Y | 8305003 | 8305053 |
| Y | 2805544 | 2806526 | Y | 8305723 | 8305728 |
| Y | 2808798 | 2809288 | Y | 8305853 | 8305973 |
| Y | 2810533 | 2811538 | Y | 8307248 | 8307443 |
| Y | 2816457 | 2816722 | Y | 8309228 | 8309673 |
| Y | 2817786 | 2817986 | Y | 8310158 | 8310273 |
| Y | 2819683 | 2821461 | Y | 8311108 | 8311388 |
| Y | 2822424 | 2823436 | Y | 8312023 | 8312068 |
| Y | 2823844 | 2824046 | Y | 8312313 | 8312463 |
| Y | 2824336 | 2824486 | Y | 8312968 | 8313053 |
| Y | 2824716 | 2831128 | Y | 8313198 | 8313253 |
| Y | 2835805 | 2836130 | Y | 8313453 | 8314223 |
| Y | 2837576 | 2837756 | Y | 8314618 | 8314833 |
| Y | 2839845 | 2840301 | Y | 8315033 | 8315283 |
| Y | 2840790 | 2844678 | Y | 8315568 | 8315618 |
| Y | 2845388 | 2845788 | Y | 8316891 | 8316976 |
| Y | 2852799 | 2853660 | Y | 8317151 | 8317216 |
| Y | 2853920 | 2853960 | Y | 8318536 | 8318701 |
| Y | 2854465 | 2854485 | Y | 8319836 | 8320226 |
| Y | 2855972 | 2856447 | Y | 8320531 | 8320616 |
| Y | 2857788 | 2857958 | Y | 8323591 | 8323711 |
| Y | 2860476 | 2861395 | Y | 8324411 | 8324426 |
| Y | 2863911 | 2864001 | Y | 8325016 | 8325306 |
| Y | 2864401 | 2865246 | Y | 8325471 | 8325531 |
| Y | 2865862 | 2865907 | Y | 8326216 | 8327589 |
| Y | 2866405 | 2867202 | Y | 8327714 | 8328049 |
| Y | 2867912 | 2871963 | Y | 8328319 | 8328457 |
| Y | 2872497 | 2872657 | Y | 8328752 | 8331198 |
| Y | 2873149 | 2873259 | Y | 8331518 | 8331828 |
| Y | 2873995 | 2874319 | Y | 8331863 | 8331915 |
| Y | 2875198 | 2876764 | Y | 8334766 | 8335406 |
| Y | 2878759 | 2878909 | Y | 8340420 | 8340455 |
| Y | 2879019 | 2879099 | Y | 8340770 | 8343710 |
| Y | 2884339 | 2884872 | Y | 8344246 | 8344336 |
| Y | 2885537 | 2885712 | Y | 8344481 | 8344701 |
| Y | 2885967 | 2886067 | Y | 8344846 | 8345996 |
| Y | 2886860 | 2886865 | Y | 8346186 | 8346466 |
| Y | 2887451 | 2887556 | Y | 8346875 | 8350763 |
| Y | 2888558 | 2892208 | Y | 8352796 | 8352926 |
| Y | 2893113 | 2893879 | Y | 8354434 | 8354529 |
| Y | 2894229 | 2895212 | Y | 8357242 | 8357412 |
| Y | 2896193 | 2897289 | Y | 8358167 | 8359472 |
| Y | 2897679 | 2898136 | Y | 8359692 | 8359712 |
| Y | 2898756 | 2898941 | Y | 8360177 | 8360452 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 2899226 | 2899291 | Y | 8361052 | 8362542 |
| Y | 2899441 | 2899501 | Y | 8363412 | 8363832 |
| Y | 2900164 | 2901430 | Y | 8364217 | 8364428 |
| Y | 2903170 | 2906517 | Y | 8364893 | 8364993 |
| Y | 2908450 | 2910754 | Y | 8365463 | 8365953 |
| Y | 2911634 | 2911953 | Y | 8366278 | 8366403 |
| Y | 2915826 | 2915886 | Y | 8368033 | 8368183 |
| Y | 2919816 | 2920832 | Y | 8368318 | 8368888 |
| Y | 2920947 | 2921032 | Y | 8369633 | 8369758 |
| Y | 2921693 | 2922289 | Y | 8369973 | 8370693 |
| Y | 2923977 | 2925829 | Y | 8371138 | 8371213 |
| Y | 2927240 | 2927435 | Y | 8371683 | 8373687 |
| Y | 2928155 | 2928442 | Y | 8374592 | 8374772 |
| Y | 2929222 | 2929947 | Y | 8375187 | 8375407 |
| Y | 2930618 | 2932723 | Y | 8375612 | 8376412 |
| Y | 2932913 | 2933358 | Y | 8378267 | 8378557 |
| Y | 2933543 | 2933713 | Y | 8379287 | 8379402 |
| Y | 2934433 | 2934583 | Y | 8379742 | 8380612 |
| Y | 2934818 | 2934868 | Y | 8380832 | 8381017 |
| Y | 2935108 | 2935363 | Y | 8386930 | 8387395 |
| Y | 2935583 | 2935643 | Y | 8387845 | 8388910 |
| Y | 2935923 | 2936653 | Y | 8388950 | 8389190 |
| Y | 2938738 | 2939876 | Y | 8389450 | 8389490 |
| Y | 2940521 | 2940676 | Y | 8389835 | 8389935 |
| Y | 2942360 | 2942415 | Y | 8390075 | 8390150 |
| Y | 2943615 | 2943750 | Y | 8390580 | 8390720 |
| Y | 2943780 | 2943955 | Y | 8391120 | 8391170 |
| Y | 2949274 | 2949649 | Y | 8391526 | 8392087 |
| Y | 2949999 | 2950059 | Y | 8392382 | 8392502 |
| Y | 2950279 | 2950459 | Y | 8392782 | 8393142 |
| Y | 2950564 | 2950569 | Y | 8393382 | 8393427 |
| Y | 2951609 | 2952204 | Y | 8394862 | 8394937 |
| Y | 2953243 | 2962011 | Y | 8396497 | 8396737 |
| Y | 2962918 | 2964070 | Y | 8397192 | 8397982 |
| Y | 2965325 | 2966429 | Y | 8398337 | 8398557 |
| Y | 2967254 | 2967324 | Y | 8399132 | 8399267 |
| Y | 2968425 | 2968705 | Y | 8399822 | 8399962 |
| Y | 2972023 | 2973213 | Y | 8400652 | 8400977 |
| Y | 2973363 | 2973468 | Y | 8404557 | 8406337 |
| Y | 2974623 | 2976519 | Y | 8407112 | 8407263 |
| Y | 2982836 | 3134074 | Y | 8407953 | 8408513 |
| Y | 3134329 | 3134389 | Y | 8409478 | 8411798 |
| Y | 3134604 | 3134679 | Y | 8412848 | 8413203 |
| Y | 3134864 | 3158495 | Y | 8413628 | 8413688 |
| Y | 3173613 | 3213190 | Y | 8413868 | 8414143 |
| Y | 3219196 | 3219446 | Y | 8415562 | 8416657 |
| Y | 3219541 | 3219781 | Y | 8417227 | 8417617 |
| Y | 3220746 | 3305648 | Y | 8418087 | 8418172 |
| Y | 3311467 | 3322844 | Y | 8419472 | 8419742 |
| Y | 3333337 | 3334587 | Y | 8420112 | 8420187 |
| Y | 3340465 | 3417325 | Y | 8420567 | 8420587 |
| Y | 3425733 | 3450322 | Y | 8421737 | 8421902 |
| Y | 3453881 | 3453886 | Y | 8422353 | 8422713 |
| Y | 3455335 | 3455340 | Y | 8423703 | 8424513 |
| Y | 3459125 | 3462962 | Y | 8425188 | 8425568 |

The chromosomal positon was obtained from UCSC genome browser (http://genome.ucsc.edu/) build 36.

APPENDIX E: Chromosome Y

| Chr | Start | End | | Chr | Start | End |
|---|---|---|---|---|---|---|
| Y | 3465092 | 3540165 | | Y | 8426228 | 8426413 |
| Y | 3568144 | 3712660 | | Y | 8433817 | 8433967 |
| Y | 3724348 | 3735050 | | Y | 8434724 | 8437279 |
| Y | 3738501 | 3738696 | | Y | 8437544 | 8437639 |
| Y | 3739591 | 3765859 | | Y | 8439758 | 8441083 |
| Y | 3773125 | 3778126 | | Y | 8441493 | 8441878 |
| Y | 3778876 | 3778951 | | Y | 8442218 | 8442728 |
| Y | 3779666 | 3781140 | | Y | 8443193 | 8443448 |
| Y | 3781925 | 3781990 | | Y | 8444593 | 8444833 |
| Y | 3784790 | 3784940 | | Y | 8446713 | 8448793 |
| Y | 3790821 | 3793537 | | Y | 8451417 | 8457625 |
| Y | 3796203 | 3913567 | | Y | 8458155 | 8463951 |
| Y | 3934063 | 3935503 | | Y | 8464411 | 8464651 |
| Y | 3944459 | 4123766 | | Y | 8465071 | 8465426 |
| Y | 4131040 | 4133625 | | Y | 8466541 | 8466621 |
| Y | 4138815 | 4139555 | | Y | 8466816 | 8467091 |
| Y | 4139610 | 4139665 | | Y | 8467596 | 8470627 |
| Y | 4140870 | 4174613 | | Y | 8471347 | 8471917 |
| Y | 4171265 | 4171295 | | Y | 8472672 | 8476857 |
| Y | 4175988 | 4221799 | | Y | 8477357 | 8535182 |
| Y | 4226031 | 4367418 | | Y | 8536142 | 8538007 |
| Y | 4393805 | 4421238 | | Y | 8538392 | 8538882 |
| Y | 4428351 | 4429811 | | Y | 8540060 | 8540145 |
| Y | 4431396 | 4431626 | | Y | 8540570 | 8540605 |
| Y | 4463216 | 4511328 | | Y | 8540695 | 8540700 |
| Y | 4523280 | 4554984 | | Y | 8542016 | 8543181 |
| Y | 4578248 | 4729704 | | Y | 8543971 | 8552506 |
| Y | 4732386 | 4850901 | | Y | 8553261 | 8560719 |
| Y | 4886500 | 4926483 | | Y | 8560999 | 8561049 |
| Y | 4932814 | 4932869 | | Y | 8561324 | 8561854 |
| Y | 4934620 | 5096670 | | Y | 8562085 | 8566135 |
| Y | 5114975 | 5248943 | | Y | 8566635 | 8579177 |
| Y | 5264269 | 5270427 | | Y | 8581057 | 8585001 |
| Y | 5279778 | 5279788 | | Y | 8585626 | 8589869 |
| Y | 5283521 | 5418333 | | Y | 8590459 | 8611108 |
| Y | 5421640 | 5421730 | | Y | 8611508 | 8611548 |
| Y | 5422155 | 5422455 | | Y | 8611633 | 8616150 |
| Y | 5428493 | 5709619 | | Y | 8617355 | 8640354 |
| Y | 5710849 | 5720698 | | Y | 8640544 | 8640624 |
| Y | 5728979 | 5734352 | | Y | 8642913 | 8643324 |
| Y | 5747726 | 5815224 | | Y | 8644029 | 8645629 |
| Y | 5819245 | 5897976 | | Y | 8645909 | 8646029 |
| Y | 5902997 | 6046182 | | Y | 8646609 | 8647219 |
| Y | 6050456 | 6062525 | | Y | 8647914 | 8669238 |
| Y | 6065337 | 6122484 | | Y | 8670144 | 8703973 |
| Y | 6124599 | 6151273 | | Y | 8706565 | 8706765 |
| Y | 6155217 | 6162526 | | Y | 8707070 | 8707855 |
| Y | 6195189 | 6195549 | | Y | 8708270 | 8708335 |
| Y | 6410499 | 6411594 | | Y | 8708765 | 8709440 |
| Y | 6423354 | 6424635 | | Y | 8711257 | 8714779 |
| Y | 6427457 | 6430937 | | Y | 8716198 | 8716918 |
| Y | 6431882 | 6438541 | | Y | 8717473 | 8717698 |
| Y | 6446623 | 6457715 | | Y | 8717743 | 8723292 |
| Y | 6464073 | 6464503 | | Y | 8724647 | 8725472 |
| Y | 6465683 | 6477826 | | Y | 8727934 | 8728584 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 6484411 | 6485101 | | | Y | 8729009 | 8730094 |
| Y | 6485496 | 6514639 | | | Y | 8730729 | 8731004 |
| Y | 6515409 | 6515519 | | | Y | 8732269 | 8733029 |
| Y | 6518125 | 6649501 | | | Y | 8733679 | 8734219 |
| Y | 6653413 | 6654038 | | | Y | 8735584 | 8736249 |
| Y | 6654500 | 6679916 | | | Y | 8737149 | 8737214 |
| Y | 6680606 | 6680691 | | | Y | 8740596 | 8740721 |
| Y | 6686881 | 6686966 | | | Y | 8741151 | 8744106 |
| Y | 6687772 | 6687807 | | | Y | 8745416 | 8747656 |
| Y | 6688652 | 6688757 | | | Y | 8748512 | 8748812 |
| Y | 6688842 | 6688902 | | | Y | 8749845 | 8752139 |
| Y | 6690894 | 6691514 | | | Y | 8755004 | 8755444 |
| Y | 6692419 | 6693218 | | | Y | 8756624 | 8756714 |
| Y | 6693733 | 6693758 | | | Y | 8756999 | 8757169 |
| Y | 6695525 | 6696100 | | | Y | 8758424 | 8758464 |
| Y | 6703440 | 6703560 | | | Y | 8758624 | 8759881 |
| Y | 6704098 | 6704128 | | | Y | 8760261 | 8762527 |
| Y | 6704378 | 6709568 | | | Y | 8764712 | 8774084 |
| Y | 6713744 | 6714415 | | | Y | 8775665 | 8776031 |
| Y | 6716954 | 6717044 | | | Y | 8776177 | 8777866 |
| Y | 6717298 | 6717368 | | | Y | 8778638 | 8790758 |
| Y | 6718416 | 6719041 | | | Y | 8792684 | 8792779 |
| Y | 6719996 | 6720901 | | | Y | 8794917 | 8796612 |
| Y | 6721211 | 6721336 | | | Y | 8797757 | 8798047 |
| Y | 6721991 | 6734169 | | | Y | 8799506 | 8802928 |
| Y | 6735704 | 6737228 | | | Y | 8803748 | 8805890 |
| Y | 6737463 | 6737558 | | | Y | 8807040 | 8807835 |
| Y | 6737833 | 6737878 | | | Y | 8809255 | 8809520 |
| Y | 6738338 | 6738583 | | | Y | 8809780 | 8818558 |
| Y | 6739548 | 6739768 | | | Y | 8819753 | 8820353 |
| Y | 6740378 | 6740833 | | | Y | 8820901 | 8821006 |
| Y | 6747927 | 6754940 | | | Y | 8822626 | 8822986 |
| Y | 6755850 | 6755895 | | | Y | 8824131 | 8824506 |
| Y | 6756160 | 6756305 | | | Y | 8824933 | 8825458 |
| Y | 6758195 | 6758729 | | | Y | 8827903 | 8828253 |
| Y | 6759687 | 6759762 | | | Y | 8829119 | 8829974 |
| Y | 6760057 | 6760107 | | | Y | 8831124 | 8832404 |
| Y | 6760212 | 6760302 | | | Y | 8835369 | 8835895 |
| Y | 6763562 | 6763927 | | | Y | 8836310 | 8836335 |
| Y | 6764357 | 6764637 | | | Y | 8838261 | 8839946 |
| Y | 6766087 | 6766152 | | | Y | 8842422 | 8843146 |
| Y | 6766856 | 6767016 | | | Y | 8844176 | 8844872 |
| Y | 6768344 | 6774443 | | | Y | 8848388 | 8852116 |
| Y | 6774453 | 6774648 | | | Y | 8852376 | 8853346 |
| Y | 6775399 | 6776179 | | | Y | 8853796 | 8855411 |
| Y | 6776304 | 6776369 | | | Y | 8856256 | 8856421 |
| Y | 6776519 | 6777569 | | | Y | 8856496 | 8858705 |
| Y | 6778119 | 6778854 | | | Y | 8860685 | 8862630 |
| Y | 6780452 | 6788601 | | | Y | 8864764 | 8866071 |
| Y | 6790006 | 6790826 | | | Y | 8868811 | 8880920 |
| Y | 6791621 | 6791931 | | | Y | 8883058 | 8883563 |
| Y | 6793047 | 6795575 | | | Y | 8884036 | 8887499 |
| Y | 6796341 | 6797566 | | | Y | 8888049 | 8888514 |
| Y | 6798482 | 6798677 | | | Y | 8889158 | 8889298 |
| Y | 6799433 | 6799658 | | | Y | 8889423 | 8889518 |

The chromosomal positon was obtained from UCSC genome browser (http://genome.ucsc.edu/) build 36.

APPENDIX E: Chromosome Y
Page 36 of 58

| Chr | Start | End | Chr | Start | End |
|---|---|---|---|---|---|
| Y | 6801017 | 6804479 | Y | 8890394 | 8891375 |
| Y | 6805404 | 6805574 | Y | 8891970 | 8893625 |
| Y | 6806074 | 6806544 | Y | 8894492 | 8894692 |
| Y | 6808414 | 6812550 | Y | 8896060 | 8898020 |
| Y | 6813618 | 6814418 | Y | 8898365 | 8898565 |
| Y | 6814938 | 6815323 | Y | 8899145 | 8899540 |
| Y | 6816439 | 6817487 | Y | 8901310 | 8901370 |
| Y | 6818059 | 6818469 | Y | 8901880 | 8905377 |
| Y | 6818924 | 6818999 | Y | 8907845 | 8908001 |
| Y | 6820024 | 6820804 | Y | 8911311 | 8911776 |
| Y | 6821394 | 6821534 | Y | 8912751 | 8913286 |
| Y | 6822414 | 6822539 | Y | 8917344 | 8920499 |
| Y | 6824219 | 6824584 | Y | 8921034 | 8923074 |
| Y | 6825294 | 6825464 | Y | 8924404 | 8924854 |
| Y | 6826888 | 6826928 | Y | 8926440 | 8926565 |
| Y | 6827373 | 6827423 | Y | 8927590 | 8927630 |
| Y | 6831221 | 6831431 | Y | 8928435 | 8956243 |
| Y | 6833171 | 6833436 | Y | 8956558 | 8957984 |
| Y | 6836546 | 6836926 | Y | 8958659 | 8959094 |
| Y | 6838759 | 6838824 | Y | 8960739 | 8963818 |
| Y | 6839205 | 6839361 | Y | 8964906 | 8966461 |
| Y | 6841153 | 6841378 | Y | 8967951 | 8968021 |
| Y | 6842993 | 6843375 | Y | 8968351 | 8968416 |
| Y | 6843570 | 6843735 | Y | 8972409 | 8972724 |
| Y | 6847313 | 6847678 | Y | 8973959 | 8974419 |
| Y | 6847948 | 6848308 | Y | 9027222 | 9031056 |
| Y | 6849491 | 6849726 | Y | 9035596 | 9036318 |
| Y | 6853227 | 6853287 | Y | 9044993 | 9047498 |
| Y | 6853992 | 6855900 | Y | 9049828 | 9050288 |
| Y | 6858074 | 6858504 | Y | 9050508 | 9050773 |
| Y | 6859579 | 6859938 | Y | 9055590 | 9057479 |
| Y | 6860848 | 6860918 | Y | 9058469 | 9062182 |
| Y | 6861398 | 6864362 | Y | 9063996 | 9065201 |
| Y | 6865652 | 6866372 | Y | 9065716 | 9072382 |
| Y | 6868742 | 6868792 | Y | 9075722 | 9076117 |
| Y | 6868927 | 6869872 | Y | 9076702 | 9077894 |
| Y | 6870432 | 6870797 | Y | 9079654 | 9079734 |
| Y | 6871237 | 6871815 | Y | 9081046 | 9081346 |
| Y | 6872750 | 6873712 | Y | 9083558 | 9084711 |
| Y | 6875354 | 6878696 | Y | 9086065 | 9087829 |
| Y | 6888095 | 6890989 | Y | 9095821 | 9103024 |
| Y | 6893715 | 6893900 | Y | 9104821 | 9105256 |
| Y | 6895300 | 6895360 | Y | 9106381 | 9109512 |
| Y | 6896645 | 6897066 | Y | 9112412 | 9114262 |
| Y | 6897316 | 6897711 | Y | 9117957 | 9118977 |
| Y | 6898295 | 6898961 | Y | 9120117 | 9121077 |
| Y | 6899046 | 6899121 | Y | 9121178 | 9121303 |
| Y | 6899176 | 6899221 | Y | 9124528 | 9124973 |
| Y | 6899961 | 6900416 | Y | 9127823 | 9128373 |
| Y | 6901006 | 6902286 | Y | 9128613 | 9128703 |
| Y | 6903886 | 6905899 | Y | 9130819 | 9131569 |
| Y | 6906714 | 6906934 | Y | 9131964 | 9132394 |
| Y | 6908224 | 6908374 | Y | 9134418 | 9135512 |
| Y | 6909004 | 6909604 | Y | 9137557 | 9137602 |
| Y | 6911264 | 6911289 | Y | 9137852 | 9137887 |

The chromosomal positon was obtained from UCSC genome browser (http://genome.ucsc.edu/) build 36.

APPENDIX E: Chromosome Y
Page 37 of 58

| Chr | Start | End | | Chr | Start | End |
|---|---|---|---|---|---|---|
| Y | 6912649 | 6914609 | | Y | 9141627 | 9141877 |
| Y | 6915662 | 6916359 | | Y | 9144414 | 9145829 |
| Y | 6919219 | 6919919 | | Y | 9147305 | 9147962 |
| Y | 6920549 | 6920669 | | Y | 9148052 | 9148497 |
| Y | 6920929 | 6921372 | | Y | 9150086 | 9150096 |
| Y | 6921945 | 6922320 | | Y | 9150381 | 9151813 |
| Y | 6922917 | 6923552 | | Y | 9155451 | 9159381 |
| Y | 6924280 | 6924985 | | Y | 9160169 | 9171814 |
| Y | 6925799 | 6925969 | | Y | 9174605 | 9174620 |
| Y | 6926174 | 6926849 | | Y | 9176025 | 9195185 |
| Y | 6927374 | 6927464 | | Y | 9199055 | 9199300 |
| Y | 6927574 | 6928165 | | Y | 9199720 | 9200603 |
| Y | 6932758 | 6932778 | | Y | 9201998 | 9207953 |
| Y | 6933503 | 6933723 | | Y | 9208090 | 9208205 |
| Y | 6933753 | 6933908 | | Y | 9208645 | 9208900 |
| Y | 6934241 | 6935336 | | Y | 9209595 | 9217502 |
| Y | 6937271 | 6937386 | | Y | 9220941 | 9221259 |
| Y | 6939022 | 6939087 | | Y | 9222389 | 9224324 |
| Y | 6939747 | 6939982 | | Y | 9225019 | 9225609 |
| Y | 6940437 | 6940532 | | Y | 9228794 | 9230472 |
| Y | 6941102 | 6941627 | | Y | 9230971 | 9985373 |
| Y | 6941927 | 6942247 | | Y | 9986131 | 9986136 |
| Y | 6943351 | 6944446 | | Y | 9986261 | 9986276 |
| Y | 6945744 | 6945879 | | Y | 9986296 | 9988376 |
| Y | 6946074 | 6946449 | | Y | 9989997 | 9990007 |
| Y | 6946824 | 6946939 | | Y | 9991412 | 9993837 |
| Y | 6947139 | 6947769 | | Y | 9994032 | 9996527 |
| Y | 6949104 | 6949398 | | Y | 9996852 | 9999962 |
| Y | 6950214 | 6950585 | | Y | 10000905 | 10001150 |
| Y | 6951120 | 6951320 | | Y | 10002670 | 10005125 |
| Y | 6953363 | 6953568 | | Y | 10005500 | 10005645 |
| Y | 6953713 | 6953918 | | Y | 10006408 | 10006597 |
| Y | 6954268 | 6954333 | | Y | 10007182 | 10008669 |
| Y | 6956303 | 6957919 | | Y | 10009384 | 10010616 |
| Y | 6958719 | 6959144 | | Y | 10012015 | 10012130 |
| Y | 6959399 | 6959559 | | Y | 10013350 | 10014934 |
| Y | 6959884 | 6959989 | | Y | 10015976 | 10018272 |
| Y | 6964023 | 6965223 | | Y | 10025598 | 10026283 |
| Y | 6965913 | 6966058 | | Y | 10027674 | 10027989 |
| Y | 6966173 | 6967033 | | Y | 10028374 | 10028404 |
| Y | 6967643 | 6970393 | | Y | 10028609 | 10028810 |
| Y | 6971835 | 6972198 | | Y | 10029870 | 10033533 |
| Y | 6973048 | 6973173 | | Y | 10035068 | 10045706 |
| Y | 6973888 | 6973968 | | Y | 10046003 | 10046143 |
| Y | 6974240 | 6974340 | | Y | 10047999 | 10048664 |
| Y | 6974430 | 6978816 | | Y | 10049599 | 10050034 |
| Y | 6979617 | 6980293 | | Y | 10050819 | 10051588 |
| Y | 6981518 | 6981573 | | Y | 10052263 | 10053738 |
| Y | 6986974 | 6989391 | | Y | 10055529 | 10055888 |
| Y | 6992163 | 6994333 | | Y | 10057690 | 10058040 |
| Y | 6995613 | 6997238 | | Y | 10058330 | 10058430 |
| Y | 6998113 | 6998328 | | Y | 10059447 | 10059687 |
| Y | 7000816 | 7000931 | | Y | 10060740 | 10061060 |
| Y | 7001326 | 7001441 | | Y | 10061180 | 10061832 |
| Y | 7002256 | 7002554 | | Y | 10065227 | 10065317 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 7003424 | 7003499 | Y | 10065772 | 10067462 |
| Y | 7003829 | 7003889 | Y | 10070358 | 10070683 |
| Y | 7005027 | 7007227 | Y | 10070853 | 10072248 |
| Y | 7007497 | 7007607 | Y | 10073388 | 10075093 |
| Y | 7007662 | 7007697 | Y | 10075813 | 10076875 |
| Y | 7009057 | 7009222 | Y | 10094760 | 10094815 |
| Y | 7010062 | 7010472 | Y | 10094880 | 10094980 |
| Y | 7011698 | 7012003 | Y | 10095065 | 10105820 |
| Y | 7013602 | 7013697 | Y | 10113502 | 10114292 |
| Y | 7015402 | 7015467 | Y | 10122681 | 10131344 |
| Y | 7017219 | 7017374 | Y | 10131849 | 10133269 |
| Y | 7018714 | 7018784 | Y | 10250272 | 10258841 |
| Y | 7020290 | 7020570 | Y | 10355150 | 10367752 |
| Y | 7020765 | 7020825 | Y | 10368457 | 10373549 |
| Y | 7021085 | 7023516 | Y | 10374866 | 10380785 |
| Y | 7024681 | 7024856 | Y | 10381779 | 10382426 |
| Y | 7025061 | 7025181 | Y | 10385866 | 10386486 |
| Y | 7026521 | 7026786 | Y | 10388418 | 10388683 |
| Y | 7027209 | 7027279 | Y | 10395709 | 10396593 |
| Y | 7027582 | 7027642 | Y | 10399862 | 10400387 |
| Y | 7028372 | 7028492 | Y | 10404401 | 10405263 |
| Y | 7028912 | 7028957 | Y | 10405443 | 10405538 |
| Y | 7031422 | 7031512 | Y | 10406364 | 10406704 |
| Y | 7033070 | 7033730 | Y | 10406834 | 10406974 |
| Y | 7034835 | 7034895 | Y | 10407405 | 10407666 |
| Y | 7036673 | 7036793 | Y | 10408448 | 10416098 |
| Y | 7040867 | 7043314 | Y | 10419099 | 10419544 |
| Y | 7045664 | 7045759 | Y | 10421785 | 10423595 |
| Y | 7046194 | 7046299 | Y | 10423985 | 10423990 |
| Y | 7046969 | 7047997 | Y | 10424075 | 10424095 |
| Y | 7048152 | 7048567 | Y | 10424325 | 10424380 |
| Y | 7050368 | 7050413 | Y | 10425200 | 10427410 |
| Y | 7051523 | 7051718 | Y | 10427690 | 10427770 |
| Y | 7053120 | 7053565 | Y | 10429275 | 10429380 |
| Y | 7054535 | 7055415 | Y | 10431235 | 10432070 |
| Y | 7056550 | 7057644 | Y | 10432475 | 10433027 |
| Y | 7069048 | 7069148 | Y | 10434673 | 10435358 |
| Y | 7069677 | 7070324 | Y | 10436728 | 10438253 |
| Y | 7071645 | 7072040 | Y | 10439253 | 10439381 |
| Y | 7074466 | 7075281 | Y | 10441103 | 10441143 |
| Y | 7079896 | 7080356 | Y | 10443722 | 10443927 |
| Y | 7091807 | 7092162 | Y | 10445279 | 10445534 |
| Y | 7092886 | 7094042 | Y | 10446189 | 10447240 |
| Y | 7094758 | 7094893 | Y | 10447690 | 10448066 |
| Y | 7095483 | 7096742 | Y | 10450197 | 10451072 |
| Y | 7096937 | 7097097 | Y | 10452117 | 10452517 |
| Y | 7097517 | 7097752 | Y | 10454370 | 10454485 |
| Y | 7099797 | 7100287 | Y | 10454976 | 10455831 |
| Y | 7101382 | 7101837 | Y | 10456201 | 10456286 |
| Y | 7103292 | 7103833 | Y | 10458116 | 10462272 |
| Y | 7106455 | 7106640 | Y | 10463256 | 10463436 |
| Y | 7107275 | 7107560 | Y | 10464181 | 10468128 |
| Y | 7107765 | 7107775 | Y | 10469228 | 10469888 |
| Y | 7109305 | 7109390 | Y | 10471379 | 10471824 |
| Y | 7110020 | 7110297 | Y | 10474185 | 10474490 |

The chromosomal positon was obtained from UCSC genome browser (http://genome.ucsc.edu/) build 36.

APPENDIX E: Chromosome Y
Page 39 of 58

| Chr | Start | End | Chr | Start | End |
|---|---|---|---|---|---|
| Y | 7110982 | 7111002 | Y | 10476865 | 10476875 |
| Y | 7111147 | 7111517 | Y | 10479559 | 10479654 |
| Y | 7111867 | 7112097 | Y | 10479984 | 10480650 |
| Y | 7114881 | 7115096 | Y | 10480760 | 10480927 |
| Y | 7115801 | 7116890 | Y | 10482272 | 10482322 |
| Y | 7117150 | 7117245 | Y | 10482482 | 10482572 |
| Y | 7117375 | 7117435 | Y | 10482756 | 10484401 |
| Y | 7124835 | 7125615 | Y | 10485926 | 10486701 |
| Y | 7126725 | 7128893 | Y | 10489901 | 10492502 |
| Y | 7130158 | 7130848 | Y | 10492782 | 10493047 |
| Y | 7131168 | 7131243 | Y | 10493562 | 10495252 |
| Y | 7131353 | 7131903 | Y | 10496636 | 10497411 |
| Y | 7132773 | 7133028 | Y | 10503638 | 10504071 |
| Y | 7133988 | 7134778 | Y | 10504391 | 10504676 |
| Y | 7135443 | 7135513 | Y | 10504846 | 10505516 |
| Y | 7139959 | 7140029 | Y | 10506681 | 10508266 |
| Y | 7142311 | 7142341 | Y | 10510818 | 10511109 |
| Y | 7146997 | 7147767 | Y | 10511259 | 10511374 |
| Y | 7150381 | 7150906 | Y | 10511529 | 10511754 |
| Y | 7151626 | 7151666 | Y | 10512024 | 10512099 |
| Y | 7152683 | 7152898 | Y | 10512329 | 10515829 |
| Y | 7153733 | 7154578 | Y | 10515979 | 10516109 |
| Y | 7155495 | 7155859 | Y | 10516349 | 10517889 |
| Y | 7156535 | 7157814 | Y | 10520279 | 10535564 |
| Y | 7162308 | 7162343 | Y | 10535779 | 10535879 |
| Y | 7165606 | 7166691 | Y | 10537539 | 10538541 |
| Y | 7168554 | 7168839 | Y | 10542345 | 10545462 |
| Y | 7170122 | 7170157 | Y | 10546832 | 10547422 |
| Y | 7185384 | 7185409 | Y | 10548847 | 10549414 |
| Y | 7187224 | 7187249 | Y | 10549819 | 10553425 |
| Y | 7188511 | 7188936 | Y | 10554880 | 10557368 |
| Y | 7191559 | 7191699 | Y | 10560748 | 10564425 |
| Y | 7193219 | 7193561 | Y | 10564980 | 10570669 |
| Y | 7193696 | 7196120 | Y | 10572824 | 10573464 |
| Y | 7196215 | 7196590 | Y | 10574629 | 10575034 |
| Y | 7198944 | 7199468 | Y | 10578378 | 10588046 |
| Y | 7201229 | 7201539 | Y | 10589531 | 10590226 |
| Y | 7203362 | 7203787 | Y | 10591041 | 10591391 |
| Y | 7207212 | 7207982 | Y | 10592780 | 10594730 |
| Y | 7211260 | 7213660 | Y | 10595050 | 10595175 |
| Y | 7219387 | 7219667 | Y | 10595330 | 10595455 |
| Y | 7224892 | 7224972 | Y | 10597200 | 10598365 |
| Y | 7228207 | 7229017 | Y | 10598930 | 10599395 |
| Y | 7231563 | 7232948 | Y | 10604010 | 10605376 |
| Y | 7233048 | 7233473 | Y | 10605536 | 10605841 |
| Y | 7237282 | 7238327 | Y | 10606471 | 10607574 |
| Y | 7238522 | 7238767 | Y | 10614038 | 10614663 |
| Y | 7238817 | 7238927 | Y | 10615431 | 10615676 |
| Y | 7242364 | 7242739 | Y | 10615796 | 10616361 |
| Y | 7245733 | 7245893 | Y | 10620824 | 10621482 |
| Y | 7249462 | 7249527 | Y | 10635845 | 10637780 |
| Y | 7250222 | 7251775 | Y | 10638500 | 10638560 |
| Y | 7252080 | 7252325 | Y | 10638852 | 10639017 |
| Y | 7253125 | 7253430 | Y | 10639087 | 10639932 |
| Y | 7254060 | 7254105 | Y | 10645150 | 10645235 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 7258289 | 7258894 | | | Y | 10646695 | 10647050 |
| | | | | | Y | 10649249 | 10649509 |
| | | | | | Y | 10649854 | 11247088 |
| Y | 11658165 | 11665034 | | | Y | 16670514 | 16670937 |
| Y | 11665864 | 11666014 | | | Y | 16671232 | 16671537 |
| Y | 11668922 | 11673097 | | | Y | 16676411 | 16676631 |
| Y | 11675523 | 11678626 | | | Y | 16678406 | 16679445 |
| Y | 11680838 | 11681573 | | | Y | 16680500 | 16680695 |
| Y | 11689951 | 11691266 | | | Y | 16681986 | 16684142 |
| Y | 11693565 | 11694245 | | | Y | 16685962 | 16686812 |
| Y | 11697053 | 11699273 | | | Y | 16687952 | 16688287 |
| Y | 11711131 | 11720000 | | | Y | 16691007 | 16691767 |
| Y | 11764526 | 11770706 | | | Y | 16699535 | 16702480 |
| Y | 11816964 | 11820345 | | | Y | 16703276 | 16705325 |
| Y | 11830159 | 11833170 | | | Y | 16707718 | 16708369 |
| Y | 11860060 | 11860895 | | | Y | 16714891 | 16715096 |
| Y | 11868178 | 11883172 | | | Y | 16723859 | 16724494 |
| Y | 11894451 | 11905244 | | | Y | 16725445 | 16726070 |
| Y | 11919911 | 11922186 | | | Y | 16727225 | 16727475 |
| Y | 11924403 | 11930118 | | | Y | 16728960 | 16729260 |
| Y | 11931845 | 11936779 | | | Y | 16735420 | 16735690 |
| Y | 11939045 | 11952003 | | | Y | 16745236 | 16746492 |
| Y | 11955084 | 11965687 | | | Y | 16747237 | 16747927 |
| Y | 11969947 | 11972391 | | | Y | 16748902 | 16749187 |
| Y | 12012335 | 12014768 | | | Y | 16749867 | 16750282 |
| Y | 12024720 | 12026286 | | | Y | 16751252 | 16754102 |
| Y | 12031192 | 12046830 | | | Y | 16758619 | 16760062 |
| Y | 12062799 | 12063211 | | | Y | 16761411 | 16761566 |
| Y | 12073817 | 12075418 | | | Y | 16762281 | 16762489 |
| Y | 12089965 | 12094216 | | | Y | 16766962 | 16767362 |
| Y | 12097901 | 12101944 | | | Y | 16767672 | 16767917 |
| Y | 12313624 | 12313699 | | | Y | 16775159 | 16776689 |
| Y | 12381664 | 12383814 | | | Y | 16892797 | 16893147 |
| Y | 12411735 | 12413176 | | | Y | 16894986 | 16895406 |
| Y | 12417366 | 12424635 | | | Y | 16896781 | 16897411 |
| Y | 12431971 | 12434111 | | | Y | 16905051 | 16905656 |
| Y | 12439028 | 12441420 | | | Y | 16906256 | 16907928 |
| Y | 12446468 | 12447693 | | | Y | 16915151 | 16915441 |
| Y | 12451443 | 12469864 | | | Y | 16917785 | 16923136 |
| Y | 12483366 | 12485426 | | | Y | 16926806 | 16927814 |
| Y | 12497924 | 12499184 | | | Y | 16929674 | 16930251 |
| Y | 12500505 | 12501330 | | | Y | 16933520 | 16934290 |
| Y | 12508529 | 12510214 | | | Y | 16936164 | 16936639 |
| Y | 12513521 | 12514595 | | | Y | 17047819 | 17054809 |
| Y | 12526903 | 12528678 | | | Y | 17058052 | 17058157 |
| Y | 12531281 | 12531571 | | | Y | 17061308 | 17061529 |
| Y | 12533353 | 12534217 | | | Y | 17063024 | 17064774 |
| Y | 12534437 | 12534737 | | | Y | 17065519 | 17067282 |
| Y | 12536624 | 12536769 | | | Y | 17071974 | 17073183 |
| Y | 12538619 | 12539334 | | | Y | 17075107 | 17077873 |
| Y | 12540565 | 12540610 | | | Y | 17081526 | 17081891 |
| Y | 12542292 | 12543132 | | | Y | 17083151 | 17085391 |
| Y | 12545326 | 12545476 | | | Y | 17086416 | 17088177 |
| Y | 12546516 | 12547056 | | | Y | 17090252 | 17092674 |
| Y | 12548511 | 12548771 | | | Y | 17094285 | 17095678 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 12553422 | 12555152 | | | Y | 17103876 | 17104401 |
| Y | 12557022 | 12558643 | | | Y | 17105386 | 17106602 |
| Y | 12560957 | 12562552 | | | Y | 17109482 | 17111480 |
| Y | 12571857 | 12573334 | | | Y | 17111720 | 17112136 |
| Y | 12573884 | 12575729 | | | Y | 17115171 | 17117346 |
| Y | 12578168 | 12580693 | | | Y | 17119483 | 17119985 |
| Y | 12581849 | 12582744 | | | Y | 17122992 | 17124175 |
| Y | 12583999 | 12584224 | | | Y | 17125909 | 17126846 |
| Y | 12585384 | 12585579 | | | Y | 17129292 | 17129977 |
| Y | 12586385 | 12587082 | | | Y | 17144507 | 17145921 |
| Y | 12590593 | 12591178 | | | Y | 17149834 | 17151149 |
| Y | 12593903 | 12594843 | | | Y | 17152925 | 17153650 |
| Y | 12595138 | 12595528 | | | Y | 17155138 | 17156453 |
| Y | 12596298 | 12598686 | | | Y | 17158476 | 17158776 |
| Y | 12600176 | 12600581 | | | Y | 17164794 | 17170255 |
| Y | 12601346 | 12601996 | | | Y | 17173861 | 17175678 |
| Y | 12602301 | 12604413 | | | Y | 17179968 | 17180128 |
| Y | 12605798 | 12608131 | | | Y | 17184229 | 17184674 |
| Y | 12613426 | 12613671 | | | Y | 17186744 | 17189169 |
| Y | 12615764 | 12616949 | | | Y | 17189662 | 17190891 |
| Y | 12619081 | 12619251 | | | Y | 17193647 | 17193802 |
| Y | 12627207 | 12627442 | | | Y | 17195781 | 17196076 |
| Y | 12635681 | 12636331 | | | Y | 17196626 | 17199913 |
| Y | 12645719 | 12646699 | | | Y | 17200678 | 17200788 |
| Y | 12651411 | 12651796 | | | Y | 17202875 | 17203640 |
| Y | 12655549 | 12658070 | | | Y | 17204710 | 17204750 |
| Y | 12662175 | 12662720 | | | Y | 17210088 | 17213300 |
| Y | 12668303 | 12668498 | | | Y | 17213565 | 17214635 |
| Y | 12678711 | 12679479 | | | Y | 17215960 | 17216331 |
| Y | 12681514 | 12682748 | | | Y | 17220224 | 17221219 |
| Y | 12682768 | 12685314 | | | Y | 17222762 | 17224101 |
| Y | 12691826 | 12695016 | | | Y | 17225151 | 17225931 |
| Y | 12697469 | 12697694 | | | Y | 17228635 | 17228960 |
| Y | 12698869 | 12699059 | | | Y | 17229821 | 17230471 |
| Y | 12702223 | 12702363 | | | Y | 17233784 | 17233859 |
| Y | 12703288 | 12703528 | | | Y | 17235110 | 17236017 |
| Y | 12704158 | 12705578 | | | Y | 17240537 | 17241937 |
| Y | 12708560 | 12709255 | | | Y | 17245881 | 17248311 |
| Y | 12710305 | 12711575 | | | Y | 17248766 | 17250201 |
| Y | 12716771 | 12717709 | | | Y | 17252062 | 17252875 |
| Y | 12721678 | 12722733 | | | Y | 17256817 | 17257232 |
| Y | 12726752 | 12727232 | | | Y | 17259997 | 17264852 |
| Y | 12730248 | 12730333 | | | Y | 17267694 | 17267949 |
| Y | 12731845 | 12732220 | | | Y | 17271110 | 17271730 |
| Y | 12735223 | 12735768 | | | Y | 17274486 | 17275361 |
| Y | 12739443 | 12740578 | | | Y | 17281927 | 17282312 |
| Y | 12741538 | 12741793 | | | Y | 17283422 | 17283532 |
| Y | 12745020 | 12745125 | | | Y | 17284542 | 17285482 |
| Y | 12753058 | 12753538 | | | Y | 17291611 | 17292321 |
| Y | 12758022 | 12758678 | | | Y | 17296333 | 17296588 |
| Y | 12772645 | 12773085 | | | Y | 17297358 | 17298073 |
| Y | 12791669 | 12791789 | | | Y | 17298388 | 17299503 |
| Y | 12792029 | 12792764 | | | Y | 17300753 | 17301695 |
| Y | 12794224 | 12795943 | | | Y | 17302450 | 17302780 |
| Y | 12798115 | 12803390 | | | Y | 17303895 | 17304145 |

The chromosomal positon was obtained from UCSC genome browser (http://genome.ucsc.edu/) build 36.

APPENDIX E: Chromosome Y
Page 42 of 58

| Chr | Start | End | | | Chr | Start | End |
|---|---|---|---|---|---|---|---|
| Y | 12807501 | 12808976 | | | Y | 17311790 | 17312045 |
| Y | 12809467 | 12809732 | | | Y | 17316685 | 17317135 |
| Y | 12817856 | 12818997 | | | Y | 17318620 | 17318780 |
| Y | 12820978 | 12824017 | | | Y | 17321466 | 17322558 |
| Y | 12828908 | 12829018 | | | Y | 17329069 | 17329413 |
| Y | 12829793 | 12830478 | | | Y | 17329578 | 17330338 |
| Y | 12831488 | 12832328 | | | Y | 17330798 | 17331389 |
| Y | 12842836 | 12843126 | | | Y | 17332569 | 17332929 |
| Y | 12844387 | 12846607 | | | Y | 17333635 | 17333755 |
| Y | 12853337 | 12853986 | | | Y | 17334505 | 17334715 |
| Y | 12855477 | 12855702 | | | Y | 17336485 | 17336815 |
| Y | 12856382 | 12857017 | | | Y | 17340170 | 17341900 |
| Y | 12858841 | 12863090 | | | Y | 17345704 | 17346719 |
| Y | 12864825 | 12868761 | | | Y | 17349591 | 17350366 |
| Y | 12869498 | 12870458 | | | Y | 17350930 | 17351235 |
| Y | 12874301 | 12878244 | | | Y | 17359569 | 17360969 |
| Y | 12886263 | 12891511 | | | Y | 17368220 | 17371101 |
| Y | 12899489 | 12899724 | | | Y | 17375266 | 17376115 |
| Y | 12902440 | 12902635 | | | Y | 17377417 | 17377737 |
| Y | 12905107 | 12905362 | | | Y | 17391967 | 17392597 |
| Y | 12905652 | 12910438 | | | Y | 17393823 | 17394625 |
| Y | 12911273 | 12912148 | | | Y | 17399133 | 17399318 |
| Y | 12913414 | 12914109 | | | Y | 17402227 | 17402572 |
| Y | 12915914 | 12916820 | | | Y | 17404531 | 17404836 |
| Y | 12917892 | 12918538 | | | Y | 17406366 | 17408961 |
| Y | 12920601 | 12921256 | | | Y | 17418170 | 17418475 |
| Y | 12927981 | 12928352 | | | Y | 17418650 | 17419329 |
| Y | 12929567 | 12929947 | | | Y | 17422460 | 17425285 |
| Y | 12932927 | 12934052 | | | Y | 17428745 | 17430337 |
| Y | 12939468 | 12939783 | | | Y | 17442382 | 17443585 |
| Y | 12943972 | 12949059 | | | Y | 17451273 | 17452539 |
| Y | 12952319 | 12953134 | | | Y | 17453971 | 17456172 |
| Y | 12953699 | 12954729 | | | Y | 17457657 | 17458882 |
| Y | 12955829 | 12955969 | | | Y | 17469314 | 17469774 |
| Y | 12957355 | 12957815 | | | Y | 17471139 | 17471892 |
| Y | 12968264 | 12969438 | | | Y | 17473520 | 17474715 |
| Y | 12979045 | 12981242 | | | Y | 17486333 | 17486503 |
| Y | 12988683 | 12989393 | | | Y | 17489273 | 17489408 |
| Y | 12996168 | 12996548 | | | Y | 17491263 | 17491543 |
| Y | 12997493 | 12999130 | | | Y | 17492077 | 17492842 |
| Y | 13012897 | 13015017 | | | Y | 17494187 | 17494299 |
| Y | 13029968 | 13030333 | | | Y | 17496265 | 17498485 |
| Y | 13043974 | 13044304 | | | Y | 17504354 | 17504781 |
| Y | 13048293 | 13049213 | | | Y | 17505201 | 17505901 |
| Y | 13050148 | 13051209 | | | Y | 17509057 | 17509753 |
| Y | 13053623 | 13055460 | | | Y | 17511142 | 17512282 |
| Y | 13063202 | 13063617 | | | Y | 17513899 | 17514664 |
| Y | 13065017 | 13066547 | | | Y | 17520841 | 17521281 |
| Y | 13070837 | 13073102 | | | Y | 17529928 | 17530178 |
| Y | 13080061 | 13080221 | | | Y | 17532335 | 17533646 |
| Y | 13083681 | 13086802 | | | Y | 17544214 | 17545609 |
| Y | 13089440 | 13090040 | | | Y | 17547053 | 17548959 |
| Y | 13100966 | 13101541 | | | Y | 17555389 | 17555564 |
| Y | 13109596 | 13111551 | | | Y | 17566251 | 17566476 |
| Y | 13113059 | 13113799 | | | Y | 17577945 | 17579385 |

The chromosomal positon was obtained from UCSC genome browser (http://genome.ucsc.edu/) build 36.

APPENDIX E: Chromosome Y
Page 43 of 58

| Chr | Start | End | Chr | Start | End |
|---|---|---|---|---|---|
| Y | 13114274 | 13115088 | Y | 17585571 | 17585886 |
| Y | 13118848 | 13119358 | Y | 17586952 | 17588973 |
| Y | 13137632 | 13138280 | Y | 17595804 | 17596109 |
| Y | 13146539 | 13148449 | Y | 17599308 | 17599558 |
| Y | 13150331 | 13151526 | Y | 17601805 | 17602345 |
| Y | 13152568 | 13153496 | Y | 17602675 | 17602910 |
| Y | 13155274 | 13155911 | Y | 17603856 | 17604799 |
| Y | 13158026 | 13161789 | Y | 17605834 | 17606480 |
| Y | 13166644 | 13166834 | Y | 17614423 | 17614568 |
| Y | 13172708 | 13177055 | Y | 17617060 | 17618835 |
| Y | 13207399 | 13207921 | Y | 17624147 | 17624377 |
| Y | 13209630 | 13215116 | Y | 17624382 | 17624522 |
| Y | 13223719 | 13223827 | Y | 17627817 | 17628602 |
| Y | 13233102 | 13233452 | Y | 17629760 | 17631098 |
| Y | 13238505 | 13239042 | Y | 17639247 | 17639422 |
| Y | 13240729 | 13240819 | Y | 17643246 | 17643808 |
| Y | 13242664 | 13242789 | Y | 17644592 | 17645388 |
| Y | 13243970 | 13244085 | Y | 17645693 | 17646219 |
| Y | 13256645 | 13257292 | Y | 17649659 | 17649734 |
| Y | 13258386 | 13259041 | Y | 17662166 | 17662791 |
| Y | 13260844 | 13261934 | Y | 17673883 | 17674810 |
| Y | 13262534 | 13262624 | Y | 17681428 | 17689178 |
| Y | 13262999 | 13265635 | Y | 17690846 | 17692621 |
| Y | 13276837 | 13276977 | Y | 17693713 | 17696329 |
| Y | 13282496 | 13284889 | Y | 17697491 | 17698121 |
| Y | 13287136 | 13287572 | Y | 17701727 | 17702628 |
| Y | 13295235 | 13296655 | Y | 17703553 | 17704928 |
| Y | 13301138 | 13301719 | Y | 17705458 | 17706573 |
| Y | 13305181 | 13306110 | Y | 17709270 | 17709890 |
| Y | 13306776 | 13307757 | Y | 17709960 | 17710295 |
| Y | 13310993 | 13311123 | Y | 17711770 | 17712010 |
| Y | 13315654 | 13317968 | Y | 17712614 | 17714074 |
| Y | 13321197 | 13321882 | Y | 17716897 | 17717007 |
| Y | 13330603 | 13331494 | Y | 17722678 | 17724113 |
| Y | 13333773 | 13334960 | Y | 17726226 | 17726856 |
| Y | 13338777 | 13339137 | Y | 17730950 | 17731090 |
| Y | 13340382 | 13341047 | Y | 17733277 | 17733952 |
| Y | 13346817 | 13347867 | Y | 17734887 | 17736212 |
| Y | 13355815 | 13355985 | Y | 17737802 | 17738118 |
| Y | 13357340 | 13358055 | Y | 17739579 | 17739794 |
| Y | 13359140 | 13359633 | Y | 17743731 | 17744031 |
| Y | 13360235 | 13362211 | Y | 17744441 | 17748996 |
| Y | 13365658 | 13365763 | Y | 17751454 | 17751764 |
| Y | 13367172 | 13367437 | Y | 17753774 | 17754759 |
| Y | 13370341 | 13370631 | Y | 17755929 | 17756354 |
| Y | 13371757 | 13372042 | Y | 17757665 | 17760015 |
| Y | 13377343 | 13377728 | Y | 17768015 | 17770016 |
| Y | 13378538 | 13379408 | Y | 17770845 | 17772550 |
| Y | 13383787 | 13384862 | Y | 17773291 | 17774616 |
| Y | 13394993 | 13395223 | Y | 17775496 | 17775621 |
| Y | 13395907 | 13396382 | Y | 17783104 | 17786222 |
| Y | 13397830 | 13398648 | Y | 17786647 | 17787302 |
| Y | 13399750 | 13399957 | Y | 17788304 | 17788635 |
| Y | 13408237 | 13408472 | Y | 17790440 | 17790510 |
| Y | 13408767 | 13409047 | Y | 17791220 | 17792645 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 13409242 | 13409877 | Y | 17793590 | 17794460 |
| Y | 13411815 | 13412100 | Y | 17797420 | 17797752 |
| Y | 13415878 | 13416813 | Y | 17800692 | 17801007 |
| Y | 13420732 | 13420937 | Y | 17801481 | 17801826 |
| Y | 13424768 | 13426838 | Y | 17804632 | 17806529 |
| Y | 13429647 | 13429987 | Y | 17818679 | 17818754 |
| Y | 13433584 | 13434178 | Y | 17819179 | 17820831 |
| Y | 13437210 | 13437405 | Y | 17825668 | 17825928 |
| Y | 13438862 | 13439062 | Y | 17828290 | 17828635 |
| Y | 13442048 | 13442493 | Y | 17828805 | 17829580 |
| Y | 13445109 | 13445927 | Y | 17830629 | 17831139 |
| Y | 13449724 | 13449874 | Y | 17831724 | 17832651 |
| Y | 13456081 | 13456231 | Y | 17842109 | 17842349 |
| Y | 13460417 | 13461022 | Y | 17844414 | 17844704 |
| Y | 13461832 | 13464744 | Y | 17846084 | 17846234 |
| Y | 13465459 | 13465724 | Y | 17850454 | 17851439 |
| Y | 13466869 | 13468054 | Y | 17852454 | 17852649 |
| Y | 13476092 | 13476412 | Y | 17853687 | 17853922 |
| Y | 13481758 | 13482508 | Y | 17860049 | 17864898 |
| Y | 13488108 | 13488433 | Y | 17866405 | 17866620 |
| Y | 13490101 | 13492086 | Y | 17868660 | 17869615 |
| Y | 13493742 | 13494327 | Y | 17870225 | 17871171 |
| Y | 13496348 | 13497198 | Y | 17872256 | 17873101 |
| Y | 13501035 | 13502005 | Y | 17874236 | 17874546 |
| Y | 13504322 | 13504542 | Y | 17879422 | 17880468 |
| Y | 13505247 | 13505643 | Y | 17884513 | 17884653 |
| Y | 13506343 | 13507294 | Y | 17887254 | 17888424 |
| Y | 13508905 | 13509120 | Y | 17890186 | 17891297 |
| Y | 13513553 | 13516314 | Y | 17892302 | 17898377 |
| Y | 13516969 | 13519561 | Y | 17899686 | 17901652 |
| Y | 13522897 | 13523557 | Y | 17908182 | 17908674 |
| Y | 13525930 | 13527823 | Y | 17910490 | 17910686 |
| Y | 13530434 | 13530771 | Y | 17912360 | 17913015 |
| Y | 13533159 | 13534255 | Y | 17914600 | 17914900 |
| Y | 13537169 | 13537509 | Y | 17917722 | 17917927 |
| Y | 13543708 | 13544198 | Y | 17918898 | 17919028 |
| Y | 13544788 | 13544898 | Y | 17920653 | 17921098 |
| Y | 13546653 | 13549592 | Y | 17925571 | 17925866 |
| Y | 13552860 | 13553225 | Y | 17928510 | 17929410 |
| Y | 13556284 | 13556474 | Y | 17939134 | 17939344 |
| Y | 13558236 | 13560112 | Y | 17941158 | 17942080 |
| Y | 13562587 | 13564754 | Y | 17945409 | 17945764 |
| Y | 13567850 | 13568680 | Y | 17948605 | 17949175 |
| Y | 13571553 | 13573603 | Y | 17949770 | 17949995 |
| Y | 13574579 | 13576859 | Y | 17950125 | 17950625 |
| Y | 13577414 | 13579407 | Y | 17950740 | 17950975 |
| Y | 13580536 | 13582194 | Y | 17951490 | 17951730 |
| Y | 13586113 | 13586818 | Y | 17952010 | 17952175 |
| Y | 13587068 | 13587594 | Y | 17952890 | 17954767 |
| Y | 13588029 | 13589849 | Y | 17955171 | 17955486 |
| Y | 13595262 | 13595602 | Y | 17957782 | 17959677 |
| Y | 13597738 | 13598313 | Y | 17961292 | 17961698 |
| Y | 13600394 | 13601364 | Y | 17962773 | 17964158 |
| Y | 13603978 | 13604798 | Y | 17965173 | 17967951 |
| Y | 13605679 | 13606944 | Y | 17970091 | 17970861 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 13616392 | 13617236 | | | Y | 17973993 | 17975683 |
| Y | 13620262 | 13620477 | | | Y | 17975938 | 17978981 |
| Y | 13632619 | 13633266 | | | Y | 17980846 | 17981651 |
| Y | 13644402 | 13645177 | | | Y | 17983254 | 17984842 |
| Y | 13648539 | 13649490 | | | Y | 17991245 | 17991580 |
| Y | 13649890 | 13649905 | | | Y | 17992240 | 17992390 |
| Y | 13662913 | 13664368 | | | Y | 17999755 | 17999845 |
| Y | 13664993 | 13666952 | | | Y | 18003780 | 18004865 |
| Y | 13668938 | 13671045 | | | Y | 18008138 | 18009206 |
| Y | 13675144 | 13675359 | | | Y | 18011692 | 18014691 |
| Y | 13676374 | 13679109 | | | Y | 18017911 | 18023512 |
| Y | 13679929 | 13680589 | | | Y | 18024407 | 18024482 |
| Y | 13682007 | 13683365 | | | Y | 18033050 | 18033630 |
| Y | 13691416 | 13692471 | | | Y | 18036149 | 18037302 |
| Y | 13700596 | 13701533 | | | Y | 18038138 | 18039458 |
| Y | 13703515 | 13705045 | | | Y | 18043295 | 18045520 |
| Y | 13706602 | 13708936 | | | Y | 18045828 | 18046787 |
| Y | 13712673 | 13715001 | | | Y | 18054310 | 18054825 |
| Y | 13721588 | 13722013 | | | Y | 18055070 | 18056115 |
| Y | 13727330 | 13728968 | | | Y | 18057407 | 18057887 |
| Y | 13736254 | 13738219 | | | Y | 18072187 | 18072397 |
| Y | 13747611 | 13748371 | | | Y | 18073395 | 18074235 |
| Y | 13749466 | 13749642 | | | Y | 18075663 | 18075878 |
| Y | 13762591 | 13763422 | | | Y | 18076897 | 18077022 |
| Y | 13764989 | 13765499 | | | Y | 18572675 | 18574760 |
| Y | 13771189 | 13773024 | | | Y | 19261770 | 19263571 |
| Y | 13776508 | 13778504 | | | Y | 19264466 | 19264757 |
| Y | 13781471 | 13781901 | | | Y | 19270442 | 19270502 |
| Y | 13783726 | 13784324 | | | Y | 19271782 | 19272262 |
| Y | 13786382 | 13786881 | | | Y | 19273652 | 19274507 |
| Y | 13787572 | 13787737 | | | Y | 19278033 | 19278628 |
| Y | 13794841 | 13795586 | | | Y | 19280595 | 19283235 |
| Y | 13799149 | 13799994 | | | Y | 19285412 | 19285602 |
| Y | 13807075 | 13807160 | | | Y | 19286523 | 19291009 |
| Y | 13815420 | 13816628 | | | Y | 19293220 | 19293760 |
| Y | 13823617 | 13824134 | | | Y | 19296220 | 19296901 |
| Y | 13825587 | 13826262 | | | Y | 19299212 | 19299862 |
| Y | 13827187 | 13828647 | | | Y | 19494861 | 19495613 |
| Y | 13832227 | 13832647 | | | Y | 19500286 | 19500561 |
| Y | 13835901 | 13837616 | | | Y | 19504406 | 19507810 |
| Y | 13837906 | 13838126 | | | Y | 19509684 | 19509814 |
| Y | 13839559 | 13839745 | | | Y | 19512769 | 19521707 |
| Y | 13848525 | 13849561 | | | Y | 19522412 | 19522622 |
| Y | 13850859 | 13851389 | | | Y | 19524873 | 19526838 |
| Y | 13852382 | 13852717 | | | Y | 19531039 | 19535491 |
| Y | 13854278 | 13854653 | | | Y | 19544296 | 19544856 |
| Y | 13858761 | 13859571 | | | Y | 19554287 | 19556933 |
| Y | 13865596 | 13866196 | | | Y | 19557083 | 19557503 |
| Y | 13868516 | 13870769 | | | Y | 19561016 | 19561561 |
| Y | 13872226 | 13873128 | | | Y | 19563093 | 19563329 |
| Y | 13881065 | 13882125 | | | Y | 19573004 | 19573249 |
| Y | 13882725 | 13883026 | | | Y | 19573804 | 19573899 |
| Y | 13883571 | 13883761 | | | Y | 19588755 | 19589205 |
| Y | 13892989 | 13893663 | | | Y | 19591748 | 19592601 |
| Y | 13894220 | 13896777 | | | Y | 19597354 | 19597704 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 13905093 | 13905548 | Y | 19601089 | 19601174 |
| Y | 13907848 | 13908408 | Y | 19601409 | 19602401 |
| Y | 13917800 | 13918160 | Y | 19603625 | 19603810 |
| Y | 13925108 | 13925998 | Y | 19604310 | 19604595 |
| Y | 13929952 | 13931161 | Y | 19605385 | 19605575 |
| Y | 13931701 | 13932569 | Y | 19606395 | 19607084 |
| Y | 13936274 | 13936584 | Y | 19617050 | 19617190 |
| Y | 13939516 | 13942378 | Y | 19617770 | 19618210 |
| Y | 13943343 | 13944169 | Y | 19618590 | 19619538 |
| Y | 13948331 | 13950863 | Y | 19622230 | 19622580 |
| Y | 13955361 | 13956966 | Y | 19623940 | 19624035 |
| Y | 13957801 | 13958581 | Y | 19631719 | 19632496 |
| Y | 13961299 | 13961836 | Y | 19632894 | 19633134 |
| Y | 13962371 | 13963001 | Y | 19637903 | 19638729 |
| Y | 13964151 | 13964321 | Y | 19640488 | 19640918 |
| Y | 13965211 | 13966570 | Y | 19643046 | 19643595 |
| Y | 13967600 | 13967990 | Y | 19648043 | 19648183 |
| Y | 13969927 | 13970072 | Y | 19649702 | 19651016 |
| Y | 13970557 | 13970762 | Y | 19652617 | 19653644 |
| Y | 13972665 | 13972870 | Y | 19669689 | 19669904 |
| Y | 13976758 | 13977343 | Y | 19672814 | 19674079 |
| Y | 13981912 | 13982487 | Y | 19674524 | 19675177 |
| Y | 13991062 | 13991522 | Y | 19677036 | 19677696 |
| Y | 13996963 | 13997679 | Y | 19678546 | 19681098 |
| Y | 13997944 | 13998250 | Y | 19682436 | 19683676 |
| Y | 14011152 | 14012644 | Y | 19684742 | 19687401 |
| Y | 14015355 | 14015555 | Y | 19689709 | 19690621 |
| Y | 14018090 | 14019702 | Y | 19696727 | 19697428 |
| Y | 14027779 | 14031451 | Y | 19698549 | 19699084 |
| Y | 14037994 | 14038064 | Y | 19710163 | 19710408 |
| Y | 14038964 | 14040570 | Y | 19711989 | 19714720 |
| Y | 14041370 | 14041755 | Y | 19718921 | 19719116 |
| Y | 14042530 | 14043515 | Y | 19722383 | 19722822 |
| Y | 14044419 | 14045374 | Y | 19724926 | 19725276 |
| Y | 14046739 | 14046904 | Y | 19740800 | 19741840 |
| Y | 14049800 | 14050465 | Y | 19744799 | 19747049 |
| Y | 14053685 | 14054270 | Y | 19748681 | 19749201 |
| Y | 14056580 | 14059028 | Y | 19756476 | 19756761 |
| Y | 14059542 | 14061952 | Y | 19758231 | 19758336 |
| Y | 14062737 | 14062987 | Y | 19761038 | 19761613 |
| Y | 14064524 | 14065489 | Y | 19770503 | 19770778 |
| Y | 14071127 | 14071542 | Y | 19771153 | 19771353 |
| Y | 14072512 | 14073078 | Y | 19772233 | 19773603 |
| Y | 14091033 | 14091178 | Y | 19777521 | 19778677 |
| Y | 14097596 | 14098501 | Y | 19788953 | 19789871 |
| Y | 14099598 | 14101768 | Y | 19791332 | 19791487 |
| Y | 14102208 | 14102842 | Y | 19791897 | 19792287 |
| Y | 14109900 | 14112333 | Y | 19793013 | 19793475 |
| Y | 14112783 | 14113198 | Y | 19801585 | 19802065 |
| Y | 14114259 | 14114419 | Y | 19802485 | 19802775 |
| Y | 14116610 | 14116915 | Y | 19816670 | 19817292 |
| Y | 14119106 | 14120036 | Y | 19819966 | 19820281 |
| Y | 14123552 | 14124172 | Y | 19823040 | 19826467 |
| Y | 14125757 | 14126737 | Y | 19829234 | 19830174 |
| Y | 14128240 | 14130187 | Y | 19832258 | 19833054 |

The chromosomal positon was obtained from UCSC genome browser (http://genome.ucsc.edu/) build 36.

APPENDIX E: Chromosome Y
Page 47 of 58

| Chr | Start | End | | | Chr | Start | End |
|---|---|---|---|---|---|---|---|
| Y | 14131207 | 14131382 | | | Y | 19833699 | 19834279 |
| Y | 14133609 | 14134359 | | | Y | 19843915 | 19844860 |
| Y | 14141784 | 14141959 | | | Y | 19847134 | 19847854 |
| Y | 14143092 | 14144982 | | | Y | 19850294 | 19850444 |
| Y | 14151987 | 14153512 | | | Y | 19854957 | 19855162 |
| Y | 14157628 | 14158878 | | | Y | 19855911 | 19856406 |
| Y | 14160223 | 14161778 | | | Y | 19858256 | 19859712 |
| Y | 14165315 | 14165925 | | | Y | 19861087 | 19861795 |
| Y | 14173685 | 14174450 | | | Y | 19874884 | 19875464 |
| Y | 14175374 | 14175504 | | | Y | 19882489 | 19883004 |
| Y | 14177565 | 14177710 | | | Y | 19884532 | 19885209 |
| Y | 14178997 | 14187738 | | | Y | 19888450 | 19888905 |
| Y | 14188363 | 14188518 | | | Y | 19889285 | 19889690 |
| Y | 14190727 | 14191317 | | | Y | 19891509 | 19891884 |
| Y | 14193068 | 14193183 | | | Y | 19896460 | 19896940 |
| Y | 14200244 | 14200414 | | | Y | 19898782 | 19899827 |
| Y | 14201914 | 14202184 | | | Y | 19900623 | 19900743 |
| Y | 14203964 | 14204079 | | | Y | 19902728 | 19903634 |
| Y | 14210877 | 14210952 | | | Y | 19919305 | 19920030 |
| Y | 14214960 | 14215995 | | | Y | 19920320 | 19921168 |
| Y | 14216750 | 14217865 | | | Y | 19926006 | 19926201 |
| Y | 14218455 | 14218570 | | | Y | 19927008 | 19928218 |
| Y | 14220760 | 14222065 | | | Y | 19929151 | 19930101 |
| Y | 14223010 | 14224455 | | | Y | 19930791 | 19931919 |
| Y | 14225345 | 14225590 | | | Y | 19938249 | 19939110 |
| Y | 14225905 | 14226140 | | | Y | 19941010 | 19941285 |
| Y | 14227709 | 14228145 | | | Y | 19941750 | 19941965 |
| Y | 14228465 | 14229290 | | | Y | 19942994 | 19943339 |
| Y | 14229730 | 14230180 | | | Y | 19943819 | 19944044 |
| Y | 14232490 | 14233555 | | | Y | 19945430 | 19946045 |
| Y | 14234895 | 14235420 | | | Y | 19951389 | 19953615 |
| Y | 14237561 | 14238258 | | | Y | 19966320 | 19966590 |
| Y | 14245993 | 14246113 | | | Y | 19969221 | 19972691 |
| Y | 14247370 | 14248426 | | | Y | 19974285 | 19974952 |
| Y | 14256381 | 14257526 | | | Y | 19975829 | 19976189 |
| Y | 14262543 | 14264291 | | | Y | 19978249 | 19978534 |
| Y | 14266197 | 14267712 | | | Y | 19979109 | 19979359 |
| Y | 14273572 | 14275243 | | | Y | 19988541 | 19989856 |
| Y | 14279257 | 14280297 | | | Y | 19992067 | 19994431 |
| Y | 14283650 | 14283730 | | | Y | 20003673 | 20004498 |
| Y | 14286455 | 14287110 | | | Y | 20012016 | 20013756 |
| Y | 14288960 | 14289130 | | | Y | 20017009 | 20017464 |
| Y | 14292396 | 14292831 | | | Y | 20020399 | 20021242 |
| Y | 14294067 | 14294852 | | | Y | 20022703 | 20023431 |
| Y | 14297330 | 14298696 | | | Y | 20027269 | 20028999 |
| Y | 14311498 | 14312393 | | | Y | 20029750 | 20030153 |
| Y | 14319851 | 14321121 | | | Y | 20032393 | 20033822 |
| Y | 14322449 | 14322854 | | | Y | 20050858 | 20051144 |
| Y | 14323844 | 14324479 | | | Y | 20053264 | 20053469 |
| Y | 14325199 | 14326799 | | | Y | 20054509 | 20054959 |
| Y | 14329962 | 14330127 | | | Y | 20055704 | 20055979 |
| Y | 14337176 | 14337671 | | | Y | 20066490 | 20066925 |
| Y | 14338836 | 14339036 | | | Y | 20067958 | 20069629 |
| Y | 14339393 | 14339778 | | | Y | 20070784 | 20070954 |
| Y | 14342456 | 14343061 | | | Y | 20073678 | 20074008 |

The chromosomal positon was obtained from UCSC genome browser (http://genome.ucsc.edu/) build 36.

APPENDIX E: Chromosome Y

| Chr | Start | End | | Chr | Start | End |
|---|---|---|---|---|---|---|
| Y | 14352251 | 14352781 | | Y | 20078233 | 20078478 |
| Y | 14353527 | 14353702 | | Y | 20082006 | 20082470 |
| Y | 14356587 | 14357332 | | Y | 20083398 | 20083719 |
| Y | 14357782 | 14358242 | | Y | 20085230 | 20085720 |
| Y | 14359520 | 14360165 | | Y | 20087090 | 20096756 |
| Y | 14361179 | 14361684 | | Y | 20099585 | 20100610 |
| Y | 14369111 | 14369266 | | Y | 20103020 | 20105035 |
| Y | 14371056 | 14372251 | | Y | 20105715 | 20106345 |
| Y | 14374312 | 14374717 | | Y | 20112466 | 20113754 |
| Y | 14376131 | 14377381 | | Y | 20116703 | 20117458 |
| Y | 14380688 | 14382183 | | Y | 20118148 | 20118233 |
| Y | 14384090 | 14385175 | | Y | 20118848 | 20121276 |
| Y | 14387168 | 14388238 | | Y | 20123033 | 20123283 |
| Y | 14389688 | 14390033 | | Y | 20123938 | 20124423 |
| Y | 14409015 | 14410050 | | Y | 20125334 | 20127016 |
| Y | 14410535 | 14411059 | | Y | 20134999 | 20135384 |
| Y | 14419340 | 14419705 | | Y | 20141191 | 20142316 |
| Y | 14420165 | 14421315 | | Y | 20143981 | 20145031 |
| Y | 14422686 | 14423331 | | Y | 20147850 | 20149120 |
| Y | 14435780 | 14437065 | | Y | 20152239 | 20152439 |
| Y | 14439311 | 14439916 | | Y | 20153722 | 20154047 |
| Y | 14440111 | 14440771 | | Y | 20161048 | 20161243 |
| Y | 14447431 | 14448031 | | Y | 20162748 | 20164083 |
| Y | 14454021 | 14455786 | | Y | 20166623 | 20167418 |
| Y | 14458956 | 14460754 | | Y | 20170568 | 20171332 |
| Y | 14465525 | 14466085 | | Y | 20171637 | 20171817 |
| Y | 14474774 | 14475159 | | Y | 20172459 | 20172609 |
| Y | 14475894 | 14476744 | | Y | 20173369 | 20173776 |
| Y | 14477715 | 14477985 | | Y | 20174243 | 20174553 |
| Y | 14482643 | 14482918 | | Y | 20175872 | 20176962 |
| Y | 14483393 | 14483613 | | Y | 20178744 | 20180987 |
| Y | 14488368 | 14488803 | | Y | 20183412 | 20184483 |
| Y | 14489948 | 14490509 | | Y | 20188052 | 20188302 |
| Y | 14491264 | 14491982 | | Y | 20189182 | 20189812 |
| Y | 14498655 | 14498915 | | Y | 20192474 | 20192693 |
| Y | 14499225 | 14500281 | | Y | 20198557 | 20199067 |
| Y | 14501885 | 14502400 | | Y | 20200412 | 20201202 |
| Y | 14505320 | 14505830 | | Y | 20209053 | 20209573 |
| Y | 14508652 | 14508862 | | Y | 20210643 | 20211033 |
| Y | 14536972 | 14537657 | | Y | 20211243 | 20211698 |
| Y | 14540357 | 14541042 | | Y | 20212693 | 20213294 |
| Y | 14548579 | 14549273 | | Y | 20214189 | 20214579 |
| Y | 14565402 | 14566477 | | Y | 20214964 | 20215908 |
| Y | 14568766 | 14570396 | | Y | 20216468 | 20216953 |
| Y | 14580026 | 14582368 | | Y | 20221778 | 20222318 |
| Y | 14594149 | 14594414 | | Y | 20223618 | 20225126 |
| Y | 14596138 | 14597157 | | Y | 20225791 | 20226747 |
| Y | 14598625 | 14598870 | | Y | 20232283 | 20232601 |
| Y | 14603470 | 14605730 | | Y | 20235483 | 20238408 |
| Y | 14642338 | 14642448 | | Y | 20239543 | 20240188 |
| Y | 14643093 | 14643378 | | Y | 20240643 | 20240733 |
| Y | 14680534 | 14681589 | | Y | 20244383 | 20247392 |
| Y | 14682429 | 14682814 | | Y | 20251946 | 20252814 |
| Y | 14683104 | 14683244 | | Y | 20257875 | 20259129 |
| Y | 14684927 | 14685773 | | Y | 20260119 | 20260449 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 14687464 | 14688190 | | | Y | 20268465 | 20270205 |
| Y | 14688315 | 14688725 | | | Y | 20271240 | 20273254 |
| Y | 14689546 | 14690276 | | | Y | 20273314 | 20273784 |
| Y | 14692594 | 14692654 | | | Y | 20275448 | 20277093 |
| Y | 14693419 | 14694539 | | | Y | 20281595 | 20282200 |
| Y | 14694859 | 14695069 | | | Y | 20284620 | 20285020 |
| Y | 14699808 | 14702678 | | | Y | 20286895 | 20287574 |
| Y | 14704308 | 14704818 | | | Y | 20296306 | 20296811 |
| Y | 14707493 | 14708018 | | | Y | 20298081 | 20304632 |
| Y | 14708603 | 14709068 | | | Y | 20309863 | 20310578 |
| Y | 14710243 | 14710483 | | | Y | 20313713 | 20313999 |
| Y | 14710863 | 14710953 | | | Y | 20328130 | 20328415 |
| Y | 14711263 | 14711333 | | | Y | 20330330 | 20330555 |
| Y | 14712002 | 14712737 | | | Y | 20331225 | 20331685 |
| Y | 14713882 | 14714152 | | | Y | 20337061 | 20337651 |
| Y | 14714392 | 14715132 | | | Y | 20341025 | 20341521 |
| Y | 14720762 | 14720962 | | | Y | 20341876 | 20342146 |
| Y | 14722672 | 14722817 | | | Y | 20348047 | 20349379 |
| Y | 14726562 | 14727736 | | | Y | 20354296 | 20354631 |
| Y | 14730677 | 14730953 | | | Y | 20356711 | 20356906 |
| Y | 14734622 | 14736338 | | | Y | 20357427 | 20357967 |
| Y | 14736408 | 14737198 | | | Y | 20358427 | 20359014 |
| Y | 14745824 | 14746104 | | | Y | 20365337 | 20366298 |
| Y | 14762272 | 14762497 | | | Y | 20367280 | 20370122 |
| Y | 14762772 | 14762997 | | | Y | 20376070 | 20376550 |
| Y | 14763627 | 14763897 | | | Y | 20383024 | 20384325 |
| Y | 14765722 | 14765897 | | | Y | 20387751 | 20387871 |
| Y | 14768992 | 14769237 | | | Y | 20390166 | 20390647 |
| Y | 14770785 | 14771110 | | | Y | 20392401 | 20392766 |
| Y | 14772565 | 14772914 | | | Y | 20394812 | 20396657 |
| Y | 14773634 | 14776941 | | | Y | 20397255 | 20398305 |
| Y | 14777927 | 14778342 | | | Y | 20398755 | 20399977 |
| Y | 14782552 | 14782797 | | | Y | 20412856 | 20422877 |
| Y | 14783512 | 14784127 | | | Y | 20429325 | 20429700 |
| Y | 14787104 | 14788004 | | | Y | 20430262 | 20431363 |
| Y | 14790384 | 14790899 | | | Y | 20431918 | 20433308 |
| Y | 14792805 | 14793825 | | | Y | 20433748 | 20434128 |
| Y | 14795711 | 14798678 | | | Y | 20436283 | 20437173 |
| Y | 14802760 | 14802905 | | | Y | 20438198 | 20438772 |
| Y | 14805514 | 14806184 | | | Y | 20439975 | 20440590 |
| Y | 14809415 | 14809635 | | | Y | 20441180 | 20441670 |
| Y | 14815728 | 14816048 | | | Y | 20442315 | 20442410 |
| Y | 14823019 | 14825094 | | | Y | 20443056 | 20450238 |
| Y | 14833995 | 14835085 | | | Y | 20452543 | 20452943 |
| Y | 14837158 | 14837918 | | | Y | 20454203 | 20454958 |
| Y | 14838363 | 14838760 | | | Y | 20462038 | 20462293 |
| Y | 14839705 | 14841845 | | | Y | 20462857 | 20462982 |
| Y | 14842758 | 14843179 | | | Y | 20463702 | 20464012 |
| Y | 14843290 | 14843455 | | | Y | 20465033 | 20465108 |
| Y | 14843625 | 14843815 | | | Y | 20466758 | 20466928 |
| Y | 14844515 | 14844645 | | | Y | 20467508 | 20467908 |
| Y | 14848242 | 14849347 | | | Y | 20468288 | 20468798 |
| Y | 14858228 | 14858553 | | | Y | 20478429 | 20479084 |
| Y | 14861967 | 14866871 | | | Y | 20480795 | 20481527 |
| Y | 14867586 | 14867736 | | | Y | 20482002 | 20482550 |

The chromosomal positon was obtained from UCSC genome browser (http://genome.ucsc.edu/) build 36.

APPENDIX E: Chromosome Y

| Chr | Start | End | Chr | Start | End |
|---|---|---|---|---|---|
| Y | 14869741 | 14870331 | Y | 20483536 | 20484541 |
| Y | 14872729 | 14873639 | Y | 20484914 | 20485956 |
| Y | 14874809 | 14875429 | Y | 20488384 | 20488844 |
| Y | 14876685 | 14877155 | Y | 20490283 | 20493464 |
| Y | 14877926 | 14878806 | Y | 20495016 | 20498153 |
| Y | 14880811 | 14881066 | Y | 20499015 | 20499644 |
| Y | 14884211 | 14884656 | Y | 20500475 | 20501240 |
| Y | 14886600 | 14887090 | Y | 20501660 | 20502530 |
| Y | 14887570 | 14887900 | Y | 20503208 | 20503413 |
| Y | 14896168 | 14896593 | Y | 20506954 | 20510152 |
| Y | 14899292 | 14899407 | Y | 20512197 | 20514984 |
| Y | 14899627 | 14899972 | Y | 20517991 | 20518716 |
| Y | 14901742 | 14901972 | Y | 20521306 | 20521736 |
| Y | 14902293 | 14903429 | Y | 20522450 | 20526660 |
| Y | 14910737 | 14911430 | Y | 20530029 | 20530204 |
| Y | 14913675 | 14914535 | Y | 20530989 | 20533249 |
| Y | 14917566 | 14917936 | Y | 20535951 | 20536116 |
| Y | 14927853 | 14928218 | Y | 20537421 | 20540685 |
| Y | 14947654 | 14948364 | Y | 20547172 | 20547820 |
| Y | 14956303 | 14956658 | Y | 20549339 | 20550682 |
| Y | 14956993 | 14958083 | Y | 20552622 | 20552962 |
| Y | 14961614 | 14962099 | Y | 20554710 | 20559655 |
| Y | 14962764 | 14963524 | Y | 20560775 | 20566892 |
| Y | 14964214 | 14965464 | Y | 20567472 | 20568479 |
| Y | 14968741 | 14969316 | Y | 20568629 | 20569579 |
| Y | 14971646 | 14972006 | Y | 20570119 | 20571646 |
| Y | 14973491 | 14975056 | Y | 20575619 | 20576079 |
| Y | 14981505 | 14984344 | Y | 20578499 | 20579989 |
| Y | 14986368 | 14986758 | Y | 20580559 | 20581354 |
| Y | 14988670 | 14989135 | Y | 20583319 | 20584629 |
| Y | 14990709 | 14991182 | Y | 20585329 | 20586004 |
| Y | 15001144 | 15001894 | Y | 20587214 | 20590779 |
| Y | 15003474 | 15003564 | Y | 20595896 | 20596051 |
| Y | 15004249 | 15004944 | Y | 20600875 | 20601600 |
| Y | 15006624 | 15006799 | Y | 20604431 | 20604866 |
| Y | 15017134 | 15019068 | Y | 20607655 | 20609120 |
| Y | 15020913 | 15021483 | Y | 20616663 | 20616723 |
| Y | 15026308 | 15027074 | Y | 20617603 | 20619132 |
| Y | 15029097 | 15029217 | Y | 20622007 | 20623092 |
| Y | 15032866 | 15033637 | Y | 20639743 | 20640328 |
| Y | 15034422 | 15034597 | Y | 20642896 | 20643537 |
| Y | 15036206 | 15036679 | Y | 20646187 | 20646633 |
| Y | 15039019 | 15039079 | Y | 20647693 | 20647983 |
| Y | 15039799 | 15040693 | Y | 20648666 | 20651459 |
| Y | 15041827 | 15042137 | Y | 20667211 | 20671984 |
| Y | 15043397 | 15043697 | Y | 20672677 | 20673463 |
| Y | 15044397 | 15046784 | Y | 20676010 | 20922335 |
| Y | 15050864 | 15051119 | Y | 20922795 | 20922975 |
| Y | 15058351 | 15058671 | Y | 20923615 | 20929865 |
| Y | 15063659 | 15064279 | Y | 20931067 | 20931485 |
| Y | 15064489 | 15065359 | Y | 20932620 | 20938510 |
| Y | 15070382 | 15070837 | Y | 20945932 | 20948134 |
| Y | 15071642 | 15073256 | Y | 20959543 | 20962756 |
| Y | 15079922 | 15080462 | Y | 20965299 | 20966069 |
| Y | 15085094 | 15085364 | Y | 20966852 | 20968835 |

The chromosomal positon was obtained from UCSC genome browser (http://genome.ucsc.edu/) build 36.

APPENDIX E: Chromosome Y
Page 51 of 58

| Chr | Start | End | | | Chr | Start | End |
|---|---|---|---|---|---|---|---|
| Y | 15089426 | 15090201 | | | Y | 20969425 | 20969585 |
| Y | 15095045 | 15095325 | | | Y | 20970735 | 20971475 |
| Y | 15096789 | 15097259 | | | Y | 20976356 | 20977011 |
| Y | 15098719 | 15099104 | | | Y | 20979705 | 20980100 |
| Y | 15099304 | 15099434 | | | Y | 20981219 | 20981314 |
| Y | 15103287 | 15105262 | | | Y | 20985641 | 20990760 |
| Y | 15109870 | 15110030 | | | Y | 20991362 | 20992137 |
| Y | 15116499 | 15117724 | | | Y | 20993027 | 20993187 |
| Y | 15118669 | 15119467 | | | Y | 20994152 | 20994407 |
| Y | 15123684 | 15123819 | | | Y | 20994652 | 20995557 |
| Y | 15136051 | 15136186 | | | Y | 20997512 | 20997832 |
| Y | 15136841 | 15137623 | | | Y | 21004345 | 21004515 |
| Y | 15139976 | 15140386 | | | Y | 21005195 | 21006240 |
| Y | 15142345 | 15142670 | | | Y | 21007265 | 21012213 |
| Y | 15143315 | 15143405 | | | Y | 21014318 | 21015057 |
| Y | 15143720 | 15143880 | | | Y | 21017477 | 21017642 |
| Y | 15144125 | 15144410 | | | Y | 21018302 | 21018943 |
| Y | 15145095 | 15145315 | | | Y | 21019003 | 21021157 |
| Y | 15146458 | 15146610 | | | Y | 21022146 | 21022311 |
| Y | 15157088 | 15157878 | | | Y | 21022566 | 21022946 |
| Y | 15158299 | 15158834 | | | Y | 21026437 | 21027165 |
| Y | 15160684 | 15160799 | | | Y | 21034874 | 21035704 |
| Y | 15168385 | 15168705 | | | Y | 21036771 | 21040676 |
| Y | 15173186 | 15175341 | | | Y | 21042603 | 21043434 |
| Y | 15177855 | 15179390 | | | Y | 21043724 | 21044054 |
| Y | 15188307 | 15188462 | | | Y | 21048276 | 21048628 |
| Y | 15198161 | 15199981 | | | Y | 21054587 | 21057392 |
| Y | 15200526 | 15200686 | | | Y | 21058486 | 21059176 |
| Y | 15202755 | 15203105 | | | Y | 21061579 | 21062039 |
| Y | 15204396 | 15206046 | | | Y | 21063244 | 21063574 |
| Y | 15208774 | 15209129 | | | Y | 21064859 | 21065829 |
| Y | 15225354 | 15225814 | | | Y | 21067069 | 21070625 |
| Y | 15228169 | 15228614 | | | Y | 21071220 | 21071830 |
| Y | 15242570 | 15243700 | | | Y | 21072840 | 21073385 |
| Y | 15244150 | 15244822 | | | Y | 21081757 | 21083095 |
| Y | 15245067 | 15245684 | | | Y | 21089265 | 21089810 |
| Y | 15250737 | 15251767 | | | Y | 21092798 | 21094437 |
| Y | 15255993 | 15256463 | | | Y | 21109040 | 21110536 |
| Y | 15257582 | 15258264 | | | Y | 21112285 | 21112660 |
| Y | 15260985 | 15262490 | | | Y | 21113514 | 21115633 |
| Y | 15262781 | 15263006 | | | Y | 21117247 | 21117692 |
| Y | 15267179 | 15267914 | | | Y | 21118642 | 21119057 |
| Y | 15270843 | 15271728 | | | Y | 21125205 | 21125490 |
| Y | 15272378 | 15273634 | | | Y | 21127912 | 21128232 |
| Y | 15276818 | 15277283 | | | Y | 21129414 | 21129756 |
| Y | 15280190 | 15280440 | | | Y | 21132072 | 21132887 |
| Y | 15281535 | 15282210 | | | Y | 21133722 | 21134152 |
| Y | 15286636 | 15286956 | | | Y | 21135318 | 21135968 |
| Y | 15289453 | 15290503 | | | Y | 21138379 | 21140226 |
| Y | 15290708 | 15292420 | | | Y | 21141449 | 21141794 |
| Y | 15296362 | 15296697 | | | Y | 21142390 | 21142815 |
| Y | 15298462 | 15298876 | | | Y | 21145105 | 21145250 |
| Y | 15301030 | 15301270 | | | Y | 21146118 | 21147758 |
| Y | 15302775 | 15302870 | | | Y | 21150310 | 21150470 |
| Y | 15304657 | 15304897 | | | Y | 21151459 | 21152290 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 15305177 | 15305282 | | | Y | 21159001 | 21160137 |
| Y | 15307017 | 15307497 | | | Y | 21167152 | 21167622 |
| Y | 15311523 | 15311913 | | | Y | 21168022 | 21168547 |
| Y | 15315341 | 15315581 | | | Y | 21170616 | 21171246 |
| Y | 15316276 | 15317766 | | | Y | 21173300 | 21174115 |
| Y | 15322274 | 15322549 | | | Y | 21179161 | 21182811 |
| Y | 15326355 | 15326600 | | | Y | 21183887 | 21185915 |
| Y | 15327608 | 15328903 | | | Y | 21192388 | 21192774 |
| Y | 15330345 | 15331120 | | | Y | 21193759 | 21194339 |
| Y | 15331455 | 15331970 | | | Y | 21201223 | 21201688 |
| Y | 15332385 | 15332635 | | | Y | 21212374 | 21212839 |
| Y | 15333605 | 15333895 | | | Y | 21214045 | 21214339 |
| Y | 15337889 | 15342022 | | | Y | 21214994 | 21220537 |
| Y | 15342462 | 15343779 | | | Y | 21223467 | 21224935 |
| Y | 15348456 | 15348791 | | | Y | 21226158 | 21227158 |
| Y | 15351718 | 15351893 | | | Y | 21227643 | 21227778 |
| Y | 15355032 | 15355572 | | | Y | 21238077 | 21240775 |
| Y | 15360661 | 15360796 | | | Y | 21241495 | 21241951 |
| Y | 15362761 | 15364313 | | | Y | 21245346 | 21245781 |
| Y | 15365021 | 15365976 | | | Y | 21253581 | 21253721 |
| Y | 15367281 | 15369511 | | | Y | 21255858 | 21256268 |
| Y | 15373519 | 15374024 | | | Y | 21259405 | 21260077 |
| Y | 15375052 | 15376327 | | | Y | 21267941 | 21271506 |
| Y | 15380973 | 15381653 | | | Y | 21275057 | 21278735 |
| Y | 15383224 | 15383730 | | | Y | 21278820 | 21283197 |
| Y | 15384145 | 15384430 | | | Y | 21284105 | 21284521 |
| Y | 15385320 | 15385415 | | | Y | 21289170 | 21290240 |
| Y | 15385530 | 15385670 | | | Y | 21294730 | 21295556 |
| Y | 15386930 | 15388240 | | | Y | 21296702 | 21297723 |
| Y | 15389736 | 15389791 | | | Y | 21298255 | 21299290 |
| Y | 15396794 | 15397159 | | | Y | 21300045 | 21303425 |
| Y | 15397389 | 15398986 | | | Y | 21305894 | 21309444 |
| Y | 15399826 | 15400021 | | | Y | 21310529 | 21312255 |
| Y | 15408622 | 15408852 | | | Y | 21314175 | 21320381 |
| Y | 15409117 | 15409742 | | | Y | 21322396 | 21324123 |
| Y | 15412492 | 15413769 | | | Y | 21326671 | 21328031 |
| Y | 15418910 | 15419530 | | | Y | 21328456 | 21330433 |
| Y | 15421561 | 15422456 | | | Y | 21331948 | 21332374 |
| Y | 15423716 | 15424634 | | | Y | 21333019 | 21334139 |
| Y | 15427815 | 15428600 | | | Y | 21334459 | 21334722 |
| Y | 15436502 | 15437472 | | | Y | 21336174 | 21336804 |
| Y | 15449718 | 15449868 | | | Y | 21337749 | 21341245 |
| Y | 15459536 | 15460016 | | | Y | 21342790 | 21343290 |
| Y | 15463352 | 15463647 | | | Y | 21347374 | 21348641 |
| Y | 15466187 | 15467297 | | | Y | 21349431 | 21349736 |
| Y | 15467537 | 15468462 | | | Y | 21350238 | 21352449 |
| Y | 15470725 | 15471786 | | | Y | 21352687 | 21353054 |
| Y | 15472770 | 15474374 | | | Y | 21353834 | 21356174 |
| Y | 15475359 | 15475935 | | | Y | 21362252 | 21367644 |
| Y | 15476370 | 15476965 | | | Y | 21368419 | 21369984 |
| Y | 15477150 | 15477933 | | | Y | 21378062 | 21379252 |
| Y | 15478563 | 15478733 | | | Y | 21384855 | 21386420 |
| Y | 15491767 | 15492152 | | | Y | 21401081 | 21403515 |
| Y | 15495572 | 15496067 | | | Y | 21407862 | 21408575 |
| Y | 15499749 | 15501891 | | | Y | 21411958 | 21414901 |

The chromosomal positon was obtained from UCSC genome browser (http://genome.ucsc.edu/) build 36.

APPENDIX E: Chromosome Y
Page 53 of 58

| Chr | Start | End | | | Chr | Start | End |
|---|---|---|---|---|---|---|---|
| Y | 15514326 | 15514461 | | | Y | 21420810 | 21422120 |
| Y | 15516675 | 15517305 | | | Y | 21429605 | 21429995 |
| Y | 15518400 | 15518635 | | | Y | 21430685 | 21431690 |
| Y | 15519478 | 15519988 | | | Y | 21432827 | 21433112 |
| Y | 15521338 | 15522275 | | | Y | 21434859 | 21441353 |
| Y | 15523846 | 15525156 | | | Y | 21441673 | 21442433 |
| Y | 15527795 | 15528260 | | | Y | 21444223 | 21444573 |
| Y | 15529540 | 15530692 | | | Y | 21451541 | 21451862 |
| Y | 15530937 | 15531237 | | | Y | 21454063 | 21454358 |
| Y | 15539456 | 15539636 | | | Y | 21463340 | 21466818 |
| Y | 15549778 | 15550638 | | | Y | 21467278 | 21467778 |
| Y | 15551555 | 15553615 | | | Y | 21469773 | 21470028 |
| Y | 15558214 | 15558344 | | | Y | 21477243 | 21478045 |
| Y | 15559342 | 15559539 | | | Y | 21478305 | 21478655 |
| Y | 15561847 | 15562802 | | | Y | 21489146 | 21489956 |
| Y | 15563157 | 15564440 | | | Y | 21523240 | 21523500 |
| Y | 15583130 | 15584918 | | | Y | 21523920 | 21525145 |
| Y | 15585467 | 15585717 | | | Y | 21526850 | 21527441 |
| Y | 15586724 | 15588367 | | | Y | 21531348 | 21531468 |
| Y | 15589656 | 15591625 | | | Y | 21532328 | 21532558 |
| Y | 15595797 | 15596118 | | | Y | 21533009 | 21534489 |
| Y | 15597273 | 15598573 | | | Y | 21535004 | 21535364 |
| Y | 15599958 | 15600203 | | | Y | 21536184 | 21537580 |
| Y | 15602255 | 15602550 | | | Y | 21540071 | 21540286 |
| Y | 15604456 | 15605781 | | | Y | 21543861 | 21544576 |
| Y | 15611672 | 15612742 | | | Y | 21556712 | 21557292 |
| Y | 15621118 | 15622685 | | | Y | 21558745 | 21560060 |
| Y | 15630486 | 15630976 | | | Y | 21564972 | 21565504 |
| Y | 15640976 | 15641231 | | | Y | 21567244 | 21568254 |
| Y | 15642011 | 15642526 | | | Y | 21569044 | 21569434 |
| Y | 15643687 | 15644447 | | | Y | 21571579 | 21571894 |
| Y | 15647134 | 15647319 | | | Y | 21573609 | 21573784 |
| Y | 15650256 | 15650516 | | | Y | 21573944 | 21574139 |
| Y | 15652248 | 15652598 | | | Y | 21575404 | 21576094 |
| Y | 15653737 | 15655027 | | | Y | 21593053 | 21593533 |
| Y | 15660943 | 15662313 | | | Y | 21599555 | 21603620 |
| Y | 15666591 | 15666666 | | | Y | 21617904 | 21617919 |
| Y | 15676435 | 15676830 | | | Y | 21641435 | 21641665 |
| Y | 15677764 | 15679427 | | | Y | 21642705 | 21642930 |
| Y | 15686986 | 15687351 | | | Y | 21644456 | 21647841 |
| Y | 15688411 | 15689611 | | | Y | 21648201 | 21651031 |
| Y | 15694413 | 15695640 | | | Y | 21653766 | 21654641 |
| Y | 15697064 | 15698819 | | | Y | 21655476 | 21659185 |
| Y | 15699584 | 15700304 | | | Y | 21661605 | 21661945 |
| Y | 15706670 | 15707025 | | | Y | 21663455 | 21664500 |
| Y | 15708107 | 15708242 | | | Y | 21671363 | 21671628 |
| Y | 15710689 | 15711014 | | | Y | 21673656 | 21674166 |
| Y | 15711559 | 15711589 | | | Y | 21674621 | 21676143 |
| Y | 15711599 | 15712194 | | | Y | 21678788 | 21679206 |
| Y | 15713383 | 15714278 | | | Y | 21682524 | 21682719 |
| Y | 15715623 | 15716534 | | | Y | 21689459 | 21690979 |
| Y | 15725959 | 15726609 | | | Y | 21693072 | 21693362 |
| Y | 15727124 | 15727364 | | | Y | 21702479 | 21702679 |
| Y | 15734062 | 15741296 | | | Y | 21704096 | 21705756 |
| Y | 15743152 | 15744272 | | | Y | 21706351 | 21706871 |

The chromosomal positon was obtained from UCSC genome browser (http://genome.ucsc.edu/) build 36.

APPENDIX E: Chromosome Y

| Chr | Start | End | | | Chr | Start | End |
|---|---|---|---|---|---|---|---|
| Y | 15745211 | 15745591 | | | Y | 21707516 | 21707646 |
| Y | 15746411 | 15748534 | | | Y | 21714385 | 21716308 |
| Y | 15750194 | 15750969 | | | Y | 21718176 | 21719391 |
| Y | 15751719 | 15752578 | | | Y | 21722188 | 21722788 |
| Y | 15766448 | 15769106 | | | Y | 21723774 | 21723974 |
| Y | 15781241 | 15781456 | | | Y | 21724819 | 21726212 |
| Y | 15783901 | 15784166 | | | Y | 21734018 | 21734403 |
| Y | 15787027 | 15787057 | | | Y | 21735578 | 21735968 |
| Y | 15787142 | 15789707 | | | Y | 21737224 | 21738357 |
| Y | 15792179 | 15793222 | | | Y | 21740029 | 21740657 |
| Y | 15800906 | 15801421 | | | Y | 21741112 | 21741377 |
| Y | 15802446 | 15802711 | | | Y | 21746381 | 21747211 |
| Y | 15805301 | 15805936 | | | Y | 21752227 | 21752592 |
| Y | 15808058 | 15808846 | | | Y | 21762436 | 21762891 |
| Y | 15812073 | 15812898 | | | Y | 21763511 | 21763876 |
| Y | 15815013 | 15816578 | | | Y | 21769785 | 21774751 |
| Y | 15816853 | 15817978 | | | Y | 21776037 | 21777703 |
| Y | 15818728 | 15819914 | | | Y | 21778023 | 21778423 |
| Y | 15826674 | 15829510 | | | Y | 21783304 | 21783923 |
| Y | 15834967 | 15835832 | | | Y | 21787501 | 21788827 |
| Y | 15837337 | 15837647 | | | Y | 21790130 | 21791619 |
| Y | 15838117 | 15838412 | | | Y | 21792299 | 21792724 |
| Y | 15838872 | 15839107 | | | Y | 21795399 | 21795559 |
| Y | 15841107 | 15841622 | | | Y | 21797890 | 21798295 |
| Y | 15844915 | 15845075 | | | Y | 21799700 | 21800160 |
| Y | 15851221 | 15853426 | | | Y | 21801294 | 21803554 |
| Y | 15855981 | 15857271 | | | Y | 21806211 | 21810817 |
| Y | 15859213 | 15860088 | | | Y | 21811137 | 21811452 |
| Y | 15861133 | 15861198 | | | Y | 21814579 | 21817679 |
| Y | 15862111 | 15862546 | | | Y | 21818034 | 21818364 |
| Y | 15868422 | 15868838 | | | Y | 21819314 | 21819529 |
| Y | 15870156 | 15871070 | | | Y | 21822806 | 21822866 |
| Y | 15872141 | 15872491 | | | Y | 21823046 | 21824526 |
| Y | 15873841 | 15874279 | | | Y | 21825367 | 21827304 |
| Y | 15875054 | 15878797 | | | Y | 21831081 | 21831941 |
| Y | 15880857 | 15881247 | | | Y | 21833430 | 21833845 |
| Y | 15892821 | 15894141 | | | Y | 21835101 | 21835341 |
| Y | 15898546 | 15901228 | | | Y | 21836975 | 21839752 |
| Y | 15903677 | 15905197 | | | Y | 21840359 | 21842470 |
| Y | 15911084 | 15912448 | | | Y | 21844335 | 21844682 |
| Y | 15913963 | 15914523 | | | Y | 21846548 | 21846608 |
| Y | 15916037 | 15917127 | | | Y | 21848036 | 21848928 |
| Y | 15918611 | 15919140 | | | Y | 21852626 | 21854026 |
| Y | 15920885 | 15922869 | | | Y | 21854921 | 21855129 |
| Y | 15926281 | 15926658 | | | Y | 21859462 | 21860007 |
| Y | 15927688 | 15928098 | | | Y | 21860127 | 21860192 |
| Y | 15930473 | 15930843 | | | Y | 21861262 | 21862427 |
| Y | 15932733 | 15933323 | | | Y | 21864203 | 21864782 |
| Y | 15949067 | 15949862 | | | Y | 21865667 | 21866727 |
| Y | 15950532 | 15950997 | | | Y | 21870683 | 21870973 |
| Y | 15952322 | 15955542 | | | Y | 21872663 | 21872893 |
| Y | 15966377 | 15969862 | | | Y | 21876255 | 21878205 |
| Y | 15970217 | 15970597 | | | Y | 21881376 | 21881741 |
| Y | 15971582 | 15971980 | | | Y | 21892683 | 21893343 |
| Y | 15977290 | 15980099 | | | Y | 21900728 | 21901813 |

The chromosomal positon was obtained from UCSC genome browser (http://genome.ucsc.edu/) build 36.

APPENDIX E: Chromosome Y
Page 55 of 58

| Chr | Start | End | | Chr | Start | End |
|---|---|---|---|---|---|---|
| Y | 15980694 | 15980784 | | Y | 21907974 | 21908379 |
| Y | 15981105 | 15981751 | | Y | 21909659 | 21911674 |
| Y | 15983701 | 15983956 | | Y | 21913216 | 21913576 |
| Y | 15985095 | 15985445 | | Y | 21915137 | 21915727 |
| Y | 15987345 | 15990481 | | Y | 21915992 | 21916512 |
| Y | 16002865 | 16003335 | | Y | 21920162 | 21920382 |
| Y | 16003605 | 16008332 | | Y | 21939688 | 21940638 |
| Y | 16014097 | 16014552 | | Y | 21942542 | 21942942 |
| Y | 16016447 | 16017002 | | Y | 21944901 | 21949335 |
| Y | 16018597 | 16022888 | | Y | 21956329 | 21956789 |
| Y | 16028484 | 16033694 | | Y | 21957269 | 21958944 |
| Y | 16036910 | 16037510 | | Y | 21960634 | 21963764 |
| Y | 16040561 | 16040976 | | Y | 21967219 | 21968437 |
| Y | 16041993 | 16043290 | | Y | 21970061 | 21971466 |
| Y | 16043530 | 16043817 | | Y | 21972975 | 21974473 |
| Y | 16046137 | 16046893 | | Y | 21975972 | 21977427 |
| Y | 16056577 | 16056677 | | Y | 21980443 | 21981583 |
| Y | 16059338 | 16060533 | | Y | 21984569 | 21986664 |
| Y | 16061626 | 16062921 | | Y | 21992001 | 21992731 |
| Y | 16063086 | 16063156 | | Y | 21995971 | 21996226 |
| Y | 16063636 | 16063696 | | Y | 21997826 | 22001022 |
| Y | 16065275 | 16066500 | | Y | 22002449 | 22002579 |
| Y | 16067525 | 16069670 | | Y | 22003070 | 22003605 |
| Y | 16069720 | 16070365 | | Y | 22014455 | 22018205 |
| Y | 16072071 | 16072636 | | Y | 22021739 | 22022713 |
| Y | 16080691 | 16081071 | | Y | 22023358 | 22026987 |
| Y | 16082948 | 16083193 | | Y | 22027932 | 22028032 |
| Y | 16084806 | 16085248 | | Y | 22029197 | 22029657 |
| Y | 16086536 | 16088537 | | Y | 22031392 | 22031692 |
| Y | 16091181 | 16092211 | | Y | 22033987 | 22034292 |
| Y | 16092721 | 16094165 | | Y | 22035404 | 22037024 |
| Y | 16095720 | 16096790 | | Y | 22037484 | 22038199 |
| Y | 16099348 | 16101248 | | Y | 22039744 | 22040249 |
| Y | 16104532 | 16104787 | | Y | 22040504 | 22043628 |
| Y | 16105498 | 16106028 | | Y | 22044133 | 22044668 |
| Y | 16106308 | 16108742 | | Y | 22046893 | 22049286 |
| Y | 16109682 | 16111229 | | Y | 22049539 | 22049720 |
| Y | 16113909 | 16114234 | | Y | 22050471 | 22050481 |
| Y | 16115385 | 16115770 | | Y | 22052874 | 22053314 |
| Y | 16117101 | 16117486 | | Y | 22056140 | 22058901 |
| Y | 16117651 | 16118487 | | Y | 22059756 | 22061236 |
| Y | 16120875 | 16121440 | | Y | 22063653 | 22167252 |
| Y | 16122881 | 16124316 | | Y | 22169594 | 22176134 |
| Y | 16128470 | 16130985 | | Y | 22176709 | 22178164 |
| Y | 16132636 | 16139629 | | Y | 22179488 | 22180373 |
| Y | 16141622 | 16142241 | | Y | 22188013 | 22188113 |
| Y | 16153276 | 16154462 | | Y | 22192384 | 22193664 |
| Y | 16157350 | 16158469 | | Y | 22203102 | 22203402 |
| Y | 16160331 | 16160426 | | Y | 22206881 | 22207291 |
| Y | 16161363 | 16162078 | | Y | 22207846 | 22208136 |
| Y | 16162903 | 16163073 | | Y | 22208496 | 22210186 |
| Y | 16164253 | 16165103 | | Y | 22213874 | 22215179 |
| Y | 16165804 | 16166389 | | Y | 22218248 | 22219938 |
| Y | 16170145 | 16170895 | | Y | 22221708 | 22223888 |
| Y | 16172955 | 16173580 | | Y | 22226528 | 22232418 |

The chromosomal positon was obtained from UCSC genome browser (http://genome.ucsc.edu/) build 36.

APPENDIX E: Chromosome Y
Page 56 of 58

| Chr | Start | End | | | Chr | Start | End |
|---|---|---|---|---|---|---|---|
| Y | 16174562 | 16175022 | | | Y | 22252861 | 22253881 |
| Y | 16178654 | 16179429 | | | Y | 22255509 | 22256864 |
| Y | 16180804 | 16181174 | | | Y | 22262696 | 22267471 |
| Y | 16182506 | 16182856 | | | Y | 22267771 | 22274972 |
| Y | 16184287 | 16185319 | | | Y | 22281634 | 22283554 |
| Y | 16186321 | 16186396 | | | Y | 22293487 | 22294817 |
| Y | 16188147 | 16189213 | | | Y | 22305975 | 22307225 |
| Y | 16190083 | 16190298 | | | Y | 22308399 | 22308759 |
| Y | 16196565 | 16199416 | | | Y | 22309874 | 22310689 |
| Y | 16199606 | 16199761 | | | Y | 22371058 | 22371188 |
| Y | 16202036 | 16202766 | | | Y | 22372333 | 22372948 |
| Y | 16204805 | 16205316 | | | Y | 22375981 | 22401240 |
| Y | 16214360 | 16214995 | | | Y | 22404890 | 22667626 |
| Y | 16217555 | 16219641 | | | Y | 22765569 | 22766044 |
| Y | 16221301 | 16221421 | | | Y | 22768239 | 22768364 |
| Y | 16222051 | 16222946 | | | Y | 22775308 | 22775698 |
| Y | 16224592 | 16225857 | | | Y | 22777314 | 22780630 |
| Y | 16228167 | 16228397 | | | Y | 22789062 | 22789782 |
| Y | 16229522 | 16230202 | | | Y | 22791736 | 22798683 |
| Y | 16230802 | 16231112 | | | Y | 22800178 | 22801780 |
| Y | 16246300 | 16248252 | | | Y | 22805274 | 22806889 |
| Y | 16251892 | 16252577 | | | Y | 22808149 | 22810902 |
| Y | 16254967 | 16255132 | | | Y | 22824570 | 22824930 |
| Y | 16256332 | 16256657 | | | Y | 22828060 | 22828345 |
| Y | 16258582 | 16261171 | | | Y | 22835124 | 22835584 |
| Y | 16264973 | 16265723 | | | Y | 22838082 | 22839461 |
| Y | 16269567 | 16269702 | | | Y | 22845866 | 22847582 |
| Y | 16270437 | 16271217 | | | Y | 22850484 | 22852572 |
| Y | 16273052 | 16274047 | | | Y | 22853917 | 22855973 |
| Y | 16277334 | 16278684 | | | Y | 22860304 | 22861969 |
| Y | 16280968 | 16281363 | | | Y | 22863144 | 22863429 |
| Y | 16289442 | 16289642 | | | Y | 22863769 | 22864294 |
| Y | 16289917 | 16290397 | | | Y | 22864829 | 22866199 |
| Y | 16296920 | 16297955 | | | Y | 22877103 | 22877308 |
| Y | 16301236 | 16302426 | | | Y | 22878925 | 22883483 |
| Y | 16303286 | 16309490 | | | Y | 22884163 | 22886967 |
| Y | 16310680 | 16312161 | | | Y | 22888617 | 22892758 |
| Y | 16314496 | 16314576 | | | Y | 22902194 | 22905445 |
| Y | 16315081 | 16316676 | | | Y | 22907565 | 22908585 |
| Y | 16317231 | 16317586 | | | Y | 22920884 | 22923494 |
| Y | 16318791 | 16320336 | | | Y | 22926498 | 22927845 |
| Y | 16321006 | 16323265 | | | Y | 22928420 | 22929285 |
| Y | 16324475 | 16325790 | | | Y | 23282410 | 23284067 |
| Y | 16341228 | 16342393 | | | Y | 26873716 | 26874938 |
| Y | 16351235 | 16351731 | | | Y | 26907501 | 26908076 |
| Y | 16355315 | 16356217 | | | Y | 26964082 | 26964672 |
| Y | 16360007 | 16360357 | | | Y | 26969723 | 26998833 |
| Y | 16360372 | 16360482 | | | Y | 27044652 | 27047263 |
| Y | 16360812 | 16361954 | | | Y | 27050272 | 27051927 |
| Y | 16362254 | 16362476 | | | Y | 27052992 | 27056222 |
| Y | 16369965 | 16372466 | | | Y | 27065856 | 27069471 |
| Y | 16376448 | 16377756 | | | Y | 27087820 | 27089894 |
| Y | 16378421 | 16379325 | | | Y | 27106698 | 27110942 |
| Y | 16380740 | 16381145 | | | Y | 27116397 | 27116609 |
| Y | 16382955 | 16383460 | | | Y | 27119654 | 27120781 |

The chromosomal positon was obtained from UCSC genome browser (http://genome.ucsc.edu/) build 36.

APPENDIX E: Chromosome Y
Page 57 of 58

| Chr | Start | End | | | Chr | Start | End |
|---|---|---|---|---|---|---|---|
| Y | 16383765 | 16384653 | | | Y | 27133184 | 27135547 |
| Y | 16390298 | 16390568 | | | Y | 27143150 | 27150447 |
| Y | 16391543 | 16391858 | | | Y | 27155666 | 27156280 |
| Y | 16396799 | 16397089 | | | Y | 27163591 | 27164045 |
| Y | 16399424 | 16401154 | | | Y | 27168463 | 27168878 |
| Y | 16404266 | 16404617 | | | Y | 27175318 | 27176156 |
| Y | 16405677 | 16406482 | | | Y | 27178657 | 27179407 |
| Y | 16415015 | 16415425 | | | Y | 27179865 | 27179935 |
| Y | 16416055 | 16416150 | | | Y | 27180280 | 27180830 |
| Y | 16419530 | 16419805 | | | Y | 27183847 | 27185999 |
| Y | 16423476 | 16428969 | | | Y | 27187109 | 27190104 |
| Y | 16430806 | 16431111 | | | Y | 27192013 | 27192848 |
| Y | 16443991 | 16445205 | | | Y | 27208888 | 27209003 |
| Y | 16446741 | 16447506 | | | Y | 57377245 | 57379365 |
| Y | 16447676 | 16447976 | | | Y | 57392394 | 57411400 |
| Y | 16450992 | 16451384 | | | Y | 57412558 | 57413049 |
| Y | 16453769 | 16456003 | | | Y | 57420292 | 57422941 |
| Y | 16457609 | 16458419 | | | Y | 57426376 | 57430850 |
| Y | 16458443 | 16458608 | | | Y | 57437872 | 57442197 |
| Y | 16461056 | 16461921 | | | Y | 57446572 | 57456437 |
| Y | 16466319 | 16467764 | | | Y | 57462688 | 57463880 |
| Y | 16470887 | 16472005 | | | Y | 57470982 | 57480289 |
| Y | 16481178 | 16481738 | | | Y | 57483747 | 57486253 |
| Y | 16482453 | 16482943 | | | Y | 57487003 | 57501076 |
| Y | 16483828 | 16484553 | | | Y | 57502126 | 57502521 |
| Y | 16486573 | 16488330 | | | Y | 57505799 | 57508716 |
| Y | 16490255 | 16490515 | | | Y | 57508821 | 57509503 |
| Y | 16491948 | 16492923 | | | Y | 57510910 | 57515428 |
| Y | 16505059 | 16505374 | | | Y | 57517504 | 57517609 |
| Y | 16505749 | 16506019 | | | Y | 57519044 | 57525384 |
| Y | 16513061 | 16514411 | | | Y | 57527579 | 57528379 |
| Y | 16526652 | 16527367 | | | Y | 57531212 | 57533377 |
| Y | 16534374 | 16534664 | | | Y | 57533645 | 57534827 |
| Y | 16534931 | 16535071 | | | Y | 57537526 | 57544290 |
| Y | 16536871 | 16537603 | | | Y | 57545070 | 57545995 |
| Y | 16538300 | 16539625 | | | Y | 57548530 | 57549020 |
| Y | 16541845 | 16542295 | | | Y | 57559763 | 57560628 |
| Y | 16542735 | 16543010 | | | Y | 57563068 | 57571306 |
| Y | 16553792 | 16553907 | | | Y | 57573734 | 57583212 |
| Y | 16554933 | 16555123 | | | Y | 57585897 | 57586547 |
| Y | 16557874 | 16558254 | | | Y | 57587459 | 57589729 |
| Y | 16559349 | 16560039 | | | Y | 57591434 | 57597515 |
| Y | 16562310 | 16562585 | | | Y | 57598837 | 57599527 |
| Y | 16569965 | 16570142 | | | Y | 57603369 | 57605962 |
| Y | 16570617 | 16570842 | | | Y | 57608617 | 57609961 |
| Y | 16578397 | 16578697 | | | Y | 57613080 | 57616137 |
| Y | 16583892 | 16584062 | | | Y | 57617662 | 57619808 |
| Y | 16593151 | 16593631 | | | Y | 57622685 | 57624155 |
| Y | 16596085 | 16596863 | | | Y | 57624415 | 57625640 |
| Y | 16600003 | 16600723 | | | Y | 57626959 | 57628563 |
| Y | 16605209 | 16606484 | | | Y | 57630570 | 57633222 |
| Y | 16608709 | 16609004 | | | Y | 57637413 | 57649241 |
| Y | 16611934 | 16612597 | | | Y | 57652474 | 57669078 |
| Y | 16614566 | 16615106 | | | Y | 57670438 | 57684537 |
| Y | 16619220 | 16619838 | | | Y | 57685527 | 57689501 |

The chromosomal positon was obtained from UCSC genome browser (http://genome.ucsc.edu/) build 36.

APPENDIX E: Chromosome Y

| Chr | Start | End | | | Chr | Start | End |
|-----|-------|-----|---|---|-----|-------|-----|
| Y | 16620433 | 16620808 | | | Y | 57690029 | 57696301 |
| Y | 16622893 | 16623088 | | | Y | 57699963 | 57700960 |
| Y | 16624094 | 16625018 | | | Y | 57701520 | 57705177 |
| Y | 16626353 | 16627808 | | | Y | 57707202 | 57708437 |
| Y | 16631838 | 16632078 | | | Y | 57720734 | 57721124 |
| Y | 16635405 | 16635945 | | | Y | 57722606 | 57723622 |
| Y | 16636165 | 16636725 | | | Y | 57737329 | 57737459 |
| Y | 16637945 | 16638310 | | | Y | 57746976 | 57748666 |
| Y | 16639435 | 16646036 | | | | | |
| Y | 16658126 | 16659662 | | | | | |
| Y | 16659752 | 16660832 | | | | | |
| Y | 16664278 | 16664753 | | | | | |

The chromosomal positon was obtained from UCSC genome browser (http://genome.ucsc.edu/) build 36.

What is claimed is:

1. A method for prenatal diagnosis of trisomy 21 using a sample of maternal blood, the method comprising:
   a) obtaining a hypermethylated DNA sample by physically separating hypermethylated DNA from hypomethylated DNA in a sample of maternal blood, without chemically altering or enzymatically digesting the hypomethylated DNA or hypermethylated DNA;
   b) amplifying a plurality of differentially methylated regions (hereinafter DMRs), wherein said plurality of DMRs consists of eight regions amplified with oligonucleotide primers as follows:
      (i) a DMR comprising a sequence as shown in SEQ ID NO: 36 amplified using oligonucleotide primers comprising sequences as shown in SEQ ID NOs: 7 and 8;
      (ii) a DMR comprising a sequence as shown in SEQ ID NO: 37 amplified using oligonucleotide primers comprising sequences as shown in SEQ ID NOs: 9 and 10;
      (iii) a DMR comprising a sequence as shown in SEQ ID NO: 38 amplified using oligonucleotide primers comprising sequences as shown in SEQ ID NOs: 11 and 12;
      (iv) a DMR comprising a sequence as shown in SEQ ID NO: 39 amplified using oligonucleotide primers comprising sequences as shown in SEQ ID NOs: 13 and 14;
      (v) a DMR comprising a sequence as shown in SEQ ID NO: 40 amplified using oligonucleotide primers comprising sequences as shown in SEQ ID NOs: 15 and 16;
      (vi) a DMR comprising a sequence as shown in SEQ ID NO: 42 amplified using oligonucleotide primers comprising sequences as shown in SEQ ID NOs: 19 and 20;
      (vii) a DMR comprising a sequence as shown in SEQ ID NO: 43 amplified using oligonucleotide primers comprising sequences as shown in SEQ ID NOs: 21 and 22; and
      (viii) a DMR comprising a sequence as shown in SEQ ID NO: 44 amplified using oligonucleotide primers comprising sequences as shown in SEQ ID NOs: 23 and 24;
   c) obtaining a hypermethylation value for the hypermethylated DNA sample based on the amplification of the plurality of DMRs;
   d) comparing the hypermethylation value of the hypermethylated DNA sample to (i) a standardized normal reference hypermethylation value for a normal fetus or (ii) a range of standardized trisomy 21 reference hypermethylation values for a trisomy fetus;
   e) determining that (i) the hypermethylation value for the hypermethylated DNA sample is higher than the standardized normal reference hypermethylation value or (ii) the hypermethylation value for the hypermethylated DNA sample is within the range of the standardized trisomy 21 reference hypermethylation values; and
   f) diagnosing trisomy 21.

2. The method of claim 1, wherein the maternal blood sample is a maternal peripheral blood sample or a fractionated portion of maternal peripheral blood.

3. The method of claim 1, wherein hypermethylated DNA is separated from hypomethylated DNA using an antibody that immunoprecipitates methylated DNA.

4. The method of claim 1, wherein hypermethylated DNA is physically separated from hypomethylated DNA by Methylation DNA Immunoprecipitation.

5. The method of claim 1, wherein the hypermethylated DNA is amplified by ligation-mediated polymerase chain reaction (hereinafter LM-PCR).

6. The method of claim 5, wherein the levels of the plurality of DMRs are also determined in a total untreated maternal blood DNA sample as a control of the LM-PCR efficiency.

7. The method of claim 1, wherein the levels of the plurality of DMRs in the hypermethylated DNA sample are determined by real time quantitative polymerase chain reaction.

* * * * *

SEQUENCE LISTING

<160> NUMBER OF SEQ ID NOS: 46

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
gctggaccag aaagtgttga g                                     21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gtgtgctgct ttgcaatgtg                                        20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ggtcgagttt ttggtggtgt                                        20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ccaccgtcac tgttcctaga                                        20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cctcgtgctc gtgtctgtat                                        20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gaggaaacag cttggctctg                                        20

<210> SEQ ID NO 7
<211> LENGTH: 20
<212> TYPE: DNA
<213> ORGANISM: Artificial Sequence

```
<220> FEATURE:
<223> OTHER INFORMATION: primer

<400> SEQUENCE: 7
ctgttgcatg agagcagagg                                          20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgtcccsctc gctactatct                                          20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgcaggatat ttggcaaggt                                          20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ctgtgccggt agaaatggtt                                          20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tgaatcagtt caccgacagc                                          20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gaaacaacct ggccattctc                                          20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ccgttatatg gatgccttgg                                          20
```

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aaactgttgg gctgaactgc                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ccaggcaaga tggcttatgt                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
accatgctca gccaattttt                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
gacccagacg atacctggaa                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gctgaacaaa actcggcttc                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ccacatcctg gccatctact                                              20

<210> SEQ ID NO 20
<211> LENGTH: 20
<212> TYPE: DNA
<213> ORGANISM: Artificial Sequence
<220> FEATURE:
<223> OTHER INFORMATION: primer
```

```
<400> SEQUENCE: 20
ttccacagac agcagagacg                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tgagctcaca ggtctggaaa                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ccccacaggg ttctggtaat                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
attctccaca gggcaatgag                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ttatgtggcc tttcctcctg                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
caggaaagtg aagggagctg                                              20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
caaaacccaa tggtcaatcc                                              20

<210> SEQ ID NO 27
```

```
<211> LENGTH: 20
<212> TYPE: DNA
<213> ORGANISM: Artificial Sequence
<220> FEATURE:
<223> OTHER INFORMATION: primer

<400> SEQUENCE: 27
aatgattgtg caggtggtga                                              20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gagcgccttg agtagaggaa                                              20

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
aaggtgccca attcaaggta                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cttccccacc agtcttgaaa                                              20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
tgagagcgga tgacagattg                                              20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ggtccctccc ttttctgtct                                              20

<210> SEQ ID NO 33
<211> LENGTH: 149
<212> TYPE: DNA
<213> ORGANISM: Homo sapiens

<400> SEQUENCE: 33
gctggaccag aaagtgttga gtacctgctc atgcgtgcaa gaggaggagg gaggagcaca   60
```

```
tcactgaact tcacatgaaa ttggataccc gggattagag acagtagagg gttttggtga    120
aatcagatac acattgcaaa gcagcacac                                      149

<210> SEQ ID NO 34
<211> LENGTH: 146
<212> TYPE: DNA
<213> ORGANISM: Homo sapiens

<400> SEQUENCE: 34
ggtcgagttt ttggtggtgt tgagcggata gccggggaag ttggagtctt gtttgtggcc    60
gcctcgtgct cgtgtctgta tctaagatcc tcaggctgct ccttttttggg taaggtctgt   120 tgcttctcta ggaacagtga cggtgg                                         146

<210> SEQ ID NO 35
<211> LENGTH: 133
<212> TYPE: DNA
<213> ORGANISM: Homo sapiens

<400> SEQUENCE: 35
cctcgtgctc gtgtctgtat ctaagatcct caggctgctc ctttttgggt aaggtctgtt    60
gcttctctag gaacagtgac ggtggcagag cccgtggccc ctctctcctg tcccagagcc   120
aagctgtttc ctc                                                       133

<210> SEQ ID NO 36
<211> LENGTH: 95
<212> TYPE: DNA
<213> ORGANISM: Homo sapiens

<400> SEQUENCE: 36
ctgttgcatg agagcagagg ggagatagag agagcttaat tataggtacc cgcgtgcagc    60
taaaaggagg gccagagata gtagcgaggg ggacg                               95

<210> SEQ ID NO 37
<211> LENGTH: 127
<212> TYPE: DNA
<213> ORGANISM: Homo sapiens

<400> SEQUENCE: 37
tgcaggatat ttggcaaggt ttcttactgt tccaagtttt ttttccgaaa acctcccttg    60 aaactttttgt gcttacttgt ggtaacatac ccataatata ccctcttaac catttctacc   120
ggcacag                                                              127

<210> SEQ ID NO 38
<211> LENGTH: 104
<212> TYPE: DNA
<213> ORGANISM: Homo sapiens

<400> SEQUENCE: 38
tgaatcagtt caccgacagc cttggggaca ttcaccttgg gctccacaac ctgtcagaaa    60
tgcccccaag cccaaaggcg tcgagagaat ggccaggttg tttc                     104

<210> SEQ ID NO 39
<211> LENGTH: 127
<212> TYPE: DNA
<213> ORGANISM: Homo sapiens

<400> SEQUENCE: 39
```

```
ccgttatatg gatgccttgg ggcttggggg gtttctggca gtctgtcgag cccgaggtga    60
atgtccccaa ggctgctggt gaatcagatc cctggcgttc tccgttggca gttcagccca   120
acagttt                                                             127

<210> SEQ ID NO 40
<211> LENGTH: 144
<212> TYPE: DNA
<213> ORGANISM: Homo sapiens

<400> SEQUENCE: 40
ccaggcaaga tggcttatgt ctttaatctc agctgtttgg gaagccaagt ggaaagattg    60
cttgaggcca ggagttcaag accaacctgg ataatgtaag aagacctcgt ctctataaaa   120
aattaaaaat tggctgagca tggt                                          144

<210> SEQ ID NO 41
<211> LENGTH: 110
<212> TYPE: DNA
<213> ORGANISM: Homo sapiens

<400> SEQUENCE: 41
gacccagacg atacctggaa attatttgct catgtggcag tcactgttga ttgcctaccc    60
aaagccatta ctccttctcc ccacctaaca gaagccgagt tttgttcagc               110

<210> SEQ ID NO 42
<211> LENGTH: 101
<212> TYPE: DNA
<213> ORGANISM: Homo sapiens

<400> SEQUENCE: 42
ccacatcctg gccatctact tcctcttaaa caagaaactg gagcgctatt tgtcaggggt    60
aagtgcgacc ctagaggcga tcgtctctgc tgtctgtgga a                       101

<210> SEQ ID NO 43
<211> LENGTH: 88
<212> TYPE: DNA
<213> ORGANISM: Homo sapiens

<400> SEQUENCE: 43
tgagctcaca ggtctggaaa tggtctgaat agaaaggatt ggtctccgga ggaaagcata    60
ctcttcctat taccagaacc ctgtgggg                                       88

<210> SEQ ID NO 44
<211> LENGTH: 128
<212> TYPE: DNA
<213> ORGANISM: Homo sapiens

<400> SEQUENCE: 44
attctccaca gggcaatgag gcaagaaatt tacagcttag cctgattaat gggccaggca    60
gttaagagtt ctttgccaag ctatgagcat aatttatagt catcacggca ggaggaaagg   120
ccacataa                                                            128

<210> SEQ ID NO 45
<211> LENGTH: 79
<212> TYPE: DNA
<213> ORGANISM: Homo sapiens

<400> SEQUENCE: 45
caggaaagtg aagggagctg ccatctgcat caaacgctgc tgatgaacac ttgaactgag    60
```

-continued

```
gattgaccat tgggttttg                                              79

<210> SEQ ID NO 46
<211> LENGTH: 104
<212> TYPE: DNA
<213> ORGANISM: Homo sapiens

<400> SEQUENCE: 46
aaggtgccca attcaaggta tataaccttt aagcagcttt aacacaagag aaaccaagat    60
tagtagctgc cacccatggg gatctttcaa gactggtggg gaag                   104
```